US012698499B2

(12) United States Patent
Wherry et al.

(10) Patent No.: US 12,698,499 B2
(45) Date of Patent: Aug. 4, 2026

(54) IDENTIFYING EPIGENETIC AND TRANSCRIPTIONAL TARGETS TO PREVENT AND REVERSE T CELL EXHAUSTION

(71) Applicant: THE TRUSTEES OF THE UNIVERSITY OF PENNSYLVANIA, Philadelphia, PA (US)

(72) Inventors: E. John Wherry, Havertown, PA (US); Omar Khan, Philadelphia, PA (US); Martha Jordan, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1206 days.

(21) Appl. No.: 16/759,665

(22) PCT Filed: Oct. 26, 2018

(86) PCT No.: PCT/US2018/057852
§ 371 (c)(1),
(2) Date: Apr. 27, 2020

(87) PCT Pub. No.: WO2019/084495
PCT Pub. Date: May 2, 2019

(65) Prior Publication Data
US 2021/0071139 A1 Mar. 11, 2021

Related U.S. Application Data

(60) Provisional application No. 62/578,234, filed on Oct. 27, 2017.

(51) Int. Cl.
| | |
|---|---|
| *C12N 15/113* | (2010.01) |
| *A61K 40/11* | (2025.01) |
| *A61K 40/42* | (2025.01) |
| *A61K 40/46* | (2025.01) |
| *C12N 5/0783* | (2010.01) |
| *C12Q 1/6883* | (2018.01) |

(52) U.S. Cl.
CPC ........... *C12N 15/113* (2013.01); *A61K 40/11* (2025.01); *A61K 40/42* (2025.01); *A61K 40/46* (2025.01); *C12N 5/0636* (2013.01); *C12Q 1/6883* (2013.01); *C12N 2501/505* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2013/0280220 A1* | 10/2013 | Ahmed | A61K 39/464435 435/325 |
| 2016/0272999 A1* | 9/2016 | Duchateau | A61P 35/00 |
| 2017/0183413 A1 | 6/2017 | Galetto | |

FOREIGN PATENT DOCUMENTS

| | | | | | |
|---|---|---|---|---|---|
| WO | WO-2014070874 A1 * | 5/2014 | .......... | A61K 31/713 |
| WO | 2017/049166 A1 | 3/2017 | | |
| WO | 2017/075451 A1 | 5/2017 | | |

OTHER PUBLICATIONS

Shin, et al. Immunity. Aug. 21, 2009;31(2):309-20. doi: 10.1016/j.immuni.2009.06.019. Epub Aug. 6, 2009. PMID: 19664943. (Year: 2009).*
Liblau, et al. Autoreactive CD8 T cells in organ-specific autoimmunity: emerging targets for therapeutic intervention. Immunity. Jul. 2002;17(1):1-6. doi: 10.1016/s1074-7613(02)00338-2. PMID: 12150886. (Year: 2002).*
McKinney, et al. Nature. Jul. 30, 2015;523(7562):612-6. doi: 10.1038/nature14468. Epub Jun. 29, 2015. PMID: 26123020. (Year: 2015).*
Zhu X, Li Q, Zhu X. Mechanisms of CAR T cell exhaustion and current counteraction strategies. Front Cell Dev Biol. Dec. 8, 2022;10:1034257. doi: 10.3389/fcell.2022.1034257. PMID: 36568989. (Year: 2022).*
PCT/US2018/57852—International Search Report and Written Opinion dated Mar. 15, 2019.
Wherry, et al., "Molecular signature of CD8+ T cell exhaustion during chronic viral infection", Immunity 27:670-684, Oct. 2007.
Zajac et al., "Viral immune evasion due to persistence of activated T cells without effector function", J. Exp. Med. 188:2205-2213, Dec. 21, 1998.
Barber et al., "Restoring function in exhausted CD8 T cells during chronic viral infection", Nature 439:682-687, Feb. 9, 2006.
Topalian et al., "Safety, activity, and immune correlates of anti-PD-1 antibody in cancer", New Engl. J. Med. 366:2443-2454, Jun. 28, 2012.
Porter et al., "Chimeric antigen receptor-modified T cells in chronic lymphoid leukemia.", New Engl. J. Med. 365:725-733, Aug. 25, 2011.
Long et al., "4-1BB costimulation ameliorates T cell exhaustion induced by tonic signaling of chimeric antigen receptors", Nat. Med. 21:581-590, May 4, 2015.
Pauken et al., "Epigenetic stability of exhausted T cells limits durability of reinvigoration by PD-1 blockade", Science, Dec. 2, 2016, 354(6316):1160-1165.
Doering et al., "Network analysis reveals centrally connected genes and pathways involved in CD8+ T cell exhaustion versus memory", Immunity, Dec. 14, 2012, 37:1130-1144.
Oestreich et al., "NFATc1 Regulates PD-1 Expression upon T Cell Activation", J. Immunol. Oct. 1, 2008, 181:4832-4839.
Martinez, et al., "The transcription factor NFAT promotes exhaustion of activated CD8+ T cells", Immunity, Feb. 17, 2015, 42:265-278.

(Continued)

*Primary Examiner* — Benjamin P Blumel
*Assistant Examiner* — Jeffrey Mark Sifford
(74) *Attorney, Agent, or Firm* — Saul Ewing LLP; Kathryn Doyle; Justin Crotty

(57) ABSTRACT

The present invention provides methods of preventing, reversing or increasing T cell exhaustion in a patient having a disease. The present invention also provides methods for treating a disease in a patient having the disease. The present invention also provides an engineered T cell comprising a high priority epigenetic pathway that has been targeted, and uses thereof.

9 Claims, 67 Drawing Sheets
Specification includes a Sequence Listing.

(56)　　　　References Cited

OTHER PUBLICATIONS

Subramanian, A. et al., "Gene set enrichment analysis: A knowledge-based approach for interpreting genome-wide expression profiles", Proc Natl Acad Sci USA, Oct. 25, 2005, 102, 15545-15550.

Herndler-Brandstetter, D. et al., "KLRG1 + Effector CD8 + T Cells Lose KLRG1, Differentiate into All Memory T Cell Lineages, and Convey Enhanced Protective Immunity", Apr. 17, 2018, Immunity 48, 716-729.e8.

Bengsch, B. et al., "Epigenomic-Guided Mass Cytometry Profiling Reveals Disease-Specific Features of Exhausted CD8 T Cells", Immunity, May 2018, 48, 1029-1045.e5.

Chen, X. et al., "Integration of external signaling pathways with the core transcriptional network in embryonic stem cell", Cell, Jun. 13, 2008, 133, 1106-1117.

McKinney et al., "T-cell exhaustion, co-stimulation and clinical outcome in autoimmunity and infection", Nature. Jul. 30, 2015, 523:612-616.

Wherry, "T cell exhaustion", Nat Immunol. Jun. 2011, 12(6):492-9.

Crawford et al., "Molecular and transcriptional basis of CD4+ T cell dysfunction during chronic infection", Immunity. Feb. 20, 2014,40(2):289-302.

Youngblood et al., "Chronic virus infection enforces demethylation of the locus that encodes PD-1 in antigen-specific CD8(+) T cells", Immunity. Sep. 23, 2011, 35(3):400-12.

Y. Zhang et al., "CRISPR-Cas9 mediated LAG-3 disruption in CAR-T cells", Frontiers of Medicine, Jun. 2017, 11(2):554-562.

Sen, D. R. et al., "The epigenetic landscape of T cell exhaustion", Science. Dec. 2, 2016, 354, 1165-1169.

Kao, C. et al., "Transcription factor T-bet represses expression of the inhibitory receptor PD-1 and sustains virus-specific CD8+ T cell responses during chronic infection", Nat Immunol. May 29, 2011 12, 663-671.

Chang, J. T., et al., "Molecular regulation of effector and memory T cell differentiation", Nat Immunol. Dec. 2014, 15, 1104-1115.

Beura, L. K. et al., "T Cells in Nonlymphoid Tissues Give Rise to Lymph-Node-Resident Memory T Cells", Immunity. Feb. 20, 2018, 48, 327-338.e5.

Milner, J. J. et al., "Runx3 programs CD8 + T cell residency in non-lymphoid tissues and tumours", Nature. Dec. 14, 2017, 552(7684):253-257.

Mackay, L. K. et al., "The developmental pathway for CD103(+)CD8+ tissue-resident memory T cells of skin", Nat Immunol . Dec. 2013, 14(12), 1294-1301.

M. Adli. "The CRISPR tool kit for genome editing and beyond," Nature Communications; vol. 9 (May 15, 2018), Article No. 1911.

Y. Lei, et al., "Targeted DNA methylation in vivo using an engineered dCas9-MQ1 fusion protein", Nature Communications; vol. 8 (Jul. 17, 2017), Article No. 16026.

Lee J. et al., "Reinvigorating Exhausted T Cells by Blockade of the PD-1 Pathway", Immunopathol Dis Therap. (2015) ; 6(1-2): 7-17.

Rupp, L.J.et al., "CRISPR/Cas9-mediated PD-1 disruption enhances anti-tumor efficacy of human chimeric antigen receptor T cells", Scientific Reports, Apr. 7, 2017, 7(1):1-10.

Liu, X. et al., "CRISPR-Cas9-mediated multiplex gene editing in CAR-T cells", Cell Research, Jan. 2017, 27(1):154-157.

Cyranowski, D., "Crispr gene-editing tested in a person for the first time", Nature, Nov. 15, 2016, 539(7630):479.

Collins, M. et al., "Transcriptional regulation and T cell exhaustion", Current Opinion in HIV and AIDS, Sep. 1, 2014, 9(5):459-463.

Wherry, E.J. et al., "Molecular and cellular insights into T cell exhaustion", Nature Reviews Immunology, Jul. 24, 2015, 15:486-499.

Wu, J. et al., "Unlocking the epigenetic code of T cell exhaustion", Translational Cancer Research, Mar. 2017, 6(S2):1165-1169.

Newman, D.M. et al., "Essential role for the histone acetyltransferase KAT7 in T cell development, fitness, and survival", Journal of Leukocyte Biology, Oct. 12, 2016, 887-892.

Khan, O. et al., "TOX transcriptionally and epigenetically programs CD8 + T cell exhaustion", Nature, Jul. 2019, 571(7764):211-218.

Scott, A.C. et al., "TOX is a critical regulator of tumour-specific T cell differentiation", Nature, Jul. 2019, 571(7764):270-274.

Youngblood et al., "Cutting Edge: Prolonged Exposure to HIV Reinforces a Poised Epigenetic Program for PD-1 Expression in Virus-Specific CD8 T Cells", J Immunol. 2013, 191(2):540-544.

The Extended European Search Report dated Oct. 14, 2021, of counterpart European Application No. 18869919.3.

* cited by examiner

Fig. 10B
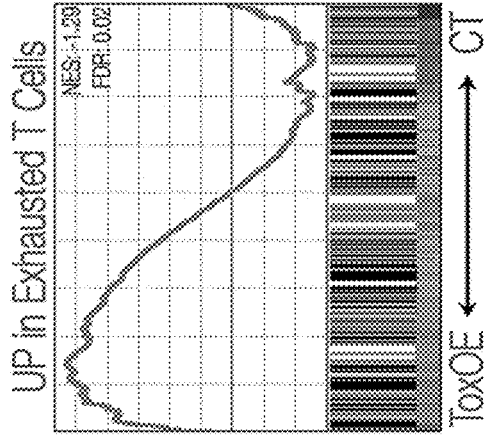
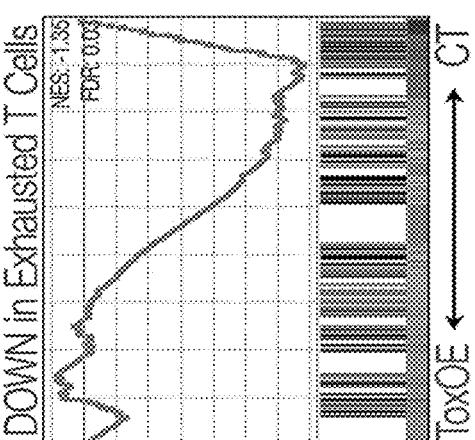
Fig. 10A
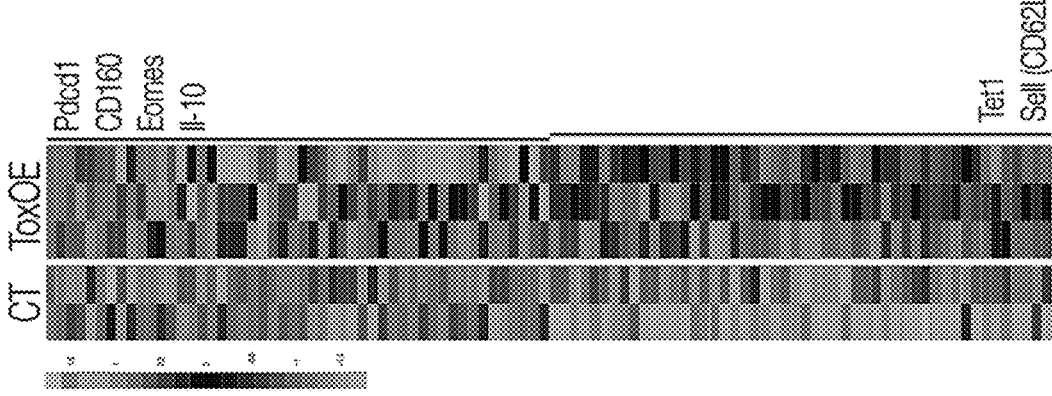

Fig. 12B

- GTF2I - General Transcription Factor 2i
- EEF1G - Eukaryotic Translation Elongation Factor 1 Gamma
- SFPQ - Splicing Factor Proline and Glutamine Rich
- SF3B3, SF3B1, SF3A3 - Splicing Factors
- RBM17 - RNA Binding Motif Protein 17
- SUB1 - SUB1 Homolog, Transcriptional Regulator
- PCNA - Proliferating Cell Nuclear Antigen
- HMGB2 - High Mobility Group Box 2
- ALYREF - Promotes dimerization of bZIP TFs —> Transcriptional elongation
- SET - Inhibitor of HAT
- RUVBL1/2 - Component of NuA4 HAT Complex
- DPY30 - Component of SET1/MLL family of H3K4 methyltransferases

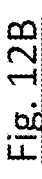
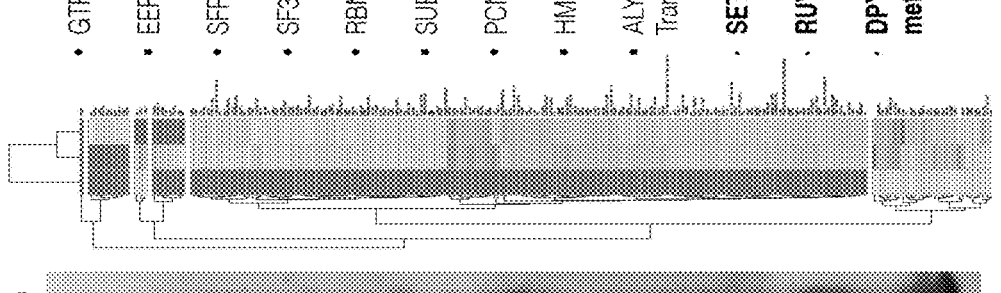

Anti-Tox

Fig. 12A

Ladder   CT Ab   Tox Ab

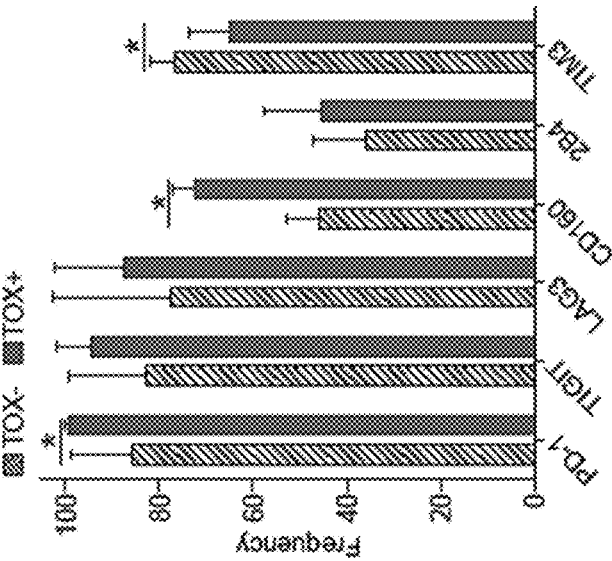
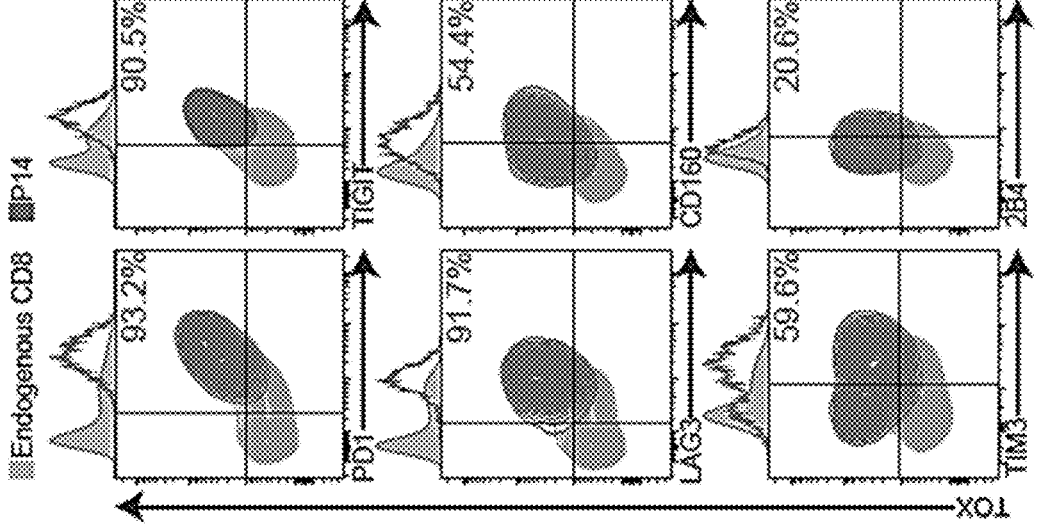
Fig. 16C

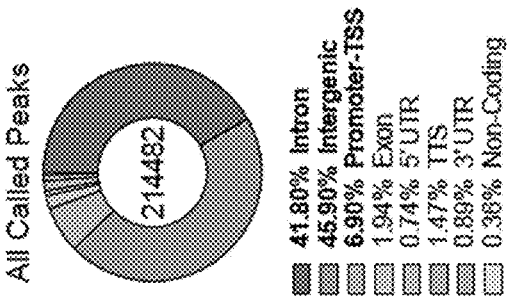
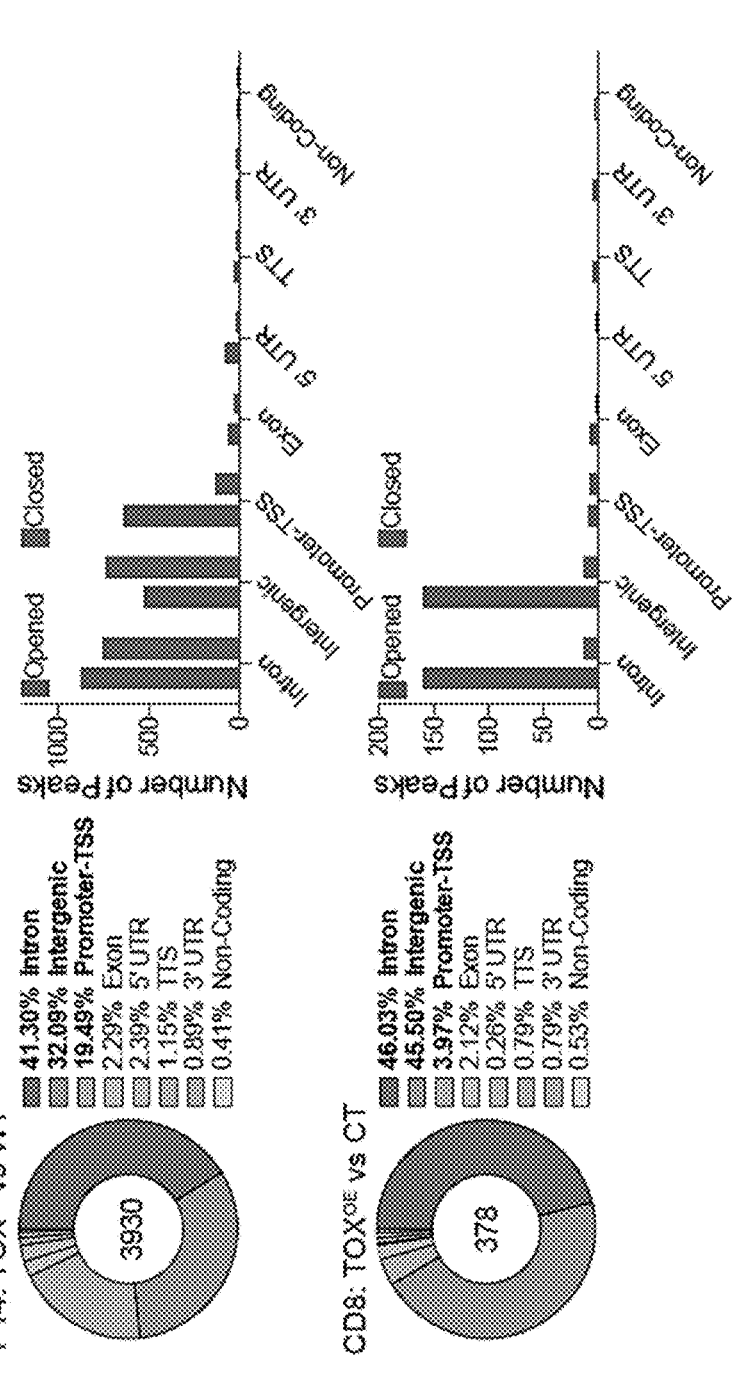
Fig. 23A

IDENTIFYING EPIGENETIC AND TRANSCRIPTIONAL TARGETS TO PREVENT AND REVERSE T CELL EXHAUSTION

CROSS-REFERENCE TO RELATED APPLICATION

This application claims priority to U.S. Provisional Application No. 62/578,234, filed Oct. 27, 2017, which is hereby incorporated by reference in its entirety.

STATEMENT REGARDING FEDERALLY SPONSORED RESEARCH OR DEVELOPMENT

This invention was made with government support under AI082292, AI129263, GM053256, AI082630, and AI105343 awarded by the National Institutes of Health. The government has certain rights in the invention.

BACKGROUND

T cell exhaustion, which is an acquired state of T cell dysfunction, is a hallmark of cancer and chronic viral infection (Wherry et al. (2007) *Immunity* 27:670-684; Zajac et al. (1998) *J Exp. Med.* 188:2205-2213). Recently, treatments to reverse T cell exhaustion in cancer have proven strikingly effective (Barber et al. (2006) *Nature* 439:682-687; Topalian et al. (2012) *New Engl. J Med.* 366:2443-2454). Chimeric antigen receptor (CAR)-T cell therapy has also proven highly effective for hematologic malignancies (Porter et al. (2011) *New Engl. J Med.* 365:725-733), but the development of exhaustion in engineered T cells to treat solid tumors remains a significant barrier to its broader use (Long et al. (2015) *Nat. Med.* 21:581-590). Identifying mechanisms that regulate T cell exhaustion could improve the efficacy of immune checkpoint blockade and adoptive T cell therapy for cancer immunotherapy (Barber et al. (2006) *Nature* 439:682-687; Topalian et al. (2012) *New Engl. J. Med.* 366:2443-2454; Porter et al. (2011)*New Engl. J. Med.* 365:725-733).

Current strategies for modulating T cell exhaustion rely on directly modulating expression of effector gene expression products, such as immune checkpoints, and such modulation produces undesired side effects since physiological levels of such effector gene expression products are often required for normal T cell function. In addition, such strategies are vulnerable to drug resistance and can lead to immunopathology. Accordingly, there is a great need in the art to identify compositions and methods useful for modulating expression of effector gene expression products in T cells as well as modulating genes that impact durability, homing and migration, transcriptional control (including transcription factors and epigenetic regulators), and metabolic control mechanisms. There remains a need for methods for modulating gene expression programs to guide the differentiation state of a T cell away from exhaustion and towards effector or memory fates.

BRIEF SUMMARY

Provided is a method of making an improved cell therapy composition for use in treating a disease, comprising the steps of.
    (a) obtaining a sample comprising lymphocytes from a
      subject;

(b) reducing or eliminating expression of one or more genes required for the induction and/or maintenance of exhausted CD8+ T lymphocytes ($T_{EX}$) in the lymphocytes; and
    (c) engineering the lymphocytes to target a therapeutically relevant antigen; wherein the disease is selected from cancer and infection.

In some embodiments, the sample comprising T cells from the subject comprises blood, ascites, pleural effusion, lymph, mucus, broncho-alveolar lavage, or tissue. In some embodiments, the sample comprising T cells from the subject comprises CD8+ T cells, tumor-associated lymphocytes, or tumor-infiltrating lymphocytes (TILs). In further embodiments, expression of the one or more genes required for the induction and/or maintenance of TEX in the lymphocytes is reduced. In further embodiments, expression of the one or more genes required for the induction and/or maintenance of TEX in the lymphocytes is eliminated.

In some embodiments, expression of the one or more genes required for the induction and/or maintenance of TEX in the lymphocytes is reduced by a method selected from the group consisting of RNA interference, clustered interspersed short palindromic repeat (CRISPR)/CRISPR-associated protein (Cas) system, meganucleases, transcription activator-like effector nucleases (TALENs), Zinc-finger nucleases (ZFNs), antisense, ribozymes and CRISPR inhibition system comprising dead Cas9.

In some embodiments, expression of the one or more genes required for the induction and/or maintenance of $T_{EX}$ in the lymphocytes is eliminated by a method selected from the group consisting of RNA interference, clustered interspersed short palindromic repeat (CRISPR)/CRISPR-associated protein (Cas) system, meganucleases, transcription activator-like effector nucleases (TALENs), Zinc-finger nucleases (ZFNs), antisense, ribozymes and CRISPR inhibition system comprising dead Cas9.

In some embodiments, the disease is a viral infection. In some embodiments, the viral infection is an acute viral infection or a chronic viral infection. In some embodiments, the disease is an acute viral infection. In further embodiments, the acute viral infection comprises infection with a virus selected from the group consisting of hepatitis viruses, herpesviruses, polyoma viruses, anelloviruses, adenoviruses, retroviruses, and influenza viruses.

In some embodiments, the virus is a hepatitis virus selected from the group consisting of Hepatitis A Virus (HAV), Hepatitis B Virus (HBV), Hepatitis C Virus (HCV), Hepatitis D Virus (HDV), Hepatitis E Virus (HEV), GB Hepatitis Virus A (GBV-A), GB Hepatitis Virus B (GBV-B), and GB Hepatitis Virus C (GBV-C). In some embodiments, the virus is a herpesvirus selected from the group consisting of alpha-herpesviruses, herpes simplex virus type 1 (HSV1), herpes simplex virus type 2 (HSV2), varicella zoster virus (VZV), beta-herpesviruses, cytomegalovirus (CMV), human herpes virus 6, human herpes virus 7, gamma-herpesviruses, Epstein-Barr virus (EBV), and human herpes virus 8. In some embodiments, the virus is a polyoma virus selected from the group consisting of BK virus (BKV), JC virus (JCV), KI polyoma virus (KIPvV), WU virus (WUPyV), Merkel cell polvomavirus (MCPyV), human polyoma virus 6 (HPyV6), human polyoma virus 7 (HPyV7), trichodysplasia spinulosa virus (TSPyV), human polyoma virus 9 (HPyV9), and MW virus (MWPvV). In some embodiments, the virus is an adenovirus selected from the group consisting of adenovirus serotype A, adenovirus serotype B, adenovirus serotype C, adenovirus serotype D, adenovirus serotype E, adenovirus serotype F, and adenovirus serotype G. In some embodiments, the virus is an influenza virus selected from group consisting of influenza virus A, influenza virus B, influenza virus C, and influenza virus D In some embodiments, the disease is a chronic viral infection. In some embodiments, the chronic viral infection comprises infection with HIV, HCV or HBV. In some embodiments, the chronic viral infection is with HIV and the subject is being treated with antiretroviral therapy (ART). In some embodiments, the chronic viral infection is with a retrovirus selected from the group consisting of alpha-retroviruses, beta-retroviruses, gamma-retroviruses, delta-retroviruses, epsilon-retroviruses, lentiviruses, and spuma-viruses. In some embodiments, the retrovirus is a lentivirus selected from the group consisting of human immunodefi-ciency virus (HIV) and equine infectious anemia virus (EIAV).

In some embodiments, the infection is a bacterial infec-tion or a parasite infection.

In some embodiments, the disease is cancer.

In some embodiments, the one or more genes required for the induction and/or maintenance of TEX is a transcription factor or a gene involved in epigenetic modification of DNA. In further embodiments, the one or more genes required for induction and/or maintenance of TEX is a transcription factor. In yet further embodiments, the transcription factor is selected from the group consisting of TOX, NFAT1, NFAT2, BATF, IRF4, T-bet, Eomes, Tcf1, Blimp-1, Bcl6, Foxo1, Stat1, Stat2, Tcf4, and Ikzf2. In some embodiments, the one or transcription factor is shown in FIG. 19.

In some embodiments, the one or more genes required for induction and/or maintenance of TEX is a gene involved in epigenetic modification of DNA. In some embodiments, the gene involved in epigenetic modification of DNA is selected from the group consisting of Kat7, Ing4, mEaf6, Jade2, Tet2, Dnmt3a, Setbp1, Gcn5, Kdm4a, Ppa1, Myef2, Rcn2, Acot8, Ing4, Thoc5, Orc5, Eif5, Fubp1, Mrpl46, Ppie, env, C1qc, Tox, Dync1li1, Sap130, Mphosph10, Rbm42, Rrp8, Meaf6, Acsl4, Kat7, Hcfc1, Ccar1, Rbm34, Dnajc9, Sdcbp, Cdadc1, Cacybp, Jade2, Tox4, Tox3, Dlst, Utp14a, Rpl36, Gm8973, Pusl1, Acad9, Prrc2a, Fxr1, Srrt, Ikbkap, Rpl37a, Cad, Prrc2c, Dmap1, Zfp219, Nusap1, Kntc1, Cdc73, Zwilch, Rpl36a, Dhx30, mKIAA0890, Aldh18a1, Pno1, Metap2, Ogdh, Ptcd3, Myo6, Kifc5b, Kifc1, Ash21, Hs2st1, Cd2ap, Ing2, Gm10094, Sap18, Dido1, Eif5b, Snx9, mars, Wdhd1, Dlgap5, Tagln2, Rrplb, Ttc37, Rifl, Arg3l1, Safb, Safb2, mKIAA0138, Cdc23, Cdc27, Terf2ip, Eif4h, mKIAA0038, Ppp1r10, Trip12, Eif4g2, Zfr, Utp18, Cdk9, Sltm, Taf6, Ddx55, Chtop, Tsr1, Anln, Tpm4, Thoc2, Dap3, Larp7, Trim21, Pdlim1, Snrpb2, Pml, Hsd17b10, Mrpl3, Utp1l1, Rbm28, Mcm5, Cnot1, Tmem214, Mrto4, mg684, Orc3, Tcebl, Supt6h, Supt6, Trrap, Cdc16, Dhx29, Arhgef2, Cptla, Tmem160, Wdr82, Ccnk, Spty2d1, Skap2, copg1, Nop2, Orc1, Gnl2, Mark2, Zmym4, Rps6ka3, Rps6ka2, Rps6ka1, Nob1, Nop14, Sptbn1, Dnajb11, Dynll2, Dynll1, BC048507, Nsf, Dnajb6, Lsg1, Ddx23, Rpl28, Polr2b, Zcchc8, Rrbp1, Camk2d, Camk2b, Camk2a, Camk2g, Sugp1, Atxn2, Gm20517, Med20, Samd1, Ap3 m1, Sorbs1, Csrp1, Parp2, Aars, Sfxn1, Ipo4, Tfip11, Bazla, Tbllx, Stau1, Cpsf3, Ep400, Pds5a, Chd4, Chd5, Lmnb1, Ddx18, Nmt1, Otud4, Supt16, Supt16h, Ap3d1, Lrrfip1, Tdrd3, Rpl3, Dnmt1, Rpa2, Ahnak, Wrnip1, Ythdf1, Isy1, Ckap5, Rpl8, Ssb, Ptpn11, Srsf5, Pds5b, Add3, Rps23, Tpx2, Dst, LRWD1, Tra2b, Nup98, Yars, Rpl13, Zc3h11a, Dnaja2, Rftn1, Rpl5, Pafl, Rpl7a, Rars, Rpl14, Rpl14-ps1, Rcc1, Eif2a, Usp10, cycs, Racgap1, Luzp1, mFLJ00226, Acad12, Acadl0, Ppan, Rcc2, Terf2, Slc25a11, Xm2, Numa1, Smarca4, Wdr36, Brd1, Eif3h, Rpl26, Rpl32, Bag6, BC005685, Rpl21, Csnk2a2, Ap3b1, Slc25a3, Lztfl1, Polb, Rbm15, Gtpbp4, Acaca, Xrcc5, Thoc1, Ywhah, Sin3a, Cd3eap, Teof1, Acin1, Hnrnph1;Hnrnph2, Elmo1, Srrm2, Rpl34;Gm2178, Pfkl, Rps24, Rps24, Zw10, Umps, Emg1, Gm20425, Srprb, Hp1bp3, Slc25a4, Srp72, Kdm1a, Eif3a, Soat1, Raver1, Pnn, Leo1, Abefl, Dld, Thoc6, Gatad2a, Rsl1d1, Rpl6, Pabpn1, Cwc 27, Nol7, Abcf2, Rpl23, Bclaf1, Cwc15, Rbm25, Pop1, Ap2a1, Actr5, Rrp1, Top3b, Rpl10, Rpl10I, Ebna1bp2, Hist1h3i, Hist1h3a, H3f3a, Gatad2b, Ccdc86, Cnot10, Yme1l1 and Paxbp1.

In some embodiments, the engineering the lymphocytes to target a therapeutically relevant antigen comprises intro-duction of a recombinant T cell receptor capable of binding a desired antigen/MHC or neo-antigen/MHC combination or introduction of a chimeric antigen receptor capable of bind-ing a desired antigen. In some embodiments, the therapeu-tically relevant antigen is selected from the group consisting of CD19, PSMA, CAIX, HER2, CD30zeta, Folate receptor alpha, Mucin1 (MUC1), Hepatitis C virus E2 glycoprotein, HIV envelope glycoprotein gp120, CMV pp65, GPC3, CEA, Mesothelin, GD2, EGFR, PSMA, EpCAM, BCMA, IL-13R, FAP and CD20.

Provided is a method of treating a disease characterized by increased numbers of exhausted CD8+ effector T cells ($T_{EX}$), comprising administering an improved cell therapy composition made by the method of any of of the preceding claims.

Provided is an improved cell therapy composition com-prising engineered lymphocytes made by the process of any one of the preceding claims.

Provided is a method of treating a disease characterized by increased numbers of exhausted CD8+ effector T cells ($T_{EX}$), comprising administering an inhibitor of calcium signaling. In some embodiments, the inhibitor of calcium signaling is selected from the group consisting of FK506/tacrolimus, pimecrolimus, and cyclosporine A.

Also provided is a method of making an improved cell therapy composition for treating an autoimmune disease, comprising the steps of (a) obtaining a sample comprising auto-reactive lympho-cytes from a subject;

(b) increasing expression of one or more genes required for the induction and/or maintenance of exhausted CD8+ T lymphocytes ($T_{EX}$) in the auto-reactive lym-phocytes; and (c) engineering the lymphocytes to target a therapeutically relevant antigen.

In some embodiments, the sample comprising T cells from the subject comprises blood, ascites, pleural effusion, lymph, mucus, broncho-alveolar lavage, or tissue. In some embodiments, the sample comprising T cells from the sub-ject comprises CD8+ T cells, tumor-associated lymphocytes, or tumor-infiltrating lymphocytes (TILs). In some embodi-ments, expression of the one or more genes required for the induction and/or maintenance of $T_{EX}$ in the auto-reactive lymphocytes is increased.

Provided is an improved cell therapy composition com-prising engineered lymphocytes made by the process of any one of the preceding embodiments.

Provided is a method of treating a disease characterized by decreased numbers of exhausted CD8+ effector T cells ($T_{EX}$), comprising administering an improved cell therapy composition made by the method of any of the preceding embodiments.

Provided is a method of identifying subjects in need of T cell reinvigoration, comprising the steps of.

(a) obtaining a sample comprising lymphocytes from a subject;

(b) measuring expression of one or more genes characteristic of exhausted CD8+ effector T cells ($T_{EX}$) in the sample;

(c) comparing expression of the one or more genes characteristic of $T_{EX}$ to expression of the same one or more genes characteristic of $T_{EX}$ in a control sample comprising lymphocytes;

(d) repeating method steps (a), (b), and (c) at one or more subsequent time points;

(e) determining the subject is in need of T cell reinvigoration if expression of the one or more genes characteristic of $T_{EX}$ in the second or subsequent sample comprising lymphocytes is increased compared its expression in the first or prior sample comprising lymphocytes; or (f) determining that the subject is not in need of T cell reinvigoration if expression of the one or more genes characteristic of $T_{EX}$ in the second or subsequent sample is the same as or decreased compared to its expression in the first or prior sample comprising lymphocytes.

In some embodiments, the one or more genes characteristic of $T_{EX}$ is selected from the group consisting of TOX, NFAT1, NFAT2, BATF, IRF4, T-bet, Eomes, Tcf1, Blimp-1, Bcl6, Foxo1, Stat1, Stat2, Tcf4, and Ikzf2. In some embodiments, the one or genes characteristic of $T_{EX}$ is shown in FIG. 19.

In some embodiments, the one or more genes characteristic of $T_{EX}$ is selected from the group consisting of Kat7, Ing4, mEaf6, Jade2, Tet2, Dnmt3a, Setbp1, Gcn5, Kdm4a, Ppa1, Myef2, Rcn2, Acot8, Ing4, Thoc5, Orc5, Eif5, Fubp1, Mrpl46, Ppie, env, C1qc, Tox, Dync1li1, Sap130, Mphosph10, Rbm42, Rrp8, Meaf6, Acsl4, Kat7, Hcfc1, Ccar1, Rbm34, Dnajc9, Sdcbp, Cdadc1, Cacybp, Jade2, Tox4, Tox3, Dlst, Utp14a, Rpl36, Gm8973, Pusl1, Acad9, Prrc2a, Fxr1, Srrt, Ikbkap, Rpl37a, Cad, Prrc2c, Dmap1, Zfp219, Nusap1, Kntc1, Cdc73, Zwilch, Rpl36a, Dhx30, mKIAA0890, Aldhl8al, Pno1, Metap2, Ogdh, Ptcd3, Myo6, Kifc5b, Kifc1, Ash21, Hs2st1, Cd2ap, Ing2, Gm10094, Sap18, Dido1, Eif5b, Snx9, mars, Wdhd1, Dlgap5, TagLn2, Rrplb, Ttc37, Rifl, Arg3ll, Safb, Safb2, mKIAA0138, Cdc23, Cdc27, Terf2ip, Eif4h, mKIAA0038, Ppplr10, Trip12, Eif4g2, Zfr, Utp18, Cdk9, Sltm, Taf6, Ddx55, Chtop, Tsr1, Anln, Tpm4, Thoc2, Dap3, Larp7, Trim21, Pdlim1, Snrpb2, Pml, Hsd17b10, Mrpl3, Utp1l1, Rbm28, Mcm5, Cnot1, Tmem214, Mrto4, mg684, Orc3, Tcebl, Supt6h, Supt6, Trrap, Cdc16, Dhx29, Arhgef2, Cptla, Tmem160, Wdr82, Ccnk, Spty2d1, Skap2, copg1, Nop2, Orc1, Gnl2, Mark2, Zmym4, Rps6ka3, Rps6ka2, Rps6ka1, Nob1, Nop14, Sptbn1, Dnajb11, Dynll2, Dynll1, BC048507, Nsf, Dnajb6, Lsg1, Ddx23, Rpl28, Polr2b, Zcchc8, Rrbp1, Camk2d, Camk2b, Camk2a, Camk2g, Sugp1, Atxn2, Gm20517, Med20, Samd1, Ap3 ml, Sorbs1, Csrp1, Parp2, Aars, Sfxn1, Ipo4, Tfip11, Baz1a, Tbl1x, Stau1, Cpsf3, Ep400, Pds5a, Chd4, Chd5, Lmnb1, Ddx18, Nmt1, Otud4, Supt16, Supt16h, Ap3d1, Lrrfip1, Tdrd3, Rpl3, Dnmt1, Rpa2, Ahnak, Wrnip1, Ythdf1, Isy1, Ckap5, Rpl8, Ssb, Ptpn11, Srsf5, Pds5b, Add3, Rps23, Tpx2, Dst, LRWD1, Tra2b, Nup98, Yars, Rpl13, Zc3h11a, Dnaja2, Rftn1, Rpl5, Pafl, Rpl7a, Rars, Rpl14, Rpl14-ps1, Rcc1, Eif2a, Usp10, cycs, Racgap1, Luzp1, mFLJ00226, Acad12, Acadl0, Ppan, Rcc2, Terf2, Slc25a11, Xm2, Numa1, Smarca4, Wdr36, Brd1, Eif3h, Rpl26, Rpl32, Bag6, BC005685, Rpl21, Csnk2a2, Ap3b1, Slc25a3, Lztfl1, Polb, Rbm15, Gtpbp4, Acaca, Xrcc5, Thoc1, Ywhah, Sin3a, Cd3eap, Tcofl, Acin1, Hnmph1;Hnmph2, Elmo1, Srrm2, Rpl34;Gm2178, Pfkl, Rps24, Rps24, Zw10, Umps, Emg1, Gm20425, Srprb, Hp1bp3, Slc25a4, Srp72, Kdm1a, Eif3a, Soat1, Ravern, Pnn, Leo1, Abcf1, Dld, Thoc6, Gatad2a, Rsl1d1, Rpl6, Pabpn1, Cwc 27, Nol7, Abcf2, Rpl23, Bclaf1, Cwc15, Rbm25, Pop1, Ap2a1, Actr5, Rrp1, Top3b, Rpl10, Rpl10I, Ebna1bp2, Hist1h3i, Hist1h3a, H3f3a, Gatad2b, Ccdc86, Cnot10, Ymel11 and Paxbp1.

In some embodiments, the sample comprising T cells from the subject comprises blood, ascites, pleural effusion, lymph, mucus, broncho-alveolar lavage, or tissue.

In some embodiments, the sample comprising T cells from the subject comprises CD8+ T cells, tumor-associated lymphocytes, or tumor-infiltrating lymphocytes (TILs).

Also provided is the method of any one of the previous embodiments, further comprising administering to the subject a composition for T cell reinvigoration if it is determined that the subject is in need of T cell reinvigoration.

Also provided is the method of any one of the preceding embodiments, further comprising administering to the subject an alternative treatment if it is determined that the subject is not in need of T cell reinvigoration.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A depicta a row-normalized heatmap depicting the expression of genes with chromatin modulating function in CD8 T cells during the course of acute or chronic LCMV infection. Cluster 1 genes represent those enriched in naïve T cells, cluster 2 genes are enriched in memory T cells, and cluster 3 genes are specifically expressed during effector T cell differentiation. The genes in cluster 4 are specifically expressed during the course of chronic infection. FIG. 1B depicts a row-normalized heatmap of cluster 4, showing the names of chromatin-modulating genes associated with T cell exhaustion. FIG. 1C depicts the microarray intensities of three example genes from cluster 4, showing the transcriptional divergence during the course of acute and chronic infection.

FIG. 2A depicts a visual description of the experimental model used to measure the expression of Tox protein in acute and chronic infection. FIG. 2B depicts contour plots from the flow cytometric analysis of Tox expression in acute and chronic infection at multiple time-points. FIG. 2C depicts quantification of the frequency of P14 T cells expressing Tox in acute and chronic infection.

FIG. 4A depicts quantification of the contribution to total splenic CD8$^+$ T cells made by WT or $Tox^{KO}$ T cells during the course of Cl-13 infection. FIG. 4B depicts a histogram of Ki-67 protein levels in WT and $Tox^{KO}$ T cells 8 days post-infection with Cl-13.

FIG. 5A depicts histograms of inhibitory receptor protein expression in WT and $Tox^{KO}$ T cells 8 days post-infection with Cl-13. FIG. 5B depicts quantification of the frequency of WT and $Tox^{KO}$ T cells expressing various inhibitory receptors 8 days post-infection.

FIG. 6A depicts histograms of CD44, KLRG1, CD62L, and CD127 protein expression in WT and $Tox^{KO}$ T cells at day 8 of infection. FIG. 6B depicts quantification of the frequency of WT and $Tox^{KO}$ T cells expressing the proteins stated in FIG. 6A 8 days post-infection with Cl-13.

FIG. 7A depicts a histogram and bar graph quantification of Tcf1 protein expression in WT and $Tox^{KO}$ T cells 8 days post-infection with Cl-13. FIG. 7B depicts, in a histogram, the protein levels of Tcf1 in naïve WT and $Tox^{KO}$ T cells from the spleens of uninfected mice.

FIGS. 10A-10B illustrate that expression of Tox is sufficient to induce an exhaustion-enriched gene signature. FIG. 10A depicts a row-normalized heatmap depicting the top 200 differentially expressed genes in T cells transduced with a vector encoding Tox compared to controls. FIG. 10B depicts a gene-set enrichment analysis plot of genes enriched in in vivo exhausted CD8+ T cells (upper panel) and genes downregulated in in vivo exhausted $CD8^+$ T cells (lower panel) relative to genes enriched in Tox-overexpressing T cells (left, red) versus genes enriched in control T cells (right, blue).

FIGS. 12A-12B illustrate that Tox binds chromatin modulators and transcriptional regulators. FIG. 12A depicts a silver stain of a magnetic immunoprecipitation (IP) of Tox from lysates derived from the EL4 thymoma cell line. "CT Ab" lane utilized an isotype control IgG for IP, while the "Tox Ab" lane use a monoclonal antibody specific for Tox protein. FIG. 12B depicts a heatmap of protein intensity after immunoprecipitation and mass spectrometry analysis.

FIGS. 13A-14G illustrate that multiple epigienietic modulators, including Tox are selectively expressed in $T_{EX}$. FIG. 13A shows Multidimensional scaling analysis of transcriptional data from LCMV-specific P14 $CD8^+$ T cells from acute (Arm) or chronic (Cl-13) LCMV at indicated time points p.i. Orange denotes naive P14 cells while gray and blue denote Arm and Cl-13 infection, respectively. Inset table enumerates differentially expressed genes (False Discovery Rate, FDR <0.05) between Arm and Cl-13 at specified d.p.i. FIG. 13D shows the difference in cumulative expression of genes in cluster 1. Values were calculated by summing the normalized array intensity of each gene at all time points p.i. and subtracting Arm from Cl-13.

FIG. 14A shows dots indicating the z-score of each gene in clusters 1-5 plotted against time post-Arm or Cl-13 infection. Gray and blue lines represent the moving average of z-score across time with 95% confidence interval in P14 cells from Arm and Cl-13 infection, respectively. FIG. 14B shows expression of selected genes within cluster 1 plotted as normalized array intensity against time p.i. Gray and blue represent P14 cells from Arm and Cl-13 infection, respectively.

FIG. 15A shows that TOX protein expression was measured in P14 T cells at the indicated days post-Arm (gray) and Cl-13 (blue) infection. Frequencies of $TOX^+$ P14 cells relative to total P14 population from representative samples are depicted in plots (left) and summarized (right) FIG. 15B shows plots of $T_{EFF}$ and $T_{MEM}$ markers relative to TOX expression in P14 T cells (blue) or endogenous CD8+ T cells (gray) on d8 post Cl-13 infection (left). Frequency of $T_{MEM}$ and $T_{EFF}$ subsets within $TOX^+$ (blue) and $TOX^-$ (white) P14 T cell populations (right). FIG. 15C shows flow plots of TOX versus the transcription factors (TFs) Tbet, Eomes, and Tcf1 at d8 or d30 p.i. with Cl-13 (left). Quantification of $TF^+$ cells within the $TOX^+$ and $TOX^-$ P14 population (right). FIG. 15D shows summary data of inhibitory receptor (IR) expression in $TOX^+$ and $TOX^-$ P14 cells 30 days post-Cl-13 infection. FIGS. 15E-15F show flow plots of TOX versus PD-1 expression in tumor-infiltrating T cells (TILs) from (FIG. 15E) CT26 602 carcinoma mouse model and (FIG. 15F) human melanoma biopsy samples (left). Histograms of inhibitory receptor expression in TOX$^{LOW}$PD-1$^{LOW}$, TOX-$^{LOW}$PD-1$^{INT}$, and TOX$^{HI}$PD-1$^{HI}$ TIL populations (middle). Summarized expression of IRs in these three populations (right). All contour and histogram plots are from one representative experiment of at least 3 independent experiments with at least four mice per group. Unless otherwise noted, P14 cells were analyzed from the spleens of infected animals. Summarized experiments denote one animal per dot and error is reported as standard deviation (SD). For (FIG. 15F) (right), 5 human TIL and 11 human normal donor samples were analyzed. Asterisks indicate statistical significance (*P<0.01, P<0.001, *P<0.0001) determined by Student's t-test.

FIGS. 16A-16E illustrate TOX expression. FIG. 16A shows TOX protein expression in P14 T cells isolated from the peripheral blood at d208 p.i. with Arm (gray) or Cl-13 (blue). FIGS. 16B-16C show representative flow plots of TOX versus IR expression in P14 and endogenous CD8+ T cells following 30 days (FIG. 16B) or 8 days (FIG. 16C, top) of Cl-13 infection. Quantification of IR expression in TOX$^+$ and TOX$^-$ P14 T cell populations (FIG. 16C, bottom). FIG. 16D shows representative contour and histogram plots of TOX expression in antigen specific CD8$^+$ T cells following influenza, VSV, or *Listeria monocytogenes* infection at indicated times (left). Summarized expression of TOX in pathogen-specific T cells relative to P14 cells following Arm and Cl-13 infection (right). FIG. 16E shows flow plots of TOX versus PD-1 expression in activated CD8$^+$ CD44$^+$ T cells from control tissues or tumors. Control T cells for B16 and CT26 mouse tumor models were acquired from the spleen whereas in humans, T cells from the peripheral blood of normal donors served as the controls for melanoma TILs. All contour and histogram plots are from one representative experiment of at least three (FIGS. 16A-16C, FIG. 16E) or two (FIG. 16D) independent experiments consisting of at least four mice per group. Unless otherwise noted, P14 cells were analyzed from the spleens of infected animals. Summarized experiments denote one animal per dot and error is reported as standard deviation (SD). For (FIG. 16E, right), 5 human samples were analyzed. Asterisks indicate statistical significance (*P<0.01, P<0.001, *P<0.0001) determined by Student's t-test.

FIG. 17A shows the frequency of WT or TOX cKO T cells relative to the total CD8$^+$ T cell pool during the course of Arm (top) or Cl-13 (bottom) infection. FIG. 17B shows representative plots (left) and quantification (right) of KLRG1 and CD127 expression in WT and TOX cKO T cells. FIG. 17C shows representative histograms of IR expression (left). Quantification of IR expression reported as the ratio of the median fluorescence intensity (MFI) between TOX cKO and WT P14 T cells (right). FIG. 17D shows representative histograms and contour plots (left) and quantification (right) of cytokine expression in WT and TOX cKO P14 cells. FIG. 17E shows transcription factor expression in WT and TOX cKO P14 T cells. FIGS. 17F-17I show that CD44$^{LOW}$ Naive WT and TOX$^{-/-}$ P14 T cells were sorted, mixed at a 1:1 ratio, and adoptively transferred into a congenic WT mice, and recovered from the spleen on d8 of Cl-13 infection for RNA-seq. FIG. 17F shows a heatmap of all differentially expressed genes (FDR <0.05) in WT and 648 TOX$^{-/-}$ P14 cells. Genes associated with T$_{EFF}$ or T$_{MEM}$ are labeled. FIG. 17G shows a gene set enrichment analysis (GSEA)(Subramanian, A. et al. Gene set enrichment analysis: a knowledge-based approach for interpreting genome-wide expression profiles. *Proc Natl Acad Sci USA* 102, 15545-15550 (2005)) of the transcriptional signature enriched in TEFF from Arm (left) or Cl-13 (right) in the set of differentially expressed genes in TOX$^{-/-}$ versus WT P14 cells. FIG. 17H shows expression of genes associated with terminal short-lived TEFF (Herndler-Brandstetter, D. et al. KLRG1+ Effector CD8+ T Cells Lose KLRG1, Differentiate into All Memory T Cell Lineages, and Convey Enhanced Protective Immunity. *Immunity* 48, 716-729.e8 (2018)). FIG. 17I shows GSEA of transcriptional signatures associated with T$_N$, T$_{EFF}$, or T$_{MEM}$ compared to the differentially expressed genes in TOX$^{-/-}$ versus WT P14 cells (left). Normalized enrichment scores (NES) based on association with TOX$^{-/-}$ (green) or WT (blue) samples (right). All contour and histogram plots are from one representative experiment of at least four independent experiments consisting of at least four mice per group. Unless otherwise noted, P14 cells were analyzed from the spleens of infected animals. Summarized experiments denote one animal per dot and error is reported as SD. For (FIGS. 17F-17I), 3 biological replicates were sequenced for each condition and normalized RNA-seq counts were averaged for subsequent analysis. Asterisks indicate statistical significance (*P<0.01, P<0.001, *P<0.0001) determined by Student's t-test.

FIG. 18A shows the gating strategy used in co-adaptive transfer and infection experiments. WT P14 cells were identified by double positivity of congenic markers CD45.1 and CD45.2, while KO lines (Tox$^{Flox/Flox}$ CD4$^{Cre}$ P14, NFAT2$^{Flow/Flow}$ CD4$^{Cre}$ P14, and Tox$^{-/-}$ P14) were positive only for CD45.2. FIG. 18B shows expression of activation markers and transcription factors in naive WT, Tox$^{Flox/Flox}$ CD4$^{Cre}$P14, and NFAT2$^{Flow/Flow}$ CD4$^{Cre}$ P14 cells from the blood prior to adoptive transfer. FIG. 18C shows pair-wise analysis of transferred P14 cells during Arm (top) or Cl-13 (bottom) infection. FIG. 18D shows representative plots of WT and TOX cKO cells at d8 of Cl-13 infection (left) or d30 of Arm or Cl-13 infection (right). Histogram of TOX expression in WT (gray) and TOX cKO (blue) P14 T cells. FIG. 18E shows a representative histogram and quantification of Ki-67$^+$ frequency in WT and TOX cKO cells on d8 of Cl-13 infection. FIGS. 18F-18G show the frequency of memory populations in WT and TOX cKO P14 cells on d8 (FIG. 18F) or d30 (FIG. 18G) post Arm infection. FIG. 18H shows quantification of TF expression in WT and TOX cKO P14 T cells on d30 p.i. with Arm. FIGS. 18I-18K show representative histograms and quantification of cytokine and effector molecule (FIG. 18I), IR (FIG. 18J), and TF (FIG. 18K) expression on d8 p.i. with Arm. Quantification of IR expression reported as the ratio of the median fluorescence intensity (MFI) between TOX cKO and WT P14 T cells (FIG. 18J, right). Contour and histogram plots are from one representative experiment of at least 4 independent experiments with at least four mice per group. Unless otherwise noted, P14 cells were analyzed from the spleens of infected animals. Summarized experiments denote one animal per dot and error is reported as SD. Asterisks indicate statistical significance (*P<0.01, P<0.001, *P<0.0001) determined by pair-wise t-test with Holm-Sidak correction (FIG. 18C) or Student's t-test (FIGS. 18D-18K). "ns", not significant.

FIG. 19A shows a representative contour and histogram plots of TOX expression in CD8$^+$ T cells following 24 hours of stimulation with PMA, ionomycin, or PMA with ionomycin (left). Time course of TOX MFI following addition of stimulus; horizontal 694 dashed line indicates TOX MFI in T$_N$ (right). FIG. 19B shows ATAC-seq tracks of the Tox locus in T$_N$ (gray), T$_{EFF}$ (light blue), and T$_{EX}$ (dark blue) P14 cells compared with NFAT1 (red) and NFAT2 (orange) ChIP-seq tracks from T$_{EFF}$ (Martinez, G. J. et al. The Transcription Factor NFAT Promotes Exhaustion of Activated CD8+ T Cells. *Immunity* 42, 265-278 (2015); Martinez, G. J. et al. The Transcription Factor NFAT Promotes Exhaustion of Activated CD8+ T Cells. *Immunity* 42, 265-278 (2015)). FIG. 19C shows, as depicted in FIG. 19B, in vitro activated CD8$^+$ T cells were transduced with RV encoding NFAT2 (WT-NFAT2), a constitutively active mutant of NFAT2 (CA-NFAT2) or control GFP (CT) and differentiated with IL-2 for 6 days prior to flow cytometric analysis. Contour and histogram plots of TOX expression are shown. FIG. 19D shows that congenic WT and NFAT2$^{Flox/Flox}$ x CD4$^{Cre}$(NFAT2 cKO) P14 T cells were mixed 1:1 and adoptively transferred into congenic WT mice prior to infection with LCMV Cl-13. Representative histograms (left) and quantification (right) of the frequency of TOX$^+$, KLRG1$^+$, PD-1$^+$, and Tcf1$^+$ P14 cells on d8 p.i. FIG. 19E shows that P14 T cells were adoptively transferred into WT mice, followed by infection with Cl-13. Mice were treated with FK506 or PBS from d3-7 p.i (FIG. 19D). Representative contour plots and histograms of TOX expression following FK506 or PBS treatment (left). Summary of the frequency of TOX$^+$, KLRG1$^+$, PD-1$^+$, and Tcf1$^+$ P14 cells on d8 p.i. (right). FIG. 19F shows NFAT2 cKO P14 cells were transduced with RV encoding TOX+GFP (NFAT2 cKO+TOX) or control only GFP (NFAT2 cKO+CT) and adoptively transferred into WT congenic mice followed by infection with Cl-13 (FIG. 19E). T$_{EFF}$ makers, IRs, and TFs were evaluated on d7 p.i. FIG. 19G 57G shows P14 cells were adoptively transferred into WT congenic mice, followed by infection with Cl-13. Mice were treated with FK506 or PBS on d25-29 of infection (FIG. 19F). Protein expression was measured on d30 p.i. All contour and histogram plots are from one representative experiment of at least 3 independent experiments consisting of at least three mice per group. Unless otherwise noted, P14 cells were analyzed from the spleens of infected animals. Summarized experiments denote one animal per dot and error is reported as SD. Asterisks indicate statistical significance (*P<0.01, P<0.001, *P<0.0001) determined by Student's t-test.

FIG. 20A shows normalized microarray expression of Nfatc1 (encodes NFAT2 protein) and Nfatc2(encodes NFAT1 protein) in P14 T cells following Arm (gray) or Cl-13 (blue) infection. FIG. 20B shows that CD8$^+$ T cells were enriched from naive mice, activated with αCD3 and aCD28 antibodies for 24 hours prior to transduction with CT, WT-NFAT2 or CA-NFAT2 encoding RVs. T cells were expanded and differentiated in vitro in the presence of IL-2 for 6 days prior to analysis. FIG. 20C shows expression of activation markers and transcription factors in naive WT and NFAT2$^{Flox/Flox}$ CD4$^{Cre}$ P14 cells from the blood prior to adoptive transfer. FIG. 20D shows P14 T cells were adoptively transferred into congenic WT mice followed by infection with LCMV Cl-13. On d3-7 of infection, mice were treated with PBS or FK506 i.p. and splenocytes were harvested on d8 p.i. FIG. 20E shows NFAT2 cKO CD8$^+$ T cells were enriched from naive mice, activated with αCD3 and αCD28 and transduced RVs encoding TOX+GFP or GFP only control. Transduced T cells were expanded for 24 hours prior to cell sorting (selecting for GFP$^+$ transduced cells) and adoptive transfer into congenic Cl-13 infected mice. Protein expression was analyzed on d7 p.i. FIG. 20F shows that P14 T cells were transferred into WT mice followed by infection with Cl-13. On d25-29 p.i., recipient mice were treated with PBS or FK506 i.p. and splenocytes were harvested on d30 p.i. for analysis.

FIG. 21A shows the experimental procedure used in FIGS. 21B-21E. Naive CD8$^+$ T cells were isolated from spleens, activated with αCD3 and αCD28 antibodies for 24 hours prior to RV transduction with RVs encoding TOX+GPF (TOX$^{OE}$) or control GFP only (CT). Transduced cells were cultured in IL-2 for 6 days prior to restimulation with biotin conjugated αCD3 and αCD28 antibodies in the presence of streptavidin for 5 hours. FIG. 21B shows cytokine and PD-1 expression in transduced in vitro effector T cells following restimulation. FIG. 21C shows gene sets were developed from upregulated (red) or downregulated (blue) transcripts in TOX$^{OE}$ relative to CT. These gene sets were analyzed for enrichment in the genes differentially expressed in Arm versus Cl-13 at d8, 15, and 30 p.i.27. Normalized enrichment scores (NES) are plotted versus time p.i. (Doering, T. A. et al. Network Analysis Reveals Centrally Connected Genes and Pathways Involved in CD8+ T Cell Exhaustion versus Memory. *Immunity* 37, 1130-1144 (2012)) Positive NES imply enrichment in Cl-13, whereas negative values imply enrichment in Arm infection. FIG. 21D shows genes uniquely upregulated (red) or downregulated (blue) in T$_{EX}$ 60 were assayed for enrichment in TOX$^{OE}$or CT T cells using GSEA. FIG. 21E shows a heatmap of leading edge genes from (FIG. 21D). Key genes associated with T$_{EX}$ are labeled. FIG. 59F shows the experimental design used in FIGS. 21G-21J. NIH3T3 cells were transduced with RV encoding TOX+GFP (TOX$^{OE}$) or control GFP only (CT). Cells were cultured for 48 hours, then harvested and processed for RNA-seq analysis. FIG. 21G shows GO analysis on biological processes differentially regulated in TOX$^{OE}$ versus CT fibroblasts. FIG. 21H shows as in FIG. 21C, genes upregulated (red) or downregulated (blue) in fibroblasts were assayed for enrichment in the genes differentially expressed in CD8$^+$ T cells on d6, 8, 15, and 30 of Arm or Cl-13 infection (Doering, T. A. et al. Network Analysis Reveals Centrally Connected Genes and Pathways Involved in CD8+ T Cell Exhaustion versus Memory. *Immunity* 37, 1130-1144 (2012). FIG. 21I shows as in FIG. 21D, genes uniquely up-(red) or down-(blue) regulated in TEX were analyzed for enrichment in TOX$^{OE}$ versus CT transduced fibroblasts (Bengsch, B. et al. Epigenomic-Guided Mass Cytometry Profiling Reveals Disease-Specific Features of Exhausted CD8 T Cells. *Immunity* 48, 1029-1045.e5 (2018)). FIG. 21J shows a volcano plot of differentially expressed genes in TOX$^{OE}$ relative to CT transduced fibroblasts. Transcripts with a FDR value <0.05 are highlighted in blue. Key T$_{EX}$-associated genes, selected from the leading edge of FIG. 21I, are labeled. All contour and histogram plots are from one representative experiment of at least 3 (FIG. 21B) independent experiments consisting of cells from at least two mice per group. RNA-seq datasets were generated from at least 2 biological replicates for each condition. Error is reported as standard deviation. Asterisks indicate statistical significance (*P<0.01, P<0.001, *P<0.0001) determined by Student's t-test.

FIGS. 22A-22D show naive CD44$^{LOW}$TOX$^{-/-}$ and WT P14 T cells were sorted, mixed 1:1, and adoptively transferred into congenic WT mice followed by infection with LCMV Cl-13. On d8 p.i., TOX$^{-/-}$ and WT P14 cells were sorted and analyzed by ATAC-seq. FIG. 22A shows a heatmap of differentially accessible loci. Regions proximal to $T_{EFF}$ (black) and $T_{MEM}$ or $T_N$ (blue) T cell genes are labeled. Lines denote number of loci with changes proximal to the gene. FIG. 22B shows chromatin regions specifically accessible in $T_N$, $T_{EFF}$, $T_{MEM}$ and $T_{EX}$ (Pauken, K. E. et al. Epigenetic stability of exhausted T cells limits durability of reinvigoration by PD-1 blockade. Science 354, 1160-1165 (2016)) were analyzed for enrichment in the TOX$^{-/-}$ versus WT P14 T cells by peak set enrichment analysis (PSEA). ATAC-seq tracks of $T_{EFF}$ (FIG. 22C) or $T_{MEM}$ (FIG. 22D) associated loci from WT (gray) and TOX$^{-/-}$ (blue) cells. Peaks uniquely opened (FIG. 22C) or closed (FIG. 22D) in TOX$^{-/-}$ relative to WT T cells are highlighted in gray. FIGS. 22E, 22F show, as per the experimental outline in FIG. 21A, $T_N$ were activated with αCD3 and αCD28 antibodies, transduced with RV encoding TOX+GFP (TOX$^{OE}$) or control GFP only (CT) and subsequently expanded in IL-2 for 6 days. Transduced cells were then restimulated with αCD3 and αCD28 786 for 5 hours prior to epigenetic evaluation with ATAC-seq. FIG. 22D shows a heatmap of differentially accessible chromatin regions in TOX$^{OE}$ compared to CT cells. FIG. 22F shows PSEA of $T_N$, $T_{EFF}$, $T_{MEM}$ or $T_{EX}$-specific loci as in FIG. 60B using differentially accessible loci in TOX$^{OE}$ versus CT CD8+ T cells. FIG. 22G shows a hive plot depicting the correlation between chromatin accessibility and RNA transcription. Genes are ordered along the y-axis and ATAC-seq peaks are ordered along the x-axis, both by genomic location, starting at the plot origin. Genes that are upregulated in TOX$^{-/-}$ T cells are positioned above the origin whereas genes that are downregulated are below. Genomic loci that increase in accessibility in TOX$^{-/-}$ cells are positioned to the right of the origin while those that decrease in accessibility are on the left. Connecting lines between axes are created when ATAC-seq peaks are associated with a differentially expressed gene. Blue lines highlight concordant changes between RNA and chromatin accessibility whereas gray lines highlight discordant changes. FIGS. 22H and 22I show TOX protein was immunoprecipitated (IP) from nuclear lysate generated from EL4 thymoma cells and subjected to mass spectrometry (MS) analysis to identify bound proteins. FIG. 22H shows MiST bait-prey association score of proteins identified after TOX IP and MS. Proteins highlighted in blue are components of the HBO1 complex. Dashed line indicates limit of high-confidence hits. FIG. 22I shows STRING protein-protein interaction network analysis of proteins with a MiST score >0.80. GO biological process (BP) analysis on subsequent network is highlighted. FIG. 60J shows: Top, αTOX or polyclonal IgG control antibody were used to immunoprecipitate proteins from EL4 lysate and subsequently blotted with aKat7 antibody. Bottom, reverse IP was performed by first immunoprecipitation with αKat7, then blotting for TOX protein. FIG. 22K shows genomic locations bound by TOX or Kat7 in EL4 cells were identified by ChIP-seq and multiple transcription-factor-binding loci (MTLs) were generated by stitching peaks within 250 bp of one another. Heatmap of ChIP-seq signal intensity of TOX (left) and Kat7 (right) at genomic locations centered on TOX MTLs in a 5kb window. FIG. 22L shows IP using αTOX or control IgG in EL4 lysate, followed by blotting against TOX, histone H4, or acetylated histone H4 (H4ac). ATAC-seq and ChIP-seq datasets were generated from 3 biological replicates for each condition.

FIGS. 23A-23G illustrate ATAC-seq results. FIG. 23A shows the frequency and enumeration of ATAC-seq peaks at annotated genomic locations. Top, pie chart of the frequency of peak distribution of all differentially accessible loci in TOX$^{-/-}$ versus WT P14 T cells on d8 p.i. with Cl-13. Bar graph displays the number of open and closed genomic loci at the various annotation sites in TOX$^{-/-}$ T cells. Bottom, pie chart and bar graph of differentially accessible loci in TOX$^{OE}$ compared to CT T cells. Right, frequency of peak distribution of all peaks in CD8 T cells above background levels. FIG. 23B shows ATAC-seq tracks of $T_N$, $T_{EFF}$, $T_{MEM}$, and $T_{EX}$ cells (Pauken, K. E. et al. Epigenetic stability of exhausted T cells limits durability of reinvigoration by PD-1 blockade. Science 354, 1160-1165 (2016)) compared with tracks from CT and TOX$^{OE}$ T cells at the Pdcd1 locus (encodes PD-1 protein). Gray bar highlights the −23.8kb enhancer that is specifically open in in vivo $T_{EX}$. FIG. 23C shows Log2-fold change of RNA expression versus log 2-fold change in ATAC-seq chromatin accessibility in TOX$^{-/-}$ relative to WT P14 cells 8 days p.i. with Cl-13. Only differentially expressed genes and associated ATAC-seq peaks are shown. Dot color represents −log$_{10}$(p-value) of differentially expressed genes. Dot size signifies −log$_{10}$(p-value) of differentially accessible loci. FIG. 23D shows abundance, specificity and reproducibility plot of proteins identified by MS analysis following TOX immunoprecipitation versus IgG control in EL4 cells. Hits are colored by MiST score (blue signifies >0.75). FIG. 23E shows GO biological process enrichment of protein identified in FIG. 61D with MiST score >0.75. FIG. 23F shows frequency of TOX-bound multiple transcription-factor-binding loci (MTL)(Chen, X. et al. Integration of External Signaling Pathways with the Core Transcriptional Network in Embryonic Stem Cells. Cell 133, 1106-1117 (2008)) also bound by Kat7. Identified by ChIP-seq of both factors in EL4 cells. FIG. 23G shows IP using aTOX or control IgG in EL4 lysate, followed by blotting against histone H3 methylation and acetylation modifications.

DETAILED DESCRIPTION

Definitions

Figures 1A, 1B:
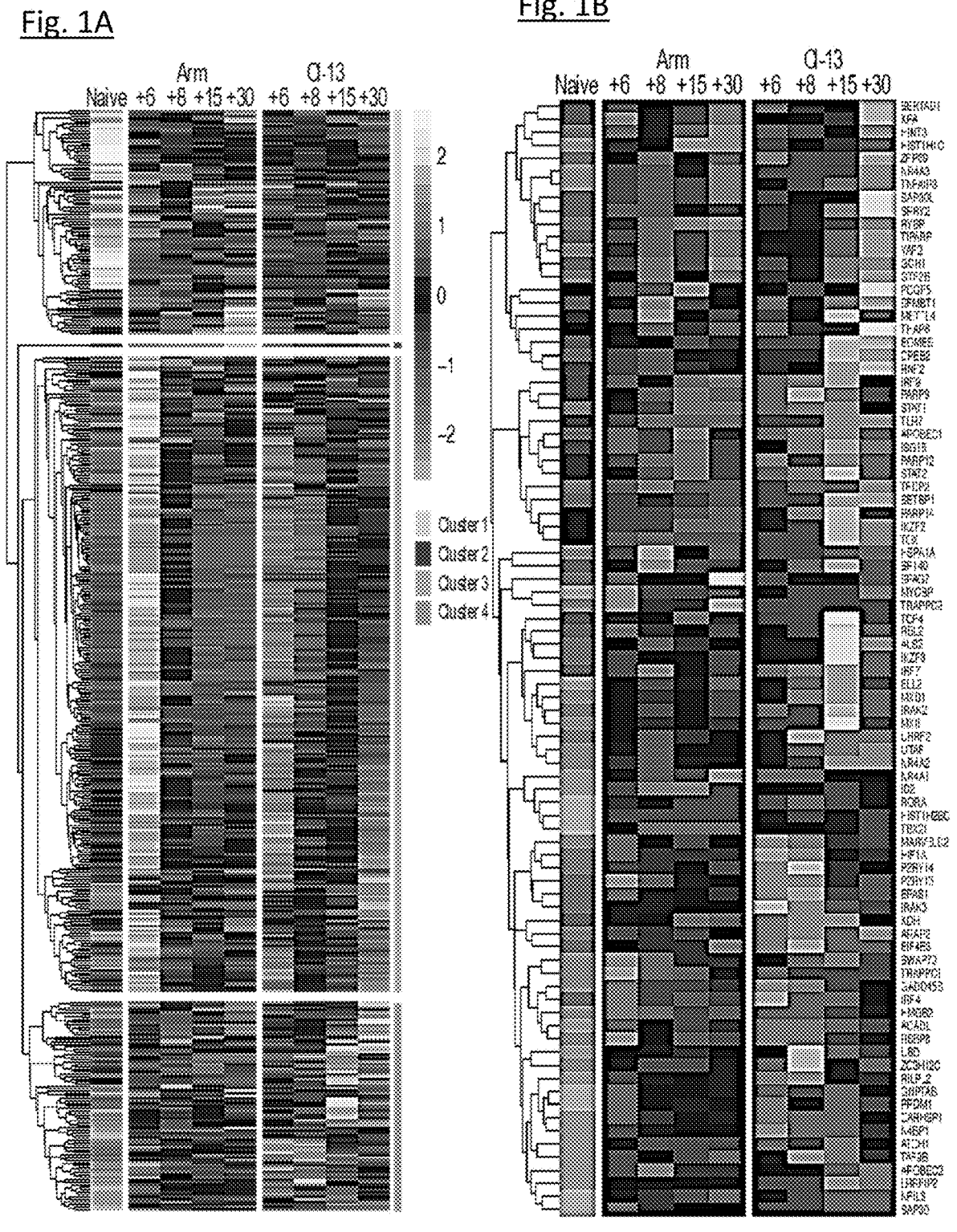
FIGS. 1A-1C illustrate that a unique set of chromatin modulators is upregulated in exhausted T cells.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20% or ±10%, in some instances ±5%, in some instances ±1%, and in some instances ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

"Activators" or "agonists" of a soluble factor are used herein to refer to molecules of agents capable of activating or increasing the levels of the soluble factor. Activators are compounds that increase, promote, induce activation, activate, or upregulate the activity or expression of soluble factor, e.g., agonists. Assays for detecting activators include, e.g., expressing the soluble factor in vitro, in cells, or cell membranes, applying putative agonist compounds, and then determining the functional effects on activity of the soluble factor, as described elsewhere herein.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are often tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

Unless otherwise specified herein, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody. The properties recited herein for antibodies and antibody fragments also apply to Fc fusion proteins described herein.

The term "antibody" as used herein also includes an "antigen-binding portion" of an antibody (or simply "antibody portion"). The term "antigen-binding portion," as used herein, refers to one or more fragments of an antibody that retain the ability to specifically bind to an antigen (e.g., PD-1 polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) Science 242: 423-426; and Huston et al. (1988) Proc. Natl. Acad. Sci. USA 85:5879-5883; and Osbourn et al. (1998) Nat. Biotechnol. 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) Human Antibodies and Hybridomas 6:93-101) and use of a cysteine residue, a marker peptide and a C-terminal polyhistidine tag to make bivalent and biotinylated scFv polypeptides (Kipriyanov, S. M., et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. Preferably, antibodies of the invention bind specifically or substantially specifically to PD-1 polypeptides or fragments thereof. They may also be selective for such antigens such that they can distinguish such antigens from closely related antigens, such as other B7 family members. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

As used herein, a "blocking" agent or an "antagonist" is one which inhibits or reduces at least one biological activity of the antigen(s) it binds. For example, an anti-PD-1 antibody binds PD-1 and inhibits the ability of PD-1 to bind one or more ligands, for example, PD-LI and/or PD-L2. In certain embodiments, the blocking antibodies or antagonist antibodies or fragments thereof described herein substantially or completely inhibit a given biological activity of the antigen(s). In certain embodiments, the term "inverse agonist" is used to refer to an agent that promotes the opposite action to normal. For example, a PD-1 inverse agonist can promote co-stimulation as opposed to co-inhibition of immune responses.

As used herein, an agent that can reverse or prevent T cell exhaustion can be, without limitation, any existing or novel epigenetic drug currently in the clinic or in development. Many of these agents are have not been used to target immune cells. They are used herein for their effects on tumor cells and infectious diseases. As used herein, an agent that can reverse or prevent T cell exhaustion can be, without limitation, any immunotherapy drug or agent including any checkpoint blockades or others agents that instigate a change in immune function.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "auto-antigen" means, in accordance with the present invention, any self-antigen which is recognized by the immune system as if it were foreign. Auto-antigens comprise, but are not limited to, cellular proteins, phosphoproteins, cellular surface proteins, cellular lipids, nucleic acids, glycoproteins, including cell surface receptors.

The term "ATAC-seq" (Assay for Transposase-Accessible Chromatin using sequencing) is a technique used in molecular biology to study chromatin accessibility. ATAC-seq can be used as a rapid and sensitive method for epigenomic analysis. ATAC-seq captures open chromatin sites and can reveal the interplay between genomic locations of open chromatin, DNA-binding proteins, individual nucleosomes and chromatin compaction at nucleotide resolution. Chromatin undergoes various structural changes during a cell cycle. Histone proteins are the basic packer and arranger of chromatin and can be modified by various post-translational modifications to alter chromatin packing (histone modification). Most of the modifications occur on the histone tail. The consequences in terms of chromatin accessibility and compaction depend on, e.g., the amino-acid that is modified and the type of modification. For example, histone acetylation generally results in loosening and increased accessibility of chromatin for replication and transcription.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others. Examples of autoimmune disease include but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pemacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

As used herein, to "alleviate" a disease means reducing the severity of one or more symptoms of the disease.

The term "biomarker" or "marker" refers to a measurable entity of the present invention that has been determined to be indicative of T cell exhaustion. For example, biomarkers described herein can be genomic regulatory regions that modulate the expression of at least one gene in a T cell. In another embodiment, biomarkers described herein can be effector genes or products thereof express by T cells and related to T cell activity and/or T cell exhaustion (e.g., high sustained PD-1 expression and/or activity in exhausted T cells. Biomarkers can also include, without limitation, cell types (e.g., engineered T cells), cell ratios (e.g., engineered T cells to exhausted T cell ratio), nucleic acids (e.g., genomic nucleic acids and/or transcribed nucleic acids) and proteins, particularly those provided in Pauken et al. Table S1 (Pauken et al. Science 2016, 354(6316):1160-1165). Biomarkers can further include immunological targets or agents that downregulate unwanted immune reactions in order to treat the immune disorder of interest as described further herein. The modulation (e.g., increase or decrease) in biomarker activity can be measured in any number of ways (e.g., according to measures described herein, including using controls, ratios, comparisons to baselines, and the like). For example, a genomic regulatory region selectively chromatin accessible in exhausted CD8+ T cells that is engineered can decrease enhancer activity on at least one gene as measured by a reduction in gene expression (e.g., gene transcription and/or translation) of the at least one gene as compared to the transcription and/or translation of the at least one gene in the same T cell type from the same organism without the engineered genomic regulatory region. The modulation in gene expression can be assessed over time. A modulation can mean a change of at least 1%, 5%, 10%, 15%, 20%, 25% 30%, 35%, 40%, 45%, 50%, 55%, 60%, 65%, 70%, 75%, 80%, 85%, 90%, 95%, 100%, 110%, 120%, 130%, 140%, 150%, 200%, 250%, 300%, 350%, 400%, 450%, 500%, 5503%), 600%, 650%, 700%, 750%, 800%, 850%, 900%, 950%, 1000%, or more, or any range in between inclusive (e.g., 5% to 100%).

It is to be noted that the biomarkers described herein can be used to refer to any combination of features described herein regarding any individual or combination of such biomarkers. For example, any combination of ortholog across organisms, sequence composition, percentage identity, sequence length, domain structure, functional activity, mutation status, etc. can be used to describe a biomarker molecule of the present invention.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "bispecific antibody" or "multispecific antibody" refers to an antibody that recognized more than one epitope. Such antibodies are useful for targeting different proteins using the same agent. Methods of making such antibodies are well-known in art (see, at least U.S. Pat. Nos. 5,798,229; 5,989,830; and Holliger et al. (2005) Nat. Biotech. 23:1126-1136).

The term "control" refers to any reference standard suitable to provide a comparison to the regulatory and/or expression products in the test sample. For efficiency, expression products are described, but the description applies equally to elements that regulate the expression products. In one embodiment, the control comprises obtaining a "control sample" from which expression product levels are detected and compared to the expression product levels from the test sample. Such a control sample may comprise any suitable sample, including but not limited to a sample from a control immune disorder patient (can be stored sample or previous sample measurement) with a known outcome; normal tissue or cells isolated from a subject, such as a normal patient or the immune disorder patient, cultured primary cells/tissues isolated from a subject such as a normal subject or the immune disorder patient, adjacent normal cells/tissues obtained from the same organ or body location of the immune disorder patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care immune disorder therapy). It will be understood by those of skill in the art that such control samples and reference standard expression product levels can be used in combination as controls in the methods of the present invention. In one embodiment, the control may comprise normal or non-immune disorder cell/tissue sample. In another preferred embodiment, the control may comprise an expression level for a set of patients, such as a set of immune disorder patients, or for a set of immune disorder patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having an immune disorder that has responded to a treatment of interest. In another embodiment, the control may also comprise a measured value for example, average level of expression of a particular gene in a population compared to the level of expression of a housekeeping gene in the same population. Such a population may comprise normal subjects, immune disorder patients who have not undergone any treatment (i.e., treatment naive), immune disorder patients undergoing standard of care therapy, or patients having an immune disorder that has responded to a treatment of interest. In another preferred embodiment, the control comprises a ratio transformation of expression product levels, including but not limited to determining a ratio of expression product levels of two cell types and/or genes in the test sample and comparing it to any suitable ratio of the same two cell types and/or genes in a reference standard; determining expression product levels of the two or more cell types and/or genes in the test sample and determining a difference in expression product levels in any suitable control; and determining expression product levels of the two or more cell types and/or genes in the test sample, normalizing their expression to expression of housekeeping cell types and/or genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with the immune disorder. In one embodiment a control expression product level is established wherein higher or lower levels of expression product relative to, for instance, a particular percentile, are used as the basis for predicting outcome. In another preferred embodiment, a control expression product level is established using expression product levels from immune disorder control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

As used herein, the term "helminth" means a parasitic worm that lives and feeds on a living host. In some embodiments, the helminth is a tapeworm, a fluke, or a roundworm. A tapeworm is a parasitic worm from the class Cestoda. It typically lives in the digestive tract of a vertebrate. A fluke is a flatworm from the class Trematoda. Flukes may cause disease in their host. Schistosomiasis is an example of a parasitic disease that is caused by a fluke. A roundworm constitutes the phylum Nematoda. Roundworms that are commonly parasitic on humans include ascarids, filarias, hookworms, pinworms and whipworms. Many roundworms cause disease in their hosts. For example, the species *Trichinella spiralis* is responsible for the disease trichinosis.

As used herein, the term "protozoan" means a single-celled eukaryotic organism. In some embodiments, the protozoan is *Acanthamoeba* spp., *Balamuthia mandrillaris*, *Blastocystis* spp., *Cryptosporidium* spp., *Dientamoeba fragilis*, *Entamoeba histolytica*, *Giardia lamblia*, *Leishmania* spp., *Naegleria fowleri*, *Plasmodium falciparum*, *Plasmodium vivax*, *Plasmodium ovale*, *Plasmodium malariae*, *Plasmodium knowlesi*, *Toxoplasma gondii*, *Trichomonas vaginalis*, *Trypanosoma* bruceii or *Trypanosoma cruzi*.

As used herein, the term "immune checkpoints" means a group of molecules on the cell surface of CD4+ and CD8+ T cells. These molecules fine-tune immune responses by down-modulating or inhibiting an anti-tumor immune response. Immune checkpoint proteins are well-known in the art and include, without limitation, CTL A-4, PD-h, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2 ILT-2, ILT-4, TIGIT, and A2aR (see, for example. WO 2012/177624). Immunotherapeutic agents that can act as immune checkpoint inhibitors useful in the methods of the present invention, include, but are not limited to, Fc fusion proteins having effector function, such as certain classes of antibodies well-known in the art.

The term "anti-immune checkpoint therapy" refers to the use of agents that inhibit immune checkpoint nucleic acids and/or proteins. Inhibition of one or more immune checkpoints can block or otherwise neutralize inhibitory signaling to promote immunomodulation. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins that block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can bind to its receptor to indirectly reduce the effective concentration of the receptor to bind to an appropriate ligand. In one embodiment, anti-PD-1 antibodies, anti-PD-LI antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

The term "influenza virus," as used herein, refers to an RNA virus that is a member of the Orthomyxoviruses family. In some embodiments, the influenza virus is selected from the genera consisting of Influenza virus A, Influenza virus B, Influenza virus C and Influenza virus D. In further embodiments, the influenza A virus is of the subtype H1N1, H1N2, H2N2 or H3N2. In further embodiments, the influenza B virus of the B/Yamagata/16/88-like lineage or the B/Victoria/2/87-like lineage.

The term "polyoma virus," as used herein, refers to an unenveloped DNA virus that is a member of the Polyomaviridae family. A polyomavirus is a DNA virus with a circular genome. Some members of the family are oncoviruses, and may cause tumors. In some embodiments, the polyoma virus is BK virus (BKV), JC virus (JCV), KI polyoma virus (KIPyV), WU virus (WUPyV), Merkel cell polyomavirus (MCPyV), human polyoma virus 6 (HPvV6), human polyoma virus 7 (HPyV7), trichodysplasia spinulosa virus (TSPyV), human polyoma virus 9 (HPvV9), or MW virus (MWPvV).

"PD-1" is an immune checkpoint inhibitor that refers to a member of the immunoglobulin gene superfamily that functions as a co-inhibitory receptor having PD-L1 and PD-L2 as known ligands. PD-1 was previously identified using a subtraction cloning based approach to select for proteins involved in apoptotic cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. Int. Immunol. 1996, 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al (1996) *Int. Imnunol.* 8:773).

The nucleic acid and amino acid sequences of a representative human PD-1 biomarker is available to the public at the GenBank database under NM 005018.2 and NP 005009.2 (see also Ishida et al. (1992) 20 *EMBO J* 11:3887; Shinohara et al. (1994) *Genomics* 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al.

23                                                                    24

*EMBO J* 1992, 11:3887; Shinohara et al. (1994) *Genonmics* 23:704; and U.S. Pat. No. 5,698,520). These features also define a larger family of polypeptides, called the immunoinhibitory receptors, which also includes gp49B, PIR-B, and the killer inhibitory receptors (KIRs) (Vivier and Daeron *Immunol. Today* 1997, 18:286). It is often assumed that the tyrosyl phosphorylated ITIM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MI-C and B7 genes (Henry et al. (1999) *Immunol. Today* 20(6): 285-8). Nucleic acid and polypeptide sequences of PD-1 orthologs in organisms other than humans are well known and include, for example, mouse PD-1 (NM 008798.2 and NP 032824.1), rat PD-1 (NM 001106927.1 and NP_001100397.1), dog PD-1 (XM_543338.3 and XP_543338.3), cow PD-1 (NM_001083506.1 and NP_001076975.1), and chicken PD-1 (XM 422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity" includes the ability of a PD-1 polypeptide to modulate an inhibitory signal in an activated immune cell, e.g., by engaging a natural PD-1 ligand on an antigen presenting cell. PD-1 transmits an inhibitory signal to an immune cell in a manner similar to CTLA4. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response. Agents that modulate PD-1 activity are well-known in the art. Representative examples include, without limitation, antibodies such as MDX-1106, Merck 3475, and CT-011. MDX-1106, also known as MDX-1106-04, ONO-4538 or BMS-936558, is a fully human IgG4 anti-PD-1 monoclonal antibody described in PCT Publ. No. WO 2006/121168 and U.S. patent Ser. No. 80/088,449. Merck 3475, also known as SCH-900475 and penbrolizumab, is a humanized IgG4 anti-PD-1 monoclonal antibody described in PCT Publ. No. WO 2009/114335; U.S. Pat. No. 8,354,509; and Hamid et al. (2013) *New Engl. J. Med.* 369:134-144. Pidilizumab (CT-011; CureTech) is a humanized IgG1 monoclonal antibody that binds to PD-1. Pidilizumab and other humanized anti-PD-1 monoclonal antibodies are disclosed in PCT Publ. No. WO 2009/101611. Similarly, AMP-224 (B7-DCIg; Amplimmune) is a PD-L2 Fe fusion soluble receptor that blocks the interaction between PD-1 and PD-L1 and is disclosed in PCT Publ. Nos. WO 2010/027827 and WO 2011/066342. Moreover, many other anti-PD-1 Fc fusion proteins are known in the art as described in U.S. Pat. No. 8,609,089; US Pat. Publ. No. 2010/028330; U.S. Pat. Publ. No. 2012-0114649; and PCT Publ. No. WO 2014/089113.

The term "PD-1 ligand" refers to binding partners of the PD-1 receptor and includes both PD-LI (Freeman et al. (2000) *J. Exp. Med.* 192:1027) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) J. Exp. Med. 192:1027 for sequence data) and PD-L2 (See Latchman et al. (2001) Nat. Immunol. 2:261 for sequence data) are members of the B7 family of polypeptides. Both PD-11 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-LI is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see, Butte et al. (2007) *Immunity* 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1 (CD80), B7-2 (CD86), inducible costimulatory ligand (ICOS-L), B7-H3, B7-H4, VISTA, B7-H6, B7h (Swallow et al. (1999) *Immunity* 11:423), and/or PD-1 ligands (e.g, PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1(see the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two B sheets, each consisting of anti-parallel B strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of B strands.

The term "immune disorders" refers to conditions characterized by an unwanted immune response. In some embodiments, the immune disorder is such that a desired anti-immune disorder response suppresses immune responses. Such conditions in which downregulation of an immune response is desired are well-known in the art and include, without limitation, situations of tissue, skin and organ transplantation, in graft-versus-host disease (GVHD), inflammation, or in autoimmune diseases, such as systemic lupus erythematosus, multiple sclerosis, allergy, hypersensitivity response, a disorder requiring improved vaccination efficiency, and a disorder requiring increased regulatory T cell production or function, as described further herein. In other embodiments, the immune disorder is such that a desired response is an increased immune response. Such conditions in which upregulation of an immune response is desired are well-known in the art and include, without limitation, disorders requiring increased CD4+ effector T cell production or function such as combating cancer, infections (e.g., parasitic, bacterial, helminthic, or viral infections), and the like. In some embodiments, the immune disorder is an autoimmune disorder. Importantly, exhaustion occurs in autoimmunity (McKinney et al. Nature. 2015, 523:612-616).

The term "acute immune disorder" refers to conditions that can be resolved by an appropriate immune response that eradicates a targeted antigen and host comprising such a targeted antigen, such as a cancer or an infection agent like a virus, bacteria, parasite, *mycoplasma*, fungus, and the like. Such conditions are relatively brief and last on the order of a few days to a few weeks.

By contrast, the term "chronic immune disorders" refers to those conditions that are not effectively cleared or eliminated by the induction of a host immune response. In chronic immune disorders, a targeted antigen (and/or host comprising the targeted antigen), such as an infectious agent or cancer cell, and the immune response reach equilibrium such that the subject maintains the targeted antigen or host comprising the targeted antigen (e.g., remains infectious or afflicted with cancer) over a long period of time (i.e., a time period of months to years or even a lifetime) without necessarily expressing symptoms. Chronic immune disorders can involve stages of both silent and productive targeted antigen maintenance without rapidly killing or even producing excessive damage of the host cells. Detection of the targeted antigen or host comprising the targeted antigen can be made according to any one of many well-known methods in the art and described, for example, in U.S. Pat. Nos. 6,368,832, 6,579,854, and 6,808,710 and U.S. Patent Application Publication Nos. 20040137577, 20030232323, 20030166531, 20030064380, 20030044768, 20030039653, 20020164600, 20020160000, 20020110836, 20020107363, and 200201067.

In some embodiments, chronic immune disorders are the result of infection, such as an infection with a virus including, but not limited to, human immunodeficiency viruses (HIV), hepatitis C viruses (HCV), T-cell leukemia viruses, Epstein-Barr virus, cytomegalovirus, herpesviruses, varicella-zoster virus, measles, papovaviruses, prions, hepatitis viruses, adenoviruses, parvoviruses, papillomaviruses, prions, and the like. In some embodiments, chronic immune disorders are the result of infection, such as an infection with a virus including, but not limited to hepatitis B virus, noroviruses, and/or anelloviruses, In some embodiments, chronic immune disorders are the result of infection with non-viral chronic infections including, but not limited to malaria, *Mycobacterium tuberculosis*, trypanasoma *cruzi, Toxoplasma gondii,* and/or leishmania *major*. Chronic immune disorders include, for example, chronic conditions and latent conditions. As used herein, chronic immune disorders can be limited to chronic conditions, latent conditions, or both.

In a "chronic condition," the targeted antigen can be detected in the subject at all times regardless of whether the signs and symptoms of the disease are present or absent, even for an extended period of time. Non-limiting examples of chronic conditions resulting from infection include hepatitis B (caused by hepatitis B virus (HBV)) and hepatitis (caused by hepatitis C virus (HCV)) adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyoma virus BK, polyoma virus JC, measles virus, rubella virus, human immunodeficiency virus (HIV), human T cell leukemia virus I, and human T cell leukemia virus II. Parasitic persistent infections can arise as a result of infection by, for example, *Leishmania, Toxoplasma, Trypanosoma, Plasmodium, Schistosoma,* Encephalitozoon, norovirus, anellovirus, *mycobacterium* species, malaria species, malaria, *Mycobacterium tuberculosis*, trypanasoma *cruzi, Toxoplasma gondii,* and/or *Leishmania major.*

A particular type of chronic condition involving infections is known as a "latent condition," where the infectious agent (such as a virus) is seemingly inactive and dormant such that the subject does not always exhibit signs or symptoms. In a latent viral infection, the virus remains in equilibrium with the host for long periods of time before symptoms again appear; however, the actual viruses cannot typically be detected until reactivation of the disease occurs. Infection latency is the ability of a pathogenic infection agent, such as a virus, to lie dormant within a cell. For example, a latent viral infection is a phase in the life cycle of certain viruses in which after initial infection, virus production ceases. However, the virus genome is not fully eradicated. The result of this is that the virus can reactivate and begin producing large amounts of viral progeny (the lytic part of the viral life cycle) without the host being infected by a new virus. The virus may stay within the host indefinitely. In one embodiment, virus latency is not identical to clinical latency, in which the virus is undergoing an incubation period but is not dormant. Non-limiting examples of latent infections include infections caused by herpes simplex virus (HSV)-1 (fever blisters), HSV-2 (genital herpes), and varicella zoster virus VZV (chickenpox-shingles).

As used herein, the term "immunotherapeutic agent" can include any molecule, peptide, antibody or other agent which can stimulate a host immune system to promote immunomodulation in the subject. Various immunotherapeutic agents are useful in the compositions and methods described herein.

The terms "inhibit" or "reverse" include the decrease, limitation, or blockage, of, for example a particular action, function, or interaction. In some embodiments, an immune disorder is "inhibited" or "reversed" if at least one symptom of the immune disorder is alleviated, terminated, slowed, or prevented. As used herein, an immune disorder is also "inhibited" or "reversed" if recurrence or spread of the immune disorder is reduced, slowed, delayed, or prevented.

An "isolated antibody" is intended to refer to an antibody that is substantially free of other antibodies having different antigenic specificities. Moreover, an isolated antibody may be substantially free of other cellular material and/or chemicals.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "KD" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. Cancer cells can spread locally or through the bloodstream and lymphatic system to other parts of the body. The term "cancer" includes premalignant, as well as malignant, cancers. The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia.

Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

By "chimeric protein" is meant any single polypeptide unit that comprises two distinct polypeptide domains, wherein the two domains are not naturally occurring within the same polypeptide unit. Typically, such chimeric proteins are made by expression of a cDNA construct but could be made by protein synthesis methods known in the art.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap with each other.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal," as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "epigenetics" is defined as heritable changes in gene activity and expression that occur without alteration in DNA sequence. These non-genetic alternations are tightly regulated by two major epigenetic modifications: chemical modifications to the cytosine residues of DNA (DNA methylation) and histone proteins associated with DNA (histone modifications). Epigenetics refers to the changes of single genes or sets of genes.

The term "epigenome" reflects the overall epigenetic state of a cell, and refers to global analyses of epigenetic markers across the entire genome. Mapping epigenetic modification patterns or profiling the epigenome in a given cell can be used as epigenetic biomarkers for clinical prediction, diagnosis, and therapeutic development.

The term "epigenetic pathway" comprises any component that contributes to the "epigenome" or epigenomic state of a cell.

As used herein "endogenous" refers to any material from or produced inside an organism, cell, tissue or system.

As used herein, the term "exogenous" refers to any material introduced to an organism, cell, tissue or system that was produced outside the organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein, is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

By the term "immune reaction," as used herein, is meant the detectable result of stimulating and/or activating an immune cell.

"Immune response," as the term is used herein, means a process that results in the activation and/or invocation of an effector function in either the T cells, B cells, natural killer (NK) cells, and/or antigen-presenting cells. Thus, an immune response, as would be understood by the skilled artisan, includes, but is not limited to, any detectable antigen-specific or allogeneic activation of a helper T cell or cytotoxic T cell response, production of antibodies, T cell-mediated activation of allergic reactions, and the like. As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

"Immune cell," as used herein includes any cell that is involved in the generation, regulation or effect of the acquired or innate immune system. Immune cells include T cells such as CD4+ cells, CD8+ cells and various other T cell subsets, B cells, natural killer cells, macrophages, monocytes and dendritic cells, and neutrophils.

The term "immune related disease" means a disease in which a component of the immune system of a mammal causes, mediates or otherwise contributes to morbidity in the mammal. Also included are diseases in which stimulation or intervention of the immune response has an ameliorative effect on progression of the disease. Included within this term are autoimmune diseases, immune-mediated inflammatory diseases, non-immune-mediated inflammatory diseases, infectious diseases, and immunodeficiency diseases. Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory and fibrotic lung diseases such as inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases include AIDS (HIV infection), hepatitis A, B, C, D, and E, bacterial infections, fungal infections, protozoal infections and parasitic infections.

The term "infectious disease" refers to a disorder caused by pathogenic (micro)organisms such as bacteria, viruses, fungi, or parasites. Infectious diseases of the present disclosure include, but are not limited to a bacterium, virus, protozoan, *mycoplasma*, fungus, yeast, parasite, or prion. For example, but not by way of limitation, the immunogen may be a human papilloma virus (see below), a herpes virus such as herpes simplex or herpes zoster, a retrovirus such as human immunodeficiency virus 1 or 2, a hepatitis virus, an influenza virus, a rhinovirus, respiratory syncytial virus, cytomegalovirus, adenovirus, *Mycoplasma pneumoniae*, a bacterium of the genus *Salmonella, Staphylococcus, Streptococcus, Enterococcus, Clostridium, Escherichia, Klebsiella, Vibrio, Mycobacterium*, amoeba, a malarial parasite, and *Trypanosoma cruzi*.

"Inhibitors" or "antagonists" of a soluble factor are used herein to refer to molecules of agents capable of inhibiting, inactivating or reducing the levels of the soluble factor. Inhibitors are compounds that, e.g., bind to, partially or totally block activity, decrease, prevent, delay activation, inactivate, desensitize, or down regulate the activity or expression of soluble factor, e.g., antagonists. Inhibitors include polypeptide inhibitors, such as antibodies, soluble receptors and the like, as well as nucleic acid inhibitors such as siRNA or antisense RNA, genetically modified versions of the soluble factor, e.g., versions with altered activity, as well as naturally occurring and synthetic soluble factor antagonists, small chemical molecules and the like. Assays for detecting inhibitors include, e.g., expressing the soluble factor in vitro, in cells, or cell membranes, applying putative antagonist compounds, and then determining the functional effects on activity of the soluble factor, as described elsewhere herein.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The phrase "level of a soluble factor" in a biological sample as used herein typically refers to the amount of protein, protein fragment or peptide levels of the soluble factor that is present in a biological sample. A "level of a soluble factor" need not be quantified, but can simply be detected, e.g., a subjective, visual detection by a human, with or without comparison to a level from a control sample or a level expected of a control sample.

By the term "modulating" an immune response, as used herein, is meant mediating a detectable increase or decrease in the level of an immune response in a mammal compared with the level of an immune response in the mammal in the absence of a treatment or compound, and/or compared with the level of an immune response in an otherwise identical but untreated mammal. The term encompasses perturbing and/or affecting a native signal or response thereby mediating a beneficial therapeutic response in a mammal, preferably, a human.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "retrovirus," as used herein, is a member of the Retroviridae. A retrovirus is a single-stranded positive-sense RNA virus. In some embodiments, the retrovirus is an alpha-retrovirus, a beta-retrovirus, a gamma-retrovirus, a delta-retrovirus, an epsilon-retrovirus, a lentivirus or a spumavirus. In some embodiments, the retrovirus is a lentivirus selected from the group consisting of human immunodeficiency virus (HIV) and equine infectious anemia virus (EIAV).

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). Examples of subjects include humans, dogs, cats, mice, rats, and transgenic species thereof.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "T cell", also known as T-lymphocyte, or thymocyte is known in the art. It is a type of white blood cell which is primarily produced in the thymus. T cells are part of the immune system and develop from stem cells in the bone marrow. They help protect the body from infection and may help fight cancer. T cells can be distinguished from other lymphocytes, such as B cells and natural killer cells, by the presence of a T-cell receptor on the cell surface. There are several subsets of T cells, of which each have a distinct function. In some embodiments, the T cell is a CD8+ T cell. The term CD8+ T cell is used interchangeably with the term CD8 T cell, herein.

The category of effector T cell is a broad one that includes various T cell types that actively respond to a stimulus, such as co-stimulation. This includes helper, killer, regulatory, and potentially other T cell types.

Antigen-naïve T cells (naïve T cells, $T_N$) expand and differentiate into memory T cells ($T_{MEM}$) and effector T cells ($T_{EFF}$) after they encounter their cognate antigen within the context of an MHC molecule on the surface of a professional antigen presenting cell (e.g. a dendritic cell).

Memory T cells are a subset of infection-as well as potentially cancer-fighting T cells (also known as a T lymphocyte) that have previously encountered and responded to their cognate antigen; thus, the term antigen-experienced T cell is often applied. Such T cells can recognize foreign invaders, such as bacteria or viruses, as well as cancer cells. Memory T cells have become "experienced" by having encountered antigen during a prior infection, encounter with cancer, or previous vaccination. At a second encounter with the invader, memory T cells can reproduce to mount a faster and stronger immune response than the first time the immune system responded to the invader. This behavior is utilized in T lymphocyte proliferation assays, which can reveal exposure to specific antigens.

Effector T cells describes a broad group of cells that includes several T cell types that actively respond to a stimulus, such as co-stimulation. This includes CD4+, CD8+, cytotoxic, helper, killer, regulatory, and potentially other T cell types.

An "exhausted T cell" ($T_{EX}$) is a T cell that instead of clearing an infection, tumor, or cancer becomes "exhausted" and unable to clear, alleviate, or reduce the infection, tumor, or cancer. An exhausted T cell can be a CD8+ T cell. An exhausted T cell can be a CD4+ T cell. Exhausted T cells have progressively lost T-cell function. "Exhaustion" or "unresponsiveness" refers to a state of a cell where the cell does not perform its usual function or activity in response to normal input signals, and includes refractivity of immune cells to stimulation, such as stimulation via an activating receptor or a cytokine. Such a function or activity includes, but is not limited to, proliferation or cell division, entrance into the cell cycle, cytokine production, cytotoxicity, trafficking, phagocytotic activity, or any combination thereof. Normal input signals can include, but are not limited to, stimulation via a receptor (e.g., T cell receptor, B cell receptor, co-stimulatory receptor, and the like).

"T-cell exhaustion", a type of immunosuppression, is characterized by deprived effector function, sustained expression of inhibitory receptors, and a distinct transcriptional state (Wherry. Nat Immunol. 2011, 12(6):492-9). T cell exhaustion comprises a state of impaired effector functions, high inhibitory receptor expression including Programmed Death-1 (PD-1, or CD279), transcriptional reprogramming, and defective immune memory (Pauken et al. Science 2016, 354(6316):1160-1165).

A "control T cell" refers to a T cell that is not an exhausted T cell. A control T cell can be, e.g., a $T_N$, $T_{EFF}$, and/or $T_{MEM}$. A population of control T cells refers to any combination of control T cells.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "transplant," as used herein, refers to cells, tissue, or an organ that is introduced into an individual. The source of the transplanted material can be cultured cells, cells from another individual, or cells from the same individual (e.g., after the cells are cultured in vitro). Exemplary organ transplants are kidney, liver, heart, lung, and pancreas.

To "treat" a disease as the term is used herein, means to reduce the frequency or severity of at least one sign or symptom of a disease or disorder experienced by a subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present disclosure provides methods and compositions for treating a disease in a patient. The compositions comprise an engineered T cell (e.g., a CD8+ T cell) comprising one or more alterations in an epigenetic pathway. In some embodiments, the alteration in the engineered T cell prevents, reverses or increases exhaustion of the T cell. In some embodiments, the epigenetic pathway is a high priority epigenetic pathway. The methods comprise administering an engineered T cell of the disclosure to the patient. In some embodiments, administration of the engineered T cell increases an immunological response in the patient. In some embodiments, the patient is treated concurrently with another treatment, e.g., immune checkpoint blockade. In some embodiments, the immune checkpoint blockade comprises treatment with at least one immune checkpoint inhibitor. In some embodiments, the at least one immune checkpoint inhibitor is an anti-PD-1, PD-L1, CTLA-4, TIM3, B7-H3, BTLA, VISTA, CD40, CEACAM1/CD66a, CD80/B7-1, CD86/B7-2, OX40/CD134, CD40 Ligand, ICOS Ligand/B7-H2, 4-1BBL/CD137L, B7-DC/PD-L2/CD273, CD39/CD73, CD200/CD200R, LAG-3, TNFR2, KIRs, IDO, IL-10, IL-27, or TIGIT/CD226/CD112/CD122R/CD94 antibody. In some embodiments, targeting a high priority epigenetic pathway changes the epigenome of the engineered T cell. In some embodiments, targeting the high priority epigenetic pathway comprises epigenetic changes in at least one of Tox, SET, RuvBl1, RuvBl2, DPY30, Tox2, Stat1, Stat2, Ikzf2, Dnmt3a, Kdm4a, Bhlhe41, Nfat2, Eomes, Nr4a2, Tcf1, T-bet, Blimp-1, Id2, Zeb2, Nr4al, Suv39 h2, Csprs, Sfmbt1, Hmgn3, Chd9, Rnf2, Ikzf3, Kmt2e, Satb1, Tet1, Tet2, Tet3, Kdm5b, Sfmbt2, Actr6, and Prmt7. Targeting a high priority epigenetic pathway comprises knocking in or knocking out transcription factors or other genes encoding proteins involved in creating, modifying or otherwise maintaining the epigenome. Targeting a high priority epigenetic pathway also comprises knocking in or knocking out regulatory sequences in the OCR domains associated with T cell exhaustion. In some embodiments, the OCR domains associated with T cell exhaustion are those listed in Table 6.

$T_{EX}$ are epigenetically committed. Current immunotherapies such as PD-1 blockade provoke transient improvement in effector functions from these cells, but do not reprogram their epigenetics. As a result, the effect of PD-1 blockade is transient and these cells return to the "ground state" of exhaustion. A major problem that this invention solves is the identification of epigenetic pathways that are involved in establishing the epigenetic ground state of exhaustion and locking these cells into an inflexible differentiation state. This invention also solves the problem of identifying genomic locations that are epigenetically modified as part of the commitment to exhaustion. Targeting such pathways and/or genomic locations, alone or in combination with other immunotherapies, would prevent or reverse the $T_{EX}$ epigenetic commitment that limits current therapies. Drugs targeting epigenetic pathways are feasible and could be applied in many therapeutic settings. For cellular therapies, some epigenetic pathways identified could be targeted genetically. Proof of concept for at least one of these major pathways is provided. Tox is a member of the High Mobility Group of chromatin associated proteins. Demonstrated herein is a key role for Tox in the early programming and continued maintenance of T cell exhaustion. Tox interacts with other key epigenetic modulators, including the SET, RuvBl1/2 and DPY30 proteins, suggesting that Tox regulates a diverse array of epigenetic mechanisms. In addition to TOX, analysis herein also identifies Tox2, Stat1, Stat2, Ikzf2, Dnmt3a, Kdm4a, Bhlhe41, Nfat2, Eomes, Nr4a2, Tcf1, T-bet, Blimp-1, Id2, Zeb2, Nr4al, Suv39 h2, Csprs, Sfmbt1, Hmgn3, Chd9, Rnf2, Ikzf3, Kmt2e, Satb1, Tet1, 2, and 3, Kdm5b, Sfmbt2, Actr6, Prmt7, genes encoding inhibitory receptors and/or T cell transcription factors, and other relevant T cell genes including PD-1, CTLA-4, LAG-3, Tim3, CD200/CD200R, Ptger2, Ptger4, T-bet, Eomes, Tox, Blimp1, BATF, AP-1 family members, IRF4, and other genes described in Wherry et al, Doering et al., and/or Crawford et al. (Wherry et al. *Immunity* 2007, 27:670-684, incorporated herein by reference in its entirety; Doering et al. *Immunity* 2012, 37:1130-1144, incorporated herein by reference in its entirety; Crawford et al. *Immunity* 2014,40 (2):289-302, incorporated herein by reference in its entirety) as potential targets. Other potential targets include, but are not limited to, at least one of SERTADI, XPA, HINT3, HIST1H1C, ZFP69, NR4A3, TNFAIP3, SAP30L, SPRY2, RYBP, TIPARP, YAf2, GCHI, GTF2B, PCGF5, SFMBT1, METTL4, THAP6, EOMES, CPEB2, IRF9, PARP9, STAT1, TLR7, APOBEC1, ISG15, PARP12, STAT2, TFDP2, SETBP1, PARP14, IKZF2, HSPA1A, SP140, SPAG7, MYCBP, TRAPPC2, TCF4, RBL2, ALS2, IKZF3, IRF7, ELL2, MXD1, IRAK2, MXl1, UHRF2, LITAF, NR4A2, NR4A1, ID2, RORA, HISTIH2BC, TBX21, MARVELD2, HIF1A, P2RYl4, P2RY13, EPAS1, IRAK3, XDH, ARAP2, EIF4E3, SWAP70, TRAPPC1, GADD45B, IRF4, HMGB2, ACADL, RBBPB, UBD, ZC3H12C, RILPL2, GNPTAB, PRDM1, CARHSP1, N4BP1, ATOH1, TAF9B, APOBEC2, LRRFIP2, NFIL3, and SAP30. Indeed, additional work on Tet2 shows a key role for this enzyme involved in DNA methylation in T cell exhaustion identifying another high priority, druggable, epigenetic pathway for modulating T cell exhaustion.

Epigenetic Pathway

As described herein, an epigenetic pathway comprises any component that contributes to the "epigenome" or epigenomic state of a cell.

The term "epigenetic pathway" refers to a combination of signals or biological components that transmit such signals that together establish and maintain a stably heritable epigenetic state. In certain embodiments, an epigenetic pathway comprises a signal originating from the environment that triggers the start of the epigenetic pathway, an epigenetic initator that receives this signal and is capable of determining the precise chromatin location and or DNA environment for establishing a particular epigenomic state, and an epigenetic maintainer that sustains that particular epigenetic state in the initial and succeeding generations.

High Priority Epigenetic Pathway

The disclosure provides methods of treating a disease in a patient, the method comprising administering an engineered T cell to the patient, the engineered T cell comprising one or more alterations in one or more high priority epigenetic pathways. In some embodiments, the alterations comprise genetic modifications introduced via genome engineering approaches or epigenetic modifications using inhibitors or activators of epigenetic regulators. In some embodiments, the high priority epigenetic pathway is or has been targeted to reverse or prevent or increase exhaustion of the T cell. In further embodiments, the high priority epigenetic pathway is or has been targeted to reverse or prevent exhaustion of the T cell. In some embodiments, the high priority epigenetic pathway has been targeted by genome engineering, e.g. by knocking out/in genes in the epigenetic pathway, or by modifying the function of protein encoding genes in epigenetic pathways. In some embodiments, the high priority epigenetic pathway is targeted by genetic engineering of the non-coding genome in locations that control expression of epigenetic regulators. For example, there are exhaustion specific enhancers that are open in a locus for an epigenetic regulator of exhaustion that may be deleted or modified that would change the expression pattern of the gene. High priority epigenetic pathways are genes, loci, or proteins that fulfill one of the following criteria: a) are genes/proteins with a known or potential role in generating or changing epigenetic marks; or b) genes with known roles in T cell exhaustion based on transcriptional profiling studies that also have distinct epigenetic modifications in exhausted T cells. In some embodiments, the high priority epigenetic pathway comprises epigenetic changes in at least one of Tox, SET, RuvBl1, RuvBl2, DPY30, Tox2, Stat1, Stat2, Ikzf2, Dnmt3a, Kdm4a, Bhlhe41, Nfat2, Eomes, Nr4a2, Tcf1, T-bet, Blimp-1, Id2, Zeb2, Nr4al, Suv39 h2, Csprs, Sfmbt1, Hmgn3, Chd9, Rnf2, Ikzf3, Kmt2e, Satb1, Tet1, Tet2, Tet3, Kdm5b, Sfmbt2, Actr6, Prmt7, genes encoding inhibitory receptors and/or T cell transcription factors, and other relevant T cell genes including PD-1, CTLA-4, LAG-3, Tim3, CD200/CD200R, Ptger2, Ptger4, T-bet, Eomes, Tox, Blimp1, BATF, AP-1 family members, IRF4, and other genes described in Wherry et al., Doering et al., and/or Crawford et al. (Wherry et al. Immunity 2007, 27:670-684, incorporated herein by reference in its entirety; Doering et al. Immunity 2012, 37:1130-1144, incorporated herein by reference in its entirety; Crawford et al. Immunity 2014,40 (2):289-302, incorporated herein by reference in its entirety).

Epigenetic Targets

In some embodiments, a target associated with an epigenetic pathway, or as used herein an "epigenetic target", is targeted within a cell. In some embodiments, the epigenetic target is at least one of Tet enzyme (e.g., Tet1, Tet2), an HDAC, Tox, Tox2, Csprs, Drud1, Sfmbt1, Chd9, Suv39 h2, Sap30L, Hmgn3, BAZ2b, Prmt6, SET, Ruvbl1/2, DPY30, MLL proteins, Ezh1/2, PRC complex, CBP, BET, and/or p300. In some embodiments, the epigenetic target is at least one of any histone acetyl transferase, deacetylase, methylase, or demethylase, or any other epigenetic modifying enzyme or chromatin modifying enzyme. In some embodiments, the epigenetic target is an enzyme or intracellular protein capable of regulating epigenetic patterns. In some embodiments, the epigenetic target is a transcription factor. In some embodiments, the epigenetic target is a cell surface protein that regulates a downstream epigenetic pathway. In some embodiments, the epigenetic target is a cell surface protein that regulates a downstream epigenetic pathway. In some embodiments, the epigenetic target is at least one of SERTADI, XPA, HINT3, HIST1H1C, ZFP69, NR4A3, TNFAIP3, SAP30L, SPRY2, RYBP, TIPARP, YAf2, GCHI, GTF2B, PCGF5, SFMBT1, METTL4, THAP6, EOMES, CPEB2, IRF9, PARP9, STAT1, TLR7, APOBEC1, ISG15, PARP12, STAT2, TFDP2, SETBP1, PARP14, IKZF2, TOX, HSPA1A, SP140, SPAG7, MYCBP, TRAPPC2, TCF4, RBL2, ALS2, IKZF3, IRF7, ELL2, MXD1, IRAK2, MXl1, UHRF2, LITAF, NR4A2, NR4A1, ID2, RORA, HIST1H2BC, TBX21, MARVELD2, HIF1A, P2RY14, P2RY13, EPAS1, IRAK3, XDH, ARAP2, EIF4E3, SWAP70, TRAPPC1, GADD45B, IRF4, HMGB2, ACADL, RBBPB, UBD, ZC3H12C, RILPL2, GNPTAB, PRDM1, CARHSP1, N4BP1, ATOH1, TAF9B, APOBEC2, LRRFIP2, NFIL3, and SAP30. In some embodiments, the cell is a T cell. In some embodiments, the cell is an exhausted T cell.

Transcriptional Targets

The epigenome provides the context in which transcription factors function. Although global epigenetic landscape information did not previously exist for exhausted T cells, studies of the Pdcd1 locus (which encodes PD1) have been informative. Analysis of the Pdcd1 promoter region in acutely resolved LCMV infection demonstrated that these regions were largely demethylated in the effector phase and then became remethylated as infection resolved and CD8+ T cell memory formed. By contrast, the Pdcd1 locus became completely demethylated in chronic LCMV infection and no remethylation was observed, even when viral titers and PD1 protein expression by exhausted CD8+ T cells decreased (Youngblood et al. Immunity. 2011, 35(3):400-12). Similar data were obtained in studies examining well-controlled HIV infection (Youngblood et al. J Immunol. 2013, 191(2): 540-4133). The present disclosure teaches that epigenetic regulation of gene expression in CD8+ T cell exhaustion can prevent or reverse exhaustion and provides evidence for a durable imprint of exhaustion in the epigenome.

In some embodiments, a transcriptional target associated with an epigenetic pathway, or as used herein a "transcriptional target", is targeted within a cell. In some embodiments, the transcriptional target is Tox, SET, RuvBl1, RuvBl2, DPY30, Tox2, Stat1, Stat2, Ikzf2, Dnmt3a, Kdm4a, Bhlhe41, Nfat2, Eomes, Nr4a2, Tcf1, T-bet, Blimp-1, Id2, Zeb2, Nr4a1, Suv39 h2, Csprs, Sfmbtl, Hmgn3, Chd9, Rnf2, Ikzf3, Kmt2e, Satb1, Tet1, Tet2, Tet3, Kdm5b, Sfmbt2, Actr6, and/or Prmt7 In some embodiments, the transcriptional target is at least one of SERTADI, XPA, HINT3, HISTIHIC, ZFP69, NR4A3, TNFAIP3, SAP30L, SPRY2, RYBP, TIPARP, YAf2, GCHI, GTF2B, PCGF5, SFMBT1, METTL4, THAP6, EOMES, CPEB2, IRF9, PARP9, STAT1, TLR7, APOBEC1, ISG15, PARP12, STAT2, TFDP2, SETBP1, PARP14, IKZF2, HSPA1A, SP140, SPAG7, MYCBP, TRAPPC2, TCF4, RBL2, ALS2, IKZF3, IRF7, ELL2, MXD1, IRAK2, MXl1, UHRF2, LITAF, NR4A2, NR4A1, ID2, RORA, HIST1H2BC, TBX21, MARVELD2, HIF1A, P2RY14, P2RY13, EPAS1, IRAK3, XDH, ARAP2, EIF4E3, SWAP70, TRAPPC1, GADD45B, IRF4, HMGB2, ACADL, RBBPB, UBD, ZC3H12C, RILPL2, GNPTAB, PRDM1, CARHSP1, N4BP1, ATOH1, TAF9B, APOBEC2, LRRFIP2, NFIL3, and SAP30. In some embodiments, the transcriptional target is at least one of Pdcd1, Ccr7, Gzmb, Lef1, Itgam, Itgax, Itgad, Cd44, Kcnj8, Lrrc9/Rtn1, Ifng, Tbx21, Cxcr5, 1110, Nlrc3, Cd200r, and/or Atp8b4. In some embodiments, the transcriptional target is A330093E20Rik, Rnfl9a, 2010010A06Rik, Cdh23, Abtb2, Dync2li1, Lrrc1, Scn1b, Man1a, Gimap3, Lef1, Col26a1, Gpr180, Fam126a, Wdyhv1, Mir6395, Gpr34, Fcgr1, Rpia, A430107P09Rik, Hbsil, Slc35b3, Tmem248, Cox7a21, BB019430, Pde5a, Sept7, Lrrc3b, Cd101, Znrf3, Znrf1, Gm6260, Prpf40a, Etsi, Scn3a, Kremen1, Fam210a, Trpml, Pip4k2a, Trnp1, Sell, Nfia, Lipa, Zc3hc1, Msgn1, Yeats4, Abcd2, Tbcidl, Kcnh8, Zfp407, Capg, Gm7538, Rgcc, Sh3bp5, Slpri, Zfp957, Mcurl, Di6Ertd472e, Trat1, Fam107b, Mbtps1, Egr3, Palm3, 9030624G23Rik, Ppp6rl, Ckap4, Rngtt, Crtc3, Peak1, Lhx2, Btg1, Serbp1, Cd2, Acoxl, Hormad2, Gm10684, Smo, A630075F10Rik, Ndst1, E030018B13Rik, Skp1a, Kcnh8, Nck2, Frmd7, Cldn10, Peli1, 2010300C02Rik, Insl5, Supt20, Slc4a4, Rph3al, Dip2c, Pm20d2, Nsg2, Rbm26, Tpk1, Stambpli, AF357399, Car2, Mir145b, Zfp592, Galnt4, Gm5083, Thnsll, Dhx40, Gm20098, Ly6i, Sugtl, Ywhaz, Rad23b, Bcor, Gm12159, Vegfa, Cacna1b, Arhgefii, 2210408F21Rik, Mettl8, Wdr73, Usp12, Art4, Clvsi, Mir6388, Diap2, Gm10532, Msi2, 4930546C10Rik, Mbnl1, Tm6sfi, Ppp2r5a, Magebl6-psi, Neurl1b, Sspn, Suv420 h1, 2410088K16Rik, Rgl2, Timm8a2, Aebp2, Maml2, Ldhal6b, Peak1, Parp2, Apbb2, Tctex1d1, Dtnb, Tspan3, 4930578N18Rik, Pced1b, Commd9, Lrrc3b, Rras2, Gm10638, 1600002D24Rik, Arsb, Ube2e2, 1700009P17Rik, P4ha2, Susd1, Cdkal1, Efcc1, Malat1, 4931403G20Rik, Tox, Arpc3, Atg10, Gpbpi, Gm5148, AI317395, Abhd2, Celsrl, Tsen2, Pfkfb3, Cycl, Mir378c, Slamf6, Btg1, Phf2, Cxcr4, Gm10789, Atl2, 6030407O03Rik, Ggnbp1, Angpt1, 9530077C05Rik, Baspl, Rapgef6, H2-Ea-ps, Fam214a, Ppfia4, Lta4h, Ets2, Slc29a1, Xpo4, Gramd3, Itfg3, Flil, Frmd6, Rbpl, Olfml3, Peli1, Srpkl, Hmgcsl, Irf2bp2, Cxxc5, Ccdc171, Cntnap2, Fance, Cblb, Cubn, Sfmbt2, Srsf3, Pepd, Dgkd, Osbpl6, Trib2, Zfand3, Dchsl, 5430421F17Rik, Fpr3, Dapll, Tratl, 0610040J01Rik, Gm14005, BC051019, Tank, Tnfsf11, Rara, Pik3c2a, Elmo1, Nck2, Bel2111, Fam78a, Gm10638, Prkcq, Gpr126, Bach2, Ttc30b, Nlk, Ube2e2, Usp3, 4932441J04Rik, Larp4b, Serbp1, Dbn1, Vav3, Derll, H2-T23, C130021I20Rik, Fbxl14, Etsi, Fgf8, Abl2, Acvrlb, Upklb, Efcabl0, Uchl3, Cd302, Cdc40, Nsg2, Tmem222, P2ry10, Klrbib, Melr, Car8, BC048403, Taf8, Atplbl, Mir30c-2, Luc712, Erbb4, Arhgdib, Ube2h, Itpr2, Vav3, Ptgfrn, D630010B17Rik, Eif2s3x, Vav3, Nfe213, Ccdc171, Fignll, 4930519F09Rik, 1700123012Rik, Acsf2, Ndufb9, Atp7a, Upp2, Ptpla, Man1a, Rgs3, Zbtb2, Trib2, Npri, Fez2, Tle4, Fucal, Cmip, Bcap29, Synel, Dmbtl, Ell, Blnk, Sepwl, Gltscrl, Erdri, Medi31, Moxdl, Btg1, Akap6, 1810053B23Rik, Rsul, Gprasp2, Art4, Gpd2, Tmlhe, A430107P09Rik, Kcnj9, Atp8al, Adam6b, 2010109I03Rik, Spred2, Raver2, Apim2, Dclrela, Rbp7, Gcci, Traf4, Satbi, Gm5538, Iii2a, Fam60a, Thrb, Elk3, Vps45, Tle4, Akapi3, Gprin3, Sox21, Empl, Wfdc2, Slc45al, Lnpep, Rapgef6, Txn2, Frmd4b, Myoz3, Zfp870, Bci6, Mvbl2b, Ntrk3, Spacal, Mir701, Cdca7, Gm5083, Slpr1, Spry4, Cck, Il6st, Hebp2, Slc43a2, Tdrd5, Gm5833, Mir7-2, Mir1931, Pdgfb, 1700052N19Rik, Nfkbiz, Gm20753, Hapln1, Rras2, Diap2, Manba, Cers6, Rasgrpl, Lnpep, Apln, Ephb2, Arpp21, Mical3, Chic2, E130114P18Rik, Ipcefl, Dyrk2, Bach2, Mir122a, B230206H07Rik, Ceacam9, A730006G06Rik, 4930542C21Rik, A430107P09Rik, Tratl, Ccr2, H2-Ob, Adm, Yeats4, Ccnel, Gpc5, Spsbl, Jrkl, Orc4, Camkmt, Nfia, Celf2, Gadd45a, Gtf2al, Nrde2, Nipa2, Rmi2, Lcor, Btg1, Atg10, D6Ertd527e, Ccm2, Dpysl2, Dirc2, Cpm, Arhgap15, A730043L09Rik, Raphl, Cst10, Slc7a13, Ramp1, Atplbl, Zfp120, Slc39a13, Zfp706, Agr2, Tagap, Mir3110, Ubash3b, Dnmt3aos, H2-Bl, Agbl1, Smc6, 1700060C20Rik, Trib2, A930005H10Rik, Btg1, Scml4, Mir196b, Efna5, Tmem14a, Kcnj15, Snrpd3, Nnmt, Ryrl, Ptk2, P2rx4, 5830428M24Rik, Commd3, Cd28, Hspbl1, BC021785, Tcf7, Cstb, Art4, Tet3, Map3kl3, Camkv, Ralbpl, 9330175M20Rik, Tgtpl, Selt, Irgc1, Tcf7, Tet1, Bnip31, Nrbf2, Nimlk, Rfx8, Tlr6, Grikl, Tox, 1700061G19Rik, Dhrs3, 4930519G04Rik, Midl, Aplar, Baspl, Aqp4, 4930415F15Rik, Aifl, Rnfl25, Fam134b, Atp13a3, Dmbtl, Mbnl1, Nfaml, Lmo4, Znrf1, Ambp, 4930523C07Rik, Bfsp2, Zfp592, Gm2447, Gm16157, Gjd3, Tgtp1, Ston2, Lypd6b, Rnf7, Zbtb2, BC051537, 4930417013Rik, Amtl, Ttc9b, Foxpl, Mir7219, Mrgprb5, Tnik, Dhrsx, Foxpl, Tubb2a, Cyb5r2, Itga4, Snx9, Fam65b, C78339, Mir7212, Ldlrapl, H2-Oa, Snx12, Tdrp, Mndl-ps, Foxpl, Gucy2c, Crebl, Scn4b, Irf4, Rftn2, Gpr125, Dpfl, Fam134b, Akap13, Tmeml08, Suclgl, Mn1, Sema4b, Gm6682, Slc46a2, Dennd3, Bach2, Sytl2, Grhl3, Smad3, 1600014C10Rik, 4930455C13Rik, 3200001D21Rik, Nup153, Grk6, Zfhx3, Fhit, Hmg20b, 4930564D02Rik, Bach2, S1c39a3, Urad, Smc1a, Maml1, Zadh2, 8030462N17Rik, Fsbp, Tmem243, Srpl4, Lix1, Tmc1, Tspanl1, Tns1, Serpinb5, 1810026B05Rik, Smad7, Mir3108, Phxr4, Tmem131, O1fr1507, Kidins220, Mir378c, Afap1, Rere, Sin3b, Efemp2, Neto2, Mir7669, Tgtp1, Gramd3, Map7d2, Chst2, Spl10, Ccdc162, Igflr, Mir3110, Dcdc2b, Dse, Dlgap2, Armc9, E230029C05Rik, Gm11944, Tnik, Kat6b, Nkiras1, Tbcel, B4galtl, Cd2ap, Tnks, Icos, Tanc1, Sikl, Torlaip2, 4930453N24Rik, Bnipl, Gm6313, 4930415F15Rik, Inpp5a, Atoh7, 2210417A02Rik, Pdss2, Lamtor3, Ptbp2, Ostml, Nrarp, Fryl, Mir1907, Gm10638, Sumol, Zfp60, 1600014C10Rik, Haao, Syde2, Ep300, Ndrg3, Tex2, Cdx2, Eefsec, Tmem131, Mir6959, Fyn, Prkcq, Mical3, Snhg7, Ambral, Rag2, Vdacl, Ptpla, Tram1, Aakl, Pebp4, Sgppl, 2410007B07Rik, Itpr2, Tulp2, Mir6395, Elovl6, Ppplr3b, Zc3 h4, Sptbn4, Rap1b, Vgll4, Kcna2, Cnot6, Tbcldl, Pde4d, Rapgef4, Fbxo47, Procal, Aim, 2310001H17Rik, Tmem131, Sh2d3c, Gtpbp8, 1700030C10Rik, Polr3b, Fam69a, Bean, 4930465M20Rik, Sbpl, Emg1, Aaedl, LOC102633315, 5930430L01Rik, Adsl, Foxp1, Gm20337, Trdmtl, Gm9920, Foxo1, Olfml3, Fyb, Pgpepll, Nsg2, Tex26, Fance, Cngbl, Rapgef2, 2010010A06Rik, 2410007B07Rik, Lbh, Pnrcl, Lad1, Mycn, Abhdl5, Cdld2, 4930428G15Rik, Hnmpll, Dnaja2, Ccr7, Mmpl5, Neto2, Bach2os, Efr3a, Rnf41, Mir7656, Znrf3, Rtkn2, Sesn1, Zp3r, Glrpl, Kdm7a, 3200001D21Rik, Pdssl, 5730403I07Rik, Mmpl5, Thrb, Zbtbl6, Vkorc1, E330009J07Rik, Dntt, 4933406J10Rik, Sim2, Lgals9, Gm12216, Grbl0, Ednra, Fam3c, Birc6, Bacel, Sfrp2, 2010107G12Rik, Zfp184, Ctso, Zfp462, Abebla, Gm6639, Mir1258, Dyrk1b, Ralb, Thrb, S100a6, Gm590, Dnajcl, Zfand3, Blm, Ikzf2, Lrrc32, Nsg2, Foxpl, Tnpol, Zfat, Specc1, Snora75, Vps45, Acp6, Sydel, Extl3, Fbxl14, Cdh26, Celf2, Cd2, Tshz2, Cntln, Fam65c, Dad1, Akap6, Gm15880, E330011021Rik, Kdfl, Gsttl, 2700046G09Rik, Sortl, Nyap2, 1700063014Rik, Cog6, Extll, Vmn2r96, 1112b, Lelatl, A430107P09Rik, Zkscanl6, Chll, Nck2, Cdyl, St6gall, Mir21c, 2810428115Rik, Cnr2, Rab44, 1700064J06Rik, Zfpl91, Peli1, Als2cl, Gnas, 2300005B03Rik, BC033916, Cd226, 1700049E22Rik, Nipall, Gimap6, Gm5086, 8430436N08Rik, Ift80, Zfp697, Svsl, 4930459C07Rik, Epcam, Zfp706, Pdella, Slc43al, Slc9a9, Tshz2, Fbxwll, Mir7046, Zpbp, 1700123012Rik, Slcl6al, Gm7457, Tcf4, Fbxl12, I19r, Galnt6, Gm5868, Panxl, Hs3st5, Jarid2, Phxr4, Dock2, Nripl, Laspl, 1700066B19Rik, Marcks, Plekha7, Wdr41, Pdss2, Gpr83, Rapgef4, Gm15910, Colq, O1fr1507, Vgll4, Fgfrlop, Fancl, Capnl, Lonp2, Rnf38, Gpaal, 1700016G22Rik, Vmn2r98, Gm7325, Gm826, Rpl31, Klrc1, Ikzf1, Crlf3, Cd44, Gypc, AU019990, Fbxl13, Tsc22d3, Tgm2, Ptpnl4, Fanec, Arhgap26, Tgfbr2, Klf2, Sept7, Ptpre, Btn2a2, 4921511117Rik, Ppp2r5a, C78339, Arhgap39, Ism1, Mpzl2, 2810459M11Rik, Dyrk2, Tspanl3, Fbxl14, Plat, Celf5, Susd3, Rps6ka2, Gtf2irdl, Naifl, Rsph3a, Tsscl, Ext1, Snora7a, Bcl2l11, Pip4k2a, Npl, Tmem236, Cox7a21, A530013C23Rik, Rgll, Pgkl, Ift80, Emidl, Inpp4b, Cldn10, Gis, Tnnil, Folr4, Gm5766, O1fr1507, Hpcall, Cyth4, St8sia6, 5430434I15Rik, Ropnll, Serinc1, Mad2ll, 4921525009Rik, A430107P09Rik, Gm11127, Tra2a, Urb2, Pgpepll, Cacnald, 5730403I07Rik, Fam49a, 1700025F24Rik, Stat1, Calm1, Kcna7, Eif1, Mir669m-2, Kdr, 1700123012Rik, Mir8099-2, Hspa8, 2010010A06Rik, Zfp53, 4930524005Rik, Abl1, Uvrag, Slc16al, Dnah7b, Golph3, Ipcefl, Usp3, Jun, Snord89, Tcf7, Rbpms, Folr4, Papss2, Spred2, Stpgl, Mgat5, Lpinl, D8Ertd82e, Dhx40, Slit3, 4933405E24Rik, Nsun6, A430107P09Rik, Apol7e, Raly, Celf2, Ndufs7, Mir6921, Kbtbdl1, Gc, Haao, Gm9054, Slc44a3, Tnfrsfl9, Lefl, Ankrdl1, Plxdcl, A430107P09Rik, Zcchc2, Zmat4, Jun, Adamtsl4, Slamf6, Adamts17, A430107P09Rik, Alox5ap, Mir6368, Ncor2, Ets1, Pmpcb, Mvk, 4922502D21Rik, 1700025G04Rik, Rgmb, Gpnmb, Stkl7b, Ceacam9, Ttcl, E130006DO1Rik, Camkmt, Ankrd63, Agtrlb, Khdrbsl, Zfp706, Cux1, 4922502D21Rik, Btbdl, Timm8a2, Itga4, Reep2, Uvrag, Cyfip2, Elovl6, Tfeb, Spag16, Tbcel, Lmo2, Rasgrpl, Fam86, Ktn1, Fbxo32, Gata3, Ly86, Ptgs2os2, Famll1a, Lrrcl6a, B430306N03Rik, Tff3, Kcnn4, Mtif3, Ldlrapl, Tmem260, Pla2rl, Baspl, Ncoa3, Nglyl, Ccdcl62, Nhsl2, Cdcl23, Hnrnpu, Arhgapl8, Zfl2, Gm6498, Bex6, B630005N14Rik, Dynltlb, Lypd6b, Clec2e, Rbml7, Pstpipl, Lrpl2, Akap2, Camk2d, Igflr, Atplal, Gsn, Rragd, Actn1, Odf3b, Nudt4, Vmn2r99, Parpl1, Adipoq, Fam221a, Il6ra, Kif23, Fabp5, Srpk2, Ikzf1, Fbxw7, Slamf9, St6gall, Vav1, Serbpl, Reepl, Agr3, Plcl2, Kcnj15, Aebp2, Gm20139, Mtx2, Sell1, Mbnl2, A430078G23Rik, Krrl, Lelatl, Zfp438, 4930487H11Rik, B4galtl, Ifngr2, Olfr221, Asb4, Gm6793, Aplml, Pdlim5, Gltscrl, 1110032F04Rik, Ankrdl3a, Abcd2, Iqsecl, Inpp5a, Pdzrn3, Akirin2, Pip4k2a, Dyrk2, Jun, 4930465M20Rik, Osbpl9, Ttc30al, Ctnnbll, Tmem243, Olig3, Ubtd2, 4930540M03Rik, Dnajc5b, Denndla, Gadd45a, Rpl8, Dapll, Cd2ap, 6430710C18Rik, Slc16a5, Rcbtb2, Hmgxb3, A630075F10Rik, Ankrd2, St8sial, Ptk2b, Paqr8, Tox, Wdr37, Stat4, Rplpl, Ccnj, Hspbpl, Mthfdll, Zcchc9, Gm13293, Camk4, Htt, Usp10, Plekha6, Gm5617, Cnksr3, Mir7218, Lcp2, Cd28, Lbp, Ncoa3, Skil, Heyl, Mir6368, Akap6, Spinl, Ccdcl74, Stambpll, Ggtal, Pifo, Stim2, Rras2, Tomm201, Gm5538, Skap2, H2-Ob, Zfp3612, Clec2d, Erdrl, Dapll, Vasp, Cytip, B4galnt3, Hamp, Mex3b, Tcf712, Vpsl3d, Alox5ap, Mtssl, Gm7457, Fam46a, Taf3, 2810408111Rik, Ms4a7, Mad2ll, Selt, Snrpf, Hcn2, Frmd4b, Hivepl, Tspanl3, Nfia, Asapl, Nt5e, Misp, Maml2, Sh3pxd2a, Ccdcl62, Setd7, Etohil, Acvrll, Fntb, Shank3, Rhoh, Prok2, Marcks, A830010M20Rik, Ywhaz, Mtss1, Gm8369, Faml88b, Atp2a2, 4933405E24Rik, 4932443119Rik, Notch2, Zc3h12b, Numb, Neb, Rampl, Zfp831, Impdh2, Grkl, 4930459C07Rik, Mir7035, Setd3, Cdc42se2, Spoll, Fam166b, Mir6419, Atp10d, C2cd5, 4933412E24Rik, Boll, Calr4, I122ra2, Slc22a16, Syde2, Fyn, Slc27a6, Stx3, Gm6313, Rbm18, Gm13293, Tbc1d8, Fabp5, 4930546C10Rik, Slc16al, Cnr2, Kcnip2, Trim69, Agbl1, Plvap, Ms4a6c, Usp38, Atl2, Sh3kbpl, Ppfibp2, Piml, Pmis2, Sh3pxd2a, Ms4a4c, Klf3, Cblb, Mir701, Dmwd, Mtss1, Cdkl3, Cabp2, Chdh, Pde4b, Ston2, Cmah, Fbxl14, Syk, Trio, Btg1, Ski, Cnot2, Stk38, Tm9sf3, 4930482G09Rik, Parpll, Jarid2, Maml3, 6430710C18Rik, Commd9, Fhit, Scamp1, Tcf7, Nefl, Ric8b, Gm3716, Scml2, Nr2f2, Ssrl, Il6st, Ankrd50, Pnmal2, Foxpl, Raver2, Ccdc64, 8430436N08Rik, Klf13, Itga5, Commd3, Mro, Ms4a7, Rock2, Encl, Rab3gapl, Nav2, Tlr, Gm7457, Elfn1, Rpl34, Agfgl, 1700020N01Rik, Irf4, Gm8369, O1fr1507, Grik4, Akap6, Mir6387, Thrb, Gm20110, Mir7670, Bag4, Gm15441, LOC101055769, Pakl, Mbd2, Ralgps2, Lipg, Gpnmb, Ubash3b, Kntc1, Aqp9, Znrf2, Cmah, Peli1, Chd7, Tmsb4x, Copbl, Gimapl, Bcaslos2, Ppapdclb, Cdcl4a, Ier5, Susd3, Birc2, Sun2, Itga5, Rlbpl, St8sial, Hectdl, Chn2, Bcaslos2, Slc39a11, Cdc7, Me3, Stkl7b, Ccr4, Peli1, Cd226, 2510009E07Rik, Sh2dla, Zfp2, Mei4, Chst2, Nipall, Tbcel, Itgb6, Tmed10, Gm4489, Tmccl, A430107P09Rik, Abtb2, Tgfbr3, Zfp704, Reep5, Apeddl, Pik3rl, Msl2, Gm20098, Eif4e3, 5430402013Rik, Tsscl, Lphn2, Kcnh8, 4921525009Rik, Fam46c, Pum2, Itsn2, Slclla2, Usp6nl, Gimapl, A430107P09Rik, Nipbl, Nrxn3, 1700042010Rik, Capn3, 4930526I15Rik, Plat, Gm15850, Dock10, Shisa2, Wbscrl6, Egfl7, Zfp957, Gm20I10, Slc4a8, Ago2, Pnp2, Tgfbr3, Hmga2, Pdlim7, Dip2c, Atplbl, Pxk, Snora26, Gm6498, Sema3d, 3300002108Rik, 9330175E14Rik, BB123696, Fibedl, Slc6a19, S100a6, Commd9, Lpar4, Cntn5, Nrli2, Panxl, Dock2, Ptov1, 5330411J11Rik, Sec24d, Ms4a4b, Eif3g, Rsbnll, Plxncl, Jarid2, 1810041L15Rik, Diap2, A630075F10Rik, Klfl3, Tlkl, Lefl, Slc4a4, 2610020H08Rik, Tbce, 9430014N10Rik, S1c16a10, 2310042E22Rik, Lrrc3b, St6gall, Tnfrsfla, U90926, Fam134b, Grxcr2, Dok5, Aldh8al, Cybrdl, Smarcbl, Jmy, Zfp608, Cdkn2aipnl, Aire, Prps2, Gm839, 4933412E24Rik, St6gall, Ube2d2b, Mab2111, Slc23a2, Keap1, Brdt, Piwil2, A930005H10Rik, Fyb, Neald, Lgals9, Zfp704, Dguok, Gm15706, Nr3cl, Med13, Rictor, Paxbp1, Mir1903, Sv2a, Slx1b, Tbcld24, Wnt5b, Ccr7, Ptk2, Mir21c, Aox4, Slc35b4, Mgat5, Zfp281, Mycn, 1700016G22Rik, Odcl, Prkcb, Atel, Ncbpl, 3300002108Rik, Ly6d, Spag16, Clkl, Atg10, 1700030L20Rik, Nsg2, Agps, Goltla, Cntn5, Cadm4, Malsul, Frmd4b, Gm6607, Cdh23, Gramd4, Slc44a2, Limd2, Lphn2, 1700010K23Rik, Lrrc66, Akap7, Peal5b, D030024E09Rik, Zscanl0, Lsm2, Kcnj13, Cdhr3, Fbxl17, Lhx2, Olfm2, Cyp2rl, Wisp3, BB123696, Nlrc4, 2010010A06Rik, Elovl6, Eeal, Mir1907, Gis, B4galnt3, Epb4.1, Tshzl, Gpr126, Rgmb, Ncs1, Tet1, Hoxal, 4930515G16Rik, Usp33, Stkl0, Klhl6, Ccdcl09b, Manba, Gm5111, Chstl5, Runx1, Rgs3, Gm4759, Ldlrad4, 4933400F21Rik, 4933406C10Rik, Diap2, Mir6403, Plin2, Zmizl, Maml3, Fam86, Hbs1l, Inpp4b, Gm14405, Mgat5, Cntn5, Ramp3, Ifnk, Pgm1, Mfsd6, Armcx1, Mir5127, Gimap6, Mir6387, Slc38a2, Gsdmcl-ps, Cd24a, Kmt2e, Csrp1, 9530052E02Rik, Stkl7b, Fyb, Lhfpl5, Atp8a2, Amn1, Sertad2, Epb4.112, Stk24, Cdkl7, Camk4, Rpa1, Zmyndl1, Efcabll, Mir491, Zc3hc1, Vps45, Rgs3, Ube2m, Tspan5, Insr, Snapel, Btg1, Cox10, Znrf1, Camk4, Ddr1, Gm11981, Sesn1, Commd8, Nripl, Polr3k, Eya3, Ppplrlb, Pcdh7, A430107P09Rik, Efecl, Mtssl, Hpn, Armcx1, Gm20139, Alg14, Secl1a, Cyb5d1, Trpml, Fam65b, 5730508B09Rik, Frmd4b, Gm10584, Gm5069, Pmepal, Sell, Mir6413, Klfl2, Rhoq, Plcl2, Prrc1, Empl, D030024E09Rik, Rnfl45, Bach2, Prkcq, Hic1, Msmol, Map3k7cl, AI854517, 4922502D21Rik, Vtila, Zcchc9, Spats2, Mir7681, Wdr89, Bel6, Cytip, Gm13293, Creb314, Peli1, Pakl, Efcabll, Usp7, 4931403G20Rik, 1700030A11Rik, Mvbl2b, Ampd3, Cubn, Baiap3, Med30, Actbl2, Kat6b, Peli1, Tmevpgl, Nsf, Hpcall, Ube4b, Faml10b, C330011F03Rik, Inadl, Sesn3, Tmem30c, Itgb6, Dlgl, Srp14, 3300005DO1Rik, Ggact, Mir21c, Cyp2sl, Mir7061, Bachl, Insr, 2410114N07Rik, H2-Ebl, Taspl, Tusc3, Irf2bp2, 1700056E22Rik, Ppp6c, Slain2, Cnn3, 6030407003Rik, Acbd6, Hmgbl, P2rx4, Cdkl9, 1700061G19Rik, Tesk2, Plxncl, Ercc3, 2010010A06Rik, Stkl7b, Tspan9, Kcnj16, Ddx10, Wnt16, Sp4, Hilpda, Slc38a6, Tgfbr2, Fggy, Suget, Begain, Mndl-ps, Ksr2, Eif2d, Ms4a4d, Stim1, Cst10, Nfatc1, Ppifos, Gng7, Mir211, Txk, 4930415F15Rik, Tmem64, Stim1, Pip5klb, Kcnj15, Commd8, Mir3108, Atpl1b, Stkl7b, Emc3, Cldn10, Akapl3, Abebla, Mthfdll, Foxkl, Rgs3, Gdnf, Micul, I17r, Arhgap35, O1fr1364, Ms4a4b, Rgs10, Flt3, Sfrp2, I19r, Sfl, Gm1604b, Galnt4, Dtnb, Supt20, Fntb, Zmyndl1, Tulp3, 2410007B07Rik, Tsenl5, Abhd2, Dgcr6, Filipl1, Ift81, 4933401D09Rik, Gtdel, Ano6, Mir1928, Peli1, Jak1, Cdk19, Synel, Il23r, Tpm2, Fam65b, Kidins220, Vav1, 9030617003Rik, C1l3, Ceacam9, Ehd2, Vten1, Dusp7, Pik3ipl, Ostml, Ppard, 01fr372, Mir7032, Npy, Phxr4, Grap2, Thrb, Wipil, Dock4, Mfsd6, Zmynd8, Mylip, Setx, Ccdcl46, I112a, Sa113, Mir7048, Haplnl, Casp3, Bbs9, Synel, Tdrd3, 4930565D16Rik, Gm20098, Tcf4, Haao, Sndl, Zfp706, Agfgl, Gm8709, Synel, 4933406J10Rik, Pik3c2b, Manba, O1fr1033, Aurkb, 9330175E14Rik, Foxo1, Sfmbt2, Bach2, Pogz, 4930459C07Rik, Phxr4, Map7d2, Gm20750, I112b, Sesn3, Psen2, Suco, Mad2ll, E030030I06Rik, Gadd45a, Abcal, Boll, 4930430F21Rik, Cstad, Lyst, Rasgrp4, 4833427F10Rik, Ehd2, 4930445N18Rik, Ppmlh, Gltscrl, Irf8, Lgil, Gm10432, H2-M10.1, Crtc3, 4930453N24Rik, Irs2, 1700042010Rik, Rabgapll, Rnfl44a, Csk, Rpia, A430090L17Rik, Mir8097, Serbpl, Mir684-1, Tcf4, Commd8, Tet3, Nrli2, Gm10190, Prkcq, Orai2, Dpy30, Sbk2, Tsscl, Cd5, Sipall2, Depla, 1810006J02Rik, Itgae, D030025E07Rik, Wibg, Bach2, Irf4, Ctnnd1, Usp7, Rftn1, Themis, 4930440I19Rik, Thrb, Nrld2, Tgtpl, Ccdcl62, Atp8b2, Speer4f, Stra8, Gm4906, Fam46c, Pagl, Etv3, Erdrl, Dhrsx, Fam65b, Gosrl, Trem2, Fblnl, Sp3, Mef2a, Beor, Map4k4, Magi2, Pak2, Rph3al, Lgi4, Pja2, Tceal3, Efcab11, Arhgap5, Extl, Smyd3, Prim2, Satb1, Stag2, Themis2, Piml, Apol8, Lrrc6, Shb, Magi2, Commd8, Zfp879, Trp53i11, Rgl1, Abcd3, Diap2, Zbtb2, C030016D13Rik, Arhgdib, A630075F10Rik, C730036E19Rik, Phc2, Adamtsl0, Inpp4b, Cd200, Itpr2, Fgfrl, Gm5434, Scn2b, D8Ertd82e, Gm2a, Ube2vl, Bend4, Lpp, Mir181a-2, Gm13293, P2ryl, Klf7, E030018B13Rik, Rhobtb2, Ddr1, Ggnbp1, Gimap7, Mamstr, Cmip, Setbp1, Fcgr4, Slcla3, Zfp608, 2810403A07Rik, Gm7538, Mir378a, Hoxal3, 2610301B20Rik, Nglyl, Sergef, Tpp2, Slc35b3, Maml3, Navl, Txk, Fam195a, Scml4, Tlr12, Gpr125, Zfp3612, Suclg2, Tec, Akap2, Rab38, C030018K13Rik, 4933433H22Rik, Osbpl11, Capn13, Ankrd50, Mir1928, Mir3108, Slc39a10, Dock2, Dip2c, Aebp2, A530046M15Rik, Gm6251, Mtx2, Exoc4, Olig3, Dph6, Emb, Xpc, Gm7538, Tnfsf8, Afap112, Cenpv, Gsn, Rbms2, E2f3, Smarcel, Foxpl, Slc37a3, Apbblip, Tex10, Bend4, Pcgf5, Trio, Klf5, Gja8, E130006D01Rik, Ncor2, Acbd6, Alg14, Scmhl, D830013020Rik, Galnt4, Ndufa6, Timm8a2, 2210010C04Rik, 4931403E22Rik, Gys2, G630090E17Rik, Dapll, Nup160, Fxyd7, Zscanl8, Bid, Serhl, Cdkl7, Lrtm2, 3930402G23Rik, Tm2d1, Snora7a, C8g, Nkap, 2410007B07Rik, I1f3, Mir7017, Gpr83, Thada, Ambral, Fance, B3galt4, Thnsl1, Etv5, Aox2, Tgm2, Man1a, Edeml, Hnrnph1, Atp6v0e2, Clec4f, Heyl, Fam3c, Stat4, Slc46al, Rpsl5a-ps6, Kdm4c, Upb1, Sik1, Nceh1, Prkcq, Btg1, Galnt2, 2010010A06Rik, Neu3, Cubn, Mir1928, Rapgef2, Nedd41, Egfl7, B3gnt2, Tgtp2, Gm13546, Extl, Pold4, Ggact, B3gnt7, Gm5868, Tlr7, Lefty2, Npff, Tcf712, D130058E03, Pagl, 4930578N18Rik, 6430710C18Rik, Fam43a, Snora8l, Cyp20al, 4922502D21Rik, Lsml, Gm10791, Kcnh2, 1700109K24Rik, Nol6, 4922502D21Rik, Trib2, Nrfl, Rgag4, 4930426L09Rik, Ppil3, Vmn2r96, Nglyl, 1810046K07Rik, Hid1, O1fr1510, Nripl, Dhtkdl, Ms4a6b, 4930583K01Rik, Atplb3, Mir7046, St8sial, Pcdh7, Micalcl, D030024E09Rik, Pold4, Coro2b, Adamtsl4, Auh, Fus, Helsl, Prkcq, Nimlk, Zdhhc14, Kcnh2, Cd37, Ttc27, Olfm2, Ubac2, Mir6387, Zfp619, Zbtb9, Gpr125, Ppp2r5a, Adgb, Pard3, Ctrl, Ddrl, Ckmt2, Lpar6, Sspn, Gm4792, 9430008C03Rik, Nglyl, Tbxl9, Heatr1, Cdcl4a, Nabpl, 8430436N08Rik, Cd247, Llph, Pex10, Eeal, Lefl, Ly75, Dockl1, Haao, Rgs3, Mndl-ps, Mamll, Stxbpl, Parpll, G530011006Rik, Mgml, Ift57, Mef2a, AI427809, Ldhb, Cdkl9, Lrrc3b, Osm, Dnajcl5, Mirlet7i, Stk38, Cep170, Rcn3, Gramdla, Mfng, Vgll4, 1700017N19Rik, Atpla3, Ptpla, Mir6962, Jun, Cdkl9, Gm10638, Zfp3612, Slc39a10, Tpd52, Mthfdll, Agbll, 4922502D21Rik, Ceacam2, Drosha, Fut8, Cox10, Dnajbl2, Thns12, Eefsec, Pgpepll, 4932441J04Rik, Fndc7, Clip1, 2700046G09Rik, Itpkb, Kremenl, Mpp6, Ccr9, Tbcb, Rictor, Gm3716, Icosl, Cpeb4, Mir7681, Kmt2c, Makl6, Glil, Actl9, Gpatch2, Sept14, Aebp2, Phlppi, Zfp957, Ap3m2, Zcchc2, C030018K13Rik, Cdkl7, Tmem217, Cog6, Dock2, 117r, Crybb2, S1c16a10, Ppplrlb, E430016F16Rik, Fbxol7, Akr1d1, D10Jhu81e, Irgel, Klf7, Pcdh7, Nipbl, Rm3, Mir7681, Arhgef33, Rhoq, Dusp5, Itga4, Palm2, Map10, Tigd2, Mfge8, Zfp580, Peli1, Trim59, F730035M05Rik, Gpr110, Lyst, S1c10a4, C230029M16, Gpnmb, Rgs3, Rab3ip, Vps54, Cox7a21, Slc7a15, Serbpl, Slc22a16, Prkch, 4933433H22Rik, Arap2, Mkll, Slc22a16, Flil, Stk24, Stard8, Arhgap29, Pcca, Treml2, Tsscl, Pgpepll, Syde2, A430107P09Rik, Foxo1, 8430436N08Rik, D030024E09Rik, Tcf7, Ifitm6, Ctso, Capzb, Lypd3, Lixi, Ccdc170, Taspl, Dnah7a, Sugt1, Pde7a, Pcnp, Klf5, Olfr1357, Ldhal6b, Kctdl2b, Cxxc5, Pkn2, Mboat2, Angpt1, N6amt2, Gm839, Bachl, Il2ra, Ankrd12, Ccdc64, Pptc7, Ikzf2, Svil, Tlr, Relli, Tma16, Mbnl1, Cyfip2, Rps6ka2, Elovl6, Dapll, Zfand3, Unc5cl, Zfp619, Sytl3, BC031361, Fam26e, Gm2799, Chst15, LOC101055769, Seppi, a, Ccdc171, Hemgn, Pik3c3, Lrp12, Capnll, Pvr, Prkcq, 4932702P03Rik, 2300002M23Rik, Tef, Foxpl, Lypd6b, 4933412E24Rik, Wnt4, Marco, Elfn2, Smim9, Dip2b, March2, Frs2, O1fr1507, Mir7219, Fbxl22, Vim, 4933432G23Rik, L3mbtll, Madlll, Calr4, Lrrc3b, Strada, Mir363, Tspan9, Esrpl, Panxl, Tgfbr2, Emb, Spata3, Exti, Calm2, AY512915, C530008M17Rik, Mitf, Wdr11, Mir5127, Selt, Gm6623, Gm684, Gm3716, Tgtp2, Sptb, Hamp2, Itgb6, Cd2ap, Prnp, Ift80, Slamf6, Pou2afl, Snx29, G530011006Rik, Wipf2, Fam134b, 4930428G15Rik, Iglll, Phxr4, Sgms2, Gm12159, Igf2bp3, Haao, Bai2, Sh3pxd2a, Scn4b, Eif4e3, Snx29, Tmem194b, Ifngr2, Gm5766, Zcchc24, Sox5os3, Efna5, *Tecta*, Mir7687, Mir6367, Itga4, Tns4, Ccm2, Wipfl, Cerk, Znrfl, Elovl5, Phtf2, 1300002E11Rik, 2210417A02Rik, Mir7061, Grhpr, Mark4, 4930564C03Rik, Svopl, Pja2, Tfdp2, Rbm11, Usp6nl, Mir6368, A430107P09Rik, Bel2, Cdc42se2, 4933433H22Rik, Apol8, Xpnpep2, Dach2, Mir205, Stard5, Fsbp, Rph3al, Vav3, Gm10125, Lpcatl, Cd2ap, Banki, Smurfi, Aox2, C230029M16, Sgmsl, Eci3, Xpnpep2, Pfkfb2, Utm, Ldlrad3, Gabrrl, Kcna2, Ywhaz, Stard13, Atp10a, S1c39a10, Whsc1l1, Gm12522, Trio, Manlcl, Hmhal, Gm10791, Kidins220, Ladi, Mir1928, Gm13710, Mir1963, *Lama*4, Pard3, Susd3, Taok3, Skor2, Matn2, Tet2, Mir7674, Ccdc64b, Fam49b, 4933412E24Rik, Thsdl, Sa113, Papss2, Tceal3, Rrebl, Klrdl, Rgs3, CstlO, Itga4, Gm20098, Smarca4, Cyp2d22, Kdm6b, Cntn5, Dyrk2, Dusp10, Srpk2, Etv5, Slc25a25, Cfl2, Micul, Etsi, Gm6559, Zfr, Mrp152, Cerk, D630010B17Rik, Extl, Cblb, Gnai2, Apol7e, Manba, Dusp10, Smim8, Mir6907, Pard3, Tmem35, Ric8b, Gm14124, Pik3rl, Gml1981, Dip2c, Plin2, Fam228a, Tlrn, Lypd6b, Zc3h12b, Abegl, Exti, Camk2g, Ptgr2, Mndl-ps, Rftn1, Sox8, Sdc3, Mab2113, Aridib, Tdrp, 4921525009Rik, Arid4b, Micu2, Ly86, Afp, Grap2, Ist1, Sh2d4b, Rad52, Mir1668, Rpgripll, Gramdla, Sgkl, Fos, Smad4, Hdac4, B3gnt3, Nr4a3, St8sial, Psg-ps1, Actl9, Pdkl, Il2ra, Irf2, Fasl, Hsdl1, Galnt5, Itk, Maml2, Erdrl, Ndufa6, Tbc1d23, Slc43a2, Iqgapl, Klf7, Bend5, Klf4, Lif, Calr4, Cnst, Ifnk, G3bp2, Tbc1d2, C030034L19Rik, Zfhx3, Bellla, Retnlb, Ap3 ml, Hlcs, Serpinfl, Gm16390, Wdr37, St8sial, Cenpu, Gm10638, Tfpi, Fabp7, Wisp3, Psmal, Tet2, A1854703, Lmo4, Ppplrlb, Mgat5, Foxp1, Gm3716, Mir6349, Tle4, Itgb8, Rabllfip4, Tbcel, Npepps, 1300002E11Rik, Celf2, 4933412E24Rik, 4930415F15Rik, Olfr1507, Itgb3, Bacel, 2010015L04Rik, Mir7656, Esrpl, Spred2, Myol0, A930001A20Rik, BC048403, Lincpint, Mturn, Shisa2, Mef2d, Rac2, Dusp6, Lefl, Tmem64, Lrigl, Atp6vlgl, 1700017N19Rik, Dfna5, Zfp286, Gimap9, Gbel, Cdc37, Pard6g, Serp2, Pid1, 4930465M20Rik, P2rx4, Opa-lin, Mir684-1, Nglyl, Ndufa4, Mir16-2, Trib2, Slc17a9, Itpripl1, Uril, Rnf32, Prlr, Lyrm7, Fbln1, Nenf, Atl2, Slfn1, Supt20, Ski, Pno1, Foxo1, Olig3, 5330411J11Rik, Eci3, Clic4, Naa30, Abcal, Mppl, Adcy6, Ptprc, Fbxo27, Ahcyl2, 1700016K19Rik, Gm14405, Drosha, Lrrc1, Mir7014, Cdkl9, Ldlrapl, Pgpepll, Fgl2, Nck2, Acvr2a, Myol0, Cblb, Gm590, Kcnq5, Col6al, 4930480M12Rik, Rad23b, Tram2, Pygol, Mir6368, A430107P09Rik, Afapi, Pip4k2a, Slc46a2, Mgat5, Slc27a6, Ntpcr, Cuedel, Rampi, Enthd1, Mir6374, Stmni-rsi, Gm684, Fblni, Lef1, Chd7, Pppir3fos, Abil, Plau, Aifll, Tesc, Edem3, Tbcel, Prdm5, Lnpep, Dyrk2, Gm6260, 4930428G15Rik, Carnsl, 8430436N08Rik, Plekha5, Hexim2, Ccr7, Foxpl, Satb1, Rpgripl, Dnm3os, Retnlb, Trami, Tmppe, Car12, Snordi4c, EtsT, Crtc3, Kcnh8, Heyl, Slc44a2, Dip2c, Ankrd44, C230029M16, Nwdl, Mrps11, Cpbl, 4930567H12Rik, Mir378c, Dnaja2, Fnbpll, Tab3, Zap70, Cenpk, Bcar3, Usp6nl, Ppp4r2, Hasi, Tbcid22a, Dync2li1, BC055111, Sepwl, Apls3, Assi, Metrnl, Rsph3a, Dpysl2, Rapgef6, Cxcr4, Mir8095, Sgsm3, Actni, Grb10, Slprl, Rasgrpl, Dnajc6, Agfgl, Map3kl5, 4930465M20Rik, Csnklg3, Trpv5, Klf3, Zfp3612, Mirl81a-1, Slc30a9, Taf3, Em12, Tsscl, 1190002N15Rik, Cdh26, Savl, Ghsr, Msra, Fam134b, Tusc3, Itpkb, Dtwd2, Frmd7, Gm20750, 4933440M02Rik, St8sial, Mir8105, Mir7681, Sntgl, Hipk2, Cd8b1, Stk24, Zmat4, Pnoc, Crebl, Trpsi, Gis, Gm15706, Ubtd2, Kifib, Pex3, Ect21, 4732490B19Rik, Calm2, Synel, Apibl, Ldha, Mmpi5, Tnks, Gm20098, Spred2, Igf2bp3, Atpla3, Pdzrn3, Qserl, Ppmll, D930032P07Rik, Vmn2r98, G530011006Rik, Ikzf1, D630010B17Rik, Mettl8, Gm590, Enthdl, Ccdci52, Ywhaq, Atp8a2, Thra, Ildri, Rpap3, Ltb, Rev31, Medi31, Dner, Ralgps2, 4930428GI5Rik, Dnajc1, Arhgap6, Faml01b, Nfaml, Ccr7, Psma6, Gm1631, Hadh, 3425401B19Rik, Irf4, Zak, Brdt, Fam71f2, Slc25a12, Ippk, Fnbpll, Rps16, 4930540M03Rik, Cd5, Ube2el, A430107P09Rik, Rapgef4, O1fr1507, Rmdn2, Lhfp, Mir1893, Lgals3, Gnl31, Whscll1, Sh2dla, BC061194, Mbnl2, Zbtb38, Golph3, 4930430F21Rik, H2-Q1, Ntrk3, Ninj2, Cd3e, Stat5b, Lbxl, 4933412E24Rik, Pten, Gm2447, Mtx2, Tmcc3, Lin28a, Cyb5a, Znrf1, Fancc, 1500015010Rik, Plekhol, Prss32, Gjd2, Gphb5, Ccr7, 4931403G20Rik, Mboatl, Dyrk2, I19r, Sos1, Etv2, Txnip, Faml10b, Rph3al, Mboat4, Plekhh2, Irf6, Thoc7, Yeats4, A430107P09Rik, Ms4a7, 4930567H12Rik, Zfp930, Zap70, Uaca, Nsg2, Myol0, Ctfl, AU015836, Mir7681, 9830132P13Rik, 1700021F07Rik, Ipo4, Icosl, Smad5, Cyp26b1, Mgarp, A430078G23Rik, Kdm6a, I730028E13Rik, Hs2st1, Tox, Akrldl, 1810010DO1Rik, Rp134, Ramp1, Helsl, Rab3ip, 4930445N18Rik, Extl3, Sox4, Gjd3, Gm14305, 1700061F12Rik, Lnpep, Wnt5b, Mark4, Stmndl, O1fr1507, A430107P09Rik, Commd8, AI427809, Mir6979, Cdc42se2, Gprl25, Tcf25, Taf8, Lelatl, Wdr89, Ptk2b, Pitpnb, Ttf2, St6gall, Maml2, Lrch3, 5430427M07Rik, Bachl, Exoc4, Mef2d, Vps37b, Wdr37, Ccr7, Fam221a, Mif, Vmnlrl57, Mpp6, Chd2, Sept6, She, Prg4, Snord83b, Gm7616, 2410114N07Rik, Wdr37, Gdpd4, Vdacl, Mir5104, Rsrcl, 4930523C07Rik, Akap2, Lyst, G6pc2, Klhl4, Slc35b4, Setbp1, Akap2, 1700072005Rik, Gm1604b, Kcnal0, Stambpll, Npas2, Dnajcl, Ddx25, 4933433H22Rik, Plcg2, 4930562F07Rik, Armc4, Foxo1, Samd91, Gm16157, Gpnmb, Tmem141, Mir6413, Gabbr2, Fgf8, Prdm2, Ikzf3, Diexf, Ccdc8, Esd, Macrodl, Tm2d1, 4930572013Rik, A130077B15Rik, Lck, Kdm2a, Rbbp8, Cd47, Gm6578, Klf2, Zfp536, Ube2e3, Aff3, Man1a, 4930413G21Rik, Crtam, Rpa1, Kcnh3, 2900008C10Rik, Tbc1d31, Snn, Malatl, Bambi-ps1, Wisp3, Mrgprb5, Gehl, Nabpl, Mettl9, Zfp3612, Mir7669, 4933401H06Rik, Prkrir, Erdrl, O1fr630, Tmem168, Gbp11, Mbnl1, Plin2, Scn2b, Car8, Nglyl, Kcna2, Dpp6, BC027231, Gosrl, 1700016L21Rik, Ccdc170, Manba, Osbpl9, Purb, Rftn2, Klf3, Cdca71, Supt71, Rgs3, Rbpms, Mir6349, 5830418P13Rik, Pkn2, Baspl, Btg2, Ifnk, 5730403107Rik, Srsfl, Kif3a, Fbxo27, Gipr, Colq, 4930540M03Rik, Pard6g, Bellla, Ezhl, Cd2, Foxql, Rybp, Pgapl, Usp10, Sh3bp5, Pmp22, Sdc3, Rnf145, Ankrd44, Tacc2, Sh3bp4, 4930465M20Rik, Slc19a3, Gm10791, Map4k4, Bhmt, Gm10190, Zdhhcl8, Mroh2b, Gpr3, Tgfbr2, Reck, Atxn713b, Nglyl, 1112rbl, Gucy2c, Gpr83, 1700025G04Rik, Arap1, Chrm3, 8430436N08Rik, Postn, Lonp2, Ly6d, Zfp516, Fam102b, Psap, Rere, Fam217a, Cox4i1, Slc7al, C9, Mir6374, Mdml, 2310043L19Rik, Fbxl17, Gm5468, Panxl, Set, Racgap1, Ppmlb, Samd12, E330009J07Rik, Cd101, Zcchc2, Gadll, Rapgef6, Steap3, Fgfrlop, Setd7, 3110056K07Rik, Gm5538, Ino80e, St6gall, Nsmcel, Ccdc64, Cxcr4, Gata3, Cerk, Chst15, Mir3089, Map4k4, Akap13, Slc30a9, Gm10790, Npffrl, Tdrp, Gm20098, Ddhd2, St8sia6, Lhx2, Syt6, Dtl, Themis, Maml2, Sh3bgrl2, Sptbn1, Fam207a, Lmna, Nfatc2, Gm12185, Arhgap6, Atg14, Macrod2, Mir3110, Fam46c, Wdr63, Ppp2rlb, Prdm9, Lphn2, Mir574, I19, Elovl6, Chd7, Pitpna, Atoh7, Mc2r, Celf2, Tdrd3, Rassf2, Gm10640, Ncoa3, Lyst, Fyb, Gm2447, Ap1ar, Stag2, Foxp1, Rock2, Pdlim1, Bin1, Gm10125, Bach2, Fbxl22, 2900005J15Rik, Rgs2, Cldn10, Lrrc8d, Rad23b, Supt20, Dgkd, Atn1, Agtrla, Pias2, Gm10791, Tmem60, Prkag2, P4ha2, Tratl, March5, Tcf7, Wbscr27, Gm6498, Histlh2bn, Zfpl20, Trubl, Mir1936, Ms4a7, Nfatc4, Lrrn3, Tratl, Sox4, Nhsll, Lin-cencl, Tmem243, St6gall, Dpysl2, Cntln, I17r, Olfr9, Erbb2ip, Rpl101, Mir211, Srbdl, Lphn2, Fam3c, Sorcs2, Thrb, Katnall, Mirl99a-1, Fbxo32, Rpap3, Arfip1, Rpl19, Itm2a, Trim56, Ier51, Btg1, Plekhbl, Rp134, Pik3rl, Mir6349, Ikbkb, Cntn5, Sh3kbpl, Btg1, Cd101, 4930523C07Rik, Qsox2, Serhl, Rfcl, Cga, Bmyc, Sla, Rev31, Fam134b, Ggact, Mir466o, 28-Feb, Akrldl, Tnfsfl1, 2310040G24Rik, Gelc, Pde4b, Dgkz, Hsbpl, Eif3k, Gipc3, Mthfdll, P2ryl, Ets1, Cxcr4, Pjal, Treml2, Ccr7, C230024C17Rik, Rps6ka5, Klf4, Cx3crl, Echdc3, Hspa8, *Lama*4, Mgll, Ophnl, Thnsl1, Disc1, Pdzrn3, Sms, Zfp704, Zfp3612, Fam105a, Mad2ll, Dazap2, Fbxl14, Vapb, Ifnab, Zgrfl, Rtkn2, Ppp2r3c, Vmn2r96, Bbs9, Ifnlr1, 1700064J06Rik, Ppplr37, Tgfbr2, Slc2a2, Lefl, Ccr7, Foxql, Gan, D6Ertd527e, Snx9, Hes7, Fbxo47, Cox10, Bend3, Sgmsl, Slc30a9, Gm3716, Foxo1, Rsbnll, Tmc1, Faml20a, Gprl8, Efhcl, Ramp3, She, Akap7, Vezfl, Dnajc3, Tnpol, Nudtl6ll, Gm19589, Ankrd60, Txk, Lix1, Dnajc6, Serinc5, Lefl, Tars, Gm3336, Bacel, Nedd41, Trib2, Gm6994, Bcl11a, Mir5127, Klrb1b, Nfix, Tigd2, Map4k2, Uxs1, Bach2, 4930583K01Rik, Klhdc9, Eepdl, Als2cl, Pard3, Wdr27, Ikzf1, Btg1, Ly6e, Prml, Tacol, Itpr2, Limk2, Bend4, Gtf3c3, Kcnh8, Cd96, Fam229b, Adamts14, Lyrm7, Fhit, Sqrdl, Fpr-rs4, Tmem260, Cd55, Mir214, Mir3093, Amigo2, Dappl, C030018K13Rik, A230028005Rik, Shf, Lefl, Nrpl, Efr3a, Tmem30b, Mynn, Tgfbr2, Nfia, Ipcefl, Atl2, Thpo, Fam49a, Mir6387, Rtkn2, Gucyla3, Chrna9, Rassf2, Clip4, Wntl0a, Opalin, Llph, Mir6995, Sorcs2, Slc2a2, Gm20110, Synel, 2810001G20Rik, 5430434I15Rik, Ppp1r37, Itgb6, Hspa8, I19r, Glrp1, 5430421F17Rik, Tstd2, Zswim2, Extl, S1c16a10, Zfp957, Slfn5, Lrch1, Scin, Card11, Ext1, Tet1, Scml4, Diap2, 4933433H22Rik, Zfp629, Tspan13, Prkcq, Zcchcl3, Cd74, E330017L17Rik, Tm2d1, Gprl26, Nrnl, Fam124b, Tubb2a, Tdrp, Tnfrsfla, Foxp1, Fam107b, Epb4.115, Fam78a, Rasal2, Mapk9, Creb312, 4930539M17Rik, Kcmf1, Ctage5, Ankrd12, Manba, Tmcl, Lmanll, Nacad, Agr3, 4933433H22Rik, Matk, H2bfm, Kcnh2, Pgrl51, Inpp4b, Kcmfl, 4933430N04Rik, Vmn2r92, Stkl7b, Foxp1, Cep5711, Lix1, Kcna10, Vangl2, Treh, Enthd1, Gm6559, Brf2, 4921525009Rik, Prkcq, Igsf3, Fut8, Limk2, 5730508B09Rik, Clasp2, Twsg1, Tmem126b, Hoxa7, Cd28, Sh3bp5, Furin, 1700001PO1Rik, Diap2, *Tecta*, Icosl, F11r, Mir7023, Fes, Map3k5, Spry4, Cd44, Ralgps1, Gm16793, Alox5ap, Mir5098, Arid1b, Ugcg, Ctla4, Snx9, Mir8095, Is12, Osbpl6, Dyrkla, Cd300a, A930011G23Rik, Fam26e, Ikzf2, Enpp6, Mir181a-1, Lyst, Grhl2, Aldh1a7, Hmgb1-rs17, 2410004B18Rik, Dnm2, Nabp1, Foxp1, Tnfrsf10b, Prkcq, Sgsm3, Agr3, 1700017N19Rik, Tle3, 4933406K04Rik, Insr, Whrn, Ets1, Lef1, Mir5618, Soat1, Ccr7, Cmss1, Ahcyl2, Mgat1, Hspa13, Znrf2, Kcnh8, Tdrp, Gm1604b, Vmn2r95, Akap6, Tbc1d22a, Lbp, Mkl1, Rsu1, Sstr2, Slc37a3, Ube2d2a, Itpka, Rnf220, Hnrnph2, Gm2933, Akap2, Pdzklip1, Wwp1, Vapb, Dyrkla, Dynltlb, Zfp365, Ssh2, R3hdml, Nek10, Zswim2, Ccdc90b, Znrf1, Ms4a5, 4933406K04Rik, Actr2, Rgmb, Ston2, Gnas, Stkl7b, Pim1, Mtr, Klhl2, Cdk15, H2-Ob, 1123r, Slain2, Tssc1, Sbk1, Ube4a, H2-T3, Gtf2ird1, Tyw5, Hbsll, Efhc1, Rpe, March6, Itga4, Fam13a, Lstl, Ankrd55, Nif311, Fam69b, Mir7674, 2810001G20Rik, Gpr19, 4930567H12Rik, Foxp1, Dgkz, Cenpf, Amigo2, Panxl, B4galt3, Pag1, Ubl3, 1110059E24Rik, Hslbp3, Slc6al9os, Mdm1, Limd2, Slc6al9, Bank1, Alg13, Wisp3, Sult5a1, Fam86, Dennd2d, Cacnb2, Tesc, Mdml, Adipoq, 1810026B05Rik, Mir325, 1700096J18Rik, D030024E09Rik, GOs2, Mir7219, Slpr1, Cxcr1, Extl, Chdl, Ly86, Dhx40, 4930564D02Rik, Dctn6, 117r, E230025N22Rik, Sgk3, Bach2, Ramp1, Syt6, Gsap, Ccdc152, Jakmip1, Atp8a1, Grap2, Dynltlf, 4921513103Rik, Gpc6, Kcna10, Ipcef1, Mir7061, Btg1, Stoml1, Zfand3, Aqp4, Zfp281, Ccr2, Nrip3, C230029M16, Tcf4, Hadh, Mthfdll, Lhfp, Gprl14, Plbd1, 1110034G24Rik, Cd79a, Gse1, Churc1, Map3k7cl, Filip11, Galnt7, Appl2, March5, Zswim6, Skap1, Tgfbr3, Slcl6a2, Palld, Atg10, Cap2, Dfna5, Tlr7, Slc24al, Hivep2, Dock4, Cd300a, Igf2bp2, A430107P09Rik, Lrm3, March2, Gm21057, Apbblip, Piga, Zbpl, A430107P09Rik, Trappc8, Zdhhcl4, Stkl7b, Sh3pxd2a, Ppifos, Chdl, Socs1, Kdr, Gramd3, Urad, Sipall1, Gm20098, P2ry2, Gas8, Sox5os3, Ccdc117, A130077B15Rik, Baspl, Zfp365, Syde2, Laptm4b, Sikl, 4933433H22Rik, Npff, Amtl, Alb, Zmyndl1, Gm20098, I19, Hadh, Sstr2, Empl, Lef1, Galnt10, 5430434115Rik, Cmah, 4631405J19Rik, Hesxl, Gm16793, Rplp0, Sall3, Xdh, St8sial, Folr4, Sp3, Rassf3, Aox2, Empl, Rragc, Proser2, Gm8817, D030028A08Rik, Btg1, Mad2ll, Upbl, 1810006J02Rik, 4932702P03Rik, Rhoh, Gm10790, Dock10, Fam166b, Pcdhl, Zbtb24, Camklg, 4933407L21Rik, Pde7a, A430093F15Rik, Pmepal, Ropnll, Grap2, Rims3, Rps6ka1, Eps15, 4930445N18Rik, 6430710C18Rik, Ppplrl3b, I121r, Mtmr2, Prex2, Atp6vOd2, Abliml, Hnmpd, Sydel, Slc16a1, Mbnl1, Sgmsl, H2-DMbl, Ly6a, Tlr1, Gm20098, Galnt5, Edeml, Fam173b, Gprl26, Nbeall, Prlr, Tmc1, Csrnp1, Atp10a, Dusp4, Lpar6, Pitpnb, Actr2, Ago2, Lphn2, Gm2447, Myol8a, Cd101, Cngbl, 1700027J07Rik, Vmn2r91, Folr4, Satb1, Man2a2, Smim14, 3300005DO1Rik, D130058E03, Angptl2, Ercc3, Tmem87a, Synel, Ptrf, Gm2447, Zscan2, Bend4, Endodl, Tgfb3, Mir6962, Rragd, 4931403G20Rik, Ddrl, Map4k3, Fabp4, Stkl7b, Gm5122, Rapgef4, Neurl1b, Pdgfrb, Cirh1a, Fnipl, E030002003Rik, Fam65b, H2-DMa, Btg1, Zc3h12b, Prkch, Sipall1, Tdrp, Adtrp, Fam129c, Runx3, Ilvbl, Tbxl9, Filip11, A430107P09Rik, Cedell, Lphn2, Spgl1, Mir6395, Foxpl, Dtnb, Mrpl13, Egln3, Fprl, Rapgef4, A130077B15Rik, Tlr7, Rbpms, Gm1966, Tmem150b, Rev31, Mad2ll, Gm1604b, Taspl, Slcl9a3, TrappcO, Ralgps2, Npasl, Ptprs, Slc36alos, Maf, Wdr12, Polr3k, Gm20750, D14Ertd670e, Fam46c, Fam46c, Ptgerl, Lelatl, Ptma, Actn2, Tspanll, Zfp879, Spred2, Satb1, Nabpl, 4930486L24Rik, Ugeg, Txk, A430107P09Rik, Hadh, Abtb2, Rbm33, Flil, Fyn, Mgat4a, Sndl, Glt8d2, H2bfm, 9130401M01Rik, Sndl, Mir3079, Pcdh7, Cngal, Tldel, Ugdh, Aven, Mir8104, Rgll, Sox6, Map3kl4, Akirin2, Mir684-2, Rfx2, Fyb, Cedc711, Ecel, Gm8884, 4921507P07Rik, Mir6933, Slc6a7, Cox7b2, Rfx4, Gm5617, Sh3kbpl, Pds5a, 9030617003Rik, Gprl26, Ctnn-bll, Prpf40a, Gpr22, Cldn10, Cdkl9, Sgk3, Rgs3, Mir6995, Cdon, Stkl7b, Samhdl, Gm16793, Lag3, Olfm2, Cyb5a, Zfp438, Akap2, Dpfl, 3110052M02Rik, Lrp6, Haao, Camk2a, Tspan9, 5430434Il5Rik, Stk24, Tlr12, A930005H10Rik, Slc4a4, U2afl, Fbxl21, Opalin, Rybp, Igsf3, Aiml, Wasf2, Rgs3, Frs2, Smok4a, Pak4, Zscan22, A430107P09Rik, Slc35b3, Serpinb5, Med30, Cdcl6, Agfgl, Tmem261, Plxnal, Myo5c, Gpr183, Suclgl, Cdkl9, 4930556N09Rik, Lpp, Tmem260, Ubqln2, Mir378b, Btla, Gm19589, Ano6, Clint1, Ube4b, O1fr1507, Rab33a, 4930523C07Rik, St6gall, 1600014K23Rik, Nnmt, Ift80, Htr3b, Rp134, Ipcefl, Psma6, Dnmt3a, Hpgds, Stxbp3a, Mir6907, 1700056E22Rik, Smad7, Mir7078, Mir181b-2, 1127ra, Stat1, C030018K13Rik, Foxql, Hpcall, Msra, Zc3havl, Tdrd6, Tnfrsf4, 4921517D22Rik, Rubie, Plekhg6, Brd4, Sortl, U90926, 4930519F09Rik, Il4ra, Smyd2, Prkch, March9, Ghsr, Rps6ka2, Rpp21, Vpsl3c, 1600002D24Rik, Fam136a, 4921511I17Rik, Spefl, Maml3, St8sial, Ssbp2, Stk4, Tnfrsfl9, Snord104, O1fr1507, Dysf, Cntn5, Cd2, Raver2, Gm10790, Pjal, Tmprss9, Klf5, Ubash3b, Tle3, Seml4, Snx4, Tert, Sptbn1, Mir326, Affl, Gm8298, Ephb2, Tec, F3, Exoc6, Sema4f, Denndla, Gmell, Gm10532, St3gall, Chd7, Gm6268, Tox, Pja2, Klhl3, Dnajcl0, Foxpl, Trp53inpl, Gtf3c3, Scd2, Atl2, Dach2, Lynxl, Candl, Cxcr4, Gm20098, Fsen3, 119r, Dph5, Sh3bp5, St6gall, Flil, Mir5127, Ubacl, Gm16793, Nsmaf, Sp6, Rnfl45, Cer7, Orail, Serbpl, St6galnac5, Tox, Cacna1b, A430035B10Rik, Alpl, H2-DMb2, Etnkl, O1fr1507, Mtr, Rgmb, Pmp22, Detn6, Flil, Mir326, Slc17a7, Seppl, Slc6a19, Cngbl, Mir7681, Cer9, Klhl4, Atp6vlg3, Clecl6a, Speer2, Gsn, Umps, Unc5cl, Aox2, Deaf8, Igf2bp3, Car2, Rnf43, Kdm7a, Tgfbr3, Eldr, BC094916, Unc80, Zmyndl1, Nabpl, Adamtsl4, Gm20139, Fgfr1, Tmem141, C130026L21Rik, D630039A03Rik, Mturn, Herc3, Gm5468, Mir6398, Fam86, Nsg2, Cblb, Erbb4, Mir7-2, Smurf1, Clecl6a, Lhx2, Tomm20, Ifngr2, Acacb, Gm10791, Bachl, Epb4.112, Tmem154, Tssel, Vdacl, Itgae, Raphl, Klf3, Pnrc1, Sell, Tdrp, Ptk2, A630072M18Rik, Slc41a3, Rabllb, Tnfrsfl0b, Lrpl2, Ptger3, Aggfl, 1700029F12Rik, Dpfl, Gm14295, Ubqln2, Coq2, Txndc8, P2ryl, 4933430H16Rik, Tctex1d1, Sfmbt2, Algl4, Thal, Etsl, Cd101, Neu3, Mob3b, Kcna2, Irs2, Mbnl1, Fntb, Nipbl, Slc16a5, Ccdc174, Ncs1, BC037032, Fryl, Lipa, Hslbp3, Cd101, Chd1, Atad1, Ppplr3fos, Pde4b, Lamtor3, Klf2, Ttc27, Dntt, 5830454E08Rik, Panxl, Cyp2r1, Rhou, Mir701, Ccr7, Arhgap26, Ankrd36, Retnlb, Themis, Med13l, Slc6al9os, Znrf2, Mettl8, Mir3108, D030025E07Rik, Mir145b, Iqsecl, Cd8b1, Clic1, 1810026B05Rik, Ptprs, Med7, Mthfdll, Dnalil, Bachl, Mgmt, Ppmlb, 4933430H16Rik, Cd401g, Txk, Cdcl4a, I19r, Slc7a15, Prkch, Srpk2, Tmbim7, Rcor1, Vtila, B3gnt2, Tmem261, Gria3, Tusc3, Rgs3, Satb1, Sept6, Setbp1, Cep68, Ric8b, Il6ra, Znrf2, Lypd6b, Tmem29, Myh9, 4921511I17Rik, Dlx1, Lhx2, and/or Chst15. In some embodiments, the transcriptional target is Irf8, Ctps, Chst15, Sipall1, 2610005L07Rik, Irf8, Etv5, Ctps, Grk5, Cd200r2, Cenpu, Atp2b2, Srfbp1, Fndc9, Tlr6, 3300005D01Rik, Vav3, Dusp5, Sipall1, Chst15, 2610005L07Rik, Cxxc5, Mrc2, Plod3, Bmpr2, Cd55, Ear2, Tmtc4, St6galnac3, Cenpa, Filip1, 6330407A03Rik, Gm10389, D8Ertd82e, Gm156, Mcf21, Enpp6, 2610005L07Rik, Cdyl2, 3300005D01Rik, Gm10389, Irf8, Mir3081, Grk5, Enpp6, Srfbpl, 3300005D01Rik, Vav3, Chst15, Sipall1, Filip1, 2610005L07Rik, Bmpr2, 4930415F15Rik, St6galnac3, Ralgapa2, Tmtc4, Abhd6, Gm10389, Zfp3611, Ctps, Atp2b2, Fndc9, Tlr6, 3300005D01Rik, Dusp5, Cxxc5, Irf8, Plod3, Bmpr2, Cd55, Ear2, St6galnac3, Cenpa, Grk5, Filip1, 6330407A03Rik, Srfbpl, Filip1, Snail, I17r, Il1r2, Ly6i, Gm5, Snail, Snail, Klrg1, Tff1, Zfp3611, Pmepa1, Urb2, Snail, Klrg1, Fchsd2, 117r, Zfp3611, and Klrg1.]In some embodiments, the cell is a T cell. In some embodiments, the cell is a CD8+ T cell. In some embodiments, the cell is an exhausted T cell.

Engineered T cell

In some embodiments, the invention provides a cell (e.g., T cell) engineered to have an altered epigenome that contributes to increased immunological response in a patient having a disease such as cancer or an infectious disease. In some embodiments, the engineered T cell of the present disclosure comprises an alteration in a high priority epigenetic pathway. In some embodiments, the T cell is an exhausted T cell ($T_{EX}$). In some embodiments, the high priority epigenetic pathway is targeted. In some embodiments, the alterations in the high priority epigenetic pathway comprise genetic modifications introduced via genome engineering approaches or epigenetic modifications using inhibitors or activators of epigenetic regulators. In some embodiments, the high priority epigenetic pathway has been targeted by genome engineering, e.g. by knocking out/in transcription factors or other genes in the epigenetic pathway, or by modifying the function of protein encoding genes in epigenetic pathways. In some embodiments, the high priority epigenetic pathway is targeted by knocking in/out regulatory sequences in the OCR domains associated with T cell exhaustion. In some embodiments, the OCR domains associated with T cell exhaustion are those listed in Table 6. In some embodiments, the targeting of the high priority epigenetic pathway prevents, reverses or increases exhaustion of the T cell. In further embodiments, the targeting of the high priority epigenetic pathway prevents or reverses exhaustion of the T cell. Targeting of the epigenetic pathway can result in a change/changes in at least one of Tox, SET, RuvBl1, RuvBl2, DPY30, Tox2, Stat1, Stat2, Ikzf2, Dnmt3a, Kdm4a, Bhlhe4l, Nfat2, Eomes, Nr4a2, Tcf1, T-bet, Blimp-1, Id2, Zeb2, Nr4al, Suv39 h2, Csprs, Sfmbt1, Hmgn3, Chd9, Rnf2, Ikzf3, Kmt2e, Satb1, Tet1, Tet2, Tet3, Kdm5b, Sfmbt2, Actr6, and Prmt7. In some embodiments, the epigenetic pathway is targeted with a drug or with genome engineering via CRISPR/Cas9 targeting.

In some embodiments, an engineered mammalian T cell of the disclosure comprises a high priority epigenetic pathway, wherein the high priority epigenetic pathway is targeted, the high priority epigenetic pathway comprises an epigenetic change in or altered expression of at least one target (e.g. epigenetic target and/or transcriptional target), and the targeting of the high priority epigenetic pathway prevents, reverses or increases exhaustion of the T cell. In further embodiments, the targeting of the high priority epigenetic pathway prevents or reverses exhaustion of the T cell. In some embodiments, the epigenetic change comprises a change in at least one of DNA accessibility, histone methylation, acetylation, phosphorylation, ubiquitylation, sumoylation, ribosylation, citrullination, and DNA methylation. DNA accessibility at key loci is known through this disclosure to be important in changing the biology of exhausted T cells. This effect may be mediated by changes in histone methylation, acetylation, phosphorylation, ubiquitylation, sumoylation, ribosylation, citrullination, and DNA methylation.

Epigenomic Signature

Exhausted T cells have a unique epigenome as compared to naïve, effector, and/or memory T cells. This unique epigenome is referred to herein as an "epigenomic signature." The epigenomic signature comprises a signature of genes uniquely expressed in $T_{EX}$.

An approach that could not only identify and enumerate, but also interrogate changes in activation state and relation to disease status could be of considerable value in monitoring patients on immunotherapies and be used to guide choices of immunotherapeutic approaches and help track immunological treatment response.

A signature of genes uniquely expressed in $T_{EX}$ is identified herein. In some embodiments, the signature of genes uniquely expressed in $T_{EX}$ comprises SERTADI, XPA, HINT3, HIST1H1C, ZFP69, NR4A3, TNFAIP3, SAP30L, SPRY2, RYBP, TIPARP, YAf2, GCHI, GTF2B, PCGF5, SFMBT1, METTL4, THAP6, EOMES, CPEB2, IRF9, PARP9, STAT1, TLR7, APOBEC1, ISG15, PARP12, STAT2, TFDP2, SETBP1, PARP14, IKZF2, TOX, HSPA1A, SP140, SPAG7, MYCBP, TRAPPC2, TCF4, RBL2, ALS2, IKZF3, IRF7, ELL2, MXD1, IRAK2, MXII, UHRF2, LITAF, NR4A2, NR4A1, ID2, RORA, HIST1H2BC, TBX21, MARVELD2, HIF1A, P2RYT4, P2RY13, EPAS1, IRAK3, XDH, ARAP2, EIF4E3, SWAP70, TRAPPC1, GADD45B, IRF4, HMGB2, ACADL, RBBPB, UBD, ZC3H12C, RILPL2, GNPTAB, PRDM1, CARHSP1, N4BP1, ATOH1, TAF9B, APOBEC2, LRRFIP2, NFIL3, and/or SAP30. In some embodiments, the signature of genes uniquely expressed in $T_{EX}$ comprises A330093E20Rik, Rnfl9a, 2010010A06Rik, Cdh23, Abtb2, Dync2li1, Lrrc1, Sen1b, Man1a, Gimap3, Lef1, Col26a1, Gpr180, Fam126a, Wdyhv1, Mir6395, Gpr34, Fcgr1, Rpia, A430107P09Rik, Hbsll, Slc35b3, Tmem248, Cox7a21, BB019430, Pde5a, Sept7, Lrrc3b, Cd101, Znrf3, Znrf1, Gm6260, Prpf40a, Etsl, Scn3a, Kremenl, Fam2l0a, Trpml, Pip4k2a, Tmpl, Sell, Nfia, Lipa, Zc3hcl, Msgnl, Yeats4, Abcd2, Tbcldl, Kcnh8, Zfp407, Capg, Gm7538, Rgcc, Sh3bp5, Slpr1, Zfp957, Mcur1, D16Ertd472e, Trat1, Fam107b, Mbtps1, Egr3, Palm3, 9030624G23Rik, Ppp6rl, Ckap4, Rngtt, Crtc3, Peak1, Lhx2, Btg1, Serbp1, Cd2, Acoxl, Hormad2, Gm10684, Smo, A630075F10Rik, Ndstl, E030018B13Rik, Skp1a, Kcnh8, Nck2, Frmd7, Cldn10, Peli1, 2010300C02Rik, Insl5, Supt20, Slc4a4, Rph3al, Dip2c, Pm20d2, Nsg2, Rbm26, Tpk1, Stambpll, AF357399, Car2, Mir145b, Zfp592, Galnt4, Gm5083, Thnsl1, Dhx40, Gm20098, Ly6i, Sugt1, Ywhaz, Rad23b, Bcor, Gm12159, Vegfa, Cacna1b, Arhgefl1, 2210408F21Rik, Mettl8, Wdr73, Usp12, Art4, Clvs1, Mir6388, Diap2, Gm10532, Msi2, 4930546C10Rik, Mbnl1, Tm6sfl, Ppp2r5a, Mageb16-ps1, Neurl1b, Sspn, Suv420 h1, 2410088K16Rik, Rgl2, Timm8a2, Aebp2, Maml2, Ldhal6b, Peak1, Parp2, Apbb2, Tetex1d1, Dtnb, Tspan3, 4930578N18Rik, Pced1b, Commd9, Lrrc3b, Rras2, Gm10638, 1600002D24Rik, Arsb, Ube2e2, 1700009P17Rik, P4ha2, Susd1, Cdkal1, Efecl, Malatl, 4931403G20Rik, Tox, Arpc3, Atg10, Gpbpl, Gm5148, A1317395, Abhd2, Celsrl, Tsen2, Pfkfb3, Cycl, Mir378c, Slamf6, Btg1, Phf2, Cxcr4, Gm10789, Atl2, 6030407003Rik, Ggnbpl, Angptl, 9530077C05Rik, Baspl, Rapgef6, H2-Ea-ps, Fam214a, Ppfia4, Lta4h, Ets2, Slc29al, Xpo4, Gramd3, Itfg3, Flil, Frmd6, Rbpl, Olfml3, Peli1, Srpkl, Hmgcsl, Irf2bp2, Cxxc5, Ccdcl71, Cntnap2, Fance, Cblb, Cubn, Sfmbt2, Srsf3, Pepd, Dgkd, Osbpl6, Trib2, Zfand3, Dchsl, 5430421F17Rik, Fpr3, Dapl1, Trat1, 0610040JO1Rik, Gm14005, BC051019, Tank, Tnfsf11, Rara, Pik3c2a, Elmo1, Nck2, Bcl2111, Fam78a, Gm10638, Prkcq, Gpr126, Bach2, Ttc30b, Nlk, Ube2e2, Usp3, 4932441J04Rik, Larp4b, Serbpl, Dbnl, Vav3, Derll, H2-T23, C130021I20Rik, Fbxl14, Etsl, Fgf8, Abl2, Acvrlb, Upklb, Efcabl0, Uchl3, Cd302, Cdc40, Nsg2, Tmem222, P2ry10, Klrb1b, Melr, Car8, BC048403, Taf8, Atplbl, Mir30c-2, Luc712, Erbb4, Arhgdib, Ube2h, Itpr2, Vav3, Ptgfrn, D630010B17Rik, Eif2s3x, Vav3, Nfe213, Ccdc171, Fignll, 4930519F09Rik, 1700123012Rik, Acsf2, Ndufb9, Atp7a, Upp2, Ptpla, Man1a, Rgs3, Zbtb2, Trib2, Npr1, Fez2, Tle4, Fuca1, Cmip, Bcap29, Syne1, Dmbt1, Ell, Blnk, Sepw1, Gltscr1, Erdr1, Medl31, Moxdl, Btg1, Akap6, 1810053B23Rik, Rsul, Gprasp2, Art4, Gpd2, Tmlhe, A430107P09Rik, Kcnj9, Atp8al, Adam6b, 2010109103Rik, Spred2, Raver2, Aplm2, Delrela, Rbp7, Gec1, Traf4, Satb1, Gm5538, 1112a, Fam60a, Thrb, Elk3, Vps45, Tle4, Akapl3, Gprin3, Sox21, Empl, Wfdc5, Slc45al, Lnpep, Rapgef6, Txn2, Frmd4b, Myoz3, Zfp870, Bel6, Mvbl2b, Ntrk3, Spacal, Mir701, Cdca7, Gm5083, Slpr1, Spry4, Cck, Il6st, Hebp2, Slc43a2, Tdrd5, Gm5833, Mir7-2, Mir1931, Pdgfb, 1700052N19Rik, Nfkbiz, Gm20753, Hapln1, Rras2, Diap2, Manba, Cers6, Rasgrpl, Lnpep, Apln, Ephb2, Arpp21, Mical3, Chic2, E130114P18Rik, Ipcefl, Dyrk2, Bach2, Mir122a, B230206H07Rik, Ceacam9, A730046G06Rik, 4930542C21Rik, A430107P09Rik, Tratl, Ccr2, H2-Ob, Adm, Yeats4, Ccnel, Gpc5, Spsbl, Jrkl, Orc4, Camkmt, Nfia, Celf2, Gadd45a, Gtf2al, Nrde2, Nipa2, Rmi2, Lcor, Btg1, Atg10, D6Ertd527e, Ccm2, Dpysl2, Dirc2, Cpm, Arhgapl5, A730043L09Rik, Raphl, Cst10, Slc7al3, Ramp1, Atplbl, Zfpl20, Slc39al3, Zfp706, Agr2, Tagap, Mir3110, Ubash3b, Dnmt3aos, H2-Bl, Agbll, Smc6, 1700060C20Rik, Trib2, A930005H10Rik, Btg1, Scml4, Mirl96b, Efna5, Tmem14a, Kcnj15, Snrpd3, Nnmt, Ryrl, Ptk2, P2rx4, 5830428M24Rik, Commd3, Cd28, Hspbll, BC021785, Tcf7, Cstb, Art4, Tet3, Map3kl3, Camkv, Ralbpl, 9330175M20Rik, Tgtpl, Selt, Irgel, Tcf7, Tet1, Bnip31, Nrbf2, Nim1k, Rfx8, Tlr6, Grikl, Tox, 1700061G19Rik, Dhrs3, 4930519G04Rik, Midl, Aplar, Basp1, Aqp4, 4930415F15Rik, Aifl, Rnfl25, Fam134b, Atpl3a3, Dmbtl, Mbnl1, Nfaml, Lmo4, Znrf1, Ambp, 4930523C07Rik, Bfsp2, Zfp592, Gm2447, Gm16157, Gjd3, Tgtpl, Ston2, Lypd6b, Rnf7, Zbtb2, BC051537, 4930417013Rik, Arntl, Ttc9b, Foxpl, Mir7219, Mrgprb5, Tnik, Dhrsx, Foxpl, Tubb2a, Cyb5r2, Itga4, Snx9, Fam65b, C78339, Mir7212, Ldlrap1, H2-Oa, Snxl2, Tdrp, Mndl-ps, Foxpl, Gucy2c, Crebl, Scn4b, Irf4, Rftn2, Gprl25, Dpfl, Fam134b, Akapl3, Tmem108, Suclgl, Mnl, Sema4b, Gm6682, Slc46a2, Dennd3, Bach2, Sytl², Grhl3, Smad3, 1600014C10Rik, 4930455C13Rik, 3200001D21Rik, Nup153, Grk6, Zfhx3, Fhit, Hmg20b, 4930564D02Rik, Bach2, Slc39a3, Urad, Smela, Mamll, Zadh2, 8030462N17Rik, Fsbp, Tmem243, Srpl4, Lixl, Tmcl, Tspanll, Tnsl, Serpinb5, 1810026B05Rik, Smad7, Mir3108, Phxr4, Tmem131, O1fr1507, Kidins220, Mir378c, Afap1, Rere, Sin3b, Efemp2, Neto2, Mir7669, Tgtpl, Gramd3, Map7d2, Chst2, Sp110, Ccdcl62, Igf1r, Mir3110, Dcdc2b, Dse, Dlgap2, Armc9, E230029C05Rik, Gm11944, Tnik, Kat6b, Nkiras1, Tbcel, B4galtl, Cd2ap, Tnks, Icos, Tanc1, Sik1, Torlaip2, 4930453N24Rik, Bnip1, Gm6313, 4930415F15Rik, Inpp5a, Atoh7, 2210417A02Rik, Pdss2, Lamtor3, Ptbp2, Ostm1, Nrarp, Fryl, Mir1907, Gm10638, Sumol, Zfp60, 1600014C10Rik, Haao, Syde2, Ep300, Ndrg3, Tex2, Cdx2, Eefsec, Tmem131, Mir6959, Fyn, Prkcq, Mical3, Snhg7, Ambral, Rag2, Vdacl, Ptpla, Tram1, Aakl, Pebp4, Sgppl, 2410007B07Rik, Itpr2, Tulp2, Mir6395, Elovl6, Ppplr3b, Zc3 h4, Sptbn4, Rap1b, Vgll4, Kcna2, Cnot6, Tbcldl, Pde4d, Rapgef4, Fbxo47, Procal, Aim, 2310001H17Rik, Tmem131, Sh2d3c, Gtpbp8, 1700030C10Rik, Polr3b, Fam69a, Bean, 4930465M20Rik, Sbpl, Emg1, Aaedl, LOC102633315, 5930430L01Rik, Adsl, Foxp1, Gm20337, Trdmtl, Gm9920, Foxo1, Olfml3, Fyb, Pgpepll, Nsg2, Tex26, Fancc, Cngbl, Rapgef2, 2010010A06Rik, 2410007B07Rik, Lbh, Pnrcl, Lad1, Mycn, Abhdl5, Cdld2, 4930428G15Rik, Hnrnpll, Dnaja2, Ccr7, Mmpl5, Neto2, Bach2os, Efr3a, Rnf41, Mir7656, Znrf3, Rtkn2, Sesn1, Zp3r, Glrpl, Kdm7a, 3200001D21Rik, Pdssl, 5730403107Rik, Mmpl5, Thrb, Zbtbl6, Vkorc1, E330009J07Rik, Dntt, 4933406J10Rik, Sim2, Lgals9, Gm12216, Grb10, Ednra, Fam3c, Birc6, Bacel, Sfrp2, 2010107G12Rik, Zfpl84, Ctso, Zfp462, Abebla, Gm6639, Mir1258, Dyrk1b, Ralb, Thrb, S100a6, Gm590, Dnajcl, Zfand3, Blm, Ikzf2, Lrrc32, Nsg2, Foxpl, Tnpol, Zfat, Speccl, Snora75, Vps45, Acp6, Sydel, Extl3, Fbxl14, Cdh26, Celf2, Cd2, Tshz2, Cntln, Fam65c, Dad1, Akap6, Gm15880, E330011021Rik, Kdfl, Gsttl, 2700046G09Rik, Sortl, Nyap2, 1700063014Rik, Cog6, Extll, Vmn2r96, 1112b, Lelatl, A430107P09Rik, Zkscanl6, Chll, Nck2, Cdyl, St6gall, Mir21c, 2810428I15Rik, Cnr2, Rab44, 1700064J06Rik, Zfpl91, Peli1, Als2cl, Gnas, 2300005B03Rik, BC033916, Cd226, 1700049E22Rik, Nipall, Gimap6, Gm5086, 8430436N08Rik, Ift80, Zfp697, Svsl, 4930459C07Rik, Epcam, Zfp706, Pdella, Slc43al, Slc9a9, Tshz2, Fbxwll, Mir7046, Zpbp, 1700123012Rik, Slcl6al, Gm7457, Tcf4, Fbxl12, I19r, Galnt6, Gm5868, Panxl, Hs3st5, Jarid2, Phxr4, Dock2, Nripl, Laspl, 1700066B19Rik, Marcks, Plekha7, Wdr41, Pdss2, Gpr83, Rapgef4, Gm15910, Colq, O1fr1507, Vgll4, Fgfrlop, Fancl, Capnl, Lonp2, Rnf38, Gpaal, 1700016G22Rik, Vmn2r98, Gm7325, Gm826, Rpl31, Kircl, Ikzf1, Crlf3, Cd44, Gypc, AU019990, Fbxl13, Tsc22d3, Tgm2, Ptpnl4, Fance, Arhgap26, Tgfbr2, Klf2, Sept7, Ptpre, Btn2a2, 4921511I17Rik, Ppp2r5a, C78339, Arhgap39, Ism1, Mpzl2, 2810459M11Rik, Dyrk2, Tspanl3, Fbxl14, Plat, Celf5, Susd3, Rps6ka2, Gtf2irdl, Naifl, Rsph3a, Tssel, Ext1, Snora7a, Bel2111, Pip4k2a, Npl, Tmem236, Cox7a21, A530013C23Rik, Rgll, Pgkl, 1ft80, Emidl, Inpp4b, Cldn10, Gis, Tnnil, Folr4, Gm5766, O1fr1507, Hpcall, Cyth4, St8sia6, 5430434115Rik, Ropnll, Serincl, Mad2ll, 4921525009Rik, A430107P09Rik, Gm11127, Tra2a, Urb2, Pgpepll, Cacnald, 5730403I07Rik, Fam49a, 1700025F24Rik, Stat1, Calm1, Kcna7, Eifl, Mir669m-2, Kdr, 1700123012Rik, Mir8099-2, Hspa8, 2010010A06Rik, Zfp53, 4930524005Rik, Abl1, Uvrag, Slcl6al, Dnah7b, Golph3, Ipcefl, Usp3, Jun, Snord89, Tcf7, Rbpms, Folr4, Papss2, Spred2, Stpgl, Mgat5, Lpinl, D8Ertd82e, Dhx40, Slit3, 4933405E24Rik, Nsun6, A430107P09Rik, Apol7e, Raly, Celf2, Ndufs7, Mir6921, Kbtbdl1, Gc, Haao, Gm9054, Slc44a3, Tnfrsfl9, Lefl, Ankrd11, Plxdc1, A430107P09Rik, Zcchc2, Zmat4, Jun, Adamtsl4, Slamf6, Adamts17, A430107P09Rik, Alox5ap, Mir6368, Ncor2, Ets1, Pmpcb, Mvk, 4922502D21Rik, 1700025G04Rik, Rgmb, Gpnmb, Stkl7b, Ceacam9, Ttcl, E130006DO1Rik, Camkmt, Ankrd63, Agtrlb, Khdrbsl, Zfp706, Cux1, 4922502D21Rik, Btbdl, Timm8a2, Itga4, Reep2, Uvrag, Cyfip2, Elovl6, Tfeb, Spag16, Tbcel, Lmo2, Rasgrpl, Fam86, Ktn1, Fbxo32, Gata3, Ly86, Ptgs2os2, Famllla, Lrrcl6a, B430306N03Rik, Tff3, Kcnn4, Mtif3, Ldlrapl, Tmem260, Pla2rl, Baspl, Ncoa3, Nglyl, Ccdcl62, Nhsl2, Cdc123, Hnrnpu, Arhgapl8, Zfl2, Gm6498, Bex6, B630005N14Rik, Dynltlb, Lypd6b, Clec2e, Rbml7, Pstpipl, Lrp12, Akap2, Camk2d, Igflr, Atplal, Gsn, Rragd, Actn1, Odf3b, Nudt4, Vmn2r99, Parp11, Adipoq, Fam221a, Il6ra, Kif23, Fabp5, Srpk2, Ikzfl, Fbxw7, Slamf9, St6gall, Vav1, Serbpl, Reepl, Agr3, Plcl2, Kcnj15, Aebp2, Gm20139, Mtx2, Selll, Mbnl2, A430078G23Rik, Krrl, Lelatl, Zfp438, 4930487H11Rik, B4galtl, Ifngr2, Olfr221, Asb4, Gm6793, Aplml, Pdlim5, Gltscrl, 1110032F04Rik, Ankrdl3a, Abcd2, Iqsecl, Inpp5a, Pdzrn3, Akirin2, Pip4k2a, Dyrk2, Jun, 4930465M20Rik, Osbpl9, Ttc30al, Ctnnbll, Tmem243, Olig3, Ubtd2, 4930540M03Rik, Dnajc5b, Denndla, Gadd45a, Rpl8, Dapll, Cd2ap, 6430710C18Rik, Slc16a5, Rcbtb2, Hmgxb3, A630075F10Rik, Ankrd2, St8sial, Ptk2b, Paqr8, Tox, Wdr37, Stat4, Rplpl, Ccnj, Hspbpl, Mthfdll, Zcchc9, Gm13293, Camk4, Htt, Usp10, Plekha6, Gm5617, Cnksr3, Mir7218, Lcp2, Cd28, Lbp, Ncoa3, Skil, Heyl, Mir6368, Akap6, Spin1, Ccdcl74, Stambpll, Ggtal, Pifo, Stim2, Rras2, Tomm201, Gm5538, Skap2, H2-Ob, Zfp3612, Clec2d, Erdrl, Dapll, Vasp, Cytip, B4galnt3, Hamp, Mex3b, Tcf712, Vpsl3d, Alox5ap, Mtss1, Gm7457, Fam46a, Taf3, 2810408I11Rik, Ms4a7, Mad2ll, Selt, Snrpf, Hcn2, Frmd4b, Hivep1, Tspan13, Nfia, Asap1, Nt5e, Misp, Maml2, Sh3pxd2a, Ccdcl62, Setd7, Etohil, Acvrl1, Fntb, Shank3, Rhoh, Prok2, Marcks, A830010M20Rik, Ywhaz, Mtss1, Gm8369, Fam188b, Atp2a2, 4933405E24Rik, 4932443I19Rik, Notch2, Zc3h12b, Numb, Neb, Ramp1, Zfp831, Impdh2, Grkl, 4930459C07Rik, Mir7035, Setd3, Cdc42se2, Spoll, Faml66b, Mir6419, Atp10d, C2cd5, 4933412E24Rik, Boll, Calr4, 1122ra2, Slc22a16, Syde2, Fyn, Slc27a6, Stx3, Gm6313, Rbml8, Gm13293, Tbcld8, Fabp5, 4930546C10Rik, Slcl6al, Cnr2, Kcnip2, Trim69, Agbll, Plvap, Ms4a6c, Usp38, Atl2, Sh3kbpl, Ppfibp2, Piml, Pmis2, Sh3pxd2a, Ms4a4c, Klf3, Cblb, Mir701, Dmwd, Mtssl, Cdkl3, Cabp2, Chdh, Pde4b, Ston2, Cmah, Fbxl14, Syk, Trio, Btg1, Ski, Cnot2, Stk38, Tm9sf3, 4930482G09Rik, Parpll, Jarid2, Maml3, 6430710C18Rik, Commd9, Fhit, Scampl, Tcf7, Ncfl, Ric8b, Gm3716, Scml2, Nr2f2, Ssrl, Il6st, Ankrd50, Pnmal2, Foxpl, Raver2, Ccdc64, 8430436N08Rik, Klfl3, Itga5, Commd3, Mro, Ms4a7, Rock2, Encl, Rab3gapl, Nav2, Tlr, Gm7457, Elfnl, Rp134, Agfgl, 1700020NO1Rik, Irf4, Gm8369, O1fr1507, Grik4, Akap6, Mir6387, Thrb, Gm20110, Mir7670, Bag4, Gm15441, LOC101055769, Pakl, Mbd2, Ralgps2, Lipg, Gpnmb, Ubash3b, Kntc1, Aqp9, Znrf2, Cmah, Peli1, Chd7, Tmsb4x, Copbl, Gimapl, Bcaslos2, Ppapdclb, Cdcl4a, Ier5, Susd3, Birc2, Sun2, Itga5, Rlbpl, St8sial, Hectdl, Chn2, Bcaslos2, Slc39all, Cdc7, Me3, Stkl7b, Ccr4, Peli1, Cd226, 2510009E07Rik, Sh2dla, Zfp2, Mei4, Chst2, Nipall, Tbcel, Itgb6, Tmed10, Gm4489, Tmccl, A430107P09Rik, Abtb2, Tgfbr3, Zfp704, Reep5, Apeddl, Pik3rl, Msl2, Gm20098, Eif4e3, 5430402013Rik, Tsscl, Lphn2, Kcnh8, 4921525009Rik, Fam46c, Pum2, Itsn2, Slclla2, Usp6nl, Gimap6, A430107P09Rik, Nipbl, Nrxn3, 1700042010Rik, Capn3, 4930526115Rik, Plat, Gm15850, Dock10, Shisa2, Wbscrl6, Egfl7, Zfp957, Gm20110, Slc4a8, Ago2, Pnp2, Tgfbr3, Hmga2, Pdlim7, Dip2c, AtpIbl, Pxk, Snora26, Gm6498, Sema3d, 3300002108Rik, 9330175E14Rik, BB123696, Fibedl, Slc6al9, S100a6, Commd9, Lpar4, Cntn5, Nrli2, Panxl, Dock2, Ptov1, 5330411J11Rik, Sec24d, Ms4a4b, Eif3g, Rsbnll, Plxncl, Jarid2, 1810041L15Rik, Diap2, A630075F10Rik, Klfl3, Tlk1, Lef1, Slc4a4, 2610020H08Rik, Tbce, 9430014N10Rik, Slcl6a10, 2310042E22Rik, Lrrc3b, St6gall, Tnfrsfla, U90926, Fam134b, Grxcr2, Dok5, Aldh8al, Cybrd1, Smarcb1, Jmy, Zfp608, Cdkn2aipnl, Aire, Prps2, Gm839, 4933412E24Rik, St6gall, Ube2d2b, Mab2111, Slc23a2, Keap1, Brdt, Piwil2, A930005H10Rik, Fyb, Neald, Lgals9, Zfp704, Dguok, Gm15706, Nr3cl, Med13, Rictor, Paxbp1, Mir1903, Sv2a, Slx1b, Tbcld24, Wnt5b, Ccr7, Ptk2, Mir21c, Aox4, Slc35b4, Mgat5, Zfp281, Mycn, 1700016G22Rik, Odcl, Prkcb, Atel, Ncbpl, 3300002I08Rik, Ly6d, Spag16, Clkl, Atg10, 1700030L20Rik, Nsg2, Agps, Goltla, Cntn5, Cadm4, Malsul, Frmd4b, Gm6607, Cdh23, Gramd4, Slc44a2, Limd2, Lphn2, 1700010K23Rik, Lrrc66, Akap7, Peal5b, D030024E09Rik, Zscanl0, Lsm2, Kcnj13, Cdhr3, Fbxl17, Lhx2, Olfm2, Cyp2rl, Wisp3, BB123696, Nlrc4, 2010010A06Rik, Elovl6, Eeal, Mir1907, Gls, B4galnt3, Epb4.1, Tshzl, Gpr126, Rgmb, Ncs1, Tet1, Hoxal, 4930515G16Rik, Usp33, Stkl0, Klhl6, Ccdcl09b, Manba, Gm5111, Chstl5, Runxl, Rgs3, Gm4759, Ldlrad4, 4933400F21Rik, 4933406C10Rik, Diap2, Mir6403, Plin2, Zmizl, Maml3, Fam86, Hbsll, Inpp4b, Gm14405, Mgat5, Cntn5, Ramp3, Ifnk, Pgml, Mfsd6, Armcx1, Mir5127, Gimap6, Mir6387, Slc38a2, Gsdmcl-ps, Cd24a, Kmt2e, Csrp1, 9530052E02Rik, Stkl7b, Fyb, Lhfpl5, Atp8a2, Amn1, Sertad2, Epb4.112, Stk24, Cdkl7, Camk4, Rpa1, Zmyndl1, Efcabl1, Mir491, Zc3hcl, Vps45, Rgs3, Ube2m, Tspan5, Insr, Snapel, Btg1, Cox10, Znrf1, Camk4, Ddrl, Gm11981, Sesn1, Commd8, Nripl, Polr3k, Eya3, Ppplrlb, Pcdh7, A430107P09Rik, Efecl, Mtssl, Hpn, Armcx1, Gm20139, Algl4, Secl1a, Cyb5d1, Trpm1, Fam65b, 5730508B09Rik, Frmd4b, Gm10584, Gm5069, Pmepa1, Sell, Mir6413, Klfl2, Rhoq, Plcl2, Prrc1, Empl, D030024E09Rik, Rnfl45, Bach2, Prkcq, Hic1, Msmol, Map3k7cl, AI854517, 4922502D21Rik, Vtila, Zcchc9, Spats2, Mir7681, Wdr89, Bel6, Cytip, Gm13293, Creb314, Peli1, Pakl, Efcabl1, Usp7, 4931403G20Rik, 1700030A11Rik, Mvbl2b, Ampd3, Cubn, Baiap3, Med30, Actbl2, Kat6b, Peli1, Tmevpgl, Nsf, Hpcall, Ube4b, Faml10b, C330011F03Rik, Inadl, Sesn3, Tmem30c, Itgb6, Dlgl, Srpl4, 3300005DO1Rik, Ggact, Mir21c, Cyp2sl, Mir7061, Bachl, Insr, 2410114N07Rik, H2-Ebl, Taspl, Tusc3, Irf2bp2, 1700056E22Rik, Ppp6c, Slain2, Cnn3, 6030407003Rik, Acbd6, Hmgbl, P2rx4, Cdkl9, 1700061G19Rik, Tesk2, Plxncl, Ercc3, 2010010A06Rik, Stkl7b, Tspan9, Kcnj16, Ddx10, Wnt16, Sp4, Hilpda, Slc38a6, Tgfbr2, Fggy, Suget, Begain, Mndl-ps, Ksr2, Eif2d, Ms4a4d, Stim1, Cst10, Nfatc1, Ppifos, Gng7, Mir211, Txk, 4930415F15Rik, Tmem64, Stim1, Pip5klb, Kcnj15, Commd8, Mir3108, Atpl1b, Stkl7b, Emc3, Cldn10, Akap13, Abebla, Mthfdll, Foxkl, Rgs3, Gdnf, Micul, I17r, Arhgap35, O1fr1364, Ms4a4b, Rgs10, Flt3, Sfrp2, I19r, Sfl, Gm1604b, Galnt4, Dtnb, Supt20, Fntb, Zmyndl1, Tulp3, 2410007B07Rik, Tsenl5, Abhd2, Dgcr6, Filipl1, Ift81, 4933401D09Rik, Gtdel, Ano6, Mir1928, Peli1, Jakl, Cdkl9, Synel, I123r, Tpm2, Fam65b, Kidins220, Vavl, 9030617003Rik, C1l3, Ceacam9, Ehd2, Vten1, Dusp7, Pik3ipl, Ostml, Ppard, 01fr372, Mir7032, Npy, Phxr4, Grap2, Thrb, Wipil, Dock4, Mfsd6, Zmynd8, Mylip, Setx, Ccdcl46, 1112a, Sall3, Mir7048, Haplnl, Casp3, Bbs9, Synel, Tdrd3, 4930565D16Rik, Gm20098, Tcf4, Haao, Sndl, Zfp706, Agfgl, Gm8709, Synel, 4933406J10Rik, Pik3c2b, Manba, O1fr1033, Aurkb, 9330175E14Rik, Foxo1, Sfmbt2, Bach2, Pogz, 4930459C07Rik, Phxr4, Map7d2, Gm20750, I112b, Sesn3, Psen2, Suco, Mad2ll, E030030I06Rik, Gadd45a, Abcal, Boll, 4930430F21Rik, Cstad, Lyst, Rasgrp4, 4833427F10Rik, Ehd2, 4930445N18Rik, Ppmlh, Gltscrl, Irf8, Lgil, Gm10432, H2-M10.1, Crtc3, 4930453N24Rik, Irs2, 1700042010Rik, Rabgapll, Rnfl44a, Csk, Rpia, A430090L17Rik, Mir8097, Serbpl, Mir684-1, Tcf4, Commd8, Tet3, Nrli2, Gm10190, Prkcq, Orai2, Dpy30, Sbk2, Tsscl, Cd5, Sipall2, Depla, 1810006J02Rik, Itgae, D030025E07Rik, Wibg, Bach2, Irf4, Ctnndl, Usp7, Rftn1, Themis, 4930440I19Rik, Thrb, Nrld2, Tgtpl, Ccdcl62, Atp8b2, Speer4f, Stra8, Gm4906, Fam46c, Pagl, Etv3, Erdrl, Dhrsx, Fam65b, Gosrl, Trem2, Fblnl, Sp3, Mef2a, Beor, Map4k4, Magi2, Pak2, Rph3al, Lgi4, Pja2, Tceal3, Efcabl1, Arhgap5, Extl, Smyd3, Prim2, Satb1, Stag2, Themis2, Piml, Apol8, Lrrc6, Shb, Magi2, Commd8, Zfp879, Trp53111, Rgll, Abcd3, Diap2, Zbtb2, C030016D13Rik, Arhgdib, A630075F10Rik, C730036E19Rik, Phc2, Adamtsl0, Inpp4b, Cd200, Itpr2, Fgfrl, Gm5434, Scn2b, D8Ertd82e, Gm2a, Ube2vl, Bend4, Lpp, Mir181a-2, Gm13293, P2ryl, Klf7, E030018B13Rik, Rhobtb2, Ddrl, Ggnbpl, Gimap7, Mamstr, Cmip, Setbp1, Fcgr4, Slcla3, Zfp608, 2810403A07Rik, Gm7538, Mir378a, Hoxal3, 2610301B20Rik, Nglyl, Sergef, Tpp2, Slc35b3, Maml3, Navl, Txk, Fam195a, Scml4, T1r12, Gpr125, Zfp3612, Suclg2, Tec, Akap2, Rab38, C030018K13Rik, 4933433H22Rik, Osbpl11, Capn13, Ankrd50, Mir1928, Mir3108, S1c39a10, Dock2, Dip2c, Aebp2, A530046M15Rik, Gm6251, Mtx2, Exoc4, Olig3, Dph6, Emb, Xpc, Gm7538, Tnfsf8, Afap112, Cenpv, Gsn, Rbms2, E2f3, Smarcel, Foxpl, S1c37a3, Apbblip, Tex10, Bend4, Pcgf5, Trio, Klf5, Gja8, E130006D01Rik, Ncor2, Acbd6, Alg14, Scmhl, D830013020Rik, Galnt4, Ndufa6, Timm8a2, 2210010C04Rik, 4931403E22Rik, Gys2, G630090E17Rik, Dapll, Nup160, Fxyd7, Zscanl8, Bid, Serhl, Cdkl7, Lrtm2, 3930402G23Rik, Tm2d1, Snora7a, C8g, Nkap, 2410007B07Rik, Il1f3, Mir7017, Gpr83, Thada, Ambral, Fance, B3galt4, Thnsl1, Etv5, Aox2, Tgm2, Man1a, Edeml, Hnrnph1, Atp6v0e2, Clec4f, Heyl, Fam3c, Stat4, Slc46al, Rps15a-ps6, Kdm4c, Upbl, Sikl, Ncehl, Prkcq, Btg1, Galnt2, 2010010A06Rik, Neu3, Cubn, Mir1928, Rapgef2, Nedd41, Egfl7, B3gnt2, Tgtp2, Gm13546, Ext1, Pold4, Ggact, B3gnt7, Gm5868, Tlr7, Lefty2, Npff, Tcf712, D130058E03, Pagl, 4930578N18Rik, 6430710C18Rik, Fam43a, Snora8l, Cyp20al, 4922502D21Rik, Lsm1, Gm10791, Kcnh2, 1700109K24Rik, Nol6, 4922502D21Rik, Trib2, Nrfl, Rgag4, 4930426L09Rik, Ppil3, Vmn2r96, Nglyl, 1810046K07Rik, Hid1, O1fr1510, Nripl, Dhtkdl, Ms4a6b, 4930583K01Rik, Atp1b3, Mir7046, St8sial, Pcdh7, Micalcl, D030024E09Rik, Pold4, Coro2b, Adamtsl4, Auh, Fus, Helsl, Prkcq, Nimlk, Zdhhcl4, Kcnh2, Cd37, Ttc27, Olfm2, Ubac2, Mir6387, Zfp619, Zbtb9, Gpr125, Ppp2r5a, Adgb, Pard3, Ctrl, Ddr1, Ckmt2, Lpar6, Sspn, Gm4792, 9430008C03Rik, Nglyl, Tbx19, Heatr1, Cdc14a, Nabpl, 8430436N08Rik, Cd247, Llph, Pex10, Eeal, Lef1, Ly75, Dockl1, Haao, Rgs3, Mndl-ps, Mamll, Stxbpl, Parpl1, G530011006Rik, Mgrn1, Ift57, Mef2a, AI427809, Ldhb, Cdkl9, Lrrc3b, Osm, Dnajcl5, Mirlet7i, Stk38, Cep170, Rcn3, Gramdla, Mfng, Vgll4, 1700017N19Rik, Atpla3, Ptpla, Mir6962, Jun, Cdkl9, Gm10638, Zfp3612, S1c39a10, Tpd52, Mthfdll, Agbll, 4922502D21Rik, Ceacam2, Drosha, Fut8, Cox10, Dnajbl2, Thns12, Eefsec, Pgpepll, 4932441J04Rik, Fndc7, Clip1, 2700046G09Rik, Itpkb, Kremenl, Mpp6, Ccr9, Tbcb, Rictor, Gm3716, Icosl, Cpeb4, Mir7681, Kmt2c, Mak16, Glil, Actl9, Gpatch2, Sept14, Aebp2, Phlppi, Zfp957, Ap3m2, Zcchc2, C030018K13Rik, Cdkl7, Tmem217, Cog6, Dock2, 117r, Crybb2, Slc16a10, Ppp1rlb, E430016F16Rik, Fbxol7, Akrldl, D10Jhu81e, Irgel, Klf7, Pcdh7, Nipbl, Rm3, Mir7681, Arhgef33, Rhoq, Dusp5, Itga4, Palm2, Map10, Tigd2, Mfge8, Zfp580, Peli1, Trim59, F730035M05Rik, Gpr110, Lyst, Slc10a4, C230029M16, Gpnmb, Rgs3, Rab3ip, Vps54, Cox7a21, Slc7a15, Serbp1, Slc22a16, Prkch, 4933433H22Rik, Arap2, Mkll, Slc22a16, Flil, Stk24, Stard8, Arhgap29, Pcca, Treml2, Tssc1, Pgpepll, Syde2, A430107P09Rik, Foxo1, 8430436N08Rik, D030024E09Rik, Tcf7, Ifitm6, Ctso, Capzb, Lypd3, Lix1, Ccdcl70, Taspl, Dnah7a, Sugt1, Pde7a, Pcnp, Klf5, Olfr1357, Ldhal6b, Kctdl2b, Cxxc5, Pkn2, Mboat2, Angpt1, N6amt2, Gm839, Bach1, Il2ra, Ankrd12, Ccdc64, Pptc7, Ikzf2, Svil, Tlr, Relll, Tmal6, Mbnl1, Cyfip2, Rps6ka2, Elovl6, Dapll, Zfand3, Unc5cl, Zfp619, Sytl³, BC031361, Fam26e, Gm2799, Chst15, LOC101055769, Sepp1, a, Ccdc171, Hemgn, Pik3c3, Lrp12, Capnll, Pvr, Prkcq, 4932702P03Rik, 2300002M23Rik, Tef, Foxpl, Lypd6b, 4933412E24Rik, Wnt4, Marco, Elfn2, Smim9, Dip2b, March2, Frs2, O1fr1507, Mir7219, Fbxl22, Vim, 4933432G23Rik, L3mbtll, Madlll, Calr4, Lrrc3b, Strada, Mir363, Tspan9, Esrpl, Panxl, Tgfbr2, Emb, Spata3, Ext1, Calm2, AY512915, C530008M17Rik, Mitf, Wdr11, Mir5127, Selt, Gm6623, Gm684, Gm3716, Tgtp2, Sptb, Hamp2, Itgb6, Cd2ap, Prnp, Ift80, Slamf6, Pou2afl, Snx29, G530011006Rik, Wipf2, Fam134b, 4930428G15Rik, Iglll, Phxr4, Sgms2, Gm12159, Igf2bp3, Haao, Bai2, Sh3pxd2a, Scn4b, Eif4e3, Snx29, Tmem194b, Ifngr2, Gm5766, Zcchc24, Sox5os3, Efna5, *Tecta*, Mir7687, Mir6367, Itga4, Tns4, Ccm2, Wipfl, Cerk, Znrfl, Elovl5, Phtf2, 1300002E11Rik, 2210417A02Rik, Mir7061, Grhpr, Mark4, 4930564C03Rik, Svopl, Pja2, Tfdp2, Rbm11, Usp6nl, Mir6368, A430107P09Rik, Bel2, Cdc42se2, 4933433H22Rik, Apol8, Xpnpep2, Dach2, Mir205, Stard5, Fsbp, Rph3al, Vav3, Gm10125, Lpcatl, Cd2ap, Bank1, Smurf1, Aox2, C230029M16, Sgmsl, Eci3, Xpnpep2, Pfkfb2, Utm, Ldlrad3, Gabrrl, Kcna2, Ywhaz, Stard13, Atp10a, Slc39a10, Whsc1ll, Gm12522, Trio, Manlcl, Hmhal, Gm10791, Kidins220, Lad1, Mir1928, Gm13710, Mir1963, *Lama*4, Pard3, Susd3, Taok3, Skor2, Matn2, Tet2, Mir7674, Ccdc64b, Fam49b, 4933412E24Rik, Thsdl, Sall3, Papss2, Tceal3, Rrebl, Klrdl, Rgs3, Cst10, Itga4, Gm20098, Smarca4, Cyp2d22, Kdm6b, Cntn5, Dyrk2, Dusp10, Srpk2, Etv5, Slc25a25, Cfl2, Micul, Ets1, Gm6559, Zfr, Mrpl52, Cerk, D630010B17Rik, Extl, Cblb, Gnai2, Apol7e, Manba, Dusp10, Smim8, Mir6907, Pard3, Tmem35, Ric8b, Gm14124, Pik3rl, Gm11981, Dip2c, Plin2, Fam228a, Tlrn, Lypd6b, Zc3h12b, Abegl, Ext1, Camk2g, Ptgr2, Mndl-ps, Rftn1, Sox8, Sdc3, Mab2113, Arid1b, Tdrp, 4921525009Rik, Arid4b, Micu2, Ly86, Afp, Grap2, Ist1, Sh2d4b, Rad52, Mir1668, Rpgripll, Gramdla, Sgkl, Fos, Smad4, Hdac4, B3gnt3, Nr4a3, St8sial, Psg-ps1, Actl9, Pdkl, Il2ra, Irf2, Fasl, Hsdll, Galnt5, Itk, Maml2, Erdrl, Ndufa6, Tbc1d23, Slc43a2, Iqgapl, Klf7, Bend5, Klf4, Lif, Calr4, Cnst, Ifnk, G3bp2, Tbc1d2, C030034L19Rik, Zfhx3, Bellla, Retnlb, Ap3 ml, Hlcs, Serpinfl, Gm16390, Wdr37, St8sial, Cenpu, Gm10638, Tfpi, Fabp7, Wisp3, Psmal, Tet2, AI854703, Lmo4, Ppplrlb, Mgat5, Foxp1, Gm3716, Mir6349, Tle4, Itgb8, Rabllfip4, Tbcel, Npepps, 1300002E11Rik, Celf2, 4933412E24Rik, 4930415F15Rik, Olfr1507, Itgb3, Bacel, 2010015L04Rik, Mir7656, Esrpl, Spred2, Myol0, A930001A20Rik, BC048403, Lincpint, Mturn, Shisa2, Mef2d, Rac2, Dusp6, Lefl, Tmem64, Lrigl, Atp6vlgl, 1700017N19Rik, Dfna5, Zfp286, Gimap9, Gbel, Cdc37, Pard6g, Serp2, Pid1, 4930465M20Rik, P2rx4, Opa-lin, Mir684-1, Nglyl, Ndufa4, Mirl6-2, Trib2, Slc17a9, Itpripll, Uril, Rnf32, Prlr, Lyrm7, Fblnl, Nenf, Atl2, Slfnl, Supt20, Ski, Pno1, Foxol, Olig3, 5330411J11Rik, Eci3, Clic4, Naa30, Abcal, Mppl, Adcy6, Ptpre, Fbxo27, Ahcyl2, 1700016K19Rik, Gm14405, Drosha, Lrrc1, Mir7014, Cdkl9, Ldlrapl, Pgpepll, Fgl2, Nck2, Acvr2a, Myol0, Cblb, Gm590, Kcnq5, Col6al, 4930480M12Rik, Rad23b, Tram2, Pygol, Mir6368, A430107P09Rik, Afap1, Pip4k2a, Slc46a2, Mgat5, Slc27a6, Ntper, Cuedel, Ramp1, Enthdl, Mir6374, Stmnl-rsl, Gm684, Fblnl, Lef1, Chd7, Ppplr3fos, Abil, Plau, Aifll, Tesc, Edem3, Tbcel, Prdm5, Lnpep, Dyrk2, Gm6260, 4930428G15Rik, Carnsl, 8430436N08Rik, Plekha5, Hexim2, Ccr7, Foxp1, Satb1, Rpgripl, Dnm3os, Retnlb, Tram1, Tmppe, Car12, Snordl4c, Ets1, Crtc3, Kcnh8, Heyl, Slc44a2, Dip2c, Ankrd44, C230029M16, Nwdl, Mrps11, Cpb1, 4930567H12Rik, Mir378c, Dnaja2, Fnbpll, Tab3, Zap70, Cenpk, Bcar3, Usp6nl, Ppp4r2, Has1, Tbc1d22a, Dync2li1, BC055111, Sepwl, Apls3, Ass1, Metml, Rsph3a, Dpysl2, Rapgef6, Cxcr4, Mir8095, Sgsm3, Actn1, Grb10, Slprl, Rasgrpl, Dnajc6, Agfgl, Map3kl5, 4930465M20Rik, Csnklg3, Trpv5, Klf3, Zfp3612, Mir181a-1, Slc30a9, Taf3, Em12, Tsscl, 1190002N15Rik, Cdh26, Savl, Ghsr, Msra, Fam134b, Tusc3, Itpkb, Dtwd2, Frmd7, Gm20750, 4933440M02Rik, St8sial, Mir8105, Mir7681, Sntgl, Hipk2, Cd8b1, Stk24, Zmat4, Pnoc, Creb1, Trps1, Gis, Gm15706, Ubtd2, Kif1b, Pex3, Ect21, 4732490B19Rik, Calm2, Syne1, Ap1b1, Ldha, Mmp15, Tnks, Gm20098, Spred2, Igf2bp3, Atpla3, Pdzm3, Qserl, Ppm1l, D930032P07Rik, Vmn2r98, G530011006Rik, Ikzf1, D630010B17Rik, Mettl8, Gm590, Enthdl, Ccdc152, Ywhaq, Atp8a2, Thra, Ildr1, Rpap3, Ltb, Rev31, Med131, Dner, Ralgps2, 4930428G15Rik, Dnajc1, Arhgap6, Faml01b, Nfaml, Ccr7, Psma6, Gm1631, Hadh, 3425401B19Rik, Irf4, Zak, Brdt, Fam71f2, Slc25a12, Ippk, Fnbpll, Rps16, 4930540M03Rik, Cd5, Ube2el, A430107P09Rik, Rapgef4, O1fr1507, Rmdn2, Lhfp, Mir1893, Lgals3, Gnl31, Whscll1, Sh2dla, BC061194, Mbnl2, Zbtb38, Golph3, 4930430F21Rik, H2-Q1, Ntrk3, Ninj2, Cd3e, Stat5b, Lbx1, 4933412E24Rik, Pten, Gm2447, Mtx2, Tmcc3, Lin28a, Cyb5a, Znrf1, Fancc, 1500015010Rik, Plekhol, Prss32, Gjd2, Gphb5, Ccr7, 4931403G20Rik, Mboatl, Dyrk2, I19r, Sos1, Etv2, Txnip, Faml10b, Rph3al, Mboat4, Plekhh2, Irf6, Thoc7, Yeats4, A430107P09Rik, Ms4a7, 4930567H12Rik, Zfp930, Zap70, Uaca, Nsg2, Myol0, Ctfl, AU015836, Mir7681, 9830132P13Rik, 1700021F07Rik, Ipo4, Icosl, Smad5, Cyp26b1, Mgarp, A430078G23Rik, Kdm6a, I730028E13Rik, Hs2stl, Tox, Akrld1, 1810010D01Rik, Rp134, Ramp1, Helsl, Rab3ip, 4930445N18Rik, Extl3, Sox4, Gjd3, Gm14305, 1700061F12Rik, Lnpep, Wnt5b, Mark4, Stmndl, O1fr1507, A430107P09Rik, Commd8, AI427809, Mir6979, Cdc42se2, Gpr125, Tcf25, Taf8, Lelatl, Wdr89, Ptk2b, Pitpnb, Ttf2, St6gall, Maml2, Lrch3, 5430427M07Rik, Bachl, Exoc4, Mef2d, Vps37b, Wdr37, Ccr7, Fam221a, Mif, Vmnlrl57, Mpp6, Chd2, Sept6, She, Prg4, Snord83b, Gm7616, 2410114N07Rik, Wdr37, Gdpd4, Vdacl, Mir5104, Rsrcl, 4930523C07Rik, Akap2, Lyst, G6pc2, Klhl4, Slc35b4, Setbp1, Akap2, 1700072005Rik, Gm1604b, Kcnal0, Stambpll, Npas2, Dnajcl, Ddx25, 4933433H22Rik, Plcg2, 4930562F07Rik, Armc4, Foxo1, Samd91, Gm16157, Gpnmb, Tmem141, Mir6413, Gabbr2, Fgf8, Prdm2, Ikzf3, Diexf, Ccdc8, Esd, Macrodl, Tm2d1, 4930572013Rik, A130077B15Rik, Lck, Kdm2a, Rbbp8, Cd47, Gm6578, Klf2, Zfp536, Ube2e3, Aff3, Man1a, 4930413G21Rik, Crtam, Rpa1, Kcnh3, 2900008C10Rik, Tbc1d31, Snn, Malatl, Bambi-ps1, Wisp3, Mrgprb5, Gehl, Nabpl, Mettl9, Zfp3612, Mir7669, 4933401H06Rik, Prkrir, Erdrl, O1fr630, Tmem168, Gbp11, Mbnl1, Plin2, Scn2b, Car8, Nglyl, Kcna2, Dpp6, BC027231, Gosrl, 1700016L21Rik, Ccdc170, Manba, Osbpl9, Purb, Rftn2, Klf3, Cdca71, Supt71, Rgs3, Rbpms, Mir6349, 5830418P13Rik, Pkn2, Baspl, Btg2, Ifnk, 5730403107Rik, Srsfl, Kif3a, Fbxo27, Gipr, Colq, 4930540M03Rik, Pard6g, Bellla, Ezhl, Cd2, Foxql, Rybp, Pgapl, Usp10, Sh3bp5, Pmp22, Sdc3, Rnf145, Ankrd44, Tacc2, Sh3bp4, 4930465M20Rik, Slc19a3, Gm10791, Map4k4, Bhmt, Gm10190, Zdhhcl8, Mroh2b, Gpr3, Tgfbr2, Reck, Atxn713b, Nglyl, I112rbl, Gucy2c, Gpr83, 1700025G04Rik, Arap1, Chrm3, 8430436N08Rik, Postn, Lonp2, Ly6d, Zfp516, Fam102b, Psap, Rere, Fam217a, Cox4il, Slc7al, C9, Mir6374, Mdml, 2310043L19Rik, Fbxl17, Gm5468, Panxl, Set, Racgap1, Ppmlb, Samd12, E330009J07Rik, Cd101, Zcchc2, Gadll, Rapgef6, Steap3, Fgfrlop, Setd7, 3110056K07Rik, Gm5538, Ino80e, St6gall, Nsmcel, Ccdc64, Cxcr4, Gata3, Cerk, Chst15, Mir3089, Map4k4, Akap13, Slc30a9, Gm10790, Npffrl, Tdrp, Gm20098, Ddhd2, St8sia6, Lhx2, Syt[6], Dtl, Themis, Maml2, Sh3bgrl2, Sptbn1, Fam207a, Lmna, Nfatc2, Gm12185, Arhgap6, Atg14, Macrod2, Mir3110, Fam46c, Wdr63, Ppp2rlb, Prdm9, Lphn2, Mir574, I19, Elovl6, Chd7, Pitpna, Atoh7, Mc2r, Celf2, Tdrd3, Rassf2, Gm10640, Ncoa3, Lyst, Fyb, Gm2447, Aplar, Stag2, Foxpl, Rock2, Pdlim1, Bin1, Gm10125, Bach2, Fbxl22, 2900005J15Rik, Rgs2, Cldn10, Lrrc8d, Rad23b, Supt20, Dgkd, Atn1, Agtrla, Pias2, Gm10791, Tmem60, Prkag2, P4ha2, Tratl, March5, Tcf7, Wbscr27, Gm6498, Histlh2bn, Zfp120, Trubl, Mir1936, Ms4a7, Nfatc4, Lrrn3, Tratl, Sox4, Nhsll, Lincenc1, Tmem243, St6gall, Dpysl2, Cntln, I17r, Olfr9, Erbb2ip, Rpl101, Mir211, Srbdl, Lphn2, Fam3c, Sorcs2, Thrb, Katnall, Mirl99a-1, Fbxo32, Rpap3, Arfip1, Rpl19, Itm2a, Trim56, Ier51, Btg1, Plekhbl, Rp134, Pik3rl, Mir6349, Ikbkb, Cntn5, Sh3kbpl, Btg1, Cd101, 4930523C07Rik, Qsox2, Serhl, Rfcl, Cga, Bmyc, Sla, Rev31, Fam134b, Ggact, Mir466o, 28-Feb, Akrldl, Tnfsfl1, 2310040G24Rik, Gelc, Pde4b, Dgkz, Hsbp1, Eif3k, Gipc3, Mthfdll, P2ryl, EtsT, Cxcr4, Pjal, Treml2, Ccr7, C230024C17Rik, Rps6ka5, Klf4, Cx3crl, Echdc3, Hspa8, *Lama*4, Mgll, Ophnl, Thnsl1, Disc1, Pdzrn3, Sms, Zfp704, Zfp3612, Fam105a, Mad2ll, Dazap2, Fbxl14, Vapb, Ifnab, Zgrfl, Rtkn2, Ppp2r3c, Vmn2r96, Bbs9, Ifnlrl, 1700064J06Rik, Ppplr37, Tgfbr2, Slc2a2, Lefl, Ccr7, Foxql, Gan, D6Ertd527e, Snx9, Hes7, Fbxo47, Cox10, Bend3, Sgmsl, Slc30a9, Gm3716, Foxo1, Rsbnll, Tmcl, Faml20a, Gprl8, Efhcl, Ramp3, She, Akap7, Vezfl, Dnajc3, Tnpol, Nudtl6ll, Gm19589, Ankrd60, Txk, Lix1, Dnajc6, Serinc5, Lefl, Tars, Gm3336, Bacel, Nedd41, Trib2, Gm6994, Bcl11a, Mir5127, Klrb1b, Nfix, Tigd2, Map4k2, Uxsl, Bach2, 4930583K01Rik, Klhdc9, Eepdl, Als2cl, Pard3, Wdr27, Ikzf1, Btg1, Ly6e, Prml, Tacol, Itpr2, Limk2, Bend4, Gtf3c3, Kcnh8, Cd96, Fam229b, Adamts14, Lyrm7, Fhit, Sqrdl, Fpr-rs4, Tmem260, Cd55, Mir214, Mir3093, Amigo2, Dappl, C030018K13Rik, A230028005Rik, Shf, Lefl, Nrpl, Efr3a, Tmem30b, Mynn, Tgfbr2, Nfia, Ipcefl, Atl2, Thpo, Fam49a, Mir6387, Rtkn2, Gucyla3, Chrna9, Rassf2, Clip4, Wnt10a, Opalin, Llph, Mir6995, Sorcs2, Slc2a2, Gm20110, Synel, 2810001G20Rik, 5430434I15Rik, Ppplr37, Itgb6, Hspa8, I19r, Glrp1, 5430421F17Rik, Tstd2, Zswim2, Extl, Slcl6a10, Zfp957, Slfh5, Lrchl, Scin, Card11, Extl, Tet1, Scml4, Diap2, 4933433H22Rik, Zfp629, Tspan13, Prkcq, Zcchcl3, Cd74, E330017L17Rik, Tm2d1, Gprl26, Nrnl, Fam124b, Tubb2a, Tdrp, Tnfrsfla, Foxpl, Fam107b, Epb4.115, Fam78a, Rasal2, Mapk9, Creb312, 4930539M17Rik, Kcmfl, Ctage5, Ankrd12, Manba, Tmc1, Lmanll, Nacad, Agr3, 4933433H22Rik, Matk, H2bfm, Kcnh2, PgrT51, Inpp4b, Kcmfl, 4933430N04Rik, Vmn2r92, Stkl7b, Foxpl, Cep5711, Lix1, KcnaTO, Vangl2, Treh, Enthdl, Gm6559, Brf2, 4921525009Rik, Prkcq, Igsf3, Fut8, Limk2, 5730508B09Rik, Clasp2, Twsgl, Tmem126b, Hoxa7, Cd28, Sh3bp5, Furin, 1700001PO1Rik, Diap2, *Tecta*, Icosl, Fllr, Mir7023, Fes, Map3k5, Spry4, Cd44, Ralgpsl, Gm16793, Alox5ap, Mir5098, Arid1b, Ugcg, Ctla4, Snx9, Mir8095, Is12, Osbpl6, Dyrkla, Cd300a, A930011G23Rik, Fam26e, Ikzf2, Enpp6, MirT81a-1, Lyst, Grhl2, Aldhla7, Hmgbl-rs17, 2410004B18Rik, Dnm2, Nabpl, Foxpl, Tnfrsfl0b, Prkcq, Sgsm3, Agr3, 1700017N19Rik, Tle3, 4933406K04Rik, Insr, Whrn, Ets1, Lefl, Mir5618, Soat1, Ccr7, Cmssl, Ahcyl2, Mgatl, Hspal3, Znrf2, Kcnh8, Tdrp, Gm1604b, Vmn2r95, Akap6, TbcTd22a, Lbp, Mkll, Rsul, Sstr2, Slc37a3, Ube2d2a, Itpka, Rnf220, Hnrnph2, Gm2933, Akap2, Pdzklipl, Wwpl, Vapb, Dyrkla, Dynltlb, Zfp365, Ssh2, R3hdml, Nek10, Zswim2, Ccdc90b, Znrf1, Ms4a5, 4933406K04Rik, Actr2, Rgmb, Ston2, Gnas, Stkl7b, Piml, Mtr, Klhl2, Cdkl5, H2-Ob, I123r, Slain2, Tsscl, Sbkl, Ube4a, H2-T3, Gtf2irdl, Tyw5, Hbs1l, Efhcl, Rpe, March6, Itga4, Fam13a, Lstl, Ankrd55, Nif311, Fam69b, Mir7674, 2810001G20Rik, Gpr19, 4930567H12Rik, Foxp1, Dgkz, Cenpf, Amigo2, Panx1, B4galt3, Pagl, Ubl3, 1110059E24Rik, Hslbp3, Slc6al9os, Mdml, Limd2, Slc6al9, Bank1, Alg13, Wisp3, Sult5al, Fam86, Dennd2d, Cacnb2, Tesc, Mdml, Adipoq, 1810026B05Rik, Mir325, 1700096J18Rik, D030024E09Rik, GOs2, Mir7219, Slprl, Cxcrl, Extl, Chdl, Ly86, Dhx40, 4930564D02Rik, Dctn6, Il7r, E230025N22Rik, Sgk3, Bach2, Ramp1, Syt[6], Gsap, Ccdc152, Jakmipl, Atp8al, Grap2, Dynltlf, 4921513I03Rik, Gpc6, Kcna10, Ipcefl, Mir7061, Btg1, Stomll, Zfand3, Aqp4, Zfp281, Ccr2, Nrip3, C230029M16, Tcf4, Hadh, Mthfdll, Lhfp, Gprl14, Plbd1, 1110034G24Rik, Cd79a, Gsel, Churc1, Map3k7cl, Filipl1, Galnt7, Appl2, March5, Zswim6, Skap1, Tgfbr3, Slcl6a2, Palld, Atg10, Cap2, Dfna5, Tlr7, Slc24al, Hivep2, Dock4, Cd300a, Igf2bp2, A430107P09Rik, Lrm3, March2, Gm21057, Apbblip, Piga, Zbpl, A430107P09Rik, Trappc8, Zdhhcl4, Stkl7b, Sh3pxd2a, Ppifos, Chdl, Socs1, Kdr, Gramd3, Urad, Sipall1, Gm20098, P2ry2, Gas8, Sox5os3, Ccdc117, A130077B15Rik, Baspl, Zfp365, Syde2, Laptm4b, Sikl, 4933433H22Rik, Npff, Amtl, Alb, Zmyndl1, Gm20098, 119, Hadh, Sstr2, Empl, Lefl, Galnt10, 5430434115Rik, Cmah, 4631405J19Rik, Hesxl, Gm16793, Rplp0, Sall3, Xdh, St8sial, Folr4, Sp3, Rassf3, Aox2, Empl, Rragc, Proser2, Gm8817, D030028A08Rik, Btg1, Mad2ll, Upbl, 1810006J02Rik, 4932702P03Rik, Rhoh, Gm10790, Dock10, Fam166b, Pcdhl, Zbtb24, Camklg, 4933407L21Rik, Pde7a, A430093F15Rik, Pmepa1, Ropnll, Grap2, Rims3, Rps6ka1, Eps15, 4930445N18Rik, 6430710C18Rik, Ppplrl3b, 112lr, Mtmr2, Prex2, Atp6vOd2, Abliml, Hnrnpd, Sydel, Slcl6al, Mbnl1, Sgmsl, H2-DMbl, Ly6a, Tlr1, Gm20098, Galnt5, Edeml, Fam173b, Gprl26, Nbeall, Prlr, Tmcl, Csrnpl, Atpl0a, Dusp4, Lpar6, Pitpnb, Actr2, Ago2, Lphn2, Gm2447, Myol8a, Cd101, Cngbl, 1700027J07Rik, Vmn2r91, Folr4, Satb1, Man2a2, Smiml4, 3300005DO1Rik, D130058E03, Angptl2, Ercc3, Tmem87a, Synel, Ptrf, Gm2447, Zscan2, Bend4, Endodl, Tgfb3, Mir6962, Rragd, 4931403G20Rik, Ddrl, Map4k3, Fabp4, Stkl7b, Gm5122, Rapgef4, NeurlIb, Pdgfrb, Cirh1a, Fnipl, E030002003Rik, Fam65b, H2-DMa, Btg1, Zc3h12b, Prkch, Sipall1, Tdrp, Adtrp, Fam129c, Runx3, Ilvbl, Tbxl9, Filipl1, A430107P09Rik, Cedell, Lphn2, Spgl1, Mir6395, Foxpl, Dtnb, Mrpl13, Egln3, Fprl, Rapgef4, A130077B15Rik, Tlr7, Rbpms, Gm1966, Tmem150b, Rev31, Mad2ll, Gm1604b, Taspl, Slcl9a3, Trappc10, Ralgps2, Npasl, Ptprs, Slc36alos, Maf, Wdrl2, Polr3k, Gm20750, D14Ertd670e, Fam46c, Fam46c, Ptgerl, Lelatl, Ptma, Actn2, Tspanl1, Zfp879, Spred2, Satb1, Nabpl, 4930486L24Rik, Ugcg, Txk, A430107P09Rik, Hadh, Abtb2, Rbm33, Fli1, Fyn, Mgat4a, Sndl, Glt8d2, H2bfm, 9130401MO1Rik, Sndl, Mir3079, Pcdh7, Cngal, Tldcl, Ugdh, Aven, Mir8104, Rgll, Sox6, Map3kl4, Akirin2, Mir684-2, Rfx2, Fyb, Ccdc711, Ecel, Gm8884, 4921507P07Rik, Mir6933, Slc6a7, Cox7b2, Rfx4, Gm5617, Sh3kbp1, Pds5a, 9030617003Rik, Gprl26, Ctnnbl1, Prpf40a, Gpr22, Cldn10, Cdk19, Sgk3, Rgs3, Mir6995, Cdon, Stkl7b, Samhdl, Gm16793, Lag3, Olfm2, Cyb5a, Zfp438, Akap2, Dpfl, 3110052M02Rik, Lrp6, Haao, Camk2a, Tspan9, 5430434Il5Rik, Stk24, Tlr12, A930005H10Rik, Slc4a4, U2afl, Fbxl21, Opalin, Rybp, Igsf3, Aiml, Wasf2, Rgs3, Frs2, Smok4a, Pak4, Zscan22, A430107P09Rik, Slc35b3, Serpinb5, Med30, Cdc16, Agfgl, Tmem261, Plxnal, Myo5c, Gpr183, Suclgl, Cdkl9, 4930556N09Rik, Lpp, Tmem260, Ubqln2, Mir378b, Btla, Gm19589, Ano6, Clinti, Ube4b, O1fr1507, Rab33a, 4930523C07Rik, St6gall, 1600014K23Rik, Nnmt, Ift80, Htr3b, Rpl34, Ipcefl, Psma6, Dnmt3a, Hpgds, Stxbp3a, Mir6907, 1700056E22Rik, Smad7, Mir7078, Mir181b-2, 1127ra, Stat1, C030018K13Rik, Foxql, Hpcall, Msra, Zc3havl, Tdrd6, Tnfrsf4, 4921517D22Rik, Rubie, Plekhg6, Brd4, Sortl, U90926, 4930519F09Rik, Il4ra, Smyd2, Prkch, March9, Ghsr, Rps6ka2, Rpp21, Vps13c, 1600002D24Rik, Fam136a, 4921511I17Rik, Spefl, Maml3, St8sial, Ssbp2, Stk4, Tnfrsfl9, Snord104, O1fr1507, Dysf, Cntn5, Cd2, Raver2, Gm10790, Pjal, Tmprss9, Klf5, Ubash3b, Tle3, Scml4, Snx4, Tert, Sptbn1, Mir326, Affl, Gm8298, Ephb2, Tec, F3, Exoc6, Sema4f, Denndla, Gmcll, Gm10532, St3gall, Chd7, Gm6268, Tox, Pja2, Klhl3, Dnajcl0, Foxpl, Trp53inp1, Gtf3c3, Scd2, Atl2, Dach2, Lynx1, Candl, Cxcr4, Gm20098, Fscn3, 119r, Dph5, Sh3bp5, St6gall, Flil, Mir5127, Ubac1, Gm16793, Nsmaf, Sp6, Rnfl45, Ccr7, Orail, Serbp1, St6galnac5, Tox, Cacnalb, A430035B10Rik, Alpl, H2-DMb2, Etnkl, O1fr1507, Mtr, Rgmb, Pmp22, Dctn6, Flil, Mir326, Slc17a7, Seppl, Slc6a19, Cngbl, Mir7681, Ccr9, Klhl4, Atp6vlg3, Clec16a, Speer2, Gsn, Umps, Unc5cl, Aox2, Dcaf8, Igf2bp3, Car2, Rnf43, Kdm7a, Tgfbr3, Eldr, BC094916, Unc80, Zmyndl1, Nabp1, Adamts14, Gm20139, Fgfrl, Tmem141, C130026L21Rik, D630039A03Rik, Mturn, Herc3, Gm5468, Mir6398, Fam86, Nsg2, Cblb, Erbb4, Mir7-2, Smurf1, Clec16a, Lhx2, Tomm20, Ifngr2, Acacb, Gm10791, Bachl, Epb4.112, Tmem154, Tsscl, Vdac1, Itgae, Raph1, Klf3, Pnrc1, Sell, Tdrp, Ptk2, A630072M18Rik, Slc41a3, Rabl1b, Tnfrsfl0b, Lrp12, Ptger3, Aggf1, 1700029F12Rik, Dpfl, Gm14295, Ubqln2, Coq2, Txndc8, P2ryl, 4933430H16Rik, Tctex1d1, Sfmbt2, Alg14, Thal, Ets1, Cd101, Neu3, Mob3b, Kcna2, Irs2, Mbnl1, Fntb, Nipbl, Slc16a5, Ccdc174, Ncs1, BC037032, Fryl, Lipa, Hslbp3, Cd101, Chd1, Atadl, Ppplr3fos, Pde4b, Lamtor3, Klf2, Ttc27, Dntt, 5830454E08Rik, Panx1, Cyp2rl, Rhou, Mir701, Ccr7, Arhgap26, Ankrd36, Retnlb, Themis, Med131, Slc6a19os, Znrf2, Mettl8, Mir3108, D030025E07Rik, Mir145b, Iqsec1, Cd8b1, Clic1, 1810026B05Rik, Ptprs, Med7, Mthfd11, Dnalil, Bach1, Mgmt, Ppmlb, 4933430H16Rik, Cd40lg, Txk, Cdc14a, I19r, Slc7a15, Prkch, Srpk2, Tmbim7, Rcor1, Vti1a, B3gnt2, Tmem261, Gria3, Tusc3, Rgs3, Satb1, Sept6, Setbp1, Cep68, Ric8b, Il6ra, Znrf2, Lypd6b, Tmem29, Myh9, 4921511I17Rik, D1x1, Lhx2, and/or Chst15. A novel approach was used that combined cross-species identification of $T_{EX}$ specific transcriptional and epigenetic changes. Genes were identified that are specifically up-regulated in $T_{EX}$ compared to canonical T cell populations (naïve, effector, memory T cells) in the lymphocytic choriomeningitis virus (LCMV) model in mice. Among this set of genes the subset that had unique $T_{EX}$ specific epigenetic changes in open chromatin regions was further selected based on ATAC-seq analyses (Pauken et al. *Science* 2016, 354(6316): 1160-1165). This signature outperforms previous exhaustion signatures because the epigenetically selected genes drive the enrichment with other datasets typically accumulating at the leading edge of signature enrichment.

Disease

T cell exhaustion, usually manifests with several characteristic features, such as progressive and hierarchical loss of effector functions, sustained upregulation and co-expression of multiple inhibitory receptors, altered expression and use of key transcription factors, metabolic derangements, and a failure to transition to quiescence and acquire antigen-independent memory T cell homeostatic responsiveness. Although T cell exhaustion was first described in chronic viral infection in mice, it has also been observed in humans during infections such as HIV and hepatitis C virus (HCV), as well as in cancer. Importantly, while T cell exhaustion prevents optimal control of infections and tumors, modulating pathways overexpressed in exhaustion—for example, by targeting programmed cell death protein 1 (PD1) and cytotoxic T lymphocyte antigen 4 (CTLA4)—can reverse this dysfunctional state and reinvigorate immune responses. However, these immune responses are rarely durable in patients. In some embodiments, the patient has a disease and is treated with an engineered T cell of the disclosure. In some embodiments, the disease is cancer. In some embodiments, the disease is an infectious disease.

In some embodiments, the disease is selected from the group consisting of cancer, viral infection, bacterial infection, and parasite infection. In further embodiments, the viral infection is with a virus selected from the group consisting of hepatitis viruses, herpesviruses, polyoma viruses, anelloviruses, adenoviruses, retroviruses, and influenza viruses. In some embodiments, the disease is a bacterial infection selected from the group consisting of *Mycobacterium tuberculosis* (MTB), *Staphylococcus aureus, Streptococcus pyogenes, Clostridium botulinum, Campylobacter jejuni, Escherichia coli, Listeria monocytogenes, Salmonella enterica, Salmonella bongori,* and *Vibrio cholera.* In some embodiments, the cancer is responsive to treatment with an immune checkpoint inhibitor. In further embodiments, the cancer responsive to treatment with immune checkpoint inhibitors is selected from the group consisting of unresectable melanoma, metastatic melanoma, Stage III melanoma, metastatic non-small cell lung cancer (NSCLC), NSCLC, recurrent squamous cell cancer of the head and neck (SCCHN), metastatic renal cell carcinoma (RCC), urothelial carcinoma, hepatocellular carcinoma (HCC), bladder cancer, colorectal cancer, ovarian cancer, and endothelial cancer. In some embodiments, any disease where a genomic signature of exhaustion is detected may be treated.

Treatments

In some embodiments, the patient is administered an engineered T cell of the disclosure wherein the T cell has been engineered to prevent, reverse or increases exhaustion of the T cell. In further embodiments, the patient is administered an engineered T cell of the disclosure that has been engineered to prevent or reverse exhaustion of the T cell. In some embodiments, the T cell has been engineered by targeting a high priority epigenetic pathway in the T cell, as described herein. In some embodiments, administering the engineered T cell increases an immunological response in the patient. In some embodiments, the patient having a disease is treated for the disease with one or more immune checkpoint inhibitors before being administered the engineered T cell. In some embodiments, the patient is treated with one or more immune checkpoint inhibitors before administering the engineered T cell. In some embodiments, the engineered T cell is administered simultaneously or concurrently with an immune checkpoint inhibitor.

Humanized Antibodies

In some embodiments, a non-human antibody can be humanized, where specific sequences or regions of the antibody are modified to increase similarity to an antibody naturally produced in a human. For instance, in the present invention, the antibody or fragment thereof may comprise a non-human mammalian scFv. In one embodiment, the antigen binding domain portion is humanized.

A humanized antibody can be produced using a variety of techniques known in the art, including but not limited to, CDR-grafting (see, e.g., European Patent No. EP 239,400;

International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, *PNAS,* 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., *J. Immunol.,* 169:1119-25 (2002), Caldas et al., Protein Eng., 13 (5): 353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp):5973s-5977s (1995), Couto et al., Cancer Res., 55(8): 1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., *J. Mol. Biol.*, 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences.

Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody. However, using certain methods of humanization, the affinity and/or specificity of binding of the antibody to the target antigen may be increased using methods of "directed evolution," as described by Wu et al., J. Mol. Biol., 294:151 (1999), the contents of which are incorporated herein by reference herein in their entirety.

T cells

During acute infections or vaccinations, naive T cells are activated and differentiate into effector T cells over the course of 1-2 weeks. This differentiation is accompanied by robust proliferation, transcriptional, epigenetic and metabolic reprogramming, and the acquisition of cardinal features of effector T cells such as effector function, altered tissue homing and dramatic numerical expansion. Following the peak of effector expansion, the resolution of inflammation and the clearance of antigen, most activated T cells die, but a subset persists and transitions into the memory T cell pool. These memory T cells downregulate much of the activation program of effector T cells, yet they maintain the ability to rapidly reactivate effector functions upon restimulation. In addition, memory T cells develop a key memory property of antigen-independent self-renewal, which is a type of stem cell-like, slow division that is driven by interleukin-7 (IL-7) and IL-15. There is considerable diversity and complexity of memory T cell subsets and differentiation following acute infections or vaccinations (for example, effector memory T cells versus central memory T cells). However, a key aspect of the development of functional, persisting memory T cells is that after the effector phase, memory development occurs in the absence of ongoing antigen stimulation and high levels of persisting inflammation (Wherry and Kurachi. Nat Rev Immunol. 2015, 15(8):486-499).

By contrast, during chronic infections and cancer—which involve persistent antigen exposure and/or inflammation—this program of memory T cell differentiation is markedly altered. An altered differentiation state, termed T cell exhaustion, usually manifests with several characteristic features, such as progressive and hierarchical loss of effector functions, sustained upregulation and co-expression of multiple inhibitory receptors, altered expression and use of key transcription factors, metabolic derangements, and a failure to transition to quiescence and acquire antigen-independent memory T cell homeostatic responsiveness. Although T cell exhaustion was first described in chronic viral infection in mice, it has also been observed in humans during infections such as HIV and hepatitis C virus (HCV), as well as in cancer. Importantly, while T cell exhaustion prevents optimal control of infections and tumors, modulating pathways overexpressed in exhaustion—for example, by targeting programmed cell death protein 1 (PD1) and cytotoxic T lymphocyte antigen 4 (CTLA4)—can reverse this dysfunctional state and reinvigorate immune responses. However, a durable clinical response often does not occur because of failure to fully reinvigorate $T_{EX}$.

Exhausted T cells

Exhausted T cells are not inert. They retain suboptimal but crucial functions that limit ongoing pathogen replication or tumor progression. Despite this host-pathogen stalemate mediated by exhausted T cells, these cells are not effective in eradicating pathogens or tumors, and there has been considerable interest in avoiding or reversing exhaustion. The demonstration that T cell exhaustion is reversible (at least at the population level) rather than a terminal or irreversible fate provides a substantial clinical opportunity to use immunotherapy to improve immunity. Although the immunological effects of these human treatments remain to be fully defined, emerging results support the notion that reversal of T cell exhaustion in humans is a causative mechanism for the marked antitumour effect that is seen in many patients receiving agents that block the PD1 pathway.

Exhausted immune cells can have a reduction of at least 10%, 15%, 20%, 25%, 30%, 35%, 40%, 45%, 50%, 55%, 60%, 65%, 70%, 75%, 80%, 85%, 90%, 95%, 99% or more in cytotoxic activity, cytokine production, proliferation, trafficking, phagocytotic activity, or any combination thereof, relative to a corresponding control immune cell of the same type. In one embodiment, a cell that is exhausted is a CD8+ T cell (e.g., an effector CD8+ T cell that is antigen-specific). CD8 cells normally proliferate (e.g., clonally expand) in response to T cell receptor and/or co-stimulatory receptor stimulation, as well as in response to cytokines such as IL-2. Thus, an exhausted CD8 T cell is one which does not proliferate and/or produce cytokines in response to normal input signals. It is well known that the exhaustion of effector functions can be delineated according to several stages, which eventually lead to terminal or full exhaustion and, ultimately, deletion (Yi et al. (2010) *Immunol.* 129:474-481; Wherry and Ahmed (2004) *J Virol.* 78:5535-5545). In the first stage, functional T cells enter a "partial exhaustion I" phase characterized by the loss of a subset of effector functions, including loss of IL-2 production, reduced TNFα production, and reduced capacity for proliferation and/or ex vivo lysis ability. In the second stage, partially exhausted T cells enter a "partial exhaustion II" phase when both IL-2 and TNFα production ceases following antigenic stimulation and IFNγ production is reduced. "Full exhaustion" or "terminal exhaustion" occurs when CD8+ T cells lose all effector functions, including the lack of production of IL-2, TNFα, and IFNγ and loss of ex vivo lytic ability and proliferative potential, following antigenic stimulation. A fully exhausted CD8+ T cell is one which does not proliferate, does not lyse target cells (cytotoxicity), and/or does not produce appropriate cytokines, such as IL-2, TNFα, or IFNγ, in response to normal input signals. Such lack of effector functions can occur when the antigen load is high and/or CD4 help is low. This hierarchical loss of function is also associated with the expression of co-inhibitor immune receptors, such as PD-1, TIM-3, LAG-3, and the like (Day et al. (2006) *Nature* 443:350-4; Trautmann et al. (2006) *Nat. Med.* 12:1198-202; and Urbani et al. (2006) *J. Virol.* 80:1398-1403). Other molecular markers distinguish the hierarchical stages of immune cell exhaustion, such as high eomesodermin (EOMES) and low TBET expression as a marker of terminally exhausted T cells (Paley et al. (2012) *Science* 338:1220-1225). Additional markers of exhausted T cells, such as the reduction of Bcl-b and the increased production of BLIMP-1 (Pdrm1).

The protective capacity of the adaptive immune system relies on efficient and coordinated transitions between cellular fates. Following initial activation by specific antigen, naive CD8$^+$ T cells proliferate extensively and undergo a highly orchestrated program of molecular rewiring and differentiation into effector CD8+ T cells (T$_{EFF}$) that can mediate protection through cytotoxicity and production of inflammatory cytokines (Kaech, S. M. & Wherry, E. J. Heterogeneity and cell-fate decisions in effector and memory CD8+ T cell differentiation during viral infection. *Immunity* 27, 393-405 (2007); Chang, J. T., Wherry, E. J. & Goldrath, A. W. Molecular regulation of effector and memory T cell differentiation. *Nat Immunol* 15, 1104-1115 (2014); Kaech, S. M. & Cui, W. Transcriptional control of effector and memory CD8+ T cell differentiation. 12, 749-761 (2012); Cui, W. & Kaech, S. M. Generation of effector CD8+ T cells and their conversion to memory T cells. *Immunol Rev* 236, 151-166 (2010)). If the infection or antigen is cleared, most of this T$_{EFF}$ pool dies, but a subset persists, undergoing additional differentiation to form a pool of long-lived, self-renewing memory T cells (T$_{MEM}$) capable of mounting rapid recall responses. In contrast, during chronic infections or cancer, when T cell stimulation persists, this program of functional T cell differentiation is diverted and T cells fail to sustain robust effector functions, instead becoming exhausted (Wherry, E. J. & Kurachi, M. Molecular and cellular insights into T cell exhaustion. *Nature Publishing Group* 15, 486-499 (2015); Wherry, E. J. T cell exhaustion. *Nat Immunol* 12, 492-499 (2011)). Exhausted CD8+ T cells (T$_{EX}$) may balance limited pathogen or tumor control while restraining damaging immunopathology, but the consequence of restrained functionality is disease persistence and possible progression (Barber, D. L. et al. Restoring function in exhausted CD8 T cells during chronic 1155 viral infection. *Nature* 439, 682-687 (2005); Frebel, H. et al. Programmed death 1 protects from fatal circulatory failure during systemic virus infection of mice. *J Ex pMed* 209, 2485-2499 (2012)). Though first described in mice infected with lymphocytic choriomeningitis virus (LCMV), it is now clear that T cell exhaustion is a common feature of many chronic infections as well as a variety of cancers in both mice and humans (Zajac, A. J. et al. Viral Immune Evasion Due to Persistence of Activated T Cells Without Effector Function. *J Exp Med* 188, 2205-2213 (1998); Gallimore, A. et al. Induction and Exhaustion of Lymphocytic Choriomeningitis Virus-specific Cytotoxic T Lymphocytes Visualized Using Soluble Tetrameric Major Histocompatibility Complex Class I-Peptide Complexes. *J Exp Med* 187, 1383-1393 (1998); Lechner, F. et al. Analysis of Successful Immune Responses in Persons Infected with Hepatitis C Virus. *J Exp Med* 191, 1499-1512 (2000). 1166 12. Shankar, P. et al. Impaired function of circulating HIV-specific CD8(+) T cells in chronic human immunodeficiency virus infection. *Blood* 96, 3094-3101 (2000)). Indeed, T$_{EX}$ are highly therapeutically relevant since these cells are a major target of checkpoint blockade mediated immune reinvigoration in human cancer patients (Pauken, K. E. & Wherry, E. J. Overcoming T cell exhaustion in infection and cancer. *Trends in Immunology* 36, 265-276 (2015); Page, D. B., Postow, M. A., Callahan, M. K., Allison, J. P. & Wolchok, J. D.; Immune Modulation in Cancer with Antibodies. *Annu. Rev. Med.* 65, 185-202 (2014); Hamid, O. et al. Safety and Tumor Responses with Lambrolizumab (Anti-PD-1) in Melanoma. *N Engl J Med* 369, 134-144 (2013); Hirano, F. et al. Blockade of B7-H1 and PD-1 bp monoclonal antibodies potentiates cancer therapeutic immunity. *Cancer Res.* 65, 1089-1096 (2005); Barber, D. L. et al. Restoring function in exhausted CD8 T cells during chronic viral infection. *Nature* 439, 682-687 (2005)).

T cell exhaustion is characterized by the progressive decline in effector function including the hierarchical loss of inflammatory cytokine production (IL-2, TNFα, IFNγ) (Wherry, E. J., Blattman, J. N., Murali-Krishna, K., van der Most, R. & Ahmed, R. Viral Persistence Alters CD8 T-Cell Immunodominance and Tissue Distribution and Results in Distinct Stages of Functional Impairment. *J Virol* 77, 4911-4927 (2003); Fuller, M. J. & Zajac, A. J. Ablation of CD8 and CD4 T Cell Responses by High Viral Loads. *J Immunol* 170, 477-486 (2003)). T$_{EX}$ also sustain high co-expression of multiple inhibitory receptors (PD-1, LAG3, TIGIT, CD160, TIM-3, 2B4) (Blackbum, S. D. et al. Coregulation of CD8+ T cell exhaustion by multiple inhibitory receptors during chronic viral infection. Nat 1186 *Immunol* 10, 29-37 (2008)), have reduced glycolytic and oxidative phosphorylation capacity (Bengsch, B. et al. Bioenergetic Insufficiencies Due to Metabolic Alterations Regulated by the Inhibitory Receptor PD-1 Are an Early Driver of CD8+ T Cell Exhaustion. *Immunity* 45, 358-373 (2016); Staron, M. M. et al. The Transcription Factor FoxO1 Sustains Expression of the Inhibitory Receptor PD-1 and Survival of Antiviral CD8+ T Cells during Chronic Infection. *Immunity* 41, 802-814 (2014)), and impaired proliferation and survival (Wherry, E. J., Blattman, J. N. & Ahmed, R. Low CD8 T-Cell Proliferative Potential and High Viral Load Limit the Effectiveness of Therapeutic Vaccination. *J Virol* 79, 8960-8968 (2005); Wherry, E. J., Barber, D. L., Kaech, S. M., Blattman, J. N. & Ahmed, R. Antigen independent memory CD8 T cells do not develop during chronic viral infection. *Proc Natl Acad Sci USA* 101, 16004-16009 (2004); Shin, H., Blackburn, S. D., Blattman, J. N. & Wherry, E. J. Viral antigen and extensive division maintain virus-specific CD8 T cells during chronic infection. J 1201 *Exp Med* 204, 941-949 (2007)). Underlying these major differences in T$_{EX}$ compared to T$_{EFF}$ and T$_{MEM}$, is a distinct transcriptional program highlighted by altered use of key transcription factors and altered transcriptional circuits (Wherry, E. J. et al. Molecular signature of CD8+ T cell exhaustion during chronic viral infection. *Immunity* 27, 670-684 (2007); Doering, T. A. et al. Network Analysis Reveals Centrally Connected Genes and Pathways Involved in CD8+ T Cell Exhaustion versus Memory. *Immunity* 37, 1130-1144 (2012); Crawford, A. et al. Molecular and Transcriptional Basis of CD4+ T Cell Dysfunction during Chronic Infection. *Immunity* 40, 289-302 (2014)). Indeed, unique networks of transcription factors (TFs) regulate different functional modules of exhaustion. T cell receptor signaling integrators including the NFAT proteins, BATF, and IRF4 have been shown to be involved in the induction of exhaustion (Grusdat, M. et al. IRF4 and BATF are critical for CD8+ T-cell function following infection with LCMV. *Cell Death and Differentiation* 21, 1050-1060 (2014); Man, K. et al. Transcription Factor IRF4 Promotes CD8+ T Cell Exhaustion and Limits the Development of Memory-like T Cells during Chronic Infection. *Immunity* 47, 1129-1141.e5 (2017); Martinez, G. J. et al. The Transcription Factor NFAT Promotes Exhaustion of Activated CD8+ T Cells. *Immunity* 42, 265-278 (2015))whereas T-bet, Eomesodermin (Eomes), and Tcf1 are involved in coordinating a proliferative hierarchy to maintain the $T_{EX}$ population once established (Im, S. J. et al. Defining CD8+ T cells that provide the proliferative burst after PD-1 therapy. *Nature* 537, 417-421 (2016); Wu, T. et al. The TCF1-Bcl6 axis counteracts type I interferon to repress exhaustion and maintain T cell stemness. Sci *Immunol* 1, eaai8593-eaai8593 (2016); Utzschneider, D. T. et al. T Cell Factor 1-Expressing Memory-like CD8+ T Cells Sustain the Immune Response to Chronic Viral Infections. *Immunity* 45, 415-427 (2016); Paley, M. A. et al. Progenitor and Terminal Subsets of CD8+ T Cells Cooperate to Contain Chronic Viral Infection. *Science* 338, 1220-1225 (2012)). In addition, Blimp-1, Bcl6, and Foxo1 regulate the locomotive and metabolic capabilities of $T_{EX}$ cells as well as the overall severity of dysfunction. In some cases, these TFs are also employed by $T_{EFF}$ or $T_{MEM}$, but with different functions and altered transcriptional connections, implying an epigenetic environment allowing the same TF to perform divergent activities. Despite this work, it has been unclear whether $T_{EX}$ are simply dysregulated $T_{EFF}$, arrested $T_{MEM}$, or whether $T_{EX}$ are a distinct cell fate. Recent epigenetic analysis, however, revealed that $T_{EX}$ differ from $T_{EFF}$ and $T_{MEM}$ by ~6000 open chromatin regions, similar to differences between other major hematopoietic lineages suggesting that $T_{EX}$ are not simply a state of activation of $T_{EFF}$ or $T_{MEM}$, but rather are a distinct immune lineage (Im, S. J. et al. Defining CD8+ T cells that provide the proliferative burst after PD-1 therapy. *Nature* 537, 417-421 (2016); Wu, T. et al. The TCF1-Bcl6 axis counteracts type I interferon to repress exhaustion and maintain T cell stemness. Sci *Immunol* 1, eaai8593-eaai8593 (2016); Utzschneider, D. T. et al. T Cell Factor 1-Expressing Memory-like CD8+ T Cells Sustain the Immune Response to Chronic Viral Infections. *Immunity* 45, 415-427 (2016); Paley, M. A. et al. Progenitor and Terminal Subsets of CD8+ T Cells Cooperate to Contain Chronic Viral Infection. *Science* 338, 1220-1225 (2012)). The mechanisms that initiate this $T_{EX}$ fate commitment and epigenetic and transcriptional programming have thus far remained poorly understood, and exhaustion-specific TFs or transcriptional programming activities have remained elusive.

Here, a requisite role for the HMG-box TF TOX in programming the early epigenetic events that drive fate commitment to the $T_{EX}$ lineage is definted. Without wishing to be bound by theory, TOX integrates early, sustained NFAT2 activity into a subsequent NFATindependent TOX-driven molecular and epigenetic $T_{EX}$ program. TOX is necessary and sufficient to induce major cellular features of $T_{EX}$ including inhibitory receptor expression, decreased function and the pattern of downstream TF expression necessary for $T_{EX}$ population maintenance. TOX is transiently and lowly expressed during many acute infections and $T_{EFF}$ and $T_{MEM}$ can form without TOX. In contrast, TOX expression is robust and sustained in $T_{EX}$ and the development of $T_{EX}$ is completely dependent on this TF. TOX interacts with major histone modifying enzyme complexes and is capable of initiating key TEx-specific epigenetic changes to function as the $T_{EX}$ lineage initiator. Thus, these data identify TOX as a critical $T_{EX}$ lineage programming transcriptional and epigenetic coordinator. These results have implications for the ontogeny of $T_{EX}$ and suggest potential therapeutics based on targeting TOX and TOX regulated epigenetic events.

Inhibitory Receptors and Treatment with Immune Checkpoint Blockade

Inhibitory receptors are crucial negative regulatory pathways that control autoreactivity and immunopathology. Although inhibitory receptors are transiently expressed in functional effector T cells during activation, higher and sustained expression of inhibitory receptors is a hallmark of exhausted T cells. The inhibitory signaling pathway mediated by PD1 in response to binding of PD1 ligand 1 (PDL1) and/or PDL2 offers an illustrative example. Whereas our understanding of the molecular mechanisms by which the inhibitory receptor PD1 controls T cell exhaustion remains incomplete, and without wishing to be bound by any theory, there are several mechanisms by which inhibitory receptors such as PD1 might regulate T cell function: first, by ectodomain competition, which refers to inhibitory receptors sequestering target receptors or ligands and/or preventing the optimal formation of microclusters and lipid rafts (for example, CTLA4); second, through modulation of intracellular mediators, which can cause local and transient intracellular attenuation of positive signals from activating receptors such as the TCR and co-stimulatory receptors; and third, through the induction of inhibitory genes.

Whereas there is some knowledge about PD1, understanding of the intracellular mechanisms of action of inhibitory receptors—including those of PD1—is incomplete. The intracellular domain of PD1 contains an immunoreceptor tyrosine-based inhibitory motif (ITIM) and an immunoreceptor tyrosine-based switch motif (ITSM). In vitro studies suggest a role for the ITSM in recruiting the tyrosine-protein phosphatase SHP1 (also known as PTPN6) and/or SHP2 (also known as PTPN11). The role of the ITIM in PD1 function remains poorly understood. Other evidence implicates a role for PD1 signaling in modulating the phosphoinositide 3-kinase (PI3K), AKT and RAS pathways, and also links PD1 to cell cycle control. Notably, much of our information about how PD1 controls T cell signaling is derived from in vitro studies of acutely activated T cells. In vivo studies of the role of PD1 during acute T cell activation and expansion suggest a possible role for PD1 signaling in either increasing mobility paralysis or decreasing migratory arrest, depending on the context. Finally, signaling downstream of PD1 may in fact induce the expression of genes that could negatively regulate the expression of effector genes, such as BATF, which encodes the activator protein 1 (AP-1) family member basic leucine zipper transcription factor ATF-like. Despite this elegant work, it is unclear how these observations relate to exhausted T cells exposed to chronic infection in vivo.

PD1 expression is rapidly upregulated upon T cell activation, and it may persist at moderate levels in healthy humans, indicating that PD1 expression alone is not a unique feature of exhausted T cells. However, during chronic infections PD1 expression can be substantially higher than observed on functional effector or memory CD8+ T cells. During chronic infection, sustained upregulation of PD1 is usually dependent on continued epitope recognition, although examples exist of residual PD1 expression even after removal of persisting antigen signaling.

In addition to PD1, exhausted T cells express a range of other cell surface inhibitory molecules. Exhausted T cells can co-express PD1 together with lymphocyte activation gene 3 protein (LAG3), 2B4 (also known as CD244), CD160, T cell immunoglobulin domain and mucin domain-containing protein 3 (TIM3; also known as HAVCR2), CTLA4 and many other inhibitory receptors. Typically, the higher the number of inhibitory receptors co-expressed by exhausted T cells, the more severe the exhaustion. Indeed, although individual expression of PD1 or other inhibitory receptors is not indicative of exhaustion, co-expression of multiple inhibitory receptors is a cardinal feature. These co-expression patterns are mechanistically relevant, as simultaneous blockade of multiple inhibitory receptors results in synergistic reversal of T cell exhaustion. This concept was demonstrated for PD1 and LAG3 in chronic LCMV infection, and for PD1 and CTLA4 in HIV infection, other infections and cancer. Many other combinations of inhibitory receptors such as PD1 and TIM3 can also co-regulate exhausted T cells. PD1 and CTLA4 blockade in patients with melanoma demonstrated impressive tumor control, and clinical trials of other combinations of agents blocking inhibitory receptors are underway (for example, ClinicalTrials.gov identifiers NCT01968109, NCT02210117 and NCT02408861, which are among >120 other trials involving the PD1 pathway). Overall, these data on the role of inhibitory receptors in co-regulation of T cell exhaustion suggest that these pathways are non-redundant. These molecules come from diverse structural families, bind ligands with distinct expression patterns and have distinct intracellular signaling domains. Thus, there is the potential to tailor or tune the type and magnitude of exhausted T cell reinvigoration.

In addition to inhibitory receptors, it has become clear that co-stimulatory receptors are involved in T cell exhaustion. For example, desensitization of co-stimulatory pathway signaling through the loss of adaptor molecules can serve as a mechanism of T cell dysfunction during chronic infection. The signaling adaptor tumor necrosis factor receptor (TNFR)-associated factor 1 (TRAF1) is downregulated in dysfunctional T cells in HIV progressors, as well as in chronic LCMV infection. Adoptive transfer of CD8+ T cells expressing TRAF1 enhanced control of chronic LCMV infection compared with transfer of TRAF1-deficient CD8+ T cells, which indicates a crucial role for TRAF1-dependent co-stimulatory pathways in this setting. It has also been possible to exploit the potential beneficial role of co-stimulation to reverse exhaustion by combining agonistic antibodies to positive co-stimulatory pathways with blockade of inhibitory pathways. 4-1BB (also known as CD137 and TNFRSF9) is a TNFR family member and positive co-stimulatory molecule that is expressed on activated T cells. Combining PD1 blockade and treatment with an agonistic antibody to 4-1BB dramatically improved exhausted T cell function and viral control. Although a simple model of positive versus negative co-stimulation during T cell exhaustion probably has mechanistic validity, the diversity of pathways and much of the experimental data suggest that specific qualitative signals may be imparted by distinct co-stimulatory and co-inhibitory pathways (Wherry and Kurachi. *Nat Rev Immunol.* 2015, 15(8):486-499).

In some embodiments, an inhibitory receptor is targeted in the patient. In some embodiments, the inhibitory receptor is targeted with an immune checkpoint inhibitor. The immune checkpoint inhibitor, without limitation, can be PD-1, PD-L1, CTLA-4, TIM3, B7-H3, BTLA, VISTA, CD40, CEACAM1/CD66a, CD80/B7-1, CD86/B7-2, OX40/CD134, CD40 Ligand, ICOS Ligand/B7-H2, 4-1BBL/CD137L, or B7-DC/PD-L2/CD273. In some embodiments, the immune checkpoint inhibitor is targeted with an anti-immune checkpoint inhibitor antibody. In some embodiments, the patient is simultaneously or concurrently treated with an anti-immune checkpoint inhibitor and an engineered T cell of the disclosure. In some embodiments, the patient is treated with an engineered T cell of the disclosure after the patient has been treated with an anti-immune checkpoint inhibitor, e.g., 1 minute, 5 minutes, 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days after treatment with an immune checkpoint inhibitor.

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out some embodiments of the present invention, and are not to be construed as limiting in any way the remainder of the disclosure.

The materials and methods employed in Examples 1-10 are now described.

Mice, Infections, and Antibody Treatment

Five to six week old female C57BL/6 and B6-Ly5.2CR (B6 mice expressing Ly5.1) were purchased from Charles River (NCI strains). C57BL/6 P14 mice were bred to B6-Ly5.2CR mice to generate P14 Ly5.1+mice as described (Odorizzi et al. *J. Exp. Med.* 2015, 212:1125-1137). LCMV strains (Armstrong (Arm) and clone 13) were propagated and titers were determined as described (Odorizzi et al. J. Exp. Med. 2015, 212:1125-1137). In some embodiments, C57BL/6 P14, Toxf/f CD4Cre+P14, and Toxf/f Ert2Cre+ P14 mice were bred in-house and backcrossed to NCI C57BL/6 mice to prevent acute rejection after transfer. LCMV strains (Armstrong (Arm) and clone 13) were propagated and titers were determined as previously described. B6 mice were infected intraperitoneally (i.p.) with $2 \times 10^5$ PFU LCMV Arm or intravenously (i.v.) with $4 \times 10^6$ PFU LCMV clone 13 to establish acute or persistent infection, respectively. In some embodiments, mice were injected IP with 2 mg of tamoxifen (Sigma) dissolved in 50:50 Kolliphor/ethanol daily between days 25-30 of infection. For all clone 13 infections, CD4 T cells were depleted by i.p. injection of 200 µg of anti-CD4 (clone GK1.5, Bio X Cell) on days $^-1$ and $^+1$ p.i. with LCMV clone 13. Anti-PD-L1 (clone 10F.9G2, Bio X Cell) or an isotype control antibody (Rat IgG2b, Bio X Cell) was administered i.p. starting between day 22-25 p.i., 200 g/injection for five injections every third day for 5 total treatments as described (Barber et al. *Nature* 2006, 439, 682-687). For some experiments vehicle (PBS) was injected as a control. For experiments where IL-7 was administered in vivo, the cytokine was complexed to anti-IL-7 to increase stability. For these experiments, IL-7/anti-IL-7 immune complexes (i.e.) were prepared as described (Boyman et al. J. Immunol. 2008, 180:7265-7275). Briefly, 1.5 pg of recombinant human IL-7 (NCI Preclinical Repository or Biolegend) and 7.5 pg of anti-human/anti-mouse IL-7 (clone m25, provided by Charlie Surh) per mouse per injection were mixed and allowed to complex for 30 min prior to diluting with PBS for injection. Complexes were administered i.p. simultaneously with anti-PD-L1 (every third day for 5 injections). All mice were maintained under specific pathogen free conditions at the University of Pennsylvania, and all protocols were approved by the Institutional Animal Care and Use Committee.

Lymphocyte Isolation and Adoptive Transfer

For experiments where P14 cells were monitored, P14 cells were isolated from the peripheral blood of P14 transgenic mice using histopaque 1083 gradients (Invitrogen), and P14 cells (500 for clone 13 experiments, and 500-2000 for Arm experiments) were adoptively transferred i.v. into 5-6 weeks old recipient B6 mice at least one day prior to infection. Similar results were obtained when comparing P14 cells to endogenous $D^bGP33^+$ and $D^bGP276^+$ cells (FIG. 5), and previous reports have shown that the number of P14 cells transferred for clone 13 experiments (500) did not impact viral load (Odorizzi et al. J. Exp. Med. 2015, 212:1125-1137; Blattman et al. *J. Virol.* 2009, 83:4386-4394). For experiments where $T_{MEM}$, $T_{EX}$, or anti-PD-L1-treated $T_{EX}$ were adoptively transferred, CD8 T cells were isolated one day post the antibody treatment period from spleens, and were enriched using CD8 T cell EasySep negative selection kits (Stem Cell Technologies) according to the manufacturer's instructions. Numbers were normalized between groups based on $D^bGP33$ tetramer staining prior to i.v. adoptive transfer into antigen free recipient mice. LCMV immune mice (day 30' p.i.) were used as antigen free recipients so endogenous LCMV-specific memory could eliminate any transferred virus as described (Angelosanto et al. *J. Virol.* 2012, 86:8161-8170). For experiments testing antigen-independent persistence, recipient mice were immune to LCMV Arm (day 30' pi). For rechallenge experiments, recipient mice had previously cleared low dose (200 PFU) infection with LCMV clone 13 V35A lacking the GP33 epitope as described (Shin, et al. *J. Exp. Med.* 2007, 204: 941-949). V35A immune mice were used for recall experiments to prevent direct competition with endogenous $D^bGP33$-specific memory CD8 T cells.

Flow Cytometry

MHC class I peptide tetramers ($D^bGP276$ and $D^bGP33$) were made as previously described or obtained from the NIH tetramer core. Antibodies were purchased from eBioscience, BD, Biolegend, Life Technologies, R&D Systems and AbD Serotec, and included CD8, CD4, B220, CD45.1, CD45.2, CD44, CD122, CD127, PD-1, 2B4, Tim-3, Lag-3, Ki-67, granzyme B, IFNγ, TNFα, and phospho-STAT5. Single cell suspensions were stained with Live/Dead Aqua (Life Technologies) according to the manufacturer's instructions prior to staining for surface antigens. Intracellular staining for Ki-67 and granzyme B was performed using the eBioscience Foxp3 fixation/permeabilization kit according to manufacturer's instructions (eBioscience). Intracellular staining for IFNγ and TNFα was performed using the BD cytofix/cytoperm kit according to manufacturer's instructions (BD) following a 5 hour in vitro restimulation with 0.2 μg/ml gp33-41 peptide (KAVYNFA™, GenScript) in the presence of brefeldin A and monensin (BD). For phosho-STAT5 detection, splenocytes were rested for 1-2 hours at 37° C. prior to stimulation. Cells were stimulated for 30 minutes with 10 ng/ml recombinant murine IL-7 or IL-15 (Peprotech). Cells were then fixed with paraformaldehyde for 15 minutes at 37° C., washed once, and immediately resuspended in Phospho Perm Buffer III (BD) and incubated for 30 minutes on ice. Cells were subsequently washed and stained according to manufacturer's instructions. Cells were collected on an LSR II flow cytometer (BD), and data were analyzed using FlowJo software (Tree Star). Sorting was conducted on a FACSAria (BD), and post-sort purities were obtained to determine sort quality.

Gene Expression by Microarray and RNA-Seq

For transcriptional profiling by microarray, CD8 T cells from spleens 1-2 days after the final treatment (after receiving 5 total treatments as described above) were enriched using magnetic beads (CD8 negative selection kit, Stem Cell Technologies) and $D^bGP276^+$ CD8 T cells were sorted on a FACSAria (BD). Four independent experiments were performed for each treatment group with 10-12 mice pooled per group per experiment. RNA was isolated with TRIzol (Life Technologies) according to manufacturer's instructions. RNA was processed, amplified, labeled, and hybridized to Affymetrix GeneChip MoGene 2.0 ST microarrays at the University of Pennsylvania Microarray Facility. Microarray data were processed and analyzed as previously described (Doering et al. *Immunity* 2012, 37:1130-1144). The heat map module in Gene Pattern was used to identify and display differentially expressed genes. Gene set enrichment analyses and leading edge metagene analyses were performed as described (Godec et al. *Immunity* 2016, 44:194-206). Metagenes for anti-PD-L1 were identified using the microarray data set comparing anti-PD-L1 to control $T_{EX}$. Metagenes for $T_{EFF}$ (Day 8 post-LCMV Arm infection), $T_{MEM}$ (Day 30 post-LCMV Arm infection), and $T_{EX}$ (Day 30 post-LCMV clone 13 infection) cells were generated by comparing to naive T cells using previously published transcriptional profiles (Doering et al. Immunity 2012, 37:1130-1144). Details of the metagene composition and comparisons can be found in Pauken et al. Table S4 (Pauken et al. *Science* 2016, 354(6316):1160-1165). To generate the effector gene list shown, we started with the top 300 genes up-regulated at Day 6 post Arm compared to naive in (Doering et al. *Immunity* 2012, 37:1130-1144). Genes that had GO membership for six of the major cell cycle terms (cell cycle, mitosis, spindle, DNA replication, mitotic cell cycle, and cell cycle) were then removed. This list is shown in Pauken et al. Table S3 (Pauken et al. *Science* 2016, 354(6316):1160-1165).

For transcriptional profiling by RNA-seq, CD8 T cells from spleens were enriched using magnetic beads (CD8 negative selection kit, Stem Cell Technologies) and P14 cells were sorted on a FACSAria (BD). P14 cells were sorted either 1 day post final treatment (with 5 doses of anti-PD-L1 or control as described above; three independent experiments for control (5-7 mice each pooled), four independent experiments for anti-PD-L1 (5-6 mice each pooled)), or long-term (two independent experiments, at 18 (5 control-treated and 7 anti-PD-L1-treated mice pooled) and 29 weeks (13 control-treated and 12 anti-PD-L1-treated mice pooled)) after the final treatment. Naïve $CD8^+$ T cells were sorted from pooled spleens from 2-3 uninfected C57BL/6 mice from two independent experiments. Cells were lysed and frozen in buffer RLT plus (RNeasy Plus Lysis Buffer, Qiagen) with 1% 2-mercaptoethanol (Sigma). Total RNA from sorted cells was extracted using the Applied Biosystems Arcturus PicoPure RNA isolation kit. Double stranded cDNA was generated using the Clontech SMRT-seq v4 method and was fragmented using the Covaris S220 in microTubes. Indexed Illumina-compatible sequencing libraries were generated from fragmented cDNA using the NEBNext Ultra II methodology. Libraries were quantified using Kapa Library QC kit for Illumina, pooled, and sequenced on an Illumina NextSeq 500 for 75 cycles (single end). Sequenced libraries were aligned to the mm10 reference genome using STAR and gene expression from RefSeq genes was quantified using Cufflinks and reported as FPKM values.

Epigenetic Profiling by ATAC-Seq

CD8 T cells were enriched using magnetic beads (CD8 negative selection kit, Stem Cell Technologies) and P14 CD8 T cells (day 8 p.i. Arm (5 spleens per experiment pooled), day 33 p.i. Arm (12-13 spleens per experiment pooled), day 35 p.i. clone 13 (15 spleens per experiment for control-treated pooled, 7 mice per experiment for anti-PD-L1-treated pooled)) or naïve CD8 T cells (from 2-3 spleens pooled) were sorted on a FACSAria (BD). Control- and anti-PD-L1-treated $T_{EX}$ cells were sorted one day after the final treatment (5 total treatments, every third day) as described above. Two independent experiments per condition were performed. ATAC-seq was performed as described (Buenrostro et al. *Nat. Methods* 2013, 10:1213-1218). Briefly, nuclei were isolated from 50,000-150,000 sorted cells per replicate using a solution of 10 mM Tris-HCl, 10 mM NaCl, 3 mM $MgCl_2$, and 0.1% IGEPAL CA-630. Immediately following nuclei isolation, the transposition reaction was conducted using Tn5 transposase and TD buffer (Illumina) for 45 minutes at 37° C. Transposed DNA fragments were purified using a Qiagen MinElute Kit, barcoded with dual indexes (Illumina Nextera) and PCR amplified using NEBNext High Fidelity 2× PCR master mix (New England Labs). The size distribution and molarity of the sequencing library were determined by using an Agilent Bioanalyzer and KAPA quantitative RT-PCR (KAPA Biosystems). Sequencing was performed using a high output, 150 cycle kit with V2 chemistry on a NextSeq 500 (Illumina). Paired-end reads were mapped to the mm10 reference genome using Bowtie2. Only concordantly mapped pairs were kept for further analysis. Peak calling was performed using MACS v1.4 to identify areas of sequence tag enrichment. BedTools was used to find common intersection between identified peaks (1 bp minimum overlap) and to create a merged peak list. ATAC-seq tag enrichment, DNA motif analysis across the merged peak list, and GO term assessment were computed using HOMER (homer.salk.edu). Principal component analysis, spectral co-clustering, and hierarchical clustering were performed using scipy, matplotlib, and scikit-learn. REVIGO was used to identify unique GO terms across different cell types. The list of peaks was filtered for some downstream analysis to remove peaks that had low enrichment across all five cell types (third quartile).

Transcription Factor Footprinting and Network Analysis

To build the integrated transcriptional network based on the unique epigenetic landscape of $T_{EX}$, Wellington bootstrap (Piper et al. BMC Genomics 2015, 16:1000) was first used to identify transcription factor (TF) binding motifs enriched in either control- or anti-PD-L1-treated $T_{EX}$ in all OCRs compared to the other cell types probed by computing 20 sets of differential footprints for all ordered pairs of the 5 cell types ($T_N$, $T_{EFF}$, $T_{MEM}$, $T_{EX}$, anti-PD-L1-treated $T_{EX}$). To analyze motif frequencies in differential footprints, a motif search was done within these footprint coordinates using annotatePeaks.pl script from HOMER (Heinz et al. Mol. Cell 2010, 38:576-589) and relative motif frequencies were calculated as described in Piper et al. (BMC Genomics 2015, 16:1000). A matrix was generated and motif scores were displayed as a heat map using the ClassNeighbors module of GenePattern (Reich et al. *Nat. Genet.* 2006, 38:500-501) to show cell-type specific TFs.

Significantly enriched TF binding motifs were subsequently validated to be included in the downstream network. TFs that were not detectable transcriptionally in the RNA-seq and/or TFs that had minimal evidence of binding to their consensus sequence with TF footprint analysis were excluded. For TF footprint validation, average profiles of the Tn5 cuts within a 200 bp window around different TF motifs were estimated and plotted using Wellington dnase_average_footprinting.py (Piper et al. Nucleic Acids Res. 2013, 41, e201). A network was then built with these validated TFs and the differentially expressed genes in $T_{EX}$ cells following anti-PD-L1 treatment from the microarray data set. Genes were included that had a LFC≥0.3. Lines connecting a TF with a target gene were based on that gene having a consensus binding motif for that TF in the region. The full list of TFs and target genes is available in Pauken et al. Table SI1 (Pauken et al. Science 2016, 354(6316):1160-1165).

To validate TFs identified in this integrated network analysis correlating the epigenetic landscape and transcriptional changes, we constructed a second network using the differentially expressed genes from the microarray following anti-PD-L1 treatment (LFC≥0.3 up or down, p<0.05) and used PSCAN to identify the TFs predicted to contain consensus binding motifs in the promoter regions of those genes (see Pauken et al. Table S12 (Pauken et al. Science 2016, 354(6316):1160-1165)). The enrichment for each TF for the differentially expressed genes was plotted as a heat map. To test the prediction that anti-PD-L1 caused a re-engagement of effector-like circuitry in $T_{EX}$, we determined genes near all OCRs in $T_{EFF}$ or $T_{EX}$ cells that contained consensus binding motifs for TFs identified in the integrated network analysis and selected additional TFs of interest including T-bet, Eomes, Prdm1 (Blimp1), and Runx1-3. We excluded genes near OCRs for which there was no transcriptional data in the microarray. The percentage of genes changed following anti-PD-L1 that contained membership in the list for the overlap between $T_{EFF}$ and $T_{EX}$ or $T_{EX}$ alone was then calculated, and the percent difference in the overlap compared to $T_{EX}$ alone was plotted.

Statistical Analysis

Statistics for flow cytometry and viral load data were analyzed using GraphPad Prism software. For comparisons between two independent conditions when only two conditions were being compared, significance was determined using unpaired Student's t tests. Paired Student's t tests were used when samples from the same mouse were being compared at two different time points as indicated in the Figure Legends. One way ANOVA tests were used when more than two groups were being compared. We first tested for normality using the D'Agostino and Pearson normality test. If all groups were determined to be normally distributed, a parametric one way ANOVA was performed, and post-test analyses of groups of interest were performed using Bonferroni's multiple comparison test. If not all groups were determined to be normally distributed, a non-parametric ANOVA (Kruskal-Wallis test) was performed, and post-test analyses of groups of interest were performed using Dunn's multiple test comparisons. P values for the ANOVA are indicated in blue next to the Y axis in each figure, and the p values for post-tests between indicated pairs are in black. P values were considered significant if less than 0.05. Asterisks used to indicate significance correspond with: $p<0.05$*, $p<0.01$, $p<0.001$*.

Patients and Specimen Collection

Patients with stage IV melanoma were enrolled for treatment with pembrolizumab (2 mg kg$^{-1}$ by infusion every 3 weeks) under an Expanded Access Program at Penn (www.clinicaltrials.gov identifier NCT02083484) or on NCT01295827 at Memorial Sloan Kettering Cancer Center ('MSKCC'). Patients consented for blood collection under the University of Pennsylvania Abramson Cancer Center's ('Penn') melanoma research program tissue collection protocol UPCC 08607 and under protocol 00-144 at MSKCC, in accordance with the Institutional Review Boards of both institutions. Peripheral blood was obtained in sodium heparin tubes before treatment and before each pembro infusion every 3 weeks for 12 weeks. Peripheral blood mononuclear cells (PBMCs) were isolated using ficoll gradient and stored using standard protocols.

Assessment of Response and Tumor Burden

Tumor burden. Total measurable tumor burden was defined as the sum of the long axis of all measurable lesions reported on the pre-therapy imaging reports. Patients with only non-measurable lesions or active brain metastasis were excluded from analysis involving clinical response and tumor burden. Assessment of clinical response and tumor burden was performed independently in a blinded fashion.

Clinical response, Penn cohort. Clinical response to anti-PD-1 therapy for the Penn cohort was determined as best response based on immune related RECIST (irRECIST) using unidimensional measurements (Nishino et al. Clin. Cancer Res. 2013,19:3936-3943). In addition, the following modifications were used. (1) Lymph node lesions with a short axis between 10 and 15 mm with a standard uptake value (SUV) of greater than 5 on PET scan were included as measurable lesions. (2) Lesions greater than 5 mm confirmed to be melanoma by biopsy were included as measurable lesions.

Clinical response, MSKCC cohort. Clinical response for the MSKCC cohort was assessed based on immune-related response criteria (Wolchok et al. Clin. Cancer Res. 2009, 15:7412-7420) using bidimensional measurements at the 12 week time point.

Flow Cytometry

Penn cohort. Cryopreserved PBMC samples from pre-treatment, cycles 1-4 (weeks 3-12) were thawed and stained with master mix of antibodies for surface stains including CD4 (Biolegend, OKT4), CD8 (ebioscience, RPA-T8), 2B4 (Beckman Coulter, IM2658), CD45RA (Biolegend, HI100), TIM-3 (F38-2E2), LAG-3 (Enzo, ALX-804-806B-C100), CXCR5-BV421 (BD, RF8B2) and CD27 (BD, L128) and intracellular stains for FOXP3 (BD, 259D/C7), CTLA-4 (BD, BNI3), Eomes (ebioscience, WD1928), T-bet (Biolegend, 4B10), GzmB (Life Tech, GB11), TCF-1-AlexaFluor647 (Biolegend, 7F11A10) and Ki67 (BD, B56). Permeabilization was performed using the FOXP3 Fixation/Permeabilization Concentrate and Diluent kit (eBioscience). PD-1 on post pembro specimens was detected using anti-human IgG4 PE (Southern Biotec). Pretreatment samples were pretreated with 25 µg ml$^{-1}$ pembro in vitro for 30 min at 37° C., washed twice and stained with standard antibody mix. Cells were resuspended in 1% paraformaldehyde until acquisition on a BD Biosciences LSR II cytometer and analyzed using FlowJo (Tree Star).

MSKCC cohort. PBMC samples at the indicated visits pre- and post-pembrolizumab treatment were thawed and stained with a fixable Aqua viability dye (Invitrogen) and a cocktail of antibodies to the following surface markers: CD8-Qdot605 (Invitrogen, 3B5), CD4-Qdot655 (Invitrogen, S3.5), PD-1-PE (BD, MIH4), LAG-3-FITC (Enzo, 17B4), ICOS-PE-Cy7 (eBioscience, ISA-3), TIM-3-APC (R&D Systems, 344823). Cells were next fixed and permeabilized with the FOXP3/Ki67 Fixation/Permeabilization Concentrate and Diluent (eBioscience), and subsequently stained intracellularly with CD3-BV570 (Biolegend, UCHT1), Ki67-AlexaFluor700 (BD), FOXP3-eFluor450 (eBioscience), and CTLA-4-PerCP-eFluor710 (eBioscience). Stained cells were acquired on a BD Biosciences LSR-Fortessa and analyzed using FlowJo software (FlowJo, LLC).

Cell Sorting

Cryopreserved PBMC samples were thawed and stained as per flow cytometry protocol (above). For RNA sequencing experiments, total CD8 T cells were sorted, using a dump/dead-CD3$^+$CD8$^+$ gating strategy. For TCR sequencing experiments, CD8 T cells were gated as above, and CD38$^+$HLA-DR$^+$ and cells that were not CD38$^+$HLA-DR$^+$ (that is, CD38$^-$HLA-DR$^-$, CD38$^+$HLA-DR$^-$, and CD38$^-$HLA-DR$^+$) were sorted. Cell sorting was performed on BD Aria Sorter.

Cytokine Analysis

Concentration of circulating plasma cytokines was analyzed using Luminex technology (EMD Millipore).

Stimulation with PMA and Ionomycin

Thawed cells were stimulated with phorbol 12-myristate 13-acetate (PMA) (Sigma) at 0.25 µg ml$^{-1}$ and ionomycin (Sigma) at 2.5 µg ml$^{-1}$ for 2-5 h in 37° C. and stained. Cytokine production was analyzed with intracellular staining using antibodies to IFNγ (Biolegend, B27) and TNF-α (Biolegend, Mab11).

Random Forest for Classification and Regression

Random forest regression and classification (RF-RC) is a multivariable non-parametric ensemble partitioning tree method that can be used to model the effect of all interactions between genes and proteins as predictors on a response variable[31]. Each model is constructed using approximately two-thirds of randomly selected samples and cross-validated on the one-third of the samples left out of the model building process ('out-of-bag' samples). After many iterations, results of all models are averaged to provide unbiased estimates of predicted values, error rates, and measures of variable importance. Performance of an RF-RC model is measured by the mean square error for regression and by misclassification error rate for classification. Flow cytometry subsets were used as possible predictors of clinical response variables. For each predictor, an importance score is determined, that measures the contribution of the variable to the error rate (higher scores are more predictive). We used the 'randomForest' R package version 4.6-12 implementation and the following parameters: 5,000 trees, node size of 1, mtry value (that is, number of variables available for splitting at each node) equal to the square root of the number of variables in the model, and the Breiman-Cutler permutation method for importance score determination. The mean decrease in accuracy is used as the importance score measure.

T-Cell Receptor Sequencing

Manual macrodissection was performed on FFPE slides, if necessary, using a scalpel and a slide stained with haematoxylin and eosin (H&E) as a guide. Tissue deparaffinization and DNA extraction were performed using standard methods. DNA was quantified using Qubit dsDNA BR Assay (Invitrogen). Peripheral blood CD8 T cells were purified and isolated from PBMCs using BD Aria Sorter. DNA extraction, amplification, library preparation, sequencing, and preliminary bioinformatics analysis was performed by Adaptive Biotechnologies. Amplification and sequencing of TCRB CDR3 was performed at a survey level resolution using the immunoSEQ Platform (Adaptive Biotechnologies).

Immunohistochemistry for PD-L1 and CD8, and Analysis

Formalin-fixed, paraffin-embedded tumors were collected at the time of surgical resection or from a biopsy. For anti-PD-L1 staining, after heat-induced antigen retrieval (Bond ER2, 20 min), the tumor slides were stained with an anti-PD-L1 antibody (E1L3N, Cell Signaling) at 1:50 dilution. To confirm specificity, the anti-PD-L1 antibody was validated by staining Hodgkin's lymphoma cells and placenta. For anti-CD8 staining, after heat-induced antigen retrieval (Bond ER1, 20 min), the tumor slides were stained with an anti-CD8 antibody (M7103, Dako) at 1:40 dilution. Tumor infiltrating CD8-positive T cells was scored as absent, minimal, mild, moderate and brisk by a blinded expert melanoma pathologist. Tumor-infiltrating CD8 T cells were also analyzed by image recognition analysis using ImageJ2. Digital slides were acquired by a Leica microscope. RGB stack images of CD8 staining were converted to greyscale, and particles (positive stain) counted using a threshold value of 100 with a size between 10 and 625 $\mu m^2$. Total area of the tumor was calculated using a tumor mask.

RNA Sequencing and Analysis

After sorting, the cells were resuspended and frozen in RLT buffer (Qiagen). RNA was isolated using the Qiagen RNeasy micro kit (74034) according to the manufacturer's protocol. RNA-seq libraries were prepared using the SMARTer Stranded Total RNA-Seq Kit for Pico Input Mammalian from Clonetech according to the manufacturer's protocol (635007). The libraries were sequenced on an Illumina NextSeq machine using a 300-cycle high-output flow cell (15057929), with a read depth between 9 million and 20.6 million paired mapped reads. The Fastq files were aligned using STAR 2.5.2a and hg19. The aligned files were processed using PORT gene-based normalization (www.github.com/itmat/Normalization). The differential gene expression was performed with Limma. Limma-voom was used to identify significantly different transcripts between groups using P value <0.05. For patients with a Ki67 peak at cycle 1 (three patients), the top 40 genes highly correlated with MKI67 were taken to create a correlative network including the top 5 genes correlating with the MKI67-correlated genes. The final network had nodes with highly correlated (absolutely value of the correlation coefficient >0.7 (abs(corr) >0.7)) values with MKI67. Cytoscape 3.4.0 was used for creation of correlation network, and metascape.org was used to enrich genes for GO biological processes. The data discussed in this publication have been deposited in NCBI Gene Expression Omnibus and are accessible through GEO Series accession number GSE96578 (www.ncbi.nlm.nih.gov/geo/query/acc.cgi?acc=GSE96578), incorporated by reference herein in its entirety.

Whole-Exome Sequencing, Mutational Burden Analysis and Neoepitope Prediction

Manual macrodissection was performed on FFPE slides, if necessary, using a scalpel and H&E-stained slide as a guide. Tissue deparaffinization and DNA extraction were performed using standard methods. DNA was quantified using Qubit dsDNA BR Assay (Invitrogen). DNA libraries were created using NEBNext Ultra DNA Library Prep Kit for Illumina (New England BioLabs) and targets were captured with SureSelect Human All Exon V6⁻ COSMIC (Agilent). HLA with OptiType and neoepitope predictions were made using Ccons 1.1 Server.

Statistical Methods and Classification and Regression Tree (CART) Analysis

For group comparisons and correlation analyses, testing was performed using PRISM 6.0. Normality of distributions was assessed using D'Agostino-Pearson omnibus normality test and variance between groups of data was assessed using the F-test. For normally distributed data, significance of mean differences was determined using two-sided paired or unpaired Student's t-tests, and for groups that differed in variance, unpaired t-test with Welch's correction was used. For non-normal data, non-parametric Mann-Whitney U-tests or Wilcoxon matched-pairs signed rank tests were used for unpaired and paired analyses, respectively. Descriptive statistics included mean, median, standard deviation and range for continuous variables and frequency and proportion for categorical variables. Correlations between continuous variables were determined by Pearson's r coefficient, whereas correlations between ordinal-scaled categorical variables were determined by Spearman's r coefficient. Overall survival was defined from the initiation of treatment to date of death or last patient contact alive and estimated by the Kaplan-Meier method. Landmark overall survival and PFS analysis was defined as overall survival and PFS starting from 6 weeks after therapy. To visually inspect the relationships between Ki67 (week 6 maximum), baseline tumor burden and clinical outcomes, we constructed simple scatter plots of Ki67 by baseline tumor burden and employed color-coded symbols for clinical outcome such as overall survival, PFS, and clinical response. In general, the mean was used for dichotomization of clinical outcomes. This included PFS and landmark PFS in the Penn dataset and landmark overall survival for MSKCC dataset. In the Penn dataset, landmark overall survival was dichotomized using a cutoff of 9.5 months, as it represented the longest complete survival time (that is, no patient with LOS <9.5 months was alive and censored for survival). The log rank test was employed to compare overall survival between patient subgroups. The ratio of Ki67 to tumor burden was associated with overall survival and was further examined by CART analysis. CART identified the optimal cut point to split this continuous variable into two homogenous subgroups according to overall survival. By this method, the optimal cut point is selected from all possible cut points. Survival and CART statistical analyses were performed using either IBM SPSS v23 or STATA v14. Similar analysis was performed for landmark PFS.

Model Selection, Principal Component Analysis and Fisher's Exact Calculation

Model selection is a method of selecting models among a set of candidate models. The R package 'leaps' version 2.9 with parameters 'nvmax=3', and 'nbest=10' was used to select the ten best models on the basis of linear regression for predicting CD8 and Ki67 expression.

Clinical parameters were used as predictor variables and Ki67 as the dependent variable. This method evaluates all one-variable, two-variable, and three-variable models and ranks best-fitting models using the Bayesian information criterion (BIC), penalized by number of variables. Lower BIC score signals a better model.

Principle component analysis was used to visualize three variables: tumor burden, Ki67, and mutational burden in two-dimensional space. R package factoMiner was used to calculate and extract the percentage of variance explained by principal components and the variables contained in each PCA variable.

Fisher's exact test was used to test the hypothesis that the probability of finding shared TCR CDR3 clonotypes (between top 10 tumor-infiltrating T-cell clones and peripheral blood, Fg-39A) among all unique sequenced peripheral blood clones was different than the probability of finding a clone in the tumor by random chance, with an theoretical estimate of 107 possible peripheral blood clonotypes. P value was calculated using the R function 'fisher.test( )'.

Adoptive Transfer of TET2cKO cells:

Mice.

B6;129S-Tet2$^{tm1.11aai}$/J (TET2$^{fl/fl}$) mice, C57BL/6J, B6.SJL-Ptprc$^a$ (CD45.1$^+$) and CD4Cre$^+$mice were obtained from Jackson Laboratories and bred at the University of Pennsylvania. TET2$^{fl/fl}$ CD4Cre$^+$ (TET2cKO) were bred to C57BL/6J mice 10 generations and then to P14 mice.

Adoptive Transfer.

Equal numbers (500) of P14 CD8$^+$ T cells from the peripheral blood of TET2cKO or wild-type P14 mice were adoptively transferred into congenic (CD45.1$^+$) hosts. The following day, host were infected with with $4 \times 10^6$ PFU LCMV clone 13 intavenously. Spleen and liver were harvested from mice 16 or 29 days post infection. Single cell suspensions were made and liver lymphocytes were further isolated using density centrifugation over a Percoll(TM) (GE Healthcare) gradient.

Flow Cytometry and Analysis.

Cells were isolated, washed and stained with indicated antibodies. Antibodies were purchased from Biolegend, Invitorgen or eBiosciences and included CD8☐-BV650 or AlexaFluor e780; CD62L PE-TexasRed, KLRG1 PE-Cy7 or FITC, CD127 PE-Cy7, PD-1 PE-Cy7, 2B4 FITC, CD45.1 AF700, CD44 BV785, Ly6C BV711, Granzyme B BV421, human Ki67-BV711, Eomes AF647, TCF-1 FITC, TbetBV605. Biotinolyted monomers specific for H2-D$^b$ restricted gp33-41 of LCMV were obtained from the NIH Tetramer Core Facility and tetramerized using their published protocol. Intracellular staining was performed using either FoxP3/Transcription Factor Staining Buffer kit (eBiosciences) according to manufacturer's instructions. Discrimination of live cell populations was performed using Live/Dead Aqua stain (Invitrogen) according to manufacturer's instructions. Flow cytometry was performed on BD LSRII and analyzed using FlowJo software. Data were graphed using Prism software.

In Vitro Effector T Cell Differentiation

To isolate naïve murine CD8 T cells, spleens were harvested from 5-6 week old C57/B16 female mice and dissociated on a 70 um filter with a syringe. Cells were washed through the filter with 3 washes of PBS and resuspended in 1 ml magnetic separation buffer (MSB, PBS with 10% FCS and 4 mM EDTA) per 100 million cells. 50ul of normal rat serum was added per ml of MSB to block non-specific antibody interactions. Subsequently, the following biotinylated antibodies were added at a 1:200 dilution: anti-CD4, anti-NK1.1, anti-CD19, anti-B220, anti-CD11c, anti-CD11a, anti-CD11b, and anti-Ter119. Antibody-cell mixture was incubated at room temperature for 15 min, prior to the addition of 125ul of streptavidin magnetic beads per 1 ml of MSB. Mixture was incubated for another 15 min at room temperature after which, total volume was brought up to 3 ml with MSB. Sample was then mixed gently and placed in a magnetic separator (StemCell) for 10 min at room temperature. Unbound fraction was decanted into a 15 ml conical tube. Sample was washed twice with 10 ml PBS and placed on ice until next step.

To generate in vitro differentiated effector cells, purified naïve CD8 T cells from the steps above were counted and resuspended at $1 \times 10^6$ cells per 1 ml of RPMI medium supplemented with 10% FCS, 50 uM beta-mercaptoethanol, 20 mM HEPES, non-essential amino acids (1:100, Invitrogen), sodium pyruvate (1:100, Invitrogen), penicillin, and streptomycin. 3 ml of cell mixture was placed in a well of 12 well cluster dish. Cells were activated for 24 hours with anti-mouse CD3e (1:1000, BioLegend), anti-mouse CD28 (1:2000, BioLegend), and 100U/ml recombinant human IL-2 (rhIL-2, Peprotech). Cells were then harvested from each well, counted, and washed 1 time in warm PBS. To differentiate activated CD8 T cells into effector cells, they were resuspended at $1 \times 10^6$ per 1 ml of supplemented RPMI and 100U/ml of rhIL-2 and 3 ml of cells were plated per well of a 6 well cluster dish. This was repeated for an additional 4 days, until a total of 6 days post-activation.

Gene Expression by Microarray and RNA-Seq

For transcriptional profiling by microarray, total RNA was isolated from sorted CD8+ T cells using TRIzol (Invitrogen, Carlsbad, CA). RNA was processed, amplified, labeled, and hybridized to Affymetrix GeneChip MoGene 1.0 st microarrays (Santa Clara, CA) by the University of Pennsylvania Microarray facility. Affymetrix Power Tools were used to process and quantile normalize fluorescent hybridization signals using Robust Multichip Averaging.

For transcriptional profiling by RNA-seq, CD8 T cells were sorted on a FACSAria (BD). Cells were lysed and frozen in buffer RLT plus (RNeasy Plus Lysis Buffer, Qiagen) with 1% 2-mercaptoethanol (Sigma). Total RNA from sorted cells was extracted using the Applied Biosystems Arcturus PicoPure RNA isolation kit. Double stranded cDNA was generated using the Clontech SMRT-seq v4 method and was fragmented using the Covaris S220 in microTubes. Indexed Illumina-compatible sequencing libraries were generated from fragmented cDNA using the NEBNext Ultra II methodology. Libraries were quantified using Kapa Library QC kit for Illumina, pooled, and sequenced on an Illumina NextSeq 500 for 75 cycles (paired-end). Sequenced libraries were aligned to the mml0 reference genome using STAR and gene expression from RefSeq genes was quantified using Cufflinks and reported as FPKM values.

Epigenetic Profiling by ATAC-Seq

ATAC-seq was performed as described previously. Briefly, nuclei were isolated from 50,000-150,000 sorted cells per replicate using a solution of 10 mM Tris-HCl, 10 mM NaCl, 3 mM MgCl$_2$, and 0.1% IGEPAL CA-630. Immediately following nuclei isolation, the transposition reaction was conducted using Tn5 transposase and TD buffer (Illumina) for 45 minutes at 37° C. Transposed DNA fragments were purified using a Qiagen MinElute Kit, barcoded with dual indexes (Illumina Nextera) and PCR amplified using NEBNext High Fidelity 2x PCR master mix (New England Labs). The size distribution and molarity of the sequencing library were determined by using an Agilent Bioanalyzer and KAPA quantitative RT-PCR (KAPA Biosystems). Sequencing was performed using a high output, 150 cycle kit with V2 chemistry on a NextSeq 500 (Illumina). Paired-end reads were mapped to the mm10 reference genome using Bowtie2. Only concordantly mapped pairs were kept for further analysis. Peak calling was performed using MACS v1.4 to identify areas of sequence tag enrichment. BedTools was used to find common intersection between identified peaks (1bp minimum overlap) and to create a merged peak list. ATAC-seq tag enrichment, DNA motif analysis across the merged peak list, and GO term assessment were computed using HOMER (homer-.salk.edu). Principal component analysis, spectral co-clustering, and hierarchical clustering were performed using scipy, matplotlib, and scikit-learn. REVIGO was used to identify unique GO terms across different cell types. The list of 8 peaks was filtered for some downstream analysis to remove peaks that had low enrichment across all five cell types (third quartile).

Sample Preparation and Mass Spectrometry Analysis

Sample Preparation

EL4 thymoma cells (ATCC) were grown in DMEM medium (Invitrogen) with 10% fetal calf serum. Cells were collected and washed 2x with warmed PBS after centrifugation. The cells were resuspended in 1 ml of Buffer A (10 mM TrisHCl pH7.5, 1.5 mM MgCl2, 10 mM KCl, 25 mM NaF, 1 mM Na3VO4, 1 mM DTT, with protease inhibitor cocktail) per 10×106 cells. Cells were incubated in Buffer A for 3 minutes on ice, centrifuged and transferred to a Dounce homogenizer in 5 ml of Buffer A. Cells were homogenized with 5 strokes of the Dounce homogenizer. Nuclei were collected by centrifugation, washed in 1 ml of Buffer A per 10×106 cells and resuspended in 1 ml of Buffer B (50 mM Tris-Cl, pH 7.4, 1.5 mM MgCl2, 20% glycerol, 420 mM NaCl, 25 mM NaF, 1 mM Na3VO4, 1 mM DTT, 400 Units/ml DNase I, with protease inhibitor cocktail) per 10×106 cells. Solution was incubated at 4 degrees for 30 min in a rotator and vortexed every 10 min. Sample was then centrifuged for 5 minutes at 3300RPM at 4 degrees. Supernatant containing nuclear extract was diluted 1:3 in Buffer D (50 mM Tris-Cl, pH 7.4 (RT), 1.5 mM MgCl2, 25 mM NaF, 1 mM Na3VO4, 0.6% NP40, 1 mM DTT, with protease inhibitor cocktail). Sample was centrifuged again and 500ul aliquots were snap frozen in liquid nitrogen prior to storage at −80 degrees.

LC-MS/MS Analysis

Sample preparation, labeling with isobaric mass tags, peptide fractionation, and mass spectrometric analyses were performed essentially as previously described. For acquisition of dose-response inhibitor data in one single multiplexed run, TMT™ (Thermo-Fisher Scientific) tags were used because they allow the acquisition of 6 point data. For immunoaffinity purifications, a maximum of four samples was compared, and iTRAQ™ reagents (Applied Biosystems) were employed for reasons of economy and coverage.

Peptide and Protein Identification and Quantification

Mascot™ 2.0 (Matrix Science) was used for protein identification using 10 ppm mass tolerance for peptide precursors and 0.8 Da (CID) tolerance for fragment ions. Carbamidomethylation of cysteine residues and iTRAQ/TMT modification of lysine residues were set as fixed modifications and S,T,Y phosphorylation, methionine oxidation, N-terminal acetylation of proteins and iTRAQ/TMT modification of peptide N-termini were set as variable modifications. The search data base consisted of a customized version of the IPI protein sequence database combined with a decoy version of this database created using a script supplied by Matrix Science. Unless stated otherwise, we accepted protein identifications as follows: i) For single spectrum to sequence assignments, we required this assignment to be the best match and a minimum Mascot score of 31 and a 10x difference of this assignment over the next best assignment. Based on these criteria, the decoy search results indicated <1% false discovery rate (FDR); ii) For multiple spectrum to sequence assignments and using the same parameters, the decoy search results indicate <0.1% false discovery rate. For protein quantification a minimum of 2 sequence assignments matching to unique peptides was required. FDR for quantified proteins was <<0.1%. Only peptides unique for identified proteins were used for relative protein quantification and are referred to in supplementary data sets as unique peptide assignments (UPA). Further, for quantification spectra matching to UPAs were filtered according to the following criteria: Mascot ion score >15, signal to background ratio of the precursor ion >4, signal to interference >0.5. Reporter ion intensities were multiplied with the ion accumulation time yielding an area value proportional to the number of reporter ions present in the mass analyzer. For compound competition binding experiments fold changes are reported based on reporter ion areas in comparison to vehicle control and were calculated using sum-based bootstrap algorithm. Fold changes were corrected for isotope purity as described and adjusted for interference caused by co-eluting nearly isobaric peaks as estimated by the signal-to-interference measure5. Absolute protein abundances, apa, were calculated by taking the average of the MS1 abundances of the three most abundant peptides for the protein in question6. Enrichment, E of a protein, P, found in an immunoprecipitation experiment over the bait protein, B, was calculated as $E=\log(apa(P)/apa(B))$ Compound profiling data was used to restrict the immunoprecipitation data to a set of reliable interactors as previously described. Heat maps and t-tests were performed using the R-package and Tableau. Cytoscape software was used for interaction network visualization.

Data Availability

RNA sequencing data that support the findings have been deposited in NCBI Gene Expression Omnibus and are accessible through GEO Series accession number GSE96578 (www.ncbi.nlm.nih.gov/geo/query/acc.cgi?acc=GSE96578). Flow cytometry, TCR sequencing, and clinical data are included in Huang et al. (Huang et al. Nature 2017, 4;545(7652):60-65, doi:10.1038/nature22079) and its Extended Data and Supplementary Information, incorporated herein by reference, in its entirety.

Results of the experiments are now described.

Example 1. Anti-PD-L1 Induces an Effector-Like Transcriptional Program in $T_{EX}$ Cells that is not Sustained after Cessation of Treatment Cellular, transcriptional, and epigenetic changes associated with PD-1 pathway blockade were interrogated using the mouse model of chronic lymphocytic choriomeningitis virus (LCMV) infection (Barber et al. Nature 2006, 439, 682-687; Pauken et al. Science 2016, 354(6316):1160-1165—Supplemental Information on *Science* online). Following anti-PD-L1 treatment, 1080 genes were up-regulated and 1686 genes were down-regulated (p<0.05, LFC≥0.2) (Pauken et al. Table S1 (Pauken et al. *Science* 2016, 354 (6316):1160-1165)). Previous studies identified transcriptional (Gubin et al. 2014, Nature 515, 577-581) or cellular (Bengsch et al. 2016, Immunity 45, 358-373; Staron et al. 2014, Immunity 41, 802-814) changes in metabolic pathways following PD-1 pathway blockade. Indeed, several metabolic genes were altered following PD-L1 blockade (Pauken et al. Table S1 (Pauken et al. Science 2016, 354 (6316):1160-1165)). Gene Set Enrichment Analysis (GSEA), however, identified more prominent changes in cell division pathways (Pauken et al. Table S2 (Pauken et al. Science 2016, 354(6316):1160-1165)) (Barber et al. Nature 2006, 439, 682-687; Patsoukis et al. 2012, Sci. Signal. 5, ra46). In addition, many effector-related genes were biased toward the anti-PD-L1 group (Pauken et al. Table S3 (Pauken et al. *Science* 2016, 354(6316):1160-1165)). Other genes of interest included Cxcl9, Illr2 and Il7r (up) and Klra9, Tnfrsf9, and Cd200r2 (down) (Pauken et al. Table S1 (Pauken et al. Science 2016, 354(6316):1160-1165)). Using Leading Edge Metagene (LEM) analysis (Godec 2016, Immunity 44, 194-206) two metagenes were identified in anti-PD-L1-treated $T_{EX}$ compared to control $T_{EX}$; one corresponding to leukocyte activation and one to cell cycle Pauken et al. Table S4 (Pauken et al. Science 2016, 354 (6316):1160-1165)). The anti-PD-L1-treated $T_{EX}$ metagenes displayed some overlap with $T_{EFF}$, largely driven by cell cycle pathways, but minimal overlap with $T_{MEM}$ (Pauken et al. Table S4 (Pauken et al. Science 2016, 354(6316):1160-1165)) suggesting limited acquisition of memory potential upon $T_{EX}$ re-invigoration.

PD-1 pathway blockade can re-activate functions in $T_{EX}$, but whether re-invigoration is sustained is unclear. Here, there was a robust re-invigoration of $T_{EX}$ as expected (Barber et al. Nature 2006, 439, 682-687), and expansion peaked ~3 weeks after initiation of blockade. By 8-11 weeks posttreatment, however, this re-invigoration was lost and the quantity, proliferation, effector function and inhibitory receptor expression of LCMV-specific CD8 T cells in the anti-PD-L1-treated mice were comparable to control-treated mice. Moreover, although anti-PD-L1 treatment reduced viral load immediately after treatment, 4 months later viral load was similar to control-treated mice. Lastly, 18-29 weeks after cessation of blockade, the transcriptional profiles of control- and anti-PD-L1-treated groups were similar (Pauken et al. Tables S5 and S6 (Pauken et al. Science 2016, 354(6316):1160-1165)). Collectively, these data indicate that when antigen remains high, $T_{EX}$ re-invigorated by PD-1 pathway blockade become "re-exhausted."

Example 2. PD-1 Pathway Blockade Moderately Improves Antigen-Independent Persistence and IL-7 Signaling in $T_{EX}$ One possible reason the effects of PD-L1 blockade were not sustained was the infection persisted. To test the idea that if the infection was cured, then anti-PD-L1 might induce differentiation into $T_{MEM}$, equal numbers of control $T_{EX}$, anti-PD-L1-treated $T_{EX}$, or $T_{MEM}$ were transferred into antigen-free mice and persistence was monitored. Consistent with previous studies (Shin, et al. J. Exp. Med. 2007, 204: 941-949; Wherry, et al. Proc. Natl. Acad. Sci. U.S.A. 2004, 101:16004-16009), $T_{EX}$ survived poorly in antigen-free recipients compared to functional $T_{MEM}$. There was a trend toward anti-PD-L1—treated $T_{EX}$ persisting moderately better, though poorly compared to $T_{MEM}$. Next, potential mechanisms for this trend were interrogated. Following PD-1 pathway blockade, interleukin (IL)-7 receptor transcripts (Il7r; CD127) increased significantly (FIG. 1D and Pauken et al. Table S1 (Pauken et al. Science 2016, 354 (6316):1160-1165)). There was also a modest increase in CD127 protein on a subset of $T_{EX}$ following anti-PD-L1. Upon stimulation with IL-7, anti-PD-L1-treated $T_{EX}$ also showed more phospho-STAT5 compared to control-treated $T_{EX}$ (FIG. 9F and FIG. 8B). In contrast, expression of the IL-15 receptor subunit CD122 and responsiveness to IL-15 in vitro were not substantially altered. These data suggest that anti-PD-L1 treatment may augment activity of the memory-biased IL7R pathway.

Treating with IL-7 starting in the effector phase can prevent development of exhaustion (Pellegrini, et al. *Cell*

2011, 144:601-613; Nanjappa, et al. *Blood* 2011, 117:5123-5132). However, later in chronic infection $T_{EX}$ respond poorly to IL-7 (Shin, et al. J. Exp. Med. 2007, 204: 941-949; Wherry, et al. Proc. Natl. Acad. Sci. U.S.A. 2004, 101: 16004-16009). Anti-PD-L1 improved IL-7R signaling, hence it was tested whether combined treatment had additional benefit. Indeed, while other aspects of the response were less affected, treatment with IL-7 and anti-PD-L1, but not IL-7 alone, resulted in more antigen-specific CD8 T cells and improved co-production of IFNγ and TNFα. Thus, it may be possible to exploit pathways upregulated by PD-L1 blockade including IL-7R to improve checkpoint blockade.

Example 3. PD-1 Pathway Blockade Fails to Restore Memory-Like Recall Capacity or Reprogram the Epigenetic Landscape of $T_{EX}$ into $T_{EFF}$ or $T_{MEM}$ Cells It was next tested whether PD-1 pathway blockade could restore robust recall potential upon re-infection, a defining property of $T_{MEM}$. Equal numbers of $D^b$GP33$^+$ CD8 $T_{EX}$, anti-PD-L1-treated $T_{EX}$, or $T_{MEM}$ were transferred into antigen-free mice, rested, and then re-challenged with Listeria monocytogenes expressing GP33-41. $T_{MEM}$ robustly expanded, and efficiently produced IFNγ. In contrast, both control- and anti-PD-L1-treated $T_{EX}$ mounted poor responses to Listeria-GP33 challenge and re-invigorated $T_{EX}$ were as defective as control $T_{EX}$ in these key properties.

After antigen withdrawal, $T_{EX}$ and anti-PD-L1-treated $T_{EX}$ failed to down-regulate PD-1, consistent with Pdcd1 locus DNA methylation and long-term expression of PD-1 (Youngblood et al. Immunity 2011, 35:400-412; Utzschneider et al. Nat. Immunol. 2013, 14:603-610; Angelosanto et al. J. Virol. 2012, 86:8161-8170). $T_{EX}$ also have lower global di-acetylated histone H3 (Zhang et al. Mol. Ther. 2014, 22:1698-1706), but how this relates to differentiation is unclear. To test whether the genome-wide epigenetic landscape of $T_{EX}$ may contribute to the lack of durable improvements following PD-1 pathway blockade, global chromatin landscape mapping was performed using ATAC-seq (Buenrostro, et al. Nat. Methods 2013, 10:1213-1218). The majority of open chromatin regions (OCRs) identified were in intergenic regions (33.3-43.3%) or introns (43.4-48.5%), as expected (Winter et al. J. Immunol. 2008,181:4832-4839). $T_{EFF}$, $T_{MEM}$, and $T_{EX}$ showed substantial chromatin remodeling compared to $T_N$ and genes with transcriptional start sites (TSS) within 20 kb of OCRs tended to be more highly expressed. OCRs at specific genes illustrated distinct patterns for $T_{EFF}$, $T_{MEM}$ and $T_{EX}$. For example, $T_{EX}$ lacked several OCRs present the Ifng locus in $T_{EFF}$ and $T_{MEM}$. Similarly, for Pdcd1, $T_{EX}$-specific OCRs were identified in the "B" and "C" regions (Staron et al. 2014, Immunity 41:802-814; Oestreich, et al. J. Immunol. 2008, 181:4832-4839; Kao et al. Nat. Immunol. 2011, 12:663-671) and a previously unidentified OCR ~23 kb from the TSS. Global hierarchical clustering and co-cluster analysis showed that $T_{EFF}$ and $T_{MEM}$ were more similar to each other than to $T_{EX}$ and that $T_{EX}$ had a distinct global epigenetic landscape. These data suggest that $T_{EX}$ may represent a distinct lineage of CD8 T cells.

Two subsets of $T_{EX}$ have been defined based on expression of Eomes, T-bet and PD-1 (Paley et al. Science 2012, 338:1220-1225; Blackburn, et al. Proc. Natl. Acad. Sci. U.S.A. 2008, 105:15016-15021) and additional heterogeneity has recently been described (He, et al. Nature 2016, 537:412-428; Im, et al. Nature 2016, 537:417-421; Utzschneider, et al. Immunity 2016, 45:415-427). The T-bet$^{hi}$Eomes$^{lo}$PD-1$^{int}$ subset can be re-invigorated by PD-1 pathway blockade while the Eomes$^{hi}$PD-1$^{hi}$ subset is more terminal and responds poorly to blocking PD-1 (Paley et al. Science 2012, 338:1220-1225; Blackburn, et al. Proc. Natl. Acad. Sci. U.S.A. 2008, 105:15016-15021). Here, T$_{EX}$ were ~80% Eomes$^{hi}$ and ~20% T-bet$^{hi}$, and this distribution changed minimally upon anti-PD-L1 treatment. The transcriptional and epigenetic profiles of T$_{EX}$ and anti-PD-L1-treated T$_{EX}$ were significantly enriched for genes from the Eomes$^{hi}$ subset (Doering, et al. Immunity 2012, 37:1130-1144). However, there was also a trend toward enrichment of genes from the PD-1$^{int}$Tbet$^{hi}$T$_{EX}$ subset in the anti-PD-L1-treated group, perhaps reflecting recent conversion of Tbet$^{hi}$ cells into Eomes$^{hi}$ cells or additional heterogeneity.

Next, the ability of PD-1 pathway blockade to reprogram the epigenetic landscape of T$_{EX}$ was examined. Hierarchical clustering, co-clustering, and principle component analysis showed considerable similarity between control and anti-PD-L1-treated T$_{EX}$. OCRs preferentially found in both T$_{EX}$ and anti-PD-L1-treated T$_{EX}$ were located near Pdcd1, Il10, Ctla4, Cxcr5 and elsewhere suggesting state-specific regulation that was not substantially altered following PD-L1 blockade. While globally the epigenetic changes were modest, co-cluster analysis identified a small subset of OCRs uniquely enriched in T$_{EX}$ (555 peaks) or anti-PD-L1-treated T$_{EX}$ (98 peaks) (FIGS. 10H to 10I; FIG. 16; and Pauken et al. Table S7 (Pauken et al. Science 2016, 354(6316):1160-1165)). Some of these genes showed the same trend epigenetically and transcriptionally (e.g., CD200r) and specific biological pathways were enriched in sets of genes near OCRs that changed.

Figure 19A:
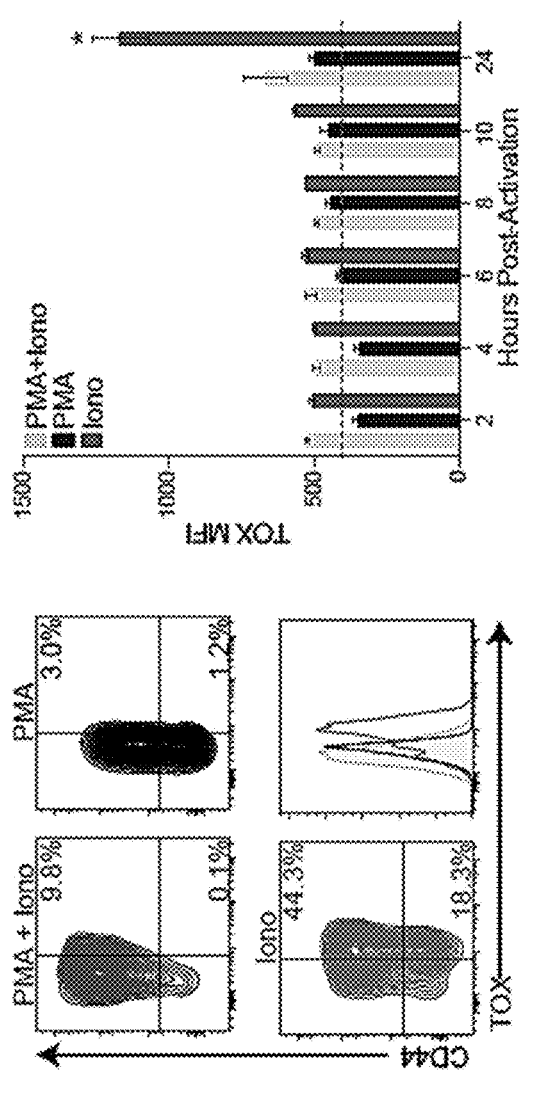
FIGS. 19A-19G illustrate that calcineurin signaling and NFAT2 are necessary and sufficient to induce TOX, but sustained expression becomes calcineurin independent.
Figure 19B:
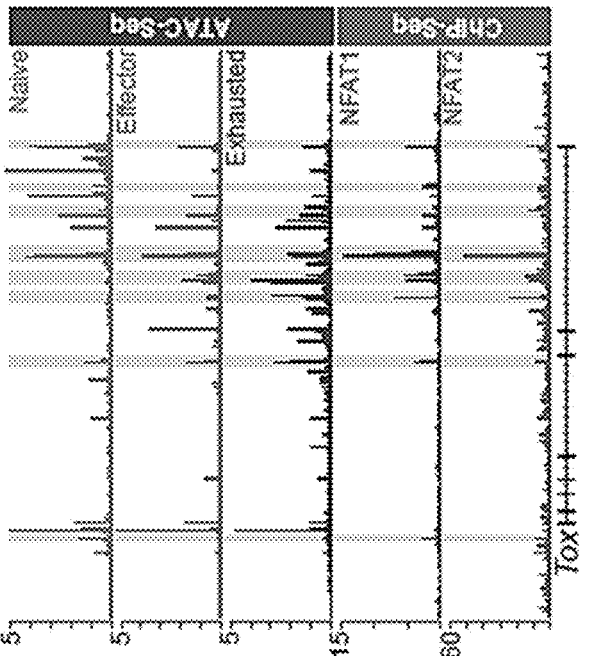

Example 4. Differential Transcription Factor Binding Following PD-1 Pathway Blockade Contributes to an Altered Transcriptional Network During T$_{EX}$ Re-Invigoration T$_{EX}$ displayed ~6000 unique OCR changes compared to T$_{EFF}$ and T$_{MEM}$ (FIGS. 10F to 10I). Thus, the ~650 OCR changes induced by PD-L1 blockade was modest by comparison. To determine whether these changes impacted specific transcriptional circuits, transcription factor (TF) motifs enriched in peaks gained (e.g., NFκB, Jun:AP1, and CTCF) or lost were identified (e.g., NFATc1, NFAT:AP1, Nur77, Eomes and Egr2). To test whether re-invigoration resulted from rewired transcriptional control within the existing T$_{EX}$ epigenetic landscape, Wellington bootstrap analysis was performed to predict TF binding activity (FIG. 19B and Pauken et al. Table S10 (Pauken et al. Science 2016, 354(6316):1160-1165)). T$_{EX}$ and anti-PD-L1-treated T$_{EX}$ were more similar to each other than to T$_N$, T$_{EFF}$ or T$_{MEM}$. However, TF motifs biased toward T$_{EX}$ or anti-PD-L1-treated T$_{EX}$ were identified (FIG. 19B and Pauken et al. Table S10 (Pauken et al. Science 2016, 354(6316):1160-1165)). TF footprinting was then performed to identify TFs with evidence of likely binding. An integrated network was then constructed for transcriptional circuitry based on predicted TF activity (Pauken et al. Table S11 (Pauken et al. Science 2016, 354(6316):1160-1165)). This network identified augmented activity of NFκB, IRFs, and bZip factors (AP-1 family) and decreased activity of NFAT, Egr2, and Nur77 upon PD-L1 blockade. Major features of this transcriptional network were recapitulated using a second network approach where additional TF families were identified (e.g., Runx, Nr2f6, Prdm1, Rarb, Pparg.Rxra and homeobox TFs; and Pauken et al. Table S12 (Pauken et al. *Science* 2016, 354(6316):1160-1165)). To further interrogate how these changes might affect a specific TF, we examined NFAT. NFAT working with AP-1 transactivates many effector-phase genes. In contrast, "partnerless" NFAT that fails to bind AP-1 induces a subset of T$_{EX}$ genes (Martinez, et al. Immunity 2015, 42:265-278). Here, upon anti-PD-L1 treatment, there was significantly reduced expression of targets of partnerless NFAT in re-invigorated T$_{EX}$, suggesting a rewiring of this transcriptional circuit following blockade.

Together these data suggested that, while PD-1 pathway blockade did not fully reprogram T$_{EX}$ into T$_{MEM}$ or T$_{EFF}$, these cells may (re)acquire some features of T$_{EFF}$ biology. One hypothesis is that upon PD-L1 blockade the rewired transcriptional network allows T$_{EX}$ to preferentially re-engage features of their epigenomic program that overlap with T$_{EFF}$. To test this idea, we separated TF target genes into those containing OCRs that were: a) unique to T$_{EFF}$; b) unique to T$_{EX}$; or c) shared between T$_{EFF}$ and T$_{EX}$. We then examined the change in genes expressed in each category following PD-L1 blockade. For several TFs including T-bet and Eomes there was no redistribution of the pattern of target gene expression (FIG. 1-9F). However, for many TFs identified above that have a key role in effector biology such as NFκB, IRF1, IRF2, Nur77 and Blimp-1 (encoded by Prdm1), there was an increase in the number of target genes expressed in the T$_{EFF}$ and T$_{EX}$ overlap group compared to the T$_{EX}$—only group upon PD-L1 blockade. Moreover, genes in the shared T$_{EFF}$ and T$_{EX}$ epigenetic module displayed a substantially greater magnitude of change in expression than genes in the T$_{EX}$ only group. These data indicate that PD-1 pathway blockade induces rewired transcriptional activity allowing T$_{EX}$ to more effectively re-engage modules of effector genes contained within the epigenetic landscape of T$_{EX}$. Specific TF circuits altered such as NFκB may have implications for co-targeting PD-1 and TNFR family pathways (Wherry et al. Nat. Rev. Immunol. 2015, 15:486-499; Sharma et al. Science 2015, 348:56-61; Ward-Kavanagh, et al. Immunity 2016, 44:1005-1019) and may be relevant for design of future therapeutics.

The data above demonstrates that in settings of severe T cell exhaustion, re-acquiring durable immune memory may be challenging, especially if tumor or viral antigen persists. However, the data also indicates that PD-1 pathway blockade may reveal opportunities to further augment T cell quality or effector activity (e.g., NFκB, IL-7R). Additional strategies such as priming new T cell responses (Sharma et al. Science 2015, 348:56-61), selectively expanding less exhausted subsets (Blackburn, et al. Proc. Natl. Acad. Sci. U.S.A. 2008, 105:15016-15021), or targeting multiple immunoregulatory or homeostatic pathways (e.g., IL-7, IL-2) simultaneously (Wherry et al. Nat. Rev. Immunol. 2015, 15:486-499; Sharma et al. Science 2015, 348:56-61) may also augment acquisition of durable immunity. These studies provide the impetus for extending epigenetic landscape mapping to human T$_{EX}$, future evaluation of checkpoint blockade combined with epigenetic modifiers, or epigenomic engineering for T cells. Thus, integrated cellular, transcriptional and epigenetic profiling of T$_{EX}$ not only reveals mechanistic insights into PD-1 pathway blockade mediated re-invigoration, but also points to key opportunities to improve long-term durability of these effects.

Example 5. CD8 T Cells Responding to Anti-PD-1 Therapy Display an Exhausted Phenotype Healthy donor versus melanoma patients were compared. Twenty-nine patients with stage IV melanoma treated with the anti-PD-1 antibody pembrolizumab (pembro) were enrolled the clinical trial described herein. All patients had previously received anti-CTLA-4 therapy. Patients were treated with pembro, and blood was obtained before therapy and every 3 weeks during therapy for a total of 12 weeks. 62% of patients did not have an objective clinical response, determined on the basis of immune RECIST (response evaluation criteria in solid tumors) criteria, consistent with published trials (Robert et al. N. Engl. J. Med. 2015, 372:2521-2532; Ribas et al. Lancet Oncol. 2015, 16:908-918).

Peripheral blood T cells from patients with melanoma were first compared to those from age-matched healthy donors using high-dimensional flow cytometry. The frequencies of CD4 and CD8 T cells, memory T-cell subsets, and CD4 and CD8 T-cell co-expression of inhibitory receptors (PD-1, CTLA-4, 2B4, and TIM-3) were similar (data not shown). However, patients with melanoma had a higher frequency of CD4$^+$FOXP3$^+$ T cells and Ki67 expression by FOXP3$^+$ cells. Ki67 expression was also increased in CD8 T cells from patients with melanoma (P<0.0001), predominantly in the PD-1$^+$ CD8 T-cell subset (P<0.0001), suggesting a pre-existing immune response.

Figure 24:
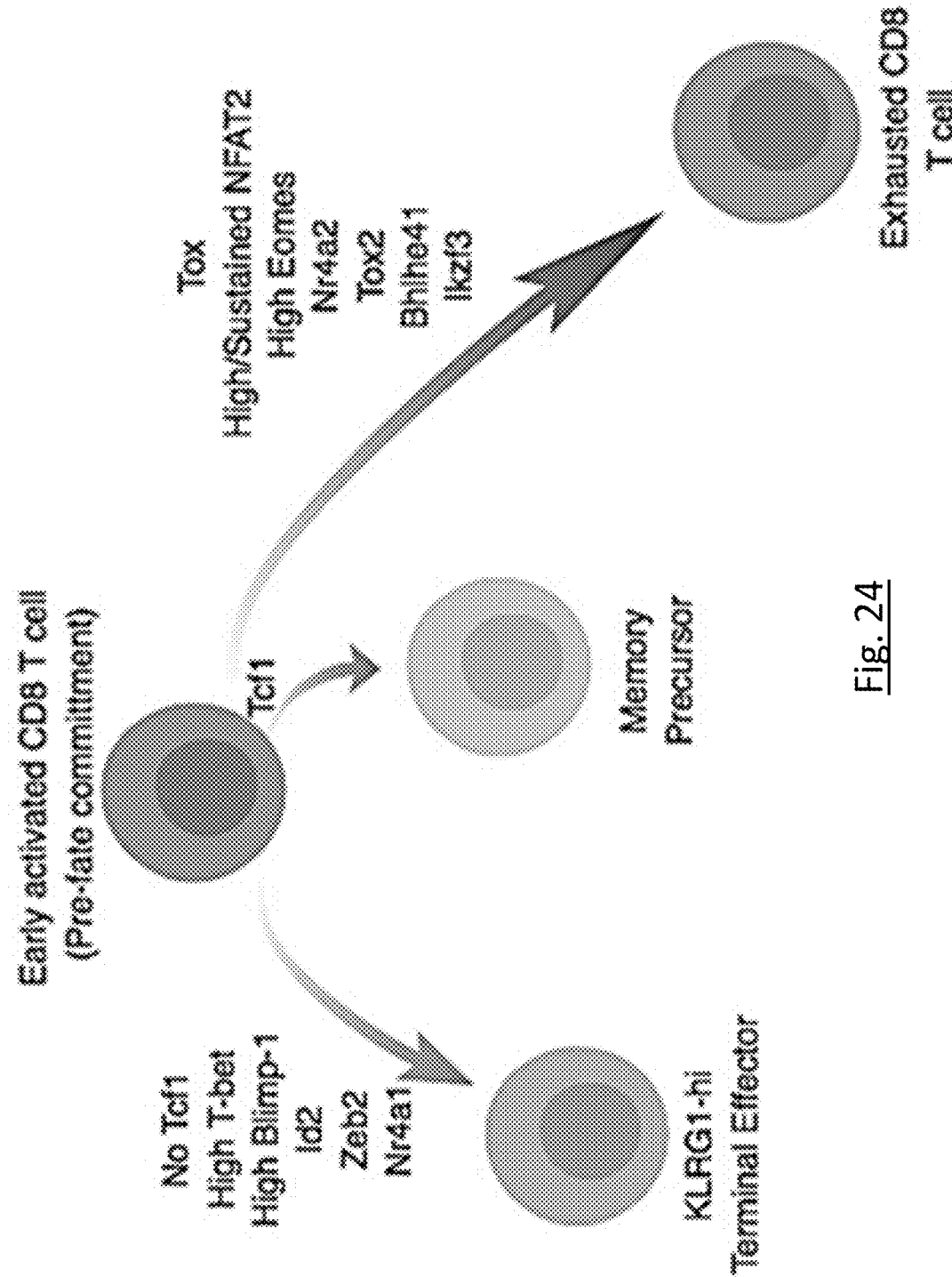
FIG. 24 illustrates factors involved in T cell fate decisions towards or away from exhaustion.

A pharmacodynamic immune response to anti-PD-1 was observed. Ki67 is a marker of cellular proliferation and T-cell reinvigoration in mouse models upon checkpoint blockade (Blackburn et al. Nat. Immunol. 2009, 10:29-37), as well as in humans receiving anti-CTLA-4 treatment plus radiation (Twyman-Saint Victor et al. *Nature* 2015, 520:373-377). Thus, changes in Ki67 expression were examined in more detail. Indeed, the frequency of Ki67$^-$ CD8 T cells was increased at 3 weeks after pembro treatment and then declined in most patients. The responding Ki67$^+$ CD8 T-cell population was largely CD45RA$^{lo}$CD27$^{hi}$ and contained cells with high expression of CTLA-4, 2B4, and PD-1 (FIG. 24C) (using an anti-IgG4 detection approach (Brahmer et al. *J. Clin. Oncol.* 2010, 28:3167-3175, see Methods). Moreover, the responding Ki67$^+$ cells were Eomes$^{hi}$ and T-bet$^{lo}$ (P<0.0001), consistent with the phenotype of T$_{EX}$ cells (Blackburn, et al. Nat. Immunol. 2009, 10:29-37; Paley, et al. Science 2012, 338:1220-1225). In contrast, the Ki67T population in healthy donors was largely Eomes$^{hi}$T-bet$^{hi}$ and CD27$^{10}$, consistent with an effector phenotype. In addition to CD8 T cells, Ki67 increased in FOXP3$^-$ CD4 T cells and FOXP3$^+$ CD4 T cells following pembro treatment, mainly in the PD-1$^+$ subset of each population. Neither FOXP3$^-$ nor FOXP3$^-$ CD4 T-cell responses correlated with clinical outcome.

The increase in Ki67 expression was most prominent in the PD-1$^+$ versus PD-1$^-$ CD8 T cells (P<0.0001). Moreover, this Ki67 response in the PD-1$^+$ subset peaked at 3 weeks after treatment compared to the PD-1$^-$ subset (P<0.0001). The time since last dose of anti-CTLA-4 therapy did not correlate with subsequent post-pembro Ki67 levels or treatment response, suggesting that the immunologic response observed in this instance was mainly due to anti-PD-1 therapy. In healthy donors, Ki67 expression by PD-1$^+$ CD8 T cells varied little over 3 weeks, changing 1.1-fold±0.37. In contrast, the majority of patients with melanoma (20 out of 27) had a biologically meaningful increase in Ki67 in their PD-1$^+$ CD8 T cells after treatment. Despite this 74% immunologic response rate, only 38% achieved a clinical response, indicating that not all patients with an immunologic response to pembro have clinical benefit.

Example 6. Exhausted-Phenotype CD8 T Cells are Preferentially Reinvigorated by Anti-PD-1 Therapy Reinvigorated T$_{EX}$ cells were detected in peripheral blood. Next, it was assessed whether CD8 T cells that co-expressed PD-1 and other inhibitory receptors provided greater precision in tracking the pharmacodynamic effects of PD-1 blockade. Circulating populations of PD-1$^+$CTLA-4$^+$ CD8 T cells were largely Eomes$^{hi}$T-bet$^{lo}$ and CD45RA$^{10}$CD27$^{hi}$. Furthermore, around 50% of PD-1$^+$ CTLA-4$^+$ cells expressed Ki67 before treatment, consistent with data on T$_{EX}$ cells in mice (Paley et al. Science 2012, 338:1220-1225), and this increased to around 75% after treatment. There was substantially lower Ki67 expression in the PD-1$^+$CTLA-4$^-$ T cells. Addition of a third inhibitory receptor (for example, 2B4) or focusing on the recently described PD-1$^+$CXCR5$^+$TCF-1$^+$ subset (Im et al. Nature 2016, 537:417-421; He et al. Nature 2016, 537:412-416) further enriched for cells responding to anti-PD-1 therapy.

Example 7. Tumor-Infiltrating T-Cell Clones in Responding Peripheral Blood CD8 T-Cell Population and Blood Ki67T CD8 T-Cell Response Correlates with Tumor Burden Responding T-cell clones from blood were found in tumor. Both neoantigen- and shared-antigen-specific T cells have been identified in the circulating PD-1V CD8 T-cell population (Gros et al. Nat. Med. 2016, 22:433-438). Moreover, there is clonal overlap between these cells in the blood and tumor-infiltrating T cells (Gros et al. Nat. Med. 2016, 22:433-438). To explore these relationships following anti-PD-1 therapy, CD8 T cells from the blood were sorted at the peak of Ki67 expression after treatment from three responders and three non-responders, and the T-cell receptor (TCR) repertoire was compared to pretreatment tumor-infiltrating T cells. Many of the top 10 tumor-infiltrating T-cell clones were readily identifiable in the blood and after therapy, including the two most abundant clones by frequency in all cases, regardless of clinical response (Table 2).

It was then determined whether these shared clones were present in the population responding to anti-PD-1 therapy. To avoid permeabilization, responding cells were sorted using expression of HLA-DR and CD38 (Miller et al. Immunity 2008, 28:710-722), rather than Ki67. Approximately 80% (mean, 80.1%) of the HLA-DR$^+$CD38$^+$ CD8 T cells expressed Ki67, and these HLA-DR$^+$CD38$^+$ cells responded with similar kinetics as Ki67T CD8 T cells (FIGS. 31B-31D). RNA-seq identified HLA-DRB1 and CD38 among the top 50 correlates of Ki67 (Table 1) and these HLA-DR$^+$CD38$^+$ cells were enriched for markers of T$_{EX}$ cells. Across six patients, 14 clones were present among the top 10 clones in both the tumor and blood. All of these (14 out of 14) were HLA-DR$^+$CD38$^+$ in the blood. Extending to the top 100 clones, 18 out of 19 clones shared between blood and tumor were HLA-DR$^+$CD38$^+$, whereas a mixture of activated and resting phenotype was found for clones that were only found in the blood and not tumor. These observations support the notion that Ki67T (HLA-DR$^+$CD38$^+$) T$_{EX}$ cells in the blood are reinvigorated by anti-PD-1 therapy and contain T-cell clones that are also present in the tumor.

It was demonstrated that T-cell reinvigoration correlates with tumor burden. Antigen burden is a key determinant of the severity of exhaustion and reinvigoration of T$_{EX}$ cells by PD-1 therapy in preclinical models (Blackburn et al. Nat. Immunol. 2009, 10:29-37; Wherry et al. J. Virol. 2003, 77:4911-4927). To test this idea in patients with melanoma, we developed a practical approach to estimate antigen burden using all measurable tumor lesions on the pretreatment imaging scan (tumor burden, see Methods). Indeed, higher tumor burden was associated with more Ki67$^+$ CD8 T cells both before and after therapy. Random forest modelling of 39 immune parameters at 3 weeks showed that Ki67$^+$ CD8 T cells were the strongest correlate of tumor burden. This correlation was also detectable before treatment, but became stronger after treatment, suggesting a pre-existing CD8 T-cell response related to tumor burden, augmented by anti-PD-1 therapy.

Example 8. Tracking CD8 T-Cell Reinvigoration in Context of Tumor Burden Predicts Response to Anti-PD-1 Therapy It is demonstrated herein that reinvigoration/tumor ratio affects clinical outcome. It was possible that larger baseline immune responses would correlate with clinical response. However, higher pretreatment Ki67 levels in PD-1$^+$ CD8 T cells were in fact an indicator of poor prognosis. A larger immune response before treatment may reflect higher tumor burden that itself is a poor prognostic indicator. Indeed patients who progressed on anti-PD-1 therapy had evidence of systemic inflammation at baseline. Random forest analysis showed that Ki67 alone did not correlate with clinical outcome (data not shown). We therefore hypothesized that it was not the absolute magnitude of reinvigoration that mattered, but rather that the ratio of $T_{EX}$-cell reinvigoration to tumor burden might better predict clinical response. To test this, we examined clinical responses in relation to the fold change of PD-1$^+$Ki67$^+$ CD8 T cells after anti-PD-1 therapy, adjusted for baseline tumor burden. Patients with longer progression-free survival (PFS) generally had a low tumor burden and clustered above the fold change of PD-1$^+$Ki67$^+$ CD8 T cells to tumor-burden regression line, suggesting that the ratio of $T_{EX}$-cell reinvigoration to tumor burden may be associated with clinical outcome. Moreover, instead of fold change that required measurements both before and after treatment, a higher ratio of Ki67$^+$ CD8 T cells to tumor burden at the post-treatment peak T-cell-response time point was associated with better clinical outcomes. Responders clustered above the PD-1$^+$ Ki67$^+$ cell to tumor-burden regression line, whereas non-responders largely fell below. Classification and regression tree (CART) analysis identified a Ki67 to tumor burden ratio of 1.94 that segregated patients by clinical outcomes as early as 6 weeks into therapy. A Ki67 to tumor burden ratio greater than 1.94 at 6 weeks was associated with better outcome by objective response rate, PFS and overall survival.

Other variables were examined by multivariate regression modelling, implicating additional roles for BRAF status that may be related to tumor-infiltrating lymphocytes upon BRAF inhibition (Wilmott et al. Clin. Cancer Res. 2012, 18:1386-1394; Knight et al. *J. Clin.* Invest. 2013, 123:1371-1381) and lactate dehydrogenase, a potential circulating proxy for tumor burden and known negative-prognostic indicator in stage IV melanoma (Balch et al. J. Clin. Oncol. 2009, 27:6199-6206). Moreover, data from a subset of patients also suggested a role for PD-L1 expression in the tumor and mutational burden, consistent with published observations (Herbst et al. Nature 2014, 515:563-567; Tumeh et al. Nature 2014, 515:568-571; Rizvi et al. Science 2015, 348:124-128). Thus, extending this modelling to include other variables will be important in the future.

Demonstrated herein are several findings relevant to the understanding of response to PD-1 blockade in patients with advanced melanoma. First, most patients have an on-target immunological effect of PD-1 blockade on CD8 T cells and this effect can be detected, longitudinally monitored and mechanistically interrogated in the peripheral blood. Second, $T_{EX}$ cells were identified as a major target of PD-1 blockade in most patients with melanoma, allowing us to develop a reinvigoration score by relating changes in circulating $T_{EX}$ cells to tumor burden. Third, most patients have a single peak of PD-1-blockade-induced immune reinvigoration, despite ongoing treatment. Fourth, these responding $T_{EX}$ cells in the blood contain TCR clonotypes shared with tumor-infiltrating T cells. Finally, we identify that the ratio of $T_{EX}$-cell reinvigoration to tumor burden can distinguish clinical outcomes and predict response. The relationship between $T_{EX}$-cell reinvigoration and tumor burden suggests a calibration of immune responses to antigen burden and raises the possibility that even robust reinvigoration by anti-PD-1 therapy may be clinically ineffective if the tumor burden is high. On the basis of these observations, it may be possible to delineate classes of predicted therapeutic failures. Tumor burden alone is not a perfect predictor of response to anti-PD-1 therapy and it has been challenging to define on-treatment predictive markers. An on-treatment biomarker is not only valuable in helping to define clinical responses as early as possible, but also in informing the type of immunological failure and tailor subsequent therapies. It is likely that other parameters such as anatomical location of metastases, PD-L1 expression and mutational phenotype will add further resolution to this relationship between T-cell reinvigoration and tumor burden. Recognizing, on the basis of tumor burden, that the amount of reinvigoration induced by PD-1 blockade in a given patient may be inadequate allows for early clinical intervention, for example with additional immune or targeted therapies (Sharma et al. Cell 2015, 161:205-214; Smyth et al. Nat. Rev. Clin. Oncol. 2016, 13:143-158). It will be important to test if the approaches reported here can be extended to other, especially less immunogenic, tumor types. However, the current study not only illustrates the on-target pharmacodynamic immune effect of PD-1 blockade and utility of blood-based immune monitoring, but also identifies a potential novel predictive biomarker and a framework for future mechanistic dissection by revealing the relationship between overall tumor burden and magnitude of immune reinvigoration by PD-1 blockade.

Example 9. Adoptive Transfer of TET2cKO Cells

To evaluate the consequence of TET2 loss in CD8+ T cells in chronic viral infection we turned to an adoptive transfer approach. Equal numbers of wild-type or TET2cKO P14 CD8$^+$ T cells were adoptively transferred into congenic (CD45.1$^+$) hosts that were subsequently infected with LCMV clone 13. Mice were analyzed at day 16 post infection. CD8+D$^b$GP276 tetramer+ T cells from the spleens of infected mice were identified and the frequency of donor cells within this population was determined. There was a significantly higher frequency of TET2cKO donor cells compared to wild-type donor cells in the spleens of host mice at this time point. The difference in absolute number of these cells trended higher in the spleen. It will be important to evaluate other organs to determine the absolute change in the expansion of wild-type versus TET2 deficient cells. These data suggest there may be a proliferative or survival advantage for T cells lacking TET2 during chronic infection. In support of the former, we found that a significantly higher percentage of donor TET2cKO P14 cells were Ki67+ as compared to wild-type donor cells. Phenotypic analysis of these populations revealed a significantly increased frequency of TCF-1+ granzyme$^-$ CD8+ DbGP276 tetramer+ T cells among TET2cKO donor cells compared to their wild-type counterparts. The transcription factor TCF-1 is highly expressed in CD8+memory cells and its expression in the setting of chronic infection appears to mark those cells that sustain the exhausted T cell population and that is responsive to expansion following PD-1 blockade (Utzschneider et al. (2016) *Immunity* 45:415-27; Im et al. (2016) *Nature* 573: 417-431). Interestingly, these cells also express high levels of Ly6C, which is expressed on memory cells and shown to be downregulated on $T_{EX}$ cells (Wherry et al. (2007) *Immunity* 27:670-684). These data suggest the loss of TET2 in CD8+ T cells during chronic infection may favor the differentiation of a more memory-like pool, which may be advantageous in the setting of immune checkpoint blockade.

Figure 1C:
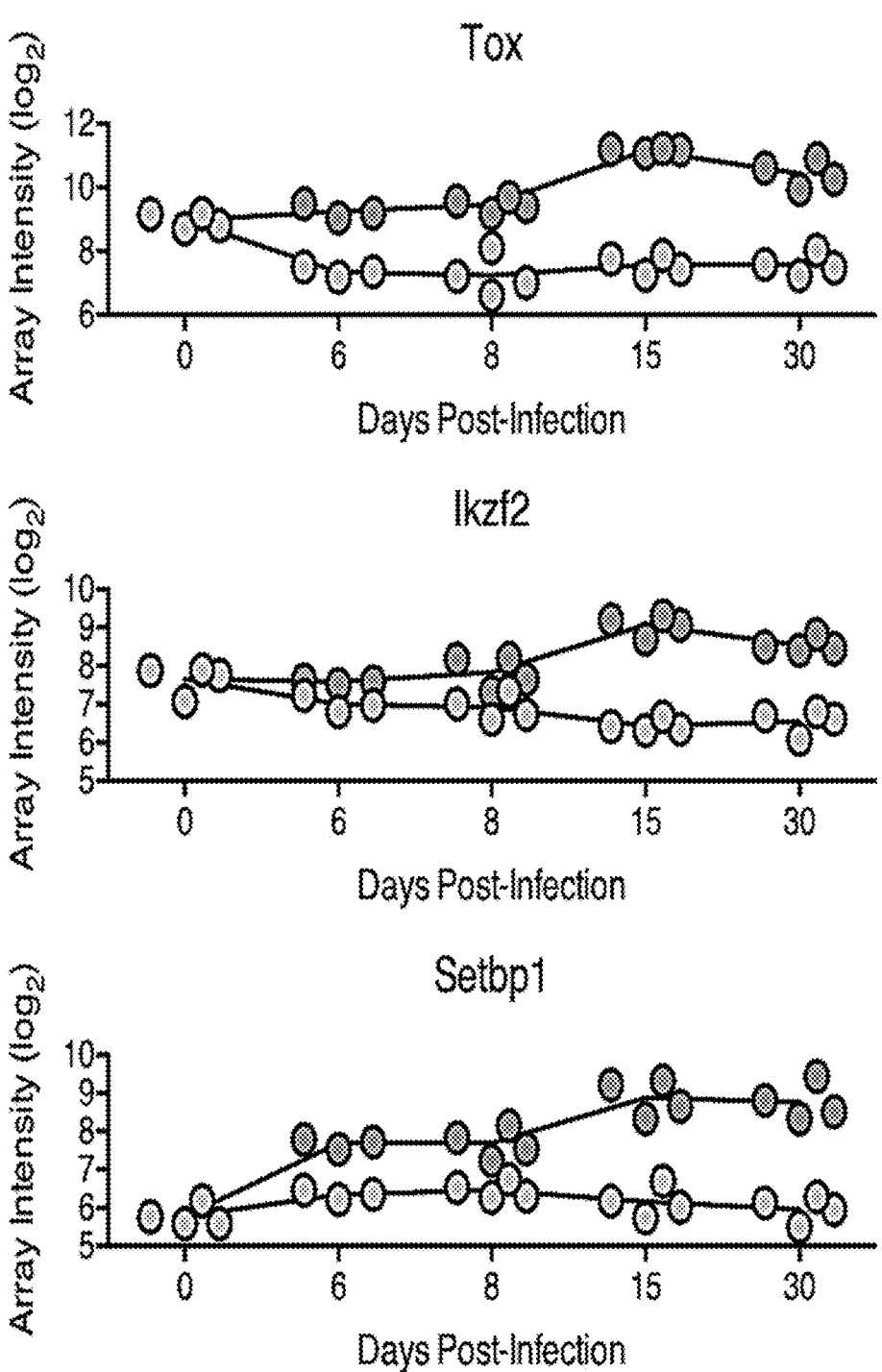
Figures 2A, 2B, 2C:
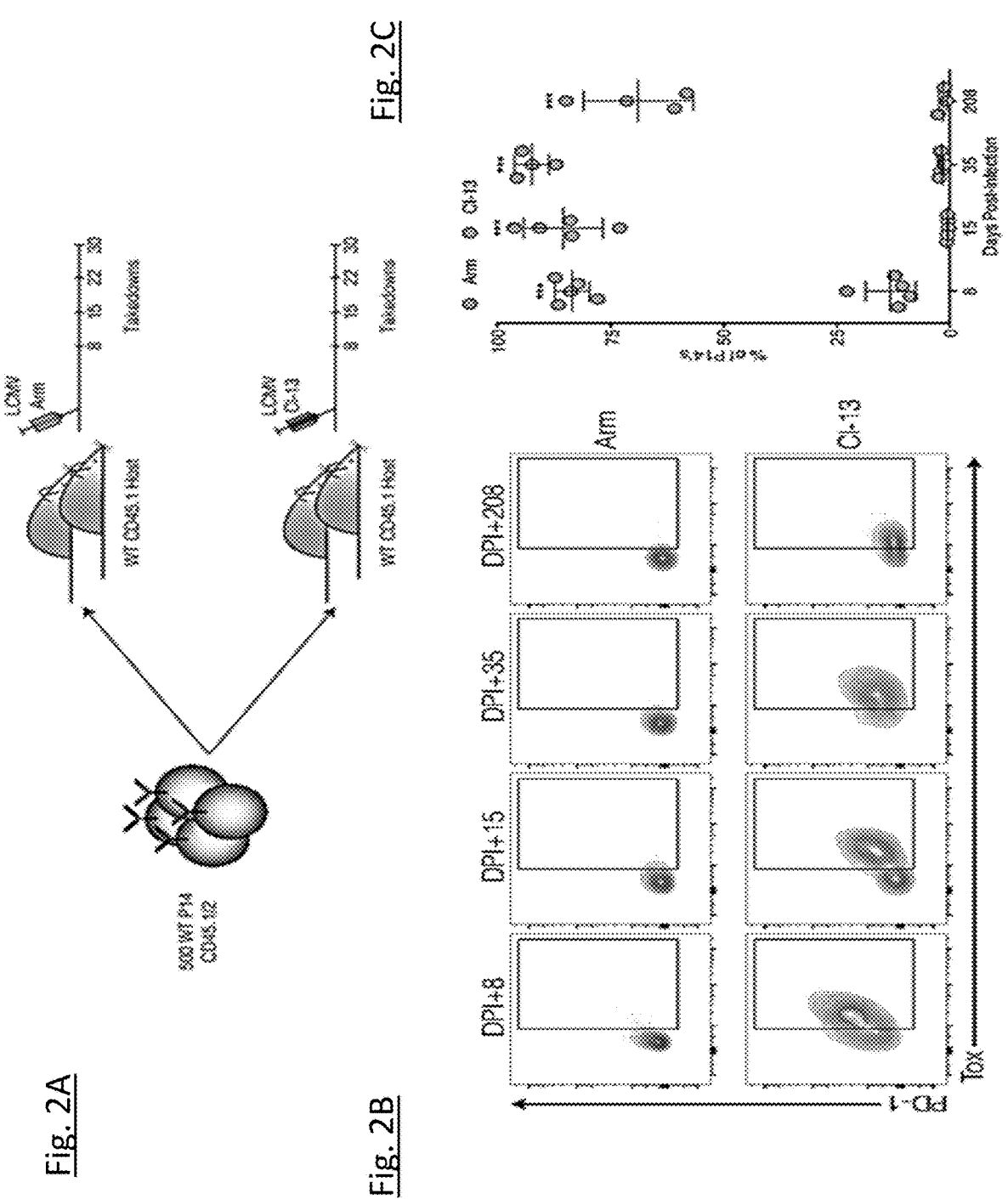
FIGS. 2A-2C illustrate that Tox expression is limited to chronic infection.

Example 10. Establishment and Maintenance of T Cell Exhaustion and Factors Involved in the Same To determine which genes with epigenetic function may play a significant role in T cell exhaustion, we utilized transcriptional data generated from P14 LCMV-specific CD8+ T cells exposed to acute or chronic variants of LCMV for 6, 8, 15 and 30 days. Genes were first filtered for those with at least one statistically significant pairwise comparison across all samples (FDR<0.05). These differentially expressed genes were filtered for those with chromatin modulating or binding function as determined by gene ontology association (GO Molecular Function: "chromatin binding", "nucleic acid binding", "nucleotide binding"; PantherDB Protein Classes: "DNA binding protein", "chromatin binding protein") and curated gene lists (Zuber et al. Nature Biotechnology. 2011, 29:79-83). Lastly, genes were filtered for minimum expression (array intensity of >6 in at least one sample) and fold change (one sample has at least a 2-fold increase in array intensity relative to all other samples). This resulted in a final list of 435 differentially expressed chromatin-modulating genes. A row-normalized heatmap of gene expression was then generated (FIG. 1A). Clustering was performed using Unweighted Pair Group Method with Arithmetic Mean on a Manhattan distance matrix. Cluster 4 genes were expressed specifically in exhausted T cells and include Tox, Ikzf2, Setbp1 (FIGS. 1B-1C). Through this analysis, we found Tox to be the most differentially expressed chromatin modulating gene. To confirm the expression results of the microarray, we utilized a P14 adoptive transfer approach to measure Tox protein expression during the course of acute and chronic infection. Five hundred P14 T cells were transferred into naïve hosts that were then infected with either LCMV Arm or Cl-13 (FIG. 2A). Flow cytometry analysis at days 8, 15, 35 and 208 post-infection suggest that Tox expression in CD8 T cells is limited to chronic infection (FIGS. 2B-2C). Indeed, Tox protein was never readily detectible in T cells exposed to acute infection.

Figure 3:
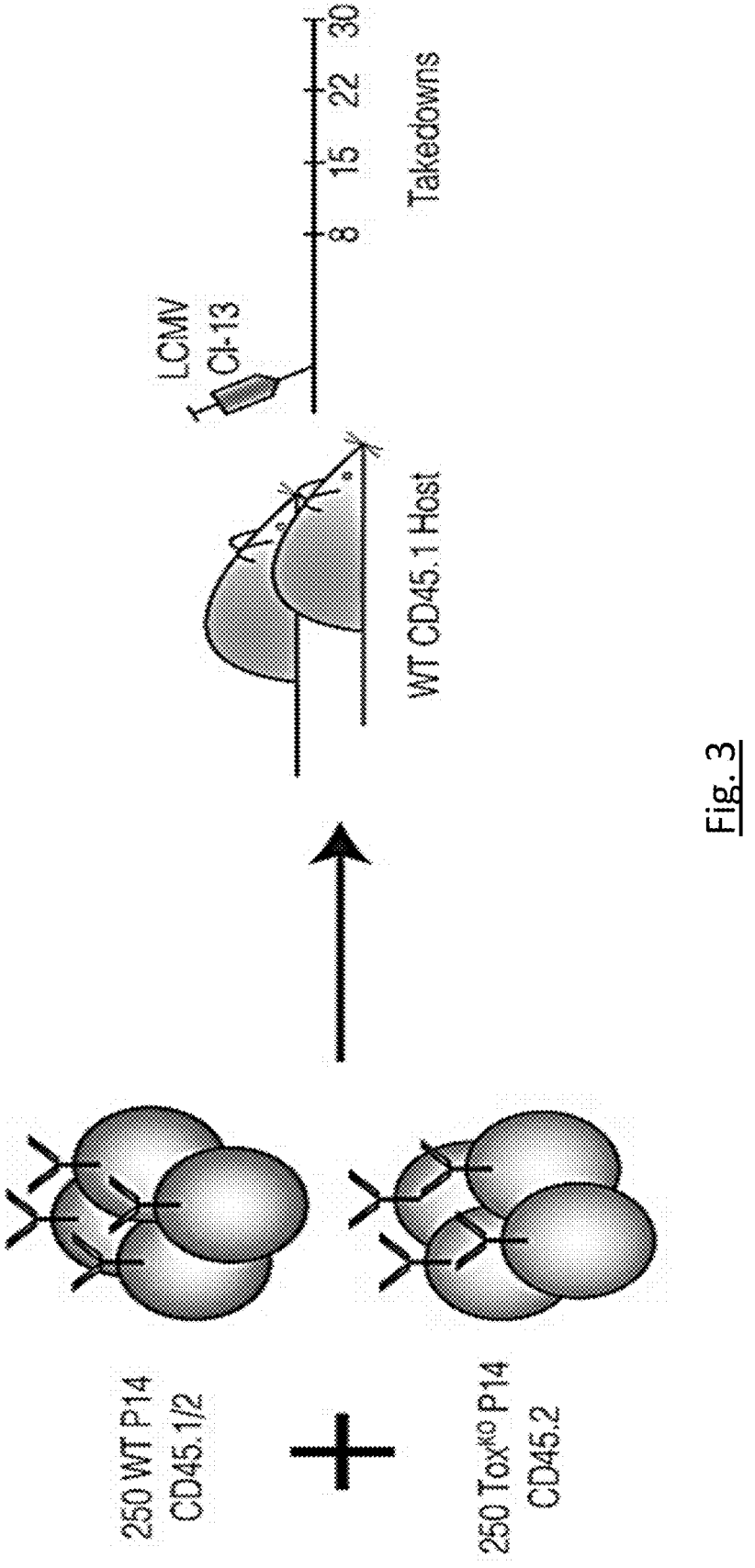
FIG. 3 illustrates a P14 co-transfer experimental model. Illustrated is a visual depiction of the model utilized to examine the behavior of Tox-deficient P14 T cells. 250 wildtype P14 T cells (WT) and 250 Tox$^{f/f}$ CD4$^{Cre+}$ P14 T cells (Tox$^{KO}$) were co-transferred into the same animal prior to infection with LCMV Cl-13. T cells from the spleen were then analyzed at the time-points indicated.
Figures 4A, 4B:
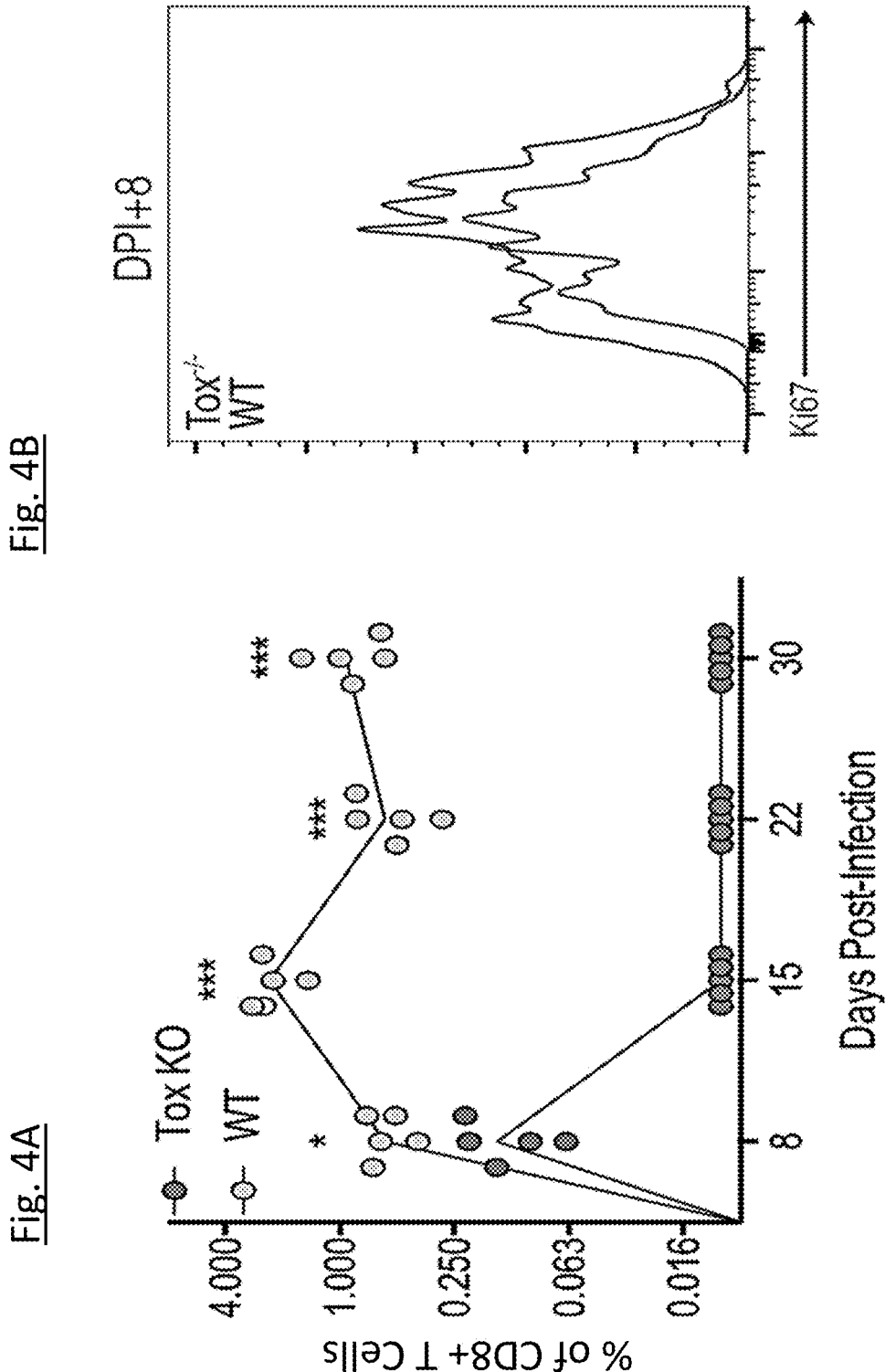
FIGS. 4A-4B illustrate that Tox-deficient T cells fail to persist during chronic infection.
Figures 5A, 5B:
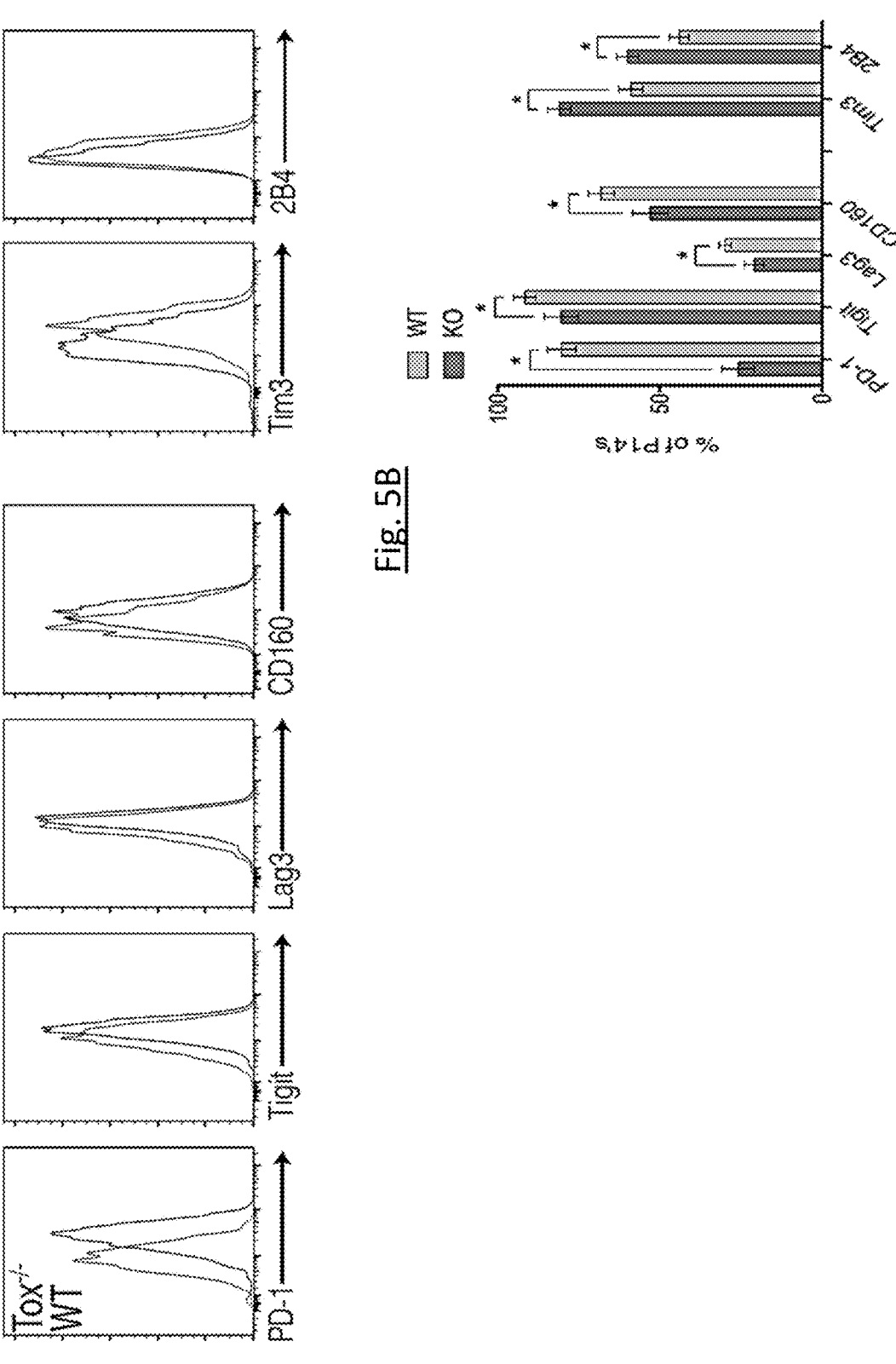
FIGS. 5A-5B illustrate that Tox deficiency results in the downregulation of multiple IRs.
Figures 6A, 6B:
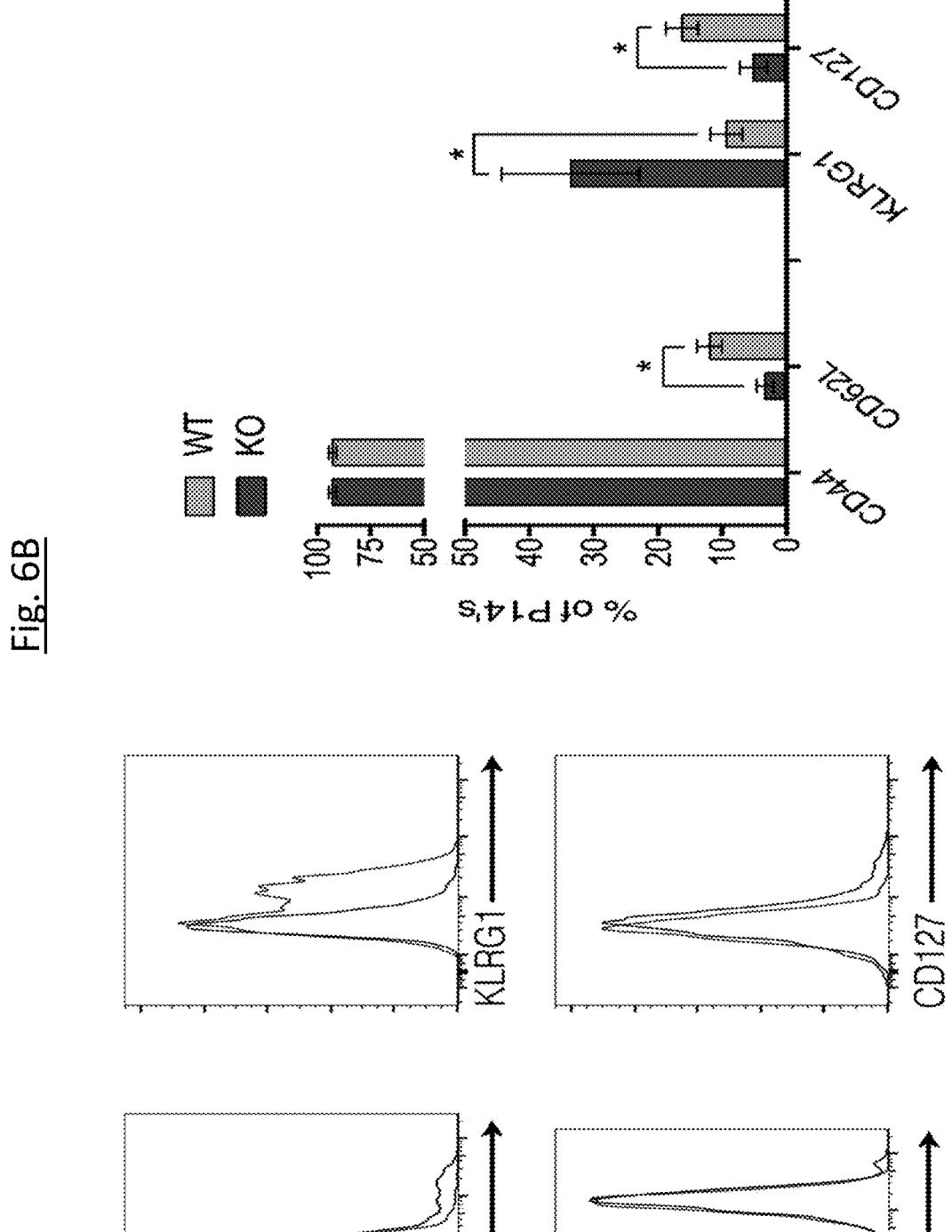
FIGS. 6A-6B illustrate that Tox represses terminal cell differentiation.
Figure 7B:
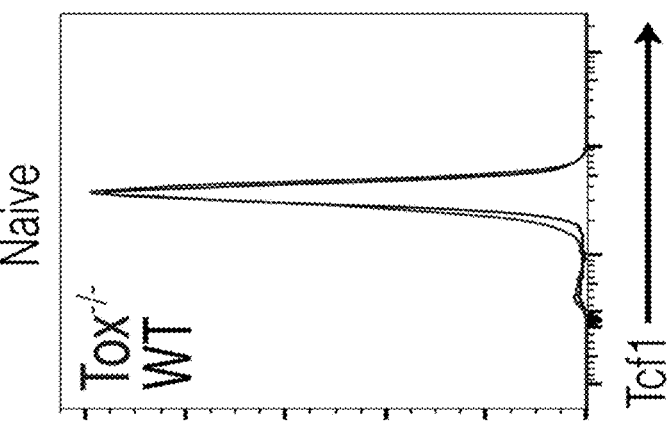
FIGS. 7A-7B illustrate that Tox is critical for the re-expression of Tcf1 in effector T cells.
Figure 7A:
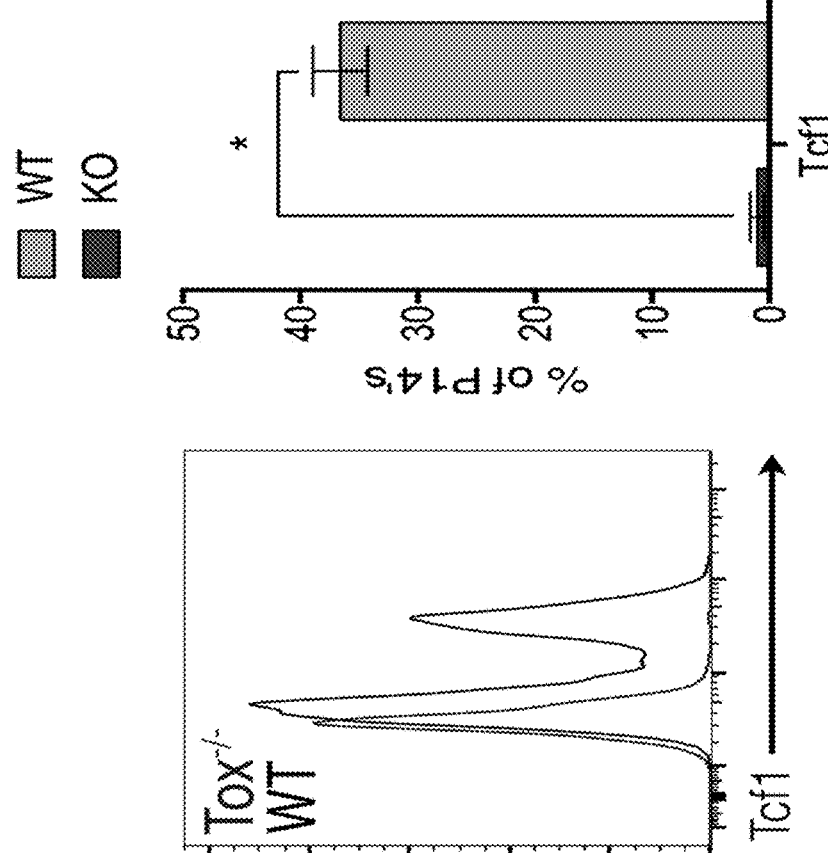

To examine the role of Tox in chronic infection, we transferred equal numbers of WT and Toxf/f CD4Cre+ P14 T cells into the same host prior to infection with LCMV Cl-13. T cells from the spleen of infected animals were then harvested at various timepoints and analyzed by flow cytometry (FIG. 3). Eight days post-infection Tox-deficient T cells proliferated and accumulated in response to chronic infection, but failed to do so to the same degree as WT T cells (FIG. 4A). Moreover, Tox-deficient T cells were dramatically depleted from Cl-13 infected animals within 15 days of infection (FIG. 4A). Interestingly, Ki-67 expression, a marker for recent cell division, was equivalent in WT and Tox-deficient T cells, suggesting that Tox may regulate the survival of T cells exposed to chronic infection (FIG. 4B). As inhibitory receptor expression during infection is critical to restrain T cell effector function and maintain prolonged responses, we next examined the expression of PD-1, Tigit, Lag3, CD160, Tim3, and 2B4 in WT and ToxKO T cells. Eight days post-infection, ToxKO cells failed to express PD-1, Tigit, Lag3, and CD160. Interestingly, expression of other inhibitory receptors, including Tim3 and 2B4, was increased in ToxKO T cells (FIGS. 5A-5B). As Tim3 and 2B4 are associated with terminal effector differentiation, we next examined the expression of surface memory and effector markers. Indeed, ToxKO T cells were enriched for a KLRG1+ terminally differentiated population relative to WT T cells. Moreover, ToxKO cells also failed to express CD62L or CD127, proteins associated with memory T cells (FIGS. 6A-6B). As transcription factors, such as Tcf1, play a critical role in suppressing terminal differentiation and maintaining long term T cell responses to chronic infection, we next examined whether ToxKO T cells regulated such pathways. Though we could not detect a difference in Tcf1 expression between WT and ToxKO naïve T cells, we found that Tox-deficient T cells failed to re-express Tcf1 8 days post-infection (FIGS. 7A-7B).

Figure 8:
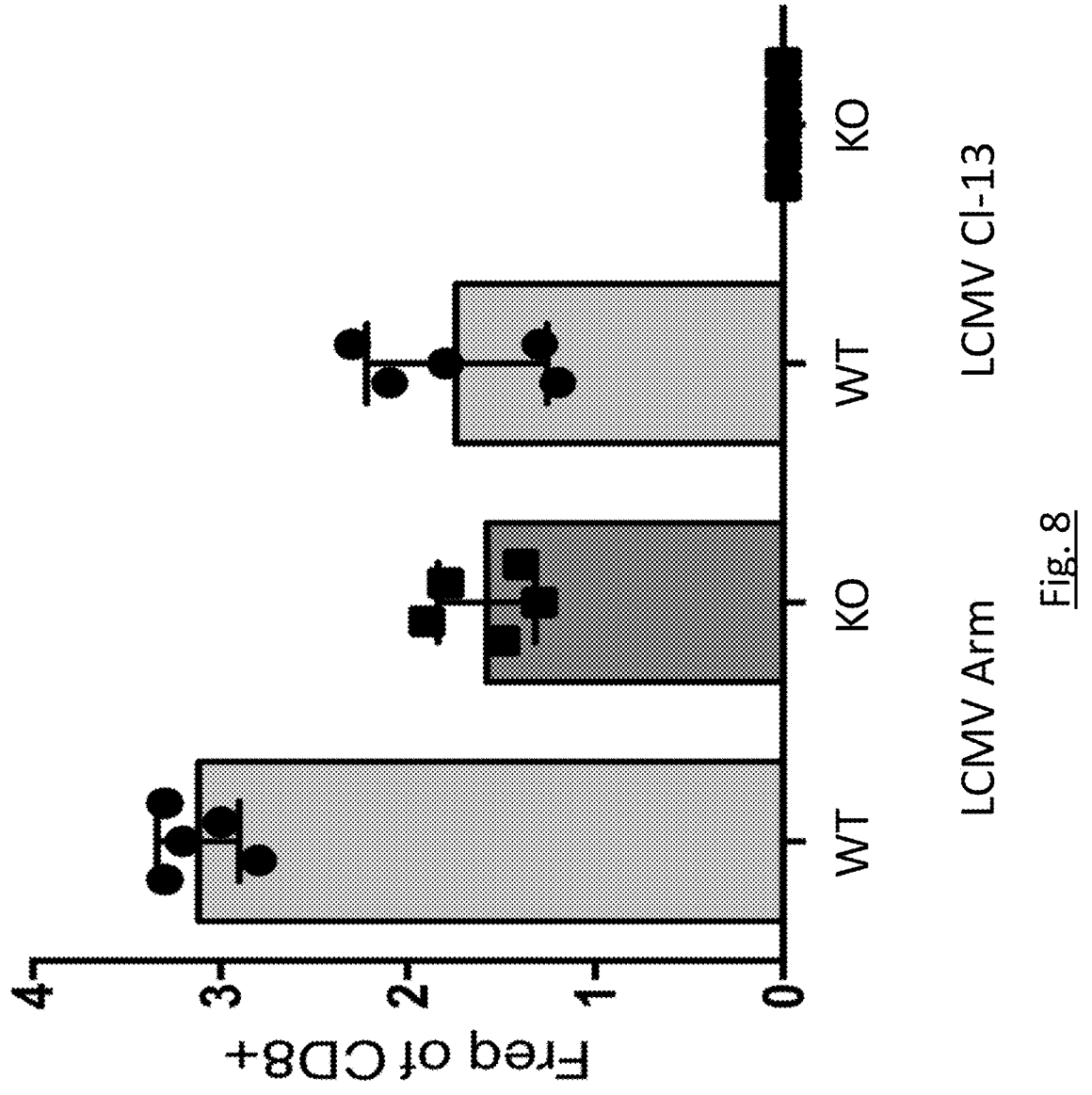
FIG. 8 depicts a graph illustrating that Tox expression is required to maintain the persistence of exhausted T cells. Illustrated is quantification of the frequency of $Ert2^{Cre+}$ P14 or $Tox^{f/f}Ert2^{Cre+}$ P14 T cells relative to the total splenic $CD8^+$ T cell pool in mice infected with LCMV Arm or Cl-13.

To elucidate whether Tox expression was also required for the maintenance of exhausted T cells, we utilized an adoptive co-transfer approach with WT and Toxf/f Ert2Cre+ P14 T cells. P14 T cells were transferred in equal amounts into hosts, which were then infected with LCMV Arm or Cl-13. From days 25-30 post-infection, hosts were treated with 2 mg of tamoxifen daily. Thirty-five days post-infection, the frequency of WT and Tox-depleted T cells was examined by flow cytometry. Loss of Tox expression in exhausted T cells resulted in a significant depletion of virus-specific P14 cells from tamoxifen-treated hosts (FIG. 8). In sum, these results suggest that Tox regulates T cell responses to chronic infection by inducing T cell exhaustion and maintaining virus-specific responses for prolonged periods of time.

Figure 9:
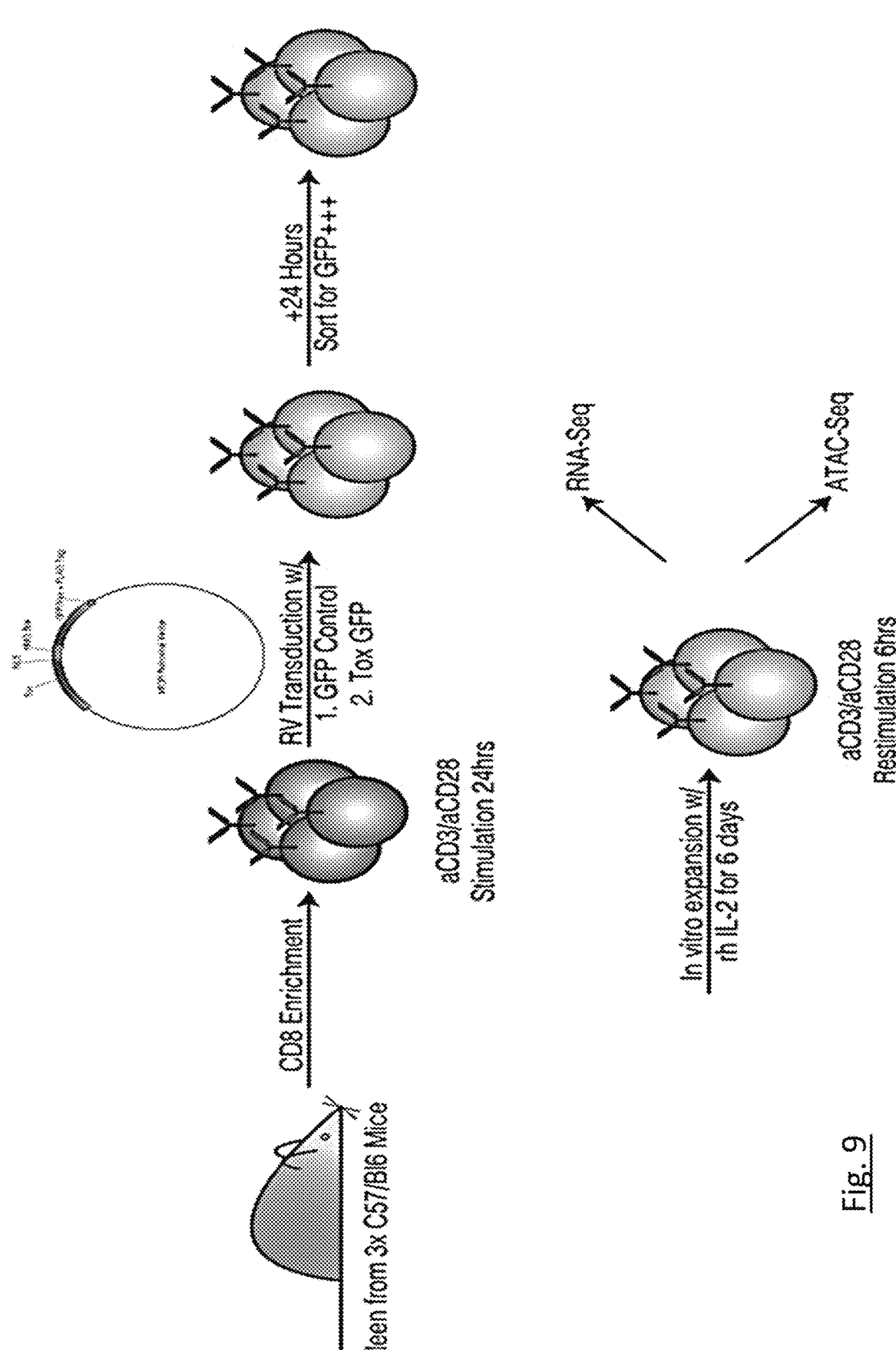
FIG. 9 depicts an experimental model for the in vitro overexpression of Tox. The model is used in some embodiments to examine the effect of Tox overexpression in in vitro-derived effector T cells. $CD8^+$ T cells were negatively enriched from the spleens of naïve WT mice, transduced with a retroviral vector encoding full-length Tox or a control vector and in vitro differentiated into effector T cells with high-dose IL-2. Six days post-activation, cells were restimulated by cross-linking CD3 and CD28 for 6 hours and subjected to RNA-Seq or ATAC-Seq.

To test whether ectopic expression of Tox was sufficient to drive exhaustion in T cells, we analyzed the transcriptional profile of naïve T cells transduced with a retroviral vector encoding Tox (FIG. 9). Over-expression of Tox resulted in the differential expression of over 2300 genes relative to T cells transduced with a control vector. Moreover, T cells over-expressing Tox were significantly enriched in genes upregulated in in vivo exhausted cells. Simultaneously, Tox expression strongly downregulated genes that are also downregulated in exhausted T cells (FIG. 10A).

Figure 11:
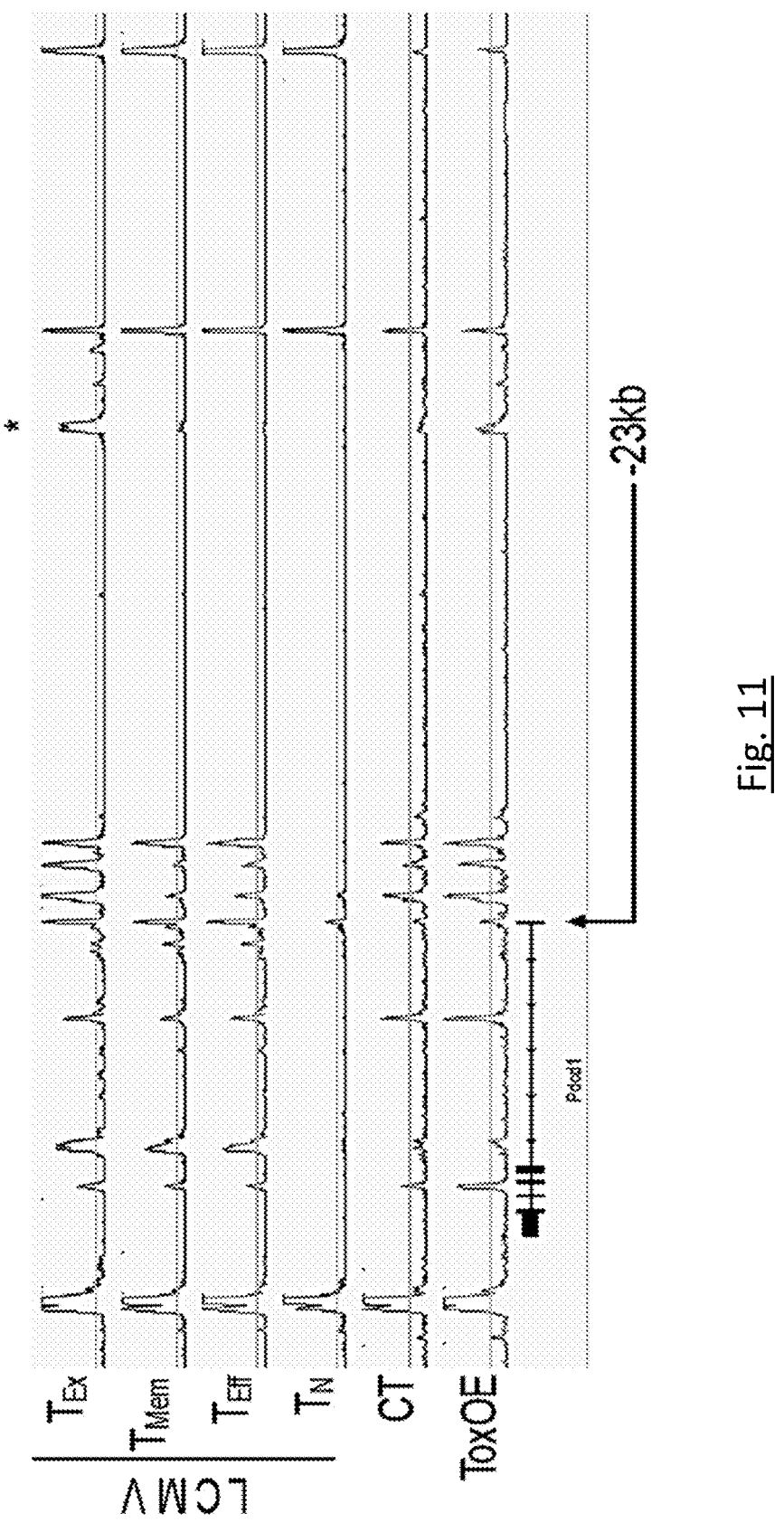
FIG. 11 depicts that Tox increases the chromatin accessibility of exhaustion-specific enhancers. Illustrated are ATAC-Seq IGV tracks of the Pdcd1 locus, which encodes the protein PD-1. The upper 4 tracks are derived from in vivo exhausted ($T_{Ex}$), memory ($T_{Mem}$), effector ($T_{Eff}$), or naïve ($T_N$) $CD8^+$ T cells from acute and chronic infection. The lower 2 tracks show the accessibility profiles of in vitro-differentiated control (CT) and Tox-overexpressing (ToxOE) $CD8^+$ T cells. The black box highlights the −23 kilobase enhancer of Pdcd1 that is uniquely "open" in exhausted and ToxOE T cells.

To examine how Tox regulates T cell exhaustion we performed ATAC-Seq in T cells over-expressing Tox. Enforced expression of Tox results in the differential accessibility of over 400 genomic loci. Of these, the −23kb enhancer of Pdcd1 was found to be "open" in T cells transduced with Tox relative to control (FIG. 11). This enhancer has been of particular interest as it is uniquely "open" only in exhausted T cells, and remains "closed" in naïve, effector, and memory T cells. These findings suggest that Tox may regulate the transcriptional signature defining T cell exhaustion by physically altering the chromatin accessibility of exhaustion-critical loci.

Lastly, to determine how Tox may be accomplishing its chromatin modulating function, we analyzed binding partners by mass spectrometry. Utilizing this approach we found that Tox binds to a host of proteins (FIG. 12A). Of these, Hmbg2, Set, Ruvbl1, Dpy30, and Hmgb1 are of particular interest due to the ability of these proteins to alter local chromatin structure (FIG. 12B).

In sum, these results suggest that Tox is central to both the establishment and maintenance of T cell exhaustion and that it acts by recruiting chromatin modulating proteins and transcription factors to loci that regulate the expression of genes that play a critical role in restraining T cell responses during protracted antigen exposure.

Tables

TABLE 1

| Gene | Corr |
|------|------|
| MKI67 | 1 |
| CTLA4 | 0.884615 |
| HLA.DQB1 | 0.884615 |
| CENPF | 0.873626 |
| RRM2 | 0.855572 |
| KIR3DX1 | 0.851243 |
| KIF19 | 0.846154 |
| ARHGAP11A | 0.82967 |
| IFI6 | 0.813187 |
| SYNGR1 | 0.802198 |
| HLA.DRB1 | 0.802198 |
| EPB41L4A | 0.801117 |
| FADS2 | 0.79952 |
| CDCA7 | 0.785127 |
| HAVCR2 | 0.78022 |
| LDLR | 0.769231 |
| FBXO5 | 0.763736 |
| ITGAD | 0.760519 |
| ALDOC | 0.758242 |
| GAMT | 0.751393 |
| CD38 | 0.747253 |
| RFC2 | 0.74553 |

TABLE 1-continued

| Gene | Corr |
|------|------|
| ORMDL3 | 0.741758 |
| COL5A3 | 0.740343 |
| TP53I11 | 0.737277 |
| HLA.K | 0.737277 |
| LMNB1 | 0.730769 |
| PRKAR1B | 0.724521 |
| CLSPN | 0.71978 |
| UBE2L6 | 0.714286 |
| BPGM | 0.714286 |
| ANKS6 | −0.70426 |
| FAM213B | −0.70621 |
| TRIO | −0.70702 |
| ZNF823 | −0.70799 |
| DKK3 | −0.71626 |
| ZNF605 | −0.72527 |
| VSIG1 | −0.72902 |
| MAMLD1 | −0.72988 |
| DBN1 | −0.73077 |
| TRBV28 | −0.73077 |
| PPAN | −0.73453 |
| PCDH1 | −0.73453 |
| C9orf89 | −0.73829 |
| RP11.173A16.2 | −0.74003 |
| CXXC5 | −0.74102 |
| RP11.213G2.3 | −0.74176 |
| GLTPD1 | −0.74176 |
| IKZF2 | −0.74725 |
| VCAN | −0.75929 |

TABLE 2

| | Nucleotide | AA | PBMC Freq (%) | TIL Freq (%) |
|---|-----------|----|------|------|
| 14784 | | | | |
| 1 | CCCCTGATCCTGGAGTCGCCCAGC CCCAACCAGACCTCTCTGTACTTCT GTGCCAGCAGTTCCTATTACGAGC AGTACTTCGGGCCG (SEQ ID NO. 1) | CASSSYYEQYF (SEQ ID NO. 31) | 8.04 | 0.31 |
| 2 | AGTGCCCATCCTGAAGACAGCAGC TTCTACATCTGCAGTGCTAGGAGC ACCGGGACTATGATTCGGGCTGAG CAGTTCTTCGGGCCA (SEQ ID NO. 2) | CSARSTGTMIRAEQFF (SEQ ID NO. 32) | 1.45 | 0.27 |
| 3 | CTGACTGTGAGCAACATGAGCCCT GAAGACAGCAGCATATATCTCTGC AGCGTCCAAGGGGGATCTCCTGAA GCTTTCTTTGGACAA (SEQ ID NO. 3) | CSVQGGSPEAFF (SEQ ID NO. 33) | 1.38 | 0.22 |
| 4 | CTAAACCTGAGCTCTCTGGAGCTG GGGGACTCAGCTTTGTATTTCTGTG CCAGCAGCGTGTTAGGGGATGAGC AGTTCTTCGGGCCA (SEQ ID NO. 4) | CASSVLGDEQFF (SEQ ID NO. 34) | 0.8 | 0.64 |
| 5 | CTGAATGTGAACGCCTTGTTGCTGG GGGACTCGGCCCTCTATCTCTGTGC CAGCAGCTTTAGGTCCGGGGAGCT GTTTTTTGGAGAA (SEQ ID NO. 5) | CASSFRSGELFF (SEQ ID NO. 35) | 0.43 | 0.25 |
| 6 | CTGCTGGGGTTGGAGTCGGCTGCT CCCTCCCAAACATCTGTGTACTTCT GTGCCAGCCGGCAGGGTTTTGGCT ACACCTTCGGTTCG (SEQ ID NO. 6) | CASRQGFGYTF (SEQ ID NO. 36) | 0.14 | 1.35 |

TABLE 2-continued

| | Nucleotide | AA | PBMC Freq (%) | TIL Freq (%) |
|---|---|---|---|---|
| 7 | ACTCTGACGATCCAGCGCACACAG CAGGAGGACTCGGCCGTGTATCTC TGTGCCAGCAGCTTAGGGTACACC ATATATTTTGGAGAG (SEQ ID NO. 7) | CASSLGYTIYF (SEQ ID NO. 37) | 0.03 | 1.56 |
| 8 | CACGCCCTGCAGCCAGAAGACTCA GCCCTGTATCTCTGCGCCAGCAGCC AAGTGCCTAGCGGCCCCTACGAGC AGTACTTCGGGCCG (SEQ ID NO. 8) | CASSQVPSGPYEQYF (SEQ ID NO. 38) | 0.03 | 0.82 |
| 9 | ACCAGTGCCCATCCTGAAGACAGC AGCTTCTACATCTGCAGTGCTCCGG GGATCGGGCGACGGGGGACTGAAG CTTTCTTTGGACAA (SEQ ID NO. 9) | CSAPGIGRRGTEAFF (SEQ ID NO. 39) | 0 | 0.27 |
| 10 | GCTGCTCCCTCCCAGACATCTGTGT ACTTCTGTGCCAGCAGTCTAACAG GGGTGGTCATATACACCGGGGAGC TGTTTTTTGGAGAA (SEQ ID NO. 10) | CASSLTGVVIYT GELFF (SEQ ID NO. 40) | 0 | 0.27 |

12288

| | Nucleotide | AA | PBMC Freq (%) | TIL Freq (%) |
|---|---|---|---|---|
| 1 | CTGAAGATCCAGCCCTCAGAACCC AGGGACTCAGCTGTGTACTTCTGTG CCAGCAGTCCCTTGGGCTACGAGC AGTACTTCGGGCCG (SEQ ID NO. 11) | CASSPLGYEQYF (SEQ ID NO. 41) | 2.37 | 0.42 |
| 2 | AGCACCTTGGAGCTGGGGGACTCG GCCCTTTATCTTTGCGCCAGCAGCG GGGGACAGGCCAGCTCCTACGAGC AGTACTTCGGGCCG (SEQ ID NO. 12) | CASSGGQASSYEQYF (SEQ ID NO. 42) | 0.3 | 0.58 |
| 3 | ATCCGGTCCACAAAGCTGGAGGAC TCAGCCATGTACTTCTGTGCCAGCA GAGGACAAGACCAGAACACTGAA GCTTTCTTTGGACAA (SEQ ID NO. 13) | CASRGQDQNTEAFF (SEQ ID NO. 43) | 0.24 | 0.89 |
| 4 | CTCAGGCTGGAGTCGGCTGCTCCCT CCCAGACATCTGTGTACTTCTGTGC CAGCAGTGAAACAGACACTGAAGC TTTCTTTGGACAA (SEQ ID NO. 14) | CASSETDTEAFF (SEQ ID NO. 44) | 0.04 | 0.51 |
| 5 | CACCTACACACCCTGCAGCCAGAA GACTCGGCCCTGTATCTCTGCGCCA GCAGCCAAATCGGGGATAAGACGG CTTTCTTTGGACAA (SEQ ID NO. 15) | CASSQIGDKTAFF (SEQ ID NO. 45) | 0.02 | |
| 6 | AAGATCCAGCCTGCAGAGCTTGGG GACTCGGCCGTGTATCTCTGTGCCA GCAGCCATACAAACACCGGGGAGC TGTTTTTTGGAGAA (SEQ ID NO. 16) | CASSHTNTGELFF (SEQ ID NO. 46) | 0.01 | 0.57 |
| 7 | TTGGAGTCGGCTGCTCCCTCCCAAA CATCTGTGTACTTCTGTGCCAGCAG TTACGGGGGACAGGGGCCTGAAGC TTTCTTTGGACAA (SEQ ID NO. 17) | CASSYGGQGPEAFF (SEQ ID NO. 47) | 0.01 | 0.44 |
| 8 | GAGATCCAGCGCACAGAGCAGGGG GACTCGGCCATGTATCTCTGTGCCA GCAGTCTAGTCGGGGGGAGGGAAG CTTTCTTTGGACAA (SEQ ID NO. 18) | CASSLVGGREAFF (SEQ ID NO. 48) | 0 | 1.3 |

TABLE 2-continued

| | Nucleotide | AA | PBMC Freq (%) | TIL Freq (%) |
|---|---|---|---|---|
| 14835 | | | | |
| 1 | CACGCCCTGCAGCCAGAAGACTCA GCCCTGTATCTCTGCGCCAGCAGCC TGGACAGGGGGTATAATCAGCCCC AGCATTTTGGTGAT (SEQ ID NO. 19) | CASSLDRGYNQPQHF (SEQ ID NO. 49) | 23.03 | 1.09 |
| 2 | CAACCTGCAAAGCTTGAGGACTCG GCCGTGTATCTCTGTGCCAGCAGCT TCAATGGGGAGATGAACACTGAAG CTTTCTTTGGACAA (SEQ ID NO. 20) | CASSFNGEMNTEAFF (SEQ ID NO. 50) | 0.01 | 1.36 |
| 13416 | | | | |
| 1 | TTGGAGATCCAGCGCACAGAGCAG GGGGACTCGGCCATGTATCTCTGT GCCAGCAGCCTTTCCTCTTCACCCC TCCACTTTGGGAAC (SEQ ID NO. 21) | CASSLSSSPLHF (SEQ ID NO. 51) | 15.16 | 1.42 |
| 2 | TCTAAGAAGCTCCTCCTCAGTGACT CTGGCTTCTATCTCTGTGCCTTCGT CAGCAGGGGAGGCGACTATGGCTA CACCTTCGGTTCG (SEQ ID NO. 22) | CAFVSRGGDYGYTF (SEQ ID NO. 52) | 14.59 | 0.65 |
| 3 | CTGAGCTCTCTGGAGCTGGGGGAC TCAGCTTTGTATTTCTGTGCCAGCA GCGCCTCCGCGTGGGCCGCTGAAG CTTTCTTTGGACAA (SEQ ID NO. 23) | CASSASAWAAEAFF (SEQ ID NO. 53) | 7.38 | 1.34 |
| 4 | ATGAGCTCCTTGGAGCTGGGGGAC TCAGCCCTGTACTTCTGTGCCAGCA GCTCGAGGACTAGGTGGAATGAGC AGTTCTTCGGGCCA (SEQ ID NO. 24) | CASSSRTRWNEQFF (SEQ ID NO. 54) | 6.73 | 0.78 |
| 5 | CTGAAGATCCAGCCCTCAGAACCC AGGGACTCAGCTGTGTACTTCTGTG CCAGCAGCAGTGCTAACTATGGCT ACACCTTCGGTTCG (SEQ ID NO. 25) | CASSSANYGYTF (SEQ ID NO. 55) | 2.26 | 1.94 |
| 6 | GAACTGAACATGAGCTCCTTGGAG CTGGGGGACTCAGCCCTGTACTTCT GTGCCAGCAGTTCATCTGATACGC AGTATTTTGGCCCA (SEQ ID NO. 26) | CASSSSDTQYF (SEQ ID NO. 56) | 0 | 0.82 |
| 13471 | | | | |
| 1 | TCTCTGGAGCTGGGGGACTCAGCT TTGTATTTCTGTGCCAGCAGCGTAG GGGACAGGGGGTCTGGAAACACCA TATATTTTGGAGAG (SEQ ID NO. 27) | CASSVGDRGSGNTIYF (SEQ ID NO. 57) | 5.8 | 0.6 |
| 2 | TCCGCTACCAGCTCCCAGACATCTG TGTACTTCTGTGCCATCAGTGACCT CGGCGGCCCGGCCGCAGATACGCA GTATTTTGGCCCA (SEQ ID NO. 28) | CAISDLGGPAADTQYF (SEQ ID NO. 58) | 0.84 | 0.29 |
| 14746 | | | | |
| 1 | CCCAGCCCCAACCAGACCTCTCTGT ACTTCTGTGCCAGCAGTTTATGGGG CGGCGGGAGCTCCTACAATGAGCA GTTCTTCGGGCCA (SEQ ID NO. 29) | CASSLWGGGSSYN EQFF (SEQ ID NO. 59) | 9.96 | 3.54 |
| 2 | CAGCCTGCAGAACTGGAGGATTCT GGAGTTTATTTCTGTGCCAGCAGCC | CASSQLTGADTEAFF (SEQ ID NO. 60) | 0.4 | 0.59 |

TABLE 2-continued

| Nucleotide | AA | PBMC Freq (%) | TIL Freq (%) |
|---|---|---|---|

AACTGACAGGGGCTGACACTGAAG
CTTTCTTTGGACAA
(SEQ ID NO. 30)

TABLE 3

| | Pre-Tumor Burden | | | | Wk3-Tumor Burden | |
|---|---|---|---|---|---|---|
| Rank | Immune Subset | IS | | Rank | Immune Subset | IS |
| 1 | CD8/Lag3+ \| Freq. of Parent (%) | 9.55 | | 1 | CD8/Ki67+ \| Freq. of Parent (%) | 32.47 |
| 2 | CD8/Ki67+ \| Freq. of Parent (%) | 9.46 | | 2 | CD4/Non-Tregs/PD1+ \| Freq. of Parent (%) | 17.58 |
| 3 | CD4 \| Freq. of Parent (%) | 5.66 | | 3 | CD8/Lag3+ \| Freq. of Parent (%) | 13.41 |
| 4 | CD4/Non-Tregs/Q4: CD45RA−, CD27− \| Freq. of Parent (%) | 4.74 | | 4 | CD4/Tregs/Tim3+ \| Freq. of Parent (%) | 11.47 |
| 5 | CD4/Tregs/Tim3+ \| Freq. of Parent (%) | 3.05 | | 5 | CD8/CTLA4+ \| Freq. of Parent (%) | 8.04 |
| 6 | CD8 \| Freq. of Parent (%) | 2.96 | | 6 | CD4/Non-Tregs/Lag3+ \| Freq. of Parent (%) | 6.75 |
| 7 | CD4/Non-Tregs/Tim3+ \| Freq. of Parent (%) | 2.57 | | 7 | CD4/Non-Tregs/Ki67+ \| Freq. of Parent (%) | 5.92 |
| 8 | CD4/Non-Tregs/Q1: CD45RA−, CD27+ \| Freq. of Parent (%) | 0.76 | | 8 | CD4/Non-Tregs/CTLA4+ \| Freq. of Parent (%) | 2.74 |
| 9 | CD8/Eomes+ \| Freq. of Parent (%) | 0.51 | | 9 | CD8/PD1+ \| Freq. of Parent (%) | 2.24 |
| 10 | CD8/Tim3+ \| Freq. of Parent (%) | 0.44 | | 10 | CD8/Tim3+ \| Freq. of Parent (%) | 1.79 |
| 11 | CD8/naïve \| Freq. of Parent (%) | 0.22 | | 11 | CD8/Eomes+ \| Freq. of Parent (%) | 0.95 |
| 12 | CD4/Non-Treg/Q3: CD45RA+, CD27− \| Freq. of Parent (%) | 0.19 | | 12 | CD4/Tregs/Tbet+ \| Freq. of Parent (%) | 0.42 |
| 13 | CD4/Non-Tregs/Q2: CD45RA+, CD27+ \| Freq. of Parent (%) | −0.04 | | 13 | CD8/naïve \| Freq. of Parent (%) | 0.24 |
| 14 | CD8/Q23: CD45RA+, CD27− \| Freq. of Parent (%) | −0.23 | | 14 | CD4/Tregs/PD1+ \| Freq. of Parent (%) | 0.23 |
| 15 | CD4/Tregs/PD1+ \| Freq. of Parent (%) | −0.54 | | 15 | CD4 \| Freq. of Parent (%) | −0.23 |
| 16 | CD8/PD1+ \| Freq. of Parent (%) | −0.61 | | 16 | CD8/Q21: CD45RA−, CD27+ \| Freq. of Parent (%) | −0.51 |
| 17 | CD8/Q24: CD45RA−, CD27− \| Freq. of Parent (%) | −0.66 | | 17 | CD8/Q22: CD45RA+, CD27+ \| Freq. of Parent (%) | −0.67 |
| 18 | CD4/Non-Tregs/Lag3+ \| Freq. of Parent (%) | −1.24 | | 18 | CD4/Tregs/GzmB+ \| Freq. of Parent (%) | −0.71 |
| 19 | CD8/Q21: CD45RA−, CD27+ \| Freq. of Parent (%) | −1.39 | | 19 | CD8/Q24: CD45RA−, CD27− \| Freq. of Parent (%) | −0.74 |
| 20 | CD8/Q22: CD45RA+, CD27+ \| Freq. of Parent (%) | −1.81 | | 20 | CD4/Tregs/naïve \| Freq. of Parent (%) | −1.01 |
| 21 | CD4/Non-Tregs/CTLA4+ \| Freq. of Parent (%) | −1.83 | | 21 | CD4/Non-Tregs/Tim3+ \| Freq. of Parent (%) | −1.10 |
| 22 | CD8/CD160+ \| Freq. of Parent (%) | −2.09 | | 22 | CD4/Non-Treg/Q3: CD45RA+, CD27− \| Freq. of Parent (%) | −1.15 |
| 23 | CD4/Non-Tregs/PD1+ \| Freq. of Parent (%) | −2.15 | | 23 | CD4/Tregs/Eomes+ \| Freq. of Parent (%) | −1.35 |
| 24 | CD4/Tregs/naïve \| Freq. of Parent (%) | −2.16 | | 24 | CD4/Non-Tregs/Q2: CD45RA+, CD27+ \| Freq. of Parent (%) | −1.38 |
| 25 | CD4/Non-Tregs/Eomes+ \| Freq. of Parent (%) | −2.19 | | 25 | CD8/CD160+ \| Freq. of Parent (%) | −1.53 |
| 26 | CD4/Non-Tregs/Ki67+ \| Freq. of Parent (%) | −2.93 | | 26 | CD4/Non-Tregs/GzmB+ \| Freq. of Parent (%) | −1.99 |
| 27 | CD4/Tregs \| Freq. of Parent (%) | −3.09 | | 27 | CD8/GzmB+ \| Freq. of Parent (%) | −2.06 |
| 28 | CD8/CTLA4+ \| Freq. of Parent (%) | −3.30 | | 28 | CD8 \| Freq. of Parent (%) | −2.19 |
| 29 | CD4/Tregs/Ki67+ \| Freq. of Parent (%) | −3.73 | | 29 | CD4/Non-Tregs/Q4: CD45RA−, CD27− \| Freq. of Parent (%) | −2.19 |
| 30 | CD4/Tregs/Eomes+ \| Freq. of Parent (%) | −3.96 | | 30 | CD4/Non-Tregs \| Freq. of Parent (%) | −2.25 |
| 31 | CD4/Tregs/Tbet+ \| Freq. of Parent (%) | −4.01 | | 31 | CD4/Tregs \| Freq. of Parent (%) | −2.28 |
| 32 | CD4/Tregs/Lag3+ \| Freq. of Parent (%) | −4.08 | | 32 | CD8/Q23: CD45RA+, CD27− \| Freq. of Parent (%) | −2.35 |
| 33 | CD8/Tbet+ \| Freq. of Parent (%) | −4.78 | | 33 | CD4/Non-Tregs/Eomes+ \| Freq. of Parent (%) | −2.43 |
| 34 | CD8/GzmB+ \| Freq. of Parent (%) | −4.82 | | 34 | CD4/Non-Tregs/Q1: CD45RA−, CD27+ \| Freq. of Parent (%) | −2.72 |
| 35 | CD4/Tregs/GzmB+ \| Freq. of Parent (%) | −4.82 | | 35 | CD4/Tregs/Ki67+ \| Freq. of Parent (%) | −2.94 |
| 36 | CD4/Non-Tregs/Tbet+ \| Freq. of Parent (%) | −7.01 | | 36 | CD4/Non-Tregs/Tbet+ \| Freq. of Parent (%) | −3.27 |
| 37 | CD4/Non-Tregs/GzmB+ \| Freq. of Parent (%) | −7.48 | | 37 | CD4/Tregs/Lag3+ \| Freq. of Parent (%) | −3.36 |
| 38 | CD4/Tregs/CTLA4+ \| Freq. of Parent (%) | −7.61 | | 38 | CD8/Tbet+ \| Freq. of Parent (%) | −3.83 |
| 39 | CD4/Non-Tregs \| Freq. of Parent (%) | −7.85 | | 39 | CD4/Tregs/CTLA4+ \| Freq. of Parent (%) | −5.76 |

| | Pre-PFS | | | | Wk3-PFS | |
|---|---|---|---|---|---|---|
| Rank | Immune Subset | IS | | Rank | Immune Subset | IS |
| 1 | CD8/CD160+ \| Freq. of Parent (%) | 30.75 | | 1 | CD4/Non-Tregs/Tbet+ \| Freq. of Parent (%) | 18.02 |
| 2 | CD8/Ki67+ \| Freq. of Parent (%) | 14.48 | | 2 | CD4/Tregs/Tbet+ \| Freq. of Parent (%) | 16.01 |
| 3 | CD4/Non-Treg/Q3: CD45RA+, CD27− \| Freq. of Parent (%) | 11.54 | | 3 | CD4/Non-Treg/Q3: CD45RA+, CD27− \| Freq. of Parent (%) | 12.41 |
| 4 | CD8/Lag3+ \| Freq. of Parent (%) | 7.30 | | 4 | CD8/CTLA4+ \| Freq. of Parent (%) | 10.32 |

TABLE 3-continued

| # | | Value | # | | Value |
|---|---|---|---|---|---|
| 5 | CD4/Non-Tregs/Q4: CD45RA−, CD27− \| Freq. of Parent (%) | 3.66 | 5 | CD4/Non-Tregs/Eomes+ \| Freq. of Parent (%) | 6.45 |
| 6 | CD4/Tregs/Lag3+ \| Freq. of Parent (%) | 3.53 | 6 | CD4/Tregs \| Freq. of Parent (%) | 3.49 |
| 7 | CD4/Non-Tregs/Ki67+ \| Freq. of Parent (%) | 3.15 | 7 | CD8/GzmB+ \| Freq. of Parent (%) | 2.84 |
| 8 | CD8/Tbet+ \| Freq. of Parent (%) | 2.71 | 8 | CD8 \| Freq. of Parent (%) | 2.36 |
| 9 | CD8/GzmB+ \| Freq. of Parent (%) | 2.04 | 9 | CD8/PD1+ \| Freq. of Parent (%) | 1.54 |
| 10 | CD4/Non-Tregs/CTLA4+ \| Freq. of Parent (%) | 1.63 | 10 | CD4/Non-Tregs \| Freq. of Parent (%) | 1.51 |
| 11 | CD4/Non-Tregs/Tbet+ \| Freq. of Parent (%) | 1.23 | 11 | CD8/Q24: CD45RA−, CD27− \| Freq. of Parent (%) | 1.34 |
| 12 | CD8/Q22: CD45RA+, CD27+ \| Freq. of Parent (%) | 0.70 | 12 | CD8/Tim3+ \| Freq. of Parent (%) | 1.16 |
| 13 | CD4/Tregs/PD1+ \| Freq. of Parent (%) | 0.47 | 13 | CD4/Non-Tregs/Ki67+ \| Freq. of Parent (%) | 0.88 |
| 14 | CD8/CTLA4+ \| Freq. of Parent (%) | 0.22 | 14 | CD8/Eomes+ \| Freq. of Parent (%) | 0.66 |
| 15 | CD8/Eomes+ \| Freq. of Parent (%) | −0.39 | 15 | CD4 \| Freq. of Parent (%) | 0.58 |
| 16 | CD4/Non-Tregs/Eomes+ \| Freq. of Parent (%) | −0.49 | 16 | CD4/Tregs/PD1+ \| Freq. of Parent (%) | 0.39 |
| 17 | CD4 \| Freq. of Parent (%) | −0.66 | 17 | CD4/Tregs/Ki67+ \| Freq. of Parent (%) | −0.38 |
| 18 | CD4/Non-Tregs/Lag3+ \| Freq. of Parent (%) | −1.02 | 18 | CD4/Tregs/Eomes+ \| Freq. of Parent (%) | −0.46 |
| 19 | CD4/Non-Tregs/Tim3+ \| Freq. of Parent (%) | −1.58 | 19 | CD8/Q22: CD45RA+, CD27+ \| Freq. of Parent (%) | −0.83 |
| 20 | CD8 \| Freq. of Parent (%) | −1.61 | 20 | CD4/Tregs/Lag3+ \| Freq. of Parent (%) | −0.91 |
| 21 | CD4/Non-Tregs/PD1+ \| Freq. of Parent (%) | −1.81 | 21 | CD4/Non-Tregs/PD1+ \| Freq. of Parent (%) | −0.92 |
| 22 | CD4/Tregs/Tim3+ \| Freq. of Parent (%) | −1.82 | 22 | CD4/Non-Tregs/GzmB+ \| Freq. of Parent (%) | −1.06 |
| 23 | CD8/Q23: CD45RA+, CD27− \| Freq. of Parent (%) | −2.14 | 23 | CD8/CD160+ \| Freq. of Parent (%) | −1.58 |
| 24 | CD4/Tregs/Ki67+ \| Freq. of Parent (%) | −2.90 | 24 | CD4/Tregs/Tim3+ \| Freq. of Parent (%) | −1.74 |
| 25 | CD4/Non-Tregs \| Freq. of Parent (%) | −2.98 | 25 | CD4/Non-Tregs/CTLA4+ \| Freq. of Parent (%) | −2.05 |
| 26 | CD4/Tregs/Tbet+ \| Freq. of Parent (%) | −3.09 | 26 | CD4/Non-Tregs/Tim3+ \| Freq. of Parent (%) | −2.28 |
| 27 | CD8/naïve \| Freq. of Parent (%) | −3.28 | 27 | CD4/Tregs/nave \| Freq. of Parent (%) | −2.42 |
| 28 | CD8/Tim3+ \| Freq. of Parent (%) | −3.60 | 28 | CD4/Non-Tregs/Lag3+ \| Freq. of Parent (%) | −2.67 |
| 29 | CD8/Q24: CD45RA−, CD27− \| Freq. of Parent (%) | −3.61 | 29 | CD8/Tbet+ \| Freq. of Parent (%) | −2.68 |
| 30 | CD4/Tregs/naïve \| Freq. of Parent (%) | −3.81 | 30 | CD4/Non-Tregs/Q2: CD45RA+, CD27+ \| Freq. of Parent (%) | −2.75 |
| 31 | CD8/Q21: CD45RA−, CD27+ \| Freq. of Parent (%) | −3.95 | 31 | CD4/Non-Tregs/Q1: CD45RA−, CD27+ \| Freq. of Parent (%) | −2.86 |
| 32 | CD4/Tregs/CTLA4+ \| Freq. of Parent (%) | −3.99 | 32 | CD4/Tregs/CTLA4+ \| Freq. of Parent (%) | −2.96 |
| 33 | CD4/Non-Tregs/Q1: CD45RA−, CD27+ \| Freq. of Parent (%) | −4.00 | 33 | CD4/Non-Tregs/Q4: CD45RA−, CD27− \| Freq. of Parent (%) | −3.02 |
| 34 | CD8/PD1+ \| Freq. of Parent (%) | −4.20 | 34 | CD4/Tregs/GzmB+ \| Freq. of Parent (%) | −3.12 |
| 35 | CD4/Tregs/GzmB+ \| Freq. of Parent (%) | −4.65 | 35 | CD8/Q23: CD45RA+, CD2− \| Freq. of Parent (%) | −3.12 |
| 36 | CD4/Tregs \| Freq. of Parent (%) | −5.03 | 36 | CD8/Q21: CD45RA−, CD27+ \| Freq. of Parent (%) | −4.06 |
| 37 | CD4/Non-Tregs/GzmB+ \| Freq. of Parent (%) | −5.20 | 37 | CD8/naïve \| Freq. of Parent (%) | −4.57 |
| 38 | CD4/Tregs/Eomes+ \| Freq. of Parent (%) | −5.83 | 38 | CD8/K167+ \| Freq. of Parent (%) | −5.08 |
| 39 | CD4/Non-Tregs/Q2: CD45RA+, CD27+ \| Freq. of Parent (%) | −6.61 | 39 | CD8/Lag3+ \| Freq. of Parent (%) | −5.30 |

The materials and methods employed in Examples 11-16 are now described.

Mice

Mice were maintained in a specific-pathogen-free facility at the University of Pennsylvania (UPenn). Experiments and procedures were performed in accordance with the Institutional Animal Care and Use Committee (IACUC) of UPenn. Mice of the following genotypes were on a C57BL/6J background and bred at UPenn or purchased from Jackson Laboratory: WT P14, TOXF$^{lox/Flox}$ x CD4$^{Cre}$ P14, TOX$^{-/-}$ P14, and NFAT2$^{Flox/Flox}$ x CD4$^{Cre}$P14. For experiments with CT26 tumors, BALB/c mice were used and ordered from Charles River. For all experiments, mice were age and sex matched and male and female mice between 6-8 weeks of age were randomly assigned to experimental groups.

Naïve Lymphocyte Isolation and Adoptive T Cell Transfer

T cell receptor transgenic GP specific CD8+ T cells (P14) were isolated from the peripheral blood of donor mice using gradient centrifugation with Histopaque-1083 (Sigma Aldrich). For experiments using LCMV infection, WT P14 cells were mixed 1:1 with congenically disparate P14 cells of the desired genotype (TOX$^{Flox/Flox}$ CD4$^{Cre}$ P14, TOX$^{-/-}$ P14, or NFAT2$^{Flox/Flox}$ CD4$^{Cre}$ P14) and a total of 500 naïve cells were adoptively transferred by tail-vein injection into 6-8-week-old recipient mice 1-5 days prior to infection.

Recipients were of a third congenic background to allow distinguishing of both donor populations from the host T cells. For experiments monitoring only WT P14 responses, 500 cells were transferred. Previous reports have shown that adoptive transfer of 500 P14 T cells prior to LCMV Cl-13 or Arm infection does not impact viral load or pathogenesis (Frebel, H. et al. Programmed death 1 protects from fatal circulatory failure during systemic virus infection of mice. J Exp Med 209, 2485-2499 (2012); Odorizzi, P. M., Pauken, K. E., Paley, M. A., Sharpe, A. & Wherry, E. J. Genetic absence of PD-1 promotes accumulation of terminally differentiated exhausted CD8+ T cells. J Exp Med 212, 1125-1137 (2015); Blattman, J. N., Wherry, E. J., Ha, S. J., van der Most, R. G. & Ahmed, R. Impact of Epitope Escape on PD-1 Expression and CD8 T-Cell Exhaustion during Chronic Infection. J Virol 83, 4386-4394 (2009)). For experiments with influenza, Listeria monocytogenes (LM), or vesicular stomatitis virus (VSV) infection, 5,000 P14 (influenza, LM) or OT-I (VSV) CD8$^+$ T cells were adoptively transferred prior to infection.

Infections, Ectopic Tumor Models, and Treatments

LCMV strains Armstrong (Arm) and clone-13 (Cl-13) were propagated and titers were determined as previously described (Odorizzi, P. M., Pauken, K. E., Paley, M. A., Sharpe, A. & Wherry, E. J. Genetic absence of PD-1 promotes accumulation of terminally differentiated exhausted CD8+ T cells. *J Exp Med* 212, 1125-1137 (2015)). C57BL/6J mice were infected intraperitoneally (i.p.) with $2\times10^5$ plaque-forming units (PFU) of LCMV Arm or intravenously (i.v.) with $4\times10^6$ PFU LMCV Cl-13. For other experiments, mice were infected with $2\times10^6$ PFU VSV-OVA (i.v.) or $1\times10^4$ colony-forming units (CFU) LM-GP33 (i.p.). For influenza infection, mice were anesthetized with isofluorane and ketamine prior to intranasal administration of 50 TCID50 PR8-GP33 (H1N1 strain) in 30ul of PBS. B16-F10 melanoma and CT26 colon carcinoma cell lines were purchased from ATCC and cultured at 37° C. in RPMI 1640 medium supplemented with 10% FBS, 100U/ml penicillin, 100U/ml streptomycin, and 2 mM L-glutamine. $2\times10^5$ tumor cells were injected subcutaneously (s.c.) on right and left flanks of mice. FK506 (Prograf, Astellas Pharma US) was prepared for injection by diluting to 1.5 mg/ml in PBS. Diluted FK506 was administered subcutaneously at a dose of 10 mg/kg from d3-7 or d25-29 of LCMV Cl-13 infection (Araki, K. et al. Pathogenic virus-specific T cells cause disease during treatment with the calcineurin inhibitor FK506: implications for transplantation. *J Exp Med* 207, 2355-2367 (2010)). For control treatments, PBS was administered s.c.

Retroviral Transduction, In Vitro Differentiation, and Cell Transfer

For retroviral (RV) transduction, CD8+ T cells were enriched from 882 spleens of donor mice using an EasySep magnetic negative selection kit (Stem Cell Technologies) and transduced as described previously (Kurachi, M. et al. Optimized retroviral transduction of mouse T cells for in vivo assessment of gene function. *Nat Protoc* 12, 1980-1998 (2017)). In brief, cells were resuspended at $10^6$/ml in "complete RPMI (cRPMI)": RPMI 1640 supplemented 10% FBS, 50 μM β-mercaptoethanol, 100U/ml penicillin, 100U/ml streptomycin, non-essential amino acids (Invitrogen), sodium pyruvate (Invitrogen), and HEPES buffer (Invitrogen). $3\times10^6$ T cells were plated in wells of a 12 well cluster dish and activated for 18-24 hours with 1 ug/ml anti-CD3ε (145-2C11, BioLegend) and 0.5ug/ml anti-CD28 (37.51, BioLegend) in the presence of 100 U/ml recombinant human IL-2 (Peprotech). Following activation, cells were resuspended at $3\times10^6$/ml in cRPMI, plated in a well of a 6 well plate and transduced with MigR1-based RV viruses in the presence of polybrene (4 μg/ml) by spin infection (2000×g for 75 minutes at 32° C.). RV supernatants were produced by co-transfecting HEK293T cells with an RV expression plasmid and pCL-Eco packaging plasmid using Lipofectamine3000 (Invitrogen).

For in vitro experiments, transduced T cells were expanded and differentiated into effector T cells (Martinez, G. J. et al. The Transcription Factor NFAT Promotes Exhaustion of Activated CD8+ T Cells. *Immunity* 42, 265-278 (2015); Pipkin, M. E. et al. Interleukin-2 and Inflammation Induce Distinct Transcriptional Programs that Promote the Differentiation of Effector Cytolytic T Cells. *Immunity* 32, 79-90 (2010)) by culturing in cRPM1 in the presence of IL-2 (100U/ml) for 5 additional days. Restimulations were performed by adding biotinylated anti-CD3ε (1 μg/ml, 145-2C11, BioLegend) and anti-CD28 (0.5 μg/ml, 37.51, BioLegend) in the presence of 25pg/ml streptavidin (Invitrogen).

For experiments involving the transfer of transduced P14 T cells into animals, mice were infected with LCMV Cl-13 on the same day as transduction. Twenty-four hours after transduction, GFP+ cells were sorted to >98% purity and transferred i.v. into infected hosts.

Preparation of Cell Suspensions and Restimulations

Following infection or tumor challenge, CD8+ T cells were isolated from spleen and draining lymph nodes by cutting samples into small pieces and homogenizing against a 70 μm cell strainer. Cells were run through cell strainer and red blood cells were lysed in ACK lysis buffer (Thermo Fisher Scientific) for 5 minutes. The cell suspension was then washed in PBS and passed through a 70 μm cell strainer an additional time. Lungs and tumors were cut into small pieces and digested for 1 hour at 37° C. in RPMI 1640 medium supplemented with 5% FBS, 100U/ml DNaseI (Sigma-Aldrich) and 0.2 mg/ml collagenase IV (Sigma-Aldrich). Samples were subsequently mechanically disrupted against a 70 μm filter and washed with PBS. Red blood cells were lysed in ACK lysis buffer for 5 minutes and samples were re-filtered through a 70 μm strainer. To assess cytokine and effector molecule production, samples were plated at $2\times10^6$/ml in cRPMI in wells of a flat-bottom 96 well dish and incubated with GP33-41 peptide in the presence of protein transport inhibitors (GolgiStop and GolgiPlug, BD Biosciences) for 5 hours at 37° C.

Human Sample Collection and Staining

Normal donor peripheral blood samples (n=10, male and female donors from the ages of 18-39) were obtained from Cellular Technology, Inc. Human melanoma tumor and PBMC samples were collected from Stage III and Stage IV melanoma patients under University of Pennsylvania Abramson Cancer Center's melanoma research program tissue collection protocol UPCC 08607 in accordance with the Institutional Review Board. Tumor samples were procured from the operating room and processed the same day using manual dissociation into single cell suspension. Tumor samples were then frozen immediately using standard freeze media, and stored in liquid nitrogen. All human samples were processed and stained as previously described (Huang, A. C. et al. T-cell invigoration to tumour burden ratio associated with anti-PD-1 response. *Nature* 545, 60-65 (2017)).

Flow Cytometry and Cell Sorting

Antibodies were procured from BioLegend: CD44 (IM7), CD62L (MEL-14), CD127 937 (A7R34), Tbet (4B10), PD-1 (RMP1-30), CD160 (7H1), TIM3 (RMT3-23), CD3ε (17A2), TNFα (MP6-XT22), CD8u (53-6.7), CD4 (RM4-5), CD45.1 (A29), CD45.2 (104); Miltenyi Biotec: TOX (REA473); Southern Biotech: KLRG1 (2F1); eBioscience: Eomes (Dan11mag), 2B4 (eBio244F4), IFNγ (XMG1.2), Granzyme B (GB 11), B220 (RA3-6B2); or from BD Biosciences: TIGIT (1G9), LAG33 (C9B7W), Tcf-1 (S33-966), 2B4 (2B4), Ki-67 (B56). Live cells were discriminated by staining with Zombie NIR dye (BioLegend). Intracellular and nuclear staining of cytokines, effector molecules, and transcription factors was performed using the FoxP3/Transcription Factor Staining Buffer Set (eBioscience) in accordance with the manufacturer's protocol. Flow cytometry data were acquired on a BD LSR II instrument and cell sorting was performed on a BD FACSAria enclosed within a laminar flow hood. Data were analyzed using FlowJo software (TreeStar).

Microarray Analysis

Microarray data (GSE41867)(Doering, T. A. et al. Network Analysis Reveals Centrally Connected Genes and Pathways Involved in CD8+ T Cell Exhaustion versus Memory. *Immunity* 37, 1130-1144 (2012)) were processed as previously described (Doering, T. A. et al. Network Analysis Reveals Centrally Connected Genes and Pathways Involved in CD8+ T Cell Exhaustion versus Memory. *Immunity* 37, 1130-1144 (2012; Pauken, K. E. et al. Epigenetic stability of exhausted T cells limits durability of reinvigoration by PD-1 blockade. *Science* 354, 1160-1165 (2016)). Genes with chromatin modulating function were identified by compiling gene lists retrieved from gene ontology associations (GO molecular functions: chromatin binding, nucleic acid binding, nucleotide binding and PANTHER protein classes: DNA binding protein, chromatin binding protein), the EpiFactors database (Medvedeva, Y. A. et al. EpiFactors: a comprehensive database of human epigenetic factors and complexes. *Database* 2015, bav067-10 (2015)), and previously identified chromatin modulators (Shi, J. et al. Discovery of cancer drug targets by CRISPR-Cas9 screening of protein domains. *Nat Biotechnol* 33, 661-667 (2015)

RNA and ATAC-Seg Sample Preparation and Sequencing

To assess the transcriptional and epigenetic impact of TOX deletion in T cells, 250 WT and 250 TOX$^{-/-}$ naive CD44$^{LOW}$CD62L$^{HI}$ P14 cells sorted from peripheral blood of donors, mixed, and co-transferred into WT mice. Recipients were subsequently infected with LCMV Cl-13 and splenocytes were harvested 8 days following infection. Ten spleens were pooled for each of the 3 replicates prior to processing, CD8$^+$ T cell enrichment (using EasySep CD8$^+$ T cell negative selection kit, Stem Cell Technologies), and staining of single cell suspensions. 100,000 WT and TOX$^{-/-}$ P14 cells were sorted to a purity of >98% for each replicate. In ectopic and enforced expression experiments, in vitro differentiated CD8$^+$ T cells transduced with TOX+GFP or control GFP only (3 biological replicates each) were sorted on GFP expression 6 days following initial activation to a purity of >98%. NIH3T3 cells were transduced with TOX+GFP or control GFP only RV viruses and cultured for 48 hours prior to cell sorting. To extract RNA, 50,000 cells were resuspended in buffer RLT supplemented with P-mercaptoethanol and processed with a RNeasy Micro Kit (Qiagen) as per the manufacturer's instructions.

Total RNA libraries were prepared using a Pico Input SMARTer Stranded Total RNA-Seq Kit™ (Takara). Extracted RNA and libraries were assessed for quality on a TapeStation 2200 instrument (Agilent). ATAC libraries were generated as described with minor changes (Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. 10, 1213-1218 (2013)). Briefly, nuclei from 50,000 cells were isolated using a lysis solution composed of 10 mM Tris-HCl, 10 mM NaCl, 3 mM MgCl$_2$, and 0.1% IGEPAL CA-630. Immediately following cell lysis, nuclei were pelleted in low-bind 1.5 ml tubes (Eppendorf) and resuspended in TD Buffer with Tn5 transposase (Illumina). Transposition reaction was performed at 37° C. for 45 minutes. DNA fragments were purified from enzyme solution using MinElute Enzyme Reaction Cleanup Kit (Qiagen). Libraries were barcoded (Nextera Index Kit, Illumina) and amplified with NEBNext High Fidelity PCR Mix (New England Biolabs). Library quality was assessed using a TapeStation instrument. RNA and ATAC libraries were quantified using a KAPA Library Quantification Kit and sequenced on an IlluminaNextSeq 550 instrument (150 bp, paired-end) on high-output flowcells.

RNA-Seg Data Processing and Analysis

FASTQ files were aligned using STAR 2.5.2a against the mm10 murine reference genome. The aligned files were processed using PORT gene-based normalization (github-.com/itmat/Normalization). Differential gene expression was performed with Limma. Limma-voom was used to identify transcripts that were significantly differentially expressed between experimental groups using a p-value <0.05.

ATAC-Seg Data Processing and Analysis

The script used for processing raw ATAC-seq FASTQ data is available at the following GitHub repository: github-.com/wherrylab/jogiles_ATAC In brief, samples were aligned to mm10 reference genome with Bowtie2. Unmapped, unpaired, and mitochrondrial reads were removed using samtools. ENCODE Blacklist regions were removed (sites.google.com/site/anshulkundaje/projects/blacklists). PCR duplicates were removed using Picard. Peak calling was performed with MACS2 with a FDR q-value=0.01. A union peak list for each experiment was created by combining all peaks in all samples; overlapping peaks were merged using bedtools merge. The number of reads in each peak was determined with bedtools coverage.

The scripts for peak set enrichment are available at: github.com/wherrylab/jogiles_ATAC. In brief, bedtools intersect was used to find overlapping peaks between the experiment and peak set of interest. Peak names between the experiment and peak set of interest were unified using custom R scripts. GSEA82 was used to calculate enrichment scores.

Chromatin Immunoprecipitation (ChIP) and ChIP-Seg Analysis

Cells were crosslinked with 1% paraformaldehyde (PFA) diluted in PBS for 15 minutes on a rotating platform. Samples were quenched with glycine and cell pellets were lysed in buffer containing 50 mM HEPES-KOH, pH 7.5, 140 mM NaCl, 1 mM EDTA, 10% glycerol, 0.5% NP-40, 0.25% Triton X-100 supplemented with protease inhibitors (ThermoFisher) for 10 minutes at 4° C. on a rotating platform. Cells were pelleted, resuspended in a second lysis buffer containing 10 mM Tris-HCl pH 8.0, 200 mM NaCl, 1 mM EDTA, 0.5 mM EGTA supplemented with protease inhibitors (ThermoFisher) for 10 minutes at room temperature (RT) on a rotating platform. Nuclei were pelleted and resuspended in a final lysis buffer containing 10 mM Tris-HCl pH 8.0, 100 mM NaCl, 1 mM EDTA, 0.5 mM EGTA, 0.10% Na-deoxycholate, 0.5% N-lauroylsarcosine and protease inhibitors. Chromatin was sheared with a Covaris sonicator. Lysates were subsequently incubated with anti-TOX (ab155768, Abcam) or anti-Kat7 (ab70183, Abcam) conjugated Dynabeads (Invitrogen) overnight at 4° C. on a rotating platform. Beads were collected by magnet and washed five times with RIPA wash buffer (50 mM HEPES-KOH pH 7.5, 500 mM LiCl, 1 mM EDTA, 1% NP-40, 0.7% Na-Deoxycholate). Samples were eluted from beads with buffer containing 50 mM Tris-HCl pH 8.0, 10 mM EDTA, and 1% SDS. Crosslinking was reversed on samples and input controls by incubating at 65° C. for 12-18 hours. DNA was purifed by sequentially incubating samples with RNase A (0.2 mg/ml in Tris-EDTA, 2 hours at 37° C.) and proteinase K (0.2 mg/ml, 2 hours at 55° C.), followed by mixing with phenol:chloroform:isoamyl alcohol and phase separation by centrifugation in Phase Lock tubes (Qiagen). Aqueous phase was transferred to a fresh tube and DNA was precipitated by incubating samples in cold ethanol at −80° C. overnight. In the experiments described herein, 25×106 EL4 cells were used per replicate per ChIP reaction.

Libraries were prepared using an NEBNext Ultra II kit with NEBNext Multiplex Oligos for Illumina Sequencers (New England Biolabs). Library quality and size distribution were assayed on a BioAnalyzer 2100 instrument (Agilent). TOX (n=3 biological replicates), Kat7 (n=2 biological replicates), and input control libraries were quantified by Qubit fluorometer and sequenced on a NextSeq550 instrument (Illumina) on high-output flowcells (150 bp, paired-end). FASTQ files were aligned to the mml0 murine reference genome with STAR 2.5.2a, converted to bam files with samtools view, then converted to bed file format using bamtoBed. MACS2 was used to perform peak calling with a FDR q-value=0.01. Genome-wide co-enrichment of TOX and Kat7 was calculated by first compiling the multiple transcription factor-binding loci (MTL) for both proteins as described (Chen, X. et al. Integration of External Signaling Pathways with the Core Transcriptional Network in Embryonic Stem Cells. Cell 133, 1106-1117 (2008)). Briefly, Kat7 peaks within 250 bp of one another were iteratively clustered to define an MTL locus. The resulting 3315 MTLs were then tested for TOX binding relative to 3315 control MTL loci (randomly assigned from sequences within 100kb of a TSS). Statistical analysis of TOX enrichment in Kat7 MTLs was performed by calculating the probability of enrichment over 1000 repeated measurements.

Immunoprecipitation and Immunoblotting

Immunoprecipitation (IP) was performed as previously described (Dou, Z. et al. Autophagy mediates degradation of nuclear lamina. Nature 527, 105-109 (2015)). Briefly, $5 \times 10^6$ EL4 cells were lysed in immunoprecipitation buffer (20 mM Tris, pH 7.5, 137 mM NaCl, 1 mM $MgCl_2$, 1 mM $CaCl_2$), 1% NP-40, 10% glycerol) supplemented with 1:100 HALT protease and phosphatase inhibitor cocktail (Thermo Scientific) and benzonase (Novagen) at 12.5 U/ml. Lysates were rotated at 4° C. for 60 minutes. Subsequently, antibody-conjugated Dynabeads (Invitrogen) were added and samples were incubated at 4° C. overnight on a rotating platform. Beads were collected by magnet and samples were washed five times with immunoprecipitation buffer. Samples were then resuspended in NuPAGE loading dye (ThermoFisher), incubated at 95° C. for 5 minutes and analyzed by Western blotting. The following antibodies were used for IP: TOX (ab155768, Abcam) and Kat7 (ab70183, Abcam) and Western blot: TOX (TXRX10, eBioscience), Kat7 (ab70183, Abcam), H3K4mel (ab8895, Abcam), H3K27me3 (ab6002, Abcam), H3K9ac (39918, Active Motif), H3K27ac (ab4729, Abcam), H4 (07-108, Millipore), and H4ac (06-866, Millipore).

Immunoprecipitation, LC-MS/MS, and Analysis

EL4 cell nuclear extract was prepared as described (Dawson, M. A. et al. Inhibition of BET recruitment to chromatin as an effective treatment for MLL-fusion leukaemia. Nature 478, 529-533 (2011)). Briefly, cells were incubated in hypotonic buffer (10 mM Tris-Cl, pH 7.4, 1.5 mM $MgCl_2$, 10 mM KCl, 25 mM NaF, 1 mM Na3VO4, 1 mM DTT, and Roche protease inhibitor cocktail) for 3 minutes. Cell pellets were subsequently spun down, resuspended in hypotonic buffer, and homogenized with 5 strokes of a Dounce homogenizer. Nuclei were collected by centrifugation and resuspended in extraction buffer (50 mM Tris-Cl, pH 7.4, 1.5 mM $MgCl_2$, 20% glycerol, 420 mM NaCl, 25 mM NaF, 1 mM $Na_3VO_4$, 1 mM DTT, 400 U/ml DNase I, and protease inhibitor cocktail). Samples were incubated for 30 minutes at 4° C. on a rotating platform. Extracts were diluted 3:1 in buffer containing 50 mM Tris-Cl, pH 7.4, 1.5 mM $MgCl_2$, 25 mM NaF, 1 mM Na3VO4, 0.6% NP-40, 1 mM DTT, and protease inhibitor cocktail. Immunopurification was carried out on 1 mg of nuclear extract using a magnetic co-IP kit (ThermoFisher) with 40pg anti-TOX (Abcam, ab155768) or control IgG antibody as per the manufacturer's instructions.

Liquid chromatography tandem mass spectrometry (LC-MS/MS) analysis was performed by the Proteomics and Metabolomics Facility at the Wistar Institute using a Q Exactive Plus mass spectrometer (ThermoFisher) coupled with a Nano-ACQUITY UPLC system (Waters). Samples were digested in-gel with trypsin and injected onto a UPLC Symmetry trap column (180 µm i.d.×2 cm packed with 5 µm C18 resin; Waters). Tryptic peptides were separated by reversed phase HPLC on a BEH C18 nanocapillary analytical column (75 µm i.d.×25 cm, 1.7 µm particle size; Waters) using a 95 minute gradient formed by solvent A (0.1% formic acid in water) and solvent B (0.1% formic acid in acetonitrile). A 30-min blank gradient was run between sample injections to minimize carryover. Eluted peptides were analyzed by the mass spectrometer set to repetitively scan m/z from 400 to 2000 in positive ion mode. The full MS scan was collected at 70,000 resolution followed by data-dependent MS/MS scans at 17,5000 resolution on the 20 most abundant ions exceeding a minimum threshold of 20,000. Peptide match was set as preferred, exclude isotopes option and charge-state screening were enabled to reject singly and unassigned charged ions. Peptide sequences were identified using MaxQuant 1.5.2.895. MS/MS spectra were searched against a UniProt human protein database using full tryptic specificity with up to two missed cleavages, static carboxamidomethylation of Cys, and variable oxidation of Met and protein N-terminal acetylation. Consensus identification lists were generated with false discovery rates of 1% at protein, and peptide levels. To generate a list of statistically significant hits, resulting iBAQ protein values from MaxQuant output were analyzed using the MiST scoring system96, which accounts for protein abundance, specificity, and reproducibility across 3 biological replicates.

Statistical Analysis

Statistical tests for flow cytometry data were performed using GraphPad Prism software. A p-value of <0.05 was considered significant in these analyses. Student's t-test (two-tailed) was used for comparisons between two independent conditions. Paired Student's t-test was used when the samples being compared originated from the same animal.

Example 11. Transcriptional Upregulation of Tox Selectively in Developing TEX

Figure 13A:
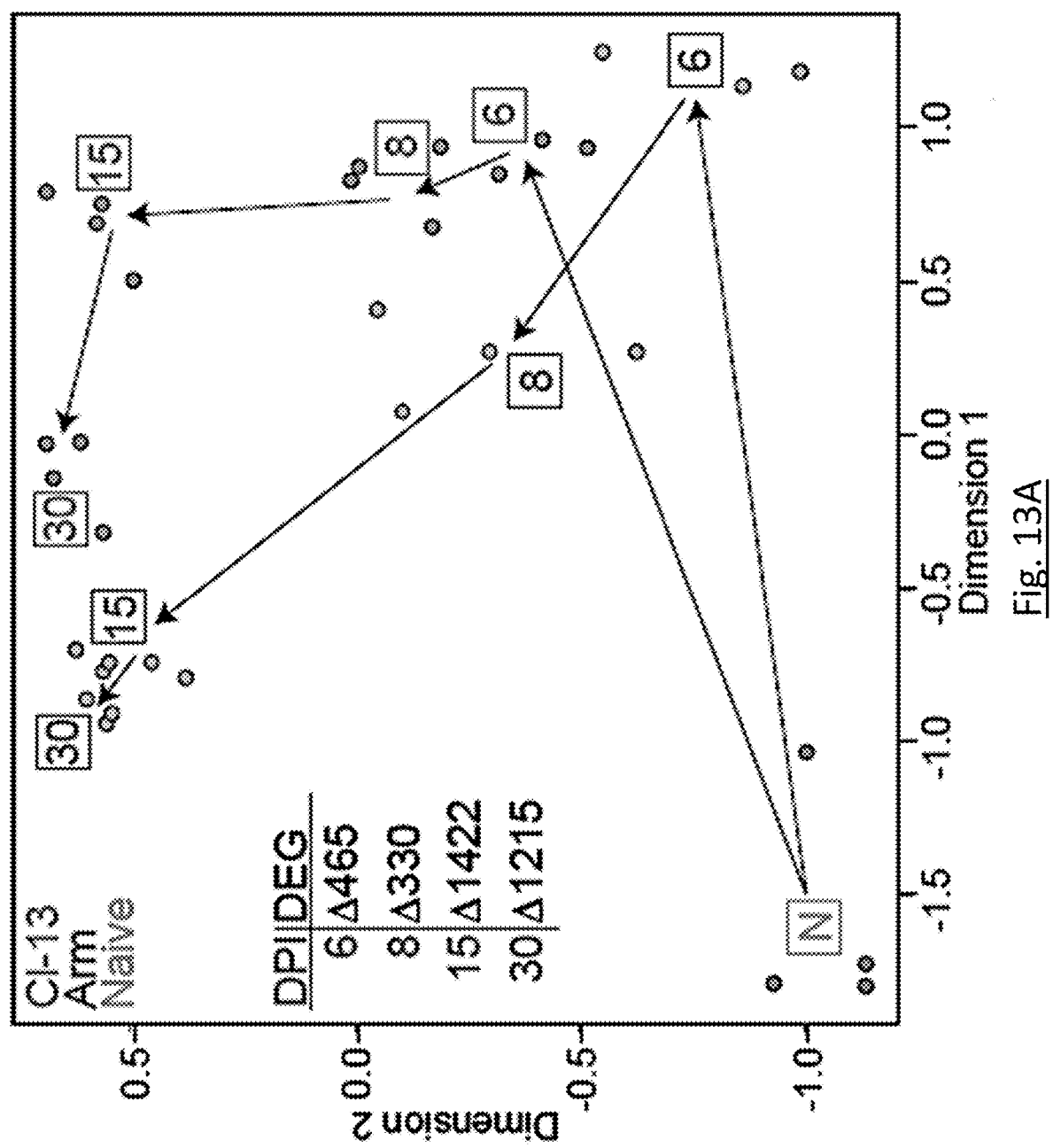
Figure 13C:
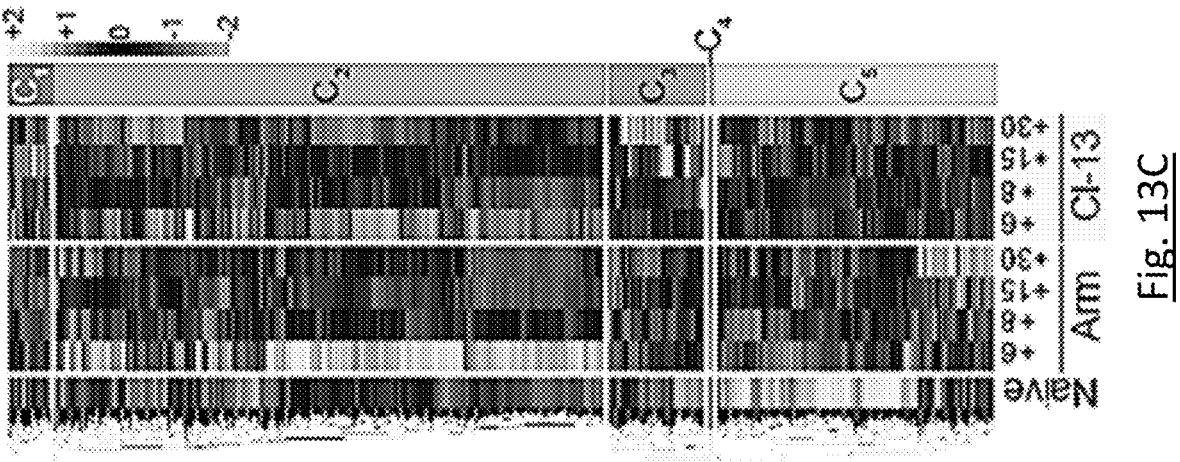
FIG. 13C shows a heatmap of differentially expressed potential chromatin modulating genes (Table 8, see methods) between naive P14 T cells and P14 T cells during Arm or Cl-13 infection. Genes are ordered by hierarchical clustering using Manhattan distance and clusters generated by k-means.
Figure 13B:
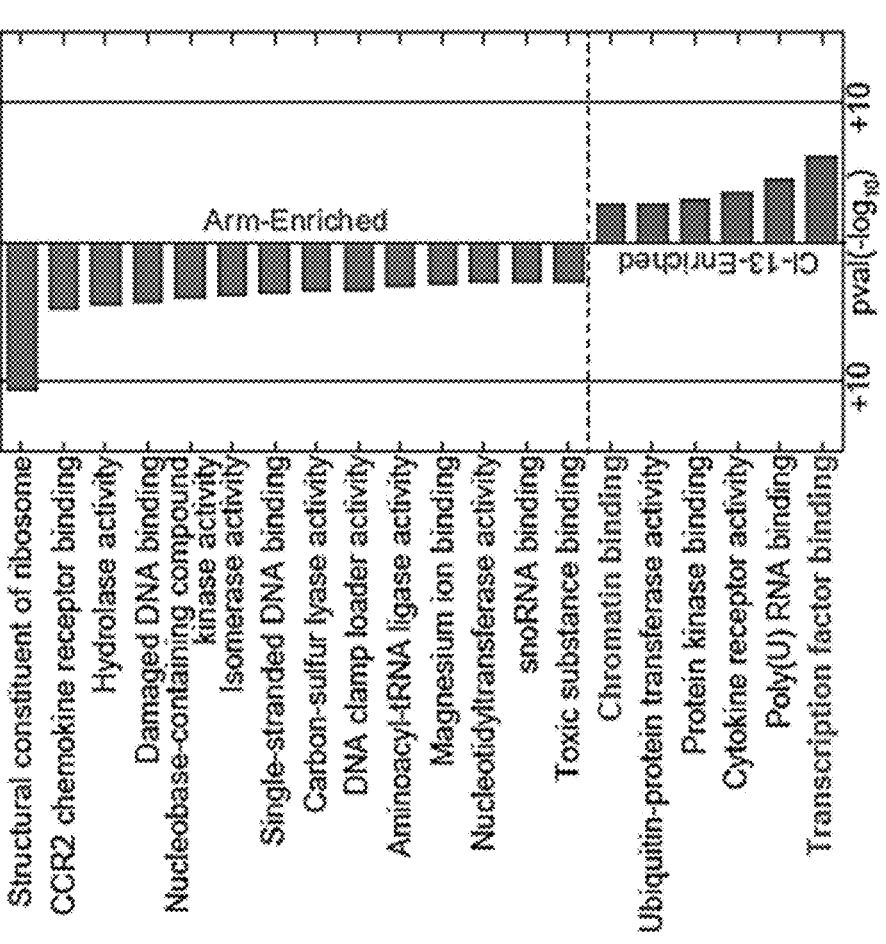
FIG. 13B shows a gene ontology (GO) analysis of differentially expressed genes 6 days post-Arm or Cl-13 infection. Gray and blue denote GO biological processes enriched in Arm and Cl-13, respectively. Categories associated with chromatin binding are highlighted in red.
Figure 13D:
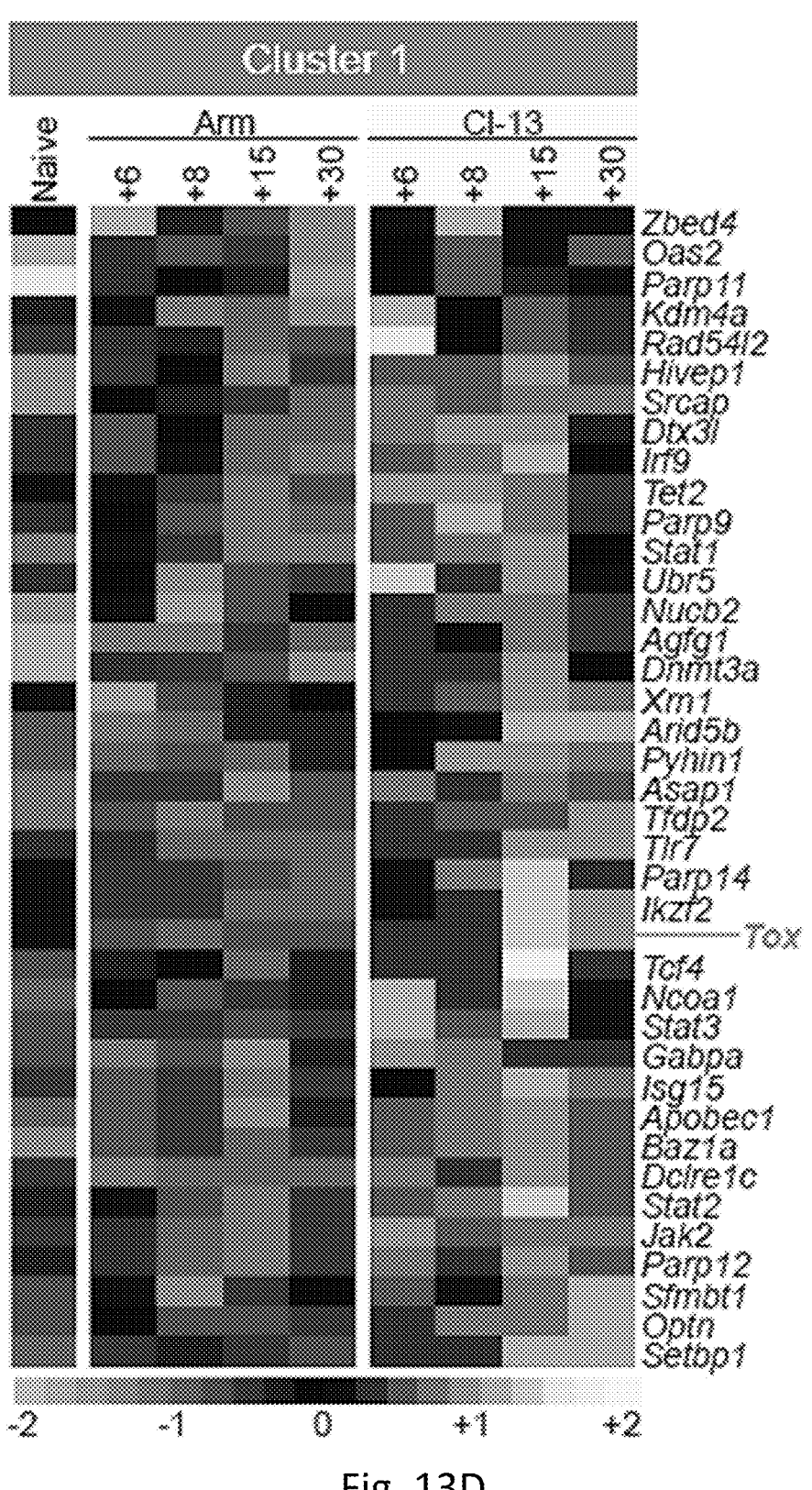
FIG. 13D shows that chromatin modulating genes in cluster 1 that are differentially expressed between Arm and Cl-13.
Figures 14A, 14B:
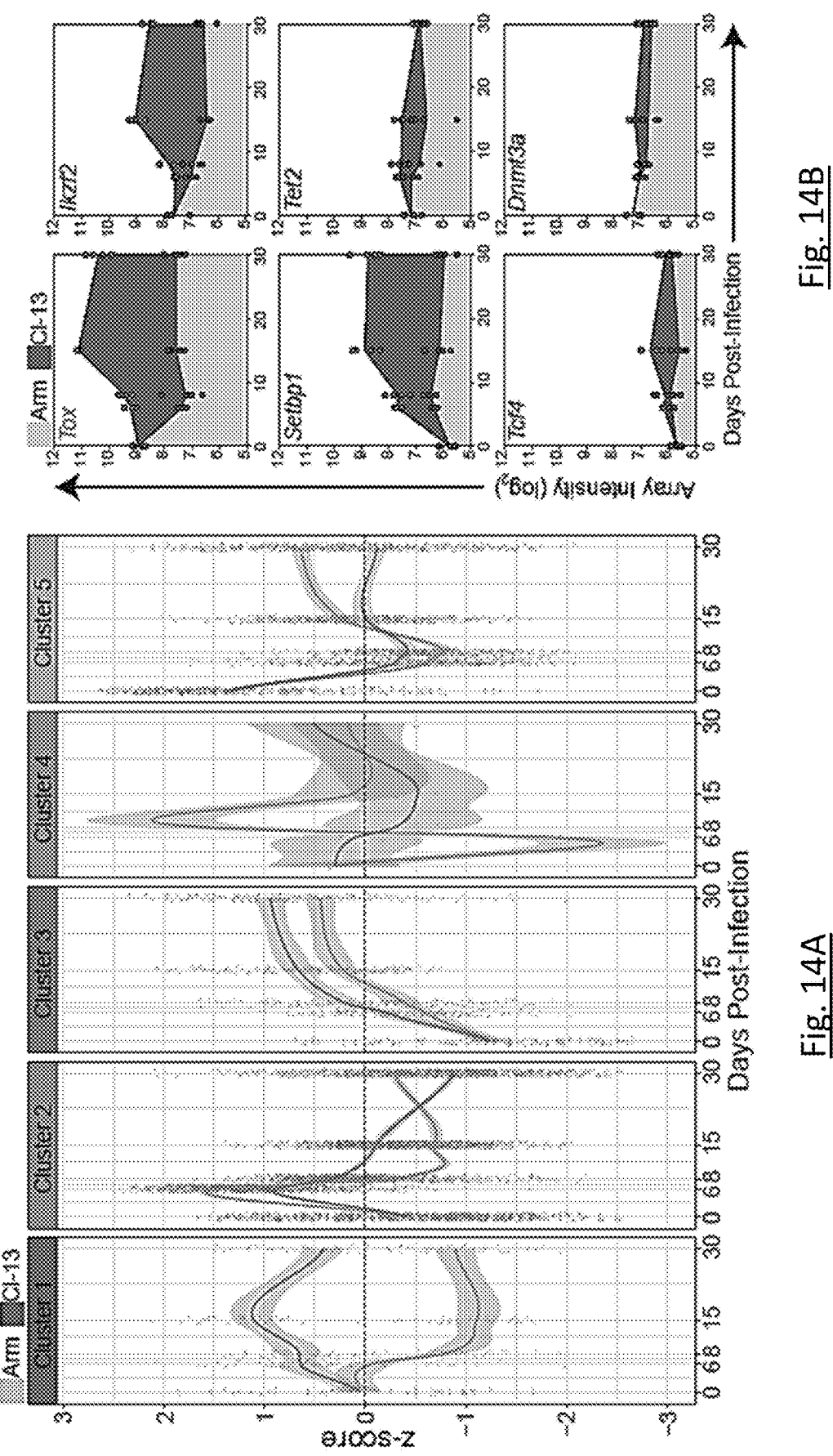
FIGS. 14A-14B illustrate z-score and gene expression data.

To identify potential molecular drivers of T cell exhaustion, we first analyzed longitudinal transcriptional data of virus-specific CD8+ T cells (using LCMV-specific TCR transgenic P14 cells) in acute (Armstrong; Arm) or chronic (clone 13; Cl-13) LCMV infection. Multidimensional scaling (MDS) analysis of gene expression data highlights dynamic changes in transcriptional signatures associated with the development of $T_{EFF}$ and $T_{MEM}$ versus $T_{EX}$ (FIG. 13A). Responses to acute and chronic infection were markedly different early, with considerable divergence of gene expression within 6 days (FIG. 13A). T cell exhaustion is associated with a unique chromatin landscape that differs from that of $T_N$,
$T_{EFF}$ or $T_{MEM}$ (Pauken, K. E. et al. Epigenetic stability of exhausted T cells limits durability of reinvigoration by PD-1 blockade. Science 354, 1160-1165 (2016); Sen, D. R. et al. The epigenetic landscape of T cell exhaustion. Science 354, 1165-1169 (2016); Philip, M. et al. Chromatin states define tumour-specific T cell dysfunction and reprogramming. Nature 545, 452-456 (2017); Scott-Browne, J. P. et al. Dynamic Changes in Chromatin Accessibility Occur in CD8+ T Cells Responding to Viral Infection. Immunity 45, 1327-1340 (2016)). Because epigenetic landscape is a key driver of cellular identity, we hypothesized that genes with chromatin modulating capacity could initiate early developmental differences and might lead to the unique transcriptional trajectories in developing $T_{MEM}$ and $T_{EX}$. Indeed, gene ontology analysis of the expression data 6 days post-infection (d.p.i.) identified differential expression of gene families with chromatin binding and transcription factor activity (FIG. 13B). Moreover, genes within these families were differentially engaged during T cell differentiation, suggesting that unique sets of chromatin modulators could have distinct roles in the early specification of different T cell fates (FIG. 13C, FIG. 14A and Table 4). Genes in cluster 1 (C1) were highly biased to CD8$^+$ T cells responding to chronic infection and this cluster included several transcription factors (Stat1, Stat2, Tcf4, Ikzf2) and chromatin modulators (Tet2, Dnmt3a) known to play key roles in maintaining T cell exhaustion (Carty, S. A. et al. The Loss of TET2 Promotes CD8+ T Cell Memory Differentiation. *J Immunol* 200, 82-91 (2018); Ghoneim, H. E. et al. De Novo Epigenetic Programs Inhibit PD-1 Blockade-Mediated T Cell Rejuvenation. *Cell* 170, 142-157.e19 (2017)) as well as several genes with previously uncharacterized functions in peripheral CD8+ T cells including Setbp1, Kdm4a, and Tox (FIG. 13D and FIGS. 14A-14B). Among these, Tox was most differentially expressed TF or potential chromatin modulator in developing $T_{EX}$ versus $T_{EFF}$ and $T_{MEM}$ from acute infection (FIG. 1E).

Figures 13E, 13F:
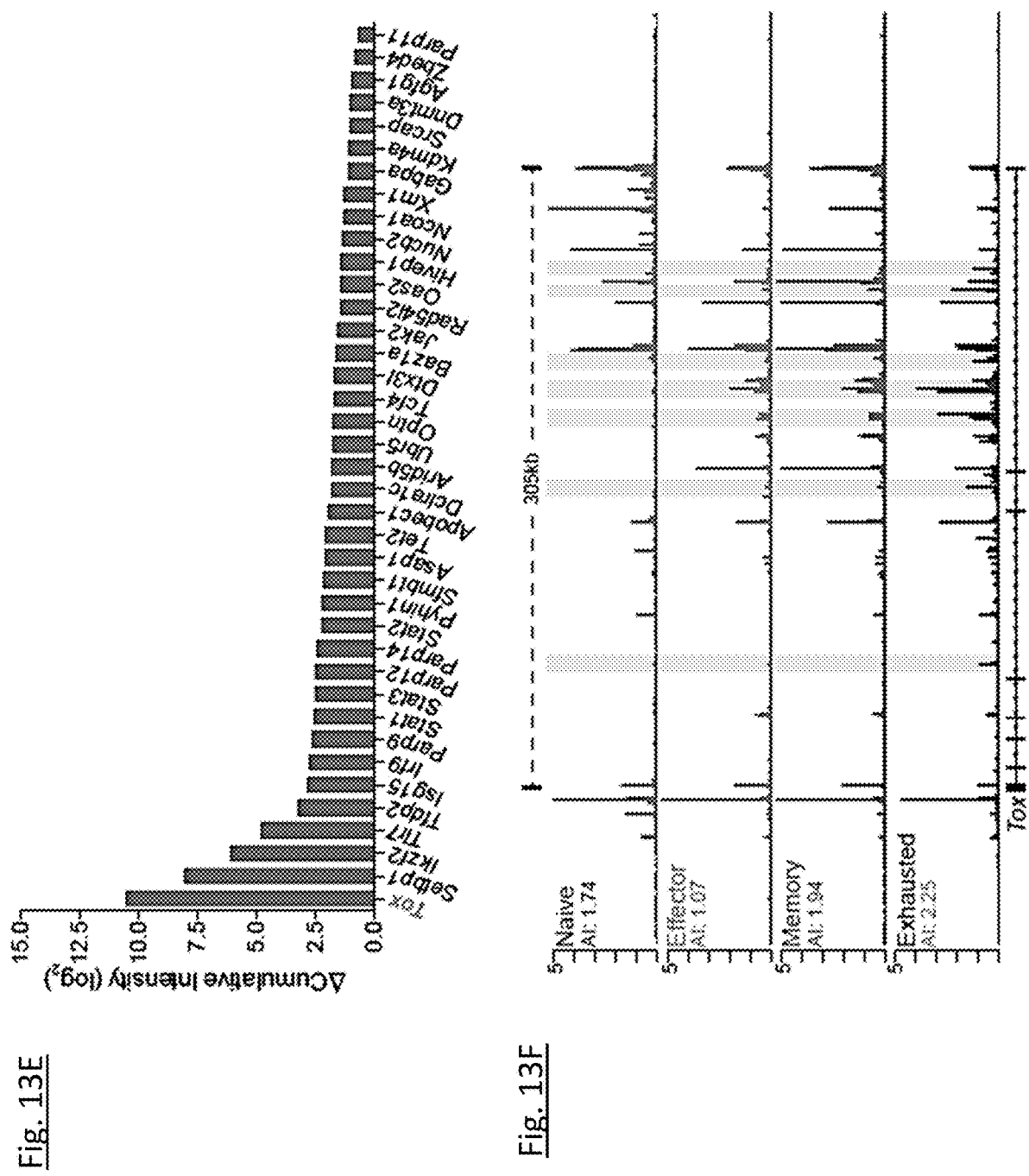
FIG. 13F shows ATAC-seq tracks of in vivo $T_N$, $T_{EFF}$, TMEM and $T_{EX}$ P14 cells at the Tox locus. Accessibility Index (AI) of each sample calculated by summing the normalized tag counts across the locus and dividing by its length.

TOX belongs to the high mobility group (HMG) family of DNA-binding proteins and is involved in the development of immune cell types including natural killer, innate lymphoid-like, and CD4$^+$ T cells (Ghoneim, H. E. et al. De Novo Epigenetic Programs Inhibit PD-1 Blockade-Mediated T Cell Rejuvenation. *Cell* 170, 142-157.e19 (2017); Aliahmad, P., Seksenyan, A. & Kaye, J. The many roles of TOX in the immunesystem. *Current Opinion in Immunology* 24, 173-177 (2012)). The role of TOX in peripheral CD8$^+$ T cell differentiation is poorly understood. Using co-expression network analyses, we previously found TOX to be the most differentially connected TF between $T_{MEM}$ and $T_{EX}$, suggesting a unique role in $T_{EX}$ (Doering, T. A. et al. Network Analysis Reveals Centrally Connected Genes and Pathways Involved in CD8+ T Cell Exhaustion versus Memory. *Immunity* 37, 1130-1144 (2012)). Because other HMG transcription factors such as Sox proteins (Bergsland, M. et al. Sequentially acting Sox transcription factors in neural lineage development. *Genes & Development* 25, 2453-2464 (2011)) and Tcf1 (Johnson, J. L. et al. Lineage-Determining Transcription Factor TCF-1 Initiates the Epigenetic Identity of T Cells. *Immunity* 48, 243-257.e10 (2018)) are involved in cellular lineage (re)programming, we examined TOX in more detail. In agreement with the substantial increase in Tox transcription early during chronic LCMV infection, chromatin accessibility of the Tox locus was also markedly increased in $T_{EX}$ cells compared to $T_{EFF}$, suggesting that the Tox locus is epigenetically reprogrammed in $T_{EX}$ (FIG. 13F). Moreover, we found that the Tox locus harbors a dense cluster of open chromatin regions, a feature that has been associated with "stretch" or "super" enhancers (SEs), that, in other settings contain a high density of H3K27ac histone marks (Whyte, W. A. et al. Master Transcription Factors and Mediator Establish Super-Enhancers at Key Cell Identity Genes. *Cell* 153, 307-319 (2013); Hnisz, D. et al. Super-Enhancers in the Control of Cell Identity and Disease. *Cell* 155, 934-947 (2013); Vahedi, G. et al. Super-enhancers delineate disease-associated regulatory nodes 1257 in T cells. *Nature* 520, 1-15 (2015)). Among loci with large stretches of open chromatin, Tox ranked much more highly in $T_{EX}$ (rank=35) compared to ranking only in the top 100

Figure 13G:
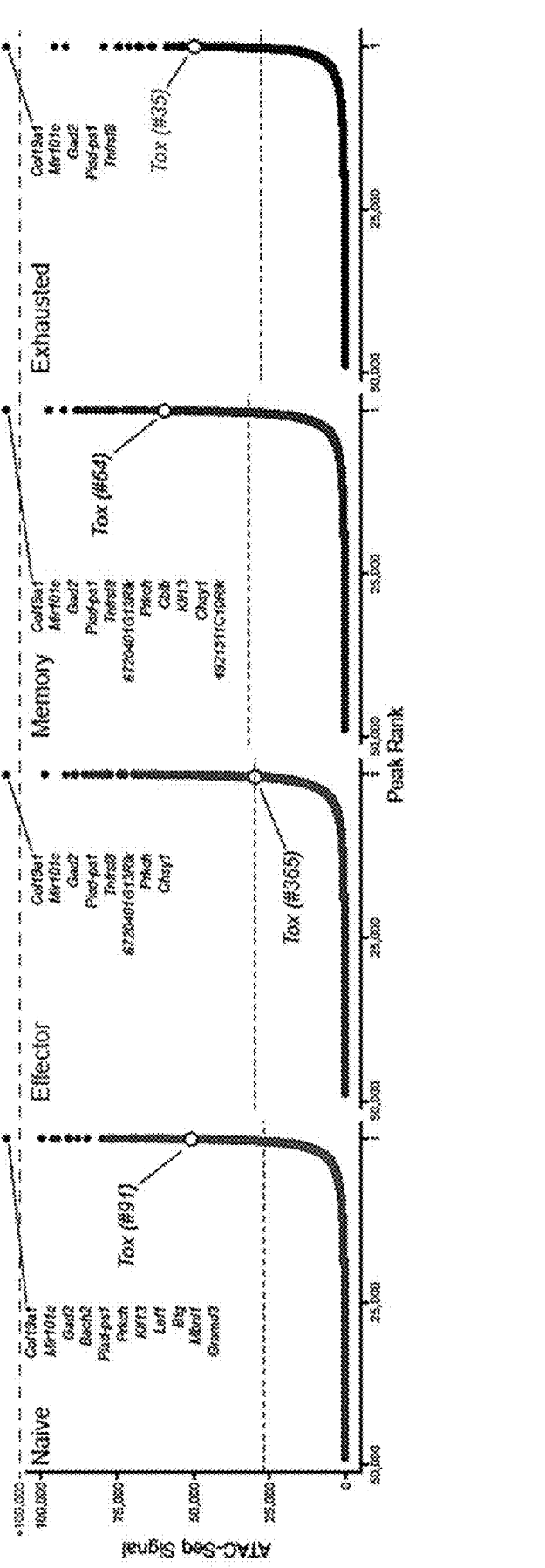
FIG. 13G shows distribution of ATAC-seq signal across loci in $T_N$, $T_{EFF}$, TMEM, and $T_{EX}$ P14 T cells. Loci above horizontal dashed lines denote putative super enhancers. Rank of the Tox locus among all identified potential super enhancers is shown.

(Rank=91 or 64) in $T_N$ and $T_{MEM}$ (FIG. 13G). These observations may be of interest as such large regions of open chromatin and SEs often demarcate genes or loci involved in cell fate decisions(Hnisz, D. et al. Super-Enhancers in the Control of Cell Identity and Disease. *Cell* 155, 934-947 (2013)). Together, these data provoke the hypothesis that TOX may act as a central node in the differentiation pathway of $T_{EX}$.

Figure 15A:
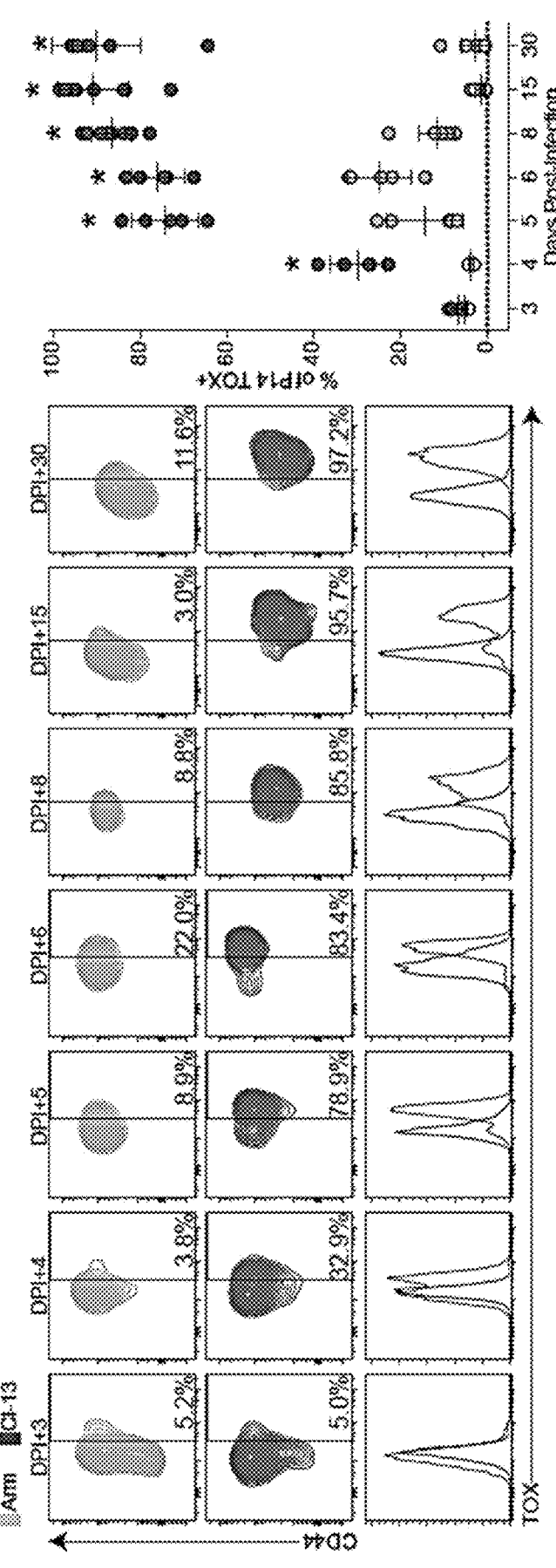
FIGS. 15A-15F illustrate that rapid and sustained TOX expression is associated with key features of exhaustion.
Figure 16B:
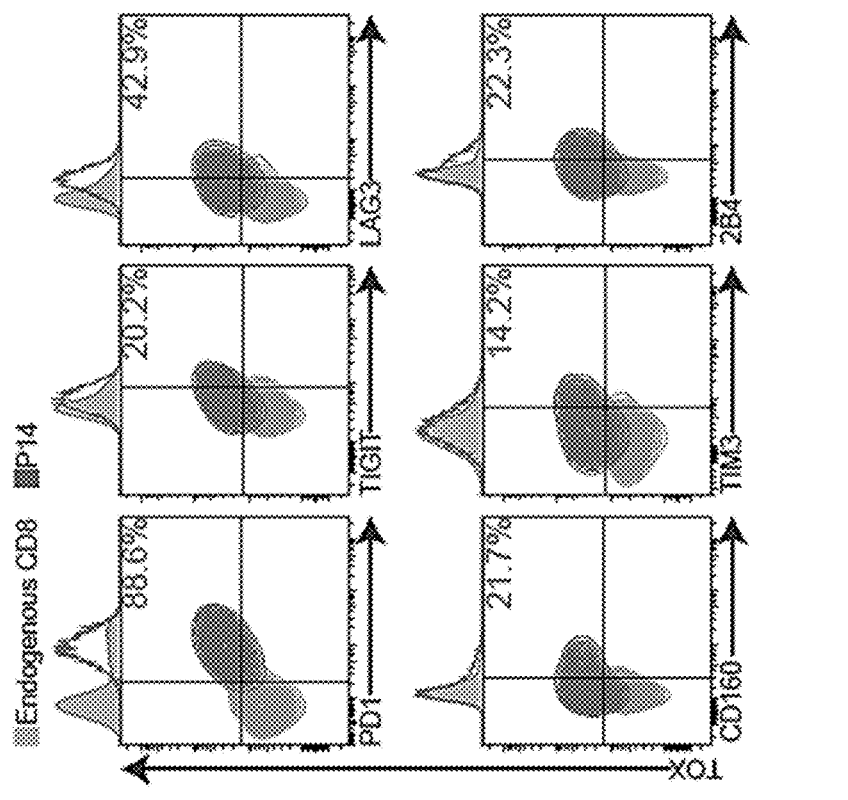
Figure 16A:
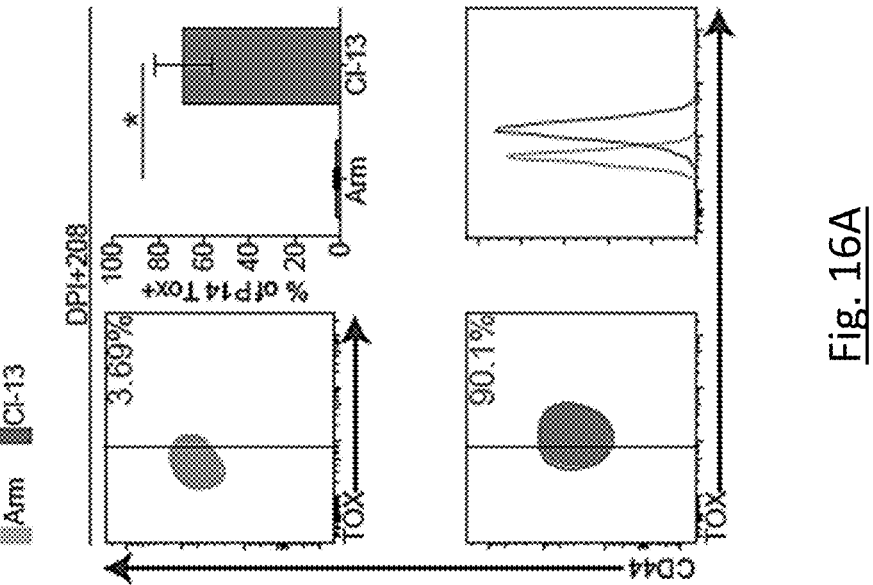

Example 12. High and Sustained TOX is Associated with $T_{EX}$ and Key Exhaustion Features in Chronic Infection and Cancer To extend the transcriptional analysis above, TOX protein expression was measured in $T_{EFF}$, $T_{MEM}$, and developing $T_{EX}$ over the course of acute or chronic LCMV infection. In agreement with the gene expression data, TOX protein levels were significantly increased within 4 days of chronic LCMV infection with ~80% of responding CD8+ T cells expressing high levels of TOX by d5 p.i. (FIG. 15A). Moreover, high TOX expression was sustained in >95% of the $T_{EX}$ population from d15 p.i. onward and remained highly expressed even >200 days p.i. (FIG. 15A and FIG. 16A). In contrast, although TOX was induced in $T_{EFF}$ responding to acutely resolving LCMV Arm infection, expression peaked 5-6 days p.i. and was limited to ~25% or less of the population. In addition, the amount of TOX protein per cell was considerably lower than in Cl-13 infection and expression was transient, returning to near baseline between d8-15 p.i. (FIG. 15A). Thus, although TOX was induced early during both acute and chronic viral infection, high and sustained TOX expression was only observed during chronic infection. Notably, the difference in TOX levels in CD8$^+$ T cells emerged before the time point when the virological outcomes were divergent (which occurs ~8 days p.i)(Wherry et al., Viral Persistence Alters CD8 T-Cell Immunodominance and Tissue Distribution and Results in Distinct Stages of Functional Impairment. *J Virol* 77:4911-4927; Odorizzi et al., Genetic absence of PD-1 promotes accumulation of terminally differentiated exhausted CD8+ T cells. *J Exp Med* 212:1125-1137 (2015)), suggesting that viral load alone was not a primary driver of differential expression.

Figure 15B:
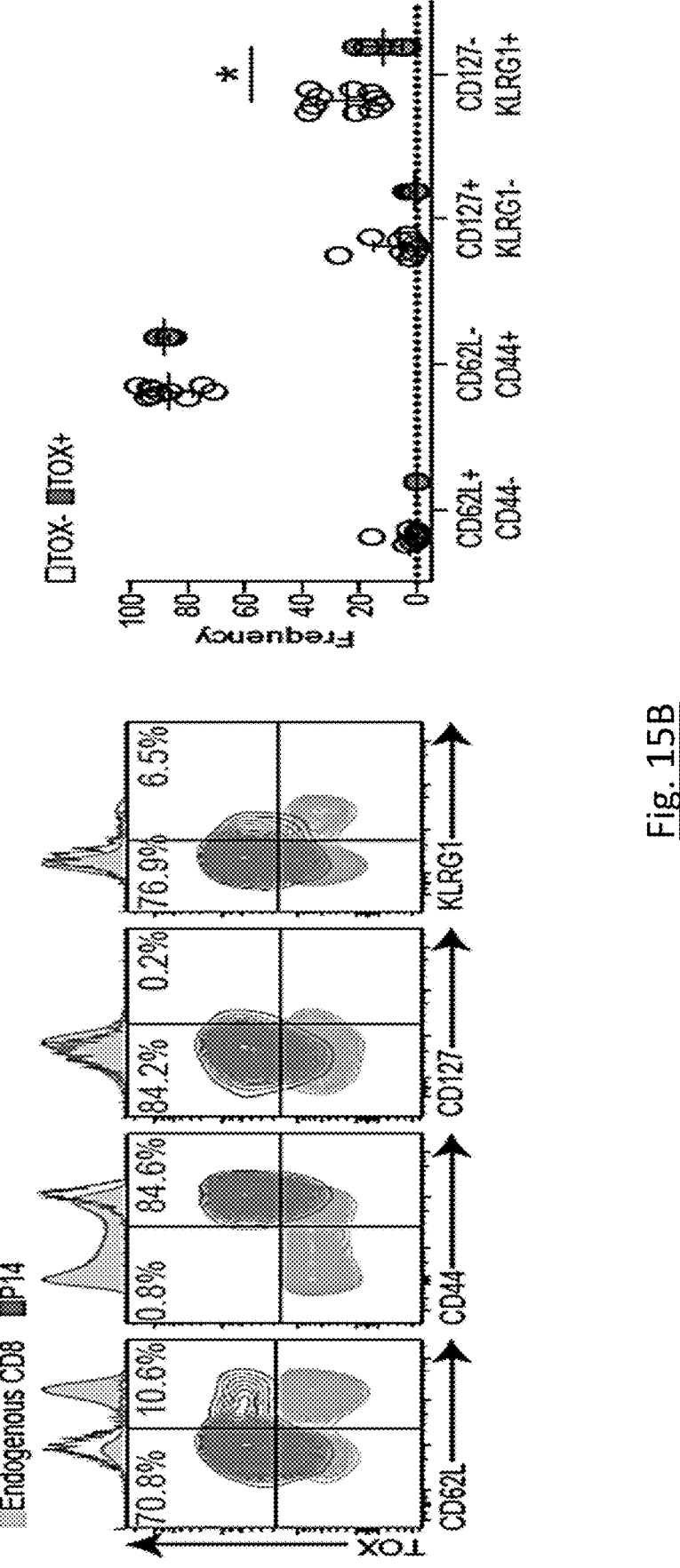
Figure 15C:
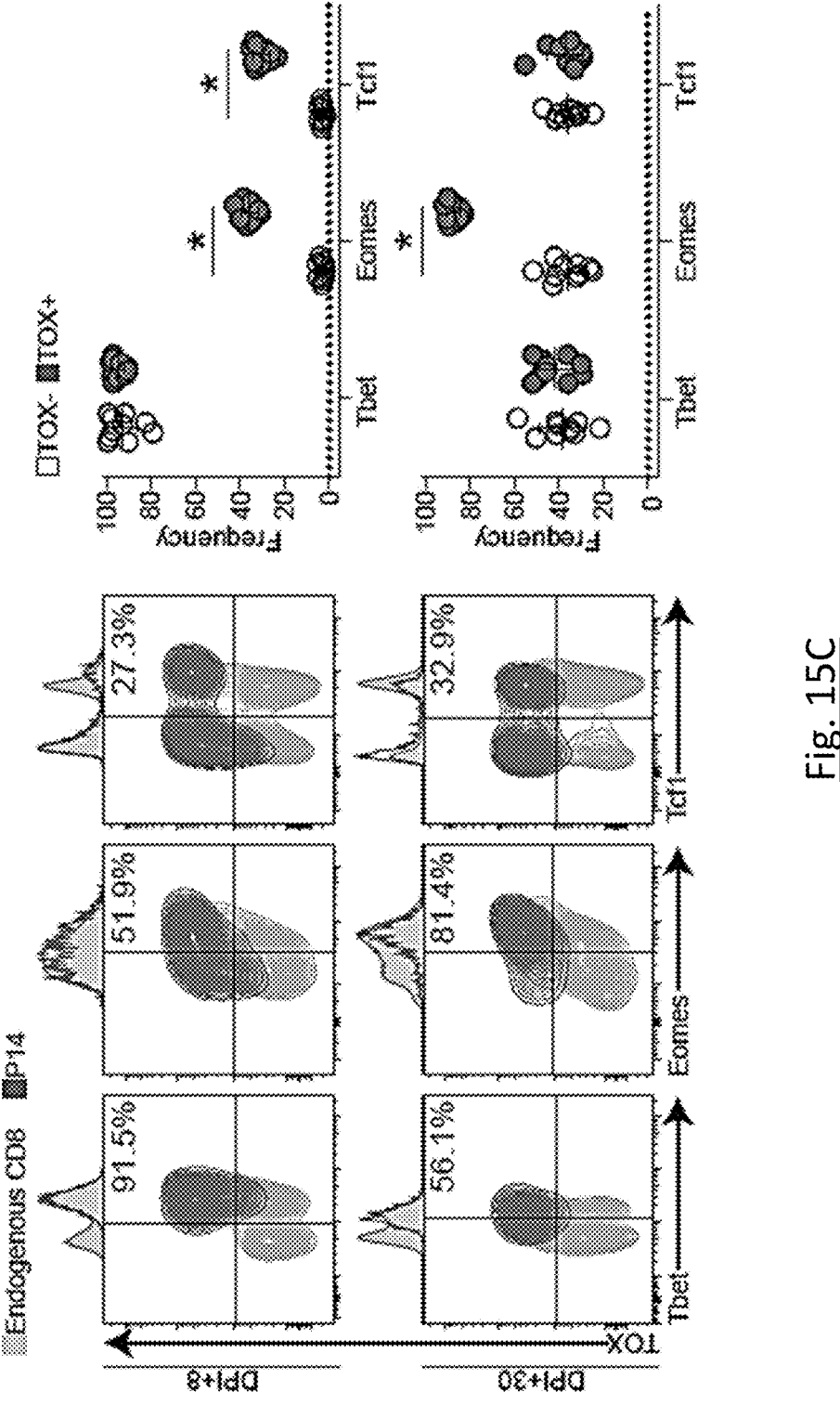
Figure 15D:
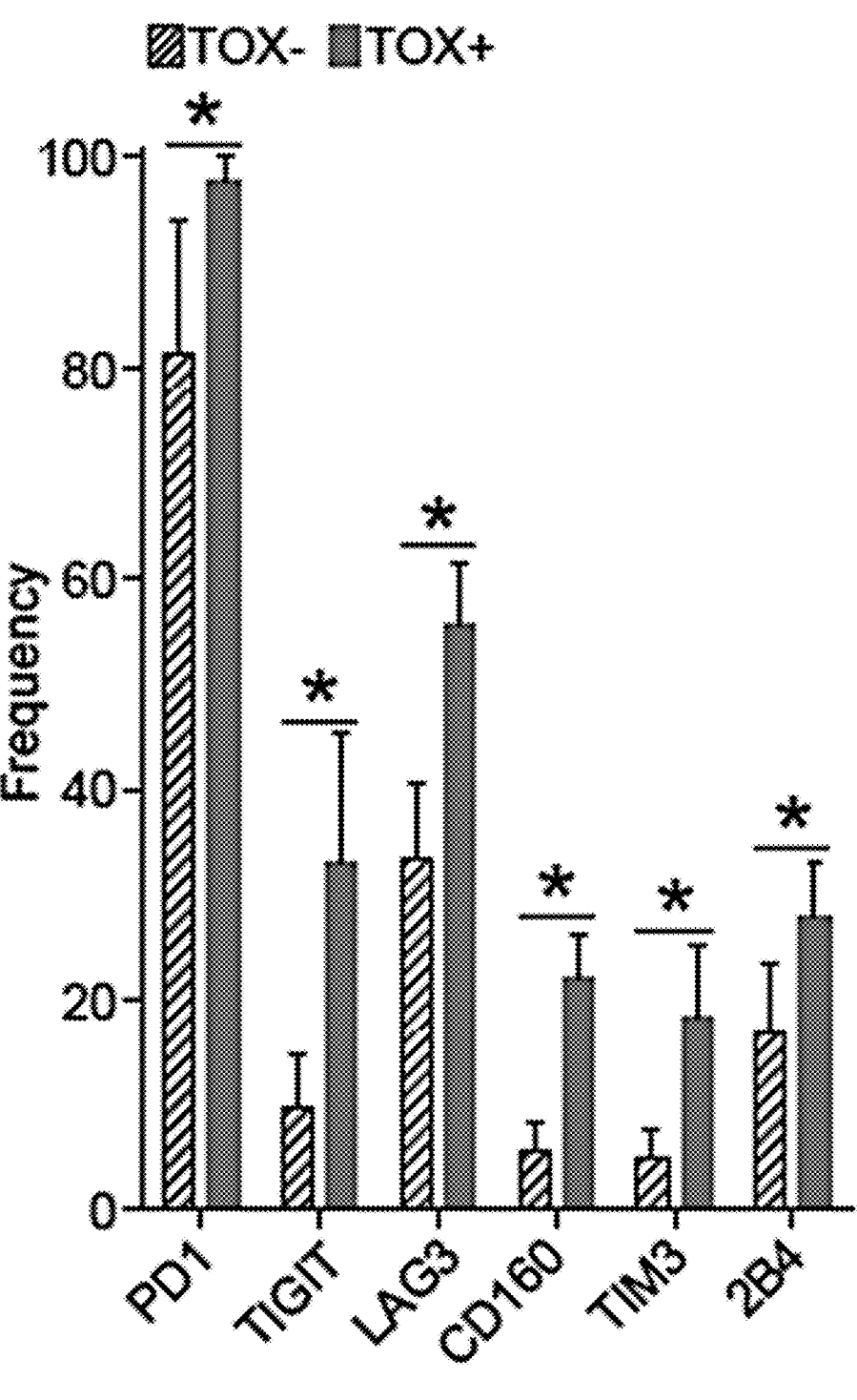

In light of these observations, we hypothesized that TOX expression during chronic infection was enriched in $T_{EX}$ cells and $T_{EX}$ precursors. Examining TOX$^-$ and TOX$^+$ virus-specific CD8$^+$ T cell populations at early time points revealed that, whereas the small population of CD127$^+$ KLRG1$^-$ cells that are the precursors to both $T_{MEM}$ and $T_{EX}$ contained both TOX$^-$ and TOX$^+$ cells, TOX$^-$ cells were enriched in the CD127$^-$KLRG1$^+$ effector pool suggesting a negative relationship between TOX and KLRG1$^+$ terminal effector cells (Chang, J. T., Wherry, E. J. & Goldrath, A. W. Molecular regulation of effector and memory T cell differentiation. *Nat Immunol* 15, 1104-1115 (2014); Joshi, N. S. et al. Inflammation directs memory precursor and short-lived effector CD8(+) T cell fates via the graded expression of T-bet transcription factor. *Immunity* 27, 281-295 (2007); Hemdler-Brandstetter, D. et al. KLRG1$^+$ Effector CD8$^+$ T Cells Lose KLRG1, Differentiate into All Memory T Cell Lineages, and Convey Enhanced Protective Immunity. *Immunity* 48, 716-729.e8 (2018)) (FIG. 15B). This KLRG1$^+$ terminal effector population is highly functional and likely important for pathogen control during acute infection. Yet, these cells are unable to generate $T_{EX}$, perhaps due to a lack of expression of transcription factors such as Tcf1 and Eomes that are critical for formation and long-term maintenance of $T_{EX}$ cells (Utzschneider, D. T. et al. T Cell Factor 1-Expressing Memory-like CD8+ T Cells Sustain the Immune Response to Chronic Viral Infections. *Immunity* 45, 415-427 (2016); Paley, M. A. et al. Progenitor and Terminal Subsets of CD8+ T Cells Cooperate to Contain Chronic Viral Infection. *Science* 338, 1220-1225 (2012); Angelosanto, J. M., Blackburn, S. D., Crawford, A. & Wherry, E. J. Progressive loss of memory T cell potential and commitment to exhaustion during chronic viral infection. *J Virol* 86, 8161-8170 (2012)). Indeed, Tcf1 and Eomes expression was confined mainly to the TOX+ cells at d8 p.i. (FIG. 15C, top). Although, the relationship between TOX and Tcf1 was not maintained later in chronic infection, the correlation between TOX and Eomes became stronger, suggesting that once exhaustion is established, TOX may be more associated with terminally differentiated (i.e. EomesHi) $T_{EX}$ cells (FIG. 15C, bottom). A defining characteristic of $T_{EX}$ is the co-expression of multiple inhibitor receptors20. TOX+ cells had high expression of PD-1, TIGIT, LAG3 and CD160 throughout chronic infection (FIG. 15D and FIGS. 16B-16C). Thus, TOX was transiently induced upon CD8+ T cell activation during acutely resolved LCMV infection, but was only expressed at high levels and sustained in the chronic infection. Moreover, TOX expression was anti-correlated with the development of KLRG1+ terminal $T_{EFF}$ and was rather associated with high co-expression of inhibitory receptors and key $T_{EX}$ TF.

Figures 15E, 15F:
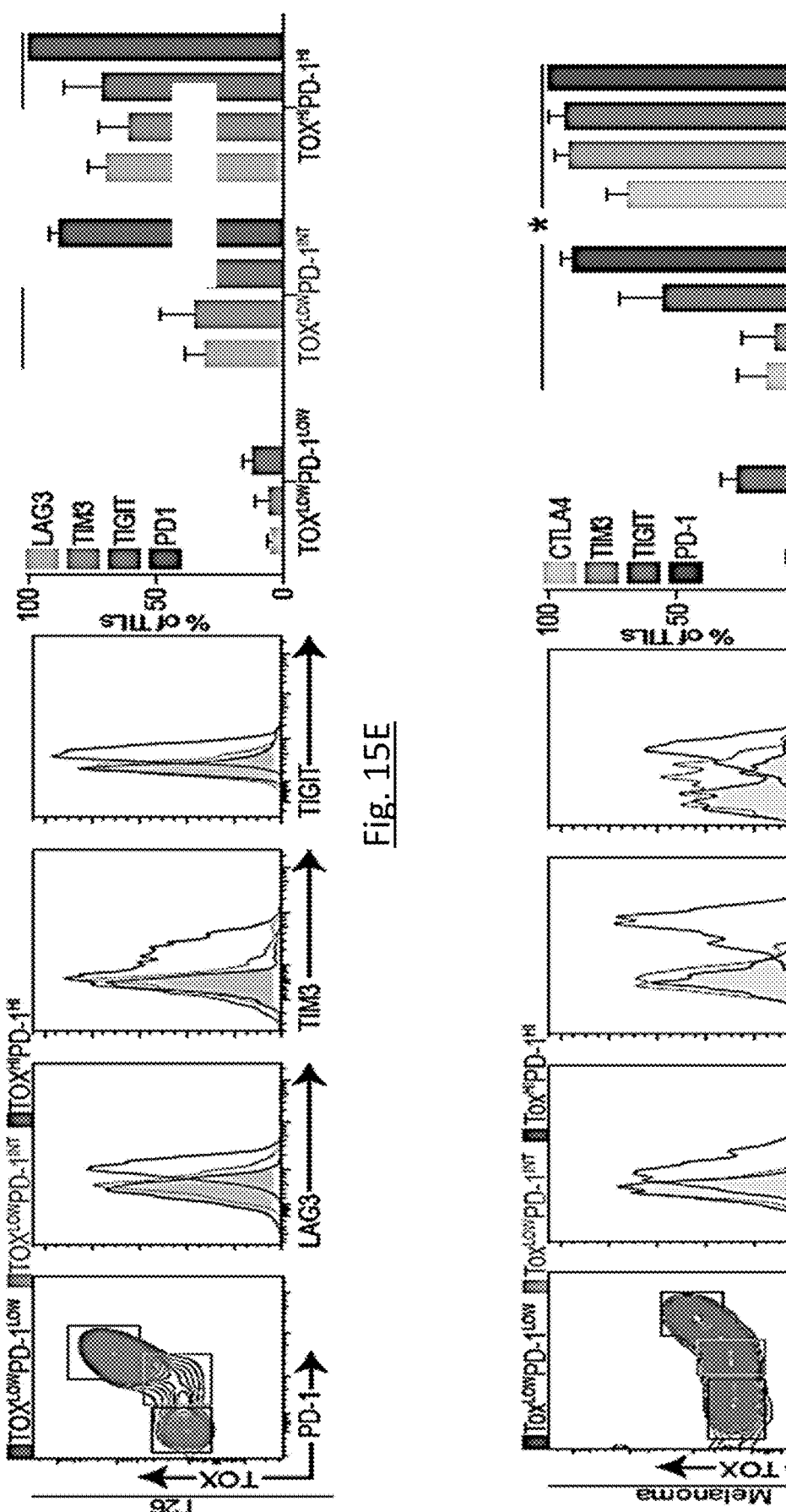
Figure 16D:
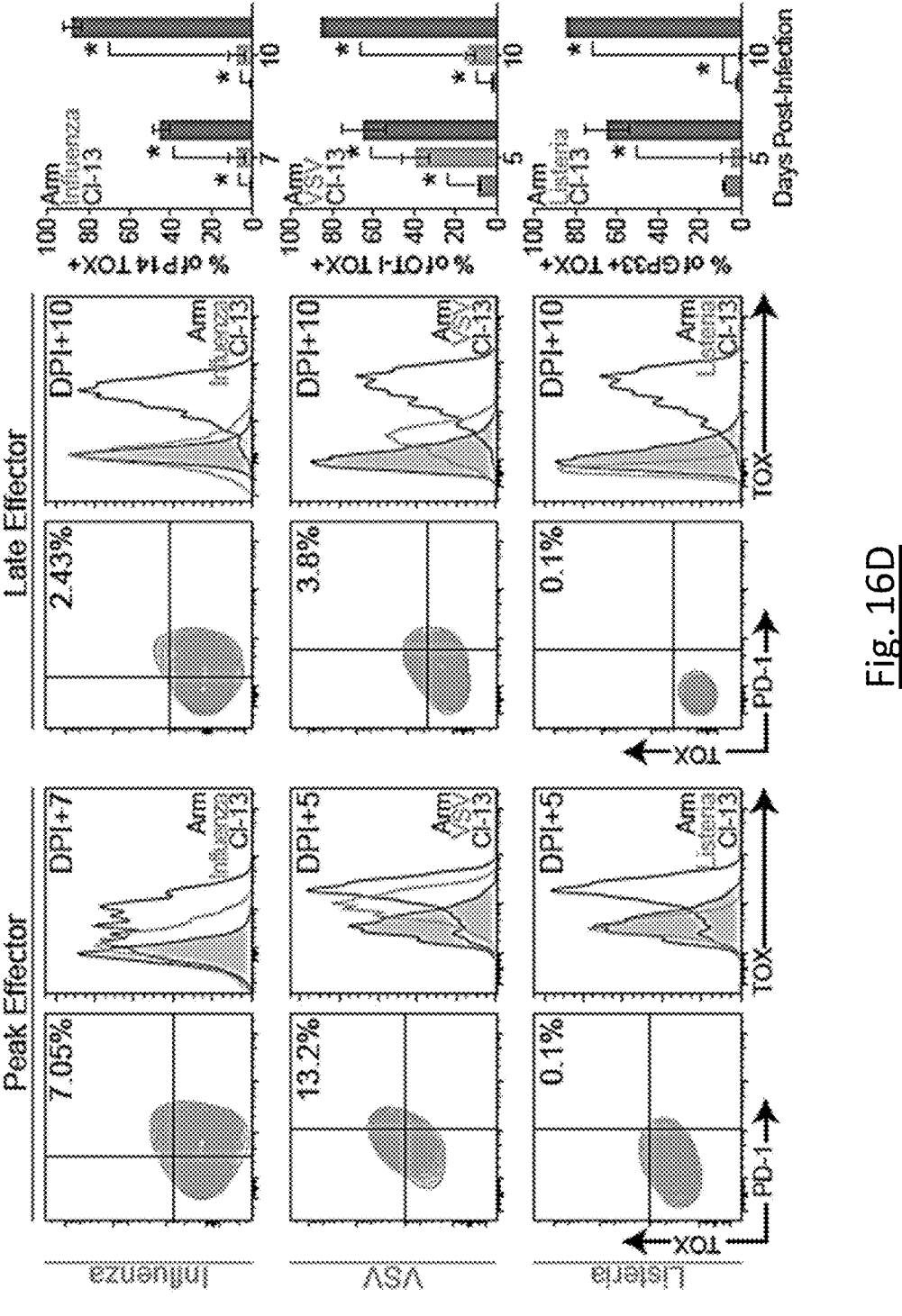
Figure 16E:
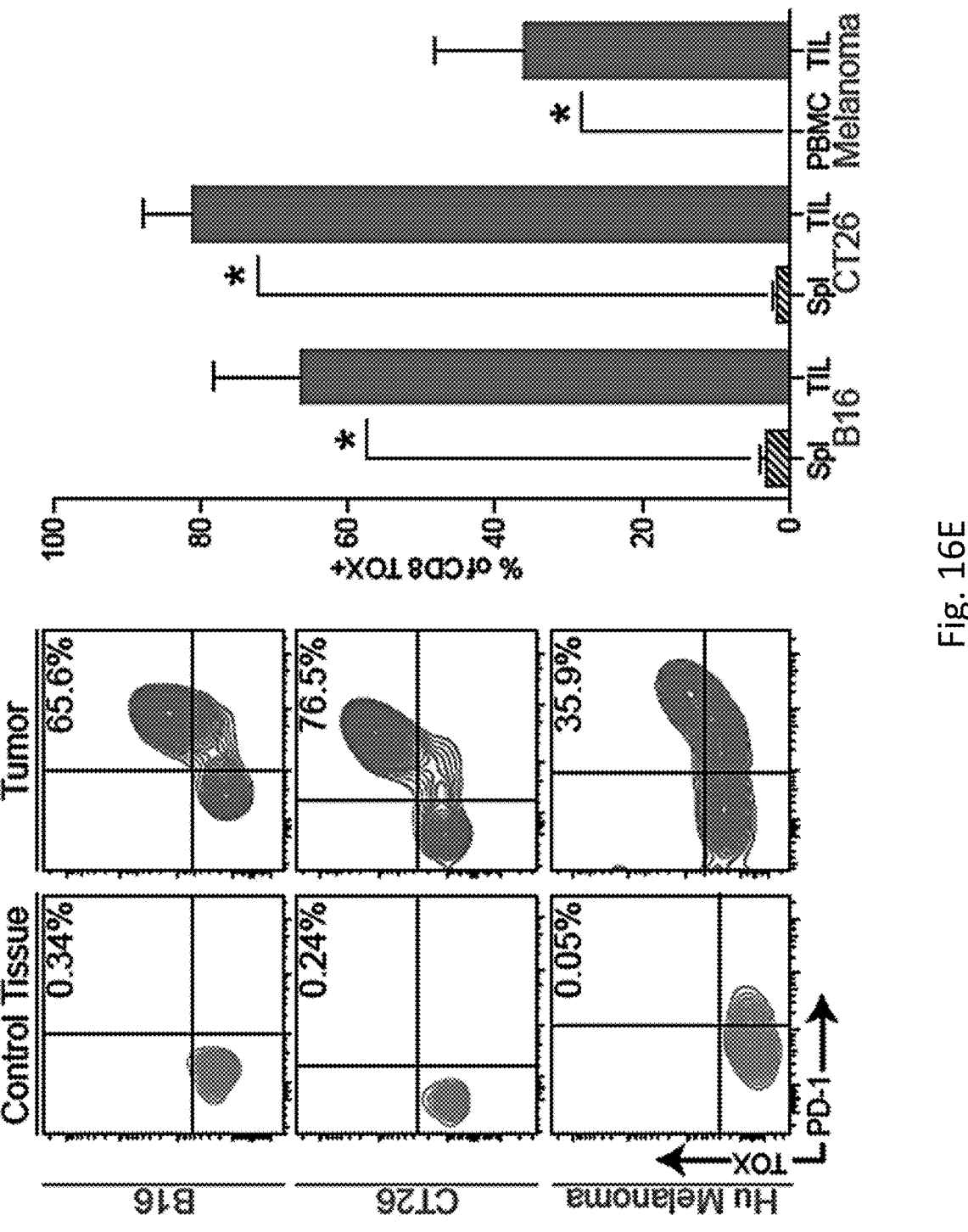

TOX expression was next examined in other acutely resolved infections and in cancer. Initial induction, but only transient expression of TOX was observed during acute infection in mice with influenza virus (Flu), vesicular stomatitis virus (VSV), and Listeriamonocytogenes (LM). As observed for acute LCMV Arm infection, TOX expression in the setting of Flu, VSV, and LM was limited to the peak of the effector phase and rapidly diminished over time (FIG. 16D). In these settings, there was a modest trend to higher TOX associating with PD-1 expression (FIG. 16D). To test other settings of chronic antigen stimulation, the B16 and CT26 mouse tumor models were used. The majority of tumor-infiltrating T cells (TILs) in both models had high levels of TOX. Additionally, a high frequency of TILs from human melanoma patients also expressed TOX protein, suggesting the association between TOX expression and sustained antigen exposure extended across species (FIG. 16E). Finally, in both mice and humans there was a strong association between high TOX expression and high co-expression of multiple inhibitory receptors including PD-1 (FIGS. 15E-15F). Thus, TOX was transiently induced in antigen-specific CD8+ T cells during acutely resolved infections, but was not sustained in the vast majority of cells. In contrast, during chronic LCMV infection and cancer, TOX was more highly expressed and robustly sustained in the vast majority of antigen-specific CD8+ T cells where it was positively correlated with high expression of inhibitory receptors. Moreover, it appears that TOX may have a similar role in T cell responses to cancer in both mice and humans.

Example 13. An Essential Role for TOX in the Generation of $T_{EX}$

Figure 18A:
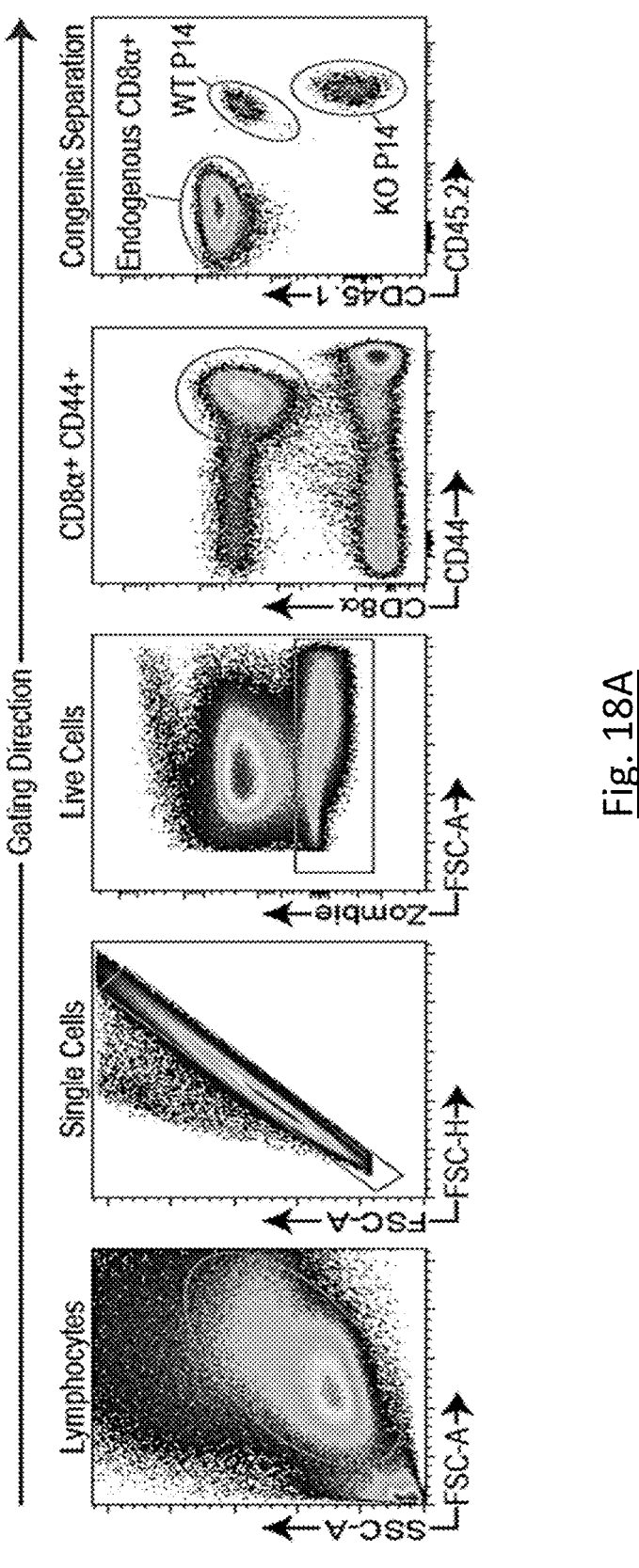
FIGS. 18A-18K-illustrate that WT and TOX cKO T cells were mixed 1:1 and adoptively transferred into congenic WT mice followed by infection with Arm (FIG. 18C, 18D, 18F-18K) or Cl-13 (FIGS. 18C-18E).
Figure 18B:
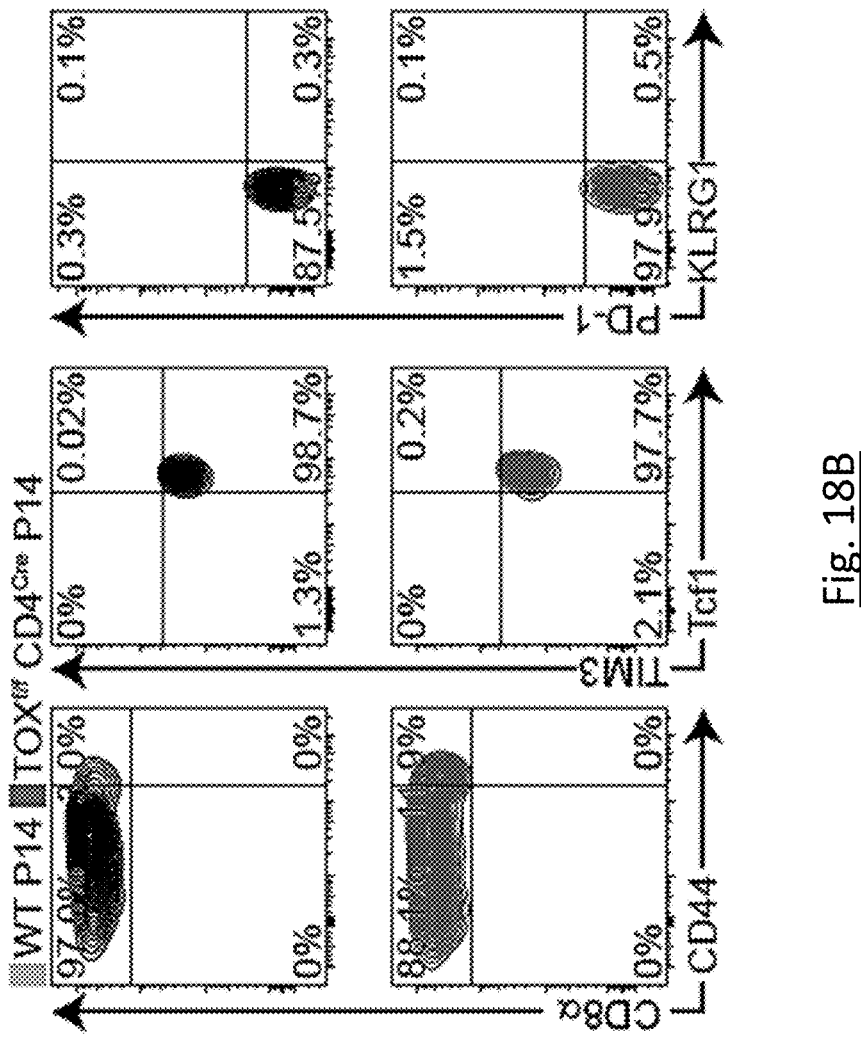

To further interrogate the role of TOX in $T_{EX}$, TOX-deficient CD8+ T cells were generated using TOX$^{Flox/Flox}$ x CD4$^{Cre}$ P14 mice (cKO). Naive P14 TOX cKO T cells were mixed 1:1 with congenically distinct control (WT) P14 cells and adoptively transferred into hosts with a third congenic background (FIG. 18A). Notably, naive TOX cKO P14 cells, compared to WT P14, had similar baseline activation and expression of inhibitory receptors (FIG. 18B). These recipient mice were then infected with LCMV Cl-13. This co-adoptive transfer approach allowed us to control for potential differences in viral load and inflammatory milieu.

Figure 17A:
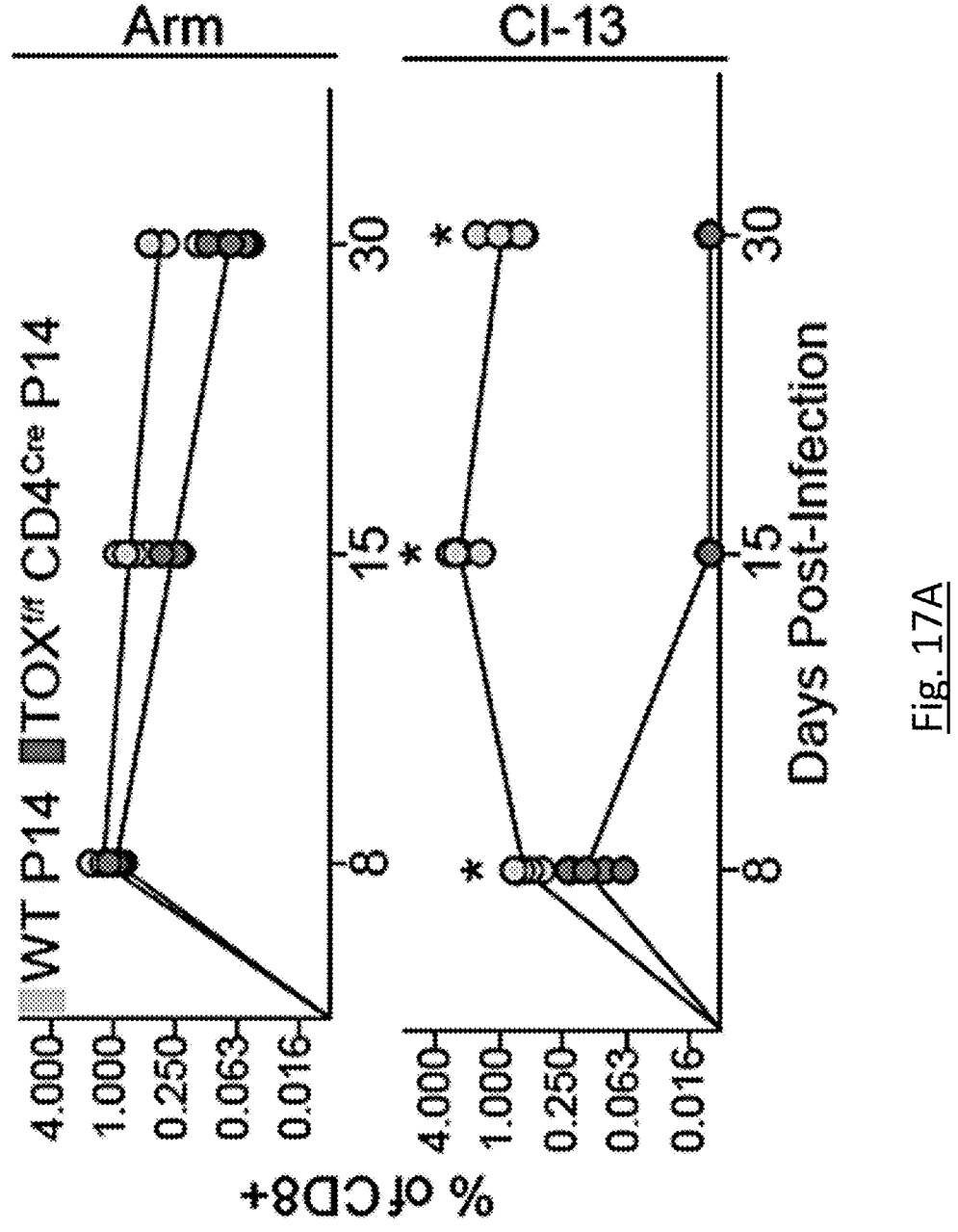
FIGS. 17A-17I illustrate that TOX is required for the development of T$_{EX}$. Congenically distinct naive WT and TOX$^{Flox/Flox}$ CD4$^{Cre}$ (TOX cKO) P14 T cells were mixed at a 1:1 ratio and adoptively transferred into WT mice with a third congenic background followed by infection with LCMV Arm or Cl-13. Spleens were harvested for analysis at indicated time points (FIG. 17A) or on d8 of Cl-13 infection (FIGS. 55B-55E).
Figure 17B:
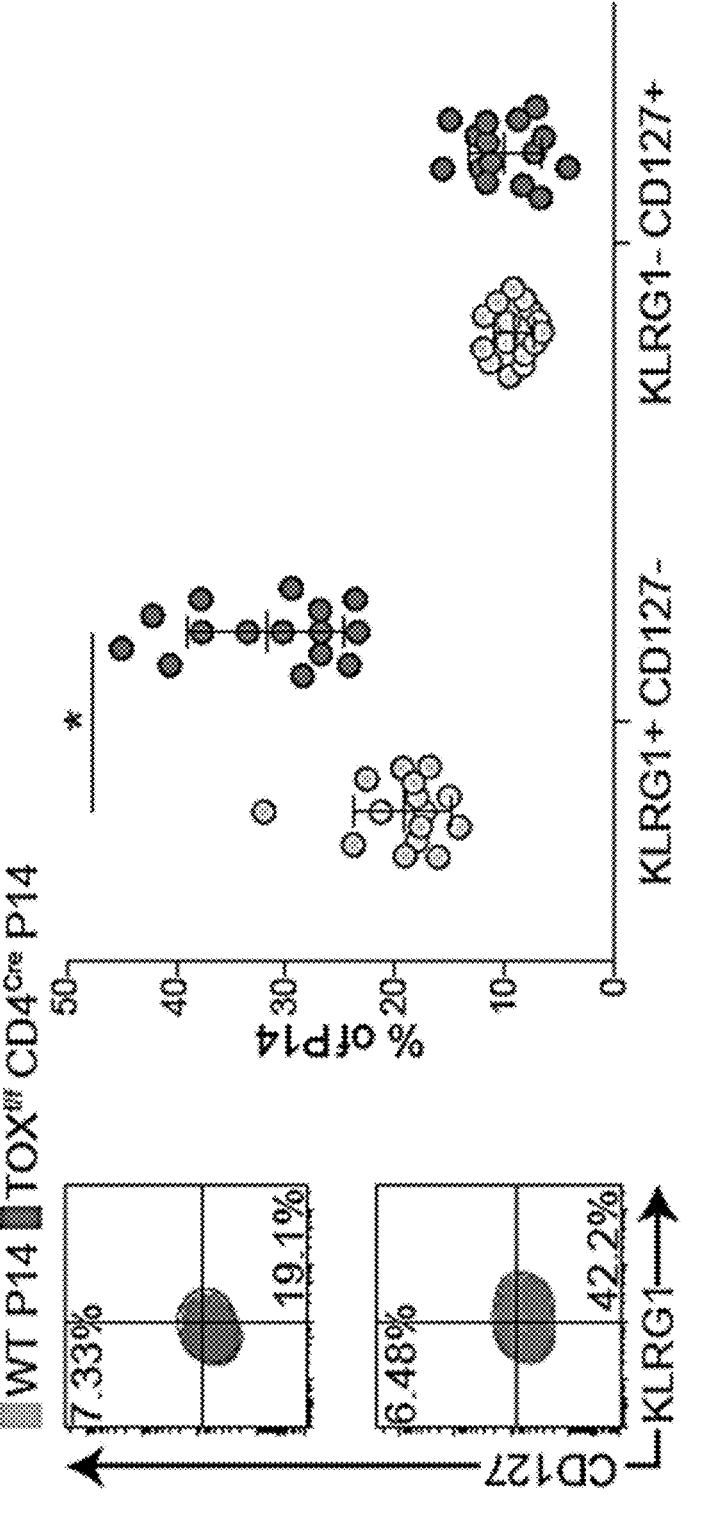
Figure 18D:
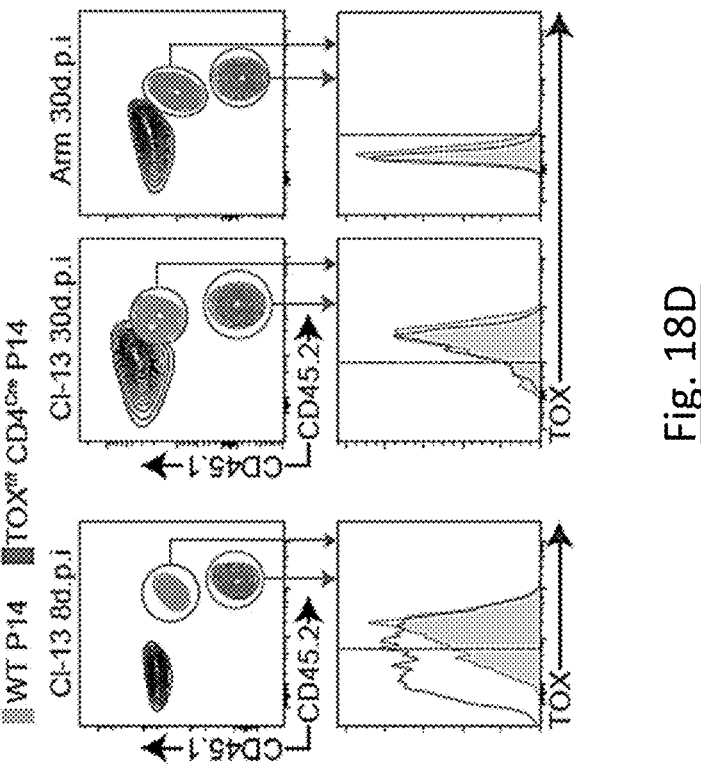
Figure 18C:
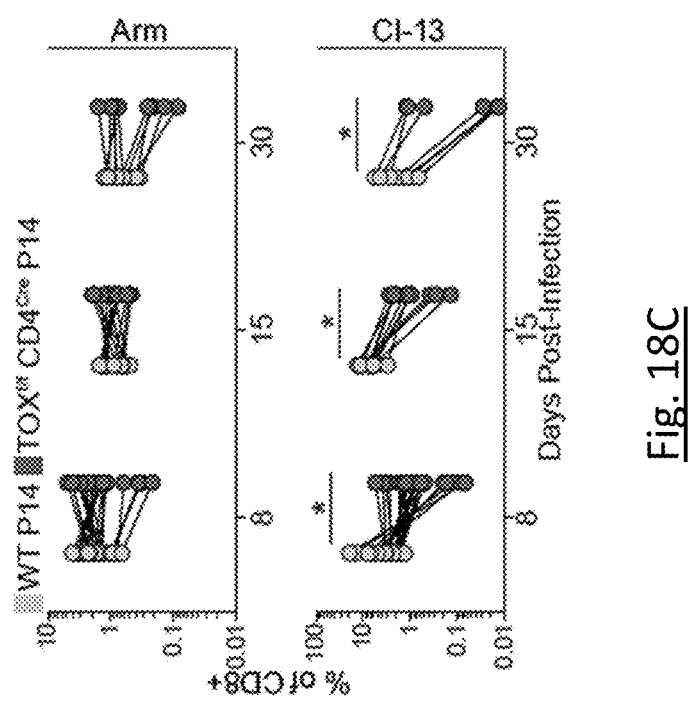
Figure 18F:
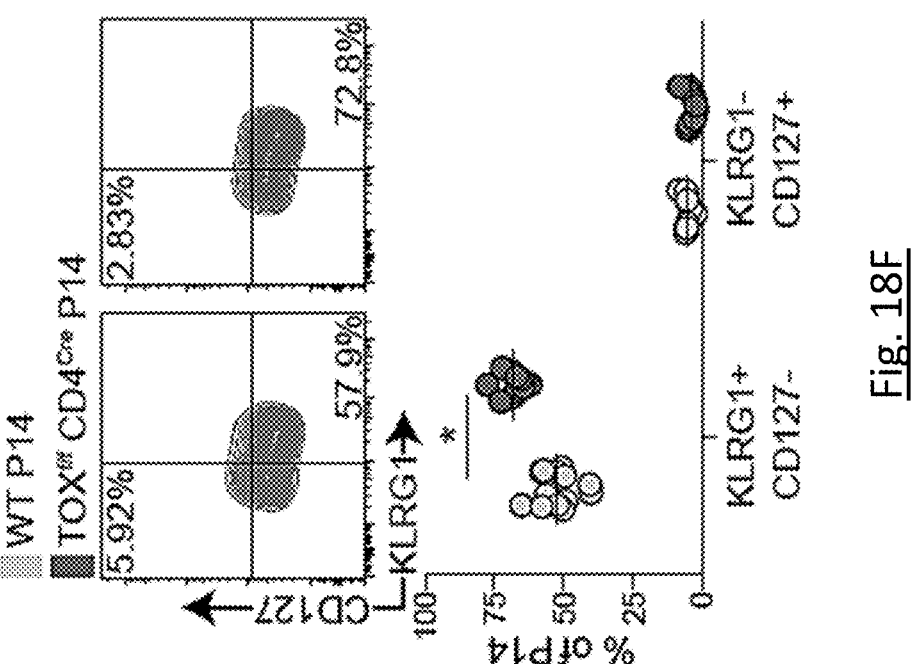
Figure 18E:
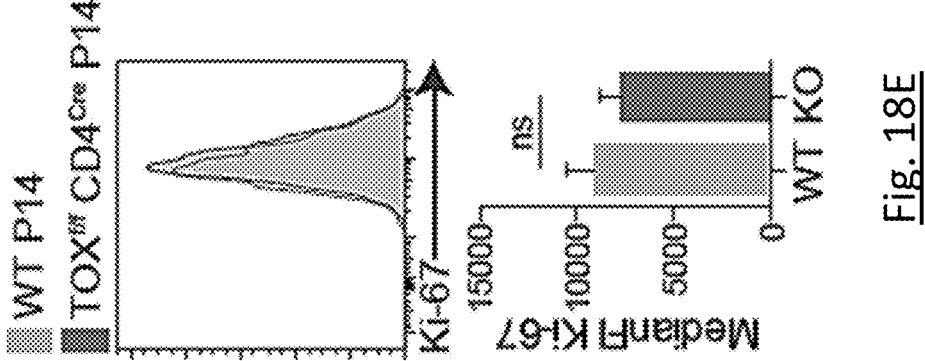

In response to chronic infection, TOX cKO P14 cells mounted an initial response, but then rapidly declined in number and were not sustained past d15 p.i. in contrast to the co-transferred WT P14 cells (FIG. 17A and FIG. 18C). This decline was not due to rejection as TOX+ escapees that failed to completely delete Tox could readily be detected and persisted throughout the course of chronic infection (FIG. 18D). Nor was this due to a difference in replicative capacity, as both TOX cKO and WT P14 cells expressed similar levels of Ki-67 (FIG. 18E). Moreover, TOX cKO P14 cells responding to acutely resolved LCMV Arm generated robust $T_{EFF}$ and $T_{MEM}$ cells that were easily detectable for at least 30 days following infection (FIG. 17A). Thus, TOX cKO CD8+ T cells were not intrinsically unable to form CD8+ T cells that could persist following acute infection including $T_{MEM}$, but rather had a specific lesion in the ability to generate of $T_{EX}$.

Figure 17C:
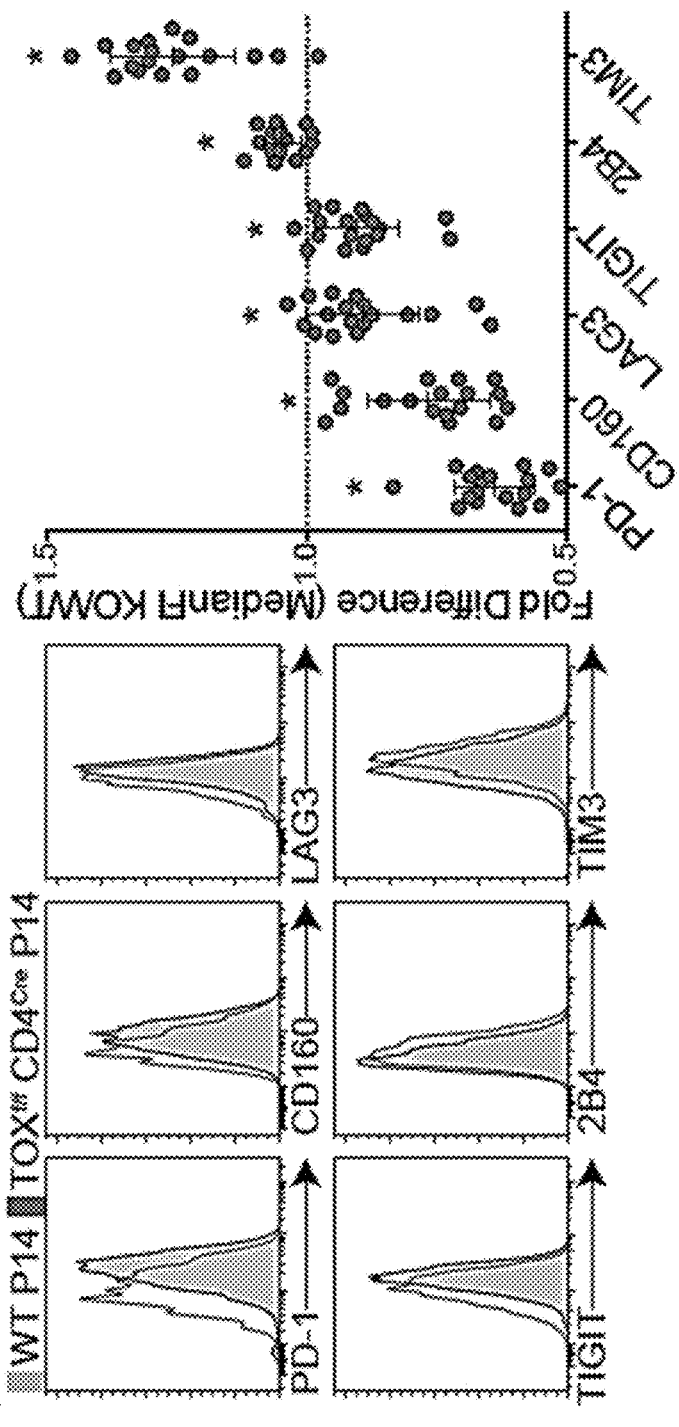
Figure 17D:
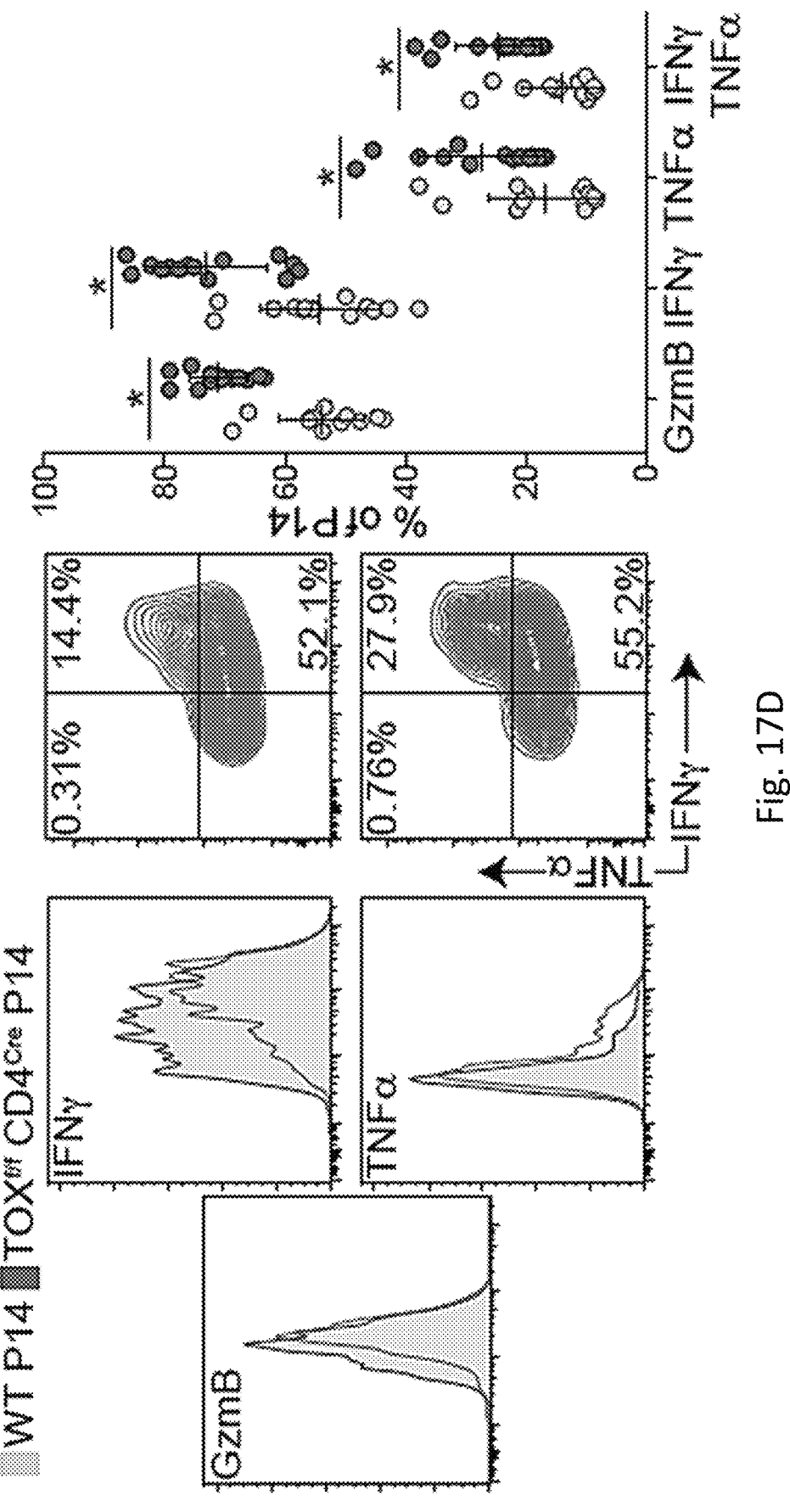
Figure 17E:
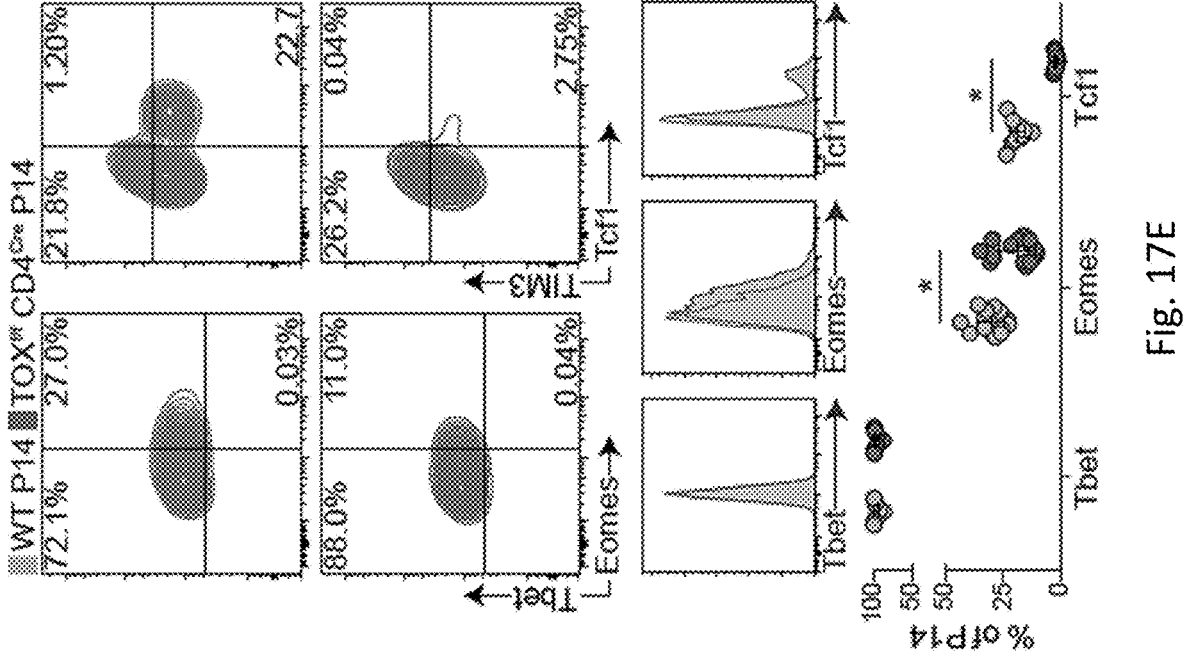
Figure 18G:
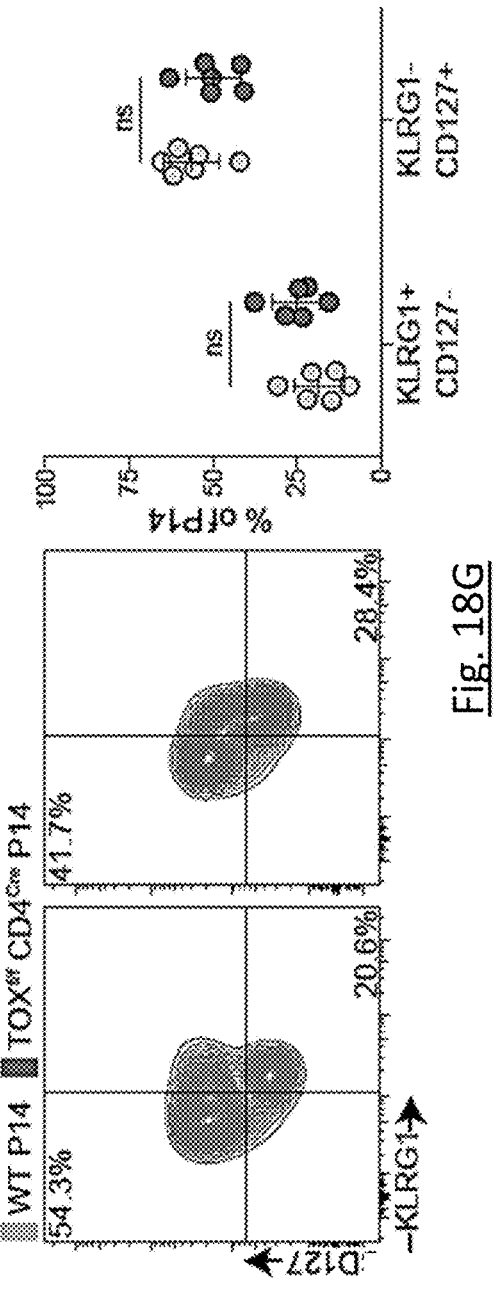
Figure 18H:
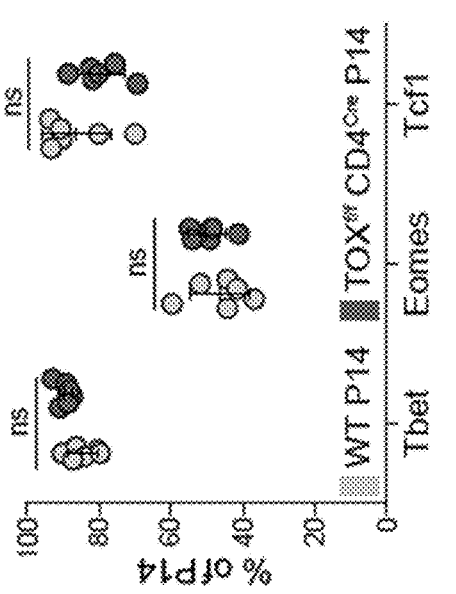
Figure 18I:
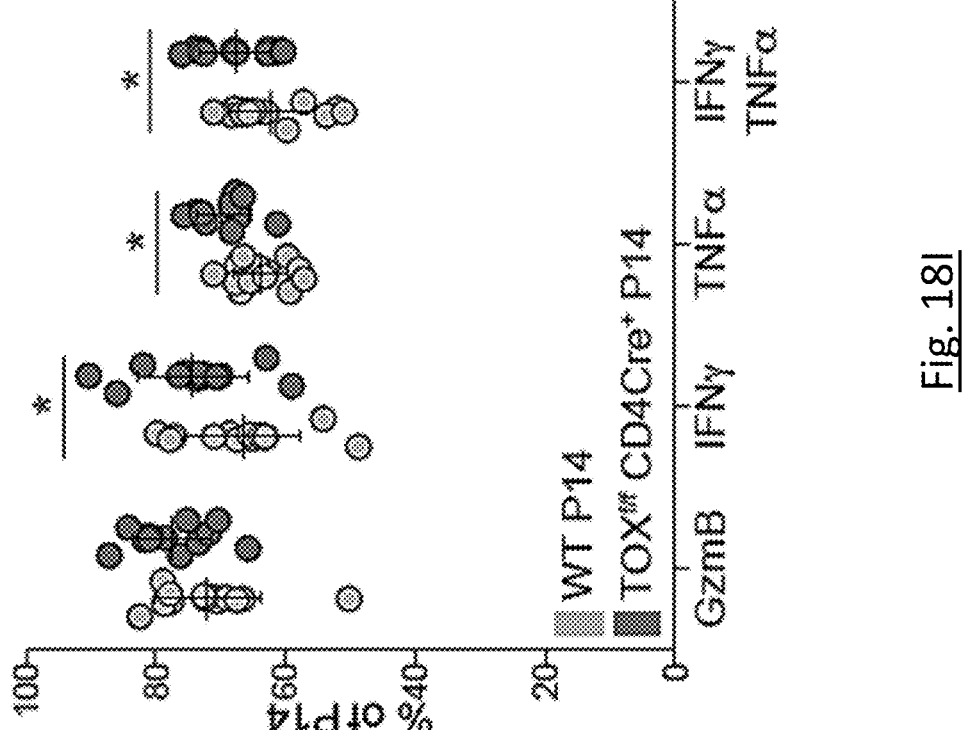
Figure 18J:
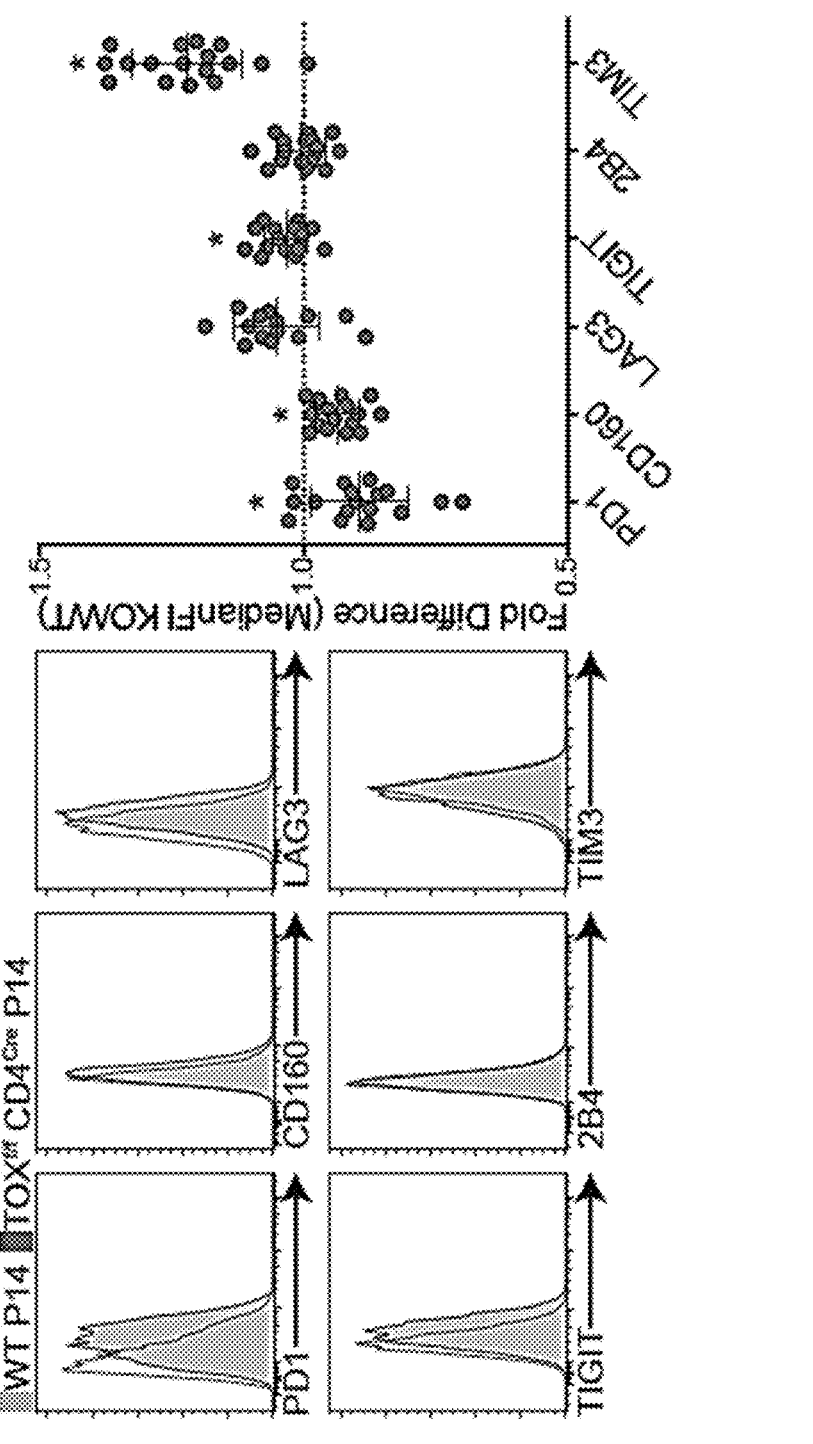
Figure 18K:
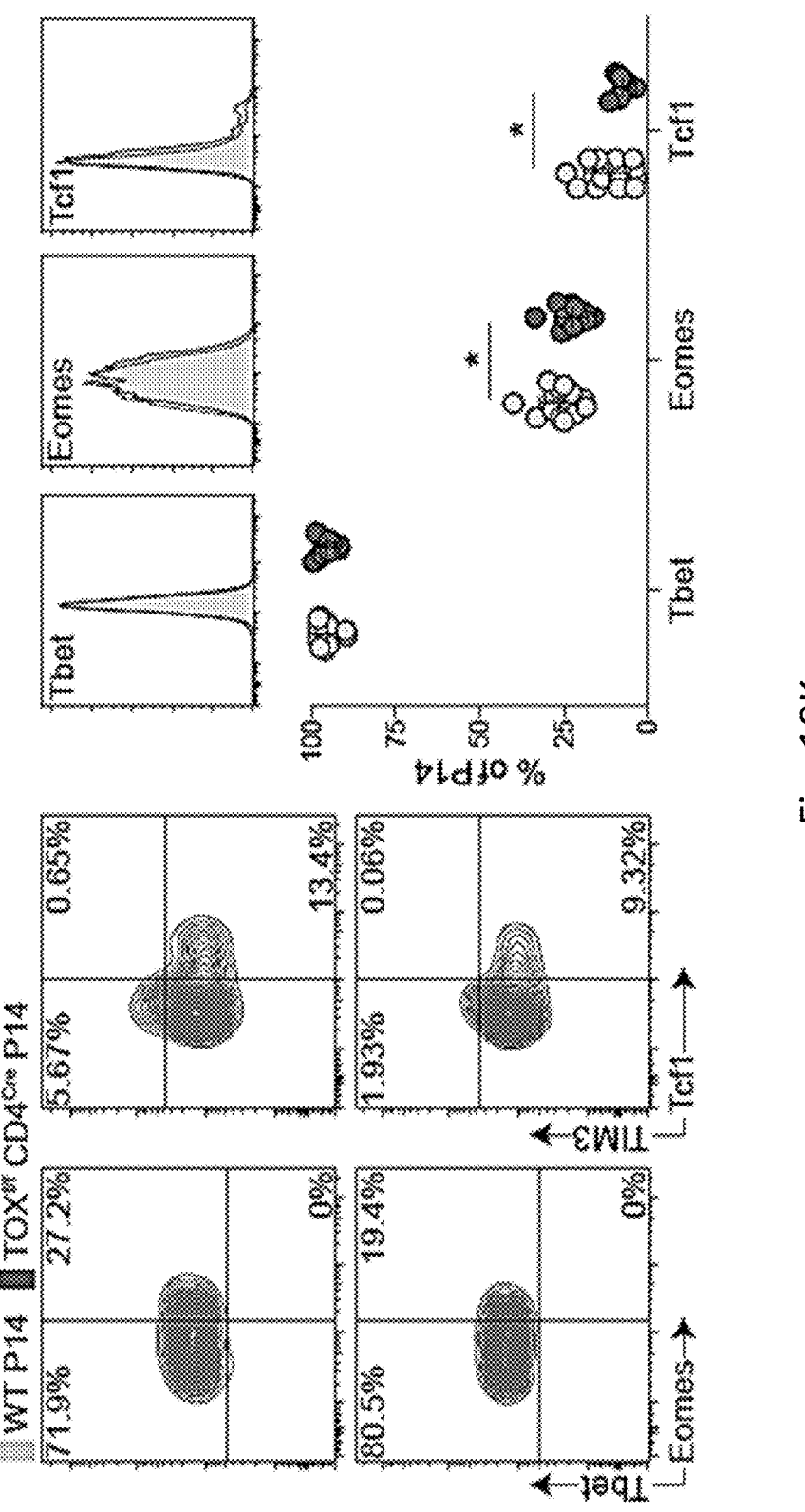

Based on the enrichment of KLRG1+ cells in the TOX⁻ fraction early during acute infection (FIG. 15B), without wishing to be bound by theory, it was posited that TOX-deficient T cells would be enriched for these terminal $T_{EFF}$ cells. Indeed, differentiation of TOX cKO P14 cells was skewed towards the generation of KLRG1+CD127⁻ $T_{EFF}$ in both acute and chronic infection (FIG. 17B and FIGS. 18F, 18I-18K). Yet, in acutely resolved Arm infection, TOX cKO effectively generated typical $T_{MEM}$ populations (FIG. 18G). In chronic infection, however, in contrast to WT P14 cells, TOX cKO cells expressed lower PD-1, CD160, LAG3, and TIGIT, though the inhibitory receptors 2B4 and TIM3 were increased without TOX at this early time point (FIG. 17C). TOX deficiency also resulted in improved function, consistent with the notion that TOX expression drives functional exhaustion (FIG. 17D). The establishment and long-term maintenance of $T_{EX}$ depends on a proliferative hierarchy mediated in part by the TFs Tcf1, T-bet and Eomes (Wu, T. et al. The TCF1-Bcl6 axis counteracts type I interferon to repress exhaustion and maintain T cell sternness. Sci *Immunol* 1, eaai8593-eaai8593 (2016); Utzschneider, D. T. et al. T Cell Factor 1-Expressing Memory-like CD8+ T Cells Sustain the Immune Response to Chronic Viral Infections. *Immunity* 45, 415-427 (2016); Paley, M. A. et al. Progenitor and Terminal Subsets of CD8+ T Cells Cooperate to Contain Chronic Viral Infection. *Science* 338, 1220-1225 (2012)). The expression of these key TFs in the absence of TOX was therefore examined in $T_{EX}$. Eomes was reduced in the absence of TOX, whereas the related TF T-bet was unaffected (FIG. 17E). Tcf1 expression was nearly ablated in TOX cKO CD8+ T cells during chronic infection with a near absence of the Tcf1+subset of $T_{EX}$ (FIG. 17E). Notably, there was no defect in Tcf1 expression by naive TOX cKO cells and TOX cKO $T_{MEM}$ generated after acute infection expressed equivalent levels of Tcf1 and Eomes compared to WT $T_{MEM}$ cells (FIG. 18B and FIG. 18H). Without wishing to be bound by theory, these data suggest that a primary defect in TOX cKO $T_{EX}$ cells is the inability to re-wire transcriptional control of Tcf1 and/or Eomes after activation and initial $T_{EX}$ precursor development.

Figure 17F:
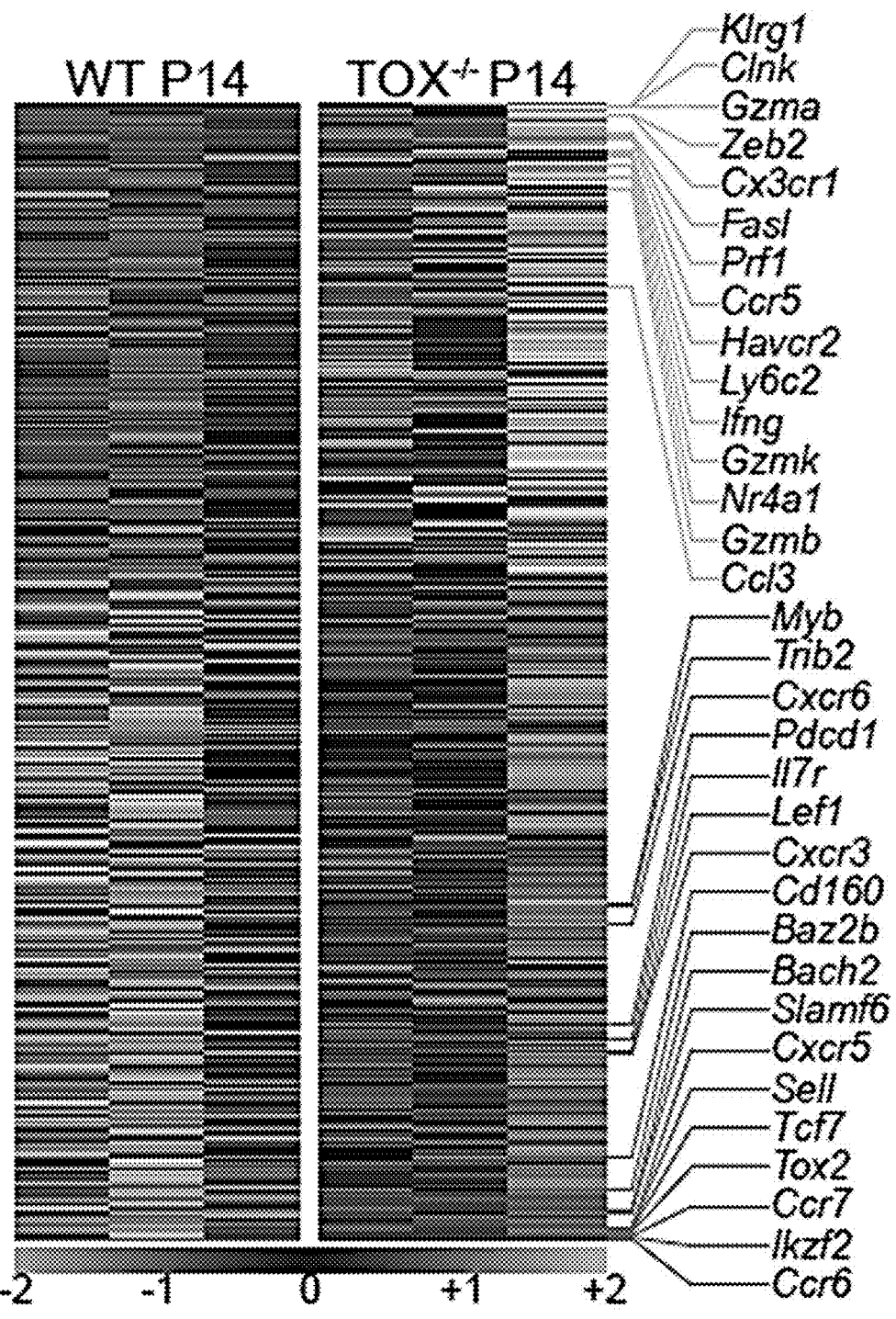
Figures 17G, 17H:
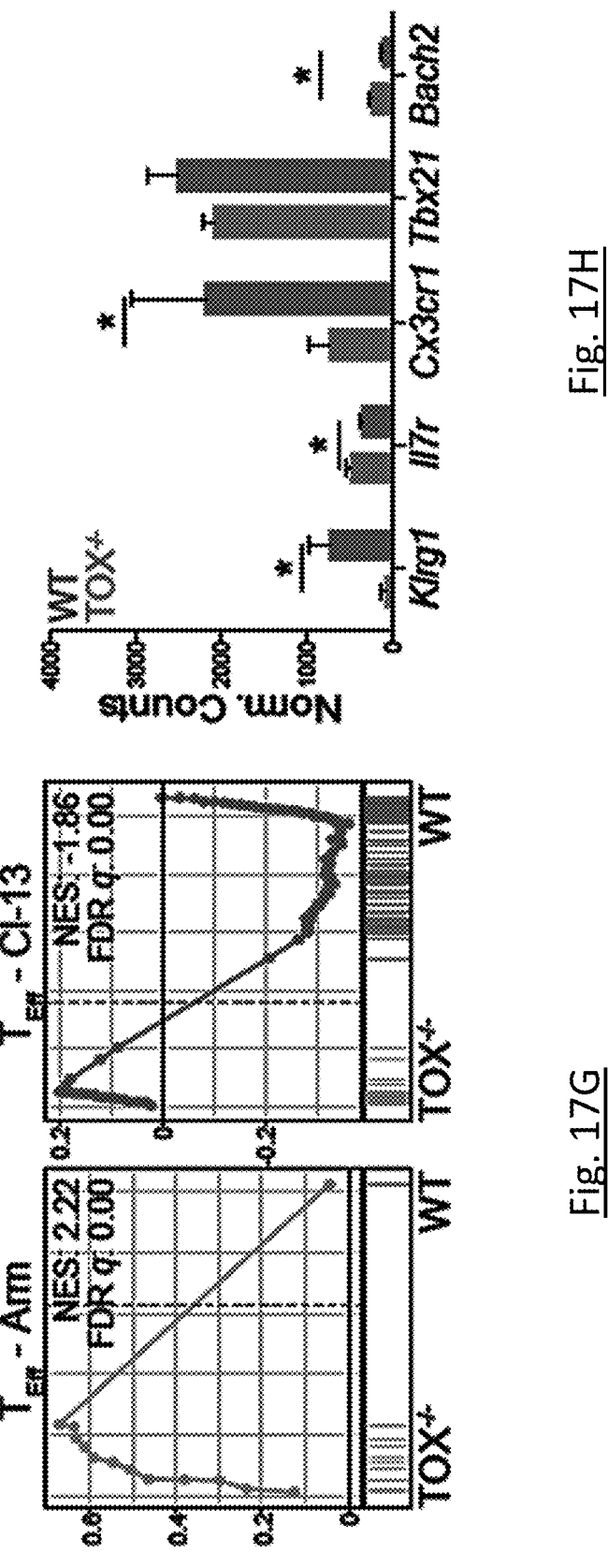
Figure 17I:
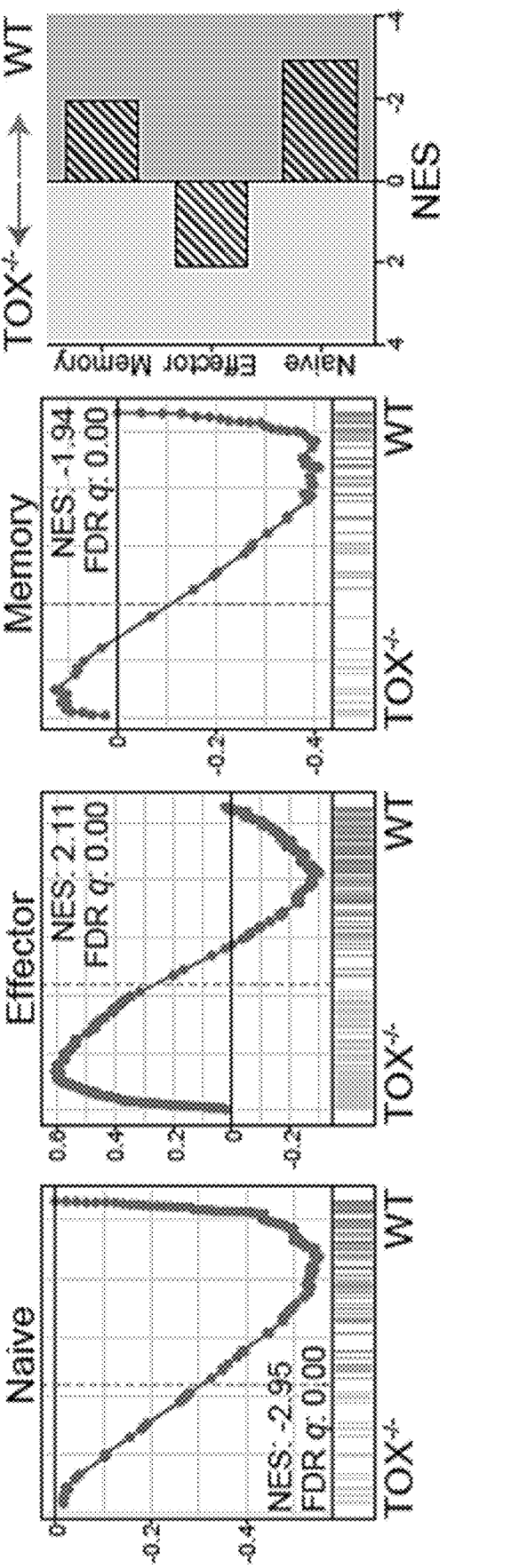

To better understand the transcriptional mechanisms downstream of TOX in $T_{EX}$, RNA-seq was performed on WT and TOX$^{-/-}$ P14 T cells isolated on d8 of Cl-13 infection. More than 3,100 genes differed between WT and TOX$^{-/-}$ CD8+ T cells at this time point. A major feature of these data was the upreglation of many $T_{EFF}$-like genes in the absence of TOX including Klrg1, Gzma, Gzmb, Cx3cr1, Zeb2 and Prf1 (FIG. 17F). In contrast, downregulated genes included Pdcd1 and Cd160, but also a number of genes associated with durability or T cell persistence including Myb, Il7r, Lef1, and Tcf7 (FIG. 17F). Indeed, in the absence of TOX in Cl-13 infection there was high enrichment for the signature from $T_{EFF}$ generated during LCMV Arm infection whereas the signature of $T_{EX}$ precursors (i.e. $T_{EFF}$ from Cl-13) was strongly depleted (FIG. 17G). Moreover, the pattern of gene expression associated with KLRG1+ short-lived terminal effectors that are incapable of giving rise to $T_{EX}$ was also observed in TOX-deficient P14 cells from Cl-13 infection (FIG. 17H-17I) (Herndler-Brandstetter, D. et al. KLRG1$^+$ Effector CD8$^+$ T Cells Lose KLRG1, 1265 Differentiate into All Memory T Cell Lineages, and Convey Enhanced Protective 1266 Immunity. *Immunity* 48, 716-729.e8 (2018); Joshi, N. S. et al. Inflammation directs memory precursor and short-lived effector CD8(+) T cell fates via the graded expression of T-bet transcription factor. *Immunity* 27, 281-295 (2007)). Without wishing to be bound by theory, collectively, these findings suggest that TOX promotes the generation of $T_{EX}$ by fostering several key developmental hallmarks of exhaustion while repressing the development of the KLRG1$^+$ $T_{EFF}$ lineage.

Figures 19C, 19D:
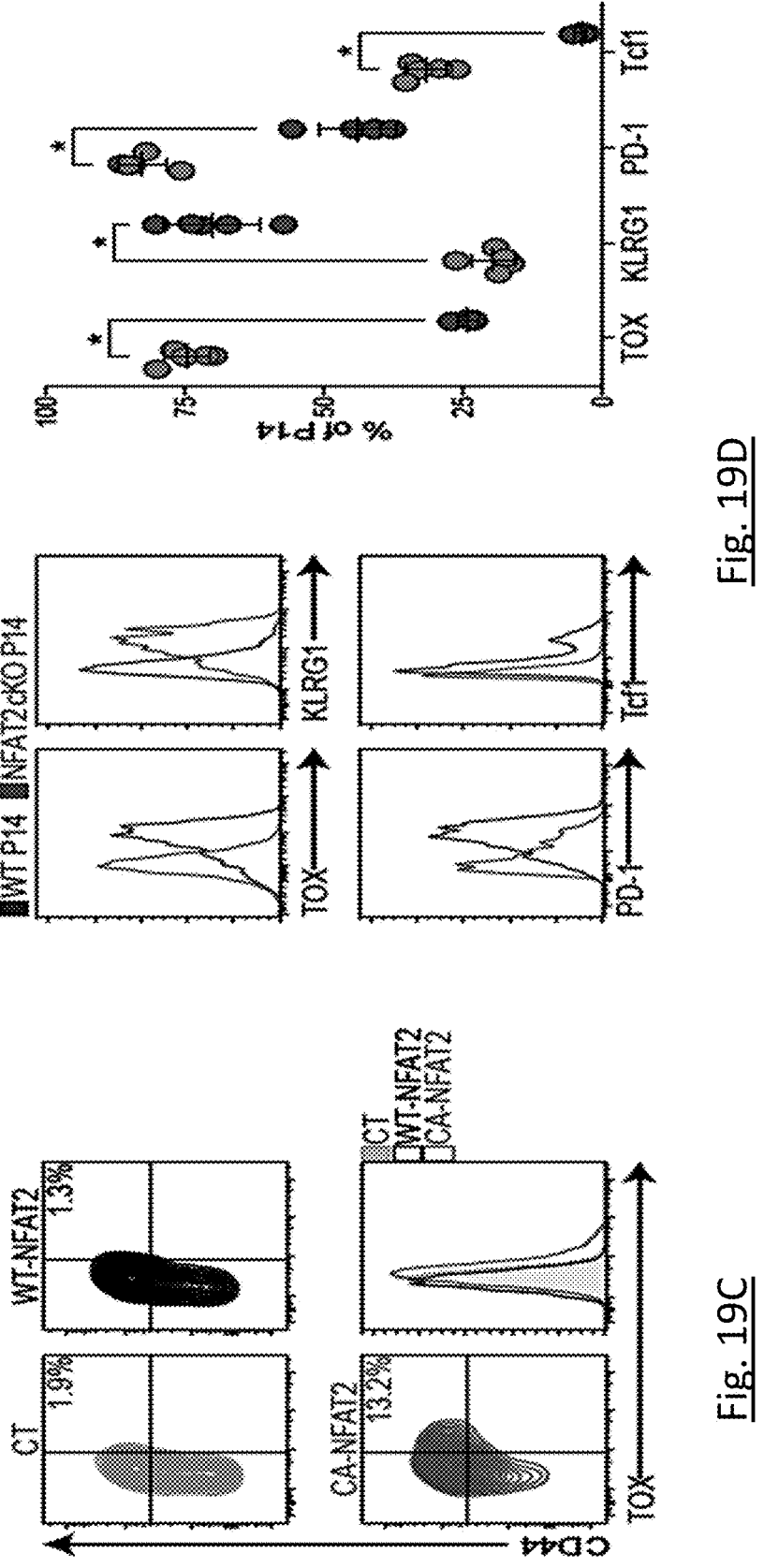
Figure 19E:
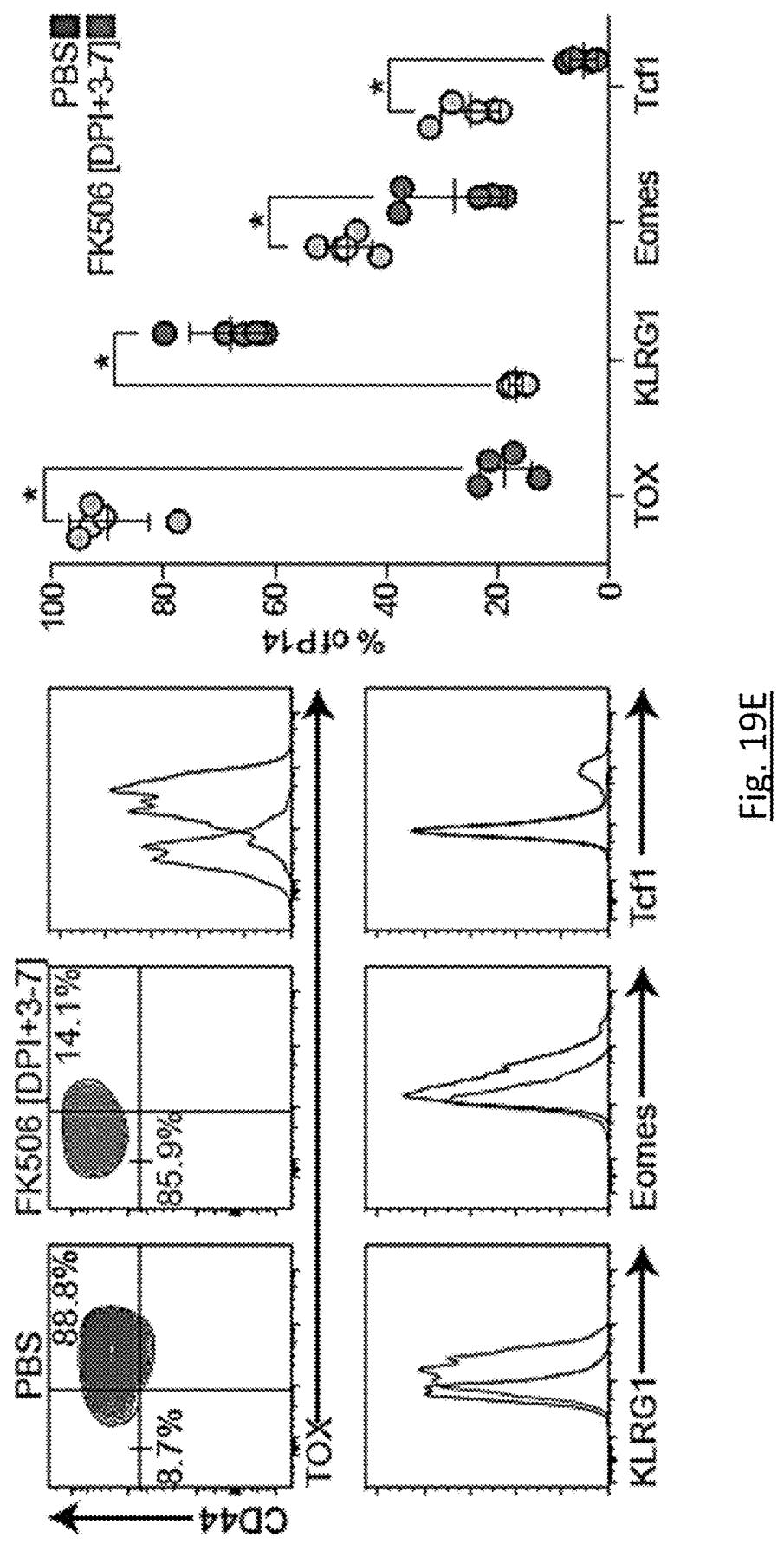
Figure 19F:
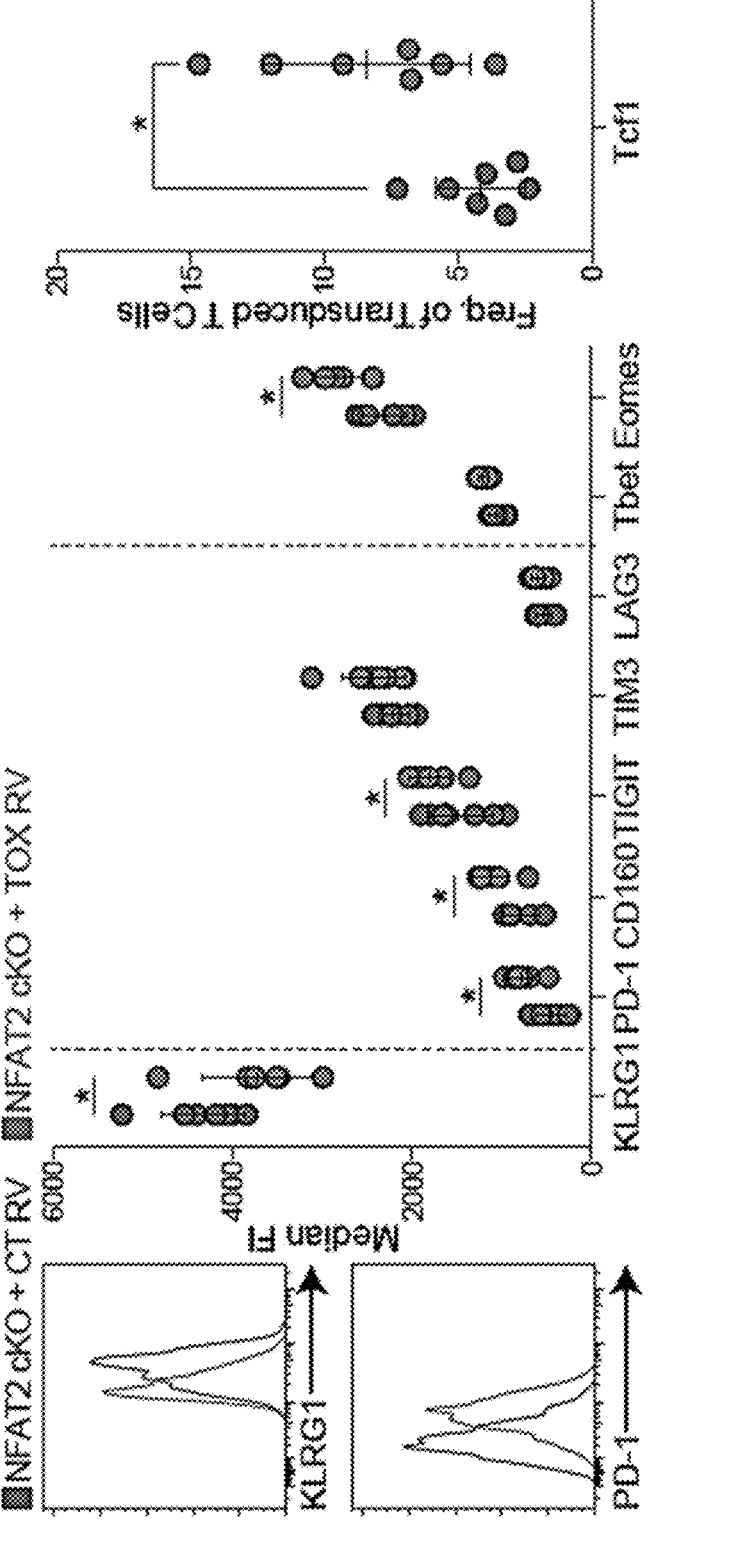
Figure 20A:
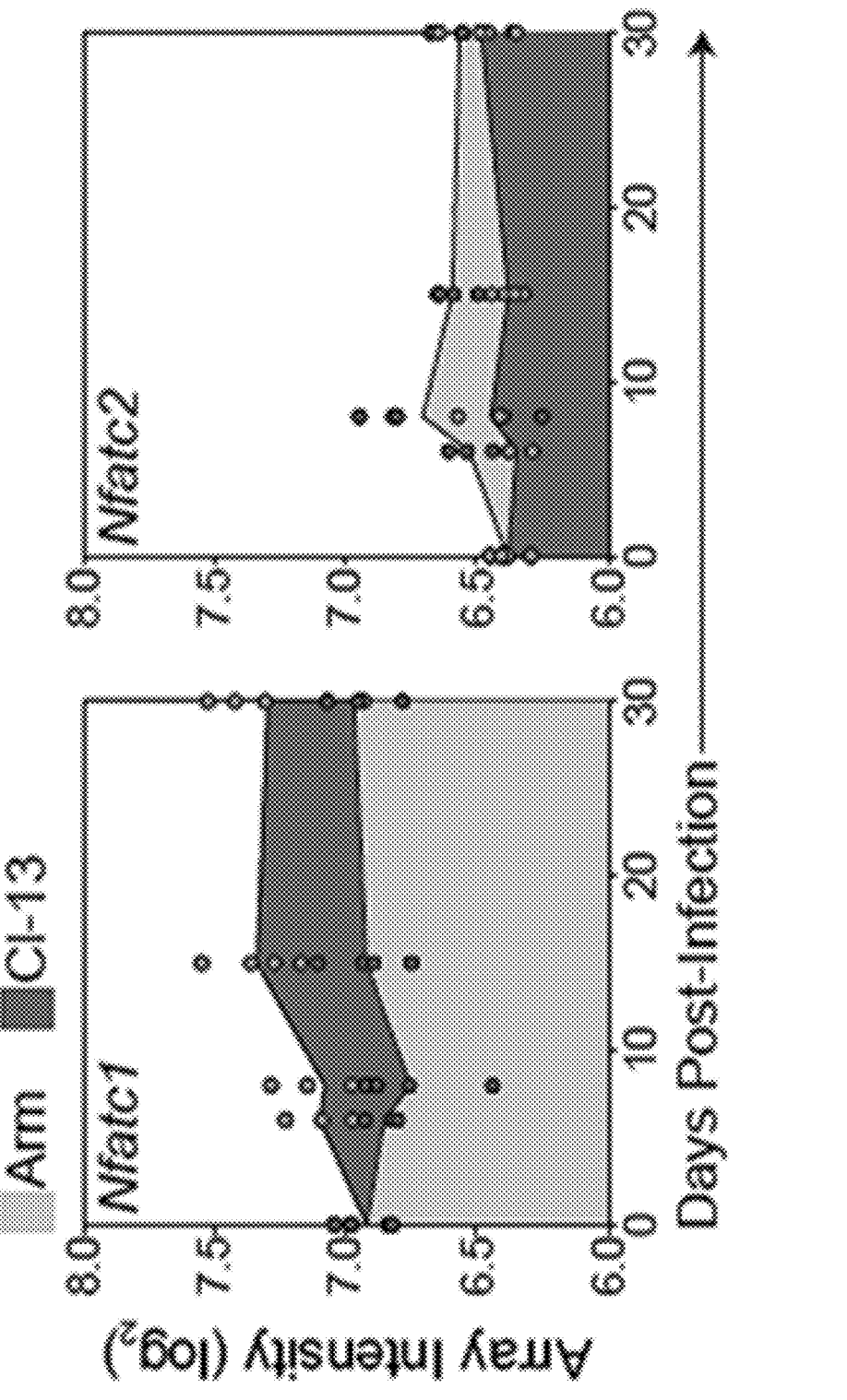
FIGS. 20A-20F show expression results in mice.
Figures 20B, 20C:
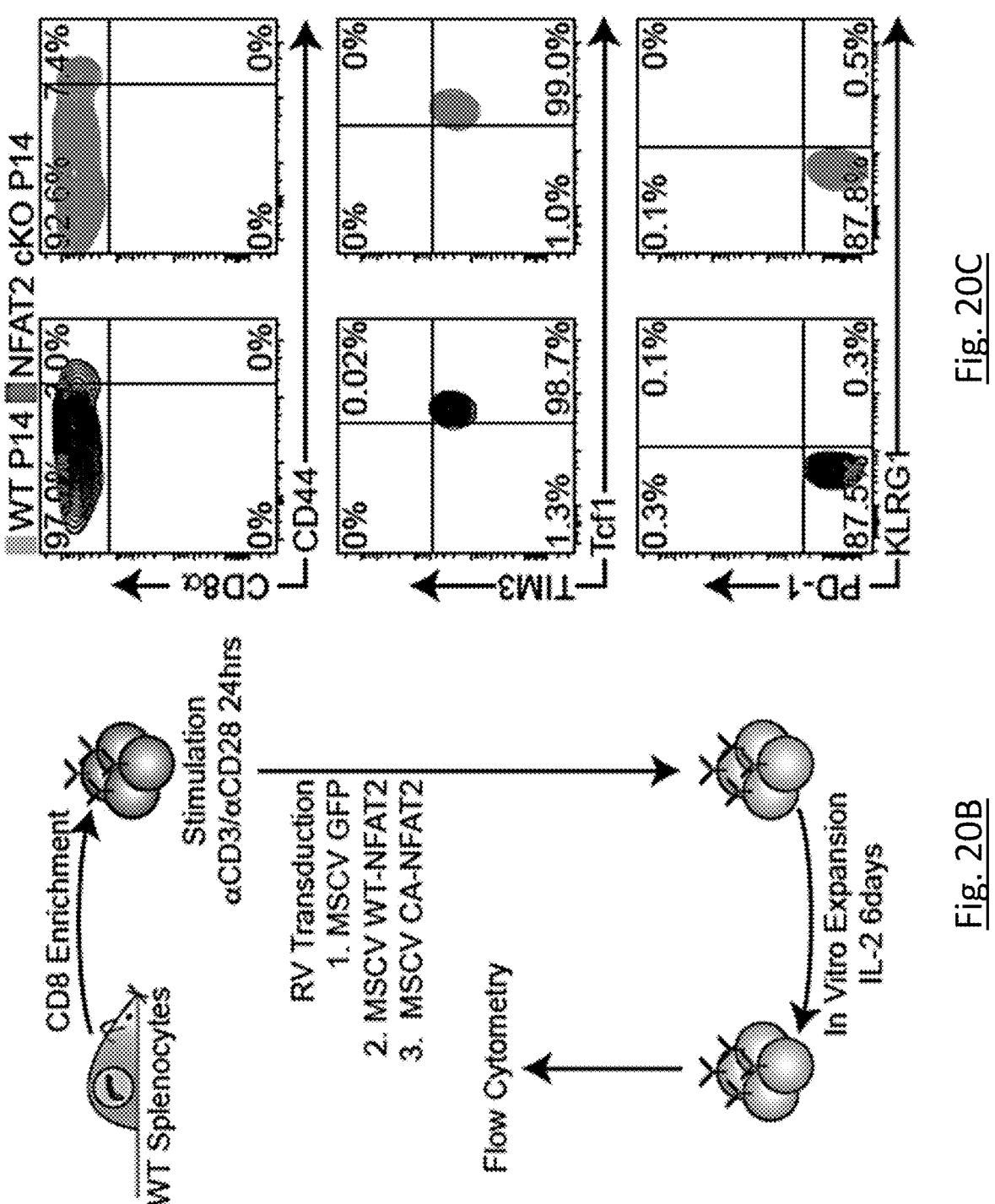
Figures 20D, 20E, 20F:
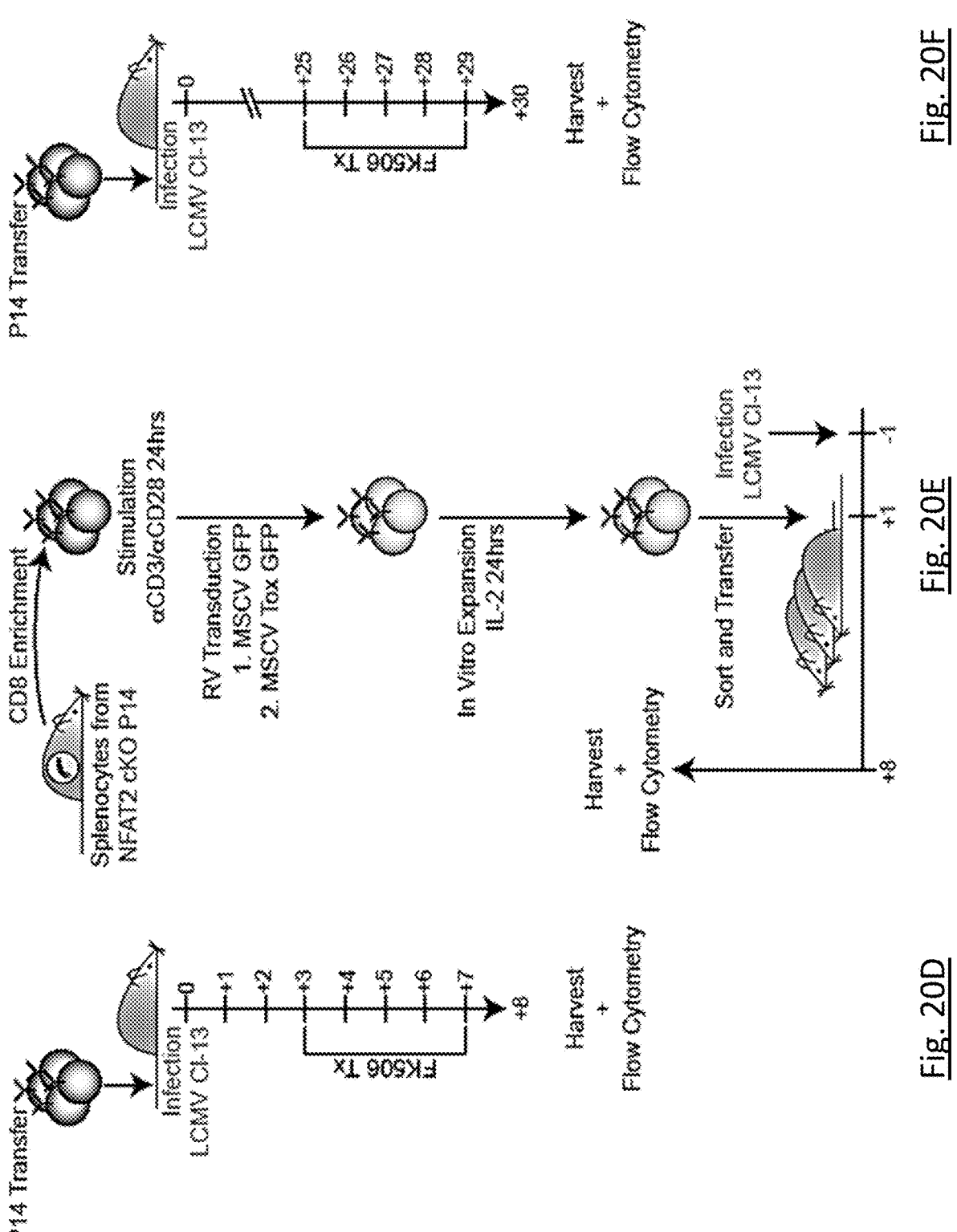
Figures 21A, 21B:
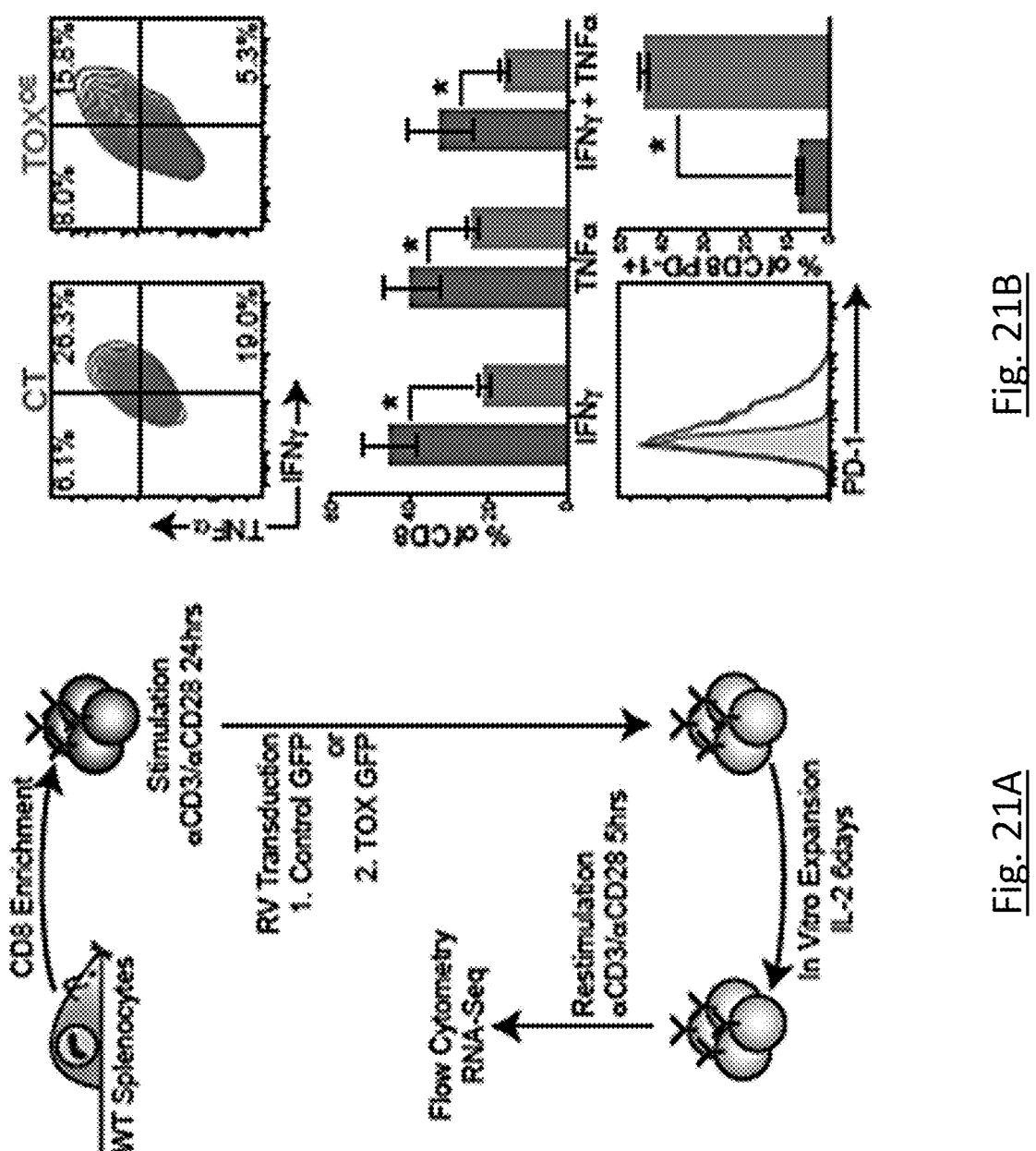
FIGS. 21A-21J illustrate that TOX enforces a T$_{EX}$ transcriptional program.

Example 14. Calcium Signaling and NFAT2 are Required for Inducing but not Sustaining TOX Expression in $T_{EX}$ The mechanisms governing the expression of TOX in developing $T_{EX}$ were assessed next. In CD4$^+$CD8$^+$ (DP) thymocytes and neurons, TOX expression is dependent on calcium and calcineurin signaling (Aliahmad, P. et al. TOX Provides a Link Between Calcineurin Activation and CD8 Lineage Commitment. *J Exp Med* 199, 1089-1099 (2004); Artegiani, B. et al. Tox: a multifunctional transcription factor and novel regulator of mammalian corticogenesis. *EMBO J* 34, 896-910 (2015)). Treatment of DP thymocytes with the diacylglycerol analogue phorbol myristate acetate (PMA) and the calcium ionophore ionomycin (Iono) or Iono alone has been shown to be capable of inducing TOX56. Here, it was discovered that Iono alone induced TOX expression in peripheral naive CD8$^+$ T cells, whereas PMA alone or addition of PMA to Iono failed to induce TOX (FIG. 21A). Without wishing to be bound by theory, these results suggested that TOX expression in mature CD8$^+$ T cells is primarily regulated by calcineurin-mediated signaling. Calcineurin signaling leads to transcriptional changes primarily through the transcription and nuclear localization of NFAT proteins (Macian, F. NFAT proteins: key regulators of T-cell development and function. *Nat Rev Immunol* 1278 5, 472-484 (2005)). Dysregulated NFAT activity, in particular NFAT functioning without canonical AP-1 as a partner (Martinez, G. J. et al. The Transcription Factor NFAT Promotes Exhaustion of Activated CD8+ T Cells. *Immunity* 42, 265-278 (2015)), has a key role in the transcriptional regulation of a subset of $T_{EX}$ genes including inhibitory receptors (including Pdcd1 and Ctla4) and transcription factors (such as Irf4, Batf, Tcf7, and Tbx21). Analysis of NFAT1 and NFAT2 DNA binding data from $T_{EFF}$ indicates that both NFATs are capable of binding to the Tox locus and that many of these NFAT-bound sites are altered in accessibility in $T_{EX}$ (FIG. 21B). Because Nfatc1 (NFAT2) is differentially expressed in $T_{EX}$ versus $T_{EFF}$ and $T_{MEM}$ (FIG. 22A), the role of this NFAT on TOX expression became the focus of the experiments described herein (Man, K. et al. Transcription Factor IRF4 Promotes CD8+ T Cell Exhaustion and Limits the Development of Memory-like T Cells during Chronic Infection. *Immunity* 47, 1129-1141.e5 (2017)). Retroviral (RV) expression of a constitutively active and nucleus-restricted CA-NFAT2 mutant induced the expression of TOX in in vitro activated CD8$^+$ T cells, whereas WT NFAT2 failed to do so (FIG. 19C and FIG. 20B) (Monticelli, S. & Rao, A. NFAT1 and NFAT2 are positive regulators of IL-4 gene transcription. *Eur. J Immunol.* 32, 2971-2978 (2002)). Moreover, P14 T cells deficient in NFAT2 (NFAT2$^{Flox/Flox}$ xCD4$^{Cre}$ P14; NFAT2 cKO) failed to express TOX in vivo during LCMV Cl-13 infection (FIG. 19D and FIG. 20C). In agreement with the TOX cKO data above, NFAT2-deficient P14 T cells, failed to generate $T_{EX}$ precursors, instead producing an abundance of $T_{EFF}$ with increased KLRG1 and lower PD-1 and Tcf1 (FIG. 19D). One potential caveat of the NFAT2 cKO, however, is altered initial T cell activation. To complement this approach, P14 containing mice were infected with LCMV Cl-13 and treated with the calcineurin inhibitor FK506 starting at d3 p.i., a time point after initial T cell activation has occurred. Treatment between d3-7 p.i. had minimal effect on overall T cell activation, as measured by CD44 expression, but significantly reduced TOX expression (FIG. 19E and FIG. 20D). Moreover, P14 cells from mice treated with FK506 phenocopied TOX-deficient T cells based on high KLRG1 and low Eomes expression and failure to express Tcf1 (FIG. 12E). Since NFAT2 could have many transcriptional effects, it was next questioned if enforced TOX expression in the absence of NFAT2 was sufficient to induce key features of exhaustion. Thus, NFAT2 cKO P14 T cells were transduced with a retrovirus expressing TOX and subsequently transferred into mice infected with LCMV Cl-13 (FIG. 20E). Expression of TOX in NFAT2-deficient T cells restored PD-1 and expression of other inhibitory receptors, increased Eomes and Tcf-1 expression and significantly reduced KLRG1 (FIG. 12). Thus, calcineurin and NFAT2 are required to induce TOX. Moreover, ectopic TOX expression in NFAT2-cKO cells can restore early $T_{EX}$ differentiation demonstrating that TOX is a major NFAT2 dependent $T_{EX}$ event during initial T cell activation.

Figure 19G:
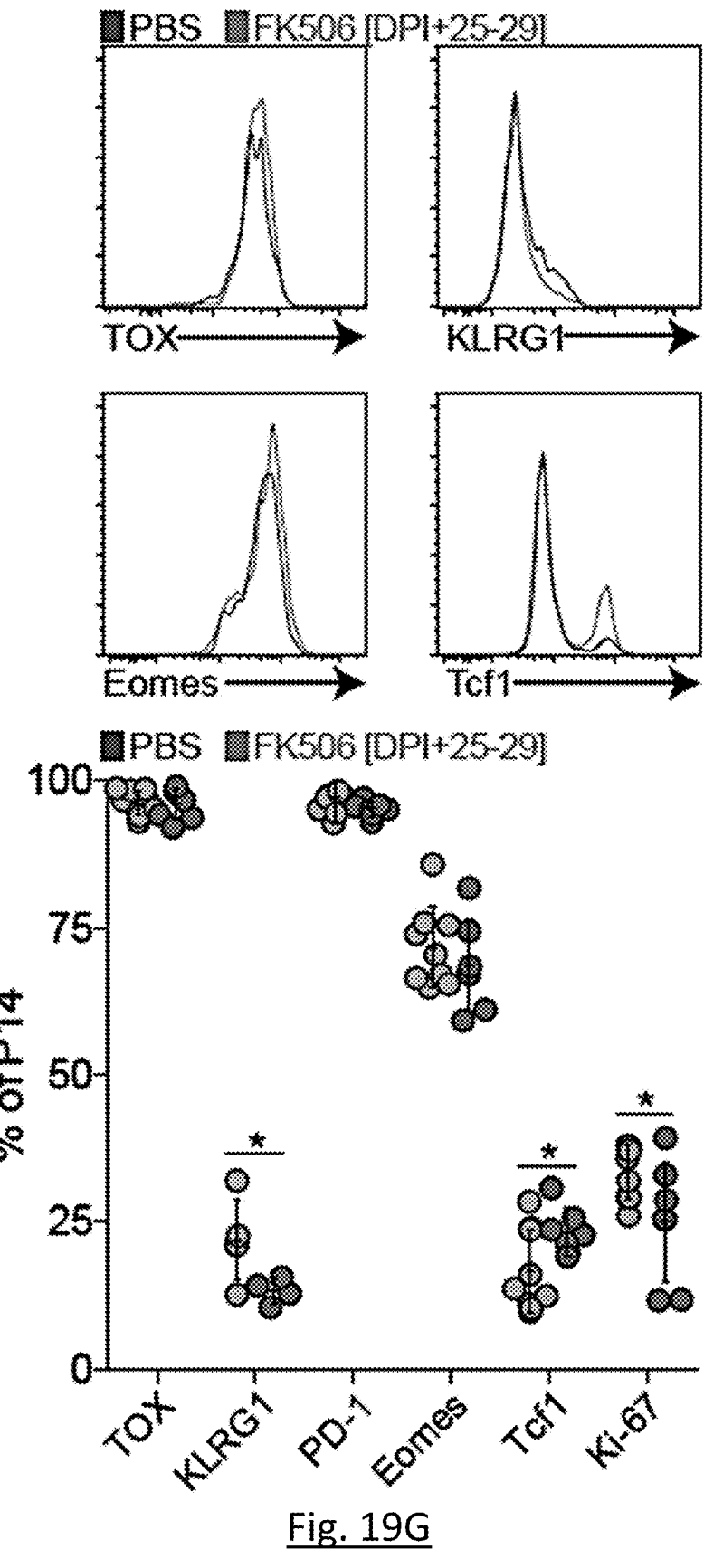

Because the TOX locus was epigenetically remodeled in $T_{EX}$ compared to $T_{EFF}$, whether continuous calcium and NFAT-mediated signaling were required for the sustained expression of TOX once exhaustion was established was tested next. Thus, calcineurin signaling was blocked in vivo between d25 and 29 of chronic infection (FIG. 20F). Treatment with FK506 during this period reduced Ki-67 in $T_{EX}$, as expected due to the requirement of TCR signaling to drive the steady state proliferative hierarchy of $T_{EX}$ (FIG. 19G) (Paley, M. A. et al. Progenitor and Terminal Subsets of CD8+ T Cells Cooperate to Contain Chronic Viral Infection. *Science* 338, 1220-1225 (2012)). Although treatment of established $T_{EX}$ in vivo slightly enriched for the progenitor $T_{EX}$ subset (KLRG1$^{Low}$Tcf1$^{Hi}$), there was little impact on TOX expression and essentially all virus-specific $T_{EX}$ remained highly TOX$^+$ (FIG. 19G). Moreover, expression of PD-1 and Eomes remained essentially unchanged (FIG. 19G). These data indicate that although initial TOX induction is reliant on NFAT2, TOX expression and the TOX-dependent $T_{EX}$ program becomes independent of calcineurin signaling once established, though TCR-driven proliferative signals may still require NFATs. Thus, after establishment of exhaustion, TOX expression becomes independent of inductive signals and is sufficient to drive PD-1 expression and repress the KLRG1$^+$ path of differentiation.

Example 15. A program of exhaustion induced by TOX

Figures 21C, 21D, 21E:
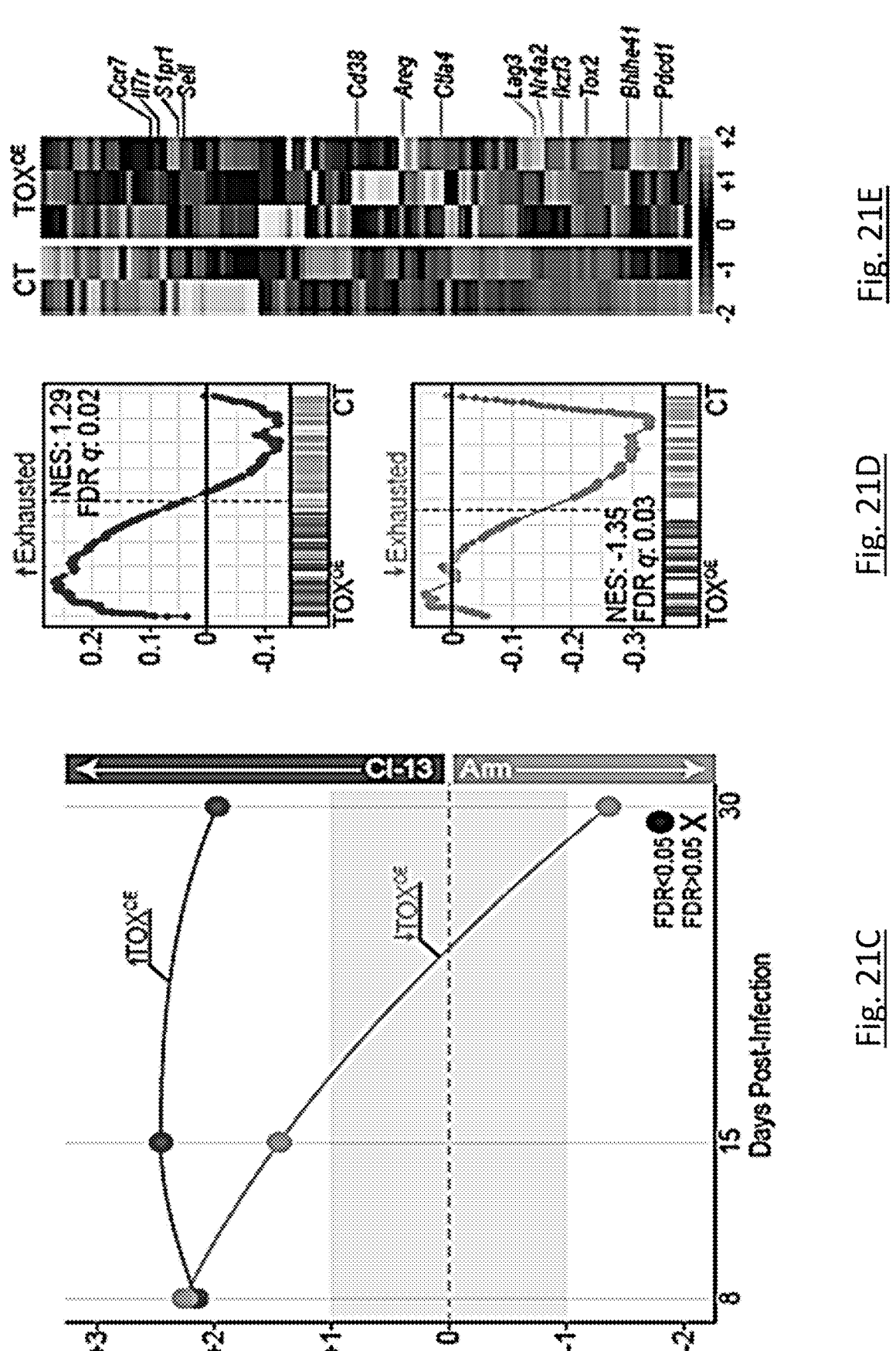

To test whether TOX expression alone was sufficient to drive exhaustion, an in vitro approach was used to enforce TOX expression in in vitro differentiated CD8+ T cells (FIG. 21A). RV expression of TOX reduced cytokine production and polyfunctionality while increasing PD-1, indicating that TOX was capable of driving these two canonical features of $T_{EX}$ (FIG. 21B) (Wherry, E. J. & Kurachi, M. Molecular and cellular insights into T cell exhaustion. *Nature Publishing Group* 15, 486-499 (2015); Wherry, E. J., Blattman, J. N., Murali-Krishna, K., van der Most, R. & Ahmed, R. Viral Persistence Alters CD8 T-Cell Immunodominance and Tissue Distribution and Results in Distinct Stages of Functional Impairment. *J Virol* 77, 4911-4927 (2003)). Transcriptional analysis of genes induced by overexpression of TOX in vitro enriched for the transcriptional signature of T cells responding to Cl-13 infection in vivo (FIG. 21C) (Doering, T. A. et al. Network Analysis Reveals Centrally Connected Genes and Pathways Involved in CD8+ T Cell Exhaustion versus Memory. *Immunity* 37, 1130-1144 (2012)). In addition, genes downregulated upon TOX expression enriched in $T_{MEM}$ signatures from acutely resolved infection (FIG. 21C). Moreover, CD8 T cells overexpressing TOX significantly enriched for the set of genes uniquely upregulated in $T_{EX}$ while expression of transcripts specifically down-regulated in $T_{EX}$ were reduced (FIG. 59D) (Bengsch, B. et al. Epigenomic-Guided Mass Cytometry Profiling Reveals Disease-Specific Features of Exhausted CD8 T Cells. *Immunity* 48, 1029-1045.e5 (2018)). Indeed, many key individual exhaustion genes such as nhibitory receptors (Pdcd1, Lag3, Ctla4) and transcription factors (Nr4a2, Ikzf3, Tox2, Bhlhe41) were induced by enforced TOX expression in vitro, whereas memory-associated genes (Ccr7, Il7r, Sell) were reduced (FIG. 21E).

Figures 21F, 21G:
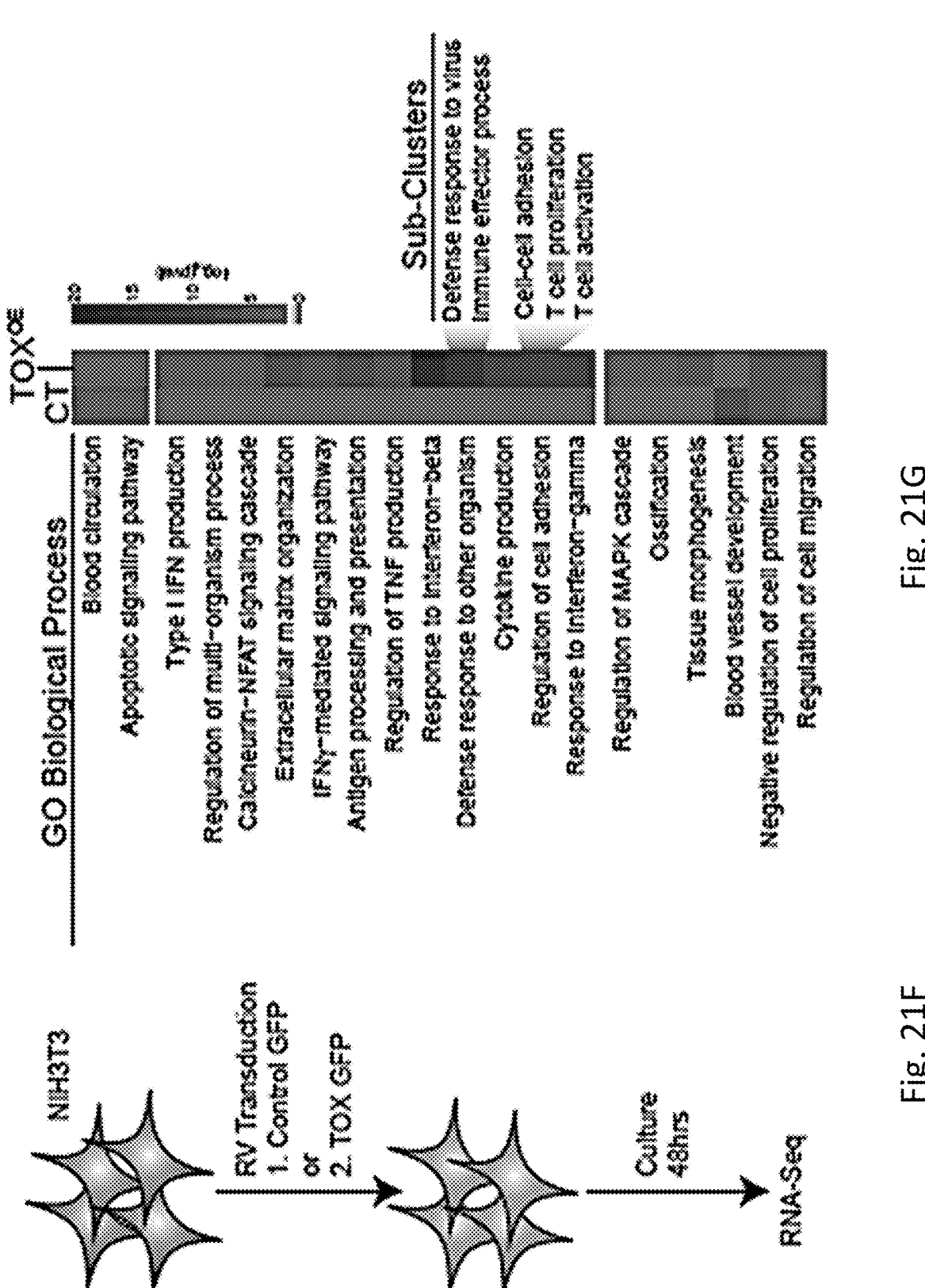
Figures 21H, 21I, 21J:
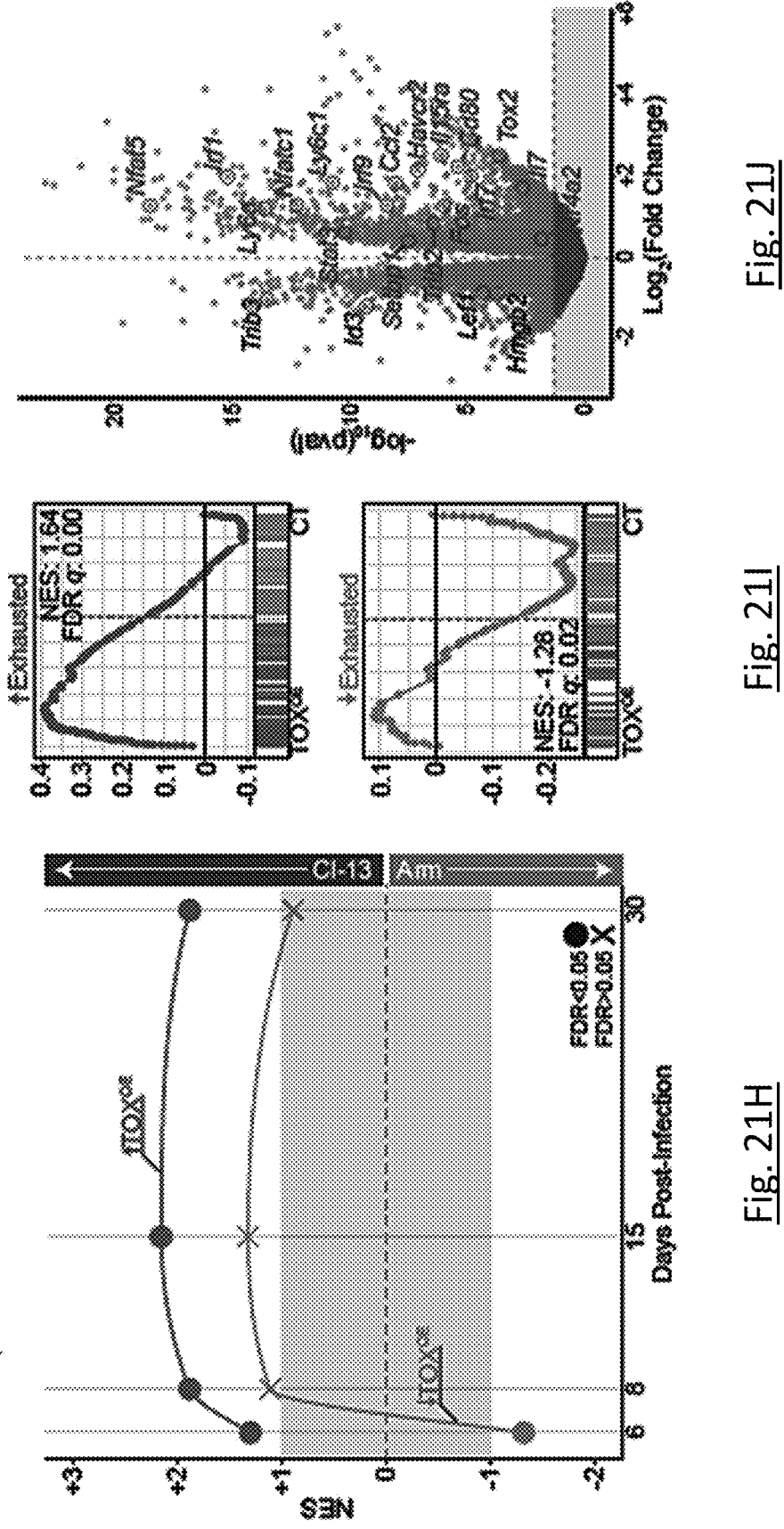

These transcriptional results in in vitro activated CD8+ T cells suggested that TOX was capable of driving a transcriptional program of exhaustion. Whether TOX-directed gene expression was subject to the regulatory environment of a T cell or displayed a broader potential for transcriptional coordination was studied next. To address this question, TOX was ectopically expressed in mouse NIH3T3 fibroblasts, which were then cultured for 48 hours and analyzed for TOX-induced transcriptional changes (FIG. 21F). Even in a cell type as distinct as fibroblasts, TOX expression induced the transcription of multiple immune pathways including those associated with inflammatory cytokine production (Irf1, Irf7, Irf9, Stat1), T cell activation and proliferation (Cd80, Ptpn22, Lyn), as well as calcineurin and NFAT signaling (Nfatc1, Nfat5, Adgrb2) (FIG. 21G, 21J). Moreover, as in CD8+ T cells, the transcriptional signature induced by TOX in fibroblasts was enriched for the signature of in vivo $T_{EX}$ and many individual genes induced by TOX in fibroblasts have potential roles in T cell exhaustion (FIG. 21H-21J). These data are reminiscent of the related HMG TF Tcf1 that has recently been shown to have a "pioneer"-like effect on chromatin architecture during T cell development (Johnson et al., Lineage-Determining Transcription Factor TCF-1 Initiates the Epigenetic Identity of T Cells. *Immunity* 48: 243-257.e10 (2018). Thus, TOX was capable of inducing a transcriptional program of $T_{EX}$ and could even do so, at least partially, in an unrelated cell type. These data suggest a potential mechanism for the TOX-dependent $T_{EX}$ transcriptional program induction if TOX is able to induce epigenetic changes that allow $T_{EX}$ associated gene expression.

Example 16. Epigenetic Programming of $T_{EX}$ by TOX

Figures 22A, 22B:
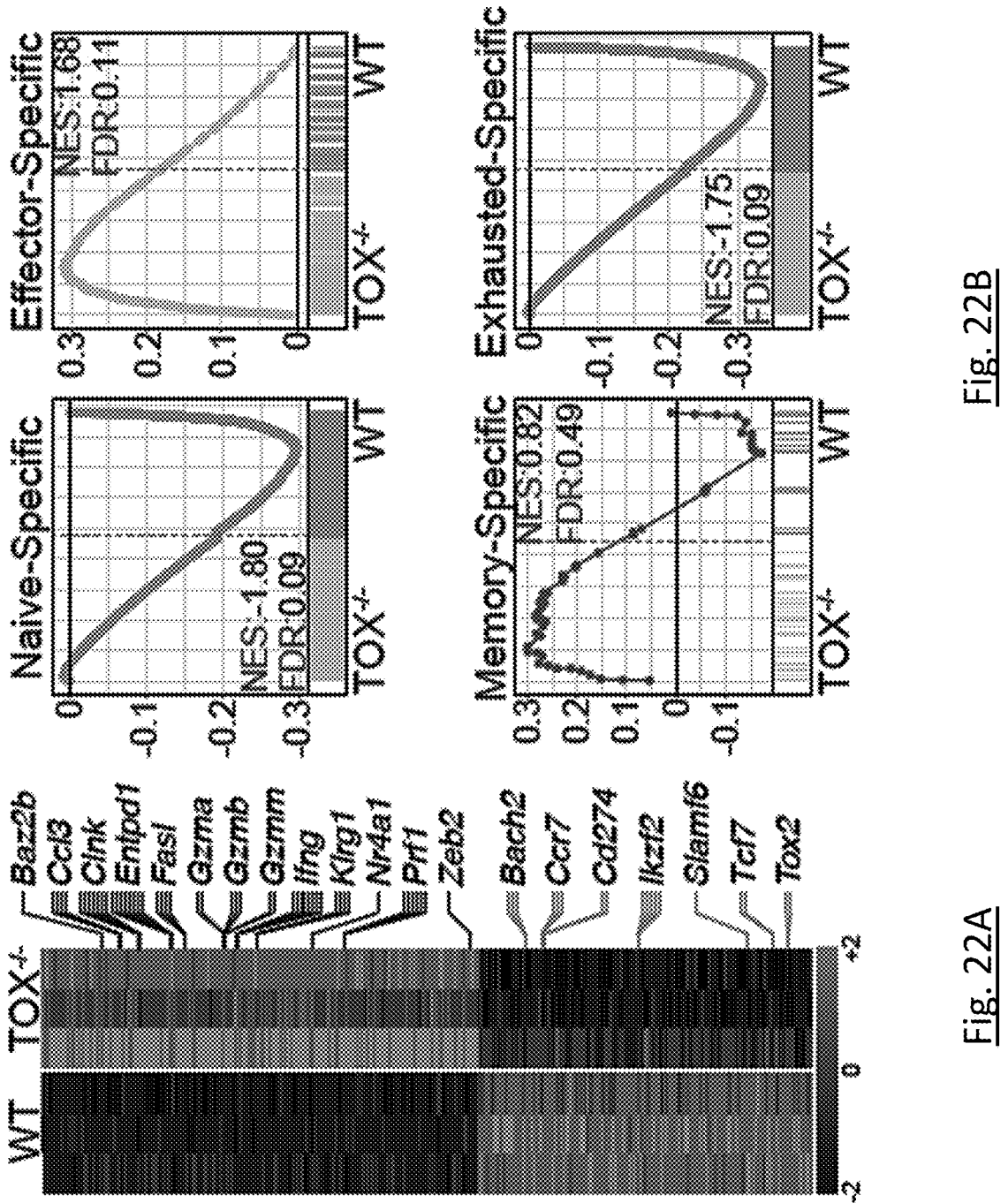
FIGS. 22A-22L illustrate that TOX induces an epigenetic signature of $T_{EX}$ by recruiting the HBO1 complex.
Figures 22C, 22D:
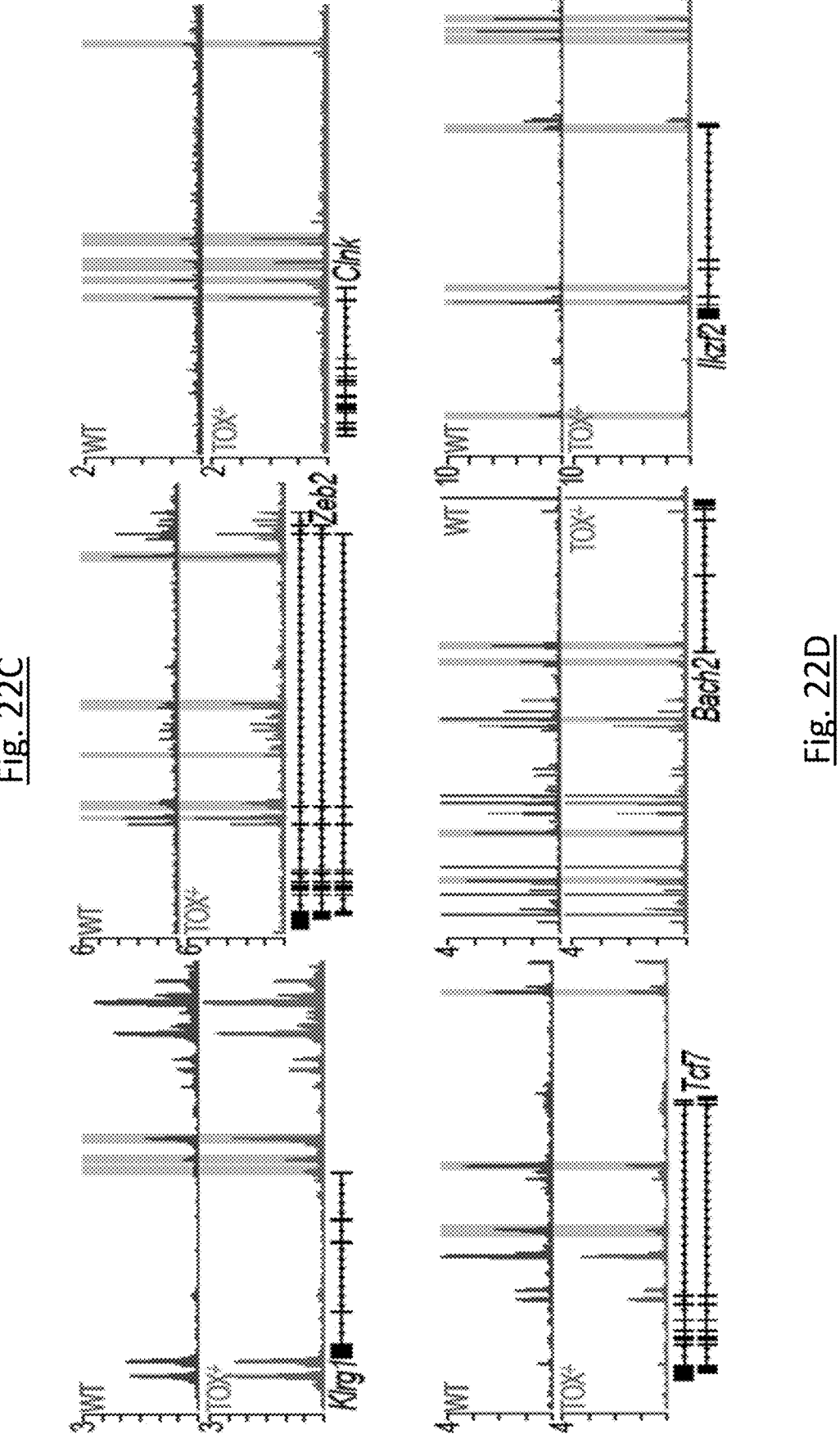

Recently it was demonstrated that $T_{EX}$ have a unique epigenetic landscape and represent a stable and distinct cellular lineage compared to $T_N$, $T_{EFF}$ and $T_{MEM}$ (Pauken, K. E. et al. Epigenetic stability of exhausted T cells limits durability of reinvigoration by PD-1 blockade. *Science* 354, 1160-1165 (2016); Sen, D. R. et al. The epigenetic landscape of T cell exhaustion. *Science* 354, 1165-1169 (2016). Philip, M. et al. Chromatin states define tumour-specific T cell dysfunction and reprogramming. *Nature* 545, 452-456 (2017). Scott-Browne, J. P. et al. Dynamic Changes in Chromatin Accessibility Occur in CD8+ T Cells Responding to Viral Infection. *Immunity* 45, 1327-1340 (2016)). Thus, whether TOX regulated this epigenetic commitment to the $T_{EX}$ fate was determined next. TOX$^{-/-}$ and WT P14 cells were adoptively transferred into congenic recipient mice followed by LCMV Cl-13 infection. Eight days p.i. WT and TOX$^{-/-}$ P14 cells were analyzed by ATAC-seq to define the epigenetic landscape changes that were TOX-dependent. In the absence of TOX there were ~4,000 regions that changed in chromatin accessibility. Over 70% of these changes were in intronic or intergenic regions consistent with enhancer elements whereas 20% were at promoters or transcription start sites (TSS) (FIG. 22A). Among these changes in the absence of TOX were increases in chromatin accessibility at many genes associated with terminal $T_{EFF}$ differentiation including Klrg1, Gzma, Gzmb, Gzmm, Zeb2, and Nr4a1 (FIG. 22A). In contrast, loci with reduced chromatin accessibility included those proximal to Tcf7 (encoding Tcf1) and other genes associated with $T_{MEM}$ and $T_{EX}$ progenitors, including Ccr7, Slamf6, Bach2, and Ikzf2 (FIG. 22A). Using a peak set enrichment approach, the epigenetic signature of TOX-deficient P14 cells at d8 of chronic infection was found to be strongly enriched for the $T_{EFF}$ signature from acute infection and depleted of the $T_{EX}$ epigenetic landscape signature (FIG. 22B). Moreover, specific peaks could be identified in many key genes that changed in a TOX-dependent manner including in the Klrg1, Zeb2 and Clnk loci that became more accessible in the absence of TOX and peaks in Tcf7, Bach2 and Ikzf2 that were strongly reduced or lost altogether (FIG. 22C, 22D).

Figure 22F:
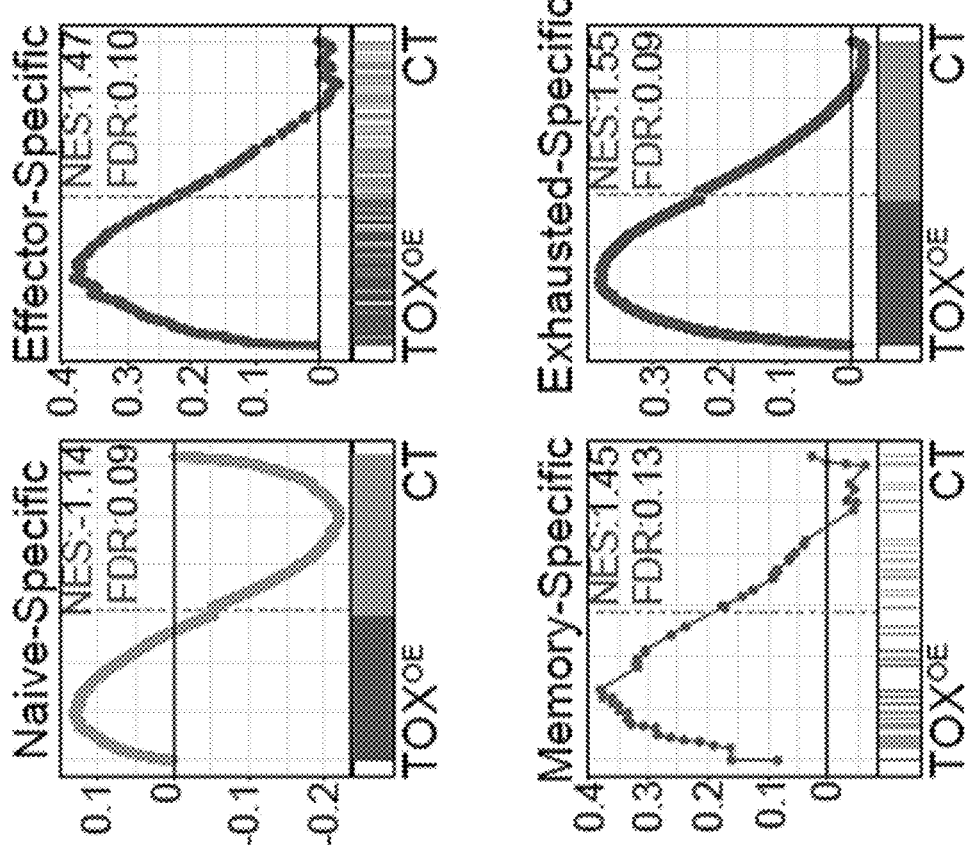
Figure 22E:
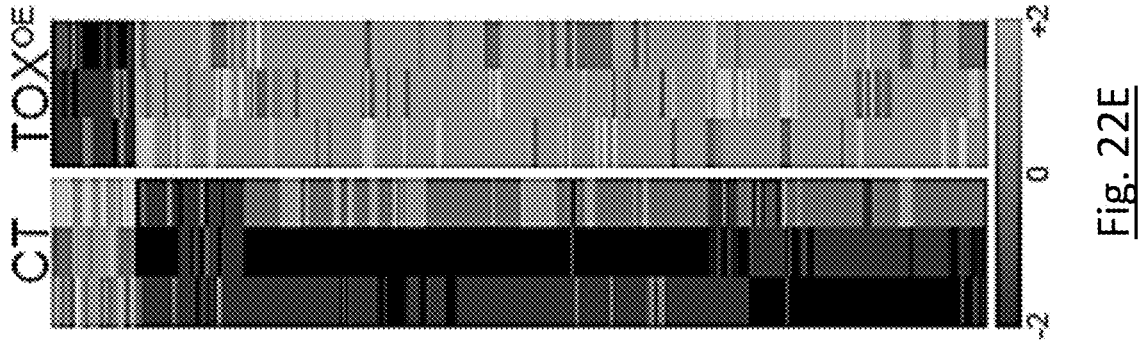
Figures 23B, 23C:
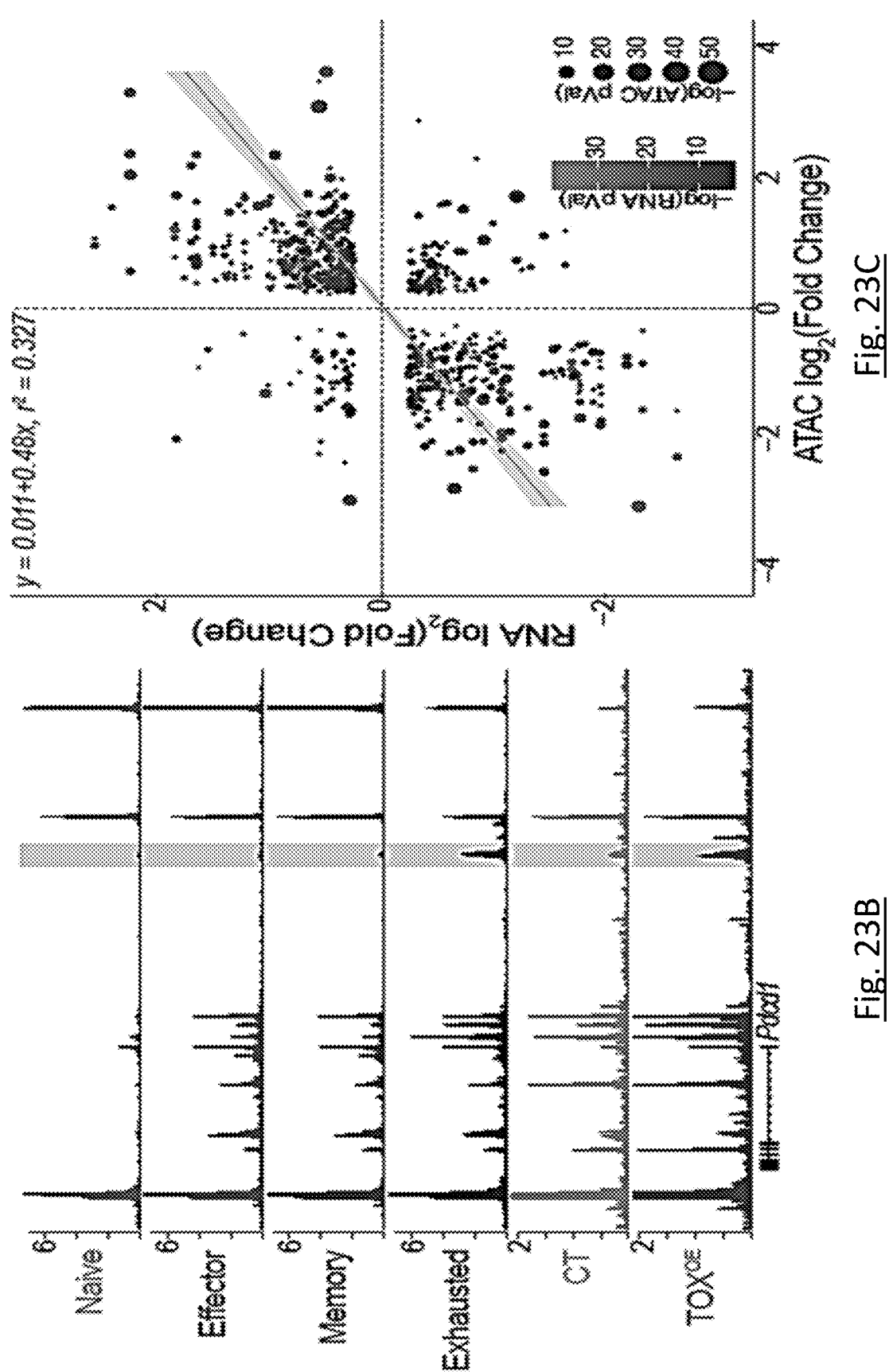

Whereas loss of TOX suggested that TOX was necessary to establish a significant proportion of the $T_{EX}$ epigenetic landscape, whether TOX expression was sufficient to induce $T_{EX}$ associated chromatin changes was studied next. To test this idea, TOX expression was forced in in vitro activated CD8+ T cells using a RV and subsequent epigenetic changes were examined 6 days later (FIG. 21A). TOX expression induced changes in chromatin accessibility in 378 sites in this short-term in vitro assay (FIG. 21A). The vast majority (91%) of these TOX-induced chromatin changes were increases in accessibility at intronic or intergenic regions (FIG. 22E and FIG. 23A). The epigenetic changes induced by TOX expression strongly enriched for the landscape observed in in vivo $T_{EX}$, but also showed overlap with $T_{EFF}$ possibly reflecting aspects of this short-term in vitro assay compared to in vivo T cell differentiation or highlighting the common epigenetic module shared between $T_{EX}$ and $T_{EFF}$ we have previously identified (Pauken, K. E. et al. Epigenetic stability of exhausted T cells limits durability of reinvigoration by PD-1 blockade. *Science* 354, 1160-1165 (2016);Sen, D. R. et al. The epigenetic landscape of T cell exhaustion. *Science* 354, 1165-1169 (2016)). However, at least one of the regions that was opened by enforced TOX expression was the $T_{EX}$-specific enhancer—23.8kb upstream of the Pdcd1 TSS (FIG. 23B) indicating at least some exhaustion-specific epigenetic changes can be induced in vitro by TOX (Pauken, K. E. et al. Epigenetic stability of exhausted T cells limits durability of reinvigoration by PD-1 blockade. *Science* 354, 1160-1165 (2016); Sen, D. R. et al. The epigenetic landscape of T cell exhaustion. *Science* 354, 1165-1169 (2016).

Figures 22G, 22H:
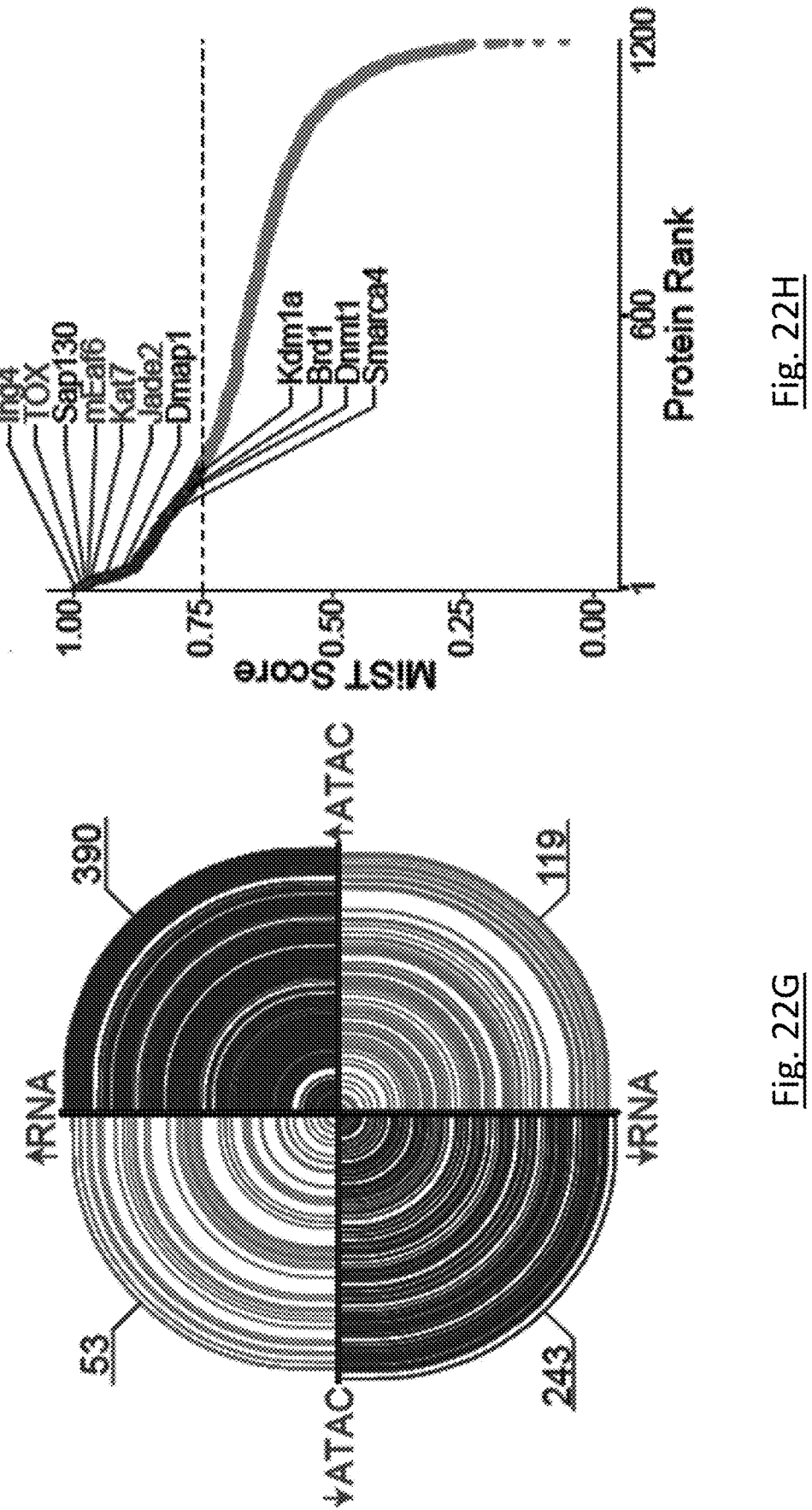
Figure 22J:
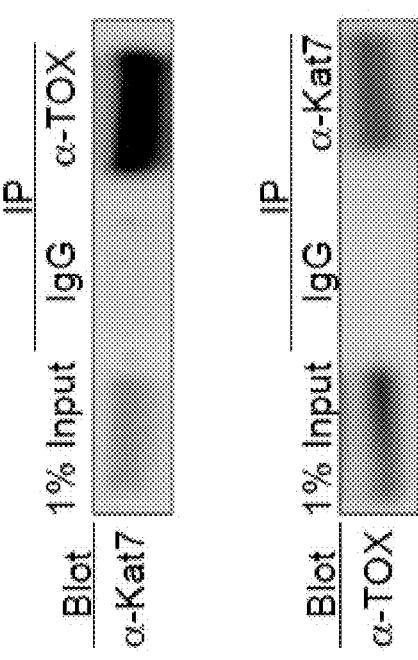
Figure 22I:
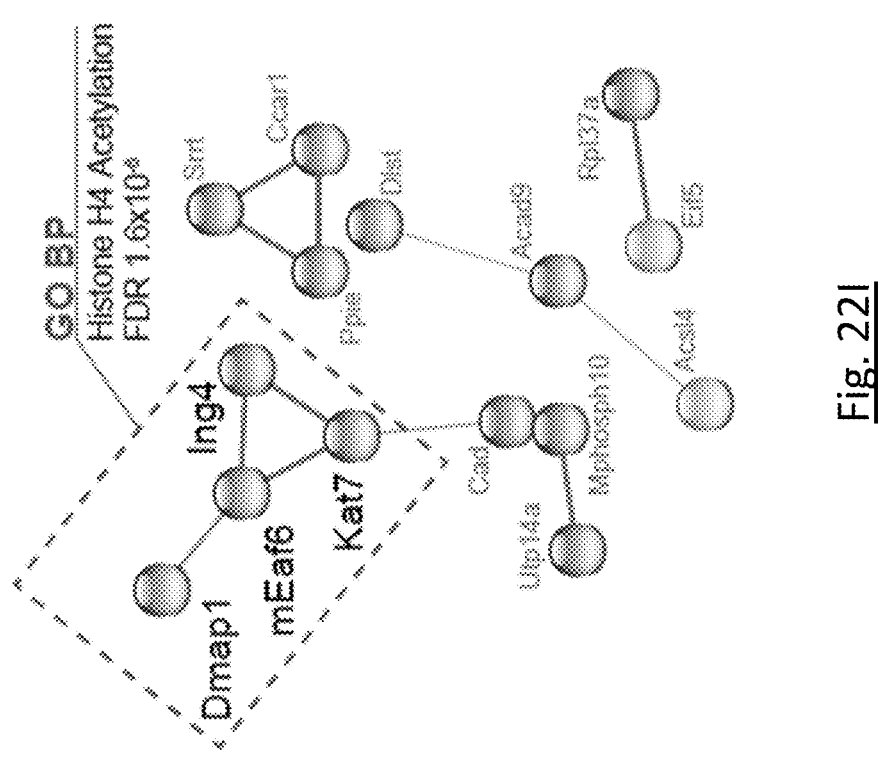
Figures 22K, 22L:
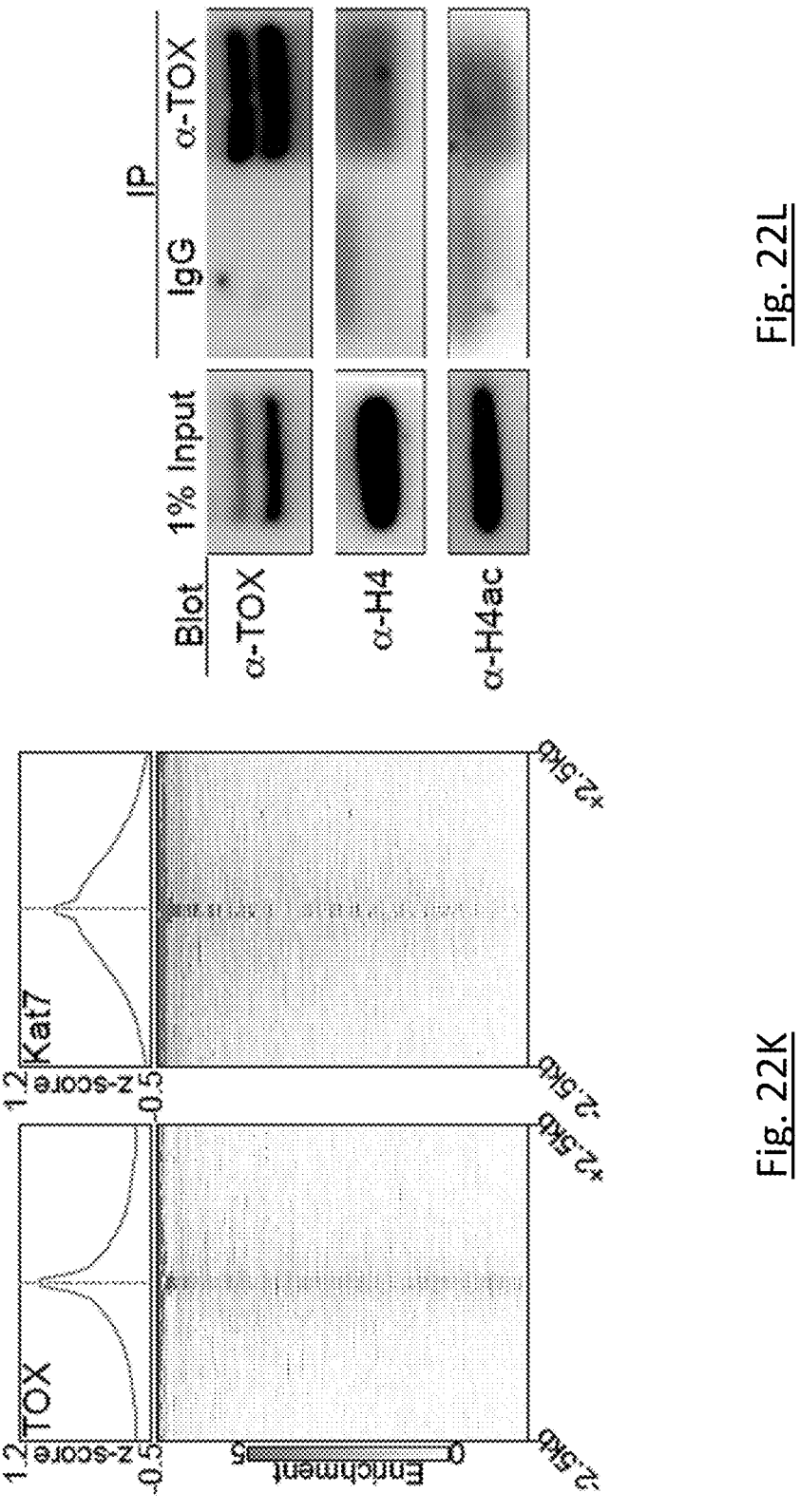
Figures 23D, 23E:
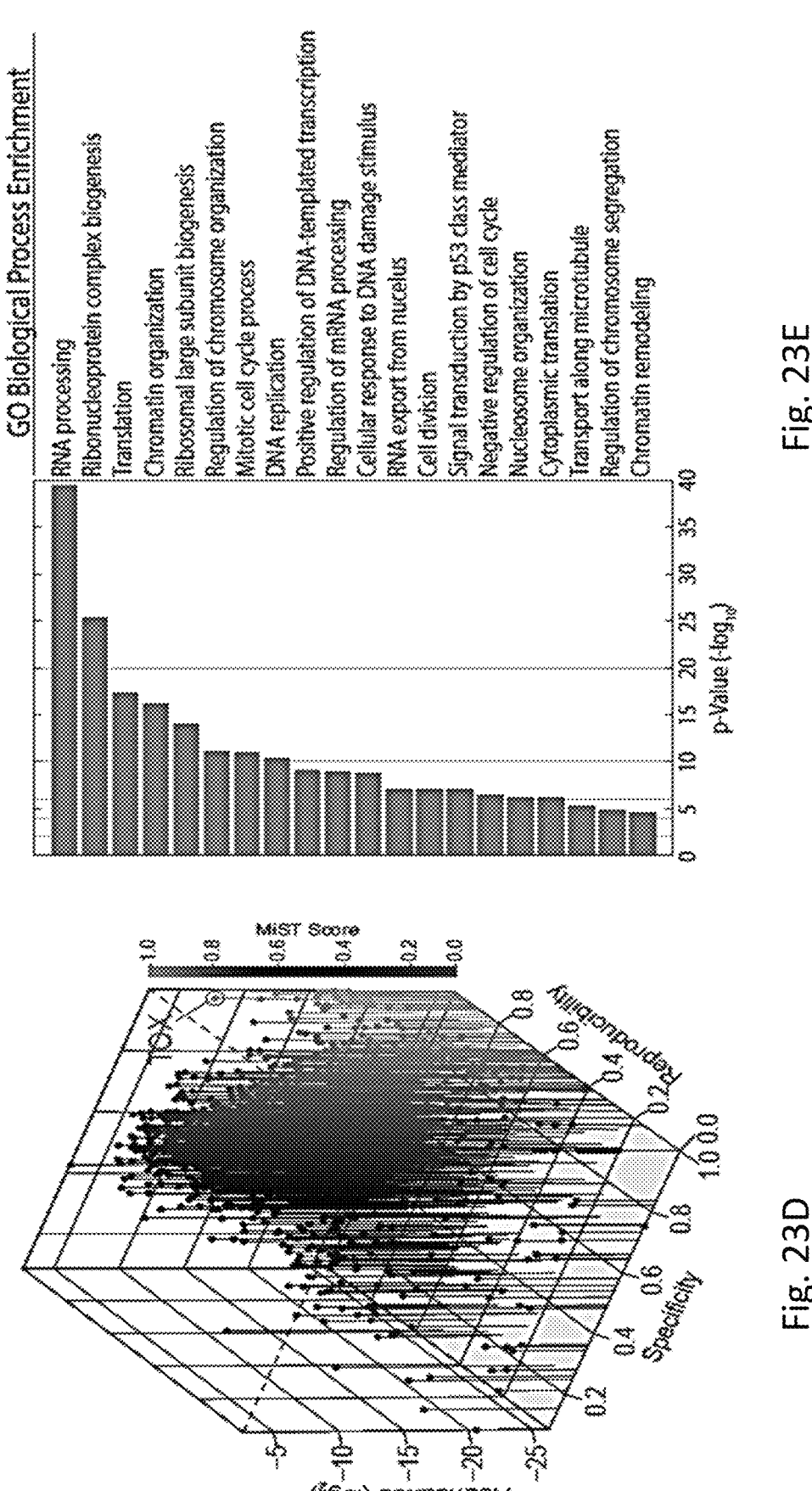
Figure 23G:
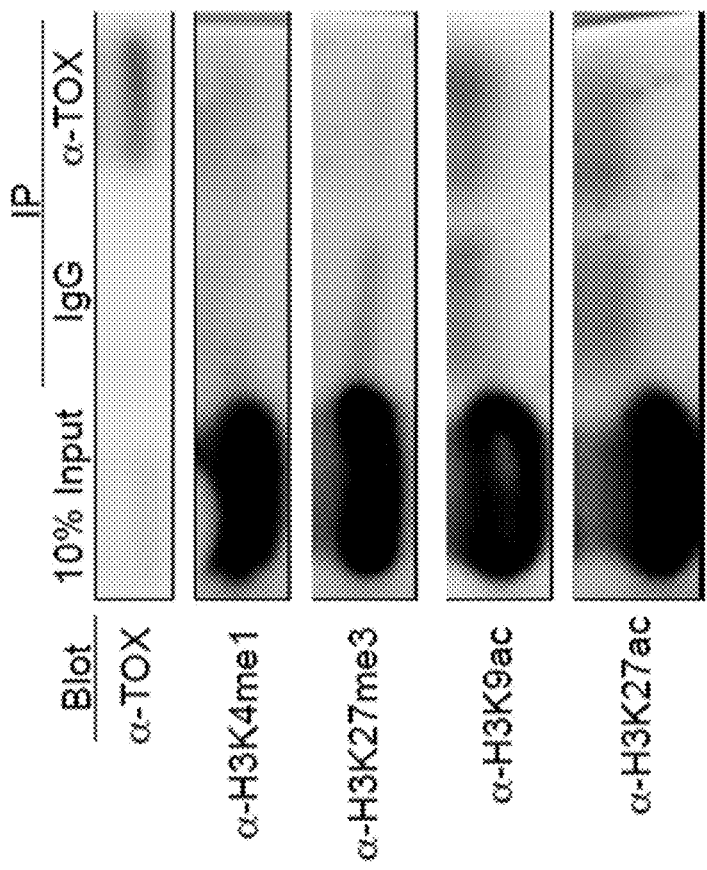
Figure 23F:
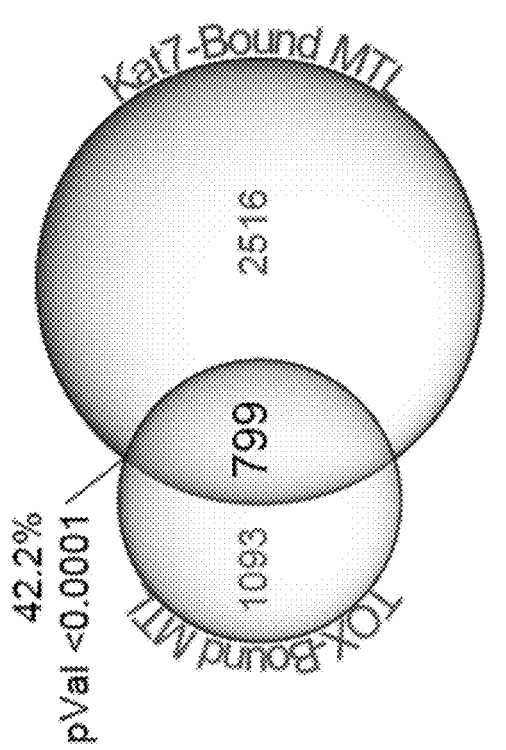

Some members of the HMG family are intrinsically capable of altering chromatin structure, though many transcriptional and histone modification changes are enabled via recruitment of additional protein complexes61. Notably, the epigenetic changes caused by TOX corresponded to functionally relevant events since there was a strong association of chromatin opening with increased gene expression and vice versa (FIG. 22G and FIG. 23C). To investigate the mechanism by which TOX-induced $T_{EX}$-related epigenetic changes, proteins bound by TOX were identified using immunoprecipitation followed by mass spectrometry (MS) (FIG. 23D). As in vivo $T_{EX}$ are difficult to generate in high numbers, EL4 thymoma cells that express high levels of TOX were used herein and have been used previously to model some features of $T_{EX}$ (Sen, D. R. et al. The epigenetic landscape of T cell exhaustion. *Science* 354, 1165-1169 (2016); Kao, C. et al. Transcription factor T-bet represses expression of the inhibitory receptor PD-1 and sustains virus-specific CD8. *Nat Immunol* 12, 663-671 (2011)). MS analysis identified proteins involved in chromatin organization and remodeling, RNA processing and translation, as well as DNA replication as major TOX binding partners (FIG. 22H, FIG. 23E). STRING protein-protein network analysis identified the HBO1 complex, involved in histone H4 and H3 acetylation, as a major TOX-bound set of proteins (FIG. 22I). Indeed, all four members of the histone H4 targeting HBO1 complex (Kat7, Ing4, mEaf6, Jade2) were found to be robustly bound to TOX (FIG. 22H, 22I) (Lalonde, M. E. et al. Exchange of associated factors directs a switch in HBO1 acetyltransferase histone tail specificity. *Genes & Development* 27, 2009-2024 (2013); Miotto, B. & Struhl, K. HBO1 Histone Acetylase Activity Is Essential for DNA Replication Licensing and Inhibited by Geminin. *Molecular Cell* 37, 57-66 (2010)). Moreover, based on co-immunoprecipitation experiments, TOX directly interacted with Kat7, the acetyl transferase component of the HBO1 complex (FIG. 22J). On a genomic level, Kat7 was found to be significantly enriched at a high proportion of TOX-bound loci including regions proximal to Tox, Tcf7, Foxo1, and Izkf1 (FIG. 22K and FIG. 22F). Moreover, TOX also co-immunoprecipitated with total and acetylated histone H4 but not with histone H3 modifications (FIG. 22L and FIG. 23G) suggesting that recruitment of the HBO1 to TOX results in histone modification and chromatin alterations. Thus, TOX is capable of directly recruiting histone modifying complexes to the epigenetic loci associated with the $T_{EX}$ lineage fate decision during chronic infection and cancer.

DISCUSSION

A long-standing question has been whether $T_{EX}$ are a type of poorly functional $T_{EFF}$ or $T_{MEM}$ or a separate and distinct lineage. Key events responsible for commitment to this distinct cell fate have remained elusive. A major role for TOX was demonstrated herein as the key inducer of canonical features of exhaustion and initiator of the $T_{EX}$-specific epigenetic program. These findings have several potential implications. First, TOX expression and the molecular events controlled by TOX could aid in more accurately detecting, quantifying and evaluating $T_{EX}$ because other $T_{EX}$ markers (e.g. PD-1) are also expressed by other activated T cells making them insufficient to define and monitor $T_{EX}$ specifically. Notably, in recent CyTOF studies of human CD8$^+$ T cells, TOX expression was found in the vast majority of $T_{EX}$ in HIV and lung cancer (Bengsch, B. et al. Epigenomic-Guided Mass Cytometry Profiling Reveals Disease-Specific Features of Exhausted CD8 T Cells. *Immunity* 48, 1029-1045.e5 (2018)). Thus, the identification of TOX as a highly $T_{EX}$ biased TF with a causal role in exhaustion may allow better identification and evaluation of $T_{EX}$ settings of human disease.

It should be noted that TOX expression is not restricted to only $T_{EX}$. Transient expression of TOX was clearly observed during acutely resolved infections, though this TOX expression may not be present for a long enough or at high enough concentrations to induce the $T_{EX}$ program. Alternatively, TOX may have distinct roles in acutely resolved infections. For example, some TOX gene expression is apparent in the early establishment of tissue resident memory cells (TRM) (Chang, J. T., Wherry, E. J. & Goldrath, A. W. Molecular regulation of effector and memory T cell differentiation. *Nat Immunol* 15, 1104-1115 (2014); Beura, L. K. et al. T Cells in Nonlymphoid Tissues Give Rise to Lymph-Node-Resident Memory T Cells. *Immunity* 48, 327-338.e5 (2018)) which notably, also arise from the KLRG1$^{LOW}$ subset of the $T_{EFF}$ population (Milner, J. J. et al. Runx3 programs CD8+ T cell residency in non-lymphoid tissues and tumours. *Nature* 1-24 (2017). doi:10.1038/nature24993; Mackay, L. K. et al. The developmental pathway for CD103+CD8+ tissue-resident memory T cells of skin. *Nat Immunol* 14, 1294-1301 (2013)), though established TRM are TOX-68. In addition, TOX is necessary for the development of CD4$^+$ T, natural killer, and innate lymphoid-like cells. Without wishing to be bound by theory, there may be a possible role for TOX in CD8$^+$ T cells in autoimmune disease. Although TOX may have roles outside of $T_{EX}$, the new data presented here highlight a previously unappreciated role for high and stable TOX expression as a distinct feature of $T_{EX}$.

A second implication is that these studies point to key molecular underpinnings of exhaustion that are relevant for understanding reversibility and re-invigoration. Without wishing to be bound by theory, re-invigoration of $T_{EX}$ following blockade PD-1 or other inhibitory receptors may occur in humans during checkpoint blockade for cancer treatment. However, such reinvigoration may change the state of the CD8$^+$ T cells, making them temporarily more functional, but does not change their fate. Indeed, PD-1 pathway blockade had little effect on modulating the epigenetic landscape and re-invigorated $T_{EX}$ reverted to the original exhausted state, an observation with potential implications for durability of checkpoint blockade effects in humans. TOX or TOX-dependent events including epigenetic landscape programming may be a major reason for this developmental inflexibility of $T_{EX}$ even following PD-1 blockade. Thus, TOX might represent a novel therapeutic target. However, the absence of TOX promotes the generation of terminal KLRG1$^{HI}$ cells, a cell fate with high functionality, but poor durability especially in settings of chronic stimulation. Thus, it may be necessary to complement TOX therapeutic targeting with strategies that also foster lineage fate re-differentiation toward the more durable $T_{MEM}$ lineage. For example, at least some KLRG1$^{HI}$ effector CD8$^+$ T cells may be able to revert to a $T_{MEM}$ developmental pathway, but additional transcriptional manipulations such as loss of Id2 might also be needed. Nevertheless, the role of TOX in $T_{EX}$ revealed here may not only aid in our understanding of the molecular, transcriptional and epigenetic basis of exhaustion, but could also lead to new therapeutic opportunities.

The link to NFAT and calcineurin for initial TOX induction is reminiscent of previous work on in vitro anergy where TCR signaling (or calcium signaling) alone induces an NFAT-dependent response-refractory state. More recent studies have shown that these events can be transcriptionally mimicked by "partnerless" NFAT working without AP-131. The relationship between in vitro anergy and in vivo exhaustion has remained poorly understood, though the partnerless NFAT transcriptional program contained a subset of key $T_{EX}$ genes. These new TOX data now may reconcile anergy and exhaustion observations through the core NFAT circuit that is required early in both settings. One difference between $T_{EX}$ and anergic or tolerant cells, however, is that $T_{EX}$, unlike anergic cells, arise from cells that have, at least initially, acquired effector functions. Thus, whereas anergic or tolerant cells might experience TOX expression in the context of a naive epigenetic landscape, developing $T_{EX}$ initiate the TOX epigenetic remodeling starting from an early $T_{EFF}$ state. This shared initial calcium-NFAT-TOX circuit might eventually lead, in the case of $T_{EX}$ in vivo, to the self-reinforcing TOX circuit that drives exhaustion which at later time points no longer requires sustained calcium signaling and NFAT.

Some of the earliest studies on exhaustion demonstrated the temporally progressive pattern of loss of function. Subsequent studies demonstrated that at early time points fate commitment to exhaustion was reversible and functional $T_{MEM}$ could form whereas after 2-4 weeks of chronic infection, the fate of $T_{EX}$ become permanently established and inflexible. The NFAT initiated, TOX-dependent feed-forward circuit described here is consistent with this progressive commitment to exhaustion and provides an explanation for the progressive fate inflexibility. These data also suggest the possibility of a multi-step process in the development of $T_{EX}$. Without wishing to be bound by theory, the data presented herein suggest that a first step may be the repression of the KLRG1$^{HI}$ cell fate by TOX and/or perhaps TOX-dependent Tcf1 expression. Once the $T_{EX}$ precursor population is preserved during the first week of chronic infection, additional epigenetic events are likely necessary over the next 1-3 weeks to ensure full fate commitment to $T_{EX}$. At least one of these events may involve a TOX-mediated self-reinforcing set of changes at the Tox locus creating an NFAT-independent transcriptional environment and ensuring long-term TOX expression. In addition, TOX epigenetically and developmentally controls the expression of many of the key genes necessary to establish the durable $T_{EX}$ proliferative hierarchy and $T_{EX}$ fate including PD-1 and other inhibitory receptors, Tcf1, Eomes and other TFs.

Many HMG family members have relatively promiscuous DNA-binding characteristics consistent with a highly GC-rich binding site reported for TOX consistent with our own analyses. Thus, it will be important in the future to further understand the TOX partners recruited and used through the $T_{EX}$ developmental program. Nevertheless, a TOX dependent progressive model of exhaustion has implications for the developmental plasticity of $T_{EX}$ and timing of therapeutics intended to prevent or reverse exhaustion.

Without wishing to be bound by theory, the observations presented herein are consistent with a model where TOX is the master regulator of $T_{EX}$ similar to other developmental programmers in immune cells. Collectively, these data demonstrate that TOX is necessary and sufficient for the development of $T_{EX}$. The identification of an epigenetic programming pathway for $T_{EX}$ opens new opportunities for mechanistic understanding and therapeutic targeting of this disease-relevant cell type. It is now possible to more accurately define $T_{EX}$ in different settings and also envision therapeutics based on modulation of TOX, HBO1, and/or Kat7 activity as well as the targeting of the TOX-dependent epigenetic changes in $T_{EX}$.

Example 17. Use of Clustered Regularly Interspaced Short Palindromic Repeats (CRISPR) Systems to Reduce or Eliminate T Cell Exhaustion CRISPR systems refer to systems useful for various types of genome editing including, but not limited to, excision of genes, mutating of genes (e.g., introduction of point mutations, frame shift mutations, and other mutations that alter expression of a gene of interest), incorporation of exogenous gene elements (e.g., introduction of exogenous coding regions, such as affinity tags, fluorescent tags, and other exogenous markers), editing via homology-directed repair (HDR) and DNA methylation. CRISPR systems, in general, use a CRISPR family enzyme (e.g., Cas9) and a guide RNA (gRNA) to direct nuclease activity (i.e., cutting of DNA) in a target specific manner within a genome. Polynucleotides useful in CRISPR systems are known to those skilled in the art and include, but are not limited to, a guide RNA (gRNA), a CRISPR RNA (crRNA), a trans-activating CRISPR RNA (tracrRNA), a single-guide crRNA and tracrRNA fusion (sgRNA), a polynucleotide encoding a CRISPR family enzyme, a CRISPR system expression vector (e.g., a vector encoding a CRISPR family enzyme, a gRNA, a crRNA, a tracrRNA, a sgRNA, or combinations thereof), or combinations thereof. CRISPR systems are described in more detail in the literature. See, e.g., M. Adli ("The CRISPR tool kit for genome editing and beyond"; *Nature Communications*; volume 9 (2018), Article number: 1911) and Y. Lei ("Targeted DNA methylation in vivo using an engineered dCas9-MQ1 fusion protein"; *Nature Communications*; volume 8 (2017), Article number: 16026), both of which are herein incorporated by reference for all that they teach.

One or more of the above-described systems are used to generate directed mutations or modifications of one or more genes or regulatory regions that are related to exhaustion, for example one or more genes in epigenetic pathways. The systems may be employed to edit (for example, delete or modify) open chromatin regions (OCRs). The systems may be employed to edit (for example, delete or modify) open chromatin regions (OCRs) listed in Table 6. The systems may be employed in vivo (i.e., within the subject) or in vitro (i.e., outside of the subject).

One or more of the above-described systems are used to generate directed mutations or modifications of Tox or Tet2 in T cells. The systems may be employed to mutate or modify Tox or Tet2 in T cells in vitro (i.e., outside of the subject) and/or in vivo (i.e., within the subject). More specifically, the directed mutations or modifications of Tox or Tet2 will be chosen such that T cell exhaustion is prevented or reduced or reversed. Similarly, the same systems may be used to modify or mutate sequences which are responsible for regulating the expression of Tox or Tet2. In addition to the engineered protein and nucleic acid systems (e.g., CRISPR/Cas9 systems with guide RNAs homologous to Tox or Tet2, and compositions for the delivery of the systems to cells) needed to make the directed mutations and modifications, modified T cells will be produced with altered expression of Tox and/or Tet2, or expression of modified versions of the Tox and/or Tet2 genes. In some instances, both the Tox and Tet2 genes and their resulting protein sequences will be mutated or modified. For example, in the case of the nucleic acid sequences encoding Tox and Tet2, the encoding nucleic acid may be mutated, or its methylation pattern changed. The mutated sequence will have altered transcription or translation efficiency relative to the wild type sequence, or the encoded protein sequence will be changed, or both, depending on the desired outcome. The change in the encoded protein sequence will affect the activity of the Tox or Tet2 gene products (or both products) by altering their activity in a manner that reduces or eliminates T cell exhaustion. The change in the encoded protein sequence may alternatively reduce the normal activity or eliminate the normal activity of one or both of the Tox or Tet2 gene products (e.g., knockout mutations). Likewise, with respect to sequences that regulate transcription of Tox or Tet2 gene products (e.g., promoter sequences), the CRISPR/Cas9 systems described above (or other systems that can direct gene mutation/modification) can be used to produce T cells where the transcription levels of the Tox or Tet2 genes, or the level of transcription of both genes, is modified such that T cell exhaustion is reduced or eliminated.

TABLE 4

| Gene-cluster associations | |
| --- | --- |
| Gene ID | Cluster ID |
| AGFG1 | 1 |
| APOBEC1 | 1 |
| ARID5B | 1 |
| ASAP1 | 1 |
| BAZ1A | 1 |
| DCLRE1C | 1 |
| DNMT3A | 1 |
| DTX3L | 1 |
| GABPA | 1 |
| HIVEP1 | 1 |
| IKZF2 | 1 |
| IRF9 | 1 |
| ISG15 | 1 |
| JAK2 | 1 |
| KDM4A | 1 |
| NCOA1 | 1 |
| NUCB2 | 1 |
| OAS2 | 1 |
| OPTN | 1 |
| PARP11 | 1 |
| PARP12 | 1 |
| PARP14 | 1 |
| PARP9 | 1 |
| PYHIN1 | 1 |
| RAD54L2 | 1 |
| SETBP1 | 1 |
| SFMBT1 | 1 |
| SRCAP | 1 |
| STAT1 | 1 |
| STAT2 | 1 |
| STAT3 | 1 |
| TCF4 | 1 |
| TET2 | 1 |
| TFDP2 | 1 |
| TLR7 | 1 |
| TOX | 1 |
| UBR5 | 1 |
| XRN1 | 1 |
| ZBED4 | 1 |
| AARSD1 | 2 |
| ABCF1 | 2 |
| ABCF2 | 2 |
| ABCF3 | 2 |
| ACADL | 2 |
| ACADM | 2 |
| ACTL6A | 2 |

TABLE 4-continued

| Gene-cluster associations | |
| --- | --- |
| Gene ID | Cluster ID |
| ADAP1 | 2 |
| AIMP1 | 2 |
| ALKBH8 | 2 |
| ANP32E | 2 |
| APEX1 | 2 |
| APITD1 | 2 |
| AQR | 2 |
| ARFGAP2 | 2 |
| ARL6IP4 | 2 |
| ASF1A | 2 |
| ASF1B | 2 |
| ASXL1 | 2 |
| ATAD2 | 2 |
| ATAD5 | 2 |
| ATOH1 | 2 |
| ATP5A1 | 2 |
| ATP5B | 2 |
| ATP6V1A | 2 |
| ATP6V1B2 | 2 |
| ATR | 2 |
| ATXN7L3 | 2 |
| AURKA | 2 |
| AURKB | 2 |
| BAP1 | 2 |
| BARD1 | 2 |
| BAZ1B | 2 |
| BCLAF1 | 2 |
| BLM | 2 |
| BRCA1 | 2 |
| BRCA2 | 2 |
| BRCC3 | 2 |
| BRD9 | 2 |
| BRE | 2 |
| BRIP1 | 2 |
| BRMS1L | 2 |
| BTF3L4 | 2 |
| BUB1 | 2 |
| BZW1 | 2 |
| C1D | 2 |
| CARHSP1 | 2 |
| CBX1 | 2 |
| CBX3 | 2 |
| CBX5 | 2 |
| CD2BP2 | 2 |
| CDC6 | 2 |
| CDCA4 | 2 |
| CDCA5 | 2 |
| CDK2 | 2 |
| CDK2AP1 | 2 |
| CDK9 | 2 |
| CDKN2AIPNL | 2 |
| CENPA | 2 |
| CHAF1A | 2 |
| CHAF1B | 2 |
| CHD1L | 2 |
| CHD4 | 2 |
| CHEK1 | 2 |
| CHUK | 2 |
| CIT | 2 |
| CNOT6 | 2 |
| COPS5 | 2 |
| CPSF2 | 2 |
| CPSF3L | 2 |
| CPSF4 | 2 |
| CPSF6 | 2 |
| CPSF7 | 2 |
| CSNK2A1 | 2 |
| CTBP1 | 2 |
| CTCF | 2 |
| CUL1 | 2 |
| CUL2 | 2 |
| CUL4B | 2 |
| CYB5R3 | 2 |
| CYB5R4 | 2 |
| DARS | 2 |
| DARS2 | 2 |

TABLE 4-continued

Gene-cluster associations

| Gene ID | Cluster ID |
|---------|------------|
| DCLRE1A | 2 |
| DCP1A | 2 |
| DDB1 | 2 |
| DDX21 | 2 |
| DEK | 2 |
| DICER1 | 2 |
| DNA2 | 2 |
| DNMT1 | 2 |
| DPF2 | 2 |
| DPY30 | 2 |
| DSCC1 | 2 |
| DZIP3 | 2 |
| E2F1 | 2 |
| E2F2 | 2 |
| E2F3 | 2 |
| E2F4 | 2 |
| E2F6 | 2 |
| E2F7 | 2 |
| E2F8 | 2 |
| EEF1G | 2 |
| EEF2 | 2 |
| EFTUD2 | 2 |
| EIF2A | 2 |
| EIF2B3 | 2 |
| EIF2B5 | 2 |
| EIF2S1 | 2 |
| EIF2S2 | 2 |
| EIF3B | 2 |
| EIF3C | 2 |
| EIF3D | 2 |
| EIF3H | 2 |
| EIF3I | 2 |
| EIF3L | 2 |
| EIF4E2 | 2 |
| EIF4G1 | 2 |
| EIF4H | 2 |
| EIF5A | 2 |
| ELP2 | 2 |
| EPAS1 | 2 |
| EPRS | 2 |
| ERCC3 | 2 |
| ERCC6L | 2 |
| ERH | 2 |
| ETS2 | 2 |
| ETV6 | 2 |
| EXO1 | 2 |
| EXOSC1 | 2 |
| EXOSC2 | 2 |
| EXOSC5 | 2 |
| EXOSC8 | 2 |
| EXOSC9 | 2 |
| EZH2 | 2 |
| FANCM | 2 |
| FBL | 2 |
| FHL2 | 2 |
| FLI1 | 2 |
| FMR1 | 2 |
| FOXM1 | 2 |
| FUS | 2 |
| G2E3 | 2 |
| G3BP1 | 2 |
| GADD45B | 2 |
| GAR1 | 2 |
| GATAD2A | 2 |
| GCDH | 2 |
| GEN1 | 2 |
| GFM2 | 2 |
| GLYR1 | 2 |
| GMEB1 | 2 |
| GMEB2 | 2 |
| GMPPA | 2 |
| GNPTAB | 2 |
| GON4L | 2 |
| GPN2 | 2 |
| GSG2 | 2 |
| GSPT1 | 2 |

TABLE 4-continued

Gene-cluster associations

| Gene ID | Cluster ID |
|---------|------------|
| GTF2E2 | 2 |
| GTF2F1 | 2 |
| GTF3C5 | 2 |
| GTPBP1 | 2 |
| H2AFX | 2 |
| H2AFY | 2 |
| H2AFZ | 2 |
| H3F3A | 2 |
| HAT1 | 2 |
| HCFC1 | 2 |
| HCLS1 | 2 |
| HDAC1 | 2 |
| HDAC3 | 2 |
| HDGF | 2 |
| HEATR1 | 2 |
| HELLS | 2 |
| HIF1A | 2 |
| HIRIP3 | 2 |
| HIST1H1A | 2 |
| HIST1H1B | 2 |
| HIST1H1E | 2 |
| HIST1H2AA | 2 |
| HIST1H2AB | 2 |
| HIST1H2BB | 2 |
| HIST1H2BH | 2 |
| HIST1H2BM | 2 |
| HIST1H3A | 2 |
| HIST3H2A | 2 |
| HJURP | 2 |
| HLTF | 2 |
| HMGA1 | 2 |
| HMGB1 | 2 |
| HMGB2 | 2 |
| HMGB3 | 2 |
| HMGN2 | 2 |
| HMGXB4 | 2 |
| HNRNPF | 2 |
| HNRNPH2 | 2 |
| HNRNPH3 | 2 |
| HP1BP3 | 2 |
| HTATSF1 | 2 |
| IGF2BP3 | 2 |
| IKBKAP | 2 |
| IKZF1 | 2 |
| ILF2 | 2 |
| ILF3 | 2 |
| IMP4 | 2 |
| INCENP | 2 |
| ING3 | 2 |
| INO80C | 2 |
| INO80E | 2 |
| IRAK3 | 2 |
| IRF1 | 2 |
| IRF4 | 2 |
| IRF8 | 2 |
| KARS | 2 |
| KAT5 | 2 |
| KHSRP | 2 |
| KLHL6 | 2 |
| LARP1 | 2 |
| LARP7 | 2 |
| LAS1L | 2 |
| LBR | 2 |
| LIG1 | 2 |
| LIN9 | 2 |
| LSM2 | 2 |
| LSM3 | 2 |
| LSM4 | 2 |
| LSM6 | 2 |
| LSM7 | 2 |
| LUC7L2 | 2 |
| MAK16 | 2 |
| MAP3K7 | 2 |
| MAPKAPK3 | 2 |
| MARVELD2 | 2 |
| MASTL | 2 |

TABLE 4-continued

Gene-cluster associations

| Gene ID | Cluster ID |
| --- | --- |
| MATR3 | 2 |
| MAX | 2 |
| MBD3 | 2 |
| MBD4 | 2 |
| MBNL3 | 2 |
| MCM10 | 2 |
| MCM2 | 2 |
| MCM3 | 2 |
| MCM4 | 2 |
| MCM5 | 2 |
| MCM6 | 2 |
| MCM7 | 2 |
| MCM8 | 2 |
| MCM9 | 2 |
| MDM2 | 2 |
| MEAF6 | 2 |
| MED27 | 2 |
| METAP1 | 2 |
| METAP2 | 2 |
| METTL14 | 2 |
| MIER3 | 2 |
| MINA | 2 |
| MLH1 | 2 |
| MORF4L2 | 2 |
| MRPL1 | 2 |
| MRPL11 | 2 |
| MRPL13 | 2 |
| MRPL16 | 2 |
| MRPL18 | 2 |
| MRPL23 | 2 |
| MRPL4 | 2 |
| MRPL44 | 2 |
| MRPS11 | 2 |
| MRPS7 | 2 |
| MSH2 | 2 |
| MSH3 | 2 |
| MSH6 | 2 |
| MSL3 | 2 |
| MTF2 | 2 |
| MTIF3 | 2 |
| MTO1 | 2 |
| MTRF1 | 2 |
| MTRF1L | 2 |
| MXD3 | 2 |
| MYB | 2 |
| MYBBP1A | 2 |
| MYBL2 | 2 |
| MYCBP | 2 |
| MYEF2 | 2 |
| N4BP1 | 2 |
| N6AMT1 | 2 |
| NAP1L1 | 2 |
| NAP1L4 | 2 |
| NARS | 2 |
| NASP | 2 |
| NAT10 | 2 |
| NBN | 2 |
| NCAPD2 | 2 |
| NCAPD3 | 2 |
| NCBP1 | 2 |
| NCBP2 | 2 |
| NCL | 2 |
| NEDD8 | 2 |
| NEIL3 | 2 |
| NFXL1 | 2 |
| NFYA | 2 |
| NFYB | 2 |
| NHP2 | 2 |
| NOC3L | 2 |
| NONO | 2 |
| NOP56 | 2 |
| NOP58 | 2 |
| NSL1 | 2 |
| NSUN2 | 2 |
| NUCB1 | 2 |
| NUDT21 | 2 |

TABLE 4-continued

Gene-cluster associations

| Gene ID | Cluster ID |
| --- | --- |
| NUP35 | 2 |
| NUPR1 | 2 |
| OTUD4 | 2 |
| OTUD6B | 2 |
| P2RY13 | 2 |
| P2RY14 | 2 |
| PA2G4 | 2 |
| PAK2 | 2 |
| PARN | 2 |
| PARP1 | 2 |
| PARP2 | 2 |
| PATL1 | 2 |
| PAXIP1 | 2 |
| PBK | 2 |
| PCBP1 | 2 |
| PCGF5 | 2 |
| PCNA | 2 |
| PDS5A | 2 |
| PDS5B | 2 |
| PEPD | 2 |
| PHF10 | 2 |
| PKN1 | 2 |
| PMS2 | 2 |
| PNPT1 | 2 |
| POLA2 | 2 |
| POLB | 2 |
| POLD2 | 2 |
| POLE2 | 2 |
| POLE3 | 2 |
| POLQ | 2 |
| POLR2D | 2 |
| POP4 | 2 |
| PPM1G | 2 |
| PPP2CA | 2 |
| PPP4C | 2 |
| PRDM1 | 2 |
| PREB | 2 |
| PRIM1 | 2 |
| PRKAA1 | 2 |
| PRKAB1 | 2 |
| PRKCD | 2 |
| PRKRIP1 | 2 |
| PRMT1 | 2 |
| PRMT5 | 2 |
| PRMT7 | 2 |
| PRPF31 | 2 |
| PRPF4 | 2 |
| PRPF40A | 2 |
| PRPF8 | 2 |
| PSMC3IP | 2 |
| PSMD14 | 2 |
| PTAFR | 2 |
| PWP1 | 2 |
| QARS | 2 |
| QRICH1 | 2 |
| RAD1 | 2 |
| RAD23B | 2 |
| RAD50 | 2 |
| RAD51 | 2 |
| RAD51C | 2 |
| RAD54B | 2 |
| RAD54L | 2 |
| RAE1 | 2 |
| RB1 | 2 |
| RBBP4 | 2 |
| RBBP7 | 2 |
| RBBP8 | 2 |
| RBM22 | 2 |
| RBMX2 | 2 |
| RCBTB2 | 2 |
| RCC1 | 2 |
| RCC2 | 2 |
| RECQL | 2 |
| RFC1 | 2 |
| RFC2 | 2 |
| RFC3 | 2 |

TABLE 4-continued

Gene-cluster associations

| Gene ID | Cluster ID |
|---------|------------|
| RFC4 | 2 |
| RFC5 | 2 |
| RILPL2 | 2 |
| RLIM | 2 |
| RMI1 | 2 |
| RNH1 | 2 |
| RNPS1 | 2 |
| RPA3 | 2 |
| RPL18 | 2 |
| RPLP0 | 2 |
| RPLP1 | 2 |
| RPP30 | 2 |
| RPS14 | 2 |
| RPS3 | 2 |
| RPS5 | 2 |
| RPS6KA3 | 2 |
| RPS6KA5 | 2 |
| RRN3 | 2 |
| RRP8 | 2 |
| RTEL1 | 2 |
| RUVBL1 | 2 |
| RUVBL2 | 2 |
| SATB1 | 2 |
| SENP1 | 2 |
| SETD8 | 2 |
| SETDB1 | 2 |
| SETDB2 | 2 |
| SF1 | 2 |
| SF3A1 | 2 |
| SF3A3 | 2 |
| SF3B3 | 2 |
| SIN3A | 2 |
| SIRT1 | 2 |
| SIRT2 | 2 |
| SIRT7 | 2 |
| SLBP | 2 |
| SMAP2 | 2 |
| SMARCA4 | 2 |
| SMARCA5 | 2 |
| SMARCB1 | 2 |
| SMARCC1 | 2 |
| SMARCD1 | 2 |
| SMARCD2 | 2 |
| SMC5 | 2 |
| SMC6 | 2 |
| SMYD2 | 2 |
| SNAPC5 | 2 |
| SND1 | 2 |
| SNRNP70 | 2 |
| SNRPA | 2 |
| SNRPD1 | 2 |
| SNRPD3 | 2 |
| SP110 | 2 |
| SPAG7 | 2 |
| SPIC | 2 |
| SPOP | 2 |
| SRBD1 | 2 |
| SRP19 | 2 |
| SSRP1 | 2 |
| STAG1 | 2 |
| STRBP | 2 |
| SUV39H1 | 2 |
| SUV39H2 | 2 |
| SUZ12 | 2 |
| SWAP70 | 2 |
| TAF1 | 2 |
| TAF10 | 2 |
| TAF12 | 2 |
| TAF2 | 2 |
| TAF5 | 2 |
| TAF6 | 2 |
| TAF9 | 2 |
| TAF9B | 2 |
| TARS | 2 |
| TARSL2 | 2 |
| TCERG1 | 2 |

TABLE 4-continued

Gene-cluster associations

| Gene ID | Cluster ID |
|---------|------------|
| TCF7L2 | 2 |
| TDG | 2 |
| TFAM | 2 |
| TFDP1 | 2 |
| TFPT | 2 |
| THOC2 | 2 |
| THOC5 | 2 |
| TIPIN | 2 |
| TOP1 | 2 |
| TOPBP1 | 2 |
| TRA2B | 2 |
| TRAPPC1 | 2 |
| TRAPPC2 | 2 |
| TRAPPC4 | 2 |
| TRMT2B | 2 |
| TRMT6 | 2 |
| TSR1 | 2 |
| TTF2 | 2 |
| TTK | 2 |
| TUFM | 2 |
| U2AF1 | 2 |
| U2AF1L4 | 2 |
| U2AF2 | 2 |
| UBA52 | 2 |
| UBC | 2 |
| UBE2N | 2 |
| UBE2T | 2 |
| UBR7 | 2 |
| UBTF | 2 |
| UCHL5 | 2 |
| UHRF1 | 2 |
| UTP6 | 2 |
| VPS72 | 2 |
| VRK1 | 2 |
| WDHD1 | 2 |
| WDR3 | 2 |
| WDR5 | 2 |
| WDR82 | 2 |
| WHSC1 | 2 |
| XDH | 2 |
| XPNPEP1 | 2 |
| XPO5 | 2 |
| XPOT | 2 |
| XRCC5 | 2 |
| XRCC6 | 2 |
| YARS | 2 |
| YEATS4 | 2 |
| YWHAB | 2 |
| YWHAE | 2 |
| YWHAZ | 2 |
| ZC3HAV1 | 2 |
| ZCCHC8 | 2 |
| ZFAND1 | 2 |
| ZMAT2 | 2 |
| ZMYND19 | 2 |
| ZNHIT1 | 2 |
| ZRANB3 | 2 |
| AFF1 | 3 |
| ALS2 | 3 |
| APOBEC2 | 3 |
| ARAP2 | 3 |
| ARID5A | 3 |
| ARNTL | 3 |
| CEBPB | 3 |
| CHD9 | 3 |
| CIR1 | 3 |
| CNOT6L | 3 |
| CPEB2 | 3 |
| CRY1 | 3 |
| DDIT3 | 3 |
| DNAJC1 | 3 |
| DNTTIP2 | 3 |
| EIF3F | 3 |
| EIF4E3 | 3 |
| ELK3 | 3 |
| ELL2 | 3 |

TABLE 4-continued

Gene-cluster associations

| Gene ID | Cluster ID |
|---|---|
| EOMES | 3 |
| GCH1 | 3 |
| GTF2B | 3 |
| H2AFV | 3 |
| HIF1AN | 3 |
| HINT3 | 3 |
| HIST1H1C | 3 |
| HIST1H2AC | 3 |
| HIST1H2BC | 3 |
| HSPA1A | 3 |
| ID2 | 3 |
| IKZF3 | 3 |
| IRAK2 | 3 |
| IRF2 | 3 |
| IRF7 | 3 |
| JDP2 | 3 |
| JUNB | 3 |
| KIN | 3 |
| LEO1 | 3 |
| LITAF | 3 |
| LRRFIP2 | 3 |
| METTL4 | 3 |
| MEX3C | 3 |
| MLLT3 | 3 |
| MTA3 | 3 |
| MXD1 | 3 |
| MXI1 | 3 |
| NFAT5 | 3 |
| NFIL3 | 3 |
| NFYC | 3 |
| NMI | 3 |
| NOD1 | 3 |
| NR3C1 | 3 |
| NR4A1 | 3 |
| NR4A2 | 3 |
| NR4A3 | 3 |
| NUP98 | 3 |
| OCEL1 | 3 |
| PER1 | 3 |
| POLN | 3 |
| PRKAB2 | 3 |
| PRKCA | 3 |
| RBL2 | 3 |
| RNF2 | 3 |
| RORA | 3 |
| RYBP | 3 |
| SAP30 | 3 |
| SAP30L | 3 |
| SERTAD1 | 3 |
| SMAD3 | 3 |
| SMAP1 | 3 |
| SP140 | 3 |
| SPRY2 | 3 |
| SPTY2D1 | 3 |
| STAT4 | 3 |
| TBX21 | 3 |
| THAP3 | 3 |
| THAP6 | 3 |
| TIPARP | 3 |
| TNFAIP3 | 3 |
| TOX2 | 3 |
| TRNT1 | 3 |
| TSC22D2 | 3 |
| UBD | 3 |
| UBE2A | 3 |
| UHRF2 | 3 |
| XPA | 3 |
| YAF2 | 3 |
| ZC3H12C | 3 |
| ZFP69 | 3 |
| ZFP90 | 3 |
| ZMYM5 | 3 |
| EID2B | 4 |
| MXD4 | 4 |
| USP3 | 4 |
| ABCE1 | 5 |

TABLE 4-continued

Gene-cluster associations

| Gene ID | Cluster ID |
|---|---|
| ABT1 | 5 |
| ACADVL | 5 |
| ACAT1 | 5 |
| ACTR6 | 5 |
| AFF3 | 5 |
| AFF4 | 5 |
| ALKBH1 | 5 |
| APPL2 | 5 |
| ARID1A | 5 |
| ARID1B | 5 |
| ARID2 | 5 |
| ARID4A | 5 |
| ARID4B | 5 |
| ASH1L | 5 |
| ASXL2 | 5 |
| ATAD2B | 5 |
| ATF7 | 5 |
| ATF7IP | 5 |
| ATM | 5 |
| ATN1 | 5 |
| ATXN3 | 5 |
| ATXN7 | 5 |
| BACH2 | 5 |
| BAZ2A | 5 |
| BAZ2B | 5 |
| BCL11B | 5 |
| BCOR | 5 |
| BDP1 | 5 |
| BPTF | 5 |
| BRD1 | 5 |
| BRWD1 | 5 |
| BZW2 | 5 |
| CARM1 | 5 |
| CBX7 | 5 |
| CCDC101 | 5 |
| CCDC130 | 5 |
| CDK7 | 5 |
| CHD1 | 5 |
| CHD2 | 5 |
| CHD3 | 5 |
| CHD6 | 5 |
| CHRAC1 | 5 |
| CLOCK | 5 |
| CNBP | 5 |
| CPSF3 | 5 |
| CREBBP | 5 |
| CRLF3 | 5 |
| CRTC2 | 5 |
| CRTC3 | 5 |
| CSTF2T | 5 |
| CUX1 | 5 |
| DCLRE1B | 5 |
| DDB2 | 5 |
| DKC1 | 5 |
| DMTF1 | 5 |
| DZIP1 | 5 |
| E2F5 | 5 |
| EEF1B2 | 5 |
| EEFSEC | 5 |
| EHMT1 | 5 |
| EID2 | 5 |
| EIF3G | 5 |
| EIF4B | 5 |
| EIF5 | 5 |
| ELF1 | 5 |
| ELK4 | 5 |
| ELP3 | 5 |
| EMG1 | 5 |
| ENOX2 | 5 |
| EP300 | 5 |
| EPC1 | 5 |
| EPC2 | 5 |
| EPM2AIP1 | 5 |
| ERAL1 | 5 |
| ERCC6 | 5 |
| ETV3 | 5 |

TABLE 4-continued

Gene-cluster associations

| Gene ID | Cluster ID |
|---|---|
| EXOSC7 | 5 |
| EYA2 | 5 |
| EZH1 | 5 |
| FAM175A | 5 |
| FAM175B | 5 |
| FBRS | 5 |
| FIZ1 | 5 |
| FOXJ2 | 5 |
| FOXK1 | 5 |
| FOXO1 | 5 |
| FOXO3 | 5 |
| FOXP1 | 5 |
| GADD45A | 5 |
| GATAD2B | 5 |
| GPATCH4 | 5 |
| GPBP1L1 | 5 |
| GPN1 | 5 |
| GPN3 | 5 |
| GRHL3 | 5 |
| GTF2I | 5 |
| GTPBP2 | 5 |
| HDAC2 | 5 |
| HDAC4 | 5 |
| HDGFRP2 | 5 |
| HDGFRP3 | 5 |
| HERC1 | 5 |
| HIST2H2BE | 5 |
| HIVEP2 | 5 |
| HMG20A | 5 |
| HUWE1 | 5 |
| HYI | 5 |
| ID3 | 5 |
| IMP3 | 5 |
| ING5 | 5 |
| INTS6 | 5 |
| IVD | 5 |
| JARID2 | 5 |
| JMJD1C | 5 |
| JMJD8 | 5 |
| JUN | 5 |
| KAT2A | 5 |
| KAT2B | 5 |
| KDM3A | 5 |
| KDM5A | 5 |
| KDM5B | 5 |
| L3MBTL3 | 5 |
| LCOR | 5 |
| LCORL | 5 |
| LDB1 | 5 |
| LEF1 | 5 |
| LIG4 | 5 |
| LRPPRC | 5 |
| LSM8 | 5 |
| LUC7L | 5 |
| MBD5 | 5 |
| MBNL2 | 5 |
| MCEE | 5 |
| MDC1 | 5 |
| MDM4 | 5 |
| MGA | 5 |
| MLLT10 | 5 |
| MLXIP | 5 |
| MPND | 5 |
| MRPS6 | 5 |
| MSL2 | 5 |
| MYC | 5 |
| MYCBP2 | 5 |
| MYSM1 | 5 |
| NANOS1 | 5 |
| NARS2 | 5 |
| NCOA3 | 5 |
| NFE2L2 | 5 |
| NFE2L3 | 5 |
| NFRKB | 5 |
| NFX1 | 5 |
| NIPBL | 5 |

TABLE 4-continued

Gene-cluster associations

| Gene ID | Cluster ID |
|---|---|
| NNT | 5 |
| NOP10 | 5 |
| NR1D2 | 5 |
| NR2C2 | 5 |
| NSD1 | 5 |
| NUFIP1 | 5 |
| OGT | 5 |
| OTUD1 | 5 |
| PAIP1 | 5 |
| PCF11 | 5 |
| PCGF1 | 5 |
| PCGF6 | 5 |
| PDCD11 | 5 |
| PDCD4 | 5 |
| PDLIM1 | 5 |
| PDP1 | 5 |
| PHC3 | 5 |
| PHF12 | 5 |
| PHF20L1 | 5 |
| PHF21A | 5 |
| PHF3 | 5 |
| PHIP | 5 |
| PHTF2 | 5 |
| POGZ | 5 |
| POLD4 | 5 |
| POLE4 | 5 |
| PPARGC1B | 5 |
| PPP4R2 | 5 |
| PPRC1 | 5 |
| PRDM2 | 5 |
| PRKDC | 5 |
| PRM3 | 5 |
| PRPF39 | 5 |
| PUM1 | 5 |
| PUM2 | 5 |
| RAD52 | 5 |
| RARA | 5 |
| RARG | 5 |
| RBBP6 | 5 |
| RBM26 | 5 |
| RCBTB1 | 5 |
| RCCD1 | 5 |
| RCOR1 | 5 |
| REST | 5 |
| RFX3 | 5 |
| RFX7 | 5 |
| RIC8B | 5 |
| RPL12 | 5 |
| RPL13 | 5 |
| RREB1 | 5 |
| RRP9 | 5 |
| SAP18 | 5 |
| SBDS | 5 |
| SCML4 | 5 |
| SENP3 | 5 |
| SETD1B | 5 |
| SETD2 | 5 |
| SETD6 | 5 |
| SETD7 | 5 |
| SETX | 5 |
| SHARPIN | 5 |
| SHPRH | 5 |
| SMAD1 | 5 |
| SMAD4 | 5 |
| SMAD5 | 5 |
| SMAD7 | 5 |
| SMARCA2 | 5 |
| SMOX | 5 |
| SMYD3 | 5 |
| SNAPC4 | 5 |
| STK4 | 5 |
| SUV420H1 | 5 |
| TAF5L | 5 |
| TAF7 | 5 |
| TAF8 | 5 |
| TCF12 | 5 |

TABLE 4-continued

| Gene-cluster associations | |
| --- | --- |
| Gene ID | Cluster ID |
| TCF20 | 5 |
| TCF7 | 5 |
| TEF | 5 |
| TET1 | 5 |
| TET3 | 5 |
| THOC1 | 5 |
| TLE4 | 5 |
| TLK2 | 5 |
| TOP2B | 5 |
| TRA2A | 5 |
| TRIM33 | 5 |
| TSC22D3 | 5 |
| UBE2H | 5 |
| UPF2 | 5 |
| USP11 | 5 |
| USP21 | 5 |
| WDR77 | 5 |
| WHSC1L1 | 5 |

TABLE 4-continued

| Gene-cluster associations | |
| --- | --- |
| Gene ID | Cluster ID |
| XPC | 5 |
| YEATS2 | 5 |
| YRDC | 5 |
| ZBTB44 | 5 |
| ZCCHC7 | 5 |
| ZFAND2A | 5 |
| ZFP1 | 5 |
| ZFP36L1 | 5 |
| ZGPAT | 5 |
| ZHX1 | 5 |
| ZHX2 | 5 |
| ZMYM2 | 5 |
| ZMYM4 | 5 |
| ZMYND11 | 5 |
| ZRSR1 | 5 |
| ZRSR2 | 5 |

TABLE 5

| Tox KO data: non-coding genomic locations epigenetically changed by Tox in an exhaustion specific manner | | | | | | | |
| --- | --- | --- | --- | --- | --- | --- | --- |
| Chromosome | Start | End | Annotation | Distance to TSS | Proximal Gene ID | Log2 Fold Change | Adjusted p-value |
| chr8 | 73123970 | 73124493 | Intron | 107719 | Mir28b | 5.15850602 | 0.00193027 |
| chr17 | 26841384 | 26841688 | Promoter-TSS | 29 | Nkx2-5 | 4.961722961 | 0.006217652 |
| chr10 | 8772489 | 8772718 | Intron | 113467 | Sash1 | 4.787449719 | 0.010430375 |
| chr7 | 84337819 | 84338153 | Intron | 72052 | Arnt2 | 4.704461923 | 0.007581916 |
| chr8 | 127233826 | 127234177 | Intron | −65611 | Pard3 | 4.681625422 | 0.010416923 |
| chr2 | 165570040 | 165570547 | Intergenic | −24735 | Eya2 | 4.486004696 | 0.016372205 |
| chr3 | 30120790 | 30121111 | Intergenic | −107746 | Mecom | 4.474618712 | 0.016846283 |
| chr17 | 66419448 | 66419986 | Intron | 30033 | Mtcl1 | 4.43896501 | 0.017143289 |
| chr12 | 54005600 | 54005878 | Intron | 198135 | Egln3 | 4.316454597 | 0.030575086 |
| chr10 | 86328154 | 86328426 | Intron | 27878 | Timp3 | 4.097054584 | 0.039804485 |
| chr17 | 5237883 | 5238116 | Intron | 180768 | Ldhal6b | 4.052175065 | 0.029574226 |
| chr5 | 5695438 | 5695806 | Intergenic | −1054 | Steap2 | 4.022603664 | 0.031834758 |
| chr19 | 20424109 | 20424552 | Intergenic | 19042 | 1500015L24Rik | 3.800456144 | 8.50E−28 |
| chr8 | 44864540 | 44865046 | Intergenic | −85415 | Fat1 | 3.799932057 | 0.047909457 |
| chr8 | 94132155 | 94132482 | Intergenic | −4886 | Mt4 | 3.660634138 | 0.030044252 |
| chr12 | 73590874 | 73591065 | Intron | 6173 | Prkch | 3.609324577 | 7.81E−15 |
| chr7 | 87204701 | 87205118 | Intergenic | −41740 | Nox4 | 3.59092549 | 0.026938724 |
| chr5 | 64030670 | 64031094 | Intergenic | −14091 | 5830416I19Rik | 3.48980091 | 1.12E−11 |
| chr6 | 51720803 | 51721191 | Intergenic | 176474 | Snx10 | 3.465557469 | 0.043202316 |
| chrY | 90742661 | 90743083 | Intergenic | 12178 | G530011O06Rik | 3.442302775 | 9.17E−05 |
| chr17 | 45359468 | 45360029 | Intergenic | 73959 | Cdc5l | 3.367508496 | 0.04054255 |
| chr4 | 9675357 | 9675611 | Intergenic | −6140 | Asph | 3.290295039 | 1.03E−09 |
| chr7 | 25831818 | 25832564 | Intergenic | −15661 | Cyp2s1 | 3.178093651 | 0.014784838 |
| chr1 | 167004656 | 167004979 | Intron | 3400 | Fam78b | 3.130032515 | 1.39E−15 |
| chr4 | 40784604 | 40785118 | Intergenic | −26926 | Smu1 | 3.096552883 | 0.029160245 |
| chr19 | 21946418 | 21946849 | Intergenic | 168293 | Tmem2 | 3.076770225 | 4.74E−24 |
| chr4 | 119008633 | 119008872 | Intergenic | 46785 | Lao1 | 2.92850791 | 0.021648726 |
| chr11 | 115970127 | 115970692 | Intergenic | −4316 | Itgb4 | 2.887929479 | 0.03792645 |
| chr4 | 32132836 | 32133245 | Intergenic | 168933 | Map3k7 | 2.882536182 | 7.18E−20 |
| chr5 | 64029601 | 64030015 | Intergenic | −15165 | 5830416I19Rik | 2.867409057 | 5.60E−11 |
| chr6 | 118629995 | 118630313 | Intron | −67898 | Ankrd26 | 2.863109924 | 0.027957498 |
| chr5 | 39155763 | 39156195 | Intergenic | −279286 | Clnk | 2.860940976 | 2.35E−12 |
| chr14 | 69467896 | 69468419 | Intergenic | 44392 | Synb | 2.836856974 | 0.043676806 |
| chr1 | 167002628 | 167002814 | Intron | 1304 | Fam78b | 2.831323133 | 1.42E−06 |
| chr8 | 110793050 | 110793317 | Intron | 12741 | Il34 | 2.785078792 | 0.049089852 |
| chr14 | 78397940 | 78398279 | Intergenic | −90066 | Tnfsf11 | 2.782285492 | 0.023893098 |
| chr9 | 23567036 | 23567565 | Intergenic | 344224 | Bmper | 2.781277228 | 0.047979754 |
| chr5 | 106628449 | 106629011 | Intron | 68100 | Zfp644 | 2.772206665 | 0.017599951 |
| chr1 | 146805956 | 146806358 | Intron | 308470 | Brinp3 | 2.755312578 | 2.07E−06 |
| chr4 | 10905111 | 10905625 | Intergenic | 30870 | 2610301B20Rik | 2.741374196 | 2.07E−10 |
| chr17 | 5567833 | 5568309 | Intron | 75471 | Zdhhc14 | 2.728745749 | 4.57E−10 |
| chr19 | 24526801 | 24527831 | Intron | 28511 | Pip5k1b | 2.724138826 | 2.08E−35 |
| chr12 | 36235549 | 36235914 | Intergenic | −17529 | Lrrc72 | 2.707446415 | 0.014370296 |
| chr14 | 101771090 | 101771427 | Intron | 41330 | Lmo7 | 2.659007489 | 0.042629391 |
| chr1 | 46408755 | 46409122 | Intergenic | −16580 | Dnah7c | 2.656322278 | 0.02533559 |
| chr18 | 11235740 | 11236185 | Intergenic | −183395 | 1010001N08Rik | 2.647047153 | 7.03E−07 |
| chr17 | 64188147 | 64188527 | Intergenic | −137665 | 1110058D11Rik | 2.608412261 | 0.037919614 |
| chr11 | 46121412 | 46121890 | Intron | −6253 | Adam19 | 2.590153061 | 3.53E−09 |
| chr19 | 56367670 | 56368086 | Intron | 22160 | Nrap | 2.580415964 | 0.018683041 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr10 | 42231229 | 42231778 | Intron | 45239 | Foxo3 | 2.576763486 | 0.019564084 |
| chr12 | 72251982 | 72252496 | Intron | −15512 | Rtn1 | 2.574010178 | 0.040317173 |
| chr17 | 80798198 | 80798564 | Intergenic | −70356 | Map4k3 | 2.55886332 | 0.043288079 |
| chr5 | 38905310 | 38905568 | Intergenic | −28746 | Clnk | 2.533914567 | 2.48E−07 |
| chr5 | 38906753 | 38907075 | Intergenic | −30221 | Clnk | 2.509009218 | 3.78E−08 |
| chr5 | 38864676 | 38865115 | Intron | 11798 | Clnk | 2.496535116 | 1.25E−25 |
| chr6 | 112796654 | 112797083 | Intron | −100198 | Rad18 | 2.453503498 | 0.028429861 |
| chr9 | 62118848 | 62119062 | Intergenic | 3639 | Mir5133 | 2.451166748 | 0.031310596 |
| chr5 | 38885170 | 38885597 | Intergenic | −8690 | Clnk | 2.446171211 | 1.59E−14 |
| chr12 | 24097144 | 24097419 | Promoter-TSS | −12 | 9030624G23Rik | 2.429977415 | 0.007761733 |
| chr10 | 16553035 | 16553568 | Intergenic | 542481 | Gm20125 | 2.412970604 | 0.014208387 |
| chr16 | 55394793 | 55395249 | Intergenic | −99710 | Mir5118 | 2.407231511 | 0.033309769 |
| chr17 | 6942527 | 6943026 | Intron | 5580 | Rsph3b | 2.389109852 | 0.020240077 |
| chr14 | 30671183 | 30671514 | Intron | 16973 | Rft1 | 2.365119565 | 0.027108923 |
| chr18 | 75471823 | 75472180 | Exon | −42644 | Gm10532 | 2.357424433 | 3.41E−05 |
| chr9 | 110659733 | 110659994 | Intron | 3360 | Ccdc12 | 2.356678893 | 4.74E−09 |
| chr4 | 9682562 | 9683082 | Intergenic | −13478 | Asph | 2.351699549 | 9.71E−09 |
| chr9 | 32901357 | 32901760 | Intergenic | 27408 | Gm27162 | 2.351097263 | 3.70E−07 |
| chr18 | 12229845 | 12230287 | Intron | 6320 | Npc1 | 2.341031466 | 1.02E−10 |
| chr9 | 79967226 | 79967407 | Intron | 10566 | Filip1 | 2.339108756 | 1.73E−05 |
| chr9 | 107701439 | 107702024 | Intron | 3860 | Sema3f | 2.327467823 | 0.037154195 |
| chr18 | 12228718 | 12228913 | Intron | 7571 | Npc1 | 2.323976897 | 5.83E−08 |
| chr16 | 92139248 | 92140077 | Intergenic | 81326 | Mrps6 | 2.279488729 | 0.020138648 |
| chr1 | 177634228 | 177634571 | Intergenic | 8544 | 2310043L19Rik | 2.269053742 | 0.015422885 |
| chr6 | 140313937 | 140314268 | Intergenic | −109997 | Plekha5 | 2.199932941 | 2.74E−05 |
| chr10 | 26202972 | 26203293 | Intergenic | −26575 | Samd3 | 2.174984958 | 1.10E−05 |
| chr5 | 38932463 | 38932812 | Intergenic | −55944 | Clnk | 2.173954403 | 1.19E−09 |
| chr16 | 31598426 | 31599083 | Intergenic | −64689 | Dlg1 | 2.161440959 | 0.0050868 |
| chr10 | 118555057 | 118555287 | Intron | 1353 | Tmevpg1 | 2.161206131 | 2.41E−05 |
| chr18 | 78546910 | 78547641 | Intron | 49675 | Slc14a2 | 2.158777797 | 0.012248939 |
| chr11 | 3754673 | 3755066 | Intron | −32642 | Osbp2 | 2.15448571 | 0.018297582 |
| chr6 | 86772741 | 86773099 | Intron | 2194 | Anxa4 | 2.135489899 | 0.043953146 |
| chr4 | 85709664 | 85710108 | Intergenic | −344029 | Adamtsl1 | 2.13415871 | 0.004230248 |
| chr19 | 3353417 | 3354039 | Intron | 30427 | Cpt1a | 2.12937944 | 0.036191923 |
| chr10 | 122911755 | 122912214 | Intron | 73740 | Mirlet7i | 2.09348079 | 0.015460918 |
| chr2 | 156456431 | 156456790 | Intron | −18924 | Epb41l1 | 2.08182495 | 0.032986722 |
| chr16 | 29992203 | 29992727 | Intergenic | −13341 | Gm1968 | 2.070424599 | 2.53E−15 |
| chr3 | 52179654 | 52180119 | Intergenic | −74880 | Maml3 | 2.061761534 | 0.00602392 |
| chr7 | 118121059 | 118121380 | Exon | −5072 | Rps15a | 2.059841745 | 1.97E−09 |
| chr8 | 44935745 | 44936079 | Intergenic | −14296 | Fat1 | 2.045127946 | 0.01689979 |
| chr5 | 38927068 | 38927445 | Intergenic | −50563 | Clnk | 2.033796846 | 3.43E−05 |
| chr4 | 9620989 | 9621579 | 3' UTR | 22433 | Asph | 2.03379541 | 3.21E−12 |
| chr19 | 31514278 | 31514893 | Intron | 149785 | Prkg1 | 2.031554571 | 0.040841883 |
| chr7 | 136164476 | 136164968 | Intergenic | −103602 | C030029H02Rik | 2.024041718 | 4.92E−12 |
| chr18 | 65205336 | 65205736 | Intron | −43325 | Mir122 | 2.007406854 | 0.033302642 |
| chr6 | 28929068 | 28929735 | Intergenic | −93218 | Mir129-1 | 2.003072382 | 9.07E−26 |
| chr1 | 167001227 | 167001432 | Promoter-TSS | −88 | Fam78b | 1.995816078 | 0.001385899 |
| chr11 | 119152422 | 119152758 | Intron | 1547 | Mir6934 | 1.994988123 | 0.000494719 |
| chr15 | 55417203 | 55417727 | Intron | 109715 | Col14a1 | 1.994558519 | 0.029587478 |
| chr1 | 167000443 | 167000760 | Promoter-TSS | −816 | Fam78b | 1.993042995 | 7.03E−07 |
| chr8 | 11382062 | 11382801 | Intron | −69605 | Col4a1 | 1.991049638 | 0.044771773 |
| chr10 | 83069800 | 83070313 | Intron | 84559 | Chst11 | 1.989190214 | 1.65E−08 |
| chr5 | 97986827 | 97987395 | Intron | 43851 | Antxr2 | 1.966860557 | 0.034561623 |
| chr10 | 122775029 | 122775356 | Intron | 95877 | Mir8104 | 1.964581871 | 1.48E−05 |
| chr2 | 125530544 | 125531230 | Intergenic | −24449 | Fbn1 | 1.955434808 | 0.043106808 |
| chr18 | 11236270 | 11236506 | Intergenic | −183821 | 1010001N08Rik | 1.953987913 | 1.88E−05 |
| chr18 | 80535806 | 80536095 | Intergenic | 8596 | Gm2176 | 1.946174027 | 0.018744038 |
| chr2 | 115780314 | 115780931 | Intergenic | 141897 | Mir1951 | 1.945938034 | 0.015399095 |
| chr14 | 52314234 | 52314579 | Exon | 1917 | Sall2 | 1.932528474 | 0.000289941 |
| chr18 | 69028907 | 69029461 | Intergenic | −6911 | Mir145b | 1.918411705 | 0.039777247 |
| chr18 | 62001564 | 62002322 | Intron | 48868 | Sh3tc2 | 1.912036571 | 0.03833881 |
| chr5 | 5625324 | 5626000 | Intron | 38570 | Cfap69 | 1.909649276 | 0.031759863 |
| chrX | 106149365 | 106149970 | Intron | 6392 | Tlr13 | 1.905810828 | 0.029701574 |
| chr4 | 107468109 | 107468994 | Intron | 33832 | Glis1 | 1.89663888 | 0.004771811 |
| chr7 | 136258486 | 136258721 | Intergenic | −9721 | C030029H02Rik | 1.890402291 | 0.000301726 |
| chr2 | 131878468 | 131878983 | Intergenic | −18978 | Erv3 | 1.88093418 | 5.47E−06 |
| chr4 | 84007817 | 84008273 | Intergenic | 36834 | 6030471H07Rik | 1.872966043 | 6.81E−06 |
| chr13 | 95261273 | 95261770 | Intergenic | −11185 | Pde8b | 1.87133063 | 0.045573651 |
| chr9 | 41515175 | 41515706 | Intron | −15985 | Mir100 | 1.866836325 | 0.049577039 |
| chr7 | 136270055 | 136270955 | Intron | 2181 | C030029H02Rik | 1.864677766 | 3.95E−21 |
| chr4 | 9067861 | 9068434 | Intergenic | −201170 | Clvs1 | 1.861760708 | 0.048516788 |
| chr9 | 99645471 | 99646293 | Intron | 16304 | Dzip1l | 1.854167831 | 0.045352961 |
| chr17 | 5017536 | 5017857 | Intron | 22622 | Arid1b | 1.853370122 | 0.000106296 |
| chr2 | 148407432 | 148407611 | Exon | 667 | Thbd | 1.828896148 | 0.007985817 |
| chr18 | 81496320 | 81496853 | Intergenic | 495494 | Mir5127 | 1.820379853 | 0.037031284 |
| chr12 | 19288170 | 19288976 | Intergenic | 774063 | 5730507C01Rik | 1.817725322 | 2.66E−12 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr10 | 85138209 | 85138554 | Intron | −10354 | Mterf2 | 1.817033011 | 0.001622459 |
| chr17 | 5017087 | 5017429 | Intron | 22184 | Arid1b | 1.815283159 | 3.21E−05 |
| chr12 | 102665851 | 102666091 | Intron | 19049 | Mir1936 | 1.810234609 | 0.018970351 |
| chr6 | 99066348 | 99066646 | Intron | −38199 | Foxp1 | 1.809199888 | 2.36E−07 |
| chr16 | 93246616 | 93247253 | Intergenic | 106255 | 1810053B23Rik | 1.805675015 | 1.03E−11 |
| chr11 | 119150790 | 119151435 | Exon | 3025 | Mir6934 | 1.800477688 | 2.54E−07 |
| chr7 | 36698253 | 36698465 | Intron | 241 | Tshz3 | 1.793838275 | 0.048782384 |
| chr5 | 64044822 | 64045089 | Promoter-TSS | −18 | 5830416I19Rik | 1.792264874 | 1.36E−08 |
| chr2 | 60870989 | 60871183 | Intron | 10352 | Rbms1 | 1.791602796 | 0.019350907 |
| chr11 | 43836266 | 43836790 | Promoter-TSS | −39 | Adra1b | 1.782395703 | 0.031759863 |
| chr3 | 104944692 | 104945498 | 3' UTR | 16614 | Wnt2b | 1.776185382 | 0.048997751 |
| chr1 | 13287883 | 13288201 | Intron | 84387 | Ncoa2 | 1.774206097 | 0.002316746 |
| chr10 | 96854197 | 96854698 | Intergenic | −181321 | 4930556N09Rik | 1.773809332 | 0.005132469 |
| chr7 | 136248196 | 136248581 | Intergenic | −19936 | C030029H02Rik | 1.757967032 | 5.08E−05 |
| chr11 | 49811028 | 49811615 | Intron | 17166 | Gfpt2 | 1.753411104 | 3.75E−07 |
| chr7 | 84747781 | 84748201 | Intron | 58351 | 2610206C17Rik | 1.746220319 | 0.005430295 |
| chr7 | 114101528 | 114102088 | Intron | 15973 | Rras2 | 1.742887653 | 3.29E−05 |
| chr10 | 42781675 | 42782097 | Intron | 20390 | Sec63 | 1.742681996 | 0.033348956 |
| chr1 | 166899350 | 166899854 | Intergenic | 100128 | Gm16701 | 1.742333589 | 6.99E−05 |
| chr7 | 136271080 | 136271359 | Intron | 2895 | C030029H02Rik | 1.741595299 | 1.49E−08 |
| chr19 | 40667682 | 40667905 | Intron | 8023 | Entpd1 | 1.738338407 | 0.024890155 |
| chr7 | 136152498 | 136152868 | Intergenic | −115641 | C030029H02Rik | 1.73809948 | 0.005294743 |
| chr2 | 36000029 | 36000233 | Intergenic | −20507 | Ttll11 | 1.73491001 | 0.018200341 |
| chr8 | 46781087 | 46781528 | Intron | 41562 | Irf2 | 1.734448785 | 0.027476098 |
| chr1 | 167000881 | 167001100 | Promoter-TSS | −427 | Fam78b | 1.732852839 | 2.15E−05 |
| chr19 | 37311488 | 37311846 | Intron | 18946 | Ide | 1.726914896 | 0.000106296 |
| chr14 | 78375817 | 78376395 | Intergenic | −68063 | Tnfsf11 | 1.726350282 | 0.043969277 |
| chr1 | 91352154 | 91352888 | Intron | 1448 | Klhl30 | 1.725488101 | 0.001291375 |
| chr12 | 100517453 | 100517655 | Intron | 3268 | Ttc7b | 1.724642127 | 0.009179072 |
| chr18 | 75215316 | 75216002 | Intron | 81658 | 2010010A06Rik | 1.722158242 | 1.04E−11 |
| chr5 | 66174111 | 66174301 | Intron | 17129 | 1700126H18Rik | 1.720259677 | 0.004313016 |
| chr11 | 99424391 | 99424857 | Intergenic | −2365 | Krt12 | 1.719464883 | 2.14E−13 |
| chr18 | 65349616 | 65350211 | Exon | 43975 | Alpk2 | 1.719374122 | 6.56E−07 |
| chr1 | 170110194 | 170111284 | Intergenic | −21795 | Ddr2 | 1.716716257 | 0.016539327 |
| chr5 | 113901985 | 113902290 | Intron | 6569 | Coro1c | 1.707566679 | 0.015391331 |
| chr7 | 66097823 | 66098313 | Intergenic | −11447 | Chsy1 | 1.701723241 | 6.15E−05 |
| chr6 | 31332282 | 31332812 | Intron | 66226 | Mkln1os | 1.701021198 | 0.016409125 |
| chr13 | 21811651 | 21812086 | Promoter-TSS | 84 | Hist1h4n | 1.700344535 | 8.09E−22 |
| chr1 | 161786155 | 161786333 | Intron | 2251 | Fasl | 1.695215297 | 0.006217652 |
| chr5 | 64040604 | 64041119 | Intergenic | −4112 | 5830416I19Rik | 1.692786257 | 5.32E−09 |
| chr5 | 149584356 | 149584601 | Exon | −46448 | Gm15997 | 1.691583955 | 1.89E−05 |
| chr13 | 21812187 | 21812410 | TTS | 514 | Hist1h4n | 1.689859613 | 0.000244269 |
| chr14 | 105288685 | 105288917 | Intron | 30128 | Ndfip2 | 1.685736663 | 0.00837591 |
| chr19 | 40691898 | 40692208 | Intron | 32283 | Entpd1 | 1.675895496 | 0.000278282 |
| chr2 | 120852689 | 120852933 | Intron | 2155 | AV039307 | 1.674726703 | 2.30E−08 |
| chr3 | 142330317 | 142330856 | Intron | 61264 | Pdlim5 | 1.667570159 | 0.04943311 |
| chr6 | 8640900 | 8641364 | Intron | 117326 | Ica1 | 1.665456488 | 5.60E−08 |
| chr7 | 80783588 | 80783749 | Intron | 19663 | Iqgap1 | 1.656630266 | 0.001836793 |
| chr11 | 66961461 | 66961803 | Intron | 3738 | 9130409J20Rik | 1.65624607 | 0.001165893 |
| chr10 | 88429644 | 88429877 | Intron | −29879 | Sycp3 | 1.654487165 | 0.001106195 |
| chr13 | 112067503 | 112067813 | Intergenic | 199722 | Gm15326 | 1.649906548 | 3.61E−06 |
| chr16 | 93245764 | 93246170 | Intergenic | 107222 | 1810053B23Rik | 1.635495269 | 2.04E−06 |
| chr7 | 136255502 | 136256129 | Intergenic | −12509 | C030029H02Rik | 1.631172486 | 1.81E−14 |
| chrY | 90741046 | 90741394 | Intergenic | 13830 | G530011O06Rik | 1.629527004 | 1.06E−05 |
| chr2 | 60843133 | 60843297 | Intron | 38223 | Rbms1 | 1.624449125 | 0.013152857 |
| chr1 | 160305183 | 160305389 | Intron | −9314 | Mir1927 | 1.622910947 | 0.017174156 |
| chr9 | 79921990 | 79922066 | Intron | 55854 | Filip1 | 1.619780784 | 0.002271119 |
| chr11 | 57652574 | 57652899 | Intron | 7294 | Galnt10 | 1.616333645 | 3.13E−05 |
| chr7 | 31062520 | 31062839 | Intron | 2744 | Lgi4 | 1.615389177 | 0.04015472 |
| chr3 | 21878444 | 21878736 | Intergenic | −198062 | Tbl1xr1 | 1.615337653 | 0.004939542 |
| chr11 | 92904088 | 92904631 | Intergenic | −194931 | Car10 | 1.613839878 | 3.54E−06 |
| chr12 | 93230238 | 93230594 | Intergenic | 214407 | 4930559C10Rik | 1.610496694 | 0.00117283 |
| chr12 | 113017296 | 113017396 | Intron | 2674 | Pacs2 | 1.604411999 | 0.00066989 |
| chr7 | 136254086 | 136254365 | Intergenic | −14099 | C030029H02Rik | 1.603663542 | 0.002071472 |
| chr2 | 121594495 | 121595462 | Intron | 88255 | Wdr76 | 1.601748868 | 6.04E−05 |
| chr16 | 43725617 | 43726192 | Intergenic | −36317 | Drd3 | 1.599175461 | 0.002137328 |
| chr14 | 78712575 | 78713029 | Intron | 12287 | Dgkh | 1.596103717 | 1.48E−07 |
| chr1 | 143319334 | 143319974 | Intergenic | −321043 | B3galt2 | 1.593524643 | 7.92E−06 |
| chr19 | 57988194 | 57988459 | Intron | −62841 | Mir5623 | 1.586304748 | 0.013674626 |
| chr5 | 74126397 | 74127085 | Intergenic | 33211 | Snora26 | 1.579935947 | 1.41E−15 |
| chr14 | 121313299 | 121313583 | Intron | 65789 | Stk24 | 1.577215077 | 0.00056488 |
| chr9 | 88266329 | 88266801 | Intergenic | −61044 | Nt5e | 1.577137598 | 0.023902386 |
| chr2 | 168466091 | 168466536 | Intergenic | 124052 | Nfatc2 | 1.575217533 | 0.034914444 |
| chr1 | 78448010 | 78448710 | Intron | 40537 | Farsb | 1.574481532 | 0.003963029 |
| chr19 | 46728865 | 46729463 | Intron | 21721 | As3mt | 1.57188084 | 0.002597814 |
| chr16 | 11426136 | 11426363 | Intron | 20601 | Snx29 | 1.562713908 | 0.001385899 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr2 | 150181540 | 150182024 | Promoter-TSS | 27 | Gm14139 | 1.561524982 | 1.37E−07 |
| chr6 | 99066128 | 99066321 | Intron | −37926 | Foxp1 | 1.559296243 | 0.014540108 |
| chr7 | 35992622 | 35992864 | Intergenic | −189754 | Zfp507 | 1.559073478 | 0.001957052 |
| chr6 | 82934728 | 82935202 | Intron | 4804 | Sema4f | 1.558585586 | 1.08E−09 |
| chr12 | 116205728 | 116206233 | Intergenic | 57045 | Wdr60 | 1.55049504 | 0.032485349 |
| chr5 | 34527223 | 34527432 | Intron | 1543 | Sh3bp2 | 1.550000793 | 0.001386446 |
| chr6 | 122282782 | 122282961 | Promoter-TSS | −38 | Klrg1 | 1.546994382 | 0.043749197 |
| chr12 | 85003592 | 85004012 | Intron | 7481 | Ylpm1 | 1.538465996 | 0.009390074 |
| chr9 | 21246454 | 21246623 | Intron | 1905 | S1pr5 | 1.537318064 | 0.003930761 |
| chr11 | 84913273 | 84913584 | Intron | 2928 | Znhit3 | 1.536591623 | 0.038379621 |
| chr12 | 81837475 | 81837796 | Intergenic | −22395 | Pcnx | 1.528837008 | 5.06E−06 |
| chr7 | 13031265 | 13031345 | TTS | 3472 | Chmp2a | 1.528818349 | 0.016398952 |
| chr5 | 104113582 | 104114352 | 5' UTR | 121 | Sparcl1 | 1.52153631 | 0.034050897 |
| chr1 | 133950521 | 133950818 | Intergenic | −29268 | Prelp | 1.519558179 | 0.025195994 |
| chr18 | 77746794 | 77747610 | Intergenic | 20578 | Haus1 | 1.510062128 | 6.64E−11 |
| chr3 | 129590626 | 129591116 | Intron | 58485 | Elovl6 | 1.5089611 | 4.28E−09 |
| chr19 | 37333091 | 37333237 | Intergenic | −2551 | Ide | 1.505515731 | 0.004436451 |
| chr11 | 32265243 | 32265406 | Intron | 2383 | Nprl3 | 1.50481038 | 0.027992541 |
| chr11 | 35446793 | 35447043 | Intron | −169898 | Mir218-2 | 1.494320687 | 0.02772521 |
| chr9 | 89633238 | 89633773 | Intergenic | −10519 | AF529169 | 1.492385872 | 7.59E−10 |
| chr14 | 79116563 | 79116775 | Intron | 130698 | Zfp957 | 1.487755448 | 0.027654805 |
| chr9 | 121305519 | 121305765 | Intergenic | −28470 | Ulk4 | 1.486802153 | 0.0022823 |
| chr2 | 114135219 | 114135466 | Intron | 15228 | Mir7002 | 1.483320856 | 0.000890103 |
| chr1 | 135111354 | 135111535 | Exon | −6168 | Lgr6 | 1.481339636 | 0.003057642 |
| chr13 | 98291717 | 98292182 | Intergenic | 25018 | Btf3 | 1.479696127 | 2.20E−14 |
| chr5 | 3488882 | 3489182 | Intron | −54801 | Fam133b | 1.476138701 | 0.00619996 |
| chr15 | 5539456 | 5539905 | Non-Coding | 43362 | 5430437J10Rik | 1.471031475 | 0.020031782 |
| chr1 | 193272489 | 193272934 | Exon | 477 | G0s2 | 1.470942521 | 0.001036568 |
| chr19 | 40667174 | 40667577 | Intron | 7606 | Entpd1 | 1.470111545 | 0.038016214 |
| chr1 | 91507104 | 91507485 | Intron | 12626 | Traf3ip1 | 1.469953668 | 0.00428928 |
| chr5 | 125488014 | 125488583 | Intron | 12425 | Aacs | 1.469889361 | 0.015411422 |
| chr17 | 86200327 | 86200693 | Intron | 32725 | Prkce | 1.466914081 | 0.006466683 |
| chr11 | 3507372 | 3507743 | Intergenic | −2736 | Inpp5j | 1.465546161 | 0.009716206 |
| chr4 | 154112005 | 154112463 | Intron | −15061 | Trp73 | 1.462440038 | 3.21E−05 |
| chr12 | 81862478 | 81862729 | Intron | 2573 | Pcnx | 1.45886749 | 0.003595173 |
| chr11 | 109765056 | 109765412 | Intergenic | −42978 | Fam20a | 1.456143669 | 0.001416367 |
| chr5 | 66324476 | 66324861 | Intron | 12997 | Apbb2 | 1.453788149 | 3.42E−05 |
| chr14 | 78900768 | 78901176 | Intron | 51794 | Vwa8 | 1.450582817 | 0.033598512 |
| chr7 | 114103954 | 114104262 | Intron | 13673 | Rras2 | 1.448999781 | 0.005294336 |
| chr14 | 47341864 | 47342364 | Intergenic | −31746 | Lgals3 | 1.447568221 | 0.000345621 |
| chr5 | 72736252 | 72736731 | 5' UTR | 111 | Txk | 1.445452468 | 0.009218544 |
| chr11 | 79871885 | 79872133 | Intergenic | 90378 | Utp6 | 1.442449849 | 0.004504475 |
| chr2 | 128426757 | 128427415 | Intron | 2265 | Gm14005 | 1.439959185 | 2.53E−20 |
| chr6 | 31192706 | 31193120 | Intron | 25561 | Lncpint | 1.437925762 | 1.66E−06 |
| chr6 | 144671439 | 144671569 | Intergenic | −1364 | Sox5os3 | 1.437226328 | 0.006030609 |
| chr16 | 96907689 | 96908176 | Intron | 262803 | Dscam | 1.43660111 | 2.51E−08 |
| chr11 | 104072988 | 104073148 | Intergenic | −59713 | Crhr1 | 1.435190737 | 0.001641259 |
| chr11 | 5219352 | 5219694 | Intron | −35075 | Mir3079 | 1.433418285 | 1.26E−07 |
| chr13 | 43450509 | 43450864 | Intron | 30287 | Ranbp9 | 1.432649346 | 0.003076391 |
| chr6 | 94555186 | 94555683 | Intron | 50981 | Mir7041 | 1.432398846 | 1.69E−06 |
| chr12 | 94083267 | 94083845 | Intergenic | 156218 | Mir8099-2 | 1.431008596 | 5.31E−06 |
| chr16 | 44404865 | 44405302 | Intron | 10284 | Cfap44 | 1.426775155 | 0.041551866 |
| chr16 | 17626033 | 17626435 | Intron | 6880 | Smpd4 | 1.426093835 | 1.77E−05 |
| chr15 | 88851590 | 88851762 | Intergenic | −10518 | Pim3 | 1.423717358 | 0.01199215 |
| chr2 | 150484848 | 150485642 | Promoter-TSS | −182 | Zfp345 | 1.417653065 | 6.59E−09 |
| chr10 | 118483945 | 118484101 | Intergenic | 42977 | Ifng | 1.413900784 | 0.008612993 |
| chr8 | 122295773 | 122296319 | Intron | 13905 | Zfpm1 | 1.412282229 | 0.000175201 |
| chr19 | 29937466 | 29937774 | Intron | −8170 | Il33 | 1.410534548 | 0.006217652 |
| chr1 | 131703532 | 131703809 | Intron | 14975 | Rab7b | 1.408905982 | 0.000223134 |
| chr1 | 64078440 | 64079094 | Exon | −36266 | Mir6899 | 1.407494604 | 2.96E−05 |
| chr7 | 73612348 | 73612514 | Intergenic | −54036 | 1810026B05Rik | 1.406456963 | 0.049567114 |
| chr5 | 28037042 | 28037530 | Intergenic | −34126 | Insig1 | 1.404379014 | 0.001127029 |
| chr3 | 22092689 | 22093006 | Intron | 16195 | Tbl1xr1 | 1.403985052 | 0.005960996 |
| chr12 | 110920956 | 110921364 | Intron | 31896 | Tecpr2 | 1.40334502 | 0.004798079 |
| chr8 | 85647668 | 85647891 | Exon | 43230 | Neto2 | 1.402570964 | 0.028296071 |
| chr2 | 73348308 | 73348516 | Intron | 35760 | Scrn3 | 1.40062859 | 0.004547482 |
| chr16 | 58480581 | 58480799 | Intron | 42622 | St3gal6 | 1.399651967 | 0.006942747 |
| chr10 | 54038980 | 54039130 | Intron | 36741 | Man1a | 1.397349294 | 0.001613675 |
| chr9 | 118365511 | 118365770 | Intergenic | −64199 | 4933432G23Rik | 1.395222232 | 0.03192507 |
| chr10 | 34185019 | 34185792 | Intron | 22146 | Dse | 1.390353464 | 0.030568763 |
| chr11 | 3470812 | 3471120 | Intron | −7976 | Mir3470a | 1.390185163 | 0.000161769 |
| chr1 | 135095185 | 135095659 | Intron | 9854 | Lgr6 | 1.388613275 | 8.30E−05 |
| chr8 | 123061680 | 123062030 | Intergenic | −3653 | Spg7 | 1.387250757 | 0.000337939 |
| chr1 | 106615657 | 106615852 | Intron | −69123 | Mir3473f | 1.385315041 | 0.007615918 |
| chr8 | 119800233 | 119800539 | Intergenic | −21970 | Tldc1 | 1.382206753 | 0.000254013 |
| chr11 | 120256602 | 120257395 | Intron | 24051 | Bahcc1 | 1.378711316 | 0.022132074 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr6 | 114679185 | 114679309 | Intron | 36150 | Atg7 | 1.378622021 | 0.032949126 |
| chr3 | 151891705 | 151892477 | Intergenic | −54563 | Ptgfr | 1.377722212 | 0.023690687 |
| chr16 | 77108796 | 77109119 | Intron | 94888 | Usp25 | 1.376982381 | 0.022193465 |
| chr15 | 73174196 | 73174404 | Intron | 10647 | Ago2 | 1.375584126 | 0.000224884 |
| chr11 | 83557025 | 83557197 | Intergenic | 21525 | Ccl9 | 1.375365055 | 0.008849797 |
| chr3 | 131199619 | 131199918 | Intron | 72333 | Hadh | 1.368555757 | 0.02660135 |
| chr16 | 97016474 | 97016897 | Intron | 154050 | Dscam | 1.366493105 | 0.000423452 |
| chr5 | 69484042 | 69484287 | Intergenic | 58483 | Yipf7 | 1.363640478 | 0.000289941 |
| chr2 | 126477700 | 126477909 | Intron | 13749 | Atp8b4 | 1.357571115 | 0.021067802 |
| chr8 | 88296957 | 88297254 | Intron | 2901 | Adcy7 | 1.34694551 | 6.74E−05 |
| chr1 | 179060028 | 179060850 | Intron | 457564 | Smyd3 | 1.346127943 | 0.040993657 |
| chr14 | 62351885 | 62352154 | Intron | 19914 | Rnaseh2b | 1.345199574 | 9.35E−05 |
| chr4 | 33149105 | 33149432 | Intron | 16712 | Gabrr1 | 1.344900844 | 0.00519084 |
| chr2 | 65044204 | 65044762 | Intergenic | −21717 | Grb14 | 1.344323214 | 0.013295299 |
| chr6 | 114939657 | 114940027 | Intergenic | −18090 | Vgll4 | 1.341473379 | 0.000543757 |
| chr7 | 99436024 | 99436187 | Intron | −29899 | Klhl35 | 1.340856868 | 0.032100513 |
| chr4 | 89400370 | 89400707 | Intron | −89506 | Cdkn2b | 1.338613965 | 0.000172778 |
| chr3 | 144505875 | 144506677 | Intron | 63940 | Hs2st1 | 1.3340155 | 0.024015931 |
| chr7 | 136294540 | 136294753 | Intron | 26322 | C030029H02Rik | 1.3320607 | 0.010430375 |
| chr19 | 56588182 | 56588831 | Intron | 40245 | Nhlrc2 | 1.329554917 | 4.46E−06 |
| chr14 | 70010551 | 70011014 | Intron | −66663 | Egr3 | 1.328610501 | 0.011395502 |
| chr10 | 127303192 | 127303446 | Intron | 8467 | Mars | 1.326797095 | 0.010942106 |
| chr5 | 147091639 | 147091919 | Intron | 14433 | Polr1d | 1.324710049 | 0.0453767 |
| chr7 | 66375622 | 66376372 | Intron | 5727 | Mir7057 | 1.324046069 | 3.93E−06 |
| chr9 | 79977758 | 79978037 | Promoter-TSS | −15 | Filip1 | 1.323971988 | 0.001464522 |
| chr3 | 20136854 | 20137471 | Intron | 17954 | Gyg | 1.32192205 | 0.006251066 |
| chr10 | 61300103 | 61300265 | Exon | 2348 | Prf1 | 1.319576063 | 0.005374642 |
| chr2 | 60901450 | 60902042 | Intron | −20308 | Rbms1 | 1.318759594 | 6.76E−06 |
| chr8 | 95084373 | 95084858 | Intron | 3414 | Katnb1 | 1.317100232 | 1.81E−10 |
| chr13 | 30004961 | 30005356 | Intergenic | −19095 | E2f3 | 1.315737104 | 0.000119892 |
| chr10 | 61317563 | 61318166 | Intergenic | 20028 | Prf1 | 1.315558548 | 9.90E−06 |
| chrY | 90744472 | 90744715 | Intergenic | 10457 | G530011O06Rik | 1.315357709 | 1.14E−07 |
| chr3 | 51092043 | 51093026 | Intergenic | −131913 | Noct | 1.315077511 | 0.042314948 |
| chr8 | 33618898 | 33619204 | TTS | 19430 | Ppp2cb | 1.313956085 | 0.028788668 |
| chr2 | 60870515 | 60870944 | Intron | 10709 | Rbms1 | 1.312760674 | 0.006943233 |
| chr15 | 38270597 | 38271025 | Intergenic | 29900 | Klf10 | 1.309334265 | 0.008643551 |
| chr5 | 143304889 | 143305561 | Intron | 10135 | E130309D02Rik | 1.309292943 | 0.002701739 |
| chr11 | 76748173 | 76748397 | Intron | 15270 | Gosr1 | 1.308180186 | 0.009112283 |
| chr7 | 140132254 | 140132610 | Exon | −5132 | Mtg1 | 1.306785308 | 0.007828301 |
| chr5 | 80500821 | 80500968 | Intergenic | −519677 | Adgrl3 | 1.30639756 | 0.017067839 |
| chr15 | 86079612 | 86080234 | Intron | 21196 | Gramd4 | 1.303727557 | 0.000541165 |
| chr12 | 70695136 | 70695768 | Intergenic | −130062 | Frmd6 | 1.29485294 | 3.31E−05 |
| chr11 | 9117832 | 9118707 | Promoter-TSS | 166 | Upp1 | 1.294088817 | 7.27E−06 |
| chr13 | 13968683 | 13969178 | Intron | 14256 | B3galnt2 | 1.293629701 | 0.003306637 |
| chr12 | 76841329 | 76841546 | Intron | 3970 | Fntb | 1.291134534 | 0.002406073 |
| chr10 | 83129196 | 83129538 | Intron | 143870 | Chst11 | 1.291055209 | 0.00266453 |
| chr10 | 79688697 | 79688889 | Promoter-TSS | −227 | Gzmm | 1.28998469 | 0.013413028 |
| chr5 | 86227378 | 86227908 | Intergenic | −29742 | Gnrhr | 1.28901652 | 0.045423863 |
| chr4 | 134548152 | 134548364 | Intron | 3908 | Selenon | 1.287941359 | 0.017432132 |
| chr15 | 80507083 | 80507376 | Intron | 53241 | Enthd1 | 1.285600001 | 0.032235654 |
| chr10 | 118466756 | 118466928 | Intergenic | 25796 | Ifng | 1.285480647 | 0.000326278 |
| chr2 | 20961848 | 20962170 | Intron | 5712 | Arhgap21 | 1.283939453 | 1.06E−05 |
| chr13 | 73955500 | 73955889 | Intron | −8168 | Zdhhc11 | 1.283894044 | 0.040179774 |
| chr2 | 31759625 | 31759990 | Promoter-TSS | −132 | Abl1 | 1.282234227 | 0.033139708 |
| chr15 | 10662184 | 10662569 | Intron | 51164 | Rai14 | 1.278030875 | 0.022317383 |
| chr15 | 62048888 | 62049845 | Intron | 10109 | Pvt1 | 1.277479521 | 9.65E−09 |
| chr6 | 3395852 | 3395983 | Intron | 3654 | Samd9l | 1.277300711 | 0.010884609 |
| chr13 | 114304307 | 114305203 | Intron | 83339 | Ndufs4 | 1.274784752 | 1.44E−05 |
| chr9 | 118486515 | 118486725 | TTS | 8431 | Eomes | 1.274677132 | 0.004785354 |
| chr5 | 3363001 | 3363373 | Intron | 19294 | Cdk6 | 1.271957811 | 0.001782585 |
| chr7 | 66376407 | 66376896 | Intron | 5073 | Mir7057 | 1.266156009 | 8.15E−06 |
| chr9 | 79971747 | 79971973 | Intron | 6022 | Filip1 | 1.262088812 | 0.004011754 |
| chr11 | 89031215 | 89031610 | Intergenic | 29336 | Dgke | 1.259307616 | 0.009599542 |
| chr3 | 106003582 | 106003853 | Intron | −2220 | Pifo | 1.258668074 | 0.047345528 |
| chr8 | 117174098 | 117174822 | Intron | 16325 | Gan | 1.252218757 | 6.14E−06 |
| chr5 | 69482912 | 69483258 | Intergenic | 59562 | Yipf7 | 1.252203479 | 3.10E−07 |
| chr19 | 55137126 | 55137759 | Intergenic | −37995 | Gpam | 1.250325557 | 0.006396303 |
| chr3 | 133322021 | 133322331 | Intron | 12066 | Ppa2 | 1.246807432 | 0.029402315 |
| chr19 | 53397994 | 53398097 | Intergenic | −7472 | Smndc1 | 1.24659655 | 0.045141175 |
| chr5 | 105556120 | 105556861 | Intron | 37019 | Lrrc8c | 1.245162752 | 1.91E−16 |
| chr3 | 114889740 | 114890143 | Intron | −14137 | Olfm3 | 1.243403902 | 7.04E−06 |
| chr18 | 12224934 | 12225118 | Intron | 11360 | Npc1 | 1.241971796 | 0.042174272 |
| chr9 | 63703428 | 63703736 | Intron | 54412 | Smad3 | 1.239398233 | 6.17E−05 |
| chr11 | 97435928 | 97436119 | Intergenic | −14137 | Arhgap23 | 1.239367876 | 0.00189847 |
| chr11 | 49981199 | 49981513 | Intergenic | −43975 | Rnf130 | 1.238789057 | 0.001077354 |
| chr10 | 127300652 | 127301087 | Intron | 10076 | Ddit3 | 1.23670288 | 0.000426084 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr1 | 121241612 | 121241975 | Intergenic | 85885 | Insig2 | 1.235218889 | 0.008622249 |
| chr12 | 86710326 | 86710749 | Intron | −15770 | Gm32755 | 1.235202767 | 0.024980098 |
| chr11 | 119258561 | 119259124 | Intron | −9121 | Gaa | 1.23369404 | 0.028996698 |
| chr2 | 34869475 | 34870083 | Intron | 1183 | Psmd5 | 1.232714544 | 0.0203914 |
| chr3 | 18623742 | 18624423 | Intergenic | −143605 | 4930433B08Rik | 1.232227908 | 2.13E−05 |
| chr8 | 86478819 | 86479256 | Intergenic | 87553 | Abcc12 | 1.232017203 | 0.000249826 |
| chr9 | 79948008 | 79948222 | Intron | 29767 | Filip1 | 1.230405756 | 0.000347511 |
| chr13 | 21834864 | 21834939 | TTS | 1158 | Hist1h2br | 1.228284775 | 0.028525105 |
| chr7 | 135582056 | 135582341 | Intron | −11283 | Ptpre | 1.227519403 | 0.002669245 |
| chr18 | 70534052 | 70534354 | Intergenic | −3882 | Poli | 1.224380746 | 2.72E−06 |
| chr5 | 86244827 | 86245316 | Intron | 44237 | Tmprss11c | 1.223440949 | 7.41E−08 |
| chr5 | 107533700 | 107533975 | Promoter-TSS | −874 | 1700028K03Rik | 1.223187472 | 0.005070108 |
| chr11 | 49979556 | 49979711 | 3' UTR | −45698 | Rnf130 | 1.222174708 | 0.049428826 |
| chr7 | 66373635 | 66373889 | Intron | 7962 | Mir7057 | 1.220610839 | 0.005960996 |
| chr10 | 83129709 | 83129947 | Intron | 144331 | Chst11 | 1.220079675 | 0.012734235 |
| chr10 | 88426088 | 88426178 | Intron | −33454 | Sycp3 | 1.219986186 | 0.044843565 |
| chr11 | 46116567 | 46116831 | Intron | −11205 | Adam19 | 1.216665974 | 0.002633301 |
| chr4 | 132950231 | 132950517 | Intergenic | −23721 | Fgr | 1.215540842 | 6.09E−08 |
| chr12 | 110866338 | 110866782 | Intron | 16281 | Zfp839 | 1.212313648 | 0.001782354 |
| chr12 | 16580410 | 16580671 | Intron | 9230 | Lpin1 | 1.211583955 | 0.013248735 |
| chr3 | 27456543 | 27456816 | Intron | 85328 | Ghsr | 1.207272799 | 0.000198112 |
| chr17 | 74077028 | 74077410 | Intergenic | −29303 | Srd5a2 | 1.207098088 | 0.026679446 |
| chr5 | 74523522 | 74523770 | Intron | 8096 | Scfd2 | 1.203410674 | 0.017290313 |
| chr10 | 95615727 | 95616119 | Intergenic | −51756 | Nudt4 | 1.202725967 | 0.043123566 |
| chr8 | 126210029 | 126210363 | Intergenic | −88383 | Slc35f3 | 1.20114698 | 0.049038599 |
| chr7 | 73647109 | 73647449 | Intergenic | 39284 | Gm4971 | 1.199853971 | 0.017975644 |
| chr2 | 60872519 | 60872758 | Intron | 8800 | Rbms1 | 1.195607406 | 0.005379212 |
| chr19 | 20390452 | 20390938 | Promoter-TSS | −24 | Anxa1 | 1.194731102 | 2.32E−06 |
| chr2 | 60845253 | 60845744 | Intron | 35940 | Rbms1 | 1.190683437 | 1.61E−10 |
| chr4 | 138327299 | 138327632 | Intergenic | −1169 | Pink1 | 1.188272019 | 6.89E−05 |
| chr2 | 122381821 | 122382009 | Intergenic | −12997 | Shf | 1.187713207 | 0.009640726 |
| chr14 | 72819989 | 72820349 | Intergenic | −110166 | Fndc3a | 1.185330849 | 0.000354687 |
| chr13 | 108860125 | 108860426 | Intron | 206098 | Pde4d | 1.184979848 | 0.009459817 |
| chr7 | 35991065 | 35991491 | Intergenic | −188289 | Zfp507 | 1.183919459 | 0.002032903 |
| chr6 | 122283472 | 122283981 | Promoter-TSS | −893 | Klrg1 | 1.182965888 | 1.66E−05 |
| chr4 | 135247210 | 135247571 | Intron | 25370 | Clic4 | 1.181053676 | 0.003967119 |
| chr16 | 29981588 | 29981940 | Intergenic | −2640 | Gm1968 | 1.180796645 | 2.25E−08 |
| chr10 | 88422568 | 88422737 | Intron | −36935 | Sycp3 | 1.179208511 | 0.000636567 |
| chr9 | 88539586 | 88540120 | Intergenic | −8167 | Zfp949 | 1.178447528 | 4.74E−05 |
| chr1 | 164079206 | 164079316 | Intron | 17185 | Sell | 1.175513257 | 0.031422465 |
| chr19 | 4222046 | 4222455 | Exon | 7861 | Clcf1 | 1.17443612 | 0.001361217 |
| chr14 | 105287690 | 105288290 | Intron | 29320 | Ndfip2 | 1.173094035 | 0.000757522 |
| chr13 | 53057219 | 53057484 | Intergenic | −76312 | Nfil3 | 1.172945341 | 0.002299824 |
| chr7 | 114085385 | 114085527 | Intron | 32325 | Rras2 | 1.170380163 | 0.026419528 |
| chr11 | 96963654 | 96963898 | Non-Coding | 13912 | Sp2 | 1.169593709 | 0.037785353 |
| chr15 | 66883366 | 66884304 | Intergenic | −7558 | Wisp1 | 1.169244952 | 1.27E−06 |
| chr13 | 63339970 | 63340246 | Intron | −38825 | Mir3074-1 | 1.167296458 | 0.019066417 |
| chr1 | 135594012 | 135594550 | Intergenic | −8926 | Nav1 | 1.167242359 | 6.54E−07 |
| chr14 | 60742791 | 60742956 | Intron | 9969 | Spata13 | 1.165056129 | 0.038997773 |
| chr1 | 133180968 | 133181361 | Intergenic | 49998 | Ppp1r15b | 1.16435795 | 0.004122356 |
| chr2 | 119759113 | 119759433 | Promoter-TSS | −748 | Ltk | 1.161189832 | 0.002452626 |
| chr11 | 5509366 | 5509843 | Intergenic | −11037 | Xbp1 | 1.160410069 | 0.013019069 |
| chr6 | 143326892 | 143327258 | Intergenic | 81187 | D6Ertd474e | 1.15854099 | 0.001790468 |
| chr6 | 142573105 | 142573309 | Intergenic | −1593 | Kcnj8 | 1.157941582 | 0.038436361 |
| chr19 | 57082315 | 57082781 | Intron | 36476 | Ablim1 | 1.156786595 | 0.019174126 |
| chr7 | 135650206 | 135650317 | Intron | −1638 | Ptpre | 1.155756436 | 0.02484797 |
| chr18 | 79106178 | 79106539 | Intron | 3033 | Setbp1 | 1.150784764 | 0.010519565 |
| chr2 | 143983048 | 143983327 | Intron | 28076 | Rrbp1 | 1.148603739 | 0.034571897 |
| chr10 | 39418467 | 39418704 | Intron | 48786 | Fyn | 1.148128609 | 0.002258468 |
| chr16 | 91423910 | 91424387 | Intron | 17913 | Il10rb | 1.145067505 | 0.013692577 |
| chr3 | 27462932 | 27463632 | Intron | 91931 | Ghsr | 1.144978253 | 0.000728931 |
| chr12 | 112810561 | 112810788 | Intron | 1699 | BC022687 | 1.141259068 | 0.008553893 |
| chr18 | 78142738 | 78143027 | Promoter-TSS | −763 | Slc14a1 | 1.14074335 | 0.034618128 |
| chr16 | 78502626 | 78503369 | Intergenic | −57319 | 4930478L05Rik | 1.140071677 | 0.026229965 |
| chr11 | 4823684 | 4824266 | Intron | 9160 | Nf2 | 1.139787237 | 4.23E−07 |
| chr10 | 24595279 | 24595987 | 5' UTR | 191 | Ctgf | 1.138057922 | 0.013295299 |
| chr11 | 3180194 | 3180275 | Intron | 13229 | Sfi1 | 1.132556671 | 0.037277784 |
| chr14 | 69284245 | 69284765 | Intron | 598 | Slc25a37 | 1.127600734 | 2.90E−12 |
| chr10 | 13499362 | 13499649 | Intergenic | −1523 | Fuca2 | 1.127029953 | 0.026408363 |
| chr3 | 152905015 | 152905185 | Intron | 77107 | St6galnac5 | 1.123880627 | 0.025496168 |
| chr7 | 128131079 | 128131064 | Intron | 1353 | Itgax | 1.122127421 | 0.030061881 |
| chr16 | 58519739 | 58519910 | Intron | 3488 | St3gal6 | 1.121187841 | 0.012582373 |
| chr6 | 99063874 | 99064676 | Intron | −35977 | Foxp1 | 1.120297574 | 1.54E−11 |
| chr6 | 31114310 | 31114637 | Intron | −51380 | Mir29b-1 | 1.118953462 | 0.031497052 |
| chr7 | 120722668 | 120723237 | Intron | −16605 | Vwa3a | 1.117565863 | 0.007451978 |
| chr9 | 73068279 | 73068668 | Intron | 4325 | Rab27a | 1.116850391 | 0.00083707 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr7 | 126097242 | 126097951 | Intergenic | −15185 | Gsg11 | 1.114316528 | 6.92E−06 |
| chr6 | 83774234 | 83774451 | Intron | 1470 | Tex261 | 1.114300296 | 0.029195217 |
| chr11 | 107029644 | 107029856 | Exon | 1527 | 1810010H24Rik | 1.113520755 | 0.026001317 |
| chr15 | 25494584 | 25495252 | Intergenic | 80726 | Gm5468 | 1.113204621 | 0.002268553 |
| chr1 | 64088064 | 64088573 | Intron | 33071 | Klf7 | 1.113098541 | 0.035981816 |
| chr5 | 64045237 | 64046082 | Intron | 686 | 5830416I19Rik | 1.112895247 | 6.41E−05 |
| chr19 | 44618117 | 44618561 | Intergenic | 55485 | Hif1an | 1.11261986 | 0.005021261 |
| chr5 | 136179446 | 136180108 | TTS | −9121 | Orai2 | 1.111431774 | 4.06E−07 |
| chr16 | 38369055 | 38369219 | Intron | 6947 | Popdc2 | 1.110965075 | 0.014053837 |
| chrX | 164446155 | 164446562 | Intron | 9364 | Asb11 | 1.110934535 | 0.032936635 |
| chr14 | 54138119 | 54138613 | Intergenic | 115563 | Dad1 | 1.108350384 | 0.00042852 |
| chr11 | 3481996 | 3482562 | Intergenic | −5948 | Pla2g3 | 1.106060496 | 0.035044203 |
| chr15 | 78170822 | 78171014 | Intron | 3190 | Ift27 | 1.105945593 | 0.047312529 |
| chr4 | 154127289 | 154127697 | Intron | 12715 | Trp73 | 1.104370198 | 0.017589398 |
| chr6 | 114934243 | 114934566 | Intergenic | −12652 | Vgll4 | 1.102300407 | 1.01E−06 |
| chr8 | 25131005 | 25131268 | Intergenic | 28097 | Mir8108 | 1.102051687 | 0.009273024 |
| chr8 | 77444283 | 77445011 | Intron | −72409 | 0610038B21Rik | 1.100757779 | 0.033302642 |
| chr9 | 62624527 | 62625115 | Intergenic | −53034 | Itga11 | 1.100408851 | 0.000636567 |
| chr5 | 120110106 | 120110609 | Intergenic | −6156 | Rbm19 | 1.099033542 | 0.024713472 |
| chr18 | 43477701 | 43477859 | Intergenic | −39494 | Dpysl3 | 1.097913424 | 2.16E−05 |
| chr11 | 3147343 | 3147443 | Intron | 23372 | Pisd-ps1 | 1.09099664 | 0.035912296 |
| chr7 | 89517456 | 89518557 | Promoter-TSS | −420 | Prss23 | 1.08894306 | 0.014200908 |
| chr12 | 73641226 | 73641590 | Intron | 56612 | Prkch | 1.088404483 | 0.000226657 |
| chr19 | 53414427 | 53414767 | Intergenic | −24024 | Smndc1 | 1.0879786 | 0.042263534 |
| chr1 | 153726683 | 153726864 | Intron | 11056 | C230024C17Rik | 1.087312955 | 0.049914515 |
| chr14 | 69555132 | 69555889 | Promoter-TSS | 109 | Entpd4 | 1.085960735 | 2.10E−14 |
| chr14 | 69502465 | 69503627 | Intergenic | 9503 | Synb | 1.085041039 | 3.17E−35 |
| chr12 | 111760545 | 111760814 | Intron | 1811 | Klc1 | 1.083205545 | 0.00493788 |
| chr13 | 52994324 | 52994877 | Intergenic | −13561 | Nfil3 | 1.082845486 | 0.009459817 |
| chr16 | 38368316 | 38368678 | Intron | 6307 | Popdc2 | 1.082483625 | 0.018335408 |
| chr2 | 32867417 | 32867944 | Intergenic | −8454 | Fam129b | 1.082451638 | 0.001667444 |
| chr11 | 100737106 | 100737282 | Intron | 1021 | Rab5c | 1.082047187 | 0.022870749 |
| chr14 | 69284792 | 69285345 | Promoter-TSS | 35 | Slc25a37 | 1.08125617 | 3.40E−19 |
| chr14 | 61339295 | 61339943 | TTS | 20826 | Ebpl | 1.08019903 | 4.15E−06 |
| chr9 | 123004201 | 123004671 | Intron | −16890 | Tmem42 | 1.080028525 | 0.015960039 |
| chr1 | 120099591 | 120099875 | Intergenic | 21186 | Dbi | 1.078875096 | 0.036277335 |
| chr2 | 163800852 | 163801351 | Intergenic | −19733 | Wisp2 | 1.077942805 | 0.000226628 |
| chrX | 78442181 | 78442711 | Intergenic | 72803 | 4930480E11Rik | 1.076963769 | 0.001978803 |
| chr7 | 47077945 | 47078260 | 3' UTR | 5122 | Mir7056 | 1.075395392 | 0.012215293 |
| chr19 | 20389300 | 20389584 | Intron | 1229 | Anxa1 | 1.074319845 | 0.000333523 |
| chr6 | 31518071 | 31519402 | TTS | 45201 | Podxl | 1.074143578 | 0.00016228 |
| chr11 | 5215871 | 5216088 | Intron | −38619 | Mir3079 | 1.072739408 | 0.037592667 |
| chr15 | 96377245 | 96377711 | Intron | 83365 | Scafl11 | 1.070996153 | 2.68E−06 |
| chr17 | 48467107 | 48467372 | Intron | 12338 | Unc5cl | 1.07059948 | 0.018219288 |
| chr5 | 72749021 | 72749249 | Intron | 3642 | Txk | 1.070530325 | 0.049263022 |
| chr2 | 45047415 | 45047661 | Intron | −24361 | Mir5129 | 1.070238863 | 0.020950997 |
| chr2 | 73070660 | 73071173 | Intergenic | −90470 | Sp3 | 1.067292777 | 0.014904521 |
| chr9 | 79978342 | 79978604 | Promoter-TSS | −591 | Filip1 | 1.067290489 | 0.010349536 |
| chr14 | 69336889 | 69337595 | Promoter-TSS | 91 | Entpd4 | 1.062946158 | 4.06E−07 |
| chr19 | 45578749 | 45579348 | TTS | 18433 | Dpcd | 1.060917005 | 2.56E−25 |
| chr13 | 113090848 | 113091123 | Intron | 9996 | Gzma | 1.059630886 | 0.016035897 |
| chr9 | 118059080 | 118059471 | 3' UTR | 18753 | Azi2 | 1.05768622 | 0.003417932 |
| chr15 | 85574577 | 85575028 | Intron | 3268 | Wnt7b | 1.056644831 | 0.022591962 |
| chr4 | 33110951 | 33111737 | Intergenic | −21212 | Gabrr1 | 1.056147133 | 6.26E−09 |
| chr3 | 59190372 | 59190931 | Intron | 4453 | Gpr87 | 1.054536421 | 0.021277168 |
| chr17 | 86971051 | 86971707 | Intron | 8268 | Rhoq | 1.0539291 | 2.92E−06 |
| chr6 | 108524168 | 108524715 | Intron | 34698 | Mir7661 | 1.053835203 | 7.71E−06 |
| chr16 | 32741378 | 32741880 | Intron | 5743 | Muc4 | 1.053613502 | 0.000111124 |
| chr9 | 90265382 | 90265643 | Intron | 5257 | Tbc1d2b | 1.051646803 | 0.016461072 |
| chr8 | 78746034 | 78746637 | Intergenic | 74817 | Lsm6 | 1.049816141 | 0.01557413 |
| chr14 | 57718133 | 57718581 | Intron | 16061 | Lats2 | 1.048201574 | 0.005736138 |
| chr17 | 67741366 | 67741606 | Intron | 44221 | Lama1 | 1.044411363 | 0.002823196 |
| chr2 | 35993883 | 35994766 | Intergenic | −14700 | Ttll11 | 1.043218566 | 4.26E−16 |
| chr6 | 99067488 | 99067973 | Intron | −39432 | Foxp1 | 1.042469356 | 0.002307792 |
| chr9 | 72454321 | 72454690 | Intron | 15976 | Mns1 | 1.041416414 | 0.000803099 |
| chr11 | 66421062 | 66421236 | Intron | 104977 | Shisa6 | 1.036246482 | 0.037121937 |
| chr1 | 127659984 | 127660751 | Intron | 17654 | Tmem163 | 1.034304563 | 0.000215945 |
| chr2 | 103635812 | 103636014 | Intron | 69603 | Abtb2 | 1.033593836 | 0.045150582 |
| chr19 | 24971223 | 24971758 | Intergenic | −9874 | Cbwd1 | 1.032584186 | 1.03E−12 |
| chr16 | 96370262 | 96370589 | Intron | 8661 | Igsf5 | 1.031876109 | 0.009438793 |
| chr13 | 93894212 | 93894421 | Intron | 103539 | Mir5624 | 1.031000917 | 0.000926296 |
| chr4 | 124086325 | 124086708 | Intergenic | 169083 | Rragc | 1.030831527 | 0.010114238 |
| chr2 | 60165693 | 60166271 | Intergenic | −40242 | Baz2b | 1.02730923 | 0.014853192 |
| chr7 | 24425987 | 24426267 | Intergenic | 19555 | Irgc1 | 1.027162671 | 0.003794187 |
| chr4 | 21604289 | 21604577 | Intergenic | 81530 | Prdm13 | 1.026458186 | 0.016774131 |
| chr8 | 110812994 | 110813756 | Intron | −7451 | Il34 | 1.025397569 | 0.004564903 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr14 | 69257188 | 69257476 | Intron | 27771 | Slc25a37 | 1.023532152 | 0.035670216 |
| chr13 | 21832886 | 21834082 | Promoter-TSS | −9 | Hist1h2ap | 1.021963365 | 3.26E−26 |
| chr4 | 154125358 | 154125690 | Intron | 14684 | Trp73 | 1.020912422 | 0.047748732 |
| chr18 | 82473476 | 82473675 | Intergenic | −1548 | Mbp | 1.020872127 | 0.045953855 |
| chr10 | 61327171 | 61327393 | Intron | 29446 | Prf1 | 1.020577889 | 0.028109613 |
| chr1 | 170977274 | 170977481 | Intergenic | −1306 | Fcgr2b | 1.019954152 | 0.014231131 |
| chr19 | 9106102 | 9106497 | Intergenic | −18343 | Scgb1a1 | 1.019784 | 0.020423473 |
| chr9 | 114650994 | 114651252 | Intergenic | −10923 | Cnot10 | 1.01957286 | 0.009135845 |
| chr2 | 45055911 | 45056291 | Intron | −32924 | Mir5129 | 1.018944285 | 0.005021261 |
| chr7 | 16332190 | 16332508 | Intron | 22766 | Bbc3 | 1.017390869 | 0.006447708 |
| chr2 | 120980892 | 120981360 | Intron | 4064 | Tmem62 | 1.016581699 | 0.015753827 |
| chr13 | 21809703 | 21811065 | Promoter-TSS | 17 | Hist1h2ao | 1.015018521 | 9.57E−18 |
| chr11 | 49101521 | 49101759 | Intron | 12117 | Olfr1396 | 1.014227267 | 0.049428826 |
| chr5 | 21035805 | 21036021 | Intron | 19884 | Ptpn12 | 1.014185995 | 0.042910309 |
| chr8 | 70341976 | 70342449 | Intron | 11067 | Upf1 | 1.013926896 | 1.51E−05 |
| chr5 | 97073050 | 97073392 | Intron | 38375 | Paqr3 | 1.013273212 | 1.73E−05 |
| chr5 | 124082937 | 124083309 | Exon | 12675 | Abcb9 | 1.010003746 | 6.47E−07 |
| chr11 | 106484027 | 106484185 | Intron | 3690 | Ern1 | 1.00932326 | 0.008315588 |
| chr13 | 98275578 | 98276064 | Intergenic | 12745 | Ankra2 | 1.004818473 | 0.01363811 |
| chr6 | 83440517 | 83440731 | Intron | 1054 | Tet3 | 1.003583597 | 0.024922272 |
| chr10 | 26228168 | 26228517 | Intergenic | −1365 | Samd3 | 1.002779155 | 0.000221261 |
| chr5 | 64024176 | 64024861 | Intergenic | −20455 | 5830416I19Rik | 1.002417315 | 0.000133984 |
| chr6 | 129597972 | 129598282 | Intron | 6316 | Klrd1 | 1.001897374 | 0.030103132 |
| chr3 | 107236950 | 107237218 | Intron | 2623 | Prok1 | 1.001825399 | 0.00745429 |
| chr19 | 40665851 | 40666226 | Intron | 6268 | Entpd1 | 0.998213966 | 0.004798079 |
| chr17 | 6015115 | 6015349 | Intron | 7652 | Synj2 | 0.997769765 | 0.046820151 |
| chr11 | 3330628 | 3330840 | Promoter-TSS | 3 | Pik3ip1 | 0.994770995 | 0.00177263 |
| chr5 | 121519725 | 121520263 | Exon | 1701 | Adam1a | 0.993923294 | 0.001218859 |
| chr9 | 108630758 | 108630964 | Intron | 18519 | Arih2 | 0.992247003 | 0.037321188 |
| chr17 | 3215116 | 3215443 | Intergenic | 100307 | Scaf8 | 0.991169897 | 0.042888215 |
| chr11 | 101357528 | 101357844 | Intergenic | −10030 | G6pc | 0.987088572 | 0.042566403 |
| chr7 | 66303380 | 66303545 | Intron | 78262 | Mir7057 | 0.986121844 | 0.013969821 |
| chr14 | 69543966 | 69544330 | Intergenic | 11239 | Gm16677 | 0.985802521 | 0.039443353 |
| chr11 | 79654352 | 79654729 | Intron | 20546 | Rab11fip4os2 | 0.984277181 | 1.84E−05 |
| chr13 | 108812974 | 108813780 | Intron | 159200 | Pde4d | 0.984204019 | 0.00559649 |
| chr3 | 135667202 | 135667392 | Intron | 24250 | Nfkb1 | 0.983703282 | 0.017028441 |
| chr14 | 77906780 | 77906968 | Intron | 2635 | Epsti1 | 0.982844841 | 0.01363811 |
| chr13 | 37542881 | 37543061 | Intergenic | 197626 | Ly86 | 0.981456012 | 0.046475788 |
| chr14 | 121912548 | 121912856 | Intron | 3072 | Gpr18 | 0.980505327 | 1.70E−05 |
| chr1 | 86379290 | 86379718 | Intergenic | 8637 | Nmur1 | 0.9801415 | 0.012485208 |
| chr15 | 99335886 | 99336297 | Intron | 34391 | Fmnl3 | 0.980138558 | 0.001397606 |
| chr18 | 82484805 | 82485282 | Intron | 9920 | Mbp | 0.979123275 | 0.004083515 |
| chr9 | 113731538 | 113732110 | Intergenic | −9649 | Clasp2 | 0.978952708 | 0.008291494 |
| chr18 | 79071982 | 79072604 | Intron | 37098 | Setbp1 | 0.977131052 | 2.11E−06 |
| chr11 | 16982636 | 16982869 | Intron | 25966 | Plek | 0.975142547 | 0.026571404 |
| chr10 | 58464091 | 58464350 | Exon | 17368 | Ranbp2 | 0.975056749 | 0.030165523 |
| chr8 | 83721663 | 83722472 | Intron | 1917 | Mir1668 | 0.974724256 | 1.01E−05 |
| chr9 | 103426503 | 103426742 | Non-Coding | 3044 | 5830418P13Rik | 0.972291761 | 0.025827756 |
| chr13 | 95614162 | 95614427 | Intron | 4139 | F2r | 0.97220094 | 0.026160902 |
| chr8 | 111998744 | 111999342 | Intron | −6741 | Adat1 | 0.972117662 | 0.042002753 |
| chr12 | 21476481 | 21476875 | Intergenic | −59242 | Ywhaq | 0.971783781 | 0.006671087 |
| chr17 | 12174803 | 12175155 | Intron | 55695 | Agpat4 | 0.970964352 | 0.010869561 |
| chr6 | 81934276 | 81934981 | Intron | 10959 | Gcfc2 | 0.969670885 | 0.001716625 |
| chr11 | 83628602 | 83629225 | Intergenic | 20465 | Ccl3 | 0.968991384 | 3.16E−06 |
| chr6 | 136900192 | 136901313 | Intergenic | 21428 | Erp27 | 0.96853744 | 3.43E−05 |
| chr7 | 28803492 | 28803706 | Intergenic | −7291 | Hnrnpl | 0.966742372 | 0.033982094 |
| chrX | 159826230 | 159826659 | Intron | −14024 | Sh3kbp1 | 0.965543097 | 0.04164386 |
| chr11 | 46360096 | 46360339 | Intron | 29298 | Itk | 0.964525012 | 0.033250015 |
| chr4 | 154110640 | 154111220 | Intron | −13757 | Trp73 | 0.964118128 | 0.035047946 |
| chr7 | 43434770 | 43435172 | Intron | −2167 | Nkg7 | 0.962723416 | 0.001017565 |
| chr4 | 7755507 | 7755878 | Intergenic | 195004 | 8430436N08Rik | 0.962464825 | 0.012906441 |
| chr9 | 106771435 | 106772068 | Intron | 17462 | Rad54l2 | 0.960730977 | 0.004957594 |
| chr19 | 29960436 | 29961150 | TTS | 15003 | Il33 | 0.960686901 | 6.85E−06 |
| chr13 | 51782346 | 51782939 | Intron | 11105 | Sema4d | 0.960530112 | 0.000861466 |
| chr7 | 17156818 | 17157281 | Intron | 6649 | Ceacam3 | 0.960003209 | 0.019727238 |
| chr7 | 16330194 | 16330748 | Intron | 20888 | Bbc3 | 0.959303124 | 0.000108634 |
| chr5 | 112310880 | 112311317 | Intron | −15271 | Tfip11 | 0.957624162 | 0.007451978 |
| chr18 | 70532991 | 70533254 | Intergenic | −2801 | Poli | 0.955923717 | 1.33E−06 |
| chr17 | 83995995 | 83996482 | Intergenic | −2314 | 8430430B14Rik | 0.954975604 | 0.002837782 |
| chr16 | 11461478 | 11462020 | Intron | 56101 | Snx29 | 0.954578969 | 0.001661334 |
| chr13 | 113090555 | 113090772 | Intron | 10318 | Gzma | 0.953356467 | 0.000171706 |
| chr2 | 52455587 | 52456407 | Intron | −31123 | Arl5a | 0.952828153 | 0.000175786 |
| chr5 | 122343754 | 122344189 | Intron | 10224 | Rad9b | 0.948874321 | 0.030519606 |
| chr2 | 165207871 | 165208131 | Intron | 26736 | Cdh22 | 0.948057998 | 0.033887019 |
| chr5 | 143517470 | 143517722 | Intron | 10397 | Rac1 | 0.947417366 | 0.000772671 |
| chr17 | 6745997 | 6746324 | Intron | 36620 | Ezr | 0.946735316 | 0.024655737 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr5 | 147072066 | 147072282 | Intron | 4398 | Lnx2 | 0.944347238 | 0.031297017 |
| chr5 | 124083396 | 124083648 | Intron | 12276 | Abcb9 | 0.943096947 | 0.000274427 |
| chr9 | 61671151 | 61671313 | Intergenic | 243278 | Rplp1 | 0.942899959 | 0.023180647 |
| chr15 | 72928755 | 72929587 | Intron | −118847 | Peg13 | 0.942402482 | 0.002371466 |
| chr12 | 104969502 | 104969981 | Intron | 28936 | Syne3 | 0.94140128 | 0.004172233 |
| chr1 | 46864115 | 46864698 | Intergenic | −10897 | Slc39a10 | 0.940961956 | 3.27E−05 |
| chr5 | 3373211 | 3373629 | Intron | 29527 | Cdk6 | 0.939500804 | 0.001311036 |
| chr14 | 61620298 | 61620731 | Intron | 11458 | Mir16-1 | 0.93918843 | 0.040081324 |
| chr4 | 150215923 | 150216190 | Intergenic | −14921 | Car6 | 0.939131323 | 0.041238449 |
| chr2 | 128427611 | 128427874 | Intron | 1609 | Gm14005 | 0.93884849 | 0.046003497 |
| chr9 | 121305898 | 121306120 | Intergenic | −28837 | Ulk4 | 0.938783271 | 0.017765826 |
| chr18 | 81924032 | 81924382 | Intergenic | 67873 | Mir5127 | 0.935772992 | 0.002594116 |
| chr11 | 106480439 | 106480879 | Intron | 7137 | Ern1 | 0.934795031 | 0.017641692 |
| chr4 | 86739208 | 86739660 | Intergenic | −9121 | Dennd4c | 0.933947506 | 0.013675814 |
| chr18 | 89304464 | 89304954 | Intron | 107282 | Cd226 | 0.93281562 | 0.006046733 |
| chr1 | 153307246 | 153307488 | Intron | 25419 | Lamc1 | 0.93116459 | 0.007912045 |
| chr10 | 94846736 | 94847406 | Intron | 97507 | Plxnc1 | 0.930985657 | 3.50E−05 |
| chr8 | 78742455 | 78742993 | Intergenic | 78428 | Lsm6 | 0.930479824 | 0.02533559 |
| chr18 | 35913280 | 35913863 | Intergenic | −51259 | Psd2 | 0.929595957 | 0.001198348 |
| chr13 | 113227117 | 113227447 | Intergenic | 17623 | Esm1 | 0.927891627 | 0.003711913 |
| chr14 | 69475446 | 69475792 | Intergenic | 36930 | Synb | 0.927238136 | 0.046877551 |
| chr13 | 53063239 | 53063477 | Intergenic | −82319 | Nfil3 | 0.927014171 | 0.043174256 |
| chr19 | 37109893 | 37110136 | Intron | −63829 | A330032B11Rik | 0.926858896 | 0.034576601 |
| chr13 | 53065163 | 53066034 | Intergenic | −84559 | Nfil3 | 0.926814709 | 5.60E−08 |
| chr9 | 86628892 | 86629196 | Intron | 56991 | Rwdd2a | 0.926283322 | 0.00226744 |
| chr8 | 13620092 | 13620877 | Intron | 57103 | Rasa3 | 0.926100221 | 0.001572406 |
| chr1 | 152089553 | 152089925 | Intron | 581 | 1700025G04Rik | 0.925126788 | 0.001116668 |
| chr1 | 85720322 | 85721086 | Intron | 15902 | A630001G21Rik | 0.923935595 | 0.013097942 |
| chr2 | 45023848 | 45024126 | Promoter-TSS | −810 | Mir5129 | 0.923759449 | 0.005639788 |
| chr7 | 48917395 | 48917867 | Intergenic | −36590 | E2f8 | 0.923596603 | 0.002425339 |
| chr1 | 131051113 | 131051658 | Intergenic | 31540 | Il10 | 0.922797942 | 0.001661334 |
| chr5 | 28042737 | 28043394 | Intergenic | −28347 | Insig1 | 0.922573607 | 0.00035216 |
| chr5 | 124046906 | 124047565 | Intergenic | −14975 | Vps37b | 0.921797487 | 0.000852826 |
| chr5 | 112291932 | 112292140 | Intron | 15345 | Tpst2 | 0.920675449 | 0.022826306 |
| chr19 | 37333346 | 37333896 | Intergenic | −3008 | Ide | 0.917159578 | 1.02E−07 |
| chr2 | 65133633 | 65134079 | Intron | 104770 | Cobll1 | 0.917040006 | 0.004313016 |
| chr7 | 24430594 | 24431411 | TTS | 14680 | Irgc1 | 0.914112679 | 0.000110537 |
| chr1 | 133175144 | 133175511 | Intergenic | 44161 | Ppp1r15b | 0.908413128 | 0.004193259 |
| chr12 | 112806150 | 112806365 | Intergenic | −2718 | BC022687 | 0.908177623 | 0.012688949 |
| chr16 | 58479956 | 58480540 | Intron | 43064 | St3gal6 | 0.907703459 | 0.000101395 |
| chr5 | 120139202 | 120139578 | Promoter-TSS | −127 | Gm10390 | 0.907476584 | 0.004164754 |
| chr5 | 115126633 | 115126916 | Intron | −7428 | Acads | 0.907432231 | 0.004000886 |
| chr9 | 108629573 | 108629830 | Intron | 19679 | Arih2 | 0.906052331 | 0.013764109 |
| chr8 | 88201100 | 88201347 | Intron | 2010 | Papd5 | 0.903859441 | 0.032933231 |
| chr17 | 74140213 | 74140545 | Intergenic | −92463 | Srd5a2 | 0.903486745 | 0.036938147 |
| chr10 | 96356902 | 96357960 | Intergenic | 131263 | 4930459C07Rik | 0.903384935 | 0.000202383 |
| chr7 | 118104716 | 118105018 | 3' UTR | 11280 | Rps15a | 0.903250646 | 0.035516546 |
| chr11 | 106564046 | 106564702 | Intron | 48556 | Tex2 | 0.899247772 | 8.32E−09 |
| chr2 | 73346234 | 73346996 | Intron | 33963 | Scrn3 | 0.898022953 | 0.004738929 |
| chr7 | 66303741 | 66304511 | Intron | 77598 | Mir7057 | 0.896819759 | 3.62E−08 |
| chr10 | 111583097 | 111583473 | Intergenic | 10988 | 4933440J02Rik | 0.896513943 | 0.000370106 |
| chr17 | 6746791 | 6747117 | Intron | 35826 | Ezr | 0.895236776 | 0.013648897 |
| chr13 | 113810359 | 113810766 | Intron | 16054 | Arl15 | 0.894451741 | 0.04151408 |
| chr7 | 36696867 | 36698137 | Promoter-TSS | −616 | Tshz3 | 0.893439812 | 0.034576601 |
| chr11 | 4946963 | 4947942 | Promoter-TSS | −69 | Ap1b1 | 0.893142431 | 0.000382581 |
| chr15 | 98780196 | 98781152 | Intergenic | −2524 | Wnt10b | 0.891134511 | 0.01249894 |
| chr10 | 118482607 | 118482967 | Intergenic | 41741 | Ifng | 0.887814915 | 6.29E−05 |
| chr14 | 25504969 | 25505649 | Intron | −29130 | Mir3075 | 0.886385915 | 1.77E−05 |
| chr5 | 3363416 | 3363856 | Intron | 19743 | Cdk6 | 0.884776576 | 0.016871467 |
| chr5 | 72757405 | 72757894 | Exon | −4872 | Txk | 0.88477523 | 0.00663095 |
| chr3 | 79593363 | 79593597 | Intron | 2091 | Ppid | 0.884506311 | 0.015705647 |
| chr6 | 115694484 | 115694835 | Intergenic | −18024 | Raf1 | 0.882318035 | 0.022582718 |
| chr6 | 83786337 | 83786792 | Intergenic | 7706 | Gm7443 | 0.881108166 | 0.025865707 |
| chr13 | 113807097 | 113807665 | Intron | 12873 | Arl15 | 0.879495885 | 0.002252725 |
| chr3 | 115730303 | 115730656 | Intergenic | −15424 | S1pr1 | 0.878768611 | 0.034666483 |
| chr18 | 77965001 | 77965474 | Intron | 26770 | Epg5 | 0.878574069 | 0.024741193 |
| chr6 | 87040988 | 87041326 | Intergenic | −1689 | Gfpt1 | 0.878124977 | 0.000858225 |
| chr5 | 114116551 | 114116962 | Intron | 11420 | Alkbh2 | 0.876877455 | 0.030589445 |
| chr10 | 117894157 | 117894862 | Intergenic | −30950 | 4933411E08Rik | 0.876708181 | 0.000200949 |
| chr9 | 57328461 | 57328891 | Intergenic | −62394 | 4930430J02Rik | 0.876622121 | 0.005208041 |
| chr11 | 103381682 | 103382571 | Intron | −18434 | Arhgap27 | 0.874144133 | 3.93E−06 |
| chr11 | 100879730 | 100880051 | Intron | 19406 | Stat5a | 0.872230267 | 0.002061258 |
| chr4 | 46422507 | 46422981 | Intergenic | −18561 | Hemgn | 0.869976248 | 0.014374831 |
| chr10 | 36158083 | 36158608 | Intergenic | −348462 | Hs3st5 | 0.867681242 | 0.04093247 |
| chr5 | 3491889 | 3492173 | Intron | −51802 | Fam133b | 0.866099062 | 0.018064007 |
| chr7 | 80715098 | 80715919 | Intron | −26631 | Crtc3 | 0.865807244 | 0.000223134 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr4 | 59315030 | 59315994 | Intron | 55461 | Gm12596 | 0.865334769 | 0.000646679 |
| chr11 | 106479660 | 106479880 | Intron | 8026 | Ern1 | 0.864694595 | 0.02968237 |
| chr8 | 122436193 | 122436446 | Intron | −3379 | Cyba | 0.864603069 | 0.00021257 |
| chr19 | 53824858 | 53825308 | Intron | −67148 | Pdcd4 | 0.863650573 | 0.01868855 |
| chr4 | 140989440 | 140989983 | Intron | 2838 | Atp13a2 | 0.862981432 | 9.75E−06 |
| chr6 | 144671669 | 144671924 | Intergenic | −1072 | Sox5os3 | 0.860485863 | 0.020808036 |
| chr9 | 123749582 | 123750116 | Intergenic | −17362 | Ccr9 | 0.860033528 | 5.36E−07 |
| chr5 | 115531706 | 115532274 | Intron | 25314 | Pxn | 0.859764431 | 0.023169822 |
| chr17 | 84308473 | 84308699 | Intron | −120639 | Zfp36l2 | 0.858299691 | 0.042837376 |
| chr10 | 93540741 | 93540944 | Promoter-TSS | 210 | Ccdc38 | 0.857988277 | 0.030614221 |
| chr13 | 108861757 | 108862465 | Intron | 207934 | Pde4d | 0.857353643 | 9.66E−08 |
| chr6 | 65531420 | 65531850 | Intergenic | −58763 | Tnip3 | 0.857201397 | 0.015263636 |
| chr8 | 77429423 | 77430314 | Intron | −87188 | 0610038B21Rik | 0.856106316 | 5.60E−08 |
| chr9 | 41078343 | 41078651 | Intron | −73869 | Crtam | 0.855731112 | 0.001270042 |
| chr8 | 13663041 | 13663343 | Intron | 14395 | Rasa3 | 0.854940598 | 0.002056051 |
| chr1 | 43138397 | 43138864 | Intron | 25331 | Fhl2 | 0.854290484 | 3.23E−06 |
| chr19 | 40678517 | 40678940 | Intron | 18988 | Entpd1 | 0.853048518 | 0.011635202 |
| chr18 | 56440958 | 56441294 | Intron | 8994 | Gramd3 | 0.852109519 | 0.019480032 |
| chr11 | 114911633 | 114912171 | Intergenic | 21861 | Cd300a | 0.85209541 | 0.017503037 |
| chr6 | 15729239 | 15729624 | Intron | 8770 | Mdfic | 0.851452844 | 0.037715281 |
| chr17 | 56904829 | 56905324 | Intron | 29443 | 1700061G19Rik | 0.851092604 | 0.041913635 |
| chr9 | 64564288 | 64564816 | Intron | 173204 | Rab11a | 0.850797478 | 0.001533906 |
| chr5 | 97075561 | 97076005 | Intron | 35813 | Paqr3 | 0.850777483 | 6.38E−05 |
| chr9 | 120576438 | 120576563 | Promoter-TSS | −831 | 5830454E08Rik | 0.849736979 | 0.038675809 |
| chr13 | 37432683 | 37433101 | Intergenic | 87548 | Ly86 | 0.848065643 | 0.02210353 |
| chr10 | 95297694 | 95298045 | Intron | 25840 | Cradd | 0.847637799 | 6.73E−05 |
| chr7 | 75579584 | 75579939 | Exon | 124227 | Akap13 | 0.847268658 | 0.0396537 |
| chr15 | 86172321 | 86172812 | Intron | 13575 | Cerk | 0.847106177 | 0.025454783 |
| chr2 | 60864517 | 60864731 | Intron | 16814 | Rbms1 | 0.846902148 | 0.048579857 |
| chr7 | 118252339 | 118252968 | Intergenic | 8746 | 4930583K01Rik | 0.844356796 | 0.014886249 |
| chr15 | 99644812 | 99645316 | Intron | 6592 | Racgap1 | 0.84395488 | 0.000133984 |
| chr4 | 107996727 | 107997310 | Intron | 28684 | Slc1a7 | 0.841824891 | 0.02673327 |
| chr7 | 120851437 | 120852186 | Intron | 622 | Eef2k | 0.840795003 | 0.000520742 |
| chr11 | 107432233 | 107432486 | Intron | 38361 | Pitpnc1 | 0.839330405 | 0.02089259 |
| chr2 | 167940697 | 167941051 | Intron | 8547 | Ptpn1 | 0.839156442 | 0.003057642 |
| chr15 | 97329316 | 97329714 | Intron | −82228 | Amigo2 | 0.832499542 | 0.035047946 |
| chr12 | 82214922 | 82215353 | Intron | 45121 | Sipa1l1 | 0.832424414 | 0.034017991 |
| chr11 | 116136259 | 116136652 | Intron | 2413 | Mrpl38 | 0.827606759 | 0.000508107 |
| chr7 | 106256758 | 106257033 | Intergenic | −41555 | Gvin1 | 0.827223319 | 0.002967819 |
| chr1 | 152088767 | 152089435 | Intron | 1219 | 1700025G04Rik | 0.825662961 | 0.004616245 |
| chr10 | 59919431 | 59920037 | Intergenic | 32036 | Ddit4 | 0.824776837 | 0.039005369 |
| chr4 | 133399560 | 133399936 | Intron | 29972 | Mir5122 | 0.82370003 | 0.048082268 |
| chr6 | 86823011 | 86823329 | Intergenic | 26270 | 2610306M01Rik | 0.823263234 | 0.011246898 |
| chr17 | 5492347 | 5492688 | Promoter-TSS | −83 | Zdhhc14 | 0.822909765 | 0.002030951 |
| chr9 | 45297862 | 45298162 | Intergenic | −21088 | Tmprss13 | 0.82273406 | 0.003724022 |
| chr1 | 43127684 | 43128670 | Intron | 29470 | AI597479 | 0.822484084 | 0.005496306 |
| chr2 | 155046871 | 155047109 | Intron | 27507 | Ahcy | 0.822050434 | 0.00960428 |
| chr8 | 112005243 | 112005961 | Intron | 5752 | Kars | 0.820872822 | 4.17E−05 |
| chr8 | 70744713 | 70745223 | Intron | −9711 | Rab3a | 0.820499535 | 0.004212645 |
| chr12 | 21225849 | 21226809 | Intron | 59908 | Itgb1bp1 | 0.82013146 | 3.95E−05 |
| chr1 | 192741237 | 192741518 | Intron | 29842 | Hhat | 0.818546093 | 0.007433442 |
| chr3 | 131207832 | 131208173 | Intron | 64099 | Hadh | 0.81711356 | 0.015705647 |
| chr15 | 66798186 | 66798363 | Intron | 33555 | Sla | 0.81703164 | 0.048181546 |
| chr7 | 27259689 | 27260232 | Intron | 1199 | Numbl | 0.816932768 | 0.01314826 |
| chr3 | 152908366 | 152908537 | Intron | 73756 | St6galnac5 | 0.813531759 | 0.026571404 |
| chr6 | 120181213 | 120181599 | Intron | −12417 | Ninj2 | 0.813217996 | 0.043288559 |
| chr15 | 31585213 | 31585645 | Exon | 16375 | Cct5 | 0.812277384 | 3.35E−05 |
| chr3 | 95312562 | 95313001 | Intergenic | −2409 | Cers2 | 0.811870198 | 0.034609802 |
| chr1 | 192730213 | 192730978 | Intron | 40624 | Hhat | 0.811730624 | 8.93E−06 |
| chr8 | 92357337 | 92357894 | Promoter-TSS | −181 | Irx5 | 0.811164689 | 0.008669588 |
| chr5 | 149594017 | 149594580 | Intron | 42017 | Hsph1 | 0.810973929 | 6.77E−07 |
| chr13 | 101706001 | 101706277 | Intron | −13509 | Pik3r1 | 0.810892982 | 0.000165229 |
| chr9 | 64779708 | 64780393 | Intergenic | −30961 | Dennd4a | 0.810474885 | 0.000329544 |
| chr11 | 83605398 | 83605967 | Intron | −12595 | Ccl6 | 0.809202437 | 0.033070499 |
| chr10 | 60038249 | 60038687 | Intron | 35141 | Ascc1 | 0.807887667 | 0.000326278 |
| chr10 | 43934586 | 43935191 | Intron | 33081 | Rtn4ip1 | 0.807833674 | 0.020020676 |
| chr5 | 124872918 | 124873459 | Intron | 10483 | Zfp664 | 0.805476979 | 0.004838828 |
| chr2 | 45019470 | 45020187 | Intron | 3349 | Mir5129 | 0.804637072 | 0.011428102 |
| chr4 | 154065339 | 154065666 | Intron | −22825 | Ccdc27 | 0.803658462 | 0.045226514 |
| chr7 | 4464287 | 4464755 | Promoter-TSS | −214 | Eps8l1 | 0.802161846 | 0.006045862 |
| chr5 | 151422627 | 151423301 | Intron | 16460 | Gm3704 | 0.801615894 | 0.009138178 |
| chr5 | 115751960 | 115752389 | Intergenic | −20615 | Ccdc64 | 0.800774064 | 0.024852973 |
| chr9 | 79922400 | 79922637 | Intron | 55364 | Filip1 | 0.800285454 | 0.024162515 |
| chr18 | 79067641 | 79067897 | Intron | 41622 | Setbp1 | 0.799547863 | 0.007588244 |
| chr9 | 57524521 | 57524834 | Intron | 3445 | Cox5a | 0.797628645 | 0.018661466 |
| chr12 | 3356740 | 3357151 | Intergenic | −8187 | Kif3c | 0.797225881 | 0.028029061 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr10 | 118096074 | 118096682 | Intergenic | −45409 | Mdm1 | 0.797198888 | 0.000199173 |
| chr17 | 32550925 | 32551401 | Exon | 14534 | Cyp4f16 | 0.796783429 | 0.004845583 |
| chr1 | 37469005 | 37469543 | Intron | 19331 | 4930594C11Rik | 0.795984632 | 0.042002753 |
| chr12 | 100508600 | 100509048 | Intron | 11998 | Ttc7b | 0.795793743 | 0.010553255 |
| chr6 | 72623853 | 72624543 | Intergenic | −5090 | Gm15401 | 0.795498544 | 0.00428928 |
| chr1 | 183803379 | 183803872 | Intergenic | 230373 | 1700056E22Rik | 0.795360091 | 0.012920273 |
| chr6 | 114931259 | 114931539 | Intergenic | −9647 | Vgll4 | 0.7949151 | 0.011586205 |
| chr2 | 139989639 | 139990197 | Intron | 76887 | Tasp1 | 0.794644155 | 0.002669245 |
| chr10 | 74920881 | 74921226 | Intron | −46178 | Gnaz | 0.794389886 | 0.025913718 |
| chr19 | 36918520 | 36919386 | Exon | 646 | Fgfbp3 | 0.794003844 | 0.000286252 |
| chr11 | 3167306 | 3167633 | Intron | 25994 | Sfi1 | 0.792709442 | 2.09E−05 |
| chr2 | 11360964 | 11361341 | Intron | 21663 | Gm13293 | 0.791866271 | 0.046214456 |
| chr10 | 118550169 | 118550676 | Intron | 6103 | Tmevpg1 | 0.791812891 | 3.47E−05 |
| chrX | 103393751 | 103394430 | 3' UTR | −20377 | Tsx | 0.791654783 | 0.015819667 |
| chr7 | 51743535 | 51743967 | Intergenic | −118264 | Gas2 | 0.790598939 | 0.036907059 |
| chr2 | 34982178 | 34982694 | TTS | −20664 | Traf1 | 0.790550398 | 0.015645033 |
| chr15 | 98778910 | 98779392 | Intergenic | −1001 | Wnt10b | 0.790261619 | 1.92E−07 |
| chr10 | 79691977 | 79692386 | Intron | −1645 | Gzmm | 0.787372021 | 1.47E−06 |
| chr9 | 124030724 | 124031025 | 3' UTR | 8903 | Ccr3 | 0.787137587 | 0.047020852 |
| chr7 | 13123642 | 13124201 | Intergenic | 8437 | Vmn1r87 | 0.786283561 | 0.043627864 |
| chr7 | 63919269 | 63919685 | Intron | 2585 | E030018B13Rik | 0.783010853 | 0.011677382 |
| chr2 | 143924590 | 143925194 | Intron | 9561 | Dstn | 0.781563902 | 0.001158602 |
| chr2 | 120599341 | 120600055 | 3' UTR | 9617 | Lrrc57 | 0.781051162 | 0.012815564 |
| chr2 | 160952142 | 160952522 | Intron | −39993 | Emilin3 | 0.77982492 | 0.002882941 |
| chr14 | 25476010 | 25476507 | Intron | 17073 | Zmiz1 | 0.779788597 | 0.002744456 |
| chr1 | 134962921 | 134963094 | Intron | 442 | Ube2t | 0.776718487 | 0.018101576 |
| chr6 | 114873956 | 114874474 | Intron | 47537 | Vgll4 | 0.776344315 | 0.003930761 |
| chr11 | 59397413 | 59398237 | Intergenic | −22172 | Prss38 | 0.774727385 | 0.0203914 |
| chr19 | 20409525 | 20410121 | Intron | 4535 | 1500015L24Rik | 0.774406078 | 0.036300065 |
| chr13 | 33068053 | 33068462 | Intergenic | −15846 | Serpinb1b | 0.773235884 | 0.030254094 |
| chr18 | 36672352 | 36674009 | Intron | −2869 | Sra1 | 0.772828276 | 2.13E−05 |
| chr19 | 53531440 | 53531918 | Intron | 2361 | Dusp5 | 0.770740774 | 0.002264422 |
| chr5 | 107524984 | 107525284 | Intergenic | −9577 | 1700028K03Rik | 0.770457929 | 0.003289632 |
| chr19 | 20393459 | 20394161 | Intron | −3139 | Anxa1 | 0.770166568 | 0.008355949 |
| chr3 | 107849053 | 107849303 | Intergenic | −28052 | Eps8l3 | 0.766830622 | 0.024056893 |
| chr2 | 45102967 | 45103533 | Intron | 7027 | Zeb2 | 0.765942684 | 0.000440855 |
| chrX | 48435560 | 48435903 | Intron | 27401 | Elf4 | 0.765173379 | 0.018216458 |
| chr6 | 50378411 | 50378928 | Intron | 4168 | Osbpl3 | 0.765138722 | 0.006376772 |
| chr15 | 100421030 | 100421613 | Intron | 1734 | Slc11a2 | 0.764188574 | 0.044070578 |
| chr2 | 173058262 | 173058458 | Intergenic | 36458 | Rbm38 | 0.763446783 | 0.0401742 |
| chr1 | 192735843 | 192737247 | Intron | 34674 | Hhat | 0.763126421 | 3.85E−10 |
| chr12 | 104058728 | 104058990 | Intergenic | −14416 | Serpina12 | 0.761984579 | 9.10E−05 |
| chr9 | 66713369 | 66714084 | Promoter-TSS | 40 | Car12 | 0.761023504 | 0.035126522 |
| chrY | 90761158 | 90761619 | Intergenic | −6338 | G530011O06Rik | 0.76047866 | 0.000272735 |
| chr7 | 25270144 | 25270313 | Intron | 2529 | Cic | 0.759991808 | 0.039443353 |
| chr10 | 39506263 | 39507108 | Intron | −106249 | Traf3ip2 | 0.759812025 | 3.72E−05 |
| chr5 | 124051948 | 124052536 | Intergenic | −19982 | Vps37b | 0.758700254 | 9.82E−05 |
| chr10 | 26229425 | 26229850 | Promoter-TSS | −70 | Samd3 | 0.758571605 | 0.003315902 |
| chr19 | 22915843 | 22916145 | Intron | 165389 | Mir204 | 0.758222077 | 0.049089852 |
| chr11 | 3156989 | 3157188 | Intron | 33067 | Pisd-ps1 | 0.75793041 | 0.013675814 |
| chr3 | 146686456 | 146686814 | Intergenic | −35318 | 4930503B20Rik | 0.753617215 | 0.008517624 |
| chr13 | 81401752 | 81402109 | Intron | 231214 | Adgrv1 | 0.751246911 | 0.046877551 |
| chr14 | 75005606 | 75006215 | Intron | −10117 | Rubcnl | 0.750661976 | 0.000976777 |
| chr18 | 56431722 | 56432439 | Promoter-TSS | −52 | Gramd3 | 0.750638696 | 2.20E−10 |
| chr5 | 113899209 | 113899889 | Intron | 9157 | Coro1c | 0.750001178 | 0.014294836 |
| chr8 | 13642861 | 13643591 | Intron | 34361 | Rasa3 | 0.748174857 | 0.028929805 |
| chr5 | 149606445 | 149606818 | Intron | 29684 | Hsph1 | 0.748140818 | 0.00290386 |
| chr14 | 52143939 | 52144418 | Intron | 33275 | Rpgrip1 | 0.746133428 | 0.002357666 |
| chr2 | 11797759 | 11798425 | Intergenic | 20339 | Ankrd16 | 0.745839077 | 0.016879779 |
| chr16 | 11456071 | 11456676 | Intron | 50725 | Snx29 | 0.745183985 | 5.66E−06 |
| chr19 | 36925604 | 36926607 | Promoter-TSS | 26 | Btaf1 | 0.745134223 | 7.57E−08 |
| chr4 | 11455107 | 11455549 | Intergenic | −30630 | 1110037F02Rik | 0.742894973 | 0.047020852 |
| chr17 | 34210521 | 34211060 | Intron | 6311 | Tap2 | 0.742760621 | 9.52E−05 |
| chr11 | 117220682 | 117221340 | Intron | 21350 | Sept9 | 0.742332649 | 1.05E−05 |
| chr13 | 119657016 | 119657528 | Intergenic | −22770 | 1700074H08Rik | 0.741956072 | 0.013730991 |
| chr6 | 108570324 | 108570677 | Intergenic | 52667 | 0610040F04Rik | 0.741775423 | 0.002095533 |
| chr5 | 123985131 | 123985673 | Intron | −11450 | Mir7032 | 0.74115677 | 6.97E−05 |
| chr2 | 168005682 | 168006498 | Intron | 4503 | Fam65c | 0.740766255 | 0.003818001 |
| chr11 | 11763173 | 11763707 | Intron | 45522 | Fignl1 | 0.739497402 | 0.009523527 |
| chr11 | 115416643 | 115417147 | Exon | 3024 | Atp5h | 0.738154398 | 0.000829402 |
| chr6 | 3182897 | 3183498 | Intergenic | −105322 | Gm8579 | 0.738010632 | 0.010997341 |
| chr7 | 100511472 | 100512058 | Exon | 3050 | Dnajb13 | 0.737582403 | 0.003268274 |
| chr12 | 100778920 | 100779465 | Promoter-TSS | 69 | 9030617O03Rik | 0.737435536 | 0.011668856 |
| chr1 | 127619063 | 127619684 | Intron | 58648 | Tmem163 | 0.73536632 | 0.015619126 |
| chr11 | 83568850 | 83569634 | Intergenic | 9394 | Ccl9 | 0.735295037 | 0.016880966 |
| chr18 | 65691395 | 65691798 | Intergenic | −6672 | Oacyl | 0.734580797 | 0.02827229 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr6 | 82748248 | 82748627 | Intron | 26017 | Hk2 | 0.734272216 | 0.031800017 |
| chr17 | 84226208 | 84226797 | Intron | −38555 | Zfp36l2 | 0.733600329 | 6.54E−07 |
| chr7 | 139970818 | 139971102 | Intergenic | 7795 | 6430531B16Rik | 0.733584421 | 0.001667444 |
| chr16 | 32742634 | 32743160 | Intron | 7011 | Muc4 | 0.732997089 | 0.002944669 |
| chr11 | 4205886 | 4206343 | Intron | −12137 | Gatsl3 | 0.731811289 | 0.003909741 |
| chr4 | 150894203 | 150894957 | Intergenic | 15341 | Park7 | 0.730355556 | 1.83E−07 |
| chr5 | 134612114 | 134612415 | Intron | 2761 | Lat2 | 0.73001808 | 0.026207608 |
| chr11 | 10276152 | 10276569 | Intergenic | −837656 | Vwc2 | 0.729881127 | 0.043749197 |
| chr19 | 21104381 | 21104964 | Promoter-TSS | −38 | 4930554I06Rik | 0.72943262 | 0.033566645 |
| chr10 | 84571003 | 84571424 | Intergenic | −5734 | Tcp11l2 | 0.728379648 | 0.009081553 |
| chr8 | 124066318 | 124066935 | Intergenic | 43153 | Urb2 | 0.728076845 | 0.016880966 |
| chr11 | 59418351 | 59418975 | Intron | 31293 | Snap47 | 0.727789979 | 0.000135014 |
| chr11 | 119856463 | 119856804 | Exon | −21924 | Rptoros | 0.727765793 | 0.04549403 |
| chr13 | 21831839 | 21832313 | Promoter-TSS | 82 | Hist1h4n | 0.727443518 | 8.89E−06 |
| chr4 | 139205031 | 139205283 | Intron | 11046 | Capzb | 0.723480466 | 0.028467506 |
| chr8 | 120760297 | 120761130 | Intergenic | 22074 | Irf8 | 0.722990914 | 0.003609666 |
| chr5 | 24747018 | 24747653 | Intergenic | 10508 | Crygn | 0.722910317 | 0.045981626 |
| chr12 | 108893379 | 108893684 | Promoter-TSS | −320 | Wars | 0.722625364 | 0.017143289 |
| chr2 | 165540985 | 165541319 | Intergenic | 37255 | Slc2a10 | 0.722474313 | 0.003640083 |
| chr16 | 11455631 | 11456045 | Intron | 50190 | Snx29 | 0.72214661 | 0.017054528 |
| chr1 | 161744887 | 161745329 | Intergenic | 43387 | Fasl | 0.720995659 | 0.040987032 |
| chr1 | 170978647 | 170979076 | Intergenic | −2790 | Fcgr2b | 0.719485332 | 0.00234323 |
| chr11 | 32582833 | 32583235 | Intron | 49768 | Stk10 | 0.718761332 | 0.0205938 |
| chr1 | 176823944 | 176824318 | Intron | 9471 | Sdccag8 | 0.718450978 | 0.017203744 |
| chr7 | 135580700 | 135581469 | Intron | −12397 | Ptpre | 0.717737445 | 1.56E−06 |
| chr1 | 13301378 | 13302115 | Intron | 70683 | Ncoa2 | 0.717375033 | 0.000625175 |
| chr6 | 39283679 | 39284350 | Intergenic | −77241 | Kdm7a | 0.716762924 | 0.000504284 |
| chr11 | 3169620 | 3169763 | Intron | 23772 | Sfi1 | 0.716458442 | 0.041723502 |
| chr2 | 163698431 | 163698523 | Intron | 4289 | Pkig | 0.71581421 | 0.019681338 |
| chr2 | 69716541 | 69716897 | Intergenic | −4113 | Fastkd1 | 0.715310149 | 0.012146712 |
| chr1 | 170972313 | 170972899 | Intron | 3465 | Fcgr2b | 0.712108782 | 0.000728353 |
| chr15 | 62079218 | 62079932 | Intron | 40318 | Pvt1 | 0.711991715 | 0.002156802 |
| chr1 | 165734729 | 165735154 | Intergenic | −26847 | Rcsd1 | 0.71045537 | 0.031517089 |
| chr8 | 121898163 | 121898383 | Intron | 9413 | Slc7a5 | 0.709977604 | 0.015522592 |
| chr2 | 168428502 | 168428805 | Intergenic | −159322 | Kcng1 | 0.709352789 | 0.022953816 |
| chr16 | 30184813 | 30185211 | Intergenic | 82520 | Cpn2 | 0.708964799 | 0.019057129 |
| chr9 | 61702299 | 61702932 | Intergenic | 211895 | Rplp1 | 0.708750556 | 3.78E−05 |
| chr4 | 16071208 | 16071928 | Intergenic | −57691 | Osgin2 | 0.708047829 | 0.018761172 |
| chrX | 59134954 | 59135371 | Promoter-TSS | −726 | Fgf13 | 0.706925368 | 0.043853866 |
| chr12 | 3896951 | 3897558 | Intron | 5510 | Dnmt3a | 0.706369607 | 0.002733714 |
| chr4 | 108058139 | 108058724 | Intron | −26341 | Podn | 0.706069074 | 5.39E−06 |
| chr12 | 113023001 | 113023603 | Intron | 8794 | Pacs2 | 0.704404212 | 0.000153335 |
| chr1 | 192733097 | 192733467 | Intron | 37937 | Hhat | 0.704381271 | 0.043833512 |
| chr7 | 123120586 | 123121080 | Intergenic | −3052 | Tnrc6a | 0.70422178 | 0.004564903 |
| chr11 | 119925260 | 119925588 | Intron | 11614 | Chmp6 | 0.703863433 | 0.001107311 |
| chr11 | 43365740 | 43366261 | Intergenic | 8461 | Mir146 | 0.70374845 | 0.01690875 |
| chr9 | 96772016 | 96772554 | Intron | 6723 | C430002N11Rik | 0.703308081 | 0.024852973 |
| chr4 | 151990987 | 151991319 | 3' UTR | −2167 | Thap3 | 0.701999445 | 0.037849074 |
| chr11 | 3165486 | 3165730 | Exon | 27855 | Sfi1 | 0.70101215 | 0.009085601 |
| chr7 | 118294579 | 118295101 | Intergenic | 50933 | 4930583K01Rik | 0.700731409 | 0.001667444 |
| chr6 | 112946913 | 112947557 | Promoter-TSS | 31 | Srgap3 | 0.700152092 | 0.000111124 |
| chr17 | 50069974 | 50070608 | Intron | 120206 | Rftn1 | 0.698991995 | 0.000279582 |
| chr9 | 118478399 | 118479419 | Exon | 720 | Eomes | 0.698476789 | 1.47E−07 |
| chr11 | 103372565 | 103372954 | Intron | −9067 | Arhgap27 | 0.698350553 | 0.034577733 |
| chr1 | 36162750 | 36163109 | Intron | −18616 | Mir6897 | 0.698130129 | 0.035782276 |
| chr14 | 56275776 | 56276459 | Intergenic | −13783 | Gzmb | 0.697478612 | 0.006061899 |
| chr17 | 12168336 | 12168986 | Intron | 49377 | Agpat4 | 0.695392666 | 0.034621947 |
| chr8 | 77461237 | 77461746 | Intron | −55565 | 0610038B21Rik | 0.694438151 | 0.040521725 |
| chr12 | 20990153 | 20990924 | Intergenic | −121218 | Asap2 | 0.69359146 | 4.07E−05 |
| chr15 | 27800160 | 27800622 | Intron | −118849 | Fam105a | 0.69316041 | 0.036946073 |
| chr9 | 79947389 | 79947906 | Intron | 30235 | Filip1 | 0.693031081 | 2.67E−09 |
| chr11 | 43395093 | 43395874 | Intergenic | −21022 | Mir146 | 0.69234776 | 0.008480365 |
| chr8 | 122436676 | 122437102 | Intergenic | −3949 | Cyba | 0.690661069 | 0.025209661 |
| chr9 | 58580733 | 58581161 | Intergenic | −1293 | Nptn | 0.690169999 | 5.31E−06 |
| chr16 | 38371015 | 38371321 | Intron | 8978 | Popdc2 | 0.688535194 | 0.014145686 |
| chr9 | 108104679 | 108105403 | Exon | −10561 | Apeh | 0.687635366 | 0.004738929 |
| chr12 | 19387316 | 19388264 | Intergenic | 873280 | 5730507C01Rik | 0.687501411 | 0.004667559 |
| chr11 | 118397815 | 118398180 | Intron | 3934 | Lgals3bp | 0.686011501 | 0.003909961 |
| chr2 | 35985466 | 35985908 | Intergenic | −6063 | Ttll11 | 0.685441838 | 0.008355949 |
| chr14 | 49219005 | 49219867 | Intergenic | 25992 | 1700011H14Rik | 0.684986425 | 3.29E−06 |
| chr14 | 64628153 | 64628521 | Intergenic | −24194 | Kif13b | 0.684909359 | 0.006238442 |
| chr18 | 79109048 | 79109573 | Promoter-TSS | 81 | Setbp1 | 0.684659424 | 0.036913303 |
| chr11 | 7145203 | 7145627 | Intron | 43154 | Gm11985 | 0.683295598 | 0.02187549 |
| chr13 | 93785033 | 93785676 | Intron | −5423 | Mir5624 | 0.682976679 | 0.020714872 |
| chr7 | 66273448 | 66273953 | Intron | 108024 | Mir7057 | 0.68278206 | 0.042002753 |
| chr6 | 33618600 | 33618989 | Intron | 369644 | Exoc4 | 0.68153361 | 0.01236688 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr11 | 3104691 | 3105794 | Intergenic | −18779 | Pisd-ps1 | 0.681223657 | 1.15E−08 |
| chr4 | 141210294 | 141210874 | Intergenic | −3372 | Rsg1 | 0.680175211 | 2.70E−05 |
| chr16 | 11448497 | 11449132 | Intron | 43166 | Snx29 | 0.679733365 | 0.00021703 |
| chr15 | 77741472 | 77742007 | Intergenic | 12618 | Apol9b | 0.67819181 | 0.037521273 |
| chr16 | 4922364 | 4922841 | Exon | −16509 | Nudt16l1 | 0.677808694 | 0.024741154 |
| chr1 | 74392238 | 74392493 | Intron | 756 | Ctdsp1 | 0.677311268 | 0.034099386 |
| chr18 | 67882676 | 67883206 | Intron | −50316 | Ldlrad4 | 0.677287081 | 0.00014569 |
| chr7 | 66383944 | 66384674 | Intron | −2585 | Mir7057 | 0.675761957 | 0.008599371 |
| chr4 | 33110065 | 33110631 | Intergenic | −22208 | Gabrr1 | 0.675739884 | 0.001946358 |
| chr6 | 40432921 | 40433495 | Intron | 2925 | E330009J07Rik | 0.671223819 | 3.55E−05 |
| chr5 | 112296046 | 112296524 | Intron | 19594 | Tpst2 | 0.670714723 | 0.001112873 |
| chr13 | 52849026 | 52849745 | Intron | 80292 | Auh | 0.670518106 | 0.043904613 |
| chr15 | 37346663 | 37347147 | Intron | −78649 | 4930447A16Rik | 0.670474766 | 0.025913718 |
| chr11 | 3123546 | 3124203 | Promoter-TSS | −147 | Pisd-ps1 | 0.66986752 | 5.49E−06 |
| chr18 | 54698918 | 54699379 | Intergenic | 87404 | 9330117O12Rik | 0.669112236 | 0.019789302 |
| chr19 | 41382559 | 41383178 | Intron | 2202 | Pik3ap1 | 0.668877925 | 0.009295682 |
| chr9 | 65491101 | 65491831 | Intergenic | 30529 | Spg21 | 0.668823687 | 0.041768157 |
| chr10 | 118446037 | 118446687 | TTS | 5316 | Ifng | 0.668613071 | 0.001275158 |
| chrX | 59134175 | 59134916 | Promoter-TSS | −109 | Fgf13 | 0.668527381 | 0.04476756 |
| chr14 | 73175691 | 73176186 | Intron | 30913 | Mir687 | 0.66757004 | 0.005443501 |
| chr19 | 37375715 | 37376606 | Promoter-TSS | −243 | Kifl1 | 0.667510039 | 5.37E−12 |
| chr4 | 59205257 | 59205671 | Intron | 15914 | Ugcg | 0.667252279 | 0.014231131 |
| chr7 | 65713475 | 65714075 | Intergenic | 20358 | Tm2d3 | 0.665924593 | 0.003909741 |
| chr19 | 40684143 | 40684445 | Intron | 24524 | Entpd1 | 0.664276926 | 0.02647912 |
| chr11 | 106493080 | 106493560 | Intergenic | −5524 | Ern1 | 0.663808845 | 0.04869356 |
| chr5 | 137263668 | 137264689 | Intergenic | −24076 | Ache | 0.662894806 | 0.045735226 |
| chr14 | 103345902 | 103346123 | Intron | 788 | Mycbp2 | 0.662820621 | 0.0401742 |
| chr6 | 47788328 | 47788702 | Intergenic | 15137 | Mir704 | 0.662764699 | 0.012946794 |
| chr18 | 81422476 | 81422767 | Intergenic | −436043 | Sall3 | 0.661271865 | 0.012903029 |
| chr10 | 60396823 | 60397249 | Intron | −2690 | Gm17455 | 0.660774837 | 0.014853192 |
| chr2 | 38511562 | 38512239 | Promoter-TSS | 24 | Nek6 | 0.660523573 | 0.004123519 |
| chr11 | 3164477 | 3164866 | Exon | 28792 | Sfi1 | 0.660179668 | 0.006396303 |
| chr14 | 47518519 | 47519061 | Intron | 46230 | Fbxo34 | 0.657399971 | 0.002633301 |
| chr17 | 86483948 | 86484727 | Intron | −197159 | 2010106C02Rik | 0.657164183 | 0.001875018 |
| chr4 | 135067649 | 135068232 | Intergenic | −52705 | Runx3 | 0.65677755 | 0.035280754 |
| chr1 | 164078252 | 164078807 | Intron | 16453 | Sell | 0.655401952 | 0.001530806 |
| chr11 | 115477533 | 115478479 | Intron | 2329 | Armc7 | 0.654874298 | 3.50E−14 |
| chr11 | 51931792 | 51932362 | Intergenic | −35554 | Cdkn2aipnl | 0.653641317 | 0.026442131 |
| chr3 | 107827690 | 107828333 | Intergenic | −49219 | Eps8l3 | 0.65293298 | 7.39E−08 |
| chr13 | 93786294 | 93786824 | Intron | −4218 | Mir5624 | 0.652593871 | 0.015608066 |
| chr13 | 4771225 | 4771964 | Intergenic | −162430 | Akr1e1 | 0.651868786 | 0.003386465 |
| chr1 | 134082944 | 134083540 | Intergenic | −4087 | Btg2 | 0.650331831 | 0.000295312 |
| chr6 | 114936332 | 114936904 | Intergenic | −14866 | Vgll4 | 0.649021514 | 4.08E−05 |
| chr10 | 94938840 | 94939203 | Intron | 5557 | Plxnc1 | 0.647514766 | 0.016672177 |
| chr15 | 66824702 | 66825002 | Intron | 6977 | Sla | 0.647414318 | 0.016473492 |
| chr19 | 56393391 | 56393709 | Intergenic | −3512 | Nrap | 0.646640728 | 0.047285593 |
| chr9 | 79970483 | 79971258 | Intron | 7012 | Filip1 | 0.645719505 | 1.81E−06 |
| chr11 | 52079954 | 52080484 | Intron | −18605 | Ppp2ca | 0.645711449 | 0.014816646 |
| chr11 | 98945471 | 98945662 | Intron | 5855 | Rara | 0.645107482 | 0.017089219 |
| chr14 | 64668249 | 64668516 | Intron | 15851 | Kifl3b | 0.643611452 | 0.029124464 |
| chr8 | 120051070 | 120051493 | 3' UTR | 50191 | Zdhhc7 | 0.643427851 | 0.024400331 |
| chr7 | 141088476 | 141088951 | Intron | 8944 | Pkp3 | 0.642727608 | 0.047426201 |
| chr17 | 83278725 | 83278925 | Intergenic | 63542 | Pkdcc | 0.642409204 | 0.047123224 |
| chr1 | 134065331 | 134065711 | Intergenic | 13634 | Btg2 | 0.640148095 | 0.034017991 |
| chr11 | 3153623 | 3154364 | Intron | 29972 | Pisd-ps1 | 0.639838994 | 8.71E−07 |
| chr2 | 131448065 | 131448622 | Intron | −43519 | Smox | 0.63854596 | 0.015822761 |
| chr2 | 122765013 | 122765787 | Promoter-TSS | 41 | Sqrdl | 0.637469123 | 0.000369751 |
| chr4 | 116700887 | 116701302 | Intergenic | 7291 | Mmachc | 0.636318505 | 0.021320427 |
| chr2 | 150830790 | 150831477 | 3' UTR | 44337 | Pygb | 0.636192533 | 0.01790397 |
| chr15 | 12034238 | 12034663 | Intergenic | −38443 | Sub1 | 0.634537771 | 0.038295345 |
| chr12 | 112618029 | 112618416 | Intergenic | −1825 | Adssl1 | 0.634471566 | 1.48E−05 |
| chr1 | 127611519 | 127612094 | Intron | 66215 | Tmem163 | 0.634338604 | 0.016880966 |
| chr11 | 59404141 | 59404873 | Intergenic | −28854 | Prss38 | 0.633192202 | 0.009608127 |
| chr7 | 139970354 | 139970568 | Intergenic | 8294 | 6430531B16Rik | 0.633025367 | 0.036520216 |
| chr6 | 51524978 | 51525374 | Intron | 1273 | Snx10 | 0.6327629 | 0.038081384 |
| chr6 | 31085268 | 31085693 | Intergenic | −22387 | Mir29b-1 | 0.631843254 | 0.001063543 |
| chr8 | 117289099 | 117289334 | Intron | 32197 | Cmip | 0.631498582 | 0.041425733 |
| chr9 | 56223576 | 56223960 | Intron | −62698 | Tspan3 | 0.631463778 | 8.60E−08 |
| chr1 | 71576691 | 71577325 | Intron | 19852 | Atic | 0.631213243 | 0.00813919 |
| chr5 | 125137215 | 125138370 | Intron | 41422 | Ncor2 | 0.630976168 | 0.007265956 |
| chr14 | 25161650 | 25162425 | Intergenic | −18796 | 4930572O13Rik | 0.630529955 | 0.002299824 |
| chr9 | 95959452 | 95960233 | Intron | 5082 | Xrn1 | 0.629956215 | 0.00243718 |
| chr11 | 16976961 | 16977402 | Intron | 25771 | Fbxo48 | 0.629772168 | 0.030165523 |
| chrX | 170674942 | 170675659 | Intron | 2656 | Asmt | 0.629737218 | 0.015843758 |
| chr8 | 117127138 | 117127565 | Intron | −30784 | Gan | 0.629500439 | 0.042888215 |
| chr19 | 41769124 | 41769555 | 3' UTR | 22378 | Gm19424 | 0.628030122 | 0.014413129 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr9 | 64792831 | 64793197 | Intergenic | −17997 | Dennd4a | 0.627049544 | 0.002049546 |
| chr9 | 62349259 | 62349742 | Intron | 8157 | Anp32a | 0.625956698 | 0.000429214 |
| chr1 | 127646121 | 127646822 | Intron | 31550 | Tmem163 | 0.625877671 | 1.86E−06 |
| chr2 | 147030468 | 147030992 | Intron | 17670 | Xrn2 | 0.625449671 | 0.024837082 |
| chr18 | 39250689 | 39251446 | Intron | 236178 | Nr3c1 | 0.625328024 | 0.032719547 |
| chr11 | 68726706 | 68727159 | Intron | 35017 | Myh10 | 0.624212921 | 0.038081384 |
| chr13 | 95961995 | 95962307 | Intron | −70229 | Iqgap2 | 0.623299818 | 0.006422268 |
| chr4 | 46568088 | 46568753 | Intron | −1980 | Coro2a | 0.622612654 | 0.004099265 |
| chr10 | 111583709 | 111584477 | Intergenic | 10180 | 4933440J02Rik | 0.622311522 | 0.002777959 |
| chr7 | 141562867 | 141563330 | Intron | 918 | Ap2a2 | 0.620535617 | 0.046844412 |
| chr12 | 55124194 | 55124647 | Promoter-TSS | −108 | Fam177a | 0.620188808 | 0.002476506 |
| chr4 | 109136575 | 109137110 | Intron | −18806 | Osbpl9 | 0.620059367 | 0.018300477 |
| chr6 | 49236466 | 49236615 | Intergenic | −21576 | Igf2bp3 | 0.619845669 | 0.002556671 |
| chr17 | 25211209 | 25212023 | Intron | −10966 | Unkl | 0.619018543 | 0.006703957 |
| chr5 | 113641192 | 113641384 | Intron | 9102 | Cmklr1 | 0.618478494 | 0.024542501 |
| chr11 | 95907777 | 95908198 | Intron | 6884 | B4galnt2 | 0.616505397 | 0.049063385 |
| chr8 | 86484664 | 86485289 | Intergenic | 81614 | Abcc12 | 0.616424019 | 0.034240162 |
| chr2 | 148851080 | 148851747 | Promoter-TSS | −479 | 9230104L09Rik | 0.615260021 | 0.02422574 |
| chr9 | 118082476 | 118083323 | Intron | 42377 | Azi2 | 0.61452445 | 0.022051049 |
| chr11 | 83558722 | 83559612 | Intergenic | 19469 | Ccl9 | 0.613821897 | 0.025625151 |
| chr11 | 16987594 | 16988396 | Intron | 20723 | Plek | 0.613317385 | 0.00059992 |
| chr16 | 96091541 | 96092397 | Intergenic | −9541 | Brwd1 | 0.612411598 | 0.034988692 |
| chr14 | 61589271 | 61590033 | Intergenic | −8574 | Trim13 | 0.612306323 | 0.011836845 |
| chr17 | 86122907 | 86123616 | Intron | 21914 | Srbd1 | 0.611760627 | 0.002978358 |
| chr8 | 115276078 | 115276639 | Intron | 430536 | Maf | 0.611746122 | 0.001862015 |
| chrX | 48429599 | 48429875 | Intron | 33395 | Elf4 | 0.611420666 | 0.018504877 |
| chr6 | 112948457 | 112948813 | Intergenic | −1369 | Srgap3 | 0.610913213 | 0.005522787 |
| chr12 | 13518146 | 13518712 | Intron | 109217 | Gm35725 | 0.608983062 | 0.024974569 |
| chr13 | 53001495 | 53001917 | Intergenic | −20667 | Nfil3 | 0.608027264 | 0.035992154 |
| chr7 | 66118096 | 66118469 | Intron | 8767 | Chsy1 | 0.607573531 | 0.017130472 |
| chr18 | 65697455 | 65698249 | Promoter-TSS | −416 | Oacyl | 0.607254649 | 0.012151698 |
| chr17 | 6007818 | 6008356 | Exon | 507 | Synj2 | 0.606513866 | 0.002449014 |
| chr8 | 48122773 | 48123398 | Intron | 13072 | Dctd | 0.606078975 | 0.04943311 |
| chr10 | 118395428 | 118396220 | Intergenic | −45222 | Ifng | 0.604902381 | 0.03376732 |
| chr1 | 85679891 | 85680585 | Intron | 30250 | Sp100 | 0.604539864 | 0.000482054 |
| chr16 | 11423466 | 11424147 | Intron | 18158 | Snx29 | 0.602010339 | 0.002264422 |
| chr4 | 28176791 | 28177166 | Intergenic | −636153 | Epha7 | 0.600996253 | 0.027202365 |
| chr6 | 122284653 | 122285169 | Intergenic | −2078 | Klrg1 | 0.600126223 | 0.00022046 |
| chr19 | 3943041 | 3943646 | Intron | 8157 | Unc93b1 | 0.599450999 | 0.046832066 |
| chr1 | 193338128 | 193338827 | Intron | 31805 | Camk1g | 0.598473591 | 0.001232651 |
| chr18 | 75424453 | 75424791 | Intergenic | 57257 | Smad7 | 0.598363039 | 0.03380066 |
| chrY | 90764603 | 90764965 | Intergenic | −9734 | G530011O06Rik | 0.598234709 | 6.54E−07 |
| chr4 | 41770221 | 41770679 | Promoter-TSS | −238 | Ccl27a | 0.597224721 | 6.73E−05 |
| chr18 | 79079533 | 79080446 | Intron | 29402 | Setbp1 | 0.597117579 | 1.60E−06 |
| chr14 | 47533476 | 47534191 | Intergenic | 34601 | Atg14 | 0.595179844 | 0.00125896 |
| chr6 | 128790500 | 128790826 | Intergenic | −2022 | Klrb1c | 0.595069705 | 0.027260067 |
| chr16 | 3115852 | 3116663 | Intergenic | −476141 | Olfr161 | 0.59391541 | 0.031355258 |
| chr6 | 86594798 | 86595292 | Intergenic | −33129 | Asprv1 | 0.593475745 | 0.026242604 |
| chr1 | 192778695 | 192779567 | Intergenic | −7912 | Hhat | 0.592654734 | 0.015369665 |
| chr6 | 3200764 | 3201380 | Intergenic | −87447 | Gm8579 | 0.592092641 | 0.003149128 |
| chr6 | 108503639 | 108504348 | Intron | 14250 | Mir7661 | 0.591533835 | 0.021225089 |
| chr11 | 83629661 | 83630167 | Intergenic | 19464 | Ccl3 | 0.590777356 | 0.040483512 |
| chr4 | 117136086 | 117136367 | Intergenic | −2263 | Plk3 | 0.590583763 | 0.049518994 |
| chr19 | 40687291 | 40687790 | Intron | 27770 | Entpd1 | 0.589723969 | 0.031355258 |
| chr3 | 32408473 | 32409466 | Intergenic | −27182 | Pik3ca | 0.58961047 | 0.003394324 |
| chr7 | 140983007 | 140983395 | Intergenic | 15125 | Ifitm1 | 0.588633841 | 0.01976276 |
| chr5 | 149586020 | 149586636 | Intron | −48298 | Gm15997 | 0.587545328 | 0.006046733 |
| chr9 | 123461797 | 123462189 | 3' UTR | −16708 | Limd1 | 0.58752618 | 1.13E−06 |
| chr7 | 75760348 | 75760934 | Intergenic | −87697 | Klhl25 | 0.587172291 | 0.011251992 |
| chr11 | 3141149 | 3141275 | Intron | 17191 | Pisd-ps1 | 0.586841174 | 0.020916187 |
| chr6 | 99057020 | 99057590 | Intron | −29007 | Foxp1 | 0.586305095 | 1.59E−05 |
| chr6 | 122302589 | 122303021 | Intergenic | −6205 | M6pr | 0.586211096 | 0.002882271 |
| chr3 | 89230579 | 89230924 | Exon | 1695 | Muc1 | 0.586158036 | 0.029474959 |
| chr8 | 94172184 | 94172922 | Promoter-TSS | −65 | Mt2 | 0.585837406 | 3.39E−05 |
| chr8 | 83736731 | 83737151 | Intron | 4370 | Adgre5 | 0.585022244 | 0.00559649 |
| chr1 | 91984365 | 91984930 | Intron | 183186 | Twist2 | 0.584800998 | 0.031366816 |
| chr18 | 79092538 | 79093127 | Intron | 16559 | Setbp1 | 0.584294246 | 0.01066887 |
| chr11 | 3291535 | 3291960 | Exon | 1290 | Patz1 | 0.582590777 | 0.010891252 |
| chr1 | 143465869 | 143466685 | Intergenic | −174420 | B3galt2 | 0.582452183 | 0.008916567 |
| chr4 | 149663820 | 149664328 | Promoter-TSS | −758 | Pik3cd | 0.582312871 | 0.004011754 |
| chr17 | 52168207 | 52168982 | Intergenic | 285867 | Gm20098 | 0.582289475 | 5.08E−06 |
| chrX | 76598559 | 76599130 | Intron | 4080 | Cldn34d | 0.582253488 | 0.033019 |
| chr9 | 117924681 | 117925443 | Intergenic | −115460 | Azi2 | 0.581327182 | 0.004298099 |
| chr11 | 67526493 | 67527530 | Intergenic | −5987 | Gas7 | 0.581119027 | 0.000311702 |
| chr4 | 6472810 | 6473217 | Intergenic | −18742 | Nsmaf | 0.58090001 | 0.034181884 |
| chr1 | 173437187 | 173437447 | Intron | 16713 | Aim2 | 0.579343753 | 0.021889335 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr1 | 128548535 | 128549379 | Intergenic | 43342 | Cxcr4 | 0.579280808 | 0.000416685 |
| chr6 | 97229293 | 97229741 | Intron | 18725 | Arl6ip5 | 0.579064457 | 0.038016214 |
| chr8 | 71488502 | 71488779 | 5' UTR | 537 | Gtpbp3 | 0.57863879 | 0.03268416 |
| chr7 | 135588469 | 135589239 | Intron | −4627 | Ptpre | 0.578037304 | 6.77E−09 |
| chr6 | 87504005 | 87504249 | Intron | −7800 | Arhgap25 | 0.576102357 | 0.029113064 |
| chr8 | 88592476 | 88593226 | 3' UTR | 43277 | Snx20 | 0.576079685 | 0.019967213 |
| chr13 | 51736339 | 51736934 | Intron | 57111 | Sema4d | 0.575911482 | 0.021175594 |
| chr4 | 83233842 | 83234432 | Intron | 90052 | Ttc39b | 0.575646652 | 0.023948093 |
| chr9 | 106430799 | 106431087 | Intron | 1532 | Rpl29 | 0.574455362 | 0.047020852 |
| chr16 | 98107507 | 98107770 | Intergenic | −25199 | A630089N07Rik | 0.57392051 | 0.030166715 |
| chr11 | 68465042 | 68465438 | Intron | 33115 | Pik3r5 | 0.572549032 | 0.042888215 |
| chr11 | 3157380 | 3157657 | Intron | 33497 | Pisd-ps1 | 0.572118335 | 0.046214456 |
| chr17 | 70963895 | 70963895 | Intergenic | 26739 | Myl12b | 0.571715143 | 0.006944208 |
| chr1 | 152253630 | 152254371 | Intergenic | 132682 | Tsen15 | 0.571033787 | 0.027202365 |
| chr9 | 42032470 | 42032807 | Intron | 91651 | Sorl1 | 0.570399545 | 0.027260067 |
| chr19 | 40707985 | 40708545 | Intron | 48495 | Entpd1 | 0.569470153 | 0.025347803 |
| chr10 | 88417730 | 88418049 | Intron | 38477 | Gnptab | 0.568083732 | 0.018506264 |
| chr2 | 127310029 | 127310543 | Intergenic | −25873 | Dusp2 | 0.567635648 | 0.014449212 |
| chr4 | 127015296 | 127015998 | Intergenic | −5654 | Sfpq | 0.567501122 | 0.003322494 |
| chr3 | 52297290 | 52297786 | Intron | 29201 | Foxo1 | 0.565834715 | 0.014548237 |
| chr4 | 116159722 | 116160393 | TTS | 7541 | Tspan1 | 0.564952073 | 0.009814701 |
| chr10 | 128626378 | 128626617 | Promoter-TSS | 9 | Rps26 | 0.564909081 | 0.026462047 |
| chr9 | 102572799 | 102573498 | Intergenic | 52976 | Cep63 | 0.56392151 | 0.034666483 |
| chr4 | 106590774 | 106591203 | TTS | 26250 | Lexm | 0.563654312 | 0.021225089 |
| chr7 | 106270859 | 106271300 | Intergenic | 53449 | Gm8989 | 0.563346391 | 0.030488308 |
| chr9 | 66281352 | 66281932 | Intergenic | −68808 | Herc1 | 0.562735158 | 0.000947463 |
| chr18 | 34854517 | 34854755 | Intergenic | −6571 | Egr1 | 0.562120742 | 0.040314837 |
| chr17 | 44702905 | 44703426 | Intron | 33011 | Runx2 | 0.56126009 | 0.035297229 |
| chr10 | 118404485 | 118404911 | Intergenic | −36348 | Ifng | 0.560945447 | 0.019307473 |
| chr8 | 124265650 | 124266254 | Intron | 34558 | Galnt2 | 0.560467789 | 2.93E−09 |
| chr11 | 95259091 | 95259919 | Intergenic | −2024 | Tac4 | 0.560366932 | 0.000687465 |
| chr6 | 58844172 | 58844743 | Intron | 10757 | Herc3 | 0.56014178 | 0.001875018 |
| chr4 | 106590099 | 106590683 | TTS | 26847 | Lexm | 0.559983554 | 0.02147042 |
| chr7 | 118113456 | 118114140 | Intron | 2349 | Rps15a | 0.559267884 | 0.002967819 |
| chr3 | 30601212 | 30601495 | Promoter-TSS | −734 | Mynn | 0.557965891 | 0.032629938 |
| chr6 | 28482816 | 28483189 | Intron | 2654 | Snd1 | 0.557786388 | 0.010067215 |
| chr4 | 9668619 | 9669523 | Promoter-TSS | 91 | Asph | 0.557143385 | 1.33E−05 |
| chr17 | 27203842 | 27204669 | Exon | 183 | Lemd2 | 0.556953945 | 0.001241617 |
| chr11 | 3176517 | 3176815 | Intron | 16797 | Sfi1 | 0.556196662 | 0.009179072 |
| chr5 | 125052133 | 125052951 | Intron | 49067 | Rflna | 0.55618944 | 0.000333523 |
| chr2 | 35978410 | 35979031 | Intron | 904 | Ttll11 | 0.555565639 | 0.001661334 |
| chr12 | 55199279 | 55200165 | Exon | 130 | 1700047I17Rik2 | 0.554539032 | 0.000381034 |
| chr14 | 64678053 | 64678510 | Intron | 25750 | Kif13b | 0.554322732 | 0.010606345 |
| chr12 | 55154703 | 55155734 | 5' UTR | 114 | Srp54b | 0.55349536 | 3.51E−08 |
| chr10 | 19596831 | 19597416 | Intron | 5174 | Ifngr1 | 0.553295409 | 0.002835111 |
| chr10 | 88418179 | 88418422 | Intron | 38888 | Gnptab | 0.553277414 | 0.036467288 |
| chr11 | 58959913 | 58960545 | Intergenic | −1482 | Gm12260 | 0.553187235 | 0.000558601 |
| chr17 | 39847310 | 39847400 | Non-Coding | 4358 | Rn45s | 0.552561754 | 0.001402973 |
| chr14 | 25421550 | 25422385 | Intergenic | −37218 | Zmiz1 | 0.551981409 | 0.000233337 |
| chr11 | 104609408 | 104609705 | Intron | 1566 | Itgb3 | 0.550706308 | 0.035440191 |
| chr4 | 155491012 | 155491673 | Promoter-TSS | −19 | Gnb1 | 0.549622546 | 0.03611854 |
| chrX | 169990324 | 169990687 | 3' UTR | −11588 | G530011O06Rik | 0.547833385 | 6.17E−05 |
| chr15 | 102377767 | 102378306 | Intergenic | −11765 | Sp7 | 0.547137849 | 0.000135634 |
| chr19 | 21713316 | 21714576 | Intergenic | 60637 | Abhd17b | 0.546162062 | 0.045981626 |
| chr15 | 100750201 | 100750652 | Intergenic | −11321 | Slc4a8 | 0.546076902 | 0.016003376 |
| chr7 | 4492712 | 4493283 | Intron | 8683 | Ppp1r12c | 0.545856787 | 0.02827229 |
| chr14 | 124801262 | 124802239 | Intergenic | −124623 | Fgf14 | 0.545082523 | 0.00234323 |
| chr17 | 86495684 | 86496699 | Intron | −209013 | 2010106C02Rik | 0.544283307 | 0.002509748 |
| chr2 | 71810122 | 71810449 | Intron | 23346 | Itga6 | 0.543981026 | 0.030447414 |
| chr16 | 17085412 | 17085953 | TTS | 15543 | Ypel1 | 0.543676606 | 0.047548486 |
| chr5 | 77211687 | 77212284 | Promoter-TSS | −514 | Spink2 | 0.543487847 | 0.016846283 |
| chr19 | 57994266 | 57994914 | Intron | −56577 | Mir5623 | 0.542485087 | 0.001953974 |
| chr8 | 94191240 | 94191686 | Intergenic | 12329 | Mt1 | 0.542091245 | 0.003597624 |
| chr3 | 104762107 | 104762687 | Intergenic | 15150 | Fam19a3 | 0.541960554 | 8.38E−06 |
| chr4 | 43968639 | 43968977 | Intron | 11106 | Glipr2 | 0.541363769 | 0.048304219 |
| chr18 | 80609665 | 80609882 | Intron | −65227 | Gm2176 | 0.540903055 | 0.027152923 |
| chr14 | 31661972 | 31663272 | Intron | 21565 | Btd | 0.540333239 | 0.014392872 |
| chr17 | 6016434 | 6016843 | Intron | 9058 | Synj2 | 0.540265618 | 0.049567194 |
| chr7 | 47139733 | 47140450 | Intergenic | −6407 | Ptpn5 | 0.539526535 | 0.014532952 |
| chr1 | 92468839 | 92469395 | Intron | −4575 | Mir6900 | 0.539398218 | 0.007701214 |
| chr11 | 98939569 | 98939900 | Promoter-TSS | 23 | Rara | 0.539327296 | 0.021576515 |
| chr11 | 68435541 | 68435997 | Intron | 3644 | Pik3r5 | 0.53896551 | 0.02673327 |
| chr1 | 153065702 | 153066858 | Intron | 111179 | Nmnat2 | 0.538859166 | 0.023381581 |
| chr4 | 154105356 | 154106009 | Intron | −8509 | Trp73 | 0.537966841 | 0.039124051 |
| chr13 | 113548892 | 113549608 | Intergenic | −46406 | 4921509O07Rik | 0.53757015 | 0.000998985 |
| chr11 | 3332032 | 3332678 | Intron | 1624 | Pik3ip1 | 0.537008595 | 1.99E−05 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr2 | 75634427 | 75634887 | Intergenic | −24602 | Hnrnpa3 | 0.536267665 | 0.01880293 |
| chr5 | 143976706 | 143977079 | Intergenic | 37961 | Ccz1 | 0.535611504 | 0.034912692 |
| chr10 | 81537076 | 81537741 | Intron | 7638 | Gna11 | 0.53535055 | 0.019819002 |
| chr2 | 25913167 | 25913758 | Intron | 35679 | Kcnt1 | 0.535110111 | 0.027992541 |
| chr19 | 8982698 | 8983668 | Intergenic | −6101 | Ahnak | 0.535066448 | 7.51E−05 |
| chr1 | 138157053 | 138157365 | Intron | 17917 | Ptprc | 0.534692594 | 0.029964056 |
| chr11 | 3265992 | 3266751 | Promoter-TSS | 15 | Drg1 | 0.534210469 | 0.005485782 |
| chr5 | 24029383 | 24029787 | Intron | 727 | Fam126a | 0.533811525 | 0.02673327 |
| chr2 | 168429282 | 168429941 | Intergenic | −160280 | Kcng1 | 0.533289571 | 0.000436275 |
| chr13 | 112578169 | 112578349 | Intron | 2403 | Il31ra | 0.533073976 | 0.029415788 |
| chr11 | 3335804 | 3336261 | Intron | 5301 | Pik3ip1 | 0.532674952 | 0.001983813 |
| chr7 | 101453341 | 101453832 | Intron | 2334 | Pde2a | 0.530939763 | 0.049473874 |
| chr1 | 24684022 | 24684280 | Intron | 5233 | Lmbrd1 | 0.530184947 | 0.009499403 |
| chr12 | 73656524 | 73657241 | Intron | 72086 | Prkch | 0.529734137 | 0.011241103 |
| chr1 | 153426816 | 153427213 | Intron | 1805 | Shcbp1l | 0.529483907 | 0.028631808 |
| chr13 | 93814729 | 93815469 | Intron | 24322 | Mir5624 | 0.529443867 | 0.02494861 |
| chr13 | 45964880 | 45965735 | Promoter-TSS | −316 | Atxn1 | 0.527706035 | 0.000347511 |
| chr5 | 105609684 | 105610133 | TTS | −90061 | Lrrc8d | 0.526848827 | 0.002095533 |
| chr11 | 3514505 | 3515049 | Promoter-TSS | 93 | Selenom | 0.526265801 | 0.006006008 |
| chr5 | 149604856 | 149605142 | Intron | 31316 | Hsph1 | 0.526154484 | 0.003930761 |
| chr4 | 97831131 | 97832181 | Intron | 54030 | Nfia | 0.524916122 | 0.012584554 |
| chr3 | 52927349 | 52927883 | Promoter-TSS | 50 | Gm20750 | 0.524861545 | 0.017860501 |
| chr1 | 135146389 | 135147763 | Exon | 242 | Arl8a | 0.524347305 | 0.001959888 |
| chr10 | 77540609 | 77541016 | Intron | 10464 | Itgb2 | 0.523854932 | 0.004606423 |
| chr5 | 139320517 | 139320886 | Intron | 4763 | Adap1 | 0.521478255 | 0.010422633 |
| chr14 | 103531549 | 103532780 | Intron | 18823 | Scel | 0.520797474 | 0.002594922 |
| chr9 | 107309159 | 107309524 | Intergenic | 12682 | Cish | 0.51892078 | 0.041480484 |
| chr16 | 11144170 | 11144318 | Intron | −9712 | Txndc11 | 0.518844759 | 0.005316903 |
| chr6 | 31191616 | 31192385 | Intron | 26474 | Lncpint | 0.518204953 | 0.030119604 |
| chr9 | 114775449 | 114775944 | Intron | 6297 | Cmtm7 | 0.517993086 | 0.024235063 |
| chr2 | 150451127 | 150451961 | Promoter-TSS | −43 | Zfp442 | 0.517958603 | 0.047020852 |
| chr7 | 43442258 | 43442515 | Intron | 1570 | Cldnd2 | 0.517594618 | 0.048351927 |
| chr6 | 121238232 | 121238708 | Intergenic | −7436 | Usp18 | 0.517402929 | 0.018113858 |
| chr6 | 140466290 | 140466709 | Intron | 42400 | Plekha5 | 0.517176707 | 0.032154109 |
| chr7 | 45921087 | 45921609 | Promoter-TSS | 78 | Emp3 | 0.517066575 | 0.019905413 |
| chr11 | 62551394 | 62551793 | Promoter-TSS | 89 | Gm1821 | 0.516905859 | 0.007449768 |
| chr3 | 90605080 | 90605487 | Intron | 1513 | S100a4 | 0.516770831 | 0.007732351 |
| chr8 | 122430353 | 122430607 | Intron | 2460 | Cyba | 0.516583097 | 0.032717468 |
| chr11 | 80504902 | 80505402 | Intron | 3954 | C030013C21Rik | 0.515087643 | 0.01757138 |
| chr6 | 130342007 | 130342654 | Intron | −4704 | Klra3 | 0.514456806 | 0.042805787 |
| chr7 | 126289390 | 126289744 | Intron | 16948 | Sbk1 | 0.51442088 | 0.042867803 |
| chr14 | 61327761 | 61328274 | Intergenic | 18264 | Arl11 | 0.513575459 | 0.033982094 |
| chr7 | 49762355 | 49763026 | Intron | 3178 | Htatip2 | 0.512920992 | 0.033546698 |
| chr10 | 21976276 | 21976726 | Intron | −2171 | Sgk1 | 0.512809616 | 0.020973742 |
| chr11 | 94997792 | 94998461 | Intron | 6914 | Ppp1r9b | 0.512170496 | 0.031297017 |
| chr1 | 127692978 | 127694021 | Intergenic | −15478 | Tmem163 | 0.512090531 | 0.002163727 |
| chr8 | 14990793 | 14991058 | Intron | −20100 | Kbtbd11 | 0.511921355 | 0.048821799 |
| chr9 | 86624783 | 86625349 | Intron | 53013 | Rwdd2a | 0.511351521 | 0.004445173 |
| chr4 | 132946050 | 132946907 | Intergenic | −23927 | Fam76a | 0.510554864 | 0.014034431 |
| chr10 | 128891074 | 128891739 | Exon | 309 | Gdf11 | 0.509354642 | 0.042432956 |
| chr19 | 21897165 | 21897823 | Intergenic | 119154 | Tmem2 | 0.508569063 | 0.041713871 |
| chr12 | 21472489 | 21472907 | Intergenic | −55262 | Ywhaq | 0.508162269 | 0.022760646 |
| chr19 | 38054229 | 38055389 | Promoter-TSS | −216 | Cep55 | 0.507152712 | 1.50E−06 |
| chr9 | 79815980 | 79816455 | Intron | 22576 | 4930429F24Rik | 0.507029399 | 0.024494534 |
| chrX | 169986654 | 169987216 | Intron | −8018 | G530011O06Rik | 0.506852782 | 2.92E−05 |
| chr19 | 53254360 | 53254986 | Intron | 532 | 1700001K23Rik | 0.506844593 | 0.007165124 |
| chr3 | 87840881 | 87841253 | Intergenic | −5688 | Sh2d2a | 0.50661867 | 0.003711913 |
| chr1 | 39986784 | 39987373 | Intron | 86165 | Map4k4 | 0.506601366 | 0.001101574 |
| chr17 | 6008526 | 6009032 | Intron | 1199 | Synj2 | 0.506563109 | 0.030377975 |
| chr10 | 83183596 | 83184546 | Intron | 153746 | Slc41a2 | 0.506104151 | 0.029175959 |
| chr6 | 140512133 | 140512646 | Intron | 88290 | Plekha5 | 0.504797452 | 0.042982803 |
| chr15 | 76299411 | 76300247 | Intron | 5395 | Smpd5 | 0.504627711 | 0.004270433 |
| chr2 | 168219273 | 168219983 | Intron | 10751 | Dpm1 | 0.504015356 | 0.000505221 |
| chr3 | 79181247 | 79181948 | Intergenic | −31322 | 4921511C10Rik | 0.503676426 | 0.021269644 |
| chr11 | 3181180 | 3181605 | Intron | 12071 | Sfi1 | 0.500981842 | 0.00515975 |
| chr13 | 95719509 | 95720228 | Intron | 22948 | F2rl2 | 0.500640214 | 0.009579527 |
| chr10 | 34172722 | 34173248 | Intron | 34566 | Dse | 0.500581921 | 0.008925203 |
| chr7 | 3290091 | 3290578 | Promoter-TSS | −221 | Myadm | 0.500571373 | 0.029691049 |
| chr11 | 121559434 | 121559985 | Intron | −40367 | Zfp750 | 0.498942199 | 0.02673327 |
| chr6 | 3536106 | 3536771 | Intron | 38045 | Vps50 | 0.498902145 | 0.011836845 |
| chr4 | 138257123 | 138257671 | Intron | −4854 | Kif17 | 0.498826518 | 0.041497774 |
| chr5 | 136149093 | 136149670 | 3′ UTR | 10600 | Alkbh4 | 0.497446358 | 0.016306972 |
| chr9 | 107950616 | 107951345 | Promoter-TSS | 17 | Traip | 0.497218436 | 0.032493231 |
| chrY | 90788844 | 90789038 | Intron | 3499 | Erdr1 | 0.497201934 | 0.031235546 |
| chr2 | 122348447 | 122349231 | TTS | 20079 | Shf | 0.49646003 | 0.041785028 |
| chr16 | 93585097 | 93586785 | Intron | 17874 | Setd4 | 0.49559698 | 1.33E−06 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr5 | 31713746 | 31714580 | Intron | 16113 | Bre | 0.495211942 | 0.028996698 |
| chr19 | 61266769 | 61266920 | Intergenic | −38426 | Csf2ra | 0.494064312 | 0.00511133 |
| chr1 | 176827283 | 176828045 | Intron | 8469 | Hmga2-ps1 | 0.493023577 | 0.005242494 |
| chr12 | 55229755 | 55230797 | Promoter-TSS | 108 | Srp54b | 0.492274773 | 3.27E−05 |
| chr6 | 127616872 | 127617861 | Intron | 39391 | Cracr2a | 0.492028132 | 0.007166291 |
| chr13 | 101707272 | 101707844 | Intron | −14928 | Pik3r1 | 0.491697259 | 0.000100448 |
| chr7 | 142994972 | 142995397 | Intergenic | −9862 | Tspan32 | 0.490144869 | 0.007632535 |
| chr2 | 144167141 | 144168115 | Intergenic | 21662 | Gm5535 | 0.490139757 | 0.000147032 |
| chr7 | 145340930 | 145341453 | Intergenic | 26356 | Mrgprd | 0.489931596 | 0.014366331 |
| chr10 | 3112374 | 3112624 | Intergenic | 20694 | B020014A21Rik | 0.489517874 | 0.010606601 |
| chr15 | 80024137 | 80024930 | Intergenic | −9725 | Pdgfb | 0.488734788 | 0.029174761 |
| chr14 | 59297329 | 59297831 | Promoter-TSS | −58 | Phf11a | 0.488080471 | 0.034641777 |
| chr2 | 128499614 | 128500246 | Intergenic | −70579 | Gm14005 | 0.488073925 | 0.013295299 |
| chr1 | 88267712 | 88268208 | Non-Coding | 1448 | 6430706D22Rik | 0.487453755 | 0.049688604 |
| chr18 | 74772901 | 74773613 | Intergenic | 5198 | Scarna17 | 0.487187591 | 0.017408107 |
| chr17 | 5491222 | 5491716 | Intergenic | −1131 | Zdhhc14 | 0.486966615 | 0.030447414 |
| chr11 | 3539044 | 3539711 | Promoter-TSS | −85 | Smtn | 0.486925211 | 0.011353868 |
| chr18 | 39035075 | 39035906 | Intron | 42345 | Arhgap26 | 0.486662052 | 0.011811831 |
| chr10 | 98776368 | 98776927 | Intergenic | −138505 | Atp2b1 | 0.486130124 | 0.012746989 |
| chr5 | 100573255 | 100573724 | Intergenic | −1284 | Plac8 | 0.485937171 | 0.027202365 |
| chr11 | 4594314 | 4595179 | Promoter-TSS | 69 | Mtmr3 | 0.485657092 | 0.018287317 |
| chr15 | 102147727 | 102148277 | Intron | −2573 | Soat2 | 0.484701859 | 0.021810199 |
| chr6 | 142561059 | 142562010 | Intergenic | 10080 | Kcnj8 | 0.484400256 | 0.011205083 |
| chr3 | 116466309 | 116466822 | Intergenic | 41610 | Rtca | 0.484278449 | 0.00409631 |
| chr2 | 174327282 | 174327538 | Promoter-TSS | −358 | Gnas | 0.484131696 | 0.03611854 |
| chr10 | 80763392 | 80763994 | Intron | 8487 | Dot1l | 0.484082228 | 0.007629076 |
| chr19 | 41360472 | 41361093 | Intron | 24288 | Pik3ap1 | 0.483187548 | 0.016971833 |
| chr19 | 37110409 | 37111060 | Intron | −63109 | A330032B11Rik | 0.483127376 | 0.01442617 |
| chr17 | 32364104 | 32364739 | Intron | −13844 | Akap8l | 0.482797596 | 0.033689193 |
| chr1 | 195241820 | 195242066 | Intergenic | −65228 | Cr2 | 0.482282172 | 0.013674626 |
| chr16 | 30024555 | 30025247 | Intron | 14578 | 9030404E10Rik | 0.481591633 | 0.036838357 |
| chr16 | 93552656 | 93553352 | Intergenic | 50811 | Setd4 | 0.48135004 | 0.005021261 |
| chr9 | 123518930 | 123519799 | 3′ UTR | −10518 | Sacm1l | 0.481031841 | 0.014753207 |
| chr10 | 60395539 | 60396097 | Intron | −3908 | Gm17455 | 0.481015179 | 0.042227317 |
| chr6 | 108630682 | 108631567 | Intron | −7957 | 0610040F04Rik | 0.480266785 | 0.000691262 |
| chrY | 90772053 | 90772890 | Intergenic | −12971 | Erdr1 | 0.479852042 | 1.05E−07 |
| chr1 | 164136717 | 164137007 | Intron | −14973 | F5 | 0.479087294 | 0.03625683 |
| chr1 | 40381027 | 40381365 | Intergenic | −48374 | Il1rl1 | 0.479044754 | 0.038190389 |
| chr3 | 97932148 | 97932612 | Intron | 2207 | Gm5544 | 0.478433166 | 0.004313016 |
| chr13 | 91370869 | 91371517 | Non-Coding | 16892 | A830009L08Rik | 0.478331124 | 0.00047087 |
| chr10 | 3113529 | 3114027 | Intergenic | 19415 | B020014A21Rik | 0.477662733 | 0.009459817 |
| chr11 | 83530377 | 83530739 | Promoter-TSS | −40 | Ccl5 | 0.477373108 | 0.020343067 |
| chr11 | 5098930 | 5099549 | Promoter-TSS | −34 | Rhbdd3 | 0.477301644 | 0.031412012 |
| chr8 | 124319329 | 124319595 | Intron | 88068 | Galnt2 | 0.47668105 | 0.022997705 |
| chr10 | 94848186 | 94848856 | Intron | 96057 | Plxnc1 | 0.475956602 | 0.003542712 |
| chr1 | 128830266 | 128831084 | Intergenic | −238571 | Cxcr4 | 0.474867302 | 0.023438661 |
| chr14 | 56261981 | 56262784 | Promoter-TSS | −48 | Gzmb | 0.474095177 | 0.003082008 |
| chr18 | 84798941 | 84799627 | Intergenic | −52130 | Cyb5a | 0.472381535 | 0.015229849 |
| chr11 | 102229776 | 102230602 | Promoter-TSS | −17 | Hdac5 | 0.471938082 | 0.043658454 |
| chr14 | 56296810 | 56297462 | Intergenic | −34802 | Gzmb | 0.471687667 | 0.005769387 |
| chr11 | 69411683 | 69412122 | Intron | 1773 | Kdm6b | 0.471506877 | 0.008457364 |
| chr11 | 32535636 | 32536000 | Intron | 2552 | Stk10 | 0.470847366 | 0.038675809 |
| chr15 | 76616333 | 76617573 | Promoter-TSS | −101 | Slc39a4 | 0.470595852 | 0.006447708 |
| chr18 | 75428335 | 75428869 | Intergenic | 61246 | Smad7 | 0.470318355 | 0.022746709 |
| chr3 | 108017467 | 108018695 | Promoter-TSS | −108 | Gstm1 | 0.470005614 | 0.000133984 |
| chr13 | 84347860 | 84348763 | Intergenic | 126015 | Tmem161b | 0.469907438 | 0.002015327 |
| chr11 | 79652846 | 79653745 | Intron | 21791 | Rab11fip4os2 | 0.469490303 | 0.014430893 |
| chr11 | 3201866 | 3203434 | Promoter-TSS | 67 | Eif4enif1 | 0.468699438 | 0.004083515 |
| chr4 | 140952353 | 140952869 | TTS | 5291 | Gm13031 | 0.468550622 | 0.026442131 |
| chr19 | 60182807 | 60183555 | Intergenic | 38506 | E330013P04Rik | 0.467873262 | 0.043288559 |
| chr7 | 128050719 | 128051310 | Intergenic | −11626 | Itgam | 0.467354093 | 0.007597906 |
| chr11 | 61407631 | 61408473 | Intergenic | −29977 | Slc47a1 | 0.46619527 | 0.023230382 |
| chr1 | 134962179 | 134962856 | Promoter-TSS | −48 | Ube2t | 0.46568695 | 0.000120729 |
| chr11 | 3408905 | 3409586 | Promoter-TSS | −7 | Limk2 | 0.465481377 | 0.004577774 |
| chr3 | 101277811 | 101278172 | Intron | 9948 | Cd2 | 0.465352179 | 0.012605668 |
| chr6 | 31220219 | 31220860 | Intron | 188 | 2210408F21Rik | 0.465144229 | 0.042910309 |
| chr15 | 102246759 | 102247734 | Promoter-TSS | −746 | Rarg | 0.464728147 | 0.018666299 |
| chr3 | 101285831 | 101286192 | Intron | 1928 | Cd2 | 0.464006835 | 0.014886249 |
| chr13 | 45442972 | 45443556 | Intergenic | 53522 | Mylip | 0.463972071 | 0.029368914 |
| chr7 | 135537334 | 135538234 | Promoter-TSS | −40 | Ptpre | 0.463781589 | 0.005976147 |
| chr10 | 79936918 | 79937561 | Intron | 9898 | Arid3a | 0.463674968 | 0.022988599 |
| chr11 | 104613521 | 104613854 | Intron | 5687 | Itgb3 | 0.463067535 | 0.006466683 |
| chr9 | 57439618 | 57440264 | Intron | 173 | Ppcdc | 0.462276751 | 0.0127874 |
| chr1 | 165730131 | 165730537 | Intergenic | −22240 | Rcsd1 | 0.461822651 | 0.035573592 |
| chr1 | 138954535 | 138955393 | Intergenic | −8745 | Dennd1b | 0.461596331 | 0.037321188 |
| chr11 | 88203749 | 88204832 | Promoter-TSS | −98 | Mrps23 | 0.461455402 | 0.005539897 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr5 | 124084069 | 124084607 | Intron | 11460 | Abcb9 | 0.461012135 | 0.011247026 |
| chr4 | 57954420 | 57954802 | Intron | 1800 | Txn1 | 0.460906009 | 0.036136524 |
| chr7 | 65714248 | 65714793 | Intergenic | 21103 | Tm2d3 | 0.460555905 | 0.021175594 |
| chr2 | 117373918 | 117374775 | Intergenic | −31469 | Rasgrp1 | 0.460553855 | 0.027333147 |
| chr3 | 107759812 | 107760772 | 5' UTR | 177 | Csf1 | 0.460550046 | 0.000403687 |
| chr2 | 144245249 | 144245798 | Intergenic | 20679 | Snord17 | 0.460146979 | 0.043833512 |
| chr10 | 94942747 | 94943108 | Intron | 1651 | Plxnc1 | 0.458425633 | 0.009595076 |
| chr14 | 30625995 | 30626732 | Promoter-TSS | −155 | Prkcd | 0.458221334 | 0.015416718 |
| chr11 | 60699400 | 60700200 | 5' UTR | 110 | Llgl1 | 0.458170419 | 0.0224904 |
| chr11 | 84916088 | 84916663 | Promoter-TSS | −19 | Znhit3 | 0.457554976 | 0.024995157 |
| chr15 | 76274240 | 76274995 | Intron | −4778 | Mirt2 | 0.457472769 | 0.032933231 |
| chr11 | 46072646 | 46074703 | Intron | 17690 | Adam19 | 0.457385773 | 0.002112513 |
| chr1 | 134110928 | 134111324 | Promoter-TSS | −116 | Chit1 | 0.457003508 | 0.005242494 |
| chr8 | 120667629 | 120668533 | Promoter-TSS | 31 | Emc8 | 0.456087513 | 0.000730523 |
| chr14 | 60712328 | 60712843 | Intron | −20319 | Spata13 | 0.456032189 | 0.005769387 |
| chr13 | 93764439 | 93765023 | Intergenic | −6948 | Arsb | 0.456004343 | 0.04592308 |
| chr5 | 121219958 | 121220830 | 5' UTR | 175 | Gm15800 | 0.455801598 | 0.027647066 |
| chr2 | 128318229 | 128318617 | Intron | 110928 | Gm14005 | 0.455678456 | 0.021489506 |
| chr19 | 53890960 | 53891252 | Intergenic | −1125 | Pdcd4 | 0.454989162 | 0.031056384 |
| chr1 | 184013039 | 184013806 | Intergenic | 20576 | 1700056E22Rik | 0.454360563 | 0.018465878 |
| chr11 | 86757287 | 86758389 | Promoter-TSS | −346 | Cltc | 0.453833945 | 5.63E−06 |
| chr8 | 27260043 | 27260747 | Promoter-TSS | 68 | Eif4ebp1 | 0.452144757 | 0.040368344 |
| chr5 | 115011713 | 115012479 | Intron | 572 | Sppl3 | 0.451868025 | 0.023886777 |
| chr10 | 61334414 | 61334900 | Intron | 36821 | Prf1 | 0.451429921 | 0.01236688 |
| chr7 | 79249293 | 79249942 | Intergenic | −23649 | Abhd2 | 0.450450271 | 0.028052079 |
| chr5 | 140617741 | 140618173 | Intergenic | 10616 | Lfng | 0.449302127 | 0.000981738 |
| chr19 | 53395567 | 53396115 | Intergenic | −5268 | Smndc1 | 0.449267434 | 0.021496267 |
| chr7 | 16309985 | 16310505 | Intron | 662 | Bbc3 | 0.448785937 | 0.023710444 |
| chr10 | 61296913 | 61297454 | Promoter-TSS | −653 | Prf1 | 0.448044812 | 0.012923049 |
| chr2 | 180709631 | 180710742 | Promoter-TSS | −40 | Gid8 | 0.447555484 | 0.000151739 |
| chr2 | 163642720 | 163643161 | Intron | −1910 | 0610039K10Rik | 0.44619364 | 0.042245921 |
| chr4 | 16163250 | 16164434 | Promoter-TSS | −199 | Ripk2 | 0.44612238 | 3.27E−07 |
| chrX | 50874196 | 50874749 | Intron | 33186 | Stk26 | 0.446001805 | 0.010968396 |
| chr9 | 57836621 | 57837117 | Intergenic | −2635 | Arid3b | 0.445871977 | 0.032978054 |
| chr11 | 83649061 | 83649878 | Promoter-TSS | −91 | Ccl3 | 0.44563461 | 0.001488476 |
| chr5 | 112301761 | 112302149 | Intron | −24414 | Tfip11 | 0.445280867 | 0.016083384 |
| chr19 | 10948950 | 10949476 | Promoter-TSS | 53 | Ccdc86 | 0.445276354 | 0.038997773 |
| chr10 | 96350546 | 96351624 | Intergenic | 124878 | 4930459C07Rik | 0.445201547 | 0.000120721 |
| chr6 | 92091136 | 92091579 | Promoter-TSS | −61 | Nr2c2 | 0.444919217 | 0.048181546 |
| chr19 | 46002293 | 46002616 | Intergenic | −1024 | Hps6 | 0.444314738 | 0.022272878 |
| chr1 | 97659325 | 97659812 | Intron | 2450 | D1Ertd622e | 0.443622219 | 0.040537292 |
| chr11 | 6546202 | 6547401 | Promoter-TSS | −86 | Ccm2 | 0.443392034 | 0.003561187 |
| chr1 | 131526874 | 131527236 | Promoter-TSS | 306 | Srgap2 | 0.443141978 | 0.007193179 |
| chr18 | 49979021 | 49980075 | 5' UTR | 121 | Tnfaip8 | 0.442923952 | 0.000749771 |
| chrX | 48424251 | 48425061 | Intron | 38476 | Elf4 | 0.442923593 | 0.002608444 |
| chr11 | 3648719 | 3649903 | Promoter-TSS | −183 | Morc2a | 0.442881526 | 0.000210486 |
| chr2 | 128072846 | 128073525 | Intron | −52853 | Bcl2l11 | 0.442752493 | 0.008269783 |
| chrX | 169997784 | 169998542 | Intergenic | −19246 | G530011O06Rik | 0.442323406 | 1.61E−05 |
| chr13 | 95696748 | 95697310 | 5' UTR | 109 | F2rl2 | 0.44182234 | 0.026086868 |
| chr2 | 13573258 | 13573995 | Promoter-TSS | −685 | Vim | 0.441540122 | 0.015477509 |
| chr11 | 117333871 | 117334486 | Intron | 1865 | Sept9 | 0.441424595 | 0.046097412 |
| chrX | 169991026 | 169991568 | TTS | −12380 | G530011O06Rik | 0.440884182 | 5.66E−05 |
| chr11 | 6199813 | 6200574 | 5' UTR | 258 | Nudcd3 | 0.440882066 | 0.018032192 |
| chr11 | 3913685 | 3914650 | 5' UTR | 566 | Slc35e4 | 0.440485792 | 0.027787341 |
| chr5 | 23433790 | 23434596 | Promoter-TSS | 160 | 5031425E22Rik | 0.440373614 | 0.00707221 |
| chr12 | 84192756 | 84193438 | Intron | 918 | Elmsan1 | 0.440244555 | 0.005663021 |
| chr6 | 41140750 | 41141610 | Intergenic | −105671 | 2210010C04Rik | 0.440181057 | 0.013437082 |
| chr2 | 120026727 | 120027996 | Promoter-TSS | −122 | Gm28042 | 0.440160378 | 0.001521576 |
| chr2 | 181377157 | 181377649 | Intron | −3832 | Lime1 | 0.439794955 | 0.022422872 |
| chr10 | 127654935 | 127655648 | Intron | 11412 | Nab2 | 0.439717752 | 0.042658916 |
| chr11 | 88973746 | 88974645 | Exon | 260 | Coil | 0.439199524 | 0.044619506 |
| chr18 | 75489116 | 75489714 | Intron | −25230 | Gm10532 | 0.439187179 | 0.021869051 |
| chr5 | 21248805 | 21249530 | Intron | 62900 | Gsap | 0.438657705 | 0.002938157 |
| chr4 | 117220645 | 117221399 | Intron | 30895 | Gm1661 | 0.438561386 | 0.043222648 |
| chr5 | 137745653 | 137746471 | Promoter-TSS | 93 | Tsc22d4 | 0.437929698 | 0.006943233 |
| chrY | 90765310 | 90765883 | Intergenic | −10546 | G530011O06Rik | 0.437916952 | 4.18E−06 |
| chr7 | 139974238 | 139974714 | Intron | 4279 | 6430531B16Rik | 0.437402852 | 0.001680742 |
| chr10 | 83004026 | 83004881 | Intron | 18956 | Chst11 | 0.437009575 | 0.013692577 |
| chr6 | 87037855 | 87038571 | Intergenic | −4633 | Gfpt1 | 0.436906129 | 0.015629865 |
| chr18 | 84589422 | 84590077 | Promoter-TSS | −245 | Zfp407 | 0.435633978 | 0.005580251 |
| chr10 | 128504572 | 128505258 | TTS | 5668 | A430046D13Rik | 0.435195909 | 0.042644939 |
| chr11 | 104667313 | 104668047 | 3' UTR | 59680 | Itgb3 | 0.432871512 | 0.041238449 |
| chr13 | 51792321 | 51793183 | Intron | 995 | Sema4d | 0.432858578 | 0.032553159 |
| chr11 | 115491319 | 115492135 | Promoter-TSS | 87 | Nt5c | 0.432453935 | 0.018414615 |
| chr6 | 47453855 | 47455164 | Intron | 185 | Cul1 | 0.432181557 | 0.038276343 |
| chr5 | 93205267 | 93206143 | Promoter-TSS | 790 | Ccni | 0.431805392 | 0.006517246 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr13 | 101706429 | 101706827 | Intron | −13998 | Pik3r1 | 0.431617598 | 0.012903029 |
| chr8 | 123982369 | 123983348 | 5' UTR | 264 | Abcb10 | 0.431187984 | 0.022435249 |
| chr11 | 105589211 | 105590214 | Promoter-TSS | −274 | Tanc2 | 0.431181132 | 0.008114395 |
| chr19 | 10979695 | 10980446 | Intron | −5400 | Ms4a10 | 0.431088109 | 0.024886986 |
| chr3 | 115692270 | 115692750 | Intergenic | 22545 | S1pr1 | 0.430963915 | 0.00670292 |
| chr17 | 72917305 | 72917750 | Promoter-TSS | −778 | Lbh | 0.430941557 | 0.032781245 |
| chr11 | 58322743 | 58323688 | Promoter-TSS | −102 | Zfp672 | 0.430637779 | 0.003837814 |
| chrX | 75758116 | 75758417 | Intron | 6433 | 4933407K13Rik | 0.430481141 | 0.043510989 |
| chr14 | 64732082 | 64732458 | Intron | 79739 | Kif13b | 0.430208171 | 0.025191676 |
| chr11 | 20631267 | 20632691 | Promoter-TSS | 2 | Sertad2 | 0.42999886 | 5.78E−05 |
| chr11 | 108267799 | 108269143 | Intron | 75417 | Prkca | 0.429967273 | 0.012306606 |
| chr11 | 83662203 | 83662754 | Promoter-TSS | −106 | Ccl4 | 0.429827755 | 0.001930796 |
| chr2 | 180582401 | 180583446 | Exon | 1619 | Mrgbp | 0.429386534 | 0.007762874 |
| chr17 | 6106347 | 6107037 | Promoter-TSS | −138 | Tulp4 | 0.428604789 | 0.008291494 |
| chr12 | 21480100 | 21480778 | Intergenic | −63003 | Ywhaq | 0.428309286 | 0.030055364 |
| chr15 | 84896216 | 84897018 | Intergenic | −26811 | Nup50 | 0.427896941 | 0.043868527 |
| chr3 | 108653756 | 108654249 | Promoter-TSS | 12 | Clcc1 | 0.427875898 | 0.006210736 |
| chr6 | 140508226 | 140508803 | Intron | 84415 | Plekha5 | 0.427577525 | 0.017468551 |
| chr11 | 4096498 | 4096954 | TTS | −1295 | Mtfp1 | 0.427191305 | 0.00826486 |
| chr14 | 70775977 | 70776664 | Intron | 1939 | Dok2 | 0.426652341 | 0.023230382 |
| chr3 | 135527500 | 135528249 | Intron | 42263 | Manba | 0.426583864 | 0.000312556 |
| chr14 | 47361480 | 47362462 | Intergenic | −11889 | Lgals3 | 0.426121796 | 4.08E−05 |
| chr6 | 136941405 | 136942013 | Promoter-TSS | 47 | Arhgdib | 0.426010301 | 0.049246005 |
| chrX | 48433263 | 48434058 | Intron | 29472 | Elf4 | 0.424633761 | 0.009881413 |
| chr11 | 4704056 | 4705050 | Promoter-TSS | −125 | Zmat5 | 0.423796855 | 0.013675814 |
| chr5 | 72743060 | 72743743 | Intron | −6799 | Txk | 0.423706885 | 0.046578371 |
| chr9 | 64789317 | 64789808 | Intergenic | −21449 | Dennd4a | 0.422758401 | 0.005430295 |
| chr11 | 106535735 | 106536571 | Intron | 35162 | Snord104 | 0.422574659 | 0.002796589 |
| chr13 | 63186964 | 63187984 | Intron | −52555 | 2010111I01Rik | 0.421964788 | 0.026537788 |
| chr19 | 27429391 | 27430251 | Promoter-TSS | 87 | Pum3 | 0.42196454 | 0.000597751 |
| chr15 | 52753282 | 52754028 | Intergenic | 41210 | Med30 | 0.42184631 | 0.00679102 |
| chr7 | 99979839 | 99980628 | Exon | 225 | Rnf169 | 0.421674994 | 0.023233918 |
| chr14 | 32201585 | 32202444 | Promoter-TSS | 43 | Parg | 0.421499532 | 0.037321188 |
| chr2 | 120849987 | 120850997 | Promoter-TSS | −74 | Ttbk2 | 0.421343187 | 0.008476617 |
| chr12 | 112619739 | 112620267 | Promoter-TSS | −44 | Adssl1 | 0.421334013 | 0.002814937 |
| chr1 | 182520006 | 182520608 | Intergenic | −2824 | Capn2 | 0.421037719 | 0.014145686 |
| chr2 | 180437909 | 180438567 | Intergenic | −22740 | Slco4a1 | 0.420500541 | 0.02672489 |
| chr4 | 59265139 | 59265517 | Intron | 5277 | Gm12596 | 0.419115022 | 0.008135351 |
| chr18 | 80691501 | 80692153 | Intron | 16346 | Nfatc1 | 0.418238147 | 0.039464873 |
| chr19 | 43689303 | 43690215 | Promoter-TSS | 70 | Entpd7 | 0.417934559 | 0.000123801 |
| chrX | 101639750 | 101640329 | Promoter-TSS | −12 | Ogt | 0.417913879 | 0.047654341 |
| chr19 | 12796085 | 12797029 | Promoter-TSS | −434 | Gm44505 | 0.417787894 | 3.90E−06 |
| chr7 | 66185359 | 66185765 | Intergenic | 76047 | Chsy1 | 0.417729119 | 0.032936635 |
| chr15 | 5517189 | 5517901 | Intron | 21227 | 5430437J10Rik | 0.417330767 | 0.035981816 |
| chr1 | 136136925 | 136137322 | Intron | 5722 | Kif21b | 0.417051713 | 0.03474624 |
| chrX | 103481257 | 103482203 | Non-Coding | 1503 | Xist | 0.416516108 | 0.009085601 |
| chr2 | 166553497 | 166554342 | Intergenic | 106468 | 5031425F14Rik | 0.416268871 | 0.036743958 |
| chr5 | 138257032 | 138257447 | Intron | 1757 | Lamtor4 | 0.415611395 | 0.04799046 |
| chr11 | 60222695 | 60223277 | Intergenic | −2359 | Srebf1 | 0.415582744 | 0.014734382 |
| chr8 | 92355659 | 92356561 | Promoter-TSS | 10 | Crnde | 0.415581855 | 0.000154625 |
| chr19 | 24476524 | 24477909 | Exon | 258 | Fam122a | 0.415567726 | 0.006544643 |
| chr9 | 90244360 | 90245063 | Intron | 26058 | Tbc1d2b | 0.415446633 | 0.017203744 |
| chr8 | 117074143 | 117074996 | Intron | 7880 | Pkd1l2 | 0.414814028 | 0.000291121 |
| chr9 | 110131598 | 110132562 | Promoter-TSS | 56 | Smarcc1 | 0.413531525 | 0.00297938 |
| chr11 | 97103765 | 97104525 | Intron | 11186 | Tbx21 | 0.412878432 | 0.006870536 |
| chr3 | 104780350 | 104781179 | Promoter-TSS | −292 | Ppm1j | 0.412640289 | 0.00207258 |
| chr11 | 67563014 | 67563646 | Intron | −23170 | Gas7 | 0.411554597 | 0.021378036 |
| chr1 | 173766801 | 173767732 | Promoter-TSS | −347 | Ifi204 | 0.4107429 | 0.009179072 |
| chr4 | 155891612 | 155891970 | Promoter-TSS | −29 | Pus1l | 0.410148266 | 0.039298277 |
| chr7 | 31086353 | 31086758 | Intergenic | −9858 | Fxyd3 | 0.40925053 | 0.016215823 |
| chr3 | 101274602 | 101275189 | Intergenic | 13044 | Cd2 | 0.408956426 | 0.012718856 |
| chr18 | 54900038 | 54900815 | Intron | 89754 | Zfp608 | 0.40778384 | 0.034666483 |
| chr11 | 104442165 | 104443121 | Promoter-TSS | −352 | Kansl1 | 0.407138136 | 1.66E−05 |
| chr11 | 62648163 | 62649326 | Promoter-TSS | 80 | Mmgt2 | 0.407101829 | 0.005503029 |
| chr11 | 23257269 | 23257726 | Intron | 1456 | Xpo1 | 0.407079241 | 0.001257618 |
| chr4 | 139199960 | 139200374 | Intron | 6056 | Capzb | 0.405716423 | 0.01137395 |
| chr19 | 24961312 | 24961967 | Promoter-TSS | −23 | Cbwd1 | 0.405529159 | 1.72E−05 |
| chr19 | 46572864 | 46573625 | Promoter-TSS | −121 | Sfxn2 | 0.405154669 | 0.000585884 |
| chr8 | 121898464 | 121898961 | Intron | 8974 | Slc7a5 | 0.404624677 | 0.021175594 |
| chr11 | 108068264 | 108068913 | Intron | 71740 | Mir7223 | 0.403976286 | 0.045929322 |
| chr1 | 53838093 | 53838896 | Intron | −10930 | Mir7681 | 0.402020098 | 0.045431897 |
| chr5 | 137741022 | 137741925 | Promoter-TSS | −305 | Nyap1 | 0.401427681 | 0.001925218 |
| chr13 | 22608885 | 22609636 | Intergenic | 11775 | Vmn1r206 | 0.401201879 | 0.042867803 |
| chr15 | 81819630 | 81820167 | Intron | 8484 | Tef | 0.400563253 | 0.034153879 |
| chr11 | 109720972 | 109722474 | 5' UTR | 533 | Fam20a | 0.399355103 | 0.012046622 |
| chr19 | 8953371 | 8954042 | Promoter-TSS | −126 | Tut1 | 0.399311586 | 0.006651777 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr11 | 102924715 | 102925713 | Promoter-TSS | −90 | Kif18b | 0.39886976 | 0.01548462 |
| chr6 | 47835405 | 47836483 | Intron | 283 | Zfp398 | 0.398479239 | 0.030169212 |
| chr16 | 11253691 | 11254927 | Promoter-TSS | 16 | Gspt1 | 0.39789281 | 0.000507774 |
| chr5 | 142929017 | 142929722 | Intergenic | −22615 | Actb | 0.397636597 | 0.045953855 |
| chr11 | 53769743 | 53770827 | Promoter-TSS | −188 | Irf1 | 0.39735175 | 0.003146869 |
| chr17 | 79347851 | 79348553 | Intron | 6889 | Cdc42ep3 | 0.39643315 | 0.037319453 |
| chr12 | 32168516 | 32169360 | Intergenic | 39400 | Pik3cg | 0.396359236 | 0.040841883 |
| chr8 | 104630980 | 104631708 | Promoter-TSS | −23 | Rrad | 0.396355587 | 0.036946073 |
| chr4 | 16013536 | 16014388 | Promoter-TSS | −85 | Osgin2 | 0.395114185 | 0.0016578 |
| chr4 | 150909584 | 150910134 | Promoter-TSS | 62 | Park7 | 0.39503269 | 0.01580227 |
| chr1 | 153332059 | 153333624 | Promoter-TSS | −55 | Lamc1 | 0.394307672 | 0.015692627 |
| chr19 | 56756172 | 56757104 | Intergenic | 34266 | Adrb1 | 0.393815898 | 0.000172944 |
| chr4 | 140947795 | 140948427 | Intron | 9791 | Gm13031 | 0.393175427 | 0.038698128 |
| chr5 | 114380260 | 114381050 | Promoter-TSS | 35 | Ube3b | 0.392774104 | 0.036743958 |
| chr9 | 124424019 | 124424860 | Non-Coding | 652 | 4930526I15Rik | 0.392564703 | 1.69E−05 |
| chr10 | 60388854 | 60389858 | Intron | −10370 | Gm17455 | 0.392386568 | 0.028029061 |
| chr8 | 126945464 | 126946260 | Promoter-TSS | 59 | Tomm20 | 0.392380312 | 0.005551028 |
| chr11 | 82183125 | 82183847 | Intergenic | −3674 | Ccl1 | 0.392367057 | 0.049428826 |
| chr12 | 108794105 | 108794747 | Intron | 1115 | Yy1 | 0.391695926 | 0.007445098 |
| chr4 | 11769051 | 11769687 | Intron | 11212 | Cdh17 | 0.391499486 | 0.030864066 |
| chr6 | 108536922 | 108537421 | Intron | 47428 | Mir7661 | 0.391275126 | 0.009179072 |
| chr11 | 115475456 | 115475874 | Promoter-TSS | −12 | Armc7 | 0.391180313 | 0.019466149 |
| chr11 | 5761783 | 5762587 | Promoter-TSS | 35 | Ube2d-ps | 0.391088601 | 0.048864889 |
| chr1 | 134405648 | 134406707 | Intron | 187 | Cyb5r1 | 0.390142108 | 0.009616131 |
| chr3 | 129830658 | 129831706 | 5' UTR | 214 | Gar1 | 0.389934024 | 0.001878958 |
| chr3 | 9801738 | 9802653 | Intron | 31484 | Pag1 | 0.389918998 | 0.017468551 |
| chr2 | 14073454 | 14074477 | Promoter-TSS | −31 | Stamos | 0.389640437 | 0.013692577 |
| chr5 | 134638821 | 134639820 | Promoter-TSS | 89 | Eif4h | 0.389312191 | 0.000298718 |
| chr9 | 122950575 | 122951438 | Promoter-TSS | −6 | 1110059G10Rik | 0.389298135 | 0.01775659 |
| chr19 | 42779494 | 42780185 | 5' UTR | 137 | Hps1 | 0.389033194 | 0.006198536 |
| chr7 | 143005461 | 143005784 | Promoter-TSS | −37 | Tspan32 | 0.388677357 | 0.042118389 |
| chrX | 75758898 | 75759416 | Intron | 5542 | 4933407K13Rik | 0.388591924 | 0.028296071 |
| chr11 | 117780580 | 117781776 | Promoter-TSS | −495 | Tmc6 | 0.388342243 | 0.002651937 |
| chr5 | 3300827 | 3301600 | Intergenic | −42680 | Cdk6 | 0.38882035 | 0.015705647 |
| chr5 | 33935763 | 33936811 | Promoter-TSS | −29 | Nelfa | 0.387821441 | 0.001864274 |
| chr10 | 128091447 | 128091871 | Intergenic | −1124 | Baz2a | 0.387244776 | 0.026679446 |
| chr16 | 23107631 | 23108648 | Promoter-TSS | 671 | Eif4a2 | 0.386249777 | 0.013912928 |
| chr15 | 5243957 | 5244895 | Promoter-TSS | −239 | Ptger4 | 0.385912348 | 0.000439561 |
| chr15 | 100227446 | 100228528 | 5' UTR | 128 | Atf1 | 0.385845088 | 0.046408776 |
| chr13 | 119487567 | 119488570 | Promoter-TSS | 29 | Tmem267 | 0.385423162 | 0.019789302 |
| chr6 | 73248163 | 73249080 | 5' UTR | 116 | Suclg1 | 0.385383947 | 0.002449014 |
| chr18 | 34860425 | 34861386 | Promoter-TSS | −302 | Egr1 | 0.384797349 | 6.31E−05 |
| chr11 | 87591681 | 87592605 | Promoter-TSS | −74 | Mtmr4 | 0.38462539 | 3.70E−05 |
| chr8 | 88618547 | 88619247 | Intergenic | 17231 | Snx20 | 0.384275904 | 0.013692577 |
| chr9 | 121675034 | 121675360 | Intergenic | 29832 | Sec22c | 0.383700446 | 0.007352292 |
| chr3 | 84345019 | 84345918 | Intergenic | 34453 | 4930565D16Rik | 0.383053996 | 0.04881716 |
| chr10 | 75326323 | 75327045 | Intron | 1826 | Adora2a | 0.382731439 | 0.002577435 |
| chr5 | 134184138 | 134184875 | Intron | 468 | Gtf2ird2 | 0.382255627 | 0.00028576 |
| chr10 | 34206446 | 34207815 | 5' UTR | 421 | Dse | 0.382102309 | 0.002534872 |
| chr13 | 37541516 | 37542020 | Intergenic | 196423 | Ly86 | 0.381958194 | 0.031497052 |
| chr5 | 138186933 | 138188187 | Promoter-TSS | 25 | Cnpy4 | 0.380921619 | 0.03474624 |
| chr17 | 56276692 | 56277643 | Promoter-TSS | −400 | Ticam1 | 0.380702416 | 0.010899543 |
| chr8 | 122473875 | 122474607 | Intron | 1823 | Rnf166 | 0.380618288 | 0.001029272 |
| chr7 | 98815081 | 98816611 | Intergenic | −19266 | Wnt11 | 0.380079224 | 0.006314048 |
| chr11 | 49250316 | 49251140 | Intron | 176 | Mgat1 | 0.380009251 | 0.041706418 |
| chr5 | 143975056 | 143975839 | Intergenic | 39406 | Ccz1 | 0.379731583 | 0.026571404 |
| chr6 | 108672052 | 108672758 | Intergenic | −11471 | 0610040F04Rik | 0.378995409 | 0.002210202 |
| chr13 | 90922717 | 90923646 | Promoter-TSS | 59 | Rps23 | 0.37888496 | 0.007782174 |
| chr3 | 152149304 | 152149939 | Intron | 16279 | Gipc2 | 0.378784492 | 0.038046249 |
| chr7 | 135659319 | 135660011 | Intron | −7351 | 5830432E09Rik | 0.378549822 | 0.033905958 |
| chr2 | 167349054 | 167349810 | Promoter-TSS | −254 | B4galt5 | 0.378483246 | 0.017975644 |
| chr7 | 16207058 | 16207861 | Intron | 14534 | Dhx34 | 0.377337199 | 0.001958774 |
| chr10 | 7473320 | 7474154 | Promoter-TSS | −260 | Ulbp1 | 0.376934037 | 0.019778154 |
| chr11 | 119933156 | 119933784 | Intergenic | −9622 | Baiap2 | 0.376824856 | 0.038243003 |
| chr1 | 161070309 | 161071035 | Promoter-TSS | −12 | Dars2 | 0.376627103 | 0.028718192 |
| chr11 | 104550006 | 104551027 | Promoter-TSS | 104 | Cdc27 | 0.376309337 | 0.01875797 |
| chr9 | 79918947 | 79919861 | Intron | 58478 | Filip1 | 0.376156363 | 0.01197694 |
| chr11 | 78535916 | 78536653 | Promoter-TSS | −24 | Tnfaip1 | 0.375808411 | 0.000479939 |
| chr11 | 109472966 | 109474097 | Promoter-TSS | 65 | Slc16a6 | 0.375647986 | 0.031274687 |
| chr9 | 114770225 | 114770760 | Intron | 11501 | Cmtm7 | 0.375644588 | 0.048983145 |
| chr12 | 105000814 | 105001643 | Intron | −2551 | Syne3 | 0.375582051 | 0.003640083 |
| chr11 | 23497431 | 23498485 | Promoter-TSS | 81 | Ahsa2 | 0.375334799 | 0.00125896 |
| chr7 | 141327227 | 141328427 | Promoter-TSS | −102 | Deaf1 | 0.375323287 | 0.000431527 |
| chr3 | 69205302 | 69206132 | Intergenic | −16702 | Arl14 | 0.37529932 | 0.039059596 |
| chr2 | 180070275 | 180071092 | Promoter-TSS | 90 | Mtg2 | 0.375005707 | 0.040924581 |
| chr10 | 14705090 | 14705911 | Promoter-TSS | −11 | Vta1 | 0.374900814 | 0.013542699 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr11 | 48816861 | 48817657 | 5' UTR | 132 | Trim41 | 0.374724957 | 0.001129694 |
| chr11 | 23665357 | 23666626 | Promoter-TSS | 15 | Pus10 | 0.37455869 | 0.039548234 |
| chr9 | 59655920 | 59656761 | Promoter-TSS | −28 | Pkm | 0.374463282 | 0.02210353 |
| chr19 | 53528785 | 53529536 | Promoter-TSS | −158 | Dusp5 | 0.373085658 | 0.003147917 |
| chr11 | 88047150 | 88047987 | 5' UTR | 195 | Srsf1 | 0.372659606 | 0.01664792 |
| chr3 | 5860335 | 5860530 | Intergenic | −284184 | Pex2 | 0.372067769 | 0.044494798 |
| chr11 | 60114933 | 60115660 | Intron | 10283 | Rai1 | 0.37203673 | 0.03202022 |
| chr4 | 128727247 | 128728281 | 5' UTR | 193 | Phc2 | 0.371753786 | 0.035157779 |
| chr7 | 135605040 | 135605822 | Promoter-TSS | −397 | Ptpre | 0.371501596 | 0.007270942 |
| chr18 | 80469143 | 80470582 | Promoter-TSS | −195 | Ctdp1 | 0.37141364 | 0.00024428 |
| chr13 | 96387933 | 96388549 | Promoter-TSS | −53 | Poc5 | 0.371406244 | 0.039298277 |
| chr4 | 19568952 | 19570267 | Intron | 495 | Cpne3 | 0.371284171 | 0.028763021 |
| chr11 | 119040613 | 119041480 | Promoter-TSS | −133 | Cbx8 | 0.371078651 | 0.016215048 |
| chr11 | 67052314 | 67053093 | Promoter-TSS | 33 | Sco1 | 0.370889652 | 0.002294804 |
| chr9 | 61914139 | 61914993 | Promoter-TSS | −56 | Rplp1 | 0.370484613 | 0.007762874 |
| chr4 | 141559142 | 141560209 | Intergenic | 13513 | B330016D10Rik | 0.369896768 | 0.003956624 |
| chr13 | 34874012 | 34874703 | Intergenic | −1137 | Prpf4b | 0.369678581 | 0.037121937 |
| chr18 | 80707440 | 80707945 | Intron | 481 | Nfatc1 | 0.36956298 | 0.046559068 |
| chr18 | 53744344 | 53745431 | Promoter-TSS | −340 | Cep120 | 0.369253027 | 0.001474812 |
| chr11 | 97825239 | 97825774 | Intron | −15274 | B230217C12Rik | 0.369173217 | 0.015580841 |
| chr8 | 128549612 | 128550495 | Intergenic | −135601 | Itgb1 | 0.368718688 | 0.000909021 |
| chr16 | 4077373 | 4078105 | Promoter-TSS | 71 | Trap1 | 0.368577043 | 0.010550357 |
| chr17 | 86904193 | 86904934 | Intergenic | −12785 | Tmem247 | 0.36804752 | 0.033047097 |
| chr6 | 47659220 | 47659753 | Promoter-TSS | −71 | Rn4.5s | 0.368043373 | 0.049089852 |
| chr1 | 171328693 | 171329690 | Promoter-TSS | 46 | Dedd | 0.367705832 | 0.008651685 |
| chr2 | 181519990 | 181520987 | Promoter-TSS | 3 | Dnajc5 | 0.367665218 | 0.025852968 |
| chr1 | 136685154 | 136686005 | Intron | 1950 | Gm19705 | 0.367610732 | 0.008114395 |
| chr11 | 120378137 | 120379196 | Promoter-TSS | 80 | Faap100 | 0.367597232 | 0.020098975 |
| chr2 | 25460585 | 25461265 | 5' UTR | 171 | BC029214 | 0.367279887 | 0.04611976 |
| chr8 | 86870776 | 86871313 | Intron | 14214 | N4bp1 | 0.366552179 | 0.034618128 |
| chr15 | 102150048 | 102151355 | Exon | 126 | Soat2 | 0.365857506 | 0.003930761 |
| chr6 | 120452920 | 120453574 | Intergenic | −9950 | Il17ra | 0.365121229 | 0.018602031 |
| chr17 | 8164878 | 8165928 | Promoter-TSS | −115 | Fgfr1op | 0.365083145 | 0.000746432 |
| chr18 | 52465434 | 52466081 | Promoter-TSS | 64 | Srfbp1 | 0.364923473 | 0.033202464 |
| chr13 | 43268613 | 43269383 | Intron | 35174 | Gfod1 | 0.364802318 | 0.024080238 |
| chr4 | 150921237 | 150921622 | Intron | 1274 | Tnfrsf9 | 0.364577039 | 0.04724523 |
| chr11 | 29130427 | 29131271 | Promoter-TSS | 98 | Pnpt1 | 0.36387687 | 0.041383981 |
| chr2 | 146497050 | 146498092 | Intron | 14433 | Ralgapa2 | 0.363870917 | 0.042977817 |
| chr10 | 94860720 | 94861395 | Intron | 83521 | Plxnc1 | 0.363866885 | 0.022841488 |
| chr11 | 3451810 | 3452655 | Promoter-TSS | −205 | 8430429K09Rik | 0.363686154 | 0.009273024 |
| chr10 | 118468914 | 118469505 | Intergenic | 28163 | Ifng | 0.363480847 | 0.004316481 |
| chr11 | 87404123 | 87404821 | Promoter-TSS | 23 | Rad51c | 0.363463303 | 0.010038035 |
| chr11 | 121420893 | 121421864 | Promoter-TSS | 5 | Fn3krp | 0.363147646 | 0.000886143 |
| chr19 | 34606908 | 34608054 | Promoter-TSS | −476 | Ifit3b | 0.363085754 | 0.006895538 |
| chr19 | 43752581 | 43753576 | Promoter-TSS | 55 | Cutc | 0.362929356 | 0.022419685 |
| chr17 | 46673955 | 46674635 | Promoter-TSS | −40 | Rrp36 | 0.362852368 | 0.026442131 |
| chr6 | 143099275 | 143100497 | Intron | 266 | C2cd5 | 0.36280098 | 0.040936647 |
| chr2 | 90542583 | 90543164 | Intron | 37774 | Ptprj | 0.362482572 | 0.025817773 |
| chr10 | 42761231 | 42762049 | 5' UTR | 144 | Sec63 | 0.361956122 | 0.03584575 |
| chr3 | 108084743 | 108086045 | Promoter-TSS | 8 | Ampd2 | 0.361762141 | 0.016929453 |
| chr2 | 129800271 | 129800996 | Exon | 116 | Stk35 | 0.361694238 | 0.035072976 |
| chr3 | 105958901 | 105959921 | Promoter-TSS | −87 | Wdr77 | 0.360816394 | 0.00015811 |
| chr2 | 156877742 | 156878354 | Intron | 9030 | Sla2 | 0.360636312 | 0.009507604 |
| chr10 | 41476970 | 41478018 | Intron | 1180 | Mical1 | 0.360496356 | 0.042888215 |
| chr2 | 157457131 | 157458150 | Intron | 33347 | Src | 0.36034685 | 0.032185477 |
| chr14 | 49171825 | 49172847 | Promoter-TSS | 90 | Naa30 | 0.360288629 | 0.019215502 |
| chr3 | 131056968 | 131057735 | Intergenic | −52946 | Lef1 | 0.359901049 | 0.001804917 |
| chr19 | 53408283 | 53408741 | Intergenic | −17939 | Smndc1 | 0.359059286 | 0.049514103 |
| chr9 | 48984762 | 48985704 | Promoter-TSS | −152 | Usp28 | 0.358997549 | 0.004997286 |
| chr13 | 33004175 | 33005001 | Promoter-TSS | 47 | Serpinb9 | 0.358833922 | 0.038659025 |
| chr3 | 98013115 | 98014250 | 5' UTR | 144 | Notch2 | 0.358210831 | 0.014532037 |
| chr19 | 45047374 | 45048011 | 5' UTR | 116 | Sfxn3 | 0.358165445 | 0.013016325 |
| chr3 | 142700484 | 142701321 | Promoter-TSS | −146 | Kyat3 | 0.357927386 | 0.045757195 |
| chr16 | 20672469 | 20673369 | Intron | 192 | Eif4g1 | 0.357853113 | 0.014225751 |
| chr4 | 150008378 | 150009748 | Promoter-TSS | −40 | H6pd | 0.357623564 | 0.001146815 |
| chr11 | 46436776 | 46437652 | Intron | 253 | Med7 | 0.357338633 | 0.02564782 |
| chr16 | 46022085 | 46022868 | Intergenic | −12063 | Plcxd2 | 0.357253967 | 0.032619433 |
| chr16 | 94370213 | 94371542 | Promoter-TSS | 138 | Ttc3 | 0.357001297 | 0.035981816 |
| chr11 | 117848431 | 117849500 | Promoter-TSS | −272 | Birc5 | 0.356752951 | 0.036158255 |
| chr5 | 123749101 | 123749922 | Promoter-TSS | −97 | Rsrc2 | 0.356444974 | 0.017589398 |
| chr13 | 36117257 | 36118100 | Promoter-TSS | 35 | Fars2 | 0.355890636 | 0.029388496 |
| chr13 | 93898387 | 93898876 | Intron | 107854 | Mir5624 | 0.355868747 | 0.047569335 |
| chr11 | 73198840 | 73199709 | Promoter-TSS | −208 | Shpk | 0.355547682 | 0.007912635 |
| chr11 | 83639988 | 83640747 | Intergenic | 9011 | Ccl3 | 0.355449652 | 0.0152543 |
| chr11 | 23894797 | 23895522 | 5' UTR | 111 | Papolg | 0.355293401 | 0.016306545 |
| chr4 | 135169013 | 135169725 | Intron | 48724 | Runx3 | 0.354852969 | 0.021648726 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr19 | 4012408 | 4013106 | Promoter-TSS | −2 | Ndufv1 | 0.354616422 | 0.040050544 |
| chr11 | 61493625 | 61494634 | 5' UTR | 137 | Mapk7 | 0.354435367 | 0.007161306 |
| chr4 | 129188967 | 129190349 | Promoter-TSS | 69 | S100pbp | 0.354236427 | 0.007828301 |
| chr10 | 86685041 | 86686016 | Promoter-TSS | 1 | 1810014B01Rik | 0.353687679 | 0.036300065 |
| chr1 | 194995086 | 194995589 | Intergenic | −18378 | Gm16897 | 0.353343892 | 0.0203914 |
| chr19 | 45058132 | 45058932 | Intergenic | 10956 | Sfxn3 | 0.353157861 | 0.049109655 |
| chr11 | 94210756 | 94211797 | Promoter-TSS | −178 | Tob1 | 0.352930629 | 0.001684466 |
| chr2 | 164460737 | 164461762 | Intron | 278 | Sys1 | 0.35292938 | 0.021418753 |
| chr5 | 122131146 | 122132058 | Intron | 3291 | Ccdc63 | 0.35244498 | 0.039443353 |
| chr1 | 182527896 | 182528869 | Intergenic | −10899 | Capn2 | 0.352394333 | 0.046739639 |
| chr5 | 117119772 | 117120407 | Promoter-TSS | −40 | Taok3 | 0.351828423 | 0.011906775 |
| chr19 | 41354267 | 41355009 | Intron | 30432 | Pik3ap1 | 0.351688743 | 0.022892568 |
| chr11 | 120598016 | 120598974 | Promoter-TSS | −37 | Anapc11 | 0.351484702 | 0.000408699 |
| chr5 | 91962194 | 91963459 | Promoter-TSS | −56 | Thap6 | 0.351457556 | 0.002341462 |
| chr1 | 134092747 | 134093812 | Intergenic | −14124 | Btg2 | 0.351429166 | 0.003963029 |
| chr2 | 157737119 | 157737743 | Promoter-TSS | 30 | Ctnnbl1 | 0.351072386 | 0.02827229 |
| chr16 | 23127453 | 23128303 | Promoter-TSS | −148 | Rfc4 | 0.35100476 | 0.009255627 |
| chr4 | 150924910 | 150925276 | Intron | −2906 | Tnfrsf9 | 0.349737768 | 0.036467288 |
| chr19 | 59345070 | 59346319 | Promoter-TSS | 86 | Pdzd8 | 0.349449728 | 0.013160011 |
| chr11 | 60416791 | 60417348 | Promoter-TSS | 30 | Atpaf2 | 0.349403336 | 0.020732662 |
| chr11 | 58903560 | 58904552 | Intron | 119 | Zfp39 | 0.348835009 | 0.031497052 |
| chr11 | 60777149 | 60777748 | Promoter-TSS | −77 | Smcr8 | 0.348647451 | 0.018602031 |
| chr4 | 40781779 | 40782348 | Intergenic | −24178 | Smu1 | 0.348594875 | 0.010043627 |
| chr5 | 142906475 | 142906955 | Promoter-TSS | 39 | Actb | 0.348503833 | 0.023316576 |
| chr13 | 49341032 | 49341853 | Promoter-TSS | −107 | Bicd2 | 0.348446352 | 0.012555993 |
| chr11 | 23007383 | 23008702 | Intergenic | −5345 | Fam161a | 0.34829164 | 0.036186903 |
| chr3 | 95893606 | 95894172 | Promoter-TSS | −32 | Aph1a | 0.348014668 | 0.020151381 |
| chr9 | 106202796 | 106203627 | 5' UTR | 103 | Twf2 | 0.347873733 | 0.03915286 |
| chr12 | 76537399 | 76537800 | Intron | 4039 | Plekhg3 | 0.347422341 | 0.03691442 |
| chr13 | 17694594 | 17695690 | Promoter-TSS | −271 | Mplkip | 0.346997782 | 6.41E−05 |
| chr9 | 60998201 | 60999516 | Intergenic | −18211 | Gm5122 | 0.346773602 | 0.012586256 |
| chr1 | 84839266 | 84840373 | Promoter-TSS | −22 | Fbxo36 | 0.346619595 | 0.041709058 |
| chr4 | 117124420 | 117124731 | Non-Coding | 1150 | Btbd19 | 0.346485061 | 0.02413513 |
| chr3 | 54692394 | 54693140 | Promoter-TSS | −338 | Supt20 | 0.346401214 | 0.004792879 |
| chr9 | 107280068 | 107281461 | Intron | 8632 | Mapkapk3 | 0.34630828 | 0.003928153 |
| chr6 | 114659959 | 114660784 | Intron | 17274 | Atg7 | 0.345952705 | 0.039548234 |
| chr9 | 96719370 | 96720267 | Intron | 11857 | Zbtb38 | 0.345892441 | 0.025625151 |
| chr11 | 58928060 | 58928762 | Intergenic | 10354 | Btnl10 | 0.345873784 | 0.008633212 |
| chr5 | 138084976 | 138085745 | Intron | 276 | Zkscan1 | 0.345460577 | 0.014430893 |
| chr7 | 5061961 | 5062565 | 5' UTR | 120 | U2af2 | 0.345206683 | 0.03743928 |
| chr15 | 99251483 | 99252511 | Promoter-TSS | −36 | Mcrs1 | 0.345051331 | 0.008996106 |
| chr19 | 31082596 | 31083284 | Promoter-TSS | 99 | Cstf2t | 0.345023597 | 0.014366331 |
| chr13 | 111489537 | 111490732 | Promoter-TSS | −93 | Gpbp1 | 0.344975374 | 0.000333028 |
| chr19 | 30113120 | 30114018 | Intron | 61872 | Gldc | 0.344816476 | 0.012819945 |
| chr8 | 72318677 | 72319629 | Promoter-TSS | 91 | Klf2 | 0.344731093 | 0.020242255 |
| chr11 | 72960897 | 72962036 | Exon | 297 | Atp2a3 | 0.344413847 | 0.03691442 |
| chr11 | 87755311 | 87755699 | Intergenic | −1359 | Mir142 | 0.344226091 | 0.049729455 |
| chr3 | 152920290 | 152920951 | Intron | 61587 | St6galnac5 | 0.344222243 | 0.020816974 |
| chr5 | 109556744 | 109559086 | Intron | 1078 | Crlf2 | 0.343306802 | 1.07E−05 |
| chr1 | 128592025 | 128592737 | Promoter-TSS | −82 | Cxcr4 | 0.342602215 | 0.046291118 |
| chr3 | 31094415 | 31095198 | Promoter-TSS | −252 | Skil | 0.34189284 | 0.008106126 |
| chrX | 94234306 | 94235322 | Promoter-TSS | −116 | Klhl15 | 0.34180166 | 0.030297346 |
| chr17 | 57290365 | 57291289 | Intron | 11727 | Vav1 | 0.341801164 | 0.013200935 |
| chr2 | 75703401 | 75705012 | Intron | 412 | Nfe2l2 | 0.34177543 | 3.57E−05 |
| chr19 | 45998085 | 45998702 | Promoter-TSS | 95 | 9130011E15Rik | 0.34174251 | 0.02089259 |
| chr6 | 122742096 | 122743035 | 5' UTR | 180 | Slc2a3 | 0.341706098 | 0.046877551 |
| chr1 | 180813222 | 180814483 | Promoter-TSS | −247 | H3f3a | 0.341684651 | 0.004172233 |
| chr10 | 79959809 | 79960369 | Promoter-TSS | −63 | Wdr18 | 0.341646683 | 0.021801615 |
| chr11 | 98941859 | 98942700 | Intron | 2568 | Rara | 0.341513734 | 0.012274603 |
| chr11 | 95384157 | 95385275 | Promoter-TSS | −206 | Slc35b1 | 0.341444628 | 0.019364455 |
| chr4 | 155085859 | 155086821 | Promoter-TSS | −43 | Rer1 | 0.341123315 | 0.001726634 |
| chr18 | 67280294 | 67281107 | Intergenic | −8523 | Impa2 | 0.34102545 | 0.036286358 |
| chr18 | 34624007 | 34625065 | Promoter-TSS | −88 | Kif20a | 0.340928063 | 0.017028441 |
| chr5 | 145166614 | 145167504 | Promoter-TSS | 45 | Ptcd1 | 0.340808601 | 0.011246543 |
| chr1 | 106713785 | 106714896 | Promoter-TSS | −50 | Bcl2 | 0.340478214 | 0.005830235 |
| chr11 | 20542389 | 20543413 | Promoter-TSS | −352 | Sertad2 | 0.340124487 | 0.00266453 |
| chr8 | 122611013 | 122612052 | Promoter-TSS | −45 | Galns | 0.339861347 | 0.025454783 |
| chr11 | 19923984 | 19924518 | Promoter-TSS | −191 | Spred2 | 0.339179745 | 0.047733092 |
| chr1 | 180330039 | 180331004 | Promoter-TSS | 28 | Gm5069 | 0.339156167 | 0.025872026 |
| chr5 | 125389088 | 125389819 | Intron | 564 | Ubc | 0.338511882 | 0.015843758 |
| chr2 | 18056341 | 18057517 | Promoter-TSS | −917 | Mir7655 | 0.338460014 | 0.002033388 |
| chr4 | 41124098 | 41124563 | Promoter-TSS | 9 | Nol6 | 0.337917383 | 0.010520162 |
| chr9 | 110656284 | 110656898 | Promoter-TSS | 88 | Ccdc12 | 0.337867297 | 0.020631045 |
| chr2 | 13270859 | 13271877 | Promoter-TSS | 47 | Rsu1 | 0.337826259 | 0.014053837 |
| chrX | 74243679 | 74244347 | Intron | 2521 | Flna | 0.337724648 | 0.042629391 |
| chr7 | 143599807 | 143600449 | Promoter-TSS | −38 | Cars | 0.337707426 | 0.008919766 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr8 | 128685028 | 128686398 | Promoter-TSS | 59 | Itgb1 | 0.337588284 | 0.007451978 |
| chr12 | 104056828 | 104058020 | Intergenic | −12981 | Serpina12 | 0.33746302 | 0.000198851 |
| chr17 | 86167254 | 86168116 | Promoter-TSS | −100 | Prkce | 0.337333532 | 0.045797925 |
| chr11 | 93995688 | 93996410 | Promoter-TSS | −42 | Spag9 | 0.336964618 | 0.022773896 |
| chr18 | 36744192 | 36745162 | Promoter-TSS | 21 | Ik | 0.336805678 | 0.004738929 |
| chr12 | 78861308 | 78862352 | Promoter-TSS | −192 | Atp6v1d | 0.336791342 | 0.010416625 |
| chr11 | 87470901 | 87472327 | Intron | 44023 | Tex14 | 0.336651646 | 0.02522962 |
| chr2 | 72978798 | 72979624 | Promoter-TSS | 70 | Sp3 | 0.336648647 | 0.025953965 |
| chr6 | 134792148 | 134793040 | Promoter-TSS | 34 | Dusp16 | 0.336623365 | 0.043626866 |
| chr5 | 143180476 | 143181056 | Promoter-TSS | 9 | Rbak | 0.336472836 | 0.037098315 |
| chr13 | 99344244 | 99345062 | Promoter-TSS | 25 | Ptcd2 | 0.336354697 | 0.047791828 |
| chr13 | 95618293 | 95618810 | Promoter-TSS | −118 | F2r | 0.336334458 | 0.019819002 |
| chr7 | 110121397 | 110122388 | Promoter-TSS | −167 | Wee1 | 0.3361301 | 0.021496268 |
| chr9 | 119340953 | 119341790 | Promoter-TSS | 77 | Acaa1a | 0.335681702 | 0.000181198 |
| chr5 | 149183842 | 149185136 | Promoter-TSS | −71 | Uspl1 | 0.334998101 | 0.037373832 |
| chr19 | 53464654 | 53465317 | Promoter-TSS | −189 | Mirt1 | 0.334845512 | 0.005726007 |
| chr11 | 20740784 | 20741965 | 5′ UTR | 182 | Aftph | 0.334833223 | 0.029714008 |
| chr19 | 56547946 | 56549115 | Promoter-TSS | 269 | Nhlrc2 | 0.334705284 | 0.015522592 |
| chr10 | 61297523 | 61297939 | Promoter-TSS | −105 | Prf1 | 0.334624905 | 0.04970518 |
| chr11 | 115513851 | 115514681 | Exon | 104 | Hn1 | 0.334500063 | 0.039129025 |
| chr9 | 109051590 | 109052061 | Intron | −3041 | Shisa5 | 0.334422232 | 0.001060617 |
| chr16 | 32430480 | 32431739 | Promoter-TSS | 89 | Pcyt1a | 0.334266877 | 0.035522293 |
| chr2 | 154603455 | 154604125 | Promoter-TSS | −117 | Pxmp4 | 0.334226109 | 0.003375931 |
| chr9 | 61012892 | 61013537 | Intergenic | −3855 | Gm5122 | 0.334080137 | 0.036602281 |
| chr10 | 8518200 | 8519417 | Promoter-TSS | 17 | Ust | 0.334049875 | 0.036467288 |
| chr2 | 128966988 | 128968035 | 5′ UTR | 109 | Zc3h6 | 0.33393188 | 0.02167105 |
| chr2 | 122377185 | 122377668 | Intergenic | −8508 | Shf | 0.333819263 | 0.038046249 |
| chr11 | 109859980 | 109860914 | Intergenic | 14569 | 1700023C21Rik | 0.333640856 | 0.004771811 |
| chr15 | 101246040 | 101247066 | Intergenic | −20293 | Nr4a1 | 0.333336372 | 0.001875018 |
| chr3 | 116423428 | 116424672 | Promoter-TSS | −18 | Cdc14a | 0.333022156 | 0.001661334 |
| chr8 | 126594402 | 126594899 | Intergenic | −1214 | Irf2bp2 | 0.332828652 | 0.036970269 |
| chr2 | 174328963 | 174330577 | Promoter-TSS | −300 | Gnas | 0.332687648 | 0.020283214 |
| chr5 | 29434501 | 29435366 | Exon | 266 | Nom1 | 0.332339583 | 0.045953855 |
| chr4 | 8647072 | 8647729 | Intergenic | −43006 | Chd7 | 0.332250774 | 0.029933535 |
| chr3 | 68789306 | 68790097 | Intergenic | −79885 | 1110032F04Rik | 0.332249444 | 0.033950996 |
| chr7 | 142396624 | 142397111 | Intergenic | −8997 | Ctsd | 0.332221117 | 0.030511454 |
| chr11 | 72606890 | 72607905 | 5′ UTR | 136 | Ube2g1 | 0.332108064 | 0.037798268 |
| chr4 | 156109591 | 156110365 | Promoter-TSS | −20 | 9430015G10Rik | 0.332022742 | 0.008633212 |
| chr19 | 21271678 | 21273037 | Promoter-TSS | 79 | Zfand5 | 0.331977081 | 0.013204736 |
| chr2 | 181186617 | 181187930 | Promoter-TSS | −70 | Ppdpf | 0.331364708 | 0.009796986 |
| chr12 | 73593091 | 73593813 | Intron | 8656 | Prkch | 0.3313179 | 0.009707622 |
| chr4 | 40853467 | 40854526 | 5′ UTR | 541 | B4galt1 | 0.331157577 | 0.001528917 |
| chr18 | 34931636 | 34932535 | Promoter-TSS | −82 | Etf1 | 0.331005834 | 0.001728529 |
| chr8 | 4213764 | 4214745 | Exon | 3058 | Prr36 | 0.330419772 | 0.01197694 |
| chr9 | 59616982 | 59617815 | Non-Coding | 114 | Parp6 | 0.330290578 | 0.005831399 |
| chr14 | 103033184 | 103033919 | Intron | 222 | 4933432I03Rik | 0.330217244 | 0.044494798 |
| chr5 | 112273767 | 112274282 | Intergenic | −2667 | Tpst2 | 0.330109096 | 0.034240162 |
| chr9 | 66945541 | 66946595 | Promoter-TSS | −8 | Rps27l | 0.330065393 | 0.037321188 |
| chr11 | 106036479 | 106037259 | Promoter-TSS | −3 | Dcaf7 | 0.32930442 | 0.001742115 |
| chr6 | 108659163 | 108660893 | Promoter-TSS | −601 | Bhlhe40 | 0.329089311 | 0.002842436 |
| chr7 | 19002929 | 19003481 | Promoter-TSS | −860 | Irf2bp1 | 0.328956366 | 0.036946073 |
| chr5 | 34369262 | 34369999 | Promoter-TSS | −303 | Fam193a | 0.328743263 | 0.033096032 |
| chr7 | 98702480 | 98703746 | Promoter-TSS | −185 | Gm15506 | 0.328689238 | 0.014924545 |
| chr8 | 78508425 | 78509470 | Promoter-TSS | −19 | Rbmxl1 | 0.328463425 | 0.017589398 |
| chr15 | 102230569 | 102231387 | Intron | 957 | Itgb7 | 0.328310305 | 0.010829041 |
| chr5 | 118464901 | 118465826 | Intergenic | −95356 | Med13l | 0.327887551 | 0.021034505 |
| chr10 | 127063103 | 127064021 | Promoter-TSS | −41 | Cdk4 | 0.327845355 | 0.01313644 |
| chr1 | 171643545 | 171644107 | Intron | −1926 | Mir7683 | 0.327636206 | 0.020138648 |
| chr9 | 64810780 | 64811803 | Intron | 280 | Dennd4a | 0.327555114 | 0.010520162 |
| chr5 | 138170902 | 138171516 | Promoter-TSS | 653 | Mcm7 | 0.327326151 | 0.008651685 |
| chr11 | 61761733 | 61762475 | Promoter-TSS | −16 | Prpsap2 | 0.326806198 | 0.047250711 |
| chr14 | 14345508 | 14346604 | Promoter-TSS | −439 | Il3ra | 0.326437206 | 0.001811497 |
| chr1 | 16104107 | 16106338 | Promoter-TSS | −660 | Rdh10 | 0.326423077 | 0.007226522 |
| chr7 | 141447035 | 141447924 | Promoter-TSS | −171 | Rplp2 | 0.326238385 | 0.031355258 |
| chr11 | 69995373 | 69995811 | Promoter-TSS | −174 | Phf23 | 0.325911819 | 0.048855299 |
| chr17 | 87446573 | 87447508 | Promoter-TSS | −105 | Calm2 | 0.325804575 | 0.014053837 |
| chr7 | 24883901 | 24884852 | Promoter-TSS | −338 | Rps19 | 0.325636887 | 0.02827229 |
| chr2 | 128125623 | 128126229 | Promoter-TSS | −112 | Bcl2l11 | 0.325487065 | 0.043288079 |
| chr2 | 172370357 | 172371263 | Promoter-TSS | −193 | Cstf1 | 0.325286357 | 0.008135351 |
| chr7 | 46795385 | 46796311 | Promoter-TSS | 33 | Hps5 | 0.325200511 | 0.008632716 |
| chr11 | 20112296 | 20113461 | Promoter-TSS | 73 | Actr2 | 0.325028764 | 0.001503311 |
| chr8 | 123212378 | 123213128 | Promoter-TSS | 35 | Chmp1a | 0.324738678 | 0.042330694 |
| chr11 | 20200685 | 20201540 | Promoter-TSS | −490 | Rab1a | 0.324200479 | 0.047909457 |
| chr5 | 135063848 | 135064714 | Promoter-TSS | 75 | Dnajc30 | 0.323957638 | 0.022161468 |
| chr11 | 49243707 | 49244492 | Promoter-TSS | −92 | Mgat1 | 0.323460347 | 0.003306637 |
| chr8 | 119427914 | 119428862 | Intergenic | −8774 | Osgin1 | 0.323458605 | 0.040363961 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr9 | 82975061 | 82976131 | Promoter-TSS | −107 | Phip | 0.323400639 | 0.019062993 |
| chr3 | 79567437 | 79568477 | Promoter-TSS | −278 | Fnip2 | 0.322743498 | 0.032986722 |
| chr11 | 84870338 | 84871051 | Promoter-TSS | 44 | Ggnbp2 | 0.32266118 | 0.024745652 |
| chr8 | 70776530 | 70777402 | Promoter-TSS | 104 | 2010320M18Rik | 0.322518446 | 0.041044052 |
| chr6 | 116207693 | 116208595 | Promoter-TSS | 111 | Washc2 | 0.322506305 | 0.009782226 |
| chrX | 134600723 | 134601677 | Promoter-TSS | 21 | Hnrnph2 | 0.322360638 | 0.022959556 |
| chr18 | 57249449 | 57250081 | Intron | −104968 | Prrc1 | 0.322170526 | 0.017003122 |
| chr11 | 53794670 | 53795584 | Intron | 24654 | Irf1 | 0.321755449 | 0.012190995 |
| chr1 | 118388619 | 118389688 | Promoter-TSS | 95 | Clasp1 | 0.321683503 | 0.027647066 |
| chr8 | 70673003 | 70673861 | 5' UTR | 201 | Lsm4 | 0.321508034 | 0.013187105 |
| chr12 | 85219137 | 85219936 | Promoter-TSS | 55 | Eif2b2 | 0.321312099 | 0.041551866 |
| chr10 | 82858685 | 82859550 | Promoter-TSS | −89 | Txnrd1 | 0.321267917 | 0.011421783 |
| chr6 | 37821346 | 37822244 | Intergenic | −49016 | Trim24 | 0.321214341 | 0.04988572 |
| chr5 | 138155381 | 138156144 | Promoter-TSS | −18 | Zfp113 | 0.320774002 | 0.018105389 |
| chr13 | 113828312 | 113829518 | Intron | 34407 | Arl15 | 0.320768589 | 0.002357666 |
| chr4 | 126677287 | 126678062 | Promoter-TSS | 31 | Psmb2 | 0.320673108 | 0.030555558 |
| chr9 | 120110248 | 120111056 | Intron | 253 | Slc25a38 | 0.320665092 | 0.030232854 |
| chr1 | 191906044 | 191907105 | Promoter-TSS | −207 | Slc30a1 | 0.320612801 | 0.00382355 |
| chr3 | 103789856 | 103791611 | Intron | 542 | Hipk1 | 0.320472622 | 0.023142234 |
| chr1 | 171503323 | 171503974 | 5' UTR | 170 | Alyref2 | 0.320162421 | 0.027448093 |
| chr9 | 106821659 | 106823020 | Intron | 363 | Vprbp | 0.320129143 | 0.001081462 |
| chr14 | 18238142 | 18239592 | 5' UTR | 239 | Nr1d2 | 0.320080042 | 0.010244845 |
| chr11 | 77685766 | 77686474 | Promoter-TSS | −19 | Nufip2 | 0.319975049 | 0.04784855 |
| chr8 | 109565422 | 109566314 | Promoter-TSS | −24 | Txnl4b | 0.319930213 | 0.008793429 |
| chr1 | 181841621 | 181843148 | Promoter-TSS | 17 | Lbr | 0.319781497 | 0.006726095 |
| chr5 | 36484210 | 36484840 | Promoter-TSS | −63 | Ccdc96 | 0.31922968 | 0.028631808 |
| chr5 | 139149392 | 139150774 | Promoter-TSS | −140 | Dnaaf5 | 0.318704793 | 0.011247026 |
| chr8 | 109692732 | 109693877 | Promoter-TSS | −10 | Ist1 | 0.31866795 | 0.00515975 |
| chr18 | 79063952 | 79064769 | Intron | 45031 | Setbp1 | 0.318625463 | 0.023138215 |
| chr2 | 130274025 | 130274894 | Promoter-TSS | 47 | Nop56 | 0.318313643 | 0.006293821 |
| chr18 | 82536999 | 82537464 | Intron | −17232 | Mbp | 0.318195883 | 0.034294853 |
| chr18 | 64488416 | 64489380 | Intron | 168 | Fech | 0.317998328 | 0.042867803 |
| chr7 | 30169527 | 30170014 | Promoter-TSS | 78 | Gm5113 | 0.317885827 | 0.031274687 |
| chr8 | 124721563 | 124722683 | Promoter-TSS | −16 | Arv1 | 0.3178127 | 0.039145199 |
| chr11 | 103966250 | 103967084 | Promoter-TSS | −58 | Arf2 | 0.317780043 | 0.017185305 |
| chr4 | 155868921 | 155870019 | Promoter-TSS | −30 | Cptp | 0.317410694 | 0.029113064 |
| chr7 | 144581567 | 144582687 | Exon | 309 | Fadd | 0.317096821 | 0.002371466 |
| chr8 | 126497465 | 126498142 | Intergenic | −22738 | Tarbp1 | 0.31685784 | 0.027077348 |
| chrX | 159254980 | 159256031 | Promoter-TSS | −277 | Rps6ka3 | 0.31680244 | 0.030555558 |
| chr19 | 28011034 | 28012248 | Promoter-TSS | −475 | Rfx3 | 0.316605966 | 0.013187105 |
| chr15 | 100614816 | 100616161 | Promoter-TSS | −174 | Dazap2 | 0.316554761 | 0.000100174 |
| chr6 | 114893523 | 114894178 | Intron | 27902 | Vgll4 | 0.316541696 | 0.021873897 |
| chr7 | 73558200 | 73559153 | Promoter-TSS | −281 | 1810026B05Rik | 0.316525734 | 0.001906099 |
| chr11 | 109362339 | 109363523 | 5' UTR | 137 | Gna13 | 0.316075684 | 0.044844579 |
| chr5 | 134266158 | 134266807 | Intron | −36857 | Ncf1 | 0.315573573 | 0.043658454 |
| chr12 | 85473434 | 85474170 | Promoter-TSS | −99 | Fos | 0.31551574 | 0.007270942 |
| chr12 | 91589683 | 91590659 | Promoter-TSS | 316 | Gtf2a1 | 0.315504908 | 0.034366911 |
| chr19 | 32755769 | 32756653 | Intergenic | −1366 | Pten | 0.315492964 | 0.02147042 |
| chr7 | 5060970 | 5061810 | Promoter-TSS | −753 | U2af2 | 0.315486055 | 0.017143289 |
| chr13 | 97137604 | 97138349 | Promoter-TSS | 39 | Gfm2 | 0.315471369 | 0.006582308 |
| chr7 | 101466083 | 101467155 | Intron | −8757 | Mir139 | 0.315375054 | 0.012775736 |
| chr9 | 120339872 | 120340364 | Intron | 36045 | Myrip | 0.315170519 | 0.037660631 |
| chr7 | 114069143 | 114069678 | Intron | 48371 | Rras2 | 0.315062821 | 0.036467288 |
| chr17 | 86753095 | 86753783 | Promoter-TSS | −425 | Epas1 | 0.315009346 | 0.040561676 |
| chr11 | 121706432 | 121706859 | Intron | 4218 | Metrnl | 0.314516024 | 0.026176127 |
| chr17 | 83731870 | 83732634 | Intron | 26089 | Mta3 | 0.314453906 | 0.023057534 |
| chr11 | 53350341 | 53351328 | Promoter-TSS | 67 | Aff4 | 0.314396359 | 0.041268603 |
| chr11 | 115276670 | 115277580 | Promoter-TSS | −156 | Fdxr | 0.314340931 | 0.016068062 |
| chr19 | 46396963 | 46397133 | Promoter-TSS | 12 | Sufu | 0.313684796 | 0.019905413 |
| chr11 | 118476574 | 118477320 | Promoter-TSS | −13 | Engase | 0.313559353 | 0.036913303 |
| chr5 | 31047933 | 31048753 | Promoter-TSS | 219 | Slc5a6 | 0.313167239 | 0.040613409 |
| chr8 | 71464593 | 71464998 | Promoter-TSS | −131 | Mrpl34 | 0.31300518 | 0.028370869 |
| chr13 | 75839543 | 75840482 | Exon | 126 | Glrx | 0.312590151 | 0.014482521 |
| chr13 | 73937365 | 73938659 | Promoter-TSS | 201 | Brd9 | 0.31252356 | 0.013743944 |
| chr11 | 50210036 | 50210935 | Intron | 335 | Sqstm1 | 0.312516495 | 0.028525105 |
| chr6 | 12124981 | 12125821 | Intergenic | −15821 | Gm6578 | 0.312277447 | 0.046785723 |
| chr19 | 43674700 | 43675692 | Promoter-TSS | 18 | BC037704 | 0.311968406 | 0.005240942 |
| chr13 | 91807186 | 91807992 | Intron | 107 | Zcchc9 | 0.311604247 | 0.049116123 |
| chr11 | 53300141 | 53301078 | Promoter-TSS | −130 | Hspa4 | 0.311297603 | 0.017589398 |
| chr11 | 40733348 | 40734220 | Promoter-TSS | 123 | Nudcd2 | 0.31128535 | 0.018784952 |
| chr6 | 71632478 | 71633628 | Promoter-TSS | −136 | Kdm3a | 0.311091449 | 0.001928789 |
| chr11 | 20332251 | 20333474 | Promoter-TSS | −149 | Slc1a4 | 0.310775504 | 0.008714695 |
| chr9 | 85326949 | 85328646 | Promoter-TSS | −647 | Fam46a | 0.310761157 | 0.030633067 |
| chr2 | 37358349 | 37359378 | Intron | 469 | Pdcl | 0.310759421 | 0.001059831 |
| chr17 | 31564137 | 31565047 | Promoter-TSS | −181 | Pknox1 | 0.310606063 | 0.024655737 |
| chr11 | 80476447 | 80477560 | Promoter-TSS | −43 | Cdk5r1 | 0.310362097 | 0.049836462 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr4 | 151996090 | 151996889 | Promoter-TSS | −310 | Phf13 | 0.310066453 | 0.013674626 |
| chr10 | 118470344 | 118471006 | Intergenic | 29629 | Ifng | 0.31004665 | 0.005897421 |
| chr7 | 4812132 | 4813143 | Promoter-TSS | −297 | Ube2s | 0.310041876 | 0.000906135 |
| chr11 | 53891285 | 53892156 | Promoter-TSS | −17 | Slc22a5 | 0.309971903 | 0.016824511 |
| chr19 | 57131343 | 57131864 | Intron | −12579 | Ablim1 | 0.309964211 | 0.043969277 |
| chr2 | 154569107 | 154570472 | Promoter-TSS | 103 | E2f1 | 0.309961871 | 0.025625151 |
| chr2 | 119477479 | 119478488 | Promoter-TSS | −354 | Ino80 | 0.309842821 | 0.02089891 |
| chr8 | 111853850 | 111854537 | Exon | 117 | Cfdp1 | 0.309768551 | 0.007430835 |
| chr7 | 13023886 | 13025205 | 5' UTR | 393 | Trim28 | 0.309755506 | 0.025865707 |
| chr11 | 120098499 | 120099338 | Promoter-TSS | −16 | Ndufaf8 | 0.309749305 | 0.043597089 |
| chr5 | 86065076 | 86065904 | Promoter-TSS | 93 | Cenpc1 | 0.30959108 | 0.005998594 |
| chr11 | 120713503 | 120714186 | Promoter-TSS | −36 | Cenpx | 0.309536005 | 0.023787642 |
| chr13 | 107890000 | 107891122 | Promoter-TSS | −497 | Zswim6 | 0.30947892 | 0.008896508 |
| chr11 | 22981762 | 22982616 | Promoter-TSS | 95 | Commd1 | 0.309339876 | 0.049089852 |
| chr7 | 47007906 | 47008874 | Promoter-TSS | 24 | Spty2d1 | 0.309320637 | 0.011833412 |
| chr13 | 51644758 | 51645837 | Promoter-TSS | 65 | Cks2 | 0.309049627 | 0.025865707 |
| chr3 | 135691262 | 135692070 | Promoter-TSS | −119 | Nfkb1 | 0.308993564 | 0.047058194 |
| chr15 | 100460951 | 100461981 | Intergenic | −7568 | Letmd1 | 0.308509003 | 0.047058194 |
| chr9 | 113930513 | 113931241 | Promoter-TSS | −57 | Ubp1 | 0.308357233 | 0.004892828 |
| chr9 | 123529309 | 123530211 | Promoter-TSS | −122 | Sacm1l | 0.308282532 | 0.005999978 |
| chr8 | 106210759 | 106211417 | Promoter-TSS | 34 | Prmt7 | 0.308035658 | 0.02873259 |
| chr11 | 72689710 | 72690535 | Intron | 120 | Ankfy1 | 0.307901791 | 0.04695583 |
| chr1 | 132007855 | 132008461 | Intron | 553 | Elk4 | 0.30770538 | 0.005186344 |
| chr7 | 135715734 | 135716915 | Promoter-TSS | 55 | Mki67 | 0.307693091 | 0.026537788 |
| chr6 | 47813054 | 47813874 | Promoter-TSS | 48 | Pdia4 | 0.307641049 | 0.000691262 |
| chr7 | 25718665 | 25719369 | Promoter-TSS | 36 | Ccdc97 | 0.307598058 | 0.047484622 |
| chr11 | 87461863 | 87463045 | Intron | 34863 | Tex14 | 0.307492244 | 0.002321511 |
| chr17 | 6960781 | 6961855 | Promoter-TSS | −162 | Tagap1 | 0.307450766 | 0.016173805 |
| chr5 | 30232232 | 30232919 | Promoter-TSS | −6 | Selenoi | 0.307402946 | 0.033064492 |
| chr18 | 56733801 | 56734439 | Intron | 26307 | Lmnb1 | 0.307368441 | 0.013617584 |
| chr17 | 56256266 | 56257075 | Promoter-TSS | −123 | Fem1a | 0.307358753 | 0.024886986 |
| chr4 | 116053077 | 116054025 | Intron | 325 | Nsun4 | 0.307354496 | 0.003268274 |
| chr7 | 120698998 | 120700041 | Intron | 21899 | BC030336 | 0.307225816 | 0.017765826 |
| chr11 | 20248858 | 20249797 | Promoter-TSS | 97 | Cep68 | 0.307022298 | 0.01934796 |
| chr12 | 106008395 | 106009142 | Intergenic | −1495 | Vrk1 | 0.3070026 | 0.015822761 |
| chr13 | 95987943 | 95989003 | Intron | −96551 | Iqgap2 | 0.306630282 | 0.014370296 |
| chr11 | 118418415 | 118419289 | Intron | 266 | Cant1 | 0.306356784 | 0.011677382 |
| chr13 | 41381091 | 41382262 | Intron | −22675 | Nedd9 | 0.30610573 | 0.026462047 |
| chr2 | 180256785 | 180257762 | Promoter-TSS | −106 | Rps21 | 0.305661129 | 0.012115218 |
| chr5 | 123394179 | 123394899 | Promoter-TSS | −259 | Mlxip | 0.305635584 | 0.042867803 |
| chr12 | 111537707 | 111538442 | Promoter-TSS | −27 | Eif5 | 0.305290878 | 0.000474237 |
| chr7 | 45017153 | 45018037 | Promoter-TSS | −412 | Rras | 0.305221016 | 0.004581767 |
| chr7 | 30090130 | 30090686 | 5' UTR | 102 | Zfp566 | 0.304864386 | 0.009295682 |
| chr7 | 38107360 | 38108585 | Promoter-TSS | −482 | Ccne1 | 0.304540054 | 0.005957973 |
| chr15 | 97342810 | 97343537 | Intron | −95886 | Amigo2 | 0.304390329 | 0.029845559 |
| chr10 | 19104608 | 19105442 | Intergenic | −36724 | Gm20139 | 0.304081874 | 0.0268747 |
| chr5 | 73193533 | 73194399 | Intron | 62652 | Fryl | 0.304040159 | 0.036186903 |
| chr12 | 83631862 | 83632521 | Promoter-TSS | −43 | Rbm25 | 0.303988247 | 0.042920908 |
| chr7 | 101896103 | 101897061 | Intron | 251 | Anapc15 | 0.303888355 | 0.016537764 |
| chr7 | 98656395 | 98657206 | Promoter-TSS | −231 | Emsy | 0.303784268 | 0.036602281 |
| chr1 | 178318159 | 178319304 | Promoter-TSS | −422 | Cox20 | 0.303733451 | 0.004581767 |
| chr13 | 104177952 | 104179258 | Promoter-TSS | −139 | Trappc13 | 0.303690965 | 0.046879612 |
| chr2 | 131352291 | 131353433 | Promoter-TSS | 30 | Rnf24 | 0.303681112 | 0.04076895 |
| chr19 | 53943869 | 53945070 | Promoter-TSS | 158 | Bbip1 | 0.303640105 | 0.000110358 |
| chr4 | 126202310 | 126203249 | Promoter-TSS | −69 | Thrap3 | 0.303565331 | 0.003306637 |
| chr2 | 121413384 | 121414079 | Promoter-TSS | 61 | Catsper2 | 0.303491172 | 0.018746377 |
| chr11 | 62602554 | 62603297 | Promoter-TSS | 48 | 2410006H16Rik | 0.302998366 | 0.026462047 |
| chr5 | 3595849 | 3596737 | 5' UTR | 227 | Pex1 | 0.302822938 | 0.011247026 |
| chr1 | 155972764 | 155973992 | Promoter-TSS | −123 | Cep350 | 0.302643599 | 0.016539327 |
| chr4 | 95160982 | 95161904 | Intergenic | −109221 | Jun | 0.302634201 | 0.037799105 |
| chr8 | 122281268 | 122282198 | Promoter-TSS | −408 | Zfpm1 | 0.302493773 | 0.005051351 |
| chr11 | 116130427 | 116131393 | TTS | 218 | Trim65 | 0.302394808 | 0.033950996 |
| chr4 | 48044918 | 48045419 | Promoter-TSS | −107 | Nr4a3 | 0.302221799 | 0.03366266 |
| chr2 | 91069925 | 91070849 | Promoter-TSS | −72 | Slc39a13 | 0.30211202 | 0.03146592 |
| chr5 | 137786092 | 137787043 | 5' UTR | 134 | Mepce | 0.301955405 | 0.004939542 |
| chr3 | 152907765 | 152908136 | Intron | 74257 | St6galnac5 | 0.301740128 | 0.042915292 |
| chr10 | 19591431 | 19592378 | Promoter-TSS | −45 | Ifngr1 | 0.301682994 | 0.012586256 |
| chr18 | 62548259 | 62549129 | Promoter-TSS | 49 | Fbxo38 | 0.30145858 | 0.044751382 |
| chr16 | 93831951 | 93832908 | Intron | 308 | Morc3 | 0.301092229 | 0.042867803 |
| chr4 | 126103650 | 126104168 | Promoter-TSS | −48 | Stk40 | 0.300937668 | 0.025257409 |
| chr12 | 84450730 | 84451701 | Promoter-TSS | −191 | Aldh6a1 | 0.300826034 | 0.020512489 |
| chr18 | 62977697 | 62978486 | Intron | 175 | Napg | 0.300312457 | 0.047262067 |
| chr11 | 85139683 | 85140551 | Promoter-TSS | −162 | Usp32 | 0.299931257 | 0.013331337 |
| chr11 | 121236612 | 121237541 | Promoter-TSS | −160 | Narf | 0.299779263 | 0.000333523 |
| chr11 | 103267033 | 103268078 | Promoter-TSS | −154 | Map3k14 | 0.299669767 | 0.016007317 |
| chr19 | 43524314 | 43525013 | Promoter-TSS | −58 | Got1 | 0.299436975 | 0.011906775 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr3 | 158036250 | 158037065 | Promoter-TSS | −18 | Srsf11 | 0.299421135 | 0.036938147 |
| chr1 | 161766556 | 161767513 | Intergenic | 21461 | Fasl | 0.299305956 | 0.030377975 |
| chr6 | 125008643 | 125009896 | Promoter-TSS | 31 | Zfp384 | 0.299116054 | 0.037914448 |
| chr11 | 103115886 | 103116609 | Promoter-TSS | −78 | Hexim1 | 0.299031978 | 0.016798519 |
| chr11 | 50291811 | 50292840 | Promoter-TSS | 11 | Maml1 | 0.298895736 | 0.049111229 |
| chr18 | 12640469 | 12640971 | Intergenic | −2813 | Ttc39c | 0.298857201 | 0.037521273 |
| chr19 | 46503557 | 46504589 | Intron | 2425 | Trim8 | 0.298619788 | 0.027234372 |
| chr19 | 41932658 | 41933758 | Promoter-TSS | 106 | Exosc1 | 0.298253648 | 0.009283011 |
| chr7 | 43399147 | 43400329 | Intergenic | −8542 | Siglecg | 0.298186677 | 0.020219736 |
| chr6 | 83794555 | 83795454 | Promoter-TSS | 4 | Nagk | 0.298126314 | 0.040179774 |
| chr4 | 126752939 | 126754152 | Promoter-TSS | −10 | AU040320 | 0.29779433 | 0.028810013 |
| chr11 | 93968001 | 93968761 | 5' UTR | 140 | Nme1 | 0.297637675 | 0.018227826 |
| chr5 | 146230878 | 146231983 | Promoter-TSS | −245 | Cdk8 | 0.297539858 | 0.039492701 |
| chr11 | 50325182 | 50326209 | Promoter-TSS | −22 | Canx | 0.29744136 | 0.024790494 |
| chr15 | 101224024 | 101224887 | Promoter-TSS | 248 | Grasp | 0.297287972 | 0.045112134 |
| chr5 | 136986612 | 136987761 | Promoter-TSS | 167 | Plod3 | 0.297195591 | 0.04164386 |
| chr8 | 121949981 | 121950866 | Promoter-TSS | −69 | Banp | 0.29711029 | 0.016306545 |
| chr17 | 85090091 | 85091113 | Promoter-TSS | −98 | Camkmt | 0.296996032 | 0.002143862 |
| chr4 | 116074856 | 116076342 | Promoter-TSS | 330 | Lrrc41 | 0.296939005 | 0.000716372 |
| chr16 | 18876376 | 18877417 | Promoter-TSS | 146 | Hira | 0.296754347 | 0.023233918 |
| chr14 | 62837004 | 62838188 | Promoter-TSS | −94 | Wdfy2 | 0.296548197 | 0.001667444 |
| chr2 | 154790557 | 154791574 | Promoter-TSS | −45 | Raly | 0.296475131 | 0.000691262 |
| chr18 | 35771212 | 35772228 | 5' UTR | 161 | Ube2d2a | 0.296308431 | 0.049196395 |
| chr4 | 152177629 | 152178734 | Promoter-TSS | 81 | Acot7 | 0.296252747 | 0.02040398 |
| chr13 | 80885440 | 80886504 | Intron | 2550 | Arrdc3 | 0.296177887 | 0.044863948 |
| chr10 | 115361877 | 115362794 | Promoter-TSS | −73 | Tmem19 | 0.295760954 | 0.011645216 |
| chr3 | 136669453 | 136670497 | Promoter-TSS | −91 | Ppp3ca | 0.295707735 | 0.020059137 |
| chr10 | 117376329 | 117377240 | Intron | 189 | Cpsf6 | 0.29540227 | 0.04476976 |
| chr17 | 12363465 | 12364687 | Intergenic | −14533 | Plg | 0.295266887 | 0.001759993 |
| chr12 | 76369170 | 76370668 | Promoter-TSS | −347 | Zbtb1 | 0.295263743 | 0.010878422 |
| chr5 | 108460939 | 108461741 | Promoter-TSS | 8 | Pcgf3 | 0.295214765 | 0.028071727 |
| chr2 | 122375410 | 122376007 | Intergenic | −6790 | Shf | 0.294953176 | 0.04640022 |
| chr16 | 8829302 | 8830346 | Promoter-TSS | −276 | 1810013L24Rik | 0.294910616 | 0.011811831 |
| chr17 | 24414235 | 24415115 | Promoter-TSS | 0 | Rnps1 | 0.29452686 | 0.042174272 |
| chr7 | 100371647 | 100372471 | Promoter-TSS | −163 | Ppme1 | 0.294344356 | 0.020037725 |
| chr14 | 121731646 | 121732472 | Intron | 6870 | Dock9 | 0.294244761 | 0.030502072 |
| chr1 | 93477912 | 93479419 | Promoter-TSS | 252 | Hdlbp | 0.294170667 | 0.002087696 |
| chr6 | 47594140 | 47595704 | 5' UTR | 108 | Ezh2 | 0.294124652 | 0.02827229 |
| chr14 | 103346193 | 103347141 | 5' UTR | 133 | Mycbp2 | 0.29403025 | 0.009994897 |
| chr2 | 25983000 | 25983916 | Promoter-TSS | −176 | Camsap1 | 0.293854588 | 0.026462047 |
| chr1 | 166378759 | 166380296 | Intron | 360 | Tada1 | 0.293678849 | 0.034600606 |
| chr10 | 67185533 | 67186130 | Promoter-TSS | 81 | Jmjd1c | 0.29339383 | 0.02660135 |
| chr7 | 16048160 | 16048570 | Intergenic | −23480 | Zfp541 | 0.293022207 | 0.049555747 |
| chr7 | 44848473 | 44849339 | Promoter-TSS | 173 | Tbc1d17 | 0.292787596 | 0.010284627 |
| chr14 | 122181409 | 122182035 | Promoter-TSS | 28 | Clybl | 0.292579266 | 0.041551866 |
| chr18 | 7868341 | 7869916 | Promoter-TSS | −44 | Wac | 0.292553118 | 0.028143959 |
| chr9 | 119322059 | 119323223 | Promoter-TSS | −214 | Oxsr1 | 0.292495744 | 0.004000886 |
| chr8 | 20296832 | 20297915 | Promoter-TSS | 59 | 6820431F20Rik | 0.292202058 | 0.00419104 |
| chr16 | 94568950 | 94570139 | Promoter-TSS | −662 | Dyrk1a | 0.292022599 | 0.014876885 |
| chr19 | 57099648 | 57100373 | Intron | 19014 | Ablim1 | 0.291917215 | 0.042547767 |
| chr10 | 93539724 | 93540597 | Promoter-TSS | −127 | Amdhd1 | 0.291545671 | 0.017555528 |
| chr13 | 106936246 | 106937277 | 5' UTR | 154 | Ipo11 | 0.29143502 | 0.035781518 |
| chr9 | 123509695 | 123510341 | Intron | −19864 | Sacm1l | 0.291139862 | 0.042658916 |
| chr9 | 109931157 | 109932171 | Promoter-TSS | −110 | Map4 | 0.291037448 | 0.010550357 |
| chr8 | 105565496 | 105567090 | Promoter-TSS | −253 | Atp6v0d1 | 0.290820661 | 0.015705647 |
| chr1 | 169531224 | 169532108 | Promoter-TSS | −202 | Nuf2 | 0.290269588 | 0.049676782 |
| chr9 | 108305758 | 108306974 | Promoter-TSS | 206 | Rhoa | 0.290161671 | 0.049567114 |
| chr17 | 25832781 | 25833603 | 5' UTR | 169 | Stub1 | 0.289905497 | 0.044735005 |
| chr1 | 136414894 | 136415719 | Promoter-TSS | 35 | Ddx59 | 0.289846233 | 0.021496267 |
| chr19 | 47731007 | 47731984 | Promoter-TSS | −261 | Sfr1 | 0.289821389 | 0.022051049 |
| chr16 | 94525997 | 94527214 | Promoter-TSS | 24 | Dscr3 | 0.289525999 | 0.011509523 |
| chr9 | 119983585 | 119984066 | Intron | 833 | Csrnp1 | 0.289274547 | 0.043222648 |
| chr7 | 16923784 | 16924757 | Promoter-TSS | −238 | Calm3 | 0.289139973 | 0.003417932 |
| chr13 | 108302964 | 108304136 | Intergenic | −12787 | Depdc1b | 0.289033216 | 0.044494798 |
| chr7 | 141193538 | 141194464 | Promoter-TSS | 3 | Hras | 0.288885804 | 0.025913718 |
| chr6 | 72957703 | 72958746 | Promoter-TSS | 8 | Tmsb10 | 0.288818618 | 0.011440688 |
| chr15 | 76080317 | 76081185 | Intron | 119 | Puf60 | 0.28869026 | 0.041238449 |
| chr1 | 155172836 | 155174032 | Intron | 14731 | Stx6 | 0.288187084 | 0.000715525 |
| chr2 | 180701442 | 180702530 | 5' UTR | 116 | Dido1 | 0.288153432 | 0.046476731 |
| chr19 | 38836145 | 38837420 | Exon | 203 | Tbc1d12 | 0.288131501 | 0.040490633 |
| chr8 | 88118458 | 88119289 | Intron | 114 | Cnep1r1 | 0.288119939 | 0.022075698 |
| chr11 | 95309379 | 95310665 | Intron | 224 | Kat7 | 0.287674894 | 0.007330656 |
| chr6 | 115676441 | 115677031 | Promoter-TSS | −101 | Raf1 | 0.287396709 | 0.036520216 |
| chr2 | 181287362 | 181288301 | Intron | 135 | Gmeb2 | 0.287234319 | 0.01595209 |
| chr10 | 91082092 | 91083584 | Promoter-TSS | −95 | Apaf1 | 0.287192159 | 0.011668856 |
| chr7 | 121706602 | 121707814 | Promoter-TSS | 45 | Usp31 | 0.287184738 | 0.014706997 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr1 | 63176424 | 63177383 | Promoter-TSS | 72 | Eef1b2 | 0.287178949 | 0.033070499 |
| chr8 | 70506148 | 70506991 | Exon | 170 | 2810428I15Rik | 0.28691569 | 0.044619506 |
| chr7 | 99483207 | 99484039 | Promoter-TSS | 86 | Rps3 | 0.286806154 | 0.033810523 |
| chr18 | 56707371 | 56708036 | Promoter-TSS | −110 | Lmnb1 | 0.286743391 | 0.025272967 |
| chr4 | 107066572 | 107067445 | Promoter-TSS | 20 | Cyb5rl | 0.286549251 | 0.025625151 |
| chr13 | 98814377 | 98815775 | Exon | 373 | Fcho2 | 0.286444086 | 0.021873402 |
| chr1 | 58392581 | 58394071 | Intron | 190 | Bzw1 | 0.286218394 | 0.015326824 |
| chr11 | 102296563 | 102297538 | Promoter-TSS | −421 | Atxn7l3 | 0.286086636 | 0.032949693 |
| chr9 | 40800719 | 40801608 | Promoter-TSS | −110 | Hspa8 | 0.285964286 | 0.02803968 |
| chr5 | 103691627 | 103692899 | Intergenic | −36531 | 1700016H13Rik | 0.28542486 | 0.047822338 |
| chr11 | 120672715 | 120673667 | Intron | 218 | Aspscr1 | 0.285400827 | 0.044619506 |
| chr16 | 45158211 | 45159423 | Promoter-TSS | −12 | Atg3 | 0.285348142 | 0.02714297 |
| chr8 | 11557876 | 11558586 | Promoter-TSS | −179 | Ing1 | 0.285263481 | 0.029926315 |
| chr2 | 153345125 | 153346058 | Promoter-TSS | 219 | 2500004C02Rik | 0.285246876 | 0.024574392 |
| chr6 | 145249245 | 145250798 | Promoter-TSS | 210 | Kras | 0.285156144 | 0.033365269 |
| chr11 | 29692542 | 29693349 | Promoter-TSS | 47 | Rtn4 | 0.284729818 | 0.026960022 |
| chr13 | 3537550 | 3538883 | 5' UTR | 141 | Gdi2 | 0.284665429 | 0.022943708 |
| chr5 | 143817130 | 143818239 | Intergenic | −54178 | Eif2ak1 | 0.284658369 | 0.019466149 |
| chr14 | 121878163 | 121879001 | Promoter-TSS | −24 | Ubac2 | 0.284478668 | 0.048351927 |
| chr2 | 120154280 | 120154977 | Promoter-TSS | −53 | Ehd4 | 0.284164033 | 0.024111714 |
| chr9 | 124422807 | 124423935 | Promoter-TSS | 120 | 4930526I15Rik | 0.283967992 | 0.004455147 |
| chr4 | 114986348 | 114987584 | Exon | 262 | Cmpk1 | 0.283850695 | 0.029933535 |
| chr17 | 84116295 | 84117069 | Intergenic | 38022 | 4933433H22Rik | 0.283461325 | 0.006533147 |
| chr2 | 163994764 | 163995863 | 5' UTR | 116 | Ywhab | 0.283451706 | 0.028588166 |
| chr2 | 158718912 | 158719624 | Intron | −48831 | Fam83d | 0.283415861 | 0.023316855 |
| chr5 | 150673331 | 150674653 | Intron | 165 | Pds5b | 0.283277504 | 0.043499675 |
| chr19 | 41801631 | 41802305 | Intron | 116 | Arhgap19 | 0.283043681 | 0.030016926 |
| chr12 | 80643330 | 80644660 | Promoter-TSS | 116 | Erh | 0.282991368 | 0.043969277 |
| chr4 | 133813140 | 133814715 | Intergenic | −60316 | Arid1a | 0.282900019 | 0.036892044 |
| chr5 | 24576916 | 24577941 | Promoter-TSS | 39 | Abcf2 | 0.282689188 | 0.045953855 |
| chr4 | 145221341 | 145222386 | Intron | 25007 | Tnfrsf1b | 0.282382534 | 0.018127966 |
| chr11 | 106788034 | 106789467 | Promoter-TSS | −256 | Ddx5 | 0.282225153 | 0.043597089 |
| chr4 | 116626703 | 116628135 | Promoter-TSS | 78 | Nasp | 0.282168033 | 0.03156101 |
| chr5 | 33657557 | 33658737 | Promoter-TSS | 19 | Tacc3 | 0.282162141 | 0.003858711 |
| chr9 | 54863366 | 54864380 | 5' UTR | 118 | Ireb2 | 0.282044704 | 0.040014386 |
| chr6 | 134920027 | 134920793 | Promoter-TSS | 9 | Cdkn1b | 0.281821658 | 0.033096032 |
| chr1 | 133130748 | 133131782 | Promoter-TSS | 99 | Ppp1r15b | 0.281766844 | 0.018531077 |
| chr4 | 150924093 | 150924744 | Intron | −3581 | Tnfrsf9 | 0.281734398 | 0.009707622 |
| chr9 | 90259403 | 90260289 | Intron | 10923 | Tbc1d2b | 0.281162702 | 0.043005833 |
| chr5 | 129941200 | 129942260 | Promoter-TSS | −379 | Vkorc1l1 | 0.281070712 | 0.012605668 |
| chr7 | 99140652 | 99141911 | Promoter-TSS | −137 | Uvrag | 0.280552291 | 0.013492519 |
| chr7 | 122288784 | 122290090 | Exon | 312 | Prkcb | 0.280214305 | 0.040883238 |
| chr11 | 109650695 | 109651617 | Intron | 235 | Prkar1a | 0.279850537 | 0.027701063 |
| chr17 | 87672172 | 87673199 | Exon | 128 | Msh2 | 0.279811378 | 0.01129744 |
| chr5 | 142920484 | 142921279 | Intergenic | −14127 | Actb | 0.279639771 | 0.038081384 |
| chrX | 162828900 | 162829756 | Exon | 126 | Txlng | 0.279508957 | 0.045807954 |
| chr4 | 62681286 | 62681909 | Intron | 7623 | Rgs3 | 0.279339801 | 0.010899543 |
| chr12 | 32378386 | 32379776 | Exon | 292 | Ccdc71l | 0.279304233 | 0.010533071 |
| chr1 | 190928181 | 190929303 | Exon | 237 | Angel2 | 0.279186406 | 0.021873402 |
| chr14 | 34310247 | 34311608 | Promoter-TSS | 200 | Glud1 | 0.279098492 | 0.006753985 |
| chr8 | 71468871 | 71469372 | Promoter-TSS | −73 | Dda1 | 0.278964125 | 0.037398863 |
| chr8 | 117256200 | 117257036 | Promoter-TSS | −401 | Cmip | 0.278776066 | 0.020786474 |
| chr1 | 161734171 | 161735299 | Intergenic | 53760 | Fasl | 0.278274362 | 0.028696828 |
| chr2 | 144555424 | 144556664 | Promoter-TSS | −185 | Sec23b | 0.278189226 | 0.019501536 |
| chr6 | 140623165 | 140623918 | Promoter-TSS | 39 | Aebp2 | 0.278169061 | 0.039163417 |
| chr3 | 107332973 | 107334153 | Promoter-TSS | −274 | Rbm15 | 0.278114899 | 0.001230837 |
| chr5 | 33651951 | 33652927 | TTS | 135 | Slbp | 0.277194285 | 0.024283232 |
| chr4 | 155601123 | 155602325 | 5' UTR | 308 | Slc35e2 | 0.277117075 | 0.033546698 |
| chr4 | 139192377 | 139193042 | Promoter-TSS | −190 | Capzb | 0.277067537 | 0.026380565 |
| chr7 | 102209625 | 102210873 | Promoter-TSS | −83 | Nup98 | 0.276791033 | 0.045859492 |
| chr6 | 144902401 | 144903528 | Intergenic | 145848 | Bcat1 | 0.276722232 | 0.029328954 |
| chr10 | 127290259 | 127291053 | Promoter-TSS | −137 | Ddit3 | 0.276716325 | 0.033982094 |
| chr11 | 109425295 | 109426455 | Promoter-TSS | −71 | Amz2 | 0.27654029 | 0.00023605 |
| chr8 | 72570642 | 72571482 | Promoter-TSS | −14 | Smim7 | 0.276381507 | 0.011912194 |
| chr2 | 18063800 | 18065254 | Promoter-TSS | −58 | Mllt10 | 0.276298422 | 0.041992397 |
| chr19 | 8819169 | 8820571 | Promoter-TSS | 469 | Hnrnpul2 | 0.276263758 | 0.012920273 |
| chr4 | 103114095 | 103115075 | Promoter-TSS | 195 | Mier1 | 0.276156312 | 0.013231224 |
| chr1 | 66816854 | 66818279 | Promoter-TSS | 29 | Kansl1l | 0.276057892 | 0.022591962 |
| chr11 | 32642274 | 32643175 | 5' UTR | 169 | Fbxw11 | 0.275919272 | 0.042163953 |
| chr11 | 65806515 | 65807596 | Promoter-TSS | −120 | Zkscan6 | 0.275406512 | 0.036856088 |
| chr1 | 152902234 | 152903491 | Promoter-TSS | −216 | Smg7 | 0.274617384 | 0.018703286 |
| chr8 | 116905156 | 116906507 | Intron | 15605 | Cmc2 | 0.274391236 | 0.020775476 |
| chr1 | 88277124 | 88277914 | Promoter-TSS | 38 | A730008H23Rik | 0.274174576 | 0.039773735 |
| chr4 | 119232333 | 119233454 | Promoter-TSS | −22 | P3h1 | 0.273080812 | 0.005769387 |
| chr19 | 41980510 | 41981954 | Promoter-TSS | −96 | Mms19 | 0.272876119 | 0.016846283 |
| chr7 | 5020073 | 5020907 | 5' UTR | 114 | Zfp865 | 0.272548258 | 0.047822338 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr11 | 29171957 | 29173195 | Promoter-TSS | −331 | Smek2 | 0.272471018 | 0.047250711 |
| chr18 | 67799855 | 67800759 | Promoter-TSS | 200 | Cep192 | 0.272419347 | 0.037121937 |
| chr18 | 42261812 | 42262608 | Promoter-TSS | −139 | Lars | 0.272201677 | 0.046877551 |
| chr9 | 88482099 | 88483258 | Promoter-TSS | −281 | Syncrip | 0.272018175 | 0.011909912 |
| chr5 | 150664843 | 150666080 | Intron | 151 | N4bp2l2 | 0.271996897 | 0.006697219 |
| chr7 | 25076804 | 25077524 | Promoter-TSS | −41 | Zfp574 | 0.271939729 | 0.006075501 |
| chr11 | 113683124 | 113684794 | Promoter-TSS | 192 | Fam104a | 0.271745382 | 0.004604657 |
| chr3 | 87885193 | 87886154 | Promoter-TSS | −111 | Prcc | 0.271717595 | 0.037746842 |
| chr2 | 119546910 | 119548126 | Promoter-TSS | 109 | Exd1 | 0.271688961 | 0.033905958 |
| chr4 | 152027218 | 152028100 | Promoter-TSS | 12 | Zbtb48 | 0.271652206 | 0.012741472 |
| chr14 | 14702564 | 14703609 | Promoter-TSS | 61 | Slc4a7 | 0.270950498 | 0.040841883 |
| chr8 | 80738790 | 80739946 | Promoter-TSS | 91 | Smarca5 | 0.270922873 | 0.037154195 |
| chr1 | 9748087 | 9748819 | Promoter-TSS | −71 | Vcpip1 | 0.270851126 | 0.04149342 |
| chr17 | 71474935 | 71476142 | Promoter-TSS | −195 | Smchd1 | 0.270542555 | 0.044495431 |
| chr15 | 95790043 | 95791320 | Promoter-TSS | −162 | Ano6 | 0.270341225 | 0.047979754 |
| chr11 | 70028771 | 70030154 | Intron | 10857 | Dlg4 | 0.270249088 | 0.037154195 |
| chr7 | 140035857 | 140037061 | Promoter-TSS | 68 | Zfp511 | 0.270232356 | 0.026442131 |
| chr15 | 59314580 | 59315406 | Promoter-TSS | −99 | Sqle | 0.270159509 | 0.018661466 |
| chr12 | 107921218 | 107921970 | Intron | 81820 | Bcl11b | 0.270035195 | 0.028143959 |
| chr11 | 23255207 | 23256176 | Promoter-TSS | −350 | Xpo1 | 0.269801257 | 0.008553893 |
| chr1 | 160212395 | 160213428 | Promoter-TSS | −19 | Cacybp | 0.269767845 | 0.032268657 |
| chr1 | 131527294 | 131528075 | Promoter-TSS | −219 | Fam72a | 0.269747584 | 0.001667444 |
| chr3 | 138442357 | 138443510 | Promoter-TSS | −160 | Adh5 | 0.269585323 | 0.009296778 |
| chr18 | 61554704 | 61555759 | Promoter-TSS | −351 | Csnk1a1 | 0.269442344 | 0.021043743 |
| chr5 | 145203966 | 145204679 | Promoter-TSS | −237 | Zkscan5 | 0.269424248 | 0.002906795 |
| chr17 | 71001769 | 71002969 | 5' UTR | 164 | Myl12a | 0.269125457 | 0.019364455 |
| chr15 | 98567243 | 98568212 | Promoter-TSS | −91 | Ccnt1 | 0.26899241 | 0.033640454 |
| chr9 | 31279737 | 31281353 | Intergenic | 9144 | Gm7244 | 0.268458399 | 0.003306637 |
| chr3 | 108256713 | 108257452 | 5' UTR | 156 | Psma5 | 0.268430192 | 0.046134897 |
| chr4 | 139574189 | 139574746 | Promoter-TSS | −253 | Iffo2 | 0.26820155 | 0.023540099 |
| chr15 | 9070838 | 9071977 | 5' UTR | 147 | Nadk2 | 0.267951733 | 0.045806606 |
| chr13 | 9093439 | 9094505 | Promoter-TSS | 91 | Larp4b | 0.267763858 | 0.047067273 |
| chr19 | 21652619 | 21653858 | Promoter-TSS | −71 | Abhd17b | 0.267757012 | 0.03538292 |
| chr18 | 46741250 | 46742392 | Promoter-TSS | −55 | Ap3s1 | 0.267542689 | 0.043408989 |
| chr7 | 27486710 | 27487466 | Intron | 135 | Sertad1 | 0.267340928 | 0.033402108 |
| chr7 | 19628297 | 19629637 | Intron | 471 | Relb | 0.267226587 | 0.042470067 |
| chr4 | 152325567 | 152326477 | Intron | 296 | Rpl22 | 0.267076466 | 0.032930997 |
| chr1 | 125435346 | 125436161 | Promoter-TSS | −26 | Actr3 | 0.266496753 | 0.020532689 |
| chr15 | 93274801 | 93275984 | Promoter-TSS | −213 | Gxylt1 | 0.266342038 | 0.019719292 |
| chr6 | 120038010 | 120038957 | 5' UTR | 172 | Wnk1 | 0.26626354 | 0.029174761 |
| chr10 | 5805227 | 5806230 | Promoter-TSS | −263 | Fbxo5 | 0.266021656 | 0.044110426 |
| chr15 | 9140200 | 9141228 | Promoter-TSS | 144 | Lmbrd2 | 0.26592848 | 0.038434855 |
| chr11 | 106216074 | 106217457 | Promoter-TSS | −161 | Ddx42 | 0.265664272 | 0.031834758 |
| chr5 | 24841987 | 24843212 | Promoter-TSS | −238 | Rheb | 0.265596545 | 0.006045862 |
| chr5 | 135545073 | 135545810 | Promoter-TSS | −319 | Hip1 | 0.265436631 | 0.008632716 |
| chr12 | 78225721 | 78226845 | Promoter-TSS | −372 | Gphn | 0.265314351 | 0.00957151 |
| chr11 | 87108679 | 87109477 | Promoter-TSS | −183 | Ska2 | 0.265306893 | 0.023052136 |
| chr15 | 77841847 | 77842780 | Promoter-TSS | −138 | Myh9 | 0.265209669 | 0.02507334 |
| chr2 | 180170890 | 180172009 | Promoter-TSS | −139 | Adrm1 | 0.264997885 | 0.034050897 |
| chr17 | 3114415 | 3115914 | 5' UTR | 192 | Scaf8 | 0.264886858 | 0.024986513 |
| chr10 | 121586280 | 121587786 | Promoter-TSS | −239 | Tbk1 | 0.264234771 | 0.043597089 |
| chr5 | 108629016 | 108630070 | Promoter-TSS | 234 | Gak | 0.263618877 | 0.048351927 |
| chr2 | 180273151 | 180274172 | Promoter-TSS | −196 | Cables2 | 0.263579961 | 0.000803099 |
| chr2 | 164804598 | 164805514 | Promoter-TSS | −58 | Zswim3 | 0.263443597 | 0.046365952 |
| chr1 | 156035372 | 156036738 | Promoter-TSS | 19 | Tor1aip2 | 0.263381314 | 0.005597954 |
| chr18 | 65414506 | 65415319 | Intron | −16085 | Malt1 | 0.263254872 | 0.034366911 |
| chr5 | 110839433 | 110840291 | Promoter-TSS | −85 | Hscb | 0.263084735 | 0.036101823 |
| chr15 | 38470330 | 38471382 | Intergenic | 19691 | Mir6951 | 0.263002858 | 0.017143289 |
| chr7 | 110061122 | 110062237 | Promoter-TSS | −23 | Zfp143 | 0.262905965 | 0.012115218 |
| chr12 | 118301871 | 118302575 | Promoter-TSS | −783 | Sp4 | 0.262546961 | 0.020423473 |
| chr4 | 129819672 | 129820280 | Promoter-TSS | −503 | Ptp4a2 | 0.262464186 | 0.037118736 |
| chr5 | 137628456 | 137629257 | Promoter-TSS | −267 | Lrch4 | 0.26242483 | 0.005197275 |
| chr18 | 73571931 | 73573050 | Promoter-TSS | −215 | Mex3c | 0.2622224 | 0.020056938 |
| chr3 | 101603802 | 101604990 | Intron | 311 | Atp1a1 | 0.262200019 | 0.014422389 |
| chr7 | 73617668 | 73619116 | Intergenic | −59997 | 1810026B05Rik | 0.261872155 | 0.004662629 |
| chr8 | 105170062 | 105171840 | 5' UTR | 277 | Cbfb | 0.261736263 | 0.024963601 |
| chr5 | 135962286 | 135963250 | Intron | 11708 | Ssc4d | 0.261685362 | 0.008912477 |
| chr6 | 38550937 | 38552563 | 5' UTR | 416 | Luc7l2 | 0.261512652 | 0.032423571 |
| chr16 | 4789821 | 4790597 | Promoter-TSS | −274 | Cdip1 | 0.261272935 | 0.042888215 |
| chrX | 151520255 | 151521281 | Promoter-TSS | 96 | Phf8 | 0.260914383 | 0.047909457 |
| chr8 | 75033346 | 75034490 | Intron | 232 | Tom1 | 0.260906533 | 0.012743816 |
| chr19 | 18712714 | 18713670 | Promoter-TSS | −44 | D030056L22Rik | 0.260384467 | 0.03600635 |
| chr19 | 8941556 | 8942632 | TTS | 174 | Mta2 | 0.260213201 | 0.036168409 |
| chr1 | 185362605 | 185363491 | Promoter-TSS | −47 | Eprs | 0.260202764 | 0.025865707 |
| chr5 | 143732053 | 143733027 | Promoter-TSS | −260 | Usp42 | 0.259813598 | 0.018298514 |
| chr7 | 19148912 | 19149928 | Promoter-TSS | −224 | Qpctl | 0.259004248 | 0.037805047 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr6 | 124828857 | 124830236 | Promoter-TSS | −62 | Usp5 | 0.258903398 | 0.001864274 |
| chr4 | 149697773 | 149698493 | Intron | 575 | Pik3cd | 0.258789284 | 0.028260357 |
| chr19 | 40513465 | 40514180 | Promoter-TSS | −10 | Sorbs1 | 0.258776265 | 0.030299648 |
| chr2 | 163418856 | 163419979 | Promoter-TSS | 53 | Oser1 | 0.258605185 | 0.02673327 |
| chr1 | 91052694 | 91053774 | Promoter-TSS | −210 | Lrrfip1 | 0.258501431 | 0.010341388 |
| chr5 | 137501818 | 137503257 | Promoter-TSS | −108 | Pop7 | 0.258439176 | 0.03366266 |
| chr11 | 121672766 | 121673707 | Promoter-TSS | −85 | B3gntl1 | 0.258226541 | 0.013131239 |
| chr18 | 82525818 | 82526914 | Intron | −28097 | Mbp | 0.258209039 | 0.034240162 |
| chr4 | 154160091 | 154161302 | Promoter-TSS | −12 | Tprgl | 0.258119892 | 0.043597089 |
| chr18 | 74778231 | 74780034 | Promoter-TSS | −80 | Acaa2 | 0.258071114 | 0.014366331 |
| chr3 | 103020205 | 103021544 | Intron | 328 | Csde1 | 0.257638572 | 0.019326455 |
| chr4 | 107803439 | 107804185 | Intron | 1553 | Lrp8 | 0.257521032 | 0.043288559 |
| chr16 | 15636937 | 15638670 | Promoter-TSS | −107 | Mcm4 | 0.256554682 | 0.018757473 |
| chr13 | 96542256 | 96543214 | Promoter-TSS | 0 | Col4a3bp | 0.256262023 | 0.045431897 |
| chr3 | 152395592 | 152396937 | Promoter-TSS | 261 | Zzz3 | 0.256118726 | 0.039767292 |
| chr12 | 105784293 | 105785367 | 5' UTR | 133 | Papola | 0.256049826 | 0.037121937 |
| chr4 | 151861582 | 151862833 | Promoter-TSS | −439 | Camta1 | 0.256037409 | 0.013931248 |
| chr15 | 81810158 | 81811772 | Promoter-TSS | −449 | Tef | 0.255911952 | 0.02672693 |
| chr6 | 122293807 | 122294225 | Intergenic | −11183 | Klrg1 | 0.255785948 | 0.044810735 |
| chr6 | 83506432 | 83507165 | Exon | 171 | Dguok | 0.255719972 | 0.021479226 |
| chr12 | 84772766 | 84773375 | Promoter-TSS | 42 | Npc2 | 0.255517319 | 0.036913303 |
| chr8 | 31149407 | 31150417 | Promoter-TSS | −404 | Tti2 | 0.254910024 | 0.047510815 |
| chr7 | 43436372 | 43437198 | Promoter-TSS | −353 | Nkg7 | 0.25469635 | 0.014293733 |
| chr15 | 98533750 | 98534701 | Promoter-TSS | 44 | Kansl2 | 0.254444727 | 0.008047209 |
| chr12 | 108179083 | 108180003 | Promoter-TSS | −195 | Ccnk | 0.254298588 | 0.001784704 |
| chr16 | 18811499 | 18812585 | Promoter-TSS | −70 | Cdc45 | 0.254295515 | 0.02489452 |
| chr17 | 50631191 | 50632470 | Intron | −66851 | Btg3 | 0.253754716 | 0.039522256 |
| chr5 | 143909424 | 143910306 | Promoter-TSS | −26 | Aimp2 | 0.25369454 | 0.033302642 |
| chr15 | 103272384 | 103273125 | Promoter-TSS | −164 | Copz1 | 0.253577 | 0.025454783 |
| chr18 | 46524991 | 46526591 | 5' UTR | 180 | Fem1c | 0.253167365 | 0.002166568 |
| chr11 | 96075480 | 96076213 | Promoter-TSS | −152 | Atp5g1 | 0.252566846 | 0.027234372 |
| chr3 | 131208365 | 131209268 | Intron | 63285 | Hadh | 0.252512806 | 0.031297017 |
| chr9 | 114752373 | 114753434 | Intergenic | 21700 | Cmtm6 | 0.252397067 | 0.007378889 |
| chr5 | 124075664 | 124076264 | Intron | 19844 | Abcb9 | 0.251817506 | 0.042610062 |
| chr11 | 69758095 | 69759625 | Promoter-TSS | −227 | Polr2a | 0.251711481 | 0.048609903 |
| chr10 | 11280477 | 11281670 | Promoter-TSS | −257 | Fbxo30 | 0.251553072 | 0.029096318 |
| chr9 | 121718741 | 121719595 | Promoter-TSS | −13 | Nktr | 0.251251884 | 0.028684248 |
| chr11 | 53430344 | 53431350 | Promoter-TSS | −16 | Uqcrq | 0.251158599 | 0.042018151 |
| chr17 | 8282865 | 8284320 | Promoter-TSS | −221 | Mpc1 | 0.251060084 | 0.013932137 |
| chr15 | 103239304 | 103240764 | Promoter-TSS | −218 | Cbx5 | 0.251026077 | 0.010043627 |
| chr14 | 120477338 | 120478762 | Promoter-TSS | −411 | Rap2a | 0.250859077 | 0.04089267 |
| chr19 | 46760691 | 46761889 | Promoter-TSS | −239 | Cnnm2 | 0.2508184 | 0.009683297 |
| chr15 | 5116047 | 5116886 | Promoter-TSS | −147 | Rpl37 | 0.250366794 | 0.025611835 |
| chr19 | 6979567 | 6980709 | Intron | 302 | Fkbp2 | 0.250362707 | 0.02465177 |
| chr13 | 12394809 | 12395860 | Promoter-TSS | −41 | Heatr1 | 0.250288065 | 0.043896665 |
| chr14 | 21500188 | 21501299 | Intron | 958 | Kat6b | 0.249921292 | 0.007553304 |
| chr10 | 40348569 | 40349737 | Promoter-TSS | −155 | Cdk19 | 0.24979335 | 0.013763263 |
| chr1 | 37864542 | 37865520 | Promoter-TSS | 51 | Tsga10 | 0.249105579 | 0.007085638 |
| chr1 | 93635104 | 93636172 | Promoter-TSS | 89 | Stk25 | 0.248848608 | 0.04017763 |
| chr9 | 25251557 | 25253144 | Promoter-TSS | −89 | Sept7 | 0.248813821 | 0.039194126 |
| chr11 | 55469100 | 55470074 | Promoter-TSS | −165 | G3bp1 | 0.248733972 | 0.002751614 |
| chr2 | 147012508 | 147013725 | Promoter-TSS | 56 | Xrn2 | 0.247925914 | 0.026165578 |
| chr16 | 22265261 | 22266314 | 5' UTR | 218 | Tra2b | 0.247925459 | 0.0385915 |
| chr15 | 102405254 | 102406342 | Promoter-TSS | −518 | Sp1 | 0.247909918 | 0.012115218 |
| chr10 | 99261429 | 99262291 | Intergenic | −1371 | Dusp6 | 0.24782529 | 0.030165523 |
| chr7 | 13037841 | 13038542 | Promoter-TSS | 84 | Ube2m | 0.247700452 | 0.041728296 |
| chr4 | 125127301 | 125128109 | Intron | 176 | Zc3h12a | 0.247654292 | 0.033893252 |
| chr7 | 135651786 | 135653129 | Promoter-TSS | −143 | 5830432E09Rik | 0.247643211 | 0.039443353 |
| chr7 | 113368765 | 113370164 | Promoter-TSS | −125 | Btbd10 | 0.246486884 | 0.033776775 |
| chr12 | 110991490 | 110992583 | Intergenic | −2362 | 6030440G07Rik | 0.246361915 | 0.036423958 |
| chr9 | 110653734 | 110654392 | Promoter-TSS | 98 | Nbeal2 | 0.246103496 | 0.048579857 |
| chr11 | 74829878 | 74830993 | Promoter-TSS | −489 | Mnt | 0.245850416 | 0.030456988 |
| chr3 | 152912172 | 152913157 | Intron | 69543 | St6galnac5 | 0.245616193 | 0.013904515 |
| chr9 | 102625443 | 102626950 | Promoter-TSS | −72 | Cep63 | 0.24501458 | 0.037916076 |
| chr7 | 138845618 | 138846718 | Promoter-TSS | 99 | Mapk1ip1 | 0.244450632 | 0.035979297 |
| chr10 | 42501683 | 42502822 | 5' UTR | 198 | Snx3 | 0.244398947 | 0.042977817 |
| chr10 | 5823662 | 5824868 | Promoter-TSS | −322 | Mtrf1l | 0.243937264 | 0.027234372 |
| chr1 | 179802912 | 179804189 | 5' UTR | 465 | Ahctf1 | 0.243458033 | 0.0385915 |
| chr5 | 129019391 | 129020718 | Promoter-TSS | −102 | Ran | 0.243101103 | 0.032198375 |
| chr4 | 120824990 | 120826119 | 5' UTR | 187 | Nfyc | 0.24166996 | 0.017589398 |
| chr8 | 94036676 | 94037533 | Promoter-TSS | −65 | Nudt21 | 0.241318791 | 0.043896665 |
| chr5 | 146220674 | 146221612 | Promoter-TSS | −172 | Rnf6 | 0.240949805 | 0.018666299 |
| chr5 | 76950883 | 76952074 | Promoter-TSS | 67 | Paics | 0.240455428 | 0.017975607 |
| chr6 | 113076000 | 113077612 | Promoter-TSS | 438 | Gt(ROSA)26Sor | 0.239563386 | 0.041551866 |
| chr4 | 107253184 | 107254134 | Promoter-TSS | −126 | Lrrc42 | 0.239542341 | 0.035522293 |
| chr2 | 132252560 | 132253558 | 5' UTR | 121 | Pcna | 0.239362685 | 0.0375874 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr14 | 121378264 | 121379969 | 5' UTR | 114 | Stk24 | 0.239114742 | 0.03366266 |
| chr12 | 113155566 | 113156639 | Promoter-TSS | −319 | 4930427A07Rik | 0.238677343 | 0.04785284 |
| chr11 | 64978678 | 64979568 | Promoter-TSS | 88 | Elac2 | 0.238667518 | 0.037777427 |
| chr9 | 25151174 | 25152261 | Promoter-TSS | 64 | Herpud2 | 0.238453512 | 0.041716893 |
| chr15 | 102624991 | 102625986 | Promoter-TSS | −24 | Atf7 | 0.237923965 | 0.031099454 |
| chr9 | 72985160 | 72986067 | Promoter-TSS | 109 | Ccpg1 | 0.237855547 | 0.029173201 |
| chr13 | 69610980 | 69612213 | Promoter-TSS | −133 | Srd5a1 | 0.237588939 | 0.04338803 |
| chr16 | 93777086 | 93778764 | Intron | −54196 | Morc3 | 0.236760679 | 0.032978054 |
| chr10 | 9900569 | 9902260 | Promoter-TSS | −374 | Stxbp5 | 0.236747918 | 0.02833225 |
| chr19 | 53141953 | 53143042 | Promoter-TSS | −259 | Add3 | 0.236647875 | 0.034810768 |
| chr18 | 65430281 | 65431286 | Promoter-TSS | −214 | Malt1 | 0.23613107 | 0.026462047 |
| chr17 | 74527743 | 74528898 | Promoter-TSS | 25 | Birc6 | 0.235726093 | 0.019987809 |
| chr1 | 191396876 | 191397881 | Promoter-TSS | −337 | Ppp2r5a | 0.235686453 | 0.017022061 |
| chr10 | 94035317 | 94036535 | Promoter-TSS | −75 | Fgd6 | 0.235590681 | 0.029174761 |
| chr7 | 111082028 | 111083562 | 5' UTR | 235 | Eif4g2 | 0.234293157 | 0.030441096 |
| chr2 | 180118769 | 180119846 | Promoter-TSS | −59 | Osbpl2 | 0.234151827 | 0.03207853 |
| chr1 | 180403280 | 180404314 | Intron | −73248 | Gm5069 | 0.234086122 | 0.028487082 |
| chr3 | 30601981 | 30603063 | 5' UTR | 435 | Mynn | 0.233968175 | 0.02591362 |
| chr17 | 84956961 | 84958180 | Promoter-TSS | 140 | 1110020A21Rik | 0.233947188 | 0.018465878 |
| chr17 | 72918008 | 72919484 | Intron | 441 | Lbh | 0.233425195 | 0.030169212 |
| chr11 | 119942216 | 119943325 | Promoter-TSS | −322 | Baiap2 | 0.233024386 | 0.039443353 |
| chr17 | 84790042 | 84791101 | 5' UTR | 215 | Lrpprc | 0.232959368 | 0.036637226 |
| chr13 | 54693596 | 54694679 | Promoter-TSS | −177 | Rnf44 | 0.232756177 | 0.044620982 |
| chr4 | 33247428 | 33248807 | Exon | 670 | Pnrc1 | 0.232699019 | 0.042977817 |
| chr7 | 27178253 | 27179248 | TTS | 133 | Rab4b | 0.232061607 | 0.028975974 |
| chr9 | 123850866 | 123852241 | TTS | 108 | Fyco1 | 0.231189911 | 0.033177923 |
| chr15 | 102517764 | 102518842 | 5' UTR | 111 | Tarbp2 | 0.230248852 | 0.002307792 |
| chr2 | 73892409 | 73893307 | Promoter-TSS | −219 | Atf2 | 0.22957414 | 0.043019435 |
| chr17 | 88065755 | 88066671 | Promoter-TSS | −928 | Fbxo11 | 0.228894904 | 0.014430893 |
| chr9 | 57075760 | 57076413 | Promoter-TSS | −290 | Sin3a | 0.228689429 | 0.046275288 |
| chr11 | 106083884 | 106085180 | Promoter-TSS | −370 | Map3k3 | 0.228060615 | 0.018970351 |
| chr12 | 76961851 | 76962813 | Promoter-TSS | −84 | Max | 0.226858537 | 0.034366911 |
| chr6 | 28479640 | 28480606 | Promoter-TSS | −225 | Snd1 | 0.226561442 | 0.049567114 |
| chr16 | 91728345 | 91729612 | Promoter-TSS | −176 | Cryzl1 | 0.226497299 | 0.018024716 |
| chr7 | 45922858 | 45923792 | Intergenic | −1899 | Emp3 | 0.226068856 | 0.038217683 |
| chr3 | 135437804 | 135439591 | Promoter-TSS | −32 | 4930539J05Rik | 0.224661411 | 0.041580273 |
| chr8 | 25273927 | 25275573 | Intergenic | 31520 | 5430421F17Rik | 0.223850804 | 0.049346071 |
| chr4 | 108999980 | 109001220 | Promoter-TSS | −38 | Nrd1 | 0.22284854 | 0.016295538 |
| chr10 | 82763443 | 82764489 | Intron | 175 | Nfyb | 0.221493286 | 0.039145199 |
| chr9 | 13826856 | 13828283 | Promoter-TSS | −158 | Fam76b | 0.220478472 | 0.006235885 |
| chr13 | 14062947 | 14064127 | Promoter-TSS | −49 | Ggps1 | 0.220209789 | 0.017028441 |
| chr12 | 116047359 | 116048192 | Promoter-TSS | 51 | Zfp386 | 0.218587368 | 0.025454783 |
| chr6 | 113306286 | 113306996 | Promoter-TSS | −496 | Brpf1 | 0.218421684 | 0.024713196 |
| chr10 | 95514634 | 95515595 | Promoter-TSS | −48 | Ube2n | 0.217997326 | 0.03792645 |
| chr7 | 3692702 | 3693975 | Promoter-TSS | 187 | Mboat7 | 0.217243367 | 0.046289759 |
| chr3 | 137863049 | 137864647 | Promoter-TSS | −319 | H2afz | 0.217193059 | 0.036913303 |
| chr3 | 106721453 | 106722523 | 5' UTR | 306 | Lrif1 | 0.214366127 | 0.032094988 |
| chr8 | 4677301 | 4679373 | Intergenic | 65167 | Zfp958 | 0.213889944 | 0.035670216 |
| chr14 | 67715585 | 67716352 | Promoter-TSS | −127 | Cdca2 | 0.212147872 | 0.040050544 |
| chr4 | 122885671 | 122886818 | Promoter-TSS | −187 | Cap1 | 0.211206865 | 0.004965252 |
| chr6 | 42349049 | 42350253 | Promoter-TSS | −177 | Zyx | 0.210152798 | 0.037930164 |
| chr10 | 115384253 | 115385666 | Promoter-TSS | 0 | Zfc3h1 | 0.209794346 | 0.021648726 |
| chr5 | 90223557 | 90224552 | Promoter-TSS | −58 | Cox18 | 0.207814354 | 0.046214456 |
| chr17 | 53478265 | 53480092 | 5' UTR | 140 | Rab5a | 0.204791803 | 0.039028999 |
| chr12 | 111813640 | 111814606 | Promoter-TSS | −47 | Zfyve21 | 0.204742781 | 0.03599827 |
| chr8 | 84066289 | 84066959 | Promoter-TSS | −212 | Rfx1 | 0.198451525 | 0.041103865 |
| chr1 | 180199170 | 180199889 | Intergenic | −3509 | Coq8a | −0.27528229 | 0.039834929 |
| chr7 | 110108984 | 110109616 | Intergenic | −12759 | Wee1 | −0.279150312 | 0.041497774 |
| chr13 | 102905894 | 102906929 | Intron | 146156 | 1700099I09Rik | −0.301346706 | 0.009273024 |
| chr6 | 41532235 | 41533211 | Intergenic | 10947 | Prss2 | −0.303536164 | 0.016808265 |
| chr5 | 105839764 | 105840556 | Intergenic | −36408 | Zfp326 | −0.307000161 | 0.042687775 |
| chr19 | 34877892 | 34879456 | Promoter-TSS | −757 | Pank1 | −0.320511826 | 0.005384337 |
| chr3 | 138893272 | 138894013 | Intron | 151434 | Tspan5 | −0.328540126 | 0.049060233 |
| chr6 | 140613642 | 140614295 | Intergenic | −8695 | Aebp2 | −0.333619703 | 0.030169212 |
| chr19 | 29453917 | 29454686 | Intron | 43382 | Pdcd1lg2 | −0.333876995 | 0.047569335 |
| chr6 | 122527383 | 122528109 | Intron | 14070 | Mfap5 | −0.340735532 | 0.005025157 |
| chr14 | 120404959 | 120405594 | Intron | −73185 | Rap2a | −0.344962926 | 0.047123224 |
| chr17 | 65961452 | 65962213 | Intergenic | −10645 | Twsg1 | −0.345920008 | 0.041435256 |
| chr10 | 75222257 | 75223036 | Intron | 10256 | Specc1l | −0.347546336 | 0.036467288 |
| chr12 | 108333795 | 108334535 | Promoter-TSS | −216 | Cyp46a1 | −0.348172916 | 0.012485208 |
| chr14 | 121938660 | 121939201 | Intron | −23156 | Gpr18 | −0.350955911 | 0.037978143 |
| chr15 | 93595299 | 93596380 | Promoter-TSS | 52 | Prickle1 | −0.351961493 | 0.027108923 |
| chr1 | 69544058 | 69544661 | Intron | 141601 | Ikzf2 | −0.353619861 | 0.010905258 |
| chr16 | 51674964 | 51675566 | Intergenic | −356284 | Cblb | −0.359179386 | 0.030326799 |
| chr14 | 76781313 | 76782015 | Intergenic | 104096 | 1700108F19Rik | −0.360641571 | 0.03146592 |
| chr3 | 138419340 | 138419848 | Intron | 4097 | Adh4 | −0.360680438 | 0.027202365 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr13 | 64432138 | 64433070 | Promoter-TSS | 51 | Cdk20 | −0.360735177 | 0.008916567 |
| chr10 | 75105113 | 75105522 | Intron | 44421 | Bcr | −0.361436803 | 0.040427941 |
| chr6 | 108338258 | 108338880 | Intron | 125473 | Itpr1 | −0.361817226 | 0.024837082 |
| chr18 | 32564188 | 32564785 | Intergenic | −4452 | Gypc | −0.361873143 | 0.04932333 |
| chr2 | 137116676 | 137117636 | Promoter-TSS | −636 | Jag1 | −0.362529876 | 0.03115686 |
| chr1 | 54585096 | 54585801 | Intergenic | −27764 | Pgap1 | −0.363331526 | 0.02422574 |
| chr7 | 130827697 | 130828925 | Intergenic | −37413 | Plekha1 | −0.368215018 | 0.023293583 |
| chr14 | 121822980 | 121823468 | Intergenic | −25490 | Dock9 | −0.375035846 | 0.043749197 |
| chr5 | 104859560 | 104860443 | Promoter-TSS | 67 | Zfp951 | −0.380144119 | 0.035971747 |
| chr10 | 54026623 | 54027255 | Intron | 48857 | Man1a | −0.381487704 | 0.041383981 |
| chr1 | 106612430 | 106613164 | Intron | −66166 | Mir3473f | −0.384813292 | 0.037018315 |
| chr6 | 97294030 | 97294771 | Intron | −41620 | Lmod3 | −0.386915737 | 0.003959314 |
| chr1 | 127233003 | 127233607 | Intron | 28319 | Mgat5 | −0.387899398 | 0.014590711 |
| chr5 | 149526428 | 149527076 | Intron | −1927 | Wdr95 | −0.401937312 | 0.009295682 |
| chr6 | 135065212 | 135065855 | Promoter-TSS | −129 | Gprc5a | −0.40293322 | 0.007584585 |
| chr9 | 108035227 | 108035904 | Intron | −13725 | Gmppb | −0.405660221 | 0.042263534 |
| chr17 | 45488378 | 45489246 | Intergenic | −13874 | Spats1 | −0.41073477 | 0.019096738 |
| chr4 | 116010065 | 116010640 | Intron | 7550 | Faah | −0.411385265 | 0.021496267 |
| chr2 | 33130306 | 33131459 | Intergenic | −43678 | Garnl3 | −0.41176533 | 0.034394606 |
| chr17 | 47531354 | 47531960 | Intron | 26606 | Ccnd3 | −0.413269626 | 0.002989356 |
| chr6 | 122532833 | 122533303 | Intergenic | 19392 | Mfap5 | −0.414115896 | 0.000329557 |
| chr17 | 87118893 | 87119577 | Intron | 11556 | Socs5 | −0.414892594 | 0.007546783 |
| chr11 | 90224809 | 90225656 | Intergenic | −24244 | Mmd | −0.415088097 | 0.049285363 |
| chr3 | 138420178 | 138420923 | Intron | 5053 | Adh4 | −0.41724936 | 0.019066417 |
| chr13 | 110394314 | 110395533 | Promoter-TSS | −121 | Plk2 | −0.41859324 | 0.006542279 |
| chr8 | 68156947 | 68157731 | Intergenic | −119189 | Sh2d4a | −0.419133337 | 0.0193937 |
| chr9 | 46083295 | 46083942 | Intron | 70798 | Sik3 | −0.420159516 | 0.029368914 |
| chr10 | 121316064 | 121316787 | Intergenic | −5236 | Tbc1d30 | −0.420768863 | 0.026151066 |
| chr8 | 107254985 | 107255506 | Promoter-TSS | −964 | Mir5098 | −0.42710304 | 0.038367289 |
| chr16 | 52147106 | 52147813 | Intron | 115910 | Cblb | −0.427487582 | 0.045797925 |
| chr1 | 101902082 | 101903060 | Intergenic | 746803 | Gm20268 | −0.428333286 | 0.00631187 |
| chr7 | 10494912 | 10495701 | Promoter-TSS | 75 | Zik1 | −0.4285593 | 0.028143959 |
| chr3 | 142358842 | 142359354 | Intron | 32752 | Pdlim5 | −0.428631114 | 0.035522293 |
| chr7 | 140376782 | 140377437 | Intergenic | −3501 | Olfr530 | −0.430735205 | 0.01342155 |
| chr16 | 45251758 | 45252464 | 3' UTR | 27774 | Btla | −0.431040799 | 0.024374496 |
| chr10 | 37136834 | 37137581 | Intron | 1719 | Marcks | −0.43484384 | 0.02578663 |
| chr10 | 117677129 | 117677962 | Intron | 33213 | Mdm2 | −0.439305886 | 0.042086589 |
| chr16 | 55770231 | 55770818 | Intergenic | 51614 | Nfkbiz | −0.4428539 | 0.019062993 |
| chr12 | 26068094 | 26068941 | Intergenic | 141988 | Gm29687 | −0.44984066 | 0.008996106 |
| chr2 | 43727614 | 43728172 | Intergenic | −20931 | Arhgap15 | −0.450173151 | 0.005719264 |
| chr17 | 34000218 | 34000902 | Promoter-TSS | −213 | H2-K1 | −0.453366928 | 1.23E−10 |
| chr11 | 22692708 | 22693676 | Intergenic | 166543 | B3gnt2 | −0.454219759 | 0.008761972 |
| chr15 | 96583164 | 96583940 | Intron | 58410 | Slc38a1 | −0.454513593 | 0.003546261 |
| chr15 | 62181338 | 62181989 | Intron | 37788 | H2afy3 | −0.454915256 | 0.033669391 |
| chr13 | 119599004 | 119599471 | Intron | −24582 | Ccl28 | −0.45641113 | 0.049620307 |
| chr12 | 102627528 | 102628034 | Intron | 57239 | Mir1936 | −0.456732447 | 0.029587478 |
| chrY | 90803267 | 90803682 | Intron | 18032 | Erdr1 | −0.461027096 | 0.037919614 |
| chr16 | 51704792 | 51705546 | Intergenic | −326380 | Cblb | −0.462669385 | 0.00045046 |
| chr15 | 50667229 | 50667961 | Intron | 221454 | Trps1 | −0.463767383 | 0.00676411 |
| chr4 | 71291161 | 71292248 | Intergenic | −756776 | Megf9 | −0.465732238 | 0.009459817 |
| chr4 | 120287639 | 120288314 | Promoter-TSS | −715 | Foxo6 | −0.466943997 | 0.043969277 |
| chr16 | 42190110 | 42190647 | Intergenic | 113091 | Mir6540 | −0.467746544 | 0.03691442 |
| chr9 | 32661443 | 32662134 | Intergenic | −34254 | Ets1 | −0.46809823 | 0.004752463 |
| chr13 | 85724187 | 85725234 | Intergenic | 322085 | Cox7c | −0.470030651 | 0.002906795 |
| chr18 | 84873951 | 84874807 | Intron | 22965 | Cyb5a | −0.470798242 | 0.04555012 |
| chr6 | 41546727 | 41547110 | Intergenic | 25142 | Prss2 | −0.47204096 | 0.000350164 |
| chr15 | 36396077 | 36396745 | Intergenic | 100380 | Ankrd46 | −0.473582863 | 0.024574392 |
| chr12 | 89719043 | 89719698 | Intron | −93113 | Nrxn3 | −0.474797196 | 0.02034242 |
| chr19 | 36348753 | 36349526 | Intergenic | −29928 | Pcgf5 | −0.477506992 | 0.013100566 |
| chr1 | 78538306 | 78538912 | TTS | 27549 | Mogat1 | −0.478719349 | 0.035996179 |
| chr1 | 23383021 | 23383700 | Promoter-TSS | −185 | Ogfrl1 | −0.479045229 | 0.027234372 |
| chr3 | 126660219 | 126661547 | Intron | 63932 | Camk2d | −0.481463932 | 0.000165309 |
| chr18 | 68189798 | 68190294 | Intron | 70927 | Mir7219 | −0.481641756 | 0.008899608 |
| chr10 | 84897205 | 84897940 | Intron | −20041 | Ric8b | −0.481766069 | 0.011717354 |
| chr10 | 121520882 | 121521374 | Intergenic | −44878 | Rassf3 | −0.482959612 | 0.021147467 |
| chr1 | 82282972 | 82283691 | Intron | 8108 | Irs1 | −0.484890021 | 0.01197694 |
| chr1 | 74295318 | 74296059 | Intron | 8648 | Tmbim1 | −0.491810626 | 0.00390311 |
| chr17 | 34001884 | 34002298 | Intergenic | −1744 | H2-K1 | −0.493320391 | 0.00207258 |
| chr13 | 114845733 | 114846445 | Intron | 27852 | Mocs2 | −0.497426864 | 0.01983773 |
| chr9 | 75625395 | 75626497 | Exon | 214 | Lysmd2 | −0.498620452 | 0.047067273 |
| chr16 | 25484996 | 25485656 | Intergenic | −198439 | Trp63 | −0.499403448 | 0.006121545 |
| chr16 | 21204352 | 21204884 | Promoter-TSS | −177 | Ephb3 | −0.500619385 | 0.004607734 |
| chr12 | 25305773 | 25306506 | Intergenic | 176965 | Gm17746 | −0.501954451 | 0.000593185 |
| chr11 | 34506253 | 34506989 | Intron | 191799 | Fam196b | −0.502231583 | 0.036361796 |
| chr9 | 120082532 | 120083120 | Intergenic | −9307 | Ccr8 | −0.502453407 | 0.049285363 |
| chr6 | 67158725 | 67159170 | Intergenic | −108032 | Serbp1 | −0.502477328 | 0.022997705 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr14 | 76504110 | 76504658 | Promoter-TSS | −126 | Tsc22d1 | −0.508226862 | 0.028788668 |
| chr10 | 111214662 | 111215089 | Intron | 50073 | Osbpl8 | −0.509759699 | 0.023361166 |
| chr9 | 92384144 | 92385024 | Intergenic | −72794 | Plscr4 | −0.510828569 | 0.013021742 |
| chr7 | 49601200 | 49602020 | Intron | 35225 | Dbx1 | −0.510915774 | 0.000116478 |
| chr4 | 56222086 | 56222901 | Intergenic | 518932 | Actl7b | −0.522361372 | 0.007033657 |
| chr3 | 94412883 | 94413446 | Promoter-TSS | −154 | Tdrkh | −0.523404213 | 0.000725797 |
| chr17 | 80323500 | 80324183 | Intron | 16434 | Arhgef33 | −0.527087857 | 0.019462983 |
| chr3 | 101280316 | 101280682 | Intron | 7440 | Cd2 | −0.527555423 | 0.009671557 |
| chr17 | 15825878 | 15826961 | 5′ UTR | 167 | Rgmb | −0.530444114 | 0.005707457 |
| chr4 | 149856388 | 149856837 | Intergenic | −82345 | Slc25a33 | −0.531374718 | 0.032861627 |
| chr9 | 89874366 | 89874927 | Intergenic | −35129 | Rasgrf1 | −0.532488276 | 0.000716372 |
| chr8 | 15018010 | 15018547 | Intron | 7253 | Kbtbd11 | −0.535260965 | 0.036158255 |
| chr2 | 126636000 | 126636905 | Intron | −17774 | Hdc | −0.535491937 | 0.021147467 |
| chr13 | 73469508 | 73469961 | Intron | 2351 | Lpcat1 | −0.537174546 | 0.022317383 |
| chr7 | 3451157 | 3451516 | Intergenic | 26674 | Cacng6 | −0.537296662 | 0.010968396 |
| chr5 | 75066603 | 75067645 | Intergenic | −8477 | Gsx2 | −0.537483451 | 0.0010573 |
| chr6 | 94681122 | 94681859 | Intron | 18655 | Lrig1 | −0.539285984 | 0.012946794 |
| chr10 | 67717387 | 67718168 | Intergenic | −168822 | Ado | −0.539991807 | 0.005830235 |
| chr13 | 89739303 | 89739823 | Intron | 2949 | Vcan | −0.54015732 | 0.017975644 |
| chr8 | 76901824 | 76902441 | Promoter-TSS | −376 | Nr3c2 | −0.54329119 | 0.003818001 |
| chr10 | 118172430 | 118173158 | Intergenic | 31007 | Mdm1 | −0.548851004 | 0.002070737 |
| chr14 | 118834217 | 118834711 | Intron | −20486 | Cldn10 | −0.549242837 | 0.018508937 |
| chr1 | 128398843 | 128399579 | Intron | 18205 | Dars | −0.550891439 | 0.033108403 |
| chr12 | 34990202 | 34990925 | Intergenic | 5802 | Prps1l1 | −0.551337688 | 0.002364046 |
| chr9 | 120023138 | 120023498 | Intron | 280 | Xirp1 | −0.55160381 | 0.038061636 |
| chr10 | 115332137 | 115332934 | Intergenic | −16944 | Rab21 | −0.552233384 | 0.001459081 |
| chr17 | 66073968 | 66074549 | Intron | 2788 | Ankrd12 | −0.552319717 | 0.006217652 |
| chr3 | 101047565 | 101048161 | Intron | −18368 | Cd101 | −0.554312372 | 0.022969516 |
| chr18 | 5593690 | 5594226 | Intron | −1525 | Gm10125 | −0.554593484 | 0.001274702 |
| chr1 | 193152778 | 193153424 | Promoter-TSS | −11 | Irf6 | −0.554651688 | 0.048304219 |
| chr8 | 13992451 | 13993144 | Intron | −6143 | Gm5907 | −0.555219895 | 0.023316576 |
| chr5 | 16469682 | 16470272 | Intergenic | −83518 | Hgf | −0.555383205 | 0.013931248 |
| chr10 | 107941278 | 107941873 | Intergenic | −5070 | Gm29685 | −0.556014431 | 0.020973742 |
| chr16 | 45223654 | 45224210 | Promoter-TSS | −405 | Btla | −0.556842142 | 0.049153943 |
| chr14 | 45040847 | 45041452 | Intergenic | 53038 | Ptger2 | −0.557573512 | 0.023489576 |
| chr2 | 78859955 | 78860425 | Intergenic | −8857 | Ube2e3 | −0.557870455 | 0.029328954 |
| chr4 | 156013659 | 156014068 | TTS | 168 | Tnfrsf4 | −0.558784636 | 0.001782167 |
| chr7 | 127188533 | 127189394 | Intergenic | 7114 | Cd2bp2 | −0.559132622 | 0.025498455 |
| chr5 | 77383906 | 77384534 | Intron | 23825 | Igfbp7 | −0.559575384 | 0.019789302 |
| chr9 | 13894380 | 13895104 | Intergenic | 67015 | Fam76b | −0.559858477 | 0.010332378 |
| chr5 | 122288415 | 122288855 | Intron | 4237 | Pptc7 | −0.560456838 | 0.000377944 |
| chr2 | 153292235 | 153292923 | Intron | 1163 | Kif3b | −0.561161442 | 0.006944208 |
| chr15 | 50697552 | 50698801 | Intron | 190873 | Trps1 | −0.561189395 | 1.57E−05 |
| chr6 | 108447994 | 108448771 | Intron | −41361 | Mir7661 | −0.562498233 | 0.000838574 |
| chr11 | 118363034 | 118363629 | Intergenic | −7920 | Timp2 | −0.562807129 | 0.004997988 |
| chr8 | 123807033 | 123807398 | Intron | 1219 | Rab4a | −0.563260371 | 0.038275769 |
| chr5 | 146867141 | 146868168 | Intergenic | 22583 | Rasl11a | −0.564868929 | 0.00428808 |
| chr14 | 122057846 | 122058386 | Intergenic | 23442 | Timm8a2 | −0.565179571 | 0.002095533 |
| chr8 | 34651696 | 34652242 | Intergenic | −11653 | B930018H19Rik | −0.565832117 | 0.009438793 |
| chr12 | 35534082 | 35535340 | 5′ UTR | 278 | Ahr | −0.567915383 | 0.000459667 |
| chr14 | 74918556 | 74919043 | Intron | 29078 | Lrch1 | −0.568018012 | 0.025794388 |
| chr17 | 44766285 | 44766915 | Intron | −10571 | Supt3 | −0.568371871 | 0.026642797 |
| chr4 | 6924535 | 6925218 | Intron | 65847 | Tox | −0.568726068 | 0.010886222 |
| chr6 | 125468031 | 125468672 | Intron | 26404 | Cd9 | −0.570843495 | 0.00544152 |
| chr1 | 119504278 | 119505104 | Promoter-TSS | 91 | Ralb | −0.573305678 | 4.85E−05 |
| chr10 | 93938607 | 93939198 | Intergenic | 24961 | Mir331 | −0.573354269 | 0.004262951 |
| chr2 | 163202902 | 163204010 | Intergenic | −21998 | Tox2 | −0.574342284 | 0.000148425 |
| chr9 | 111002975 | 111003745 | Intergenic | −13647 | Rtp3 | −0.575789611 | 0.016198841 |
| chr3 | 144410953 | 144411554 | Intergenic | 158963 | Hs2st1 | −0.576109862 | 0.034859639 |
| chr17 | 31693373 | 31693874 | Intergenic | 15692 | Cryaa | −0.57716171 | 0.041480484 |
| chr8 | 125343607 | 125344536 | Intergenic | 148639 | Sipa1l2 | −0.578787098 | 0.011052324 |
| chr10 | 17549636 | 17550548 | Intergenic | −173136 | Cited2 | −0.579188875 | 0.037031284 |
| chr12 | 36381330 | 36382328 | Promoter-TSS | −318 | Ispd | −0.580879879 | 0.032704923 |
| chr6 | 73210434 | 73210986 | Intron | 10921 | Dnah6 | −0.581686955 | 0.018495249 |
| chr10 | 111445985 | 111446721 | Intergenic | −26839 | Nap1l1 | −0.582333667 | 0.040521725 |
| chr1 | 87180778 | 87181298 | Intergenic | −2276 | Prss56 | −0.582344338 | 0.012464126 |
| chr1 | 171915615 | 171916171 | Intergenic | −1569 | Slamf6 | −0.582690243 | 0.028250701 |
| chr2 | 61493998 | 61494628 | Intergenic | −84273 | Tank | −0.582762182 | 0.000893424 |
| chr3 | 121723032 | 121723808 | Promoter-TSS | −117 | F3 | −0.585352255 | 0.018081572 |
| chr15 | 38709578 | 38710533 | Intergenic | 18461 | Borg | −0.585651327 | 0.002131617 |
| chr10 | 8130806 | 8131419 | Intergenic | −174989 | Tab2 | −0.586608961 | 0.019628701 |
| chr6 | 134413844 | 134414706 | Intron | 17946 | Bcl2l14 | −0.587428452 | 0.017353575 |
| chr6 | 142823052 | 142823728 | 3′ UTR | 9159 | Gm7457 | −0.58909971 | 0.007045773 |
| chr8 | 125253495 | 125254644 | Intron | 199874 | Disc1 | −0.590377041 | 0.028296071 |
| chr15 | 81302214 | 81302725 | Intergenic | −50607 | 8430426J06Rik | −0.590697096 | 0.002131617 |
| chr7 | 67950835 | 67951947 | Promoter-TSS | −866 | Igf1r | −0.590706828 | 0.004428602 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr13 | 28512516 | 28513106 | Intron | 198062 | Mir6368 | −0.591202673 | 0.043627864 |
| chr9 | 119988335 | 119988680 | Intergenic | −3849 | Csrnp1 | −0.591271383 | 0.012115218 |
| chr2 | 126309840 | 126310637 | Intergenic | 158097 | Dtwd1 | −0.591458711 | 0.002603336 |
| chr10 | 34110668 | 34111478 | Intergenic | −14554 | Fam26e | −0.591871559 | 1.92E−05 |
| chr4 | 136088535 | 136089402 | Intergenic | −35597 | Rpl11 | −0.592500162 | 0.003930761 |
| chr17 | 34001150 | 34001808 | Intergenic | −1132 | H2-K1 | −0.594411207 | 7.87E−09 |
| chr10 | 13993256 | 13993894 | Intron | 27196 | Hivep2 | −0.595510229 | 0.000794436 |
| chr2 | 46370892 | 46371447 | Intergenic | 674564 | 1700019E08Rik | −0.600171095 | 0.001025172 |
| chr17 | 73246759 | 73247285 | Intergenic | 139037 | Lclat1 | −0.600255943 | 0.00589286 |
| chr10 | 75446283 | 75446987 | Intergenic | −2875 | 4933407G14Rik | −0.601559163 | 0.037206824 |
| chr4 | 63627007 | 63627499 | Intergenic | −4824 | 1700018C11Rik | −0.602695023 | 0.03757704 |
| chr13 | 117217630 | 117217952 | Intergenic | −2782 | Emb | −0.602802424 | 0.019062993 |
| chr2 | 61578389 | 61578897 | Promoter-TSS | 57 | Tank | −0.603318167 | 0.005126016 |
| chr6 | 140598460 | 140598949 | Intergenic | −23959 | Aebp2 | −0.604329294 | 0.017765826 |
| chr12 | 38778586 | 38779149 | Intergenic | −1215 | Etv1 | −0.605121433 | 0.015822761 |
| chr5 | 92353511 | 92353910 | Intron | −4821 | Cxcl10 | −0.605425205 | 0.00428808 |
| chr3 | 159839981 | 159840904 | Intron | 747 | Wls | −0.605831276 | 0.029964056 |
| chr1 | 165242258 | 165242737 | Intergenic | −5539 | Tiprl | −0.606096837 | 0.03158356 |
| chr6 | 142507464 | 142508355 | Promoter-TSS | 48 | Ldhb | −0.607221718 | 0.003249237 |
| chr14 | 48421989 | 48422478 | Intergenic | −23890 | Tmem260 | −0.607360465 | 0.011836845 |
| chr10 | 59864170 | 59864703 | TTS | −15155 | Dnajb12 | −0.610610115 | 0.022591962 |
| chr13 | 100866358 | 100866773 | Intergenic | −33138 | Slc30a5 | −0.611517401 | 0.012151698 |
| chr8 | 116923551 | 116923976 | Intron | 2023 | Cenpn | −0.612349964 | 0.043800211 |
| chr17 | 43016372 | 43017023 | 5' UTR | 142 | Tnfrsf21 | −0.612571266 | 0.020480898 |
| chr19 | 32262585 | 32263183 | Intron | −51871 | Sgms1 | −0.613558165 | 0.021142922 |
| chr14 | 61778578 | 61779073 | Intergenic | −96452 | Dleu2 | −0.614170329 | 0.003467187 |
| chr2 | 61490777 | 61491026 | Intergenic | −87685 | Tank | −0.616375687 | 0.036054536 |
| chr1 | 193421371 | 193421796 | Intergenic | −51301 | Camk1g | −0.616896657 | 0.033834928 |
| chr2 | 122426260 | 122426664 | Promoter-TSS | −15 | Slc28a2 | −0.616933674 | 0.008067189 |
| chr19 | 24985048 | 24985348 | Intergenic | −14331 | Dock8 | −0.617807554 | 0.039138637 |
| chr15 | 97667516 | 97667946 | Intergenic | 38091 | Rpap3 | −0.61785249 | 0.005049514 |
| chr17 | 64622238 | 64622752 | Intron | 20846 | Man2a1 | −0.618178023 | 0.017051304 |
| chr10 | 84895790 | 84896202 | Exon | −21617 | Ric8b | −0.618911557 | 0.013331337 |
| chr1 | 69768604 | 69769393 | Intergenic | −57972 | Spag16 | −0.619715881 | 3.92E−06 |
| chr9 | 103134231 | 103135026 | Intron | 22554 | Rab6b | −0.619731974 | 0.001347307 |
| chr14 | 6108349 | 6108972 | Intergenic | 178590 | LOC100861615 | −0.619743501 | 0.032365536 |
| chr13 | 32899078 | 32899541 | Intergenic | −1169 | Serpinb1c | −0.622740188 | 0.023662677 |
| chr5 | 35893067 | 35893577 | Promoter-TSS | 3 | Afap1 | −0.623487622 | 0.002748711 |
| chr6 | 47621008 | 47621548 | Intergenic | −26248 | Ezh2 | −0.624570062 | 0.030308334 |
| chr15 | 55896869 | 55897606 | Intron | 9712 | Sntb1 | −0.624722968 | 0.010636747 |
| chr1 | 40055887 | 40056390 | Intergenic | −28630 | Il1r2 | −0.625126768 | 0.011619563 |
| chr13 | 41453395 | 41453900 | Intron | 33713 | Nedd9 | −0.625596568 | 0.023293583 |
| chr3 | 95909282 | 95909807 | Intergenic | −4905 | Car14 | −0.626113688 | 0.000808252 |
| chr3 | 129308200 | 129308953 | Intron | 24173 | Enpep | −0.628113981 | 0.049428826 |
| chr9 | 69349532 | 69349927 | Intron | 14518 | Gm15511 | −0.62859027 | 0.004862524 |
| chr4 | 3648700 | 3649406 | Intergenic | −7453 | 2210414B05Rik | −0.629006676 | 0.048958374 |
| chr1 | 156938796 | 156940182 | Promoter-TSS | −102 | Ralgps2 | −0.630414575 | 0.00012858 |
| chr16 | 10665135 | 10665885 | Intron | 120026 | Socs1 | −0.631485263 | 0.023233918 |
| chr2 | 6309258 | 6309890 | Intron | −13183 | Usp6nl | −0.631515298 | 0.001488476 |
| chr6 | 41130283 | 41130589 | Intergenic | −94927 | 2210010C04Rik | −0.631744812 | 0.00044559 |
| chr3 | 101651100 | 101651835 | Intergenic | −46760 | Atp1a1 | −0.633291998 | 0.019364455 |
| chr14 | 70341017 | 70341644 | Intron | 7103 | Slc39a14 | −0.634326973 | 0.005946931 |
| chr5 | 103376375 | 103377495 | Intergenic | −48257 | Ptpn13 | −0.634586411 | 0.001738227 |
| chr16 | 90330912 | 90331623 | Intergenic | −46764 | Scaf4 | −0.635056044 | 0.017203744 |
| chr2 | 6256064 | 6256855 | Intron | −43465 | Echdc3 | −0.635114858 | 0.037321188 |
| chr17 | 85908655 | 85909304 | Intergenic | −220725 | Six2 | −0.635389773 | 2.49E−05 |
| chr8 | 113656139 | 113656673 | TTS | 13193 | Syce1l | −0.636786034 | 0.007055164 |
| chr4 | 152120257 | 152121145 | TTS | 4358 | Tnfrsf25 | −0.63756707 | 1.33E−06 |
| chr14 | 76414085 | 76415406 | Promoter-TSS | −216 | Tsc22d1 | −0.63896344 | 0.000381325 |
| chr5 | 114323061 | 114323727 | Exon | 8453 | Myo1h | −0.638999331 | 0.00459569 |
| chr15 | 93513921 | 93514347 | Intron | 81757 | Prickle1 | −0.639100598 | 0.014803124 |
| chr16 | 3343258 | 3344039 | Intergenic | −248750 | Olfr161 | −0.640293221 | 0.034366911 |
| chr5 | 62778558 | 62779036 | Intergenic | −12620 | Arap2 | −0.640560364 | 0.031355258 |
| chrX | 57184842 | 57185308 | Intergenic | −15562 | Gm14718 | −0.642161676 | 0.020886818 |
| chr19 | 31210332 | 31210806 | Intron | 5827 | 8430431K14Rik | −0.643388063 | 0.008942635 |
| chr8 | 3220999 | 3221531 | Intron | 58352 | Insr | −0.64382973 | 0.021656112 |
| chr17 | 70728274 | 70729400 | Intron | 117940 | Tgif1 | −0.643851421 | 0.029587478 |
| chr9 | 120074293 | 120074931 | Intergenic | −6316 | Cx3cr1 | −0.643903375 | 0.005430295 |
| chr13 | 89740826 | 89741116 | Intron | 1541 | Vcan | −0.645438966 | 0.020279668 |
| chr6 | 72993172 | 72993678 | Intergenic | −34677 | Tmsb10 | −0.645766185 | 0.000419152 |
| chr9 | 32740845 | 32741302 | Intron | 45031 | Ets1 | −0.646326535 | 0.033519439 |
| chr10 | 120895750 | 120896350 | Intron | 2921 | Msrb3 | −0.646409779 | 0.000128111 |
| chr9 | 49485731 | 49486349 | Intron | 185 | Ttc12 | −0.648375553 | 0.016880966 |
| chr2 | 101983052 | 101983825 | Intron | 97176 | Commd9 | −0.648778353 | 0.017050654 |
| chr19 | 18747362 | 18747803 | Intergenic | −2401 | Trpm6 | −0.650551203 | 0.034901729 |
| chr3 | 37173137 | 37173760 | Intergenic | −47494 | Il2 | −0.652755522 | 0.032485349 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr2 | 4730050 | 4730562 | Intron | 12475 | Bend7 | −0.654079236 | 0.043658454 |
| chr17 | 63863450 | 63864435 | Promoter-TSS | −39 | Fer | −0.654286058 | 3.24E−05 |
| chr14 | 53553912 | 53554117 | Intergenic | 699915 | Dad1 | −0.654590116 | 0.000161769 |
| chr5 | 105239637 | 105240129 | Promoter-TSS | −350 | Gbp10 | −0.654774918 | 0.006044755 |
| chr10 | 60160904 | 60161276 | Intergenic | 34314 | Mir6906 | −0.656901108 | 0.048997751 |
| chr4 | 53227804 | 53228335 | Intergenic | −18127 | 4930522O17Rik | −0.657543319 | 0.019015153 |
| chr4 | 41240834 | 41241497 | Intron | 33970 | Ubap2 | −0.65826829 | 0.013700487 |
| chr9 | 70079838 | 70081224 | Intergenic | −42443 | Gcnt3 | −0.659626365 | 0.013675814 |
| chr18 | 20970046 | 20970619 | Intron | 25707 | Rnf125 | −0.659815441 | 0.021437406 |
| chr14 | 76569283 | 76569798 | Intergenic | −12651 | Serp2 | −0.660165968 | 0.024922272 |
| chr12 | 113427307 | 113427798 | Intergenic | −62013 | Adam6b | −0.66096055 | 4.04E−10 |
| chr10 | 60162229 | 60162881 | Intergenic | 35779 | Mir6906 | −0.661204017 | 0.000497732 |
| chr14 | 121101723 | 121102383 | Exon | 66479 | Farp1 | −0.661623481 | 0.036361796 |
| chr12 | 54203145 | 54204032 | 5' UTR | 286 | Egln3 | −0.66163586 | 0.002012584 |
| chr6 | 41538214 | 41538595 | Intergenic | 16628 | Prss2 | −0.663589622 | 0.000505221 |
| chr3 | 116200000 | 116200602 | Intergenic | 53183 | Gpr88 | −0.664243848 | 0.007026638 |
| chr19 | 17256434 | 17257271 | Intergenic | 82653 | Gcnt1 | −0.666389324 | 0.03664307 |
| chr13 | 119596393 | 119597056 | Intron | −27095 | Ccl28 | −0.666796513 | 1.59E−05 |
| chr10 | 17548664 | 17549505 | Intergenic | −174144 | Cited2 | −0.667313144 | 0.001880589 |
| chr10 | 24651017 | 24651591 | Exon | 55862 | Ctgf | −0.667379021 | 0.034912692 |
| chr2 | 152396083 | 152396540 | 3' UTR | 1735 | Sox12 | −0.667915547 | 0.009994897 |
| chr1 | 184139951 | 184140998 | Intergenic | 106013 | Dusp10 | −0.669186708 | 0.026139456 |
| chr2 | 11429519 | 11430113 | Intergenic | −31316 | 8030442B05Rik | −0.673577913 | 0.037957443 |
| chr2 | 72170477 | 72170934 | Intron | −114932 | Map3k20 | −0.674253831 | 0.009040037 |
| chr16 | 3122597 | 3123329 | Intergenic | −469435 | Olfr161 | −0.674350374 | 0.008919766 |
| chr2 | 66184545 | 66185222 | Intron | −60090 | Galnt3 | −0.674760681 | 0.001875018 |
| chr18 | 80046710 | 80047486 | Exon | 203 | Pard6g | −0.675904431 | 0.002886313 |
| chr19 | 53341589 | 53342218 | Intron | 11457 | Mxi1 | −0.675922135 | 0.026452893 |
| chr9 | 5298151 | 5299105 | 5' UTR | 111 | Casp1 | −0.676355582 | 0.016461072 |
| chr3 | 136742611 | 136743309 | Intron | 72894 | Ppp3ca | −0.677293506 | 0.000145397 |
| chr16 | 62940517 | 62940990 | Intergenic | 86446 | Pros1 | −0.67756006 | 0.011717354 |
| chr1 | 191579573 | 191579849 | Intron | 4075 | Ints7 | −0.678054358 | 0.024400331 |
| chr17 | 74869500 | 74870016 | Intergenic | −135771 | Ltbp1 | −0.679660724 | 4.85E−05 |
| chr19 | 17264641 | 17265408 | Intergenic | 74481 | Gcnt1 | −0.680043773 | 3.68E−07 |
| chr13 | 117051403 | 117051832 | Intergenic | −26101 | Parp8 | −0.680049261 | 0.007161926 |
| chr19 | 46470609 | 46471330 | Intron | −30679 | Trim8 | −0.680405479 | 0.021648726 |
| chr7 | 39655089 | 39655755 | Intergenic | 137656 | Zfp619 | −0.682318406 | 0.005083451 |
| chr8 | 81341635 | 81342172 | Promoter-TSS | −659 | Inpp4b | −0.682633789 | 0.037018315 |
| chr16 | 57402862 | 57403468 | Intron | 49888 | Filip1l | −0.68284586 | 0.001028603 |
| chr1 | 91095097 | 91095672 | Intron | 41940 | Lrrfip1 | −0.683224615 | 0.048664427 |
| chr1 | 176946849 | 176947203 | Intron | −110893 | Hmga2-ps1 | −0.68644628 | 0.046559068 |
| chr10 | 66955452 | 66955761 | Intergenic | −35222 | 1110002J07Rik | −0.68677057 | 0.032781245 |
| chr8 | 54077001 | 54077907 | Promoter-TSS | −78 | Vegfc | −0.687808844 | 0.029429653 |
| chr5 | 103519033 | 103519547 | Intron | 94098 | Ptpn13 | −0.688523071 | 0.001678837 |
| chr5 | 92373181 | 92373513 | Intron | −10051 | Cxcl11 | −0.68924195 | 0.009683297 |
| chr4 | 43822875 | 43823346 | Intergenic | −1677 | Olfr156 | −0.68947874 | 0.036743958 |
| chr14 | 53554146 | 53554553 | Intergenic | 699580 | Dad1 | −0.689837856 | 0.003930761 |
| chr3 | 37653831 | 37654787 | Intergenic | 14362 | Spry1 | −0.690104729 | 0.000207863 |
| chr8 | 79209698 | 79210343 | TTS | 38563 | 1700011L22Rik | −0.690696362 | 0.003478535 |
| chr18 | 60624098 | 60625170 | Promoter-TSS | −329 | Synpo | −0.691042067 | 0.000251698 |
| chr14 | 54223682 | 54223977 | Intergenic | 30100 | Dad1 | −0.691069127 | 9.78E−09 |
| chr3 | 101657276 | 101657667 | Intergenic | −52764 | Atp1a1 | −0.691478069 | 0.049957642 |
| chr15 | 50653274 | 50653754 | Intergenic | 235535 | Trps1 | −0.691829124 | 0.000378889 |
| chr3 | 131489670 | 131490952 | Intergenic | −74457 | Papss1 | −0.691934077 | 0.026109641 |
| chr14 | 105922547 | 105923308 | Intergenic | −26108 | Spry2 | −0.692194617 | 0.003641626 |
| chr1 | 164458225 | 164458900 | Promoter-TSS | −207 | Atp1b1 | −0.693060449 | 0.037398863 |
| chr18 | 84077442 | 84077761 | Intron | 8961 | Tshz1 | −0.693600372 | 0.037728253 |
| chr3 | 149466802 | 149467526 | Intergenic | 192427 | Gm1653 | −0.693954609 | 4.19E−07 |
| chr10 | 79417087 | 79418039 | Intergenic | −51395 | Vmn2r83 | −0.695099352 | 0.003636806 |
| chr13 | 92636843 | 92637252 | Intron | 25909 | Serinc5 | −0.696366631 | 0.00519084 |
| chr9 | 62363533 | 62364027 | Intron | 22437 | Anp32a | −0.696701122 | 9.17E−05 |
| chr16 | 49938508 | 49939273 | Intergenic | −41570 | Gm6936 | −0.697058975 | 0.003930761 |
| chr14 | 40929837 | 40930414 | Intron | 18084 | Tspan14 | −0.69719466 | 0.000134005 |
| chr1 | 138039139 | 138039612 | Intergenic | 72736 | Mir181b-1 | −0.698868571 | 0.013344501 |
| chr13 | 112354865 | 112355349 | Intron | 66589 | Ankrd55 | −0.701364134 | 0.008397535 |
| chr16 | 45025355 | 45025796 | Intergenic | −68478 | Ccdc80 | −0.701961249 | 0.000376894 |
| chr9 | 115623944 | 115624324 | Intergenic | 242315 | Mir467h | −0.701974522 | 0.0385915 |
| chr2 | 71274459 | 71274987 | 3' UTR | 62777 | Dync1i2 | −0.702348966 | 0.044145616 |
| chr19 | 24983786 | 24984397 | Intron | −15438 | Dock8 | −0.706497379 | 0.000112729 |
| chr13 | 46159105 | 46159786 | Intergenic | −114276 | Stmnd1 | −0.706769973 | 0.005928238 |
| chr11 | 6695069 | 6695673 | Intergenic | 24666 | Gm11981 | −0.706980045 | 0.000682952 |
| chr9 | 61778857 | 61779729 | Intergenic | 135217 | Rplp1 | −0.707057782 | 0.038295345 |
| chr17 | 70746724 | 70747184 | Intron | 99823 | Tgif1 | −0.707401358 | 0.046559068 |
| chr18 | 23844925 | 23845330 | Intron | 41157 | Mapre2 | −0.708013733 | 0.000406514 |
| chr3 | 104796323 | 104797163 | Intron | 7709 | Rhoc | −0.708467317 | 1.24E−07 |
| chr4 | 91376338 | 91376943 | Promoter-TSS | −144 | Elavl2 | −0.708815492 | 0.002224679 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr10 | 76798789 | 76799232 | Intron | −72966 | Col6a1 | −0.7110654 | 0.000195487 |
| chr2 | 19528881 | 19529291 | Intron | 24824 | 4921504E06Rik | −0.712502183 | 0.012190995 |
| chr2 | 91876199 | 91876700 | Intron | −45740 | Chrm4 | −0.715090265 | 0.013234174 |
| chrX | 99135739 | 99136243 | Promoter-TSS | −70 | Efnb1 | −0.715129962 | 0.006303029 |
| chr2 | 140100562 | 140101581 | Intergenic | −34266 | Tasp1 | −0.715138348 | 0.002949779 |
| chr12 | 25784188 | 25784995 | Intergenic | 425914 | Gm29687 | −0.715558441 | 1.14E−06 |
| chr5 | 134444416 | 134444790 | Intron | 11659 | Gtf2ird1 | −0.716518013 | 0.033300282 |
| chr16 | 50070599 | 50071039 | Intron | 2033 | Gm4827 | −0.717047697 | 0.034915016 |
| chr8 | 126881768 | 126882093 | Intergenic | 63991 | Tomm20 | −0.717190886 | 0.020632882 |
| chr11 | 94697482 | 94698076 | Intron | 6720 | Gm11541 | −0.717620194 | 0.022834597 |
| chr10 | 67099938 | 67100632 | Intergenic | −3297 | Reep3 | −0.717863243 | 5.18E−07 |
| chr6 | 146082547 | 146082824 | Intergenic | 148538 | Sspn | −0.718965354 | 0.000275824 |
| chr14 | 121102556 | 121103076 | Intron | 67242 | Farp1 | −0.719677048 | 0.000177425 |
| chr19 | 29374980 | 29375363 | Intron | 7733 | Cd274 | −0.72038171 | 0.000159787 |
| chr10 | 100015461 | 100016415 | 5' UTR | 117 | Kitl | −0.721075234 | 0.049346071 |
| chr6 | 65778402 | 65779656 | Promoter-TSS | 67 | Prdm5 | −0.721686604 | 0.020942602 |
| chr14 | 53173986 | 53174503 | Intergenic | −678549 | Olfr1507 | −0.722268264 | 0.029904893 |
| chr15 | 66286519 | 66287169 | Promoter-TSS | −620 | Kcnq3 | −0.722840939 | 0.047979754 |
| chr9 | 96773189 | 96773517 | Non-Coding | 7791 | C430002N11Rik | −0.724073377 | 0.00277585 |
| chr10 | 39521823 | 39522315 | Intron | −90865 | Traf3ip2 | −0.724925922 | 0.033309769 |
| chr11 | 88552969 | 88553328 | Intron | −66103 | 0610039H22Rik | −0.725420196 | 0.038584768 |
| chr17 | 37028320 | 37029129 | Intergenic | −5326 | Mog | −0.725804807 | 0.002387608 |
| chr1 | 136600643 | 136601152 | Intergenic | −24004 | Zfp281 | −0.726314706 | 0.016074523 |
| chr2 | 102981448 | 102982104 | Intergenic | −80111 | Cd44 | −0.72742567 | 1.19E−05 |
| chr17 | 34397997 | 34398358 | Promoter-TSS | −643 | BC051142 | −0.728015436 | 0.045112134 |
| chr14 | 79236241 | 79236855 | Intron | 10819 | Zfp957 | −0.72849023 | 0.031169626 |
| chr3 | 37386957 | 37387408 | Intron | 32414 | Nudt6 | −0.728541538 | 0.015471255 |
| chr6 | 134301999 | 134302677 | Intergenic | −93991 | Bcl2l14 | −0.72915933 | 0.000531663 |
| chr10 | 39517441 | 39517841 | Intron | −95293 | Traf3ip2 | −0.729518746 | 0.004293716 |
| chr19 | 24173617 | 24174506 | Promoter-TSS | 79 | Tjp2 | −0.730046404 | 0.000772671 |
| chr18 | 69196096 | 69196711 | Intergenic | −148089 | Tcf4 | −0.730479412 | 0.043853866 |
| chr11 | 20564642 | 20565438 | Intron | 21787 | Sertad2 | −0.731104926 | 0.010192043 |
| chr10 | 119001001 | 119001748 | Intergenic | −74231 | Gm38403 | −0.73153809 | 0.014540108 |
| chr5 | 99906097 | 99906698 | Intergenic | 72541 | Hnrnpd | −0.734327185 | 0.003899654 |
| chr1 | 92119286 | 92119828 | Intron | 60784 | Hdac4 | −0.73434283 | 0.018661466 |
| chr15 | 66803872 | 66804158 | Intron | 27814 | Sla | −0.735320353 | 0.043207298 |
| chr2 | 11616748 | 11617285 | Intergenic | −13817 | Rbm17 | −0.735884127 | 0.003732861 |
| chr14 | 62008652 | 62009100 | Intergenic | 284103 | Dleu7 | −0.736518886 | 0.04089267 |
| chr2 | 44804495 | 44804918 | Intron | 56916 | Gtdc1 | −0.738112047 | 0.02298365 |
| chr17 | 51879268 | 51879548 | Intergenic | −3319 | Gm20098 | −0.738411713 | 0.049188065 |
| chrX | 106704569 | 106704991 | Intron | −101101 | Cysltr1 | −0.739703963 | 0.028250701 |
| chr9 | 56655085 | 56655594 | Intron | −19691 | Lingo1 | −0.740884056 | 0.035397764 |
| chr15 | 85669286 | 85670375 | Intergenic | −33943 | Lncppara | −0.741016581 | 0.016808265 |
| chr19 | 32292486 | 32292837 | Intron | 56655 | Sgms1 | −0.741148086 | 0.012718856 |
| chr3 | 37292548 | 37293007 | Intergenic | 19669 | Cetn4 | −0.742462387 | 0.007732351 |
| chr16 | 23274125 | 23274467 | Intron | −16174 | St6gal1 | −0.743801944 | 0.034294853 |
| chr2 | 122161547 | 122161969 | Intron | 1058 | Trim69 | −0.744008976 | 0.006168101 |
| chr12 | 103331330 | 103332051 | Intron | 16731 | Fam181a | −0.74406313 | 8.25E−05 |
| chr5 | 148976890 | 148977314 | Intergenic | 18112 | 5930430L01Rik | −0.744529357 | 0.000715232 |
| chr8 | 126539364 | 126540247 | Intergenic | 53631 | Irf2bp2 | −0.746636857 | 0.000760626 |
| chr1 | 191259061 | 191259522 | Intergenic | 58827 | Nenf | −0.746979905 | 0.025625382 |
| chr9 | 78010725 | 78011231 | Intergenic | −40980 | Gcm1 | −0.74992017 | 0.00117283 |
| chr17 | 43232856 | 43233227 | Intergenic | −37306 | Adgrf1 | −0.749987613 | 0.036361796 |
| chr8 | 11008781 | 11009303 | Promoter-TSS | −612 | Irs2 | −0.750401143 | 0.000474714 |
| chr1 | 13752499 | 13752945 | Intergenic | 34207 | Gm5523 | −0.753559929 | 0.017765826 |
| chr15 | 53157094 | 53157710 | Intron | 188781 | Ext1 | −0.753651569 | 0.000408856 |
| chr2 | 77280043 | 77281367 | Promoter-TSS | −113 | Sestd1 | −0.754235748 | 3.49E−05 |
| chr10 | 14055526 | 14056038 | Intron | 89403 | Hivep2 | −0.755088757 | 0.047250711 |
| chr4 | 108310694 | 108311133 | Intergenic | −9823 | Zyg11b | −0.755882085 | 0.00599612 |
| chr2 | 84504888 | 84505485 | Intron | 1687 | Gm13710 | −0.756344075 | 0.000237031 |
| chr1 | 78591256 | 78592017 | Intergenic | −66189 | Acsl3 | −0.758755092 | 0.037206824 |
| chr12 | 107183356 | 107183701 | Intergenic | −467204 | 4933406K04Rik | −0.75983964 | 0.002371844 |
| chr6 | 115684801 | 115685619 | Intergenic | −8575 | Raf1 | −0.760416992 | 0.005021261 |
| chr12 | 103443329 | 103444148 | Promoter-TSS | −58 | Ifi27l2a | −0.761836393 | 0.001057841 |
| chr17 | 5976861 | 5977391 | Intron | 1540 | Synj2 | −0.763087475 | 0.015363158 |
| chr13 | 41614570 | 41615306 | Intron | 8722 | Tmem170b | −0.763571451 | 0.005080343 |
| chr1 | 162773648 | 162773991 | Intergenic | −33263 | Prrc2c | −0.763931944 | 0.04686659 |
| chr14 | 61787751 | 61788229 | Intergenic | −105617 | Dleu2 | −0.764153348 | 0.000326278 |
| chr3 | 101948404 | 101949001 | Intergenic | −24249 | Slc22a15 | −0.765559198 | 0.003630699 |
| chr13 | 6626630 | 6627160 | Intron | 21876 | Pfkp | −0.766098278 | 0.012588683 |
| chr8 | 40594874 | 40595666 | Intron | 39522 | Mtmr7 | −0.76668134 | 6.64E−05 |
| chr13 | 105066836 | 105067511 | Intergenic | −12243 | Rgs7bp | −0.766984428 | 0.044914663 |
| chr3 | 122728887 | 122729491 | Promoter-TSS | 31 | Pde5a | −0.767216918 | 0.048126298 |
| chr1 | 127732567 | 127733189 | Intron | 3465 | Acmsd | −0.767436035 | 0.015326824 |
| chr14 | 105895927 | 105896367 | Intron | 672 | Spry2 | −0.767459913 | 0.005197275 |
| chr4 | 63638726 | 63639197 | Intergenic | −16532 | 1700018C11Rik | −0.767820127 | 0.028454817 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr8 | 128535606 | 128536059 | Intergenic | −149822 | Itgb1 | −0.768469449 | 0.014082731 |
| chr8 | 128505996 | 128506229 | TTS | 146871 | Mir1903 | −0.769418977 | 0.029665007 |
| chr15 | 93712472 | 93712969 | Intergenic | −116829 | Prickle1 | −0.772357562 | 3.85E−06 |
| chr12 | 85712509 | 85712978 | Intergenic | 26023 | Batf | −0.772564721 | 0.033546698 |
| chr10 | 128991007 | 128991329 | TTS | 1254 | Olfr9 | −0.772750055 | 0.047748732 |
| chr10 | 48433252 | 48433825 | Intergenic | 662305 | C130030K03Rik | −0.772753944 | 0.010383644 |
| chr3 | 146192267 | 146192923 | Intron | −28366 | Lpar3 | −0.773306505 | 0.036079467 |
| chr16 | 91869176 | 91869921 | Intron | 62082 | Atp5o | −0.773965125 | 0.032100258 |
| chr9 | 92229006 | 92229747 | Intergenic | −20818 | Plscr1 | −0.776376846 | 0.00045046 |
| chr5 | 115711648 | 115712012 | Intron | 19729 | Ccdc64 | −0.77755696 | 0.003289632 |
| chr16 | 33606747 | 33607328 | Intron | −77429 | Heg1 | −0.777662845 | 0.002339371 |
| chr8 | 94827928 | 94828471 | Intron | 10141 | Ciapin1 | −0.777741626 | 0.017141863 |
| chr16 | 65814708 | 65815807 | Promoter-TSS | −376 | Vgll3 | −0.777933706 | 0.002886313 |
| chr1 | 128808435 | 128808981 | Intergenic | −216409 | Cxcr4 | −0.778608685 | 0.006527694 |
| chr9 | 92249521 | 92249776 | Promoter-TSS | −546 | Plscr1 | −0.781432799 | 0.03792645 |
| chr3 | 27710970 | 27711466 | Promoter-TSS | −779 | Fndc3b | −0.782766235 | 9.82E−05 |
| chr18 | 49721570 | 49722217 | Intron | 33708 | Dtwd2 | −0.782952118 | 0.014532037 |
| chr14 | 53047052 | 53047414 | Intergenic | −551538 | Olfr1507 | −0.7829615 | 0.002131672 |
| chr2 | 71941136 | 71941966 | Intergenic | −39664 | Rapgef4 | −0.783596485 | 2.39E−07 |
| chr19 | 21771633 | 21771964 | Intergenic | −6542 | Tmem2 | −0.783844522 | 5.44E−05 |
| chr17 | 29428879 | 29429245 | Intergenic | −61983 | Pim1 | −0.784351008 | 0.001624168 |
| chr6 | 124885897 | 124886414 | Intron | 2054 | Cd4 | −0.788236772 | 0.028921944 |
| chr5 | 99336440 | 99336860 | Intron | −83723 | Rasgef1b | −0.789003042 | 0.000106284 |
| chr15 | 91572650 | 91573532 | Exon | 170 | Slc2a13 | −0.789928873 | 0.002264422 |
| chr18 | 42307969 | 42308437 | Intron | 32850 | Rbm27 | −0.790133813 | 0.048782384 |
| chr2 | 164899692 | 164900349 | Exon | 11730 | Zfp335 | −0.790283011 | 0.020287373 |
| chr3 | 28402214 | 28402607 | Intron | −17533 | Mir466q | −0.790458552 | 0.001338713 |
| chr6 | 86644839 | 86645421 | Intergenic | 16956 | Asprv1 | −0.791270462 | 0.004703795 |
| chr9 | 51401774 | 51402212 | Intergenic | −73076 | 1810046K07Rik | −0.793834454 | 0.04671667 |
| chr12 | 73887905 | 73888713 | Intergenic | −13015 | Hif1a | −0.793902617 | 0.003082008 |
| chr1 | 164815257 | 164815823 | Intron | 18808 | Dpt | −0.794211746 | 0.009179072 |
| chr16 | 50372616 | 50373000 | Intron | 59581 | Bbx | −0.794237992 | 0.030738521 |
| chr18 | 50063211 | 50063681 | Intron | 10164 | Tnfaip8 | −0.794425745 | 0.012127012 |
| chr2 | 101628669 | 101629190 | Promoter-TSS | 57 | B230118H07Rik | −0.794578381 | 0.004219183 |
| chr8 | 126884209 | 126884723 | Intergenic | 61455 | Tomm20 | −0.794633691 | 0.002996886 |
| chr1 | 75457840 | 75458778 | Intron | 7799 | Asic4 | −0.795039549 | 0.043036455 |
| chr17 | 52560001 | 52560315 | Intergenic | −42551 | Kcnh8 | −0.795264743 | 0.006251066 |
| chr2 | 9749836 | 9750360 | Intergenic | 128502 | Gata3 | −0.795497274 | 0.019273091 |
| chr4 | 136081693 | 136082149 | Intergenic | −28550 | Rpl11 | −0.795511345 | 0.02827229 |
| chr3 | 121426120 | 121427458 | Exon | 248 | Cnn3 | −0.795515032 | 1.19E−05 |
| chr7 | 125474528 | 125475075 | Intron | 16741 | Nsmce1 | −0.795690279 | 0.001519982 |
| chr17 | 75005224 | 75006446 | 5' UTR | 306 | Ltbp1 | −0.796250983 | 0.009166385 |
| chr8 | 115770870 | 115771361 | Intergenic | −64221 | Maf | −0.796866248 | 0.000209329 |
| chr3 | 129658670 | 129659163 | Intergenic | 66170 | Egf | −0.797954606 | 0.043662043 |
| chr10 | 12821342 | 12821679 | Intron | 40225 | Utrn | −0.798720805 | 0.03833881 |
| chr6 | 82775479 | 82775747 | Intergenic | −1159 | Hk2 | −0.799096086 | 0.008793429 |
| chr2 | 72282767 | 72283203 | Intergenic | −2652 | Map3k20 | −0.800206344 | 0.011428102 |
| chr6 | 142917423 | 142917799 | Intron | 46841 | St8sia1 | −0.800447397 | 0.045124352 |
| chr3 | 37724505 | 37724875 | Promoter-TSS | −330 | Gm5148 | −0.802280984 | 0.034026324 |
| chr1 | 74570111 | 74570794 | Exon | 17576 | Zfp142 | −0.802325779 | 1.90E−09 |
| chr11 | 101885988 | 101886306 | Intron | 8207 | Meox1 | −0.802331695 | 0.016565565 |
| chr3 | 122619044 | 122619891 | Intron | 247 | Fnbp1l | −0.803243644 | 0.029307702 |
| chr19 | 21767534 | 21768140 | Intergenic | −10503 | Tmem2 | −0.80351162 | 6.14E−05 |
| chr3 | 101661633 | 101661971 | Intergenic | −57095 | Atp1a1 | −0.803703033 | 0.047251636 |
| chr6 | 145977732 | 145978396 | Intergenic | 43917 | Sspn | −0.805060773 | 0.009538726 |
| chr3 | 58517161 | 58517711 | Intergenic | −8385 | Eif2a | −0.805098033 | 0.011337335 |
| chr14 | 121107562 | 121108093 | Intron | 72253 | Farp1 | −0.805565085 | 1.77E−05 |
| chr14 | 87051172 | 87051689 | Intron | 89684 | Diaph3 | −0.806039892 | 8.54E−06 |
| chr19 | 14695359 | 14695814 | Intergenic | −97403 | Tle4 | −0.806203789 | 0.004965252 |
| chr2 | 75891926 | 75892492 | Intron | 46253 | Ttc30b | −0.806753211 | 0.023682302 |
| chr6 | 37054491 | 37054873 | Intron | −243321 | Ptn | −0.806777991 | 0.015541099 |
| chrX | 134808953 | 134809215 | 5' UTR | 137 | Armcx2 | −0.806973591 | 0.0465158 |
| chr19 | 18766370 | 18766915 | Intron | 16659 | Trpm6 | −0.807061227 | 0.001197108 |
| chr9 | 15059966 | 15060371 | Intron | −14690 | Panx1 | −0.807557871 | 0.040274608 |
| chr17 | 86872526 | 86873212 | Intergenic | −44479 | Tmem247 | −0.807626609 | 0.011386685 |
| chr6 | 67535018 | 67535466 | Exon | 580 | Tacstd2 | −0.808223667 | 0.042638266 |
| chr19 | 21773722 | 21773921 | Intergenic | −4519 | Tmem2 | −0.809104198 | 0.038482101 |
| chr3 | 132791170 | 132791610 | Intron | 87206 | Gm29811 | −0.809225984 | 0.00853488 |
| chr3 | 122122083 | 122122677 | Intron | 77920 | Abca4 | −0.809467171 | 0.004608101 |
| chr3 | 10204800 | 10205526 | Intron | 3413 | Fabp4 | −0.809935232 | 5.75E−05 |
| chr1 | 172015266 | 172015616 | Intron | 11854 | Vangl2 | −0.810169409 | 0.047614208 |
| chr10 | 53525462 | 53525992 | Intergenic | −6738 | Gm20597 | −0.811241272 | 6.10E−05 |
| chr7 | 132764917 | 132765464 | Intron | 11726 | Fam53b | −0.811395411 | 0.00606853 |
| chr18 | 60622748 | 60623584 | Intron | 1139 | Synpo | −0.812614106 | 0.038952106 |
| chr8 | 61275632 | 61276289 | Intron | 12912 | 1700001D01Rik | −0.812741867 | 0.032094988 |
| chr3 | 37387455 | 37387871 | Intron | 31933 | Nudt6 | −0.812836333 | 0.040841883 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr9 | 66988588 | 66989449 | Intergenic | −13534 | Lactb | −0.813574137 | 0.004892828 |
| chr14 | 118658092 | 118658766 | Intron | 18502 | Abcc4 | −0.814840541 | 0.001104907 |
| chr14 | 76556059 | 76557127 | Promoter-TSS | 94 | Serp2 | −0.815578619 | 0.000101712 |
| chr2 | 6557658 | 6558143 | Intron | 163762 | Celf2 | −0.816874616 | 0.00207258 |
| chr1 | 89069859 | 89070695 | Promoter-TSS | −185 | Sh3bp4 | −0.819177838 | 1.24E−06 |
| chr8 | 27172078 | 27172412 | Intron | 2401 | Rab11fip1 | −0.820018113 | 0.001057028 |
| chr1 | 131653061 | 131653479 | Intron | 14956 | Ctse | −0.820495102 | 0.030750785 |
| chr1 | 151025006 | 151025561 | Intergenic | −31848 | Hmcn1 | −0.820565488 | 0.022402791 |
| chr9 | 103336974 | 103337477 | Intron | 27754 | Cdv3 | −0.821230328 | 0.039090618 |
| chr9 | 96957297 | 96957756 | Intron | 60829 | Spsb4 | −0.822513867 | 0.005009153 |
| chr18 | 82508714 | 82509565 | Intron | 34016 | Mbp | −0.823908658 | 0.000998985 |
| chr4 | 57781933 | 57782635 | Intron | −62964 | Akap2 | −0.823961657 | 0.004172233 |
| chr6 | 56765326 | 56765655 | Intergenic | 32323 | Kbtbd2 | −0.825411854 | 0.046644347 |
| chr10 | 96586798 | 96587203 | Intergenic | −30001 | Btg1 | −0.825537054 | 0.005707457 |
| chr2 | 6378749 | 6379196 | Intron | 26236 | Usp6nl | −0.82559614 | 0.004688605 |
| chr12 | 12942222 | 12942708 | Promoter-TSS | −629 | Mycn | −0.826204901 | 0.002304195 |
| chr10 | 56106631 | 56107025 | Promoter-TSS | −89 | Msl3l2 | −0.8279783 | 0.015982025 |
| chr9 | 92274254 | 92274772 | Intergenic | −1089 | Plscr2 | −0.829008592 | 0.000408856 |
| chr11 | 108098143 | 108099007 | Intron | 101727 | Mir7223 | −0.829111629 | 0.000151798 |
| chr10 | 93188459 | 93188995 | Intron | 25942 | Mir1931 | −0.832110803 | 0.001939994 |
| chr15 | 81307989 | 81308463 | Intergenic | 52539 | Slc25a17 | −0.832445241 | 0.01796196 |
| chr2 | 102999000 | 102999634 | Intergenic | 74196 | Pdhx | −0.832581125 | 3.97E−10 |
| chr4 | 115052444 | 115053059 | Intergenic | −3675 | Tal1 | −0.833402267 | 0.042658916 |
| chr4 | 101419652 | 101420212 | Exon | 229 | Ak4 | −0.834202696 | 0.047045357 |
| chr16 | 22601417 | 22601718 | Intron | 55664 | Dgkg | −0.835029826 | 0.036720842 |
| chr11 | 52275430 | 52275929 | Intron | 6916 | Tcf7 | −0.835531308 | 0.00016136 |
| chr18 | 5819714 | 5820569 | Intergenic | −227704 | Gm10125 | −0.836123033 | 0.0189837 |
| chr4 | 145177365 | 145178204 | Intron | 12882 | Vps13d | −0.836222545 | 0.00014298 |
| chr13 | 94144521 | 94145111 | Intron | 87020 | Lhfpl2 | −0.836991556 | 0.018683041 |
| chr5 | 100916532 | 100916803 | Intergenic | 70438 | Agpat9 | −0.83781575 | 0.040841883 |
| chr12 | 102581685 | 102582239 | Intron | 27021 | Chga | −0.838147916 | 0.027152923 |
| chr4 | 55443518 | 55443949 | Intergenic | −24891 | Gm12505 | −0.838608426 | 0.040320777 |
| chr10 | 21358065 | 21358462 | Intron | −16208 | 4930455C13Rik | −0.838960911 | 0.045026161 |
| chr16 | 95798559 | 95799047 | Intergenic | 96396 | Ets2 | −0.839220364 | 0.002023347 |
| chr13 | 72639508 | 72640382 | Intergenic | 11148 | Irx2 | −0.8407529 | 0.011509523 |
| chr4 | 150087010 | 150088006 | Promoter-TSS | 5 | Gpr157 | −0.841337976 | 2.64E−07 |
| chr16 | 95860727 | 95861275 | Intron | 37712 | 1600002D24Rik | −0.84169808 | 0.000226236 |
| chr4 | 33290480 | 33290486 | Intergenic | −20024 | Rngtt | −0.842857938 | 0.008517624 |
| chr6 | 52158094 | 52158637 | Promoter-TSS | −48 | Hoxa1 | −0.84334889 | 0.018216458 |
| chr4 | 156008122 | 156008892 | Intron | −5188 | Tnfrsf4 | −0.843547607 | 0.000298478 |
| chr8 | 36028173 | 36028693 | Intergenic | −66395 | Prag1 | −0.843599727 | 0.029329248 |
| chr1 | 40847490 | 40848127 | Intron | 42207 | Tmem182 | −0.846252963 | 0.004581767 |
| chr6 | 121109965 | 121110621 | Intron | 20729 | Mical3 | −0.84687685 | 0.00029435 |
| chr1 | 120258377 | 120259163 | Intron | 6510 | Steap3 | −0.848182809 | 0.033761857 |
| chr14 | 121137226 | 121137814 | Intron | 101946 | Farp1 | −0.84915812 | 0.049586019 |
| chr14 | 53081822 | 53082182 | Intergenic | −586307 | Olfr1507 | −0.849870991 | 6.89E−05 |
| chr12 | 33284462 | 33284943 | Intergenic | −17813 | Atxn7l1 | −0.8503626 | 0.014430893 |
| chr18 | 41949235 | 41949472 | Intron | 1841 | Prelid2 | −0.850607497 | 0.016537764 |
| chr10 | 80628877 | 80629252 | Promoter-TSS | −592 | Csnk1g2 | −0.851033629 | 0.029012763 |
| chr16 | 25587411 | 25588186 | Intergenic | −95967 | Trp63 | −0.85144995 | 0.017975644 |
| chr13 | 114150980 | 114151795 | Intron | 205 | A430090L17Rik | −0.851601037 | 0.030152353 |
| chr16 | 38653287 | 38653971 | Intron | 59406 | Arhgap31 | −0.851618798 | 0.00028446 |
| chr11 | 33700678 | 33701141 | Intron | −121952 | Gabrp | −0.852282082 | 0.004012531 |
| chr1 | 69555520 | 69556162 | Intron | 130119 | Ikzf2 | −0.853818901 | 0.000333028 |
| chr9 | 32394635 | 32395177 | Intron | 921 | Kcnj1 | −0.854167458 | 0.029420038 |
| chr4 | 32163997 | 32165218 | Intergenic | 200500 | Map3k7 | −0.854199893 | 2.29E−09 |
| chr6 | 71638332 | 71638930 | Intergenic | −5714 | Kdm3a | −0.854679328 | 0.007828301 |
| chr5 | 21438305 | 21438922 | Intron | 13710 | Fam185a | −0.855155544 | 0.021292095 |
| chr15 | 51804734 | 51805288 | Intron | 60454 | Eif3h | −0.856124554 | 0.004361467 |
| chr13 | 83565672 | 83566549 | Intron | −7497 | Mef2c | −0.856637941 | 0.001267117 |
| chr5 | 151251734 | 151252654 | Intergenic | −62001 | Stard13 | −0.858351189 | 8.13E−06 |
| chr2 | 167760025 | 167760320 | Intergenic | 68995 | A530013C23Rik | −0.858838044 | 0.040593975 |
| chr5 | 91282897 | 91283399 | Promoter-TSS | −72 | Gm19619 | −0.860536547 | 0.036637768 |
| chr13 | 56476698 | 56477221 | Intergenic | 5287 | Il9 | −0.86161423 | 0.003089194 |
| chr8 | 11009444 | 11009888 | Intron | −1236 | Irs2 | −0.862173232 | 0.034240162 |
| chr6 | 145193370 | 145193765 | Intron | 17403 | Casc1 | −0.862350175 | 0.01199215 |
| chr16 | 95815819 | 95816506 | Intergenic | 82621 | 1600002D24Rik | −0.862485479 | 0.016564429 |
| chr7 | 35729582 | 35729967 | Exon | 24680 | Dpy19l3 | −0.862860662 | 0.001987482 |
| chr9 | 114440541 | 114441162 | Intron | 39756 | Tmppe | −0.864213441 | 3.80E−09 |
| chr6 | 99309182 | 99309826 | Intron | −42989 | Foxp1 | −0.864541081 | 0.024451963 |
| chr3 | 55461595 | 55462314 | 5' UTR | 196 | Dclk1 | −0.866313834 | 3.92E−08 |
| chr10 | 120197111 | 120197403 | Intron | 4280 | Irak3 | −0.866457122 | 0.022834597 |
| chr17 | 47171172 | 47171559 | Intron | 30423 | Trerf1 | −0.866458787 | 0.035867791 |
| chr2 | 70127326 | 70127615 | Intron | 88344 | Myo3b | −0.866460998 | 0.046214456 |
| chr10 | 67111861 | 67112342 | Intergenic | −15113 | Reep3 | −0.867505277 | 0.040936647 |
| chr5 | 148501219 | 148501916 | Intergenic | 51221 | Ubl3 | −0.868543973 | 2.15E−05 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr15 | 59618250 | 59618744 | Intergenic | −30157 | Trib1 | −0.86907377 | 0.030555558 |
| chr8 | 61426065 | 61426820 | Intergenic | −61292 | Cbr4 | −0.869456508 | 0.003452421 |
| chr6 | 135252333 | 135253073 | Intron | 1633 | Gsg1 | −0.869757923 | 0.002297941 |
| chr6 | 30624739 | 30625429 | Intron | 14074 | Cpa5 | −0.869811535 | 0.015566113 |
| chr10 | 84768801 | 84769124 | Intron | 12914 | Rfx4 | −0.870310719 | 0.015789473 |
| chr15 | 33082885 | 33083801 | Intron | 214 | Cpq | −0.870387695 | 0.000129376 |
| chr5 | 134330061 | 134330406 | Intergenic | −15473 | Gtf2i | −0.872079567 | 0.023682302 |
| chr2 | 77341604 | 77342265 | Intergenic | −61342 | Sestd1 | −0.872779414 | 2.09E−06 |
| chr17 | 15816354 | 15817018 | Intron | 9900 | Rgmb | −0.873675174 | 0.012190995 |
| chr1 | 69453934 | 69454307 | Intergenic | 231840 | Ikzf2 | −0.87426306 | 0.021008685 |
| chr14 | 105886660 | 105887273 | Intergenic | 9853 | Spry2 | −0.874656421 | 0.017085325 |
| chr7 | 123354822 | 123355202 | Intron | 14903 | Arhgap17 | −0.874703413 | 0.046214456 |
| chr10 | 93932870 | 93933288 | Intron | 30784 | Mir331 | −0.874760595 | 0.024079305 |
| chr5 | 151233369 | 151234021 | Intergenic | −43502 | Stard13 | −0.874811951 | 0.043643418 |
| chr5 | 86118294 | 86119033 | Intron | 46917 | Stap1 | −0.874874972 | 0.013496256 |
| chr9 | 83145767 | 83146877 | Intron | 285 | Hmgn3 | −0.875311056 | 0.015608066 |
| chr13 | 98124198 | 98124774 | Intron | 81679 | Arhgef28 | −0.877156311 | 0.013648887 |
| chr12 | 113427873 | 113428857 | Intergenic | −61200 | Adam6b | −0.880582732 | 1.13E−05 |
| chr13 | 119998712 | 119999038 | Intergenic | −48069 | B020031M17Rik | −0.88074872 | 0.049109655 |
| chr10 | 70120571 | 70121520 | Intron | 23924 | Ccdc6 | −0.881236477 | 0.032094988 |
| chr2 | 68289120 | 68289541 | Intron | 182651 | Stk39 | −0.881442373 | 0.031310596 |
| chr15 | 25805832 | 25806110 | Intron | −37327 | Fam134b | −0.882811321 | 0.029178297 |
| chr11 | 20282621 | 20283154 | Intergenic | −33463 | Cep68 | −0.883837198 | 0.049428826 |
| chr15 | 91651274 | 91651830 | Intergenic | −21672 | Lrrk2 | −0.884276523 | 0.003147917 |
| chr16 | 95809027 | 95809662 | Intergenic | 89369 | 1600002D24Rik | −0.885306401 | 0.001539354 |
| chr10 | 95914485 | 95915210 | Intergenic | −25816 | Eea1 | −0.885565416 | 9.41E−05 |
| chr11 | 111795629 | 111795916 | Intergenic | 729608 | Kcnj2 | −0.886511884 | 0.045397776 |
| chr18 | 39877833 | 39878214 | Intergenic | 104526 | Pabpc2 | −0.887047338 | 0.026462047 |
| chr18 | 54860459 | 54861240 | Intergenic | 129331 | Zfp608 | −0.887267998 | 1.99E−05 |
| chr3 | 133626384 | 133626942 | Intergenic | −82273 | Tet2 | −0.889063309 | 0.000148425 |
| chr5 | 121100814 | 121101356 | Intergenic | 90312 | Ptpn11 | −0.890089727 | 0.000267315 |
| chr16 | 95749244 | 95749954 | Intergenic | 47192 | Ets2 | −0.89068579 | 0.000385313 |
| chr8 | 126826393 | 126827300 | Intergenic | 119075 | Tomm20 | −0.891364269 | 0.016306752 |
| chr16 | 87764691 | 87765154 | Intergenic | 65968 | Bach1 | −0.894124506 | 0.033865443 |
| chr5 | 113034955 | 113035517 | Intergenic | −19698 | Grk3 | −0.894295515 | 0.003593741 |
| chr6 | 32795606 | 32796655 | Intron | −207938 | Plxna4 | −0.895763874 | 0.001645174 |
| chr3 | 9153637 | 9154174 | Intergenic | 91941 | 4930539M17Rik | −0.896121723 | 3.60E−07 |
| chr4 | 6880952 | 6881309 | Intergenic | 109593 | Tox | −0.897224516 | 0.039004343 |
| chr8 | 68734773 | 68735610 | Promoter-TSS | −45 | Csgalnact1 | −0.89771804 | 0.000189695 |
| chr3 | 27709488 | 27710883 | Intron | 254 | Fndc3b | −0.898303339 | 4.85E−05 |
| chr14 | 105895165 | 105895499 | Intron | 1487 | Spry2 | −0.898346077 | 0.013858084 |
| chr15 | 92134246 | 92134684 | Intron | 6337 | Cntn1 | −0.898775891 | 0.003442596 |
| chr8 | 61590824 | 61591696 | Promoter-TSS | −91 | Palld | −0.899243958 | 9.30E−05 |
| chr13 | 20372174 | 20372729 | Intron | −100539 | Elmo1 | −0.899744114 | 0.002534872 |
| chr10 | 126935800 | 126936260 | Intergenic | −34659 | Xrcc6bp1 | −0.899864091 | 0.019156119 |
| chr10 | 121506715 | 121507017 | Intergenic | −30616 | Rassf3 | −0.900354974 | 0.004540402 |
| chr1 | 165091771 | 165092136 | Promoter-TSS | −23 | 4930568G15Rik | −0.902849784 | 0.029587478 |
| chr13 | 31567447 | 31568120 | Intron | 9613 | Foxq1 | −0.903284385 | 0.01363811 |
| chr2 | 145794454 | 145794872 | Intron | 8547 | Rin2 | −0.903822968 | 0.034153879 |
| chr3 | 37360532 | 37361282 | Intron | 12254 | Fgf2 | −0.903925446 | 0.00025969 |
| chr8 | 91395512 | 91396207 | Intron | 82334 | Fto | −0.9044976 | 0.003587115 |
| chr9 | 44510206 | 44510710 | TTS | 11322 | Bcl9l | −0.906016691 | 0.029665007 |
| chr9 | 75645245 | 75645933 | Intron | 19857 | Lysmd2 | −0.90617952 | 0.009489706 |
| chr10 | 84928202 | 84928854 | Intron | 10915 | Ric8b | −0.906607388 | 0.042837376 |
| chr8 | 95672756 | 95673202 | Intergenic | −30058 | Ndrg4 | −0.906949421 | 0.033761857 |
| chr3 | 37205224 | 37205653 | Intergenic | 27198 | Il21 | −0.907768076 | 0.012586256 |
| chr17 | 70973273 | 70973853 | TTS | 16953 | Myl12b | −0.908180351 | 0.00192775 |
| chr10 | 67065460 | 67065908 | Intron | 31304 | Reep3 | −0.909703168 | 0.000206144 |
| chr9 | 13563444 | 13563965 | Intergenic | −56285 | Maml2 | −0.909725651 | 0.022317383 |
| chr15 | 97578112 | 97578372 | Intergenic | 127580 | Rpap3 | −0.909951256 | 0.007912635 |
| chr17 | 78086990 | 78087369 | Intergenic | −113069 | Crim1 | −0.910580005 | 0.008135351 |
| chr6 | 145373606 | 145374276 | Intergenic | −13684 | 1700073E17Rik | −0.911806521 | 1.43E−07 |
| chr14 | 7989350 | 7989811 | Intron | 4602 | Dnase1l3 | −0.912585407 | 9.32E−05 |
| chr14 | 101476974 | 101477623 | Intron | 131893 | Tbc1d4 | −0.914247935 | 0.000497524 |
| chr7 | 135542368 | 135542663 | Intron | 4691 | Ptpre | −0.915306775 | 0.003909741 |
| chr14 | 54220531 | 54220781 | Intergenic | 33273 | Dad1 | −0.915340017 | 5.63E−06 |
| chr11 | 116687878 | 116688447 | Intron | 6498 | St6galnac2 | −0.91552986 | 0.00311523 |
| chr12 | 33235400 | 33236130 | Intron | −66750 | Atxn7l1 | −0.916069433 | 0.001401308 |
| chr1 | 153691159 | 153691448 | Intron | 25630 | Rgs8 | −0.916405883 | 0.048304219 |
| chr13 | 34096049 | 34096409 | Intron | 17043 | 4930447K03Rik | −0.916605699 | 0.012003735 |
| chr15 | 91672728 | 91673515 | Promoter-TSS | −103 | Lrrk2 | −0.917947471 | 0.000109898 |
| chr12 | 54292970 | 54293769 | Intergenic | 59754 | 1700104L18Rik | −0.918094108 | 2.62E−08 |
| chr11 | 116394398 | 116394598 | Intron | 18534 | Rnf157 | −0.918124836 | 0.02507334 |
| chr15 | 53222380 | 53222776 | Intron | 123605 | Ext1 | −0.918725952 | 0.01689979 |
| chr5 | 86792822 | 86793272 | Intergenic | −11219 | Ythdc1 | −0.919137595 | 0.006121545 |
| chr7 | 39449254 | 39449800 | Promoter-TSS | 9 | Zfp939 | −0.919426439 | 1.33E−05 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr11 | 99132350 | 99132724 | Intergenic | 22540 | Ccr7 | −0.920183991 | 0.015066429 |
| chr17 | 57131780 | 57132254 | Intergenic | 17760 | Cd70 | −0.921334851 | 0.012476572 |
| chr2 | 59522110 | 59522541 | Intergenic | 37672 | Dapl1 | −0.921955782 | 0.036637226 |
| chr4 | 59895123 | 59895561 | Intron | 19714 | Slc46a2 | −0.922718517 | 0.022249003 |
| chr9 | 50547757 | 50548412 | Intron | 7054 | Bco2 | −0.922746132 | 0.0006757 |
| chr3 | 145988138 | 145988852 | Exon | 625 | Syde2 | −0.922947845 | 0.000988349 |
| chr8 | 68218396 | 68218931 | Intergenic | −57865 | Sh2d4a | −0.923210329 | 0.043597089 |
| chr2 | 177925432 | 177926038 | Promoter-TSS | −85 | Zfp972 | −0.923383458 | 2.51E−09 |
| chr19 | 34119713 | 34120611 | Intron | 19219 | Lipm | −0.923785016 | 0.000249826 |
| chr10 | 13424366 | 13424981 | Intron | −35703 | Phactr2 | −0.924193514 | 0.000281869 |
| chr18 | 14654779 | 14655230 | Intron | 27910 | Ss18 | −0.925190196 | 0.000698453 |
| chr5 | 20792154 | 20792492 | Intron | 89801 | Phtf2 | −0.925359469 | 0.037919614 |
| chr12 | 76950317 | 76950719 | Intron | 11730 | Max | −0.926792077 | 0.013692577 |
| chr8 | 122359116 | 122359745 | Intron | 1316 | Trhr2 | −0.927394009 | 0.035260239 |
| chr5 | 99339777 | 99340129 | Intron | −87026 | Rasgef1b | −0.928698285 | 0.029882262 |
| chr12 | 17726564 | 17726773 | Intron | 35854 | Hpcal1 | −0.928802297 | 0.043288079 |
| chr14 | 76579693 | 76580326 | Intergenic | −23120 | Serp2 | −0.930004081 | 2.91E−13 |
| chr18 | 49784179 | 49784604 | Intergenic | −28790 | Dtwd2 | −0.932959206 | 0.032507051 |
| chr19 | 25078142 | 25078844 | Intron | 78964 | Dock8 | −0.934841632 | 0.00207258 |
| chr13 | 85459326 | 85459741 | Intergenic | −170047 | Rasal1 | −0.935310207 | 0.014202645 |
| chr13 | 112507700 | 112508064 | Intergenic | 43812 | Il6st | −0.935694608 | 0.005688983 |
| chr13 | 107522918 | 107523636 | Intergenic | 53455 | AI197445 | −0.935744365 | 0.016104665 |
| chr12 | 8351329 | 8351754 | Intergenic | 38108 | Hs1bp3 | −0.936129953 | 0.024851569 |
| chr13 | 89742120 | 89742632 | 5' UTR | 136 | Vcan | −0.93650978 | 6.10E−05 |
| chr3 | 37370317 | 37370944 | Intron | 22009 | Fgf2 | −0.936761046 | 0.014366331 |
| chr3 | 9249715 | 9250427 | Promoter-TSS | −496 | Zbtb10 | −0.936823443 | 1.07E−05 |
| chr10 | 58299032 | 58299490 | Intron | −24205 | Lims1 | −0.937905393 | 0.000381577 |
| chr2 | 70118427 | 70119262 | Intron | 79718 | Myo3b | −0.938058667 | 0.000244176 |
| chr4 | 57730737 | 57731586 | Intron | −114087 | Akap2 | −0.938247737 | 5.34E−06 |
| chr11 | 108101346 | 108101954 | Intron | 104802 | Mir7223 | −0.938536809 | 0.00268315 |
| chr6 | 91712800 | 91713295 | Intron | 28980 | Slc6a6 | −0.939988202 | 0.02307253 |
| chr9 | 64049515 | 64050402 | Intron | 129 | 1110036E04Rik | −0.940383495 | 1.92E−07 |
| chr16 | 17694675 | 17695270 | Intron | 27928 | Med15 | −0.940850925 | 0.001028284 |
| chr15 | 54919912 | 54920386 | Promoter-TSS | −3 | Enpp2 | −0.941387432 | 0.001739915 |
| chr6 | 49130424 | 49130689 | Intron | 56761 | Malsu1 | −0.941518379 | 0.030119604 |
| chr13 | 46930112 | 46930685 | Promoter-TSS | −680 | Kifl3a | −0.942139473 | 0.049285363 |
| chr2 | 163120547 | 163121071 | Intergenic | −31208 | Gtsf1l | −0.942158556 | 0.000134005 |
| chr4 | 134160208 | 134160421 | Intron | 26861 | Cep85 | −0.942197936 | 0.044414661 |
| chr3 | 121547843 | 121548666 | Intergenic | −15910 | Slc44a3 | −0.942293497 | 0.00042852 |
| chr11 | 52268230 | 52268819 | Intron | 14071 | Tcf7 | −0.942817086 | 7.90E−05 |
| chr6 | 128296103 | 128296769 | Intron | 4377 | Tead4 | −0.943718429 | 0.043222648 |
| chr9 | 15550348 | 15551035 | Intergenic | 45196 | Smco4 | −0.946593579 | 1.76E−10 |
| chr14 | 74880777 | 74881306 | Intron | 66836 | Lrch1 | −0.946731063 | 3.03E−05 |
| chr4 | 102393501 | 102394305 | Intron | 138964 | Pde4b | −0.946881699 | 0.005730797 |
| chr2 | 131480593 | 131481089 | Intron | −11021 | Smox | −0.948126103 | 1.50E−05 |
| chr19 | 55915399 | 55915894 | Intron | 20325 | Tcf7l2 | −0.949567714 | 0.001280649 |
| chr8 | 79286441 | 79286998 | Intron | 8237 | Mmaa | −0.949625782 | 0.04481357 |
| chr6 | 145980865 | 145981529 | Intergenic | 47050 | Sspn | −0.950089964 | 0.002294804 |
| chr1 | 150099683 | 150100264 | Promoter-TSS | −58 | Ptgs2 | −0.951349439 | 0.043288559 |
| chr9 | 118678288 | 118679087 | Intron | −33005 | Itga9 | −0.951758193 | 8.51E−09 |
| chr17 | 31067091 | 31067430 | Intron | 9566 | Abcg1 | −0.95407046 | 0.005238192 |
| chr14 | 53105120 | 53105669 | Intergenic | −609699 | Olfr1507 | −0.954213301 | 0.035686613 |
| chr12 | 74894799 | 74895682 | Intergenic | 282092 | Kcnh5 | −0.955093213 | 8.16E−11 |
| chr2 | 77169897 | 77170698 | Intron | 338 | Ccdc141 | −0.955564289 | 9.81E−05 |
| chr18 | 60803553 | 60804023 | Promoter-TSS | −61 | Cd74 | −0.955972014 | 0.000649388 |
| chr7 | 4948390 | 4948832 | Intergenic | 15737 | Sbk2 | −0.95607579 | 1.66E−05 |
| chr2 | 101992885 | 101993353 | Intron | 106857 | Commd9 | −0.956434708 | 0.000378173 |
| chr10 | 89677880 | 89678468 | Intron | 8111 | Scyl2 | −0.956530093 | 0.004615357 |
| chr12 | 110381106 | 110381780 | Intergenic | −65736 | Ppp2r5c | −0.95698953 | 0.000170758 |
| chr1 | 156956229 | 156956863 | Intergenic | −16920 | Ralgps2 | −0.957062346 | 1.07E−05 |
| chr1 | 128708851 | 128709240 | Intergenic | −116746 | Cxcr4 | −0.958135822 | 0.010636747 |
| chr1 | 168432052 | 168432748 | Promoter-TSS | −231 | Pbx1 | −0.959857879 | 5.74E−07 |
| chr15 | 66702628 | 66703353 | Intron | 32220 | Tg | −0.961556188 | 0.002264422 |
| chr3 | 52647742 | 52648405 | Intergenic | −91651 | Gm2447 | −0.961922423 | 3.51E−07 |
| chrX | 134686263 | 134686707 | Promoter-TSS | −23 | B230119M05Rik | −0.962131405 | 0.018661466 |
| chr16 | 76354364 | 76354561 | Intron | 18587 | Nrip1 | −0.963691495 | 0.037730509 |
| chr14 | 79499298 | 79499783 | Intron | −16134 | Elf1 | −0.963732235 | 0.041580273 |
| chr7 | 92134166 | 92134748 | Intron | −14946 | 4930567K12Rik | −0.964450601 | 1.42E−05 |
| chr2 | 176121674 | 176122052 | Intergenic | −104702 | 2210418O10Rik | −0.964513013 | 0.020849388 |
| chr13 | 110967565 | 110968412 | Intergenic | −64142 | 4930526H09Rik | −0.964722975 | 0.021496268 |
| chr11 | 32210959 | 32211477 | Intron | 5803 | Snrnp25 | −0.96573456 | 0.005899145 |
| chr14 | 75769068 | 75769821 | Intron | −14951 | Cog3 | −0.966377834 | 2.07E−06 |
| chr8 | 40634531 | 40634975 | Promoter-TSS | 39 | Mtmr7 | −0.966957702 | 0.044909661 |
| chr2 | 131386368 | 131386708 | Intron | −33646 | Rnf24 | −0.968471396 | 0.025988331 |
| chr16 | 45093130 | 45093726 | Promoter-TSS | −625 | Ccdc80 | −0.968803882 | 0.031538791 |
| chr4 | 141426835 | 141427644 | Intergenic | 6460 | Hspb7 | −0.969845742 | 0.02827229 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr19 | 24166345 | 24166981 | Intron | 7477 | Tjp2 | −0.97023775 | 3.09E−06 |
| chr1 | 81250057 | 81250473 | Intron | 172948 | Nyap2 | −0.970684305 | 0.030308334 |
| chr10 | 93956175 | 93956718 | Intergenic | 7417 | Mir331 | −0.971659205 | 0.010976616 |
| chr5 | 135115165 | 135115667 | Intron | 8525 | Mlxipl | −0.971962642 | 1.31E−06 |
| chr13 | 112510708 | 112511090 | Intergenic | 46829 | Il6st | −0.972416963 | 0.033122472 |
| chr10 | 99210958 | 99211316 | Intergenic | −52094 | Dusp6 | −0.973025746 | 0.020581597 |
| chr16 | 92399964 | 92400568 | Promoter-TSS | −188 | Rcan1 | −0.97496856 | 0.02827229 |
| chr14 | 53072567 | 53073451 | Intergenic | −577314 | Olfr1507 | −0.976348658 | 1.02E−07 |
| chr14 | 121987705 | 121988024 | Intron | −22671 | Gpr183 | −0.976576073 | 0.017028441 |
| chr3 | 55438314 | 55439403 | Intron | −22900 | Dclk1 | −0.977641883 | 1.03E−05 |
| chr4 | 145045699 | 145045998 | Intron | 144818 | Vps13d | −0.977680317 | 0.024741154 |
| chr3 | 121967632 | 121968137 | Intron | 14558 | Arhgap29 | −0.978166373 | 2.71E−06 |
| chr8 | 86051920 | 86052344 | Intron | 211124 | Phkb | −0.978332325 | 0.008135351 |
| chr7 | 122395271 | 122395432 | Intron | 106226 | Prkcb | −0.978910653 | 0.019269517 |
| chr16 | 4469676 | 4470298 | Intergenic | −49489 | Adcy9 | −0.979052876 | 0.025817773 |
| chr15 | 64173428 | 64173775 | Intron | −113153 | Fam49b | −0.979527619 | 0.040050544 |
| chr16 | 91056368 | 91056844 | Intron | −12227 | Paxbp1 | −0.979635309 | 2.13E−06 |
| chr1 | 38665705 | 38665900 | Intergenic | −38558 | Aff3 | −0.980215596 | 0.042306713 |
| chr5 | 105798253 | 105798990 | Intron | −77947 | Zfp326 | −0.980509574 | 0.001500108 |
| chr10 | 24640538 | 24640815 | 3' UTR | 45234 | Ctgf | −0.981131637 | 0.006089205 |
| chr6 | 88717899 | 88718679 | Intergenic | −6123 | Mgll | −0.982223152 | 0.000500598 |
| chr5 | 103334163 | 103334558 | Intergenic | −35331 | 4930429D17Rik | −0.98280788 | 0.020377882 |
| chr13 | 32864560 | 32864826 | Intergenic | −13508 | Serpinb1a | −0.983017052 | 0.045226514 |
| chr13 | 28953242 | 28954042 | Promoter-TSS | 40 | Sox4 | −0.984327536 | 1.26E−05 |
| chr2 | 70919920 | 70920296 | Intergenic | −94628 | Tlk1 | −0.986050084 | 0.004330457 |
| chr16 | 45408393 | 45409089 | Intron | 312 | Cd200 | −0.986250684 | 0.001622459 |
| chr8 | 46654684 | 46654961 | Intergenic | 37531 | Casp3 | −0.986365046 | 0.041169862 |
| chr3 | 37738197 | 37738861 | Intergenic | −14169 | Gm5148 | −0.987251606 | 5.01E−05 |
| chr6 | 113486930 | 113487612 | Intron | 3702 | Creld1 | −0.987377479 | 0.037206824 |
| chr5 | 122291202 | 122291420 | Intron | 6913 | Pptc7 | −0.988292199 | 0.034670605 |
| chr2 | 158153783 | 158154624 | Intergenic | −7811 | Tgm2 | −0.989475274 | 0.002202496 |
| chr2 | 84837892 | 84838264 | Intergenic | −1330 | Slc43a1 | −0.989753883 | 0.036519093 |
| chr3 | 97004440 | 97004805 | Intergenic | −27780 | Gja5 | −0.991383472 | 0.019639009 |
| chr9 | 21305311 | 21305633 | Intron | 6861 | Ap1m2 | −0.993108074 | 0.022193262 |
| chr6 | 100601360 | 100602002 | Intron | 69476 | Shq1 | −0.993438957 | 0.048997751 |
| chr10 | 70180811 | 70181102 | Intron | −23708 | Mrln | −0.994132576 | 0.044931826 |
| chr12 | 52782802 | 52783412 | Intron | 83724 | Akap6 | −0.994975419 | 2.48E−11 |
| chr13 | 43774908 | 43775606 | Intergenic | −9855 | Cd83 | −0.995310483 | 0.00028446 |
| chr6 | 38581727 | 38582050 | Intron | 26165 | Luc7l2 | −0.996380327 | 0.04640022 |
| chr14 | 120313524 | 120313760 | Intron | 37973 | Mbnl2 | −0.99640209 | 0.024433293 |
| chr15 | 53130050 | 53130430 | Intron | 215943 | Ext1 | −0.996691082 | 0.025771281 |
| chr2 | 102733003 | 102733641 | Intron | 26884 | Slc1a2 | −0.997628351 | 0.001286412 |
| chr5 | 129190091 | 129190470 | Intron | 93530 | Adgrd1 | −0.998289542 | 0.00207258 |
| chr15 | 58175056 | 58175338 | TTS | 33831 | Wdyhv1 | −1.000043947 | 0.010961043 |
| chr7 | 30832192 | 30832613 | Intergenic | −8627 | Ffar2 | −1.000434523 | 0.014374831 |
| chr2 | 6379766 | 6380405 | Intron | 27349 | Usp6nl | −1.001487513 | 1.14E−06 |
| chr5 | 129191793 | 129192160 | Intron | 95226 | Adgrd1 | −1.001816622 | 0.001071891 |
| chr10 | 120882277 | 120882847 | Intron | 16409 | Msrb3 | −1.004031908 | 0.000233115 |
| chr18 | 43392803 | 43393841 | Promoter-TSS | 55 | Dpysl3 | −1.00421995 | 0.00022089 |
| chr10 | 72620608 | 72620899 | Intergenic | −34093 | Zwint | −1.004501913 | 0.038081384 |
| chr5 | 140871314 | 140871662 | Intergenic | −41057 | Gna12 | −1.004913042 | 0.00144726 |
| chr13 | 89670275 | 89670882 | Intron | 71934 | Vcan | −1.007476358 | 0.000348335 |
| chr5 | 96201863 | 96202214 | Intergenic | −8077 | Mrpl1 | −1.00957562 | 0.024814579 |
| chr8 | 61283322 | 61284148 | Intron | 5137 | 1700001D01Rik | −1.010164261 | 0.004436451 |
| chr13 | 99503520 | 99504000 | Intron | 12842 | Map1b | −1.011938042 | 0.00147275 |
| chr14 | 47395622 | 47396067 | Exon | 21984 | Lgals3 | −1.012255631 | 0.022997705 |
| chr14 | 53007432 | 53008189 | Intergenic | −512115 | Olfr1507 | −1.012578405 | 7.00E−05 |
| chr4 | 107652652 | 107653224 | Intergenic | 31224 | Dmrtb1 | −1.014171282 | 0.017161756 |
| chr10 | 117947705 | 117948236 | Non-Coding | 22556 | 4933411E08Rik | −1.014877417 | 2.69E−08 |
| chr5 | 15463656 | 15463859 | Intergenic | 65465 | Gm21190 | −1.015082228 | 0.035097811 |
| chr10 | 118310667 | 118311159 | Intergenic | −15875 | Iltifb | −1.015285691 | 0.002307792 |
| chr13 | 41638124 | 41638476 | 3' UTR | −11143 | Gm5082 | −1.016734906 | 0.002594116 |
| chr10 | 93868304 | 93868714 | Intron | 22691 | Metap2 | −1.01800664 | 0.00207258 |
| chr3 | 144412578 | 144412941 | Intergenic | 157457 | Hs2st1 | −1.018348143 | 0.002682097 |
| chr14 | 78356646 | 78357213 | Intergenic | −48886 | Tnfsf11 | −1.018959358 | 0.001980572 |
| chr5 | 73344252 | 73344725 | Intergenic | −5541 | Ociad2 | −1.020466087 | 0.000171706 |
| chr14 | 21112688 | 21113201 | Intron | 36792 | Adk | −1.02145385 | 5.73E−08 |
| chr6 | 108482423 | 108482890 | Intron | −7087 | Mir7661 | −1.022630932 | 0.048997751 |
| chr10 | 58529409 | 58529871 | Intron | 31703 | Ccdc138 | −1.025188992 | 0.021754248 |
| chr15 | 73117750 | 73118377 | Intron | 27651 | Chrac1 | −1.025653223 | 1.02E−07 |
| chr4 | 19317536 | 19317691 | Intron | 36866 | Cngb3 | −1.026544415 | 0.023489576 |
| chr5 | 122646100 | 122646372 | Intron | 2325 | P2rx7 | −1.028330588 | 0.017589398 |
| chr13 | 110044493 | 110044958 | Intergenic | 140916 | Mir1904 | −1.029119255 | 0.015016388 |
| chr3 | 37272446 | 37272724 | Intergenic | 39861 | Cetn4 | −1.030313916 | 0.033991552 |
| chr1 | 161309336 | 161309772 | Intergenic | −58344 | Prdx6 | −1.032144266 | 0.031353283 |
| chr13 | 43788935 | 43789532 | Intron | 4121 | Cd83 | −1.032511187 | 0.000224166 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr17 | 27814646 | 27814962 | Intron | 5738 | D17Wsu92e | −1.033251958 | 3.84E−05 |
| chr19 | 9939877 | 9940178 | Intergenic | −40494 | Incenp | −1.033427083 | 0.004963202 |
| chr4 | 99120395 | 99121090 | Exon | 173 | Dock7 | −1.033714817 | 0.000156853 |
| chr4 | 99193646 | 99194471 | Promoter-TSS | −89 | Atg4c | −1.037512546 | 2.48E−07 |
| chr1 | 36611438 | 36611903 | Intron | −18338 | Fam178b | −1.037761097 | 0.008971408 |
| chr8 | 8334405 | 8335071 | Intergenic | 326035 | Efnb2 | −1.038106223 | 0.000239284 |
| chr4 | 53217585 | 53218313 | Intergenic | −28247 | 4930522O17Rik | −1.040157976 | 0.000108634 |
| chr8 | 68112221 | 68112606 | Intergenic | −137839 | Psd3 | −1.04026508 | 0.022683616 |
| chr14 | 47169750 | 47170285 | Intron | 19385 | Gch1 | −1.040441996 | 0.000237031 |
| chr4 | 95100441 | 95100945 | Intergenic | −48471 | Jun | −1.041114896 | 0.007564777 |
| chr17 | 8190516 | 8191064 | Intron | 25272 | Fgfr1op | −1.041343491 | 0.014809871 |
| chr18 | 75697428 | 75697859 | Promoter-TSS | 53 | Ctif | −1.041373262 | 0.048036218 |
| chr17 | 74870102 | 74870549 | Intergenic | −135204 | Ltbp1 | −1.042021355 | 0.003640083 |
| chr10 | 39764515 | 39765115 | Intron | 32655 | Rev3l | −1.042556111 | 0.043853866 |
| chr1 | 93115110 | 93115497 | Intergenic | −13429 | Kif1a | −1.043253754 | 0.001530806 |
| chr1 | 20825112 | 20825367 | Intergenic | −5026 | Mcm3 | −1.043620598 | 0.001058271 |
| chr5 | 15498759 | 15499504 | Intergenic | 30091 | Gm21190 | −1.043798894 | 0.000911051 |
| chr7 | 68148202 | 68148894 | Intron | 115685 | Pgpep1l | −1.044758354 | 0.004902936 |
| chr17 | 26531630 | 26532115 | Intergenic | −23400 | Dusp1 | −1.044760254 | 4.15E−06 |
| chr18 | 67301416 | 67301876 | Intron | 12423 | Impa2 | −1.045647419 | 0.003640083 |
| chr4 | 11989853 | 11990253 | Intron | 23479 | 1700123M08Rik | −1.045857961 | 0.025913718 |
| chr14 | 65374624 | 65375315 | Intron | 16293 | Zfp395 | −1.045977844 | 0.019628701 |
| chr13 | 52083658 | 52084020 | Intergenic | −12902 | 4921525O09Rik | −1.04654257 | 0.024790494 |
| chr15 | 42674844 | 42675089 | Intron | 2011 | Angpt1 | −1.046832294 | 0.03044534 |
| chr12 | 56695369 | 56696073 | 5′ UTR | 250 | Pax9 | −1.048065808 | 0.000101229 |
| chr7 | 30940253 | 30940717 | Intergenic | 3544 | Hamp | −1.048296224 | 0.04054255 |
| chr6 | 100576233 | 100576589 | Intron | 49011 | 1700049E22Rik | −1.048398097 | 0.004678311 |
| chr1 | 183987694 | 183988123 | Intergenic | 46090 | 1700056E22Rik | −1.048714857 | 0.007161926 |
| chr5 | 151189877 | 151190417 | Promoter-TSS | 46 | Stard13 | −1.04882565 | 7.32E−05 |
| chr15 | 64163361 | 64163989 | Intron | −103227 | Fam49b | −1.050367587 | 0.020512489 |
| chr8 | 3279133 | 3279883 | 5′ UTR | 109 | Insr | −1.051364008 | 3.58E−06 |
| chr9 | 7553632 | 7554031 | Intergenic | −4598 | Mmp8 | −1.051479063 | 0.002521692 |
| chr5 | 66620251 | 66620679 | Intergenic | −1648 | Apbb2 | −1.051753453 | 0.031848911 |
| chr3 | 102203766 | 102204720 | Intron | 450 | Vangl1 | −1.055329439 | 0.042247524 |
| chr2 | 68884642 | 68884955 | Intron | 23357 | Cers6 | −1.055469895 | 0.039529177 |
| chr12 | 110386293 | 110386513 | Intergenic | −60776 | Ppp2r5c | −1.055543476 | 0.020775476 |
| chr2 | 9577885 | 9578368 | Intergenic | 300474 | Gata3 | −1.055560458 | 0.003694329 |
| chr13 | 112474332 | 112474770 | Intron | 10481 | Il6st | −1.055593244 | 0.015918691 |
| chr15 | 38120356 | 38120691 | Intergenic | −41669 | Ubr5 | −1.055700745 | 0.001384644 |
| chr10 | 75365255 | 75365607 | Intergenic | 13376 | Gm5779 | −1.056160878 | 0.000976777 |
| chr14 | 16269857 | 16270318 | Intron | −20279 | Oxsm | −1.05717577 | 0.00535314 |
| chr4 | 154935861 | 154936212 | Intergenic | −7959 | Tnfrsf14 | −1.057228858 | 2.22E−06 |
| chr7 | 79759673 | 79760144 | Intron | 16745 | Wdr93 | −1.057995682 | 0.046045144 |
| chr8 | 93864041 | 93864452 | Intron | −50691 | 4930488L21Rik | −1.058783273 | 0.024336276 |
| chr16 | 97401611 | 97402131 | Intron | 45143 | Bace2 | −1.058802664 | 4.74E−09 |
| chr4 | 120037036 | 120037287 | Intron | −124045 | Edn2 | −1.058861568 | 0.032986722 |
| chr19 | 21865844 | 21866024 | Intergenic | 87594 | Tmem2 | −1.059063569 | 0.01868855 |
| chr10 | 118787251 | 118788006 | Intergenic | 81275 | Dyrk2 | −1.060093817 | 6.29E−10 |
| chr6 | 94635237 | 94635682 | Intron | −29044 | Mir7041 | −1.061287279 | 0.036319888 |
| chr6 | 145379277 | 145379718 | Intron | −8128 | 1700073E17Rik | −1.061517243 | 0.00602392 |
| chr3 | 101066045 | 101066553 | Intron | −36804 | Cd101 | −1.062045692 | 0.026737493 |
| chr3 | 122721396 | 122721904 | Intergenic | −7508 | Pde5a | −1.062366632 | 0.046559068 |
| chr4 | 154942613 | 154943020 | Intergenic | −14739 | Tnfrsf14 | −1.063047045 | 0.003267031 |
| chr1 | 91800840 | 91801805 | Promoter-TSS | −139 | Twist2 | −1.063846632 | 0.027407545 |
| chr1 | 34236256 | 34236861 | Intron | 76228 | Dst | −1.065263145 | 0.032614844 |
| chr7 | 25209091 | 25209670 | Intron | 8345 | Mir7048 | −1.066112142 | 0.016817042 |
| chr6 | 100314101 | 100314584 | Intergenic | −26984 | Rybp | −1.066470242 | 0.001208324 |
| chr6 | 53497780 | 53498304 | Intron | −75332 | Creb5 | −1.068980548 | 0.00011206 |
| chr14 | 53045396 | 53045600 | Intergenic | −549803 | Olfr1507 | −1.069392493 | 0.023293583 |
| chr5 | 77114846 | 77115242 | Promoter-TSS | 79 | Hopx | −1.070703666 | 0.024890155 |
| chr4 | 149469522 | 149469908 | Exon | −14747 | Rbp7 | −1.070721248 | 0.01844833 |
| chr12 | 55007468 | 55008011 | Intergenic | −21403 | Baz1a | −1.072931624 | 0.031152969 |
| chr9 | 118843619 | 118844448 | Intron | −82503 | Ctdspl | −1.073543766 | 0.003930761 |
| chr4 | 88078968 | 88079311 | Intergenic | −15491 | Focad | −1.074870117 | 0.01689979 |
| chr1 | 177676707 | 177677196 | Intergenic | −34008 | 2310043L19Rik | −1.075301243 | 0.03146592 |
| chr7 | 126178819 | 126179093 | Intron | 21452 | Xpo6 | −1.075458026 | 0.047067273 |
| chr1 | 82428789 | 82429553 | Intron | 90122 | Rhbdd1 | −1.077269118 | 0.000253365 |
| chr2 | 135890941 | 135891535 | Intron | 149408 | Plcb4 | −1.077968479 | 8.38E−06 |
| chr10 | 99561120 | 99561903 | Intergenic | −47660 | Gm20110 | −1.078098899 | 5.15E−09 |
| chr4 | 141625045 | 141625627 | TTS | −1502 | Slc25a34 | −1.079124762 | 1.02E−05 |
| chr11 | 79460832 | 79461127 | Intron | 23007 | AU040972 | −1.079238456 | 0.034017991 |
| chr6 | 115955748 | 115956100 | Intron | 10993 | H1foo | −1.079266413 | 0.014082731 |
| chr15 | 53113895 | 53114403 | Intron | 232034 | Ext1 | −1.079486433 | 0.049714125 |
| chr12 | 99329111 | 99329678 | Intron | 120680 | Foxn3 | −1.079983334 | 0.000873117 |
| chr18 | 61207085 | 61207337 | Intron | 4385 | Slc26a2 | −1.082361489 | 0.000217203 |
| chr13 | 43778068 | 43778366 | Intergenic | −6895 | Cd83 | −1.082362599 | 0.039960216 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr10 | 14314646 | 14314958 | Intergenic | 230234 | Adgrg6 | −1.083093728 | 0.001503311 |
| chr12 | 36241089 | 36241487 | Intron | 12110 | Lrrc72 | −1.083553725 | 0.028579149 |
| chr3 | 37268394 | 37268692 | Intergenic | −35907 | Il21 | −1.083730323 | 0.029113064 |
| chr9 | 118285479 | 118285887 | Intergenic | −135487 | Cmc1 | −1.083960524 | 0.001585606 |
| chr13 | 89428324 | 89428851 | Intergenic | −112049 | Hapln1 | −1.084536009 | 0.008912477 |
| chr2 | 72281844 | 72282335 | Intergenic | −3548 | Map3k20 | −1.084620894 | 0.004298099 |
| chr10 | 127759481 | 127759848 | Promoter-TSS | −99 | Rdh1 | −1.086082008 | 0.000559243 |
| chr2 | 60370156 | 60370805 | Intron | 12751 | Ly75 | −1.087442683 | 0.000866988 |
| chr9 | 101249527 | 101250064 | Intron | 2037 | Ppp2r3a | −1.087883122 | 2.68E−08 |
| chr7 | 105481883 | 105482444 | Promoter-TSS | 34 | Prkcdbp | −1.088993503 | 0.027147225 |
| chr12 | 112449158 | 112449708 | Intergenic | −14095 | B020018J22Rik | −1.0903888 | 0.002796589 |
| chr4 | 5644069 | 5644749 | 5' UTR | 230 | Fam110b | −1.09061203 | 0.023011815 |
| chr1 | 191662135 | 191662701 | Intergenic | −55606 | Lpgat1 | −1.090697157 | 0.001293206 |
| chr4 | 105158096 | 105158462 | Intron | 932 | Plpp3 | −1.090747579 | 0.036114416 |
| chr17 | 8524558 | 8525146 | Intergenic | −1949 | Pde10a | −1.092767025 | 0.009295682 |
| chr4 | 120882191 | 120882524 | Intron | 4488 | Rims3 | −1.093684106 | 0.034666483 |
| chr15 | 50750986 | 50751496 | Intron | 137808 | Trps1 | −1.093871346 | 0.013764109 |
| chr7 | 16343602 | 16344039 | Intron | 34237 | Bbc3 | −1.095864571 | 0.039166167 |
| chr14 | 61773852 | 61774097 | Intergenic | −91601 | Dleu2 | −1.095941604 | 0.034666483 |
| chr16 | 36927472 | 36927876 | Intron | −7309 | Hcls1 | −1.096905178 | 0.001939994 |
| chrX | 36609080 | 36609553 | 3' UTR | 11123 | Pgrmc1 | −1.097105138 | 0.011247026 |
| chr19 | 7456896 | 7457344 | Exon | −21398 | Snord118 | −1.097147933 | 0.000144459 |
| chr1 | 131747037 | 131747604 | Intron | 3298 | Slc26a9 | −1.098599968 | 0.000737835 |
| chr2 | 17698212 | 17698543 | Intron | 32691 | Nebl | −1.098977924 | 0.029174761 |
| chr3 | 121493887 | 121494401 | Intron | 38200 | Slc44a3 | −1.099779712 | 0.006210736 |
| chr9 | 123243924 | 123244431 | Intergenic | 16612 | Tmem158 | −1.100211858 | 0.029587478 |
| chr18 | 84302499 | 84302849 | Intron | 214516 | Zadh2 | −1.100400548 | 0.002046262 |
| chr16 | 97402391 | 97402694 | Intron | 45814 | Bace2 | −1.10117547 | 1.88E−05 |
| chr4 | 63590681 | 63590962 | Intergenic | 9943 | Gm11213 | −1.101634484 | 0.01379505 |
| chr9 | 92252793 | 92252996 | Intron | 2700 | Plscr1 | −1.102558489 | 0.042496363 |
| chr17 | 35758750 | 35759130 | Intergenic | −13510 | 4833427F10Rik | −1.102998888 | 0.011696557 |
| chr13 | 84768946 | 84769391 | Intergenic | −420217 | Ccnh | −1.103144233 | 0.010166795 |
| chr7 | 67500362 | 67500829 | Intergenic | −127737 | Mef2a | −1.103697932 | 0.006107955 |
| chr12 | 99610283 | 99610996 | Intron | 17335 | 1700064M15Rik | −1.104219329 | 4.18E−06 |
| chr9 | 51213423 | 51214213 | Intron | 128 | Pou2af1 | −1.105540502 | 5.86E−07 |
| chr8 | 57828191 | 57828749 | Intron | −175415 | Galnt7 | −1.105783112 | 0.026537788 |
| chr7 | 78597396 | 78598124 | Intron | −19922 | Ntrk3 | −1.106002236 | 2.20E−07 |
| chr13 | 24230454 | 24231480 | Intron | 49823 | Carmil1 | −1.10728227 | 3.82E−05 |
| chr19 | 58850590 | 58851318 | Intron | 10030 | Hspa12a | −1.109492447 | 0.004888746 |
| chr1 | 80418721 | 80419124 | Intergenic | −27010 | 1700016L21Rik | −1.111697405 | 0.048822348 |
| chrX | 74399716 | 74400472 | Intron | 6803 | Ikbkg | −1.113617885 | 0.000504284 |
| chr15 | 61428800 | 61429154 | Intergenic | 345474 | D030024E09Rik | −1.113698829 | 0.040974243 |
| chr6 | 61179825 | 61180698 | Promoter-TSS | −64 | Ccser1 | −1.114186884 | 6.17E−07 |
| chr2 | 53088699 | 53089078 | Intron | 102299 | Prpf40a | −1.114253895 | 0.010349536 |
| chr16 | 21694412 | 21694894 | Promoter-TSS | 12 | 2510009E07Rik | −1.114482092 | 0.028684248 |
| chr10 | 121293962 | 121294431 | Intron | 16993 | Tbc1d30 | −1.114930344 | 0.003909741 |
| chr17 | 26551129 | 26551517 | Intergenic | −10189 | Ergic1 | −1.115188858 | 0.000601117 |
| chr10 | 96609365 | 96609893 | Intergenic | −7372 | Btg1 | −1.115280747 | 0.001023789 |
| chr8 | 81735738 | 81736456 | Intron | 393535 | Inpp4b | −1.115825794 | 0.014066848 |
| chr14 | 52008604 | 52008819 | Exon | 5847 | Zfp219 | −1.116051964 | 0.03146592 |
| chr17 | 8856327 | 8856796 | Intron | 6576 | Pde10a | −1.116182696 | 0.004764232 |
| chr17 | 46686000 | 46686280 | Intron | 4960 | Mea1 | −1.116288627 | 0.018078615 |
| chr9 | 114443315 | 114443723 | Intron | 42424 | Tmppe | −1.116411989 | 4.42E−09 |
| chr9 | 33186358 | 33186718 | Intergenic | −257572 | Gm27162 | −1.116791526 | 0.0102003 |
| chr4 | 136116997 | 136117565 | Intergenic | −26541 | Id3 | −1.117438653 | 0.007912635 |
| chr18 | 32569492 | 32569871 | Intergenic | −9647 | Gypc | −1.117503273 | 0.009712166 |
| chr11 | 32061953 | 32062357 | Intergenic | 39073 | Gm12108 | −1.117687978 | 0.012318715 |
| chr2 | 163166530 | 163166767 | Intergenic | −58806 | Tox2 | −1.119322375 | 0.039522256 |
| chr10 | 86794772 | 86795371 | Intron | 16066 | Nt5dc3 | −1.120044828 | 0.007535116 |
| chr7 | 96818244 | 96819134 | Intron | −17140 | Gm15413 | −1.120595967 | 1.75E−09 |
| chr2 | 126331792 | 126332137 | Intron | 159589 | Atp8b4 | −1.120785735 | 0.009114348 |
| chr12 | 109437816 | 109438293 | Intergenic | −14769 | Dlk1 | −1.120891473 | 0.000537976 |
| chr6 | 142954961 | 142955208 | Intron | 9368 | St8sia1 | −1.122667094 | 0.042018151 |
| chr10 | 68153895 | 68154321 | Intron | 124618 | Arid5b | −1.122682477 | 0.029113064 |
| chr3 | 50443441 | 50444208 | Promoter-TSS | −211 | Slc7a11 | −1.122853248 | 0.03246123 |
| chr8 | 46990977 | 46991464 | Intron | 4333 | Enpp6 | −1.122952896 | 0.001195133 |
| chr1 | 53049715 | 53050675 | Intergenic | −11445 | Mstn | −1.123533033 | 9.11E−05 |
| chr4 | 32405217 | 32405399 | Intergenic | −12127 | Bach2 | −1.124501604 | 0.015918274 |
| chr1 | 127796399 | 127796880 | Intron | 22475 | Ccnt2 | −1.124613029 | 0.004998588 |
| chr12 | 79692092 | 79692762 | Intron | 232306 | 9430078K24Rik | −1.125681023 | 6.32E−07 |
| chr14 | 45094643 | 45095058 | Intergenic | 106739 | Ptger2 | −1.127096941 | 0.017143289 |
| chr5 | 148419002 | 148419459 | Intergenic | −19326 | Slc7a1 | −1.127441458 | 0.010767574 |
| chr15 | 91191414 | 91192471 | Promoter-TSS | −135 | Abcd2 | −1.127490574 | 0.001474812 |
| chr16 | 45124588 | 45125231 | Intron | 30856 | Ccdc80 | −1.128305184 | 0.001496028 |
| chr1 | 9882942 | 9883662 | Intron | −25336 | Mcmdc2 | −1.128839475 | 6.64E−05 |
| chr6 | 61180766 | 61181047 | Promoter-TSS | −96 | A730020E08Rik | −1.130441485 | 0.042157297 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr4 | 89505294 | 89505774 | Intron | −182664 | Dmrta1 | −1.132002023 | 0.009608127 |
| chr6 | 145374481 | 145374704 | Intergenic | −13033 | 1700073E17Rik | −1.132414963 | 0.008641385 |
| chr9 | 14199953 | 14200753 | Intergenic | −75948 | Sesn3 | −1.13349233 | 0.000573467 |
| chr16 | 95750232 | 95750612 | Intergenic | 48015 | Ets2 | −1.134520659 | 0.011421783 |
| chr4 | 82513135 | 82513566 | Intron | 5361 | Gm11266 | −1.135253577 | 0.00313169 |
| chr3 | 121107470 | 121107914 | Intergenic | 64003 | Rwdd3 | −1.13564401 | 0.04297038 |
| chr12 | 109445105 | 109445475 | Intergenic | −7533 | Dlk1 | −1.137092718 | 0.034380433 |
| chrX | 57177203 | 57177769 | Intergenic | −23151 | Gm14718 | −1.140715144 | 9.20E−06 |
| chr13 | 110960048 | 110960528 | Intergenic | −56442 | 4930526H09Rik | −1.141747521 | 0.043597089 |
| chr18 | 65465611 | 65465973 | Intron | 34795 | Malt1 | −1.142498171 | 0.013496256 |
| chr3 | 78889832 | 78890322 | Intergenic | 254810 | Rapgef2 | −1.142698947 | 0.011509523 |
| chr18 | 57970237 | 57970850 | Intergenic | 91865 | Slc12a2 | −1.142714142 | 0.013131239 |
| chr17 | 70796943 | 70797880 | Intron | 49366 | Tgif1 | −1.143118541 | 1.50E−05 |
| chr17 | 23617076 | 23617445 | Intergenic | 16434 | Zscan10 | −1.144140173 | 0.00234807 |
| chr14 | 76570302 | 76570632 | Intergenic | −13578 | Serp2 | −1.145134259 | 0.018216458 |
| chr1 | 107589689 | 107590472 | Promoter-TSS | 74 | Serpinb8 | −1.145378356 | 0.027875812 |
| chr11 | 11506068 | 11506553 | Intron | 17044 | 4930415F15Rik | −1.145675543 | 1.16E−05 |
| chr2 | 128345532 | 128345904 | Intron | 83633 | Gm14005 | −1.146327778 | 0.011586205 |
| chr2 | 33215612 | 33216297 | Promoter-TSS | −7 | Angptl2 | −1.146523954 | 6.99E−08 |
| chr6 | 38120553 | 38121071 | Intron | 3774 | Atp6v0a4 | −1.14655283 | 7.92E−07 |
| chr1 | 74262509 | 74262916 | Intron | −15888 | Gpbar1 | −1.146569322 | 0.011233165 |
| chr7 | 75800630 | 75800844 | Intergenic | −47601 | Klhl25 | −1.146586212 | 0.022435249 |
| chr9 | 59338459 | 59338795 | Intron | 14881 | Bbs4 | −1.146663504 | 0.015756651 |
| chr8 | 119545170 | 119545489 | Intron | 13432 | Mbtps1 | −1.148264365 | 0.009179072 |
| chr1 | 38777371 | 38778046 | Intergenic | 43507 | Lonrf2 | −1.148833138 | 2.91E−05 |
| chr12 | 110389234 | 110389746 | Intergenic | −57689 | Ppp2r5c | −1.14962313 | 5.14E−05 |
| chr1 | 73940914 | 73941154 | Exon | −76568 | 6030407O03Rik | −1.149828384 | 0.032781245 |
| chr19 | 56858061 | 56858867 | Exon | −15952 | Vwa2 | −1.150550275 | 0.000353299 |
| chr3 | 27983831 | 27984207 | Promoter-TSS | −152 | Pld1 | −1.150849557 | 0.006555599 |
| chr19 | 10784081 | 10784406 | Intron | 43296 | A430093F15Rik | −1.151046281 | 0.003139464 |
| chr2 | 146834736 | 146835130 | Intergenic | −20956 | Kiz | −1.152155254 | 0.025209661 |
| chr2 | 153504586 | 153504954 | Intron | 25201 | Nol4l | −1.153862629 | 0.005769387 |
| chr12 | 41167712 | 41168127 | Intron | 143829 | Immp2l | −1.15420249 | 0.031056384 |
| chr1 | 191384810 | 191385153 | Intron | 12060 | Ppp2r5a | −1.155734431 | 0.039090618 |
| chr6 | 120913957 | 120914095 | Intron | 2794 | Bid | −1.156124174 | 0.021418753 |
| chr18 | 36492482 | 36493038 | Intergenic | 23045 | Hbegf | −1.157704664 | 0.000366808 |
| chr1 | 36646366 | 36646823 | Intron | 36589 | Fam178b | −1.158845654 | 0.002163727 |
| chr19 | 14437246 | 14437692 | Intergenic | 1037 | Rnu6 | −1.160415853 | 0.001717796 |
| chr16 | 25970182 | 25970569 | Intron | 135409 | P3h2 | −1.161094383 | 0.029420038 |
| chr5 | 77125040 | 77125436 | Intergenic | −10115 | Hopx | −1.162913486 | 0.006005294 |
| chr17 | 80579079 | 80579627 | Intergenic | −15519 | Cdkl4 | −1.163014937 | 1.44E−06 |
| chr9 | 48538121 | 48538776 | Intergenic | 43105 | Gm5617 | −1.163088669 | 0.012565834 |
| chr11 | 102496668 | 102497050 | Intron | −26976 | Itga2b | −1.163337709 | 0.024790494 |
| chr15 | 76053755 | 76054237 | Intron | 10892 | Mir6952 | −1.163596207 | 0.0205938 |
| chr11 | 103771502 | 103771826 | Intergenic | −2511 | Wnt3 | −1.163598577 | 0.016929453 |
| chr16 | 78591221 | 78591690 | Intergenic | −14767 | D16Ertd472e | −1.163824657 | 0.043597089 |
| chr10 | 7992653 | 7992998 | Intergenic | −36702 | Tab2 | −1.165180996 | 0.014876885 |
| chr3 | 141778266 | 141778985 | Intron | 152963 | Bmpr1b | −1.168070215 | 0.000146841 |
| chr4 | 6903696 | 6904027 | Intron | 86862 | Tox | −1.170461169 | 0.004764232 |
| chr16 | 95728592 | 95729330 | Intergenic | 26554 | Ets2 | −1.171181849 | 2.80E−12 |
| chr18 | 53417842 | 53418254 | Promoter-TSS | −41 | Ppic | −1.171315001 | 0.036743958 |
| chr9 | 124079845 | 124080389 | Intergenic | −22066 | Ccr2 | −1.171966668 | 0.026086868 |
| chr5 | 117481532 | 117482029 | Intron | 67778 | Ksr2 | −1.173870866 | 0.031490127 |
| chr11 | 5178743 | 5178976 | Intergenic | −26812 | Emid1 | −1.174022372 | 0.007275477 |
| chr18 | 54992494 | 54992781 | Intergenic | −2457 | Zfp608 | −1.174725256 | 0.000144095 |
| chr9 | 40348782 | 40349181 | Intron | 15509 | 1700110K17Rik | −1.175592205 | 0.014293733 |
| chr9 | 13509473 | 13509950 | Intergenic | 78350 | Phxr4 | −1.17586932 | 0.014876885 |
| chr8 | 68735672 | 68735830 | Promoter-TSS | −605 | Csgalnact1 | −1.177347386 | 0.044201229 |
| chr11 | 3101178 | 3101320 | Intergenic | −22772 | Pisd-ps1 | −1.177999636 | 0.009048052 |
| chr12 | 28792454 | 28793024 | Intron | 40911 | Tssc1 | −1.179021664 | 0.003611169 |
| chr10 | 59381686 | 59382035 | Intergenic | −21825 | Pla2g12b | −1.179697878 | 0.033073717 |
| chr2 | 6545554 | 6545871 | 3' UTR | 175950 | Celf2 | −1.179996022 | 0.028109732 |
| chr2 | 68319608 | 68320166 | Intron | 152064 | Stk39 | −1.180057072 | 0.001229725 |
| chr7 | 132402641 | 132403073 | Intergenic | −85702 | Chst15 | −1.180690865 | 7.49E−05 |
| chr13 | 32692508 | 32692953 | Intergenic | 89049 | Mylk4 | −1.18141391 | 0.021799899 |
| chr1 | 165075595 | 165076078 | Intron | 16094 | 4930568G15Rik | −1.182974825 | 0.018730823 |
| chr1 | 151236458 | 151236938 | Intergenic | 98664 | C730036E19Rik | −1.183192254 | 0.021810199 |
| chr1 | 156205985 | 156206389 | Intergenic | −1161 | Fam163a | −1.184525639 | 0.000231721 |
| chr10 | 21946823 | 21947386 | Intron | −31568 | Sgk1 | −1.185119413 | 0.029714008 |
| chr14 | 41050524 | 41050809 | Intron | 18408 | Dydc2 | −1.185411233 | 0.002743543 |
| chr11 | 6011225 | 6011513 | Intron | 54379 | Camk2b | −1.185682077 | 0.006525352 |
| chr6 | 37046167 | 37046695 | Intron | −235070 | Ptn | −1.186226283 | 0.01689979 |
| chr10 | 117625832 | 117626011 | Intergenic | −3579 | Cpm | −1.186493783 | 0.021810199 |
| chr7 | 125189882 | 125190528 | Intergenic | 159581 | 4933440M02Rik | −1.187089201 | 4.58E−07 |
| chr4 | 141302001 | 141302320 | Intron | 939 | Epha2 | −1.187274883 | 0.047401109 |
| chr4 | 43834621 | 43835196 | 3' UTR | 1609 | Olfr157 | −1.187701366 | 0.002214145 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr3 | 27607215 | 27608147 | Intron | −22686 | Mir3092 | −1.18812032 | 1.46E−06 |
| chr10 | 70133171 | 70133533 | Intron | 36231 | Ccdc6 | −1.188233688 | 0.003397628 |
| chr2 | 6592077 | 6592565 | Intron | 129341 | Celf2 | −1.189065747 | 0.009218826 |
| chr1 | 20912601 | 20913136 | Intron | 22246 | Paqr8 | −1.190223677 | 0.022860231 |
| chr13 | 28417439 | 28418425 | Intergenic | 275448 | Prl5a1 | −1.190329108 | 1.72E−10 |
| chr15 | 25773742 | 25774352 | Intron | −69251 | Fam134b | −1.192501595 | 0.005580251 |
| chr15 | 94478696 | 94479025 | Intergenic | 64647 | Pus7l | −1.192602007 | 0.035573592 |
| chr12 | 107640575 | 107640859 | Intergenic | 94771 | 4930465M20Rik | −1.192882377 | 0.042977817 |
| chr9 | 116152719 | 116153375 | Intron | 22316 | Tgfbr2 | −1.193108027 | 6.14E−06 |
| chr10 | 13090502 | 13091039 | Promoter-TSS | −18 | Plagl1 | −1.195900816 | 0.000248627 |
| chr2 | 132004712 | 132005224 | Intron | 25020 | Rassf2 | −1.196378924 | 0.004083515 |
| chr12 | 90576057 | 90576520 | Intergenic | 162749 | Dio2 | −1.196662004 | 0.003381181 |
| chr10 | 116913661 | 116914213 | Intron | −17058 | Myrfl | −1.19768073 | 2.07E−09 |
| chr6 | 99485858 | 99486602 | Intron | 34763 | Foxp1 | −1.197750815 | 1.79E−07 |
| chr9 | 120776455 | 120777276 | Intergenic | 138385 | 1700020M21Rik | −1.199047206 | 2.28E−12 |
| chr6 | 61300655 | 61301306 | Intron | −120170 | A730020E08Rik | −1.200032197 | 2.72E−06 |
| chr17 | 34293564 | 34293871 | Intergenic | −5946 | H2-Aa | −1.200216394 | 0.002308172 |
| chr18 | 65318945 | 65319353 | Intron | 70288 | Mir122 | −1.200562778 | 0.001295185 |
| chr3 | 157883689 | 157884538 | Intergenic | 40950 | Cth | −1.201720451 | 0.000371838 |
| chr6 | 108454518 | 108454847 | Intron | −35061 | Mir7661 | −1.201983461 | 0.022591962 |
| chr16 | 48786355 | 48786637 | Intergenic | −14540 | Trat1 | −1.202318797 | 0.028197578 |
| chr7 | 130892997 | 130893373 | Intron | −15083 | Mir7061 | −1.203103684 | 0.007779438 |
| chr10 | 96690717 | 96691304 | Intergenic | 74009 | Btg1 | −1.203383779 | 0.000552512 |
| chr18 | 60632595 | 60633134 | Intergenic | −8559 | Synpo | −1.204861534 | 0.006196906 |
| chr9 | 120091036 | 120091622 | Promoter-TSS | −804 | Ccr8 | −1.205078327 | 2.87E−05 |
| chr4 | 11887652 | 11888148 | Intergenic | 77813 | Pdp1 | −1.205539954 | 7.07E−05 |
| chr3 | 103146994 | 103147352 | Intron | 19617 | Dennd2c | −1.207306812 | 0.001786538 |
| chr11 | 22001472 | 22002151 | Promoter-TSS | −160 | Otx1 | −1.207589194 | 0.000559268 |
| chr6 | 144540977 | 144541652 | Intergenic | −131554 | Sox5os3 | −1.207780234 | 0.002796589 |
| chr5 | 105010174 | 105010741 | Intergenic | −27740 | Abcg3 | −1.207902461 | 5.21E−05 |
| chr15 | 85347076 | 85347701 | Intron | 11007 | Atxn10 | −1.2079853 | 0.001129694 |
| chr18 | 69614216 | 69614630 | Intron | 268702 | Tcf4 | −1.210795366 | 0.002765871 |
| chr7 | 49245789 | 49246451 | Promoter-TSS | −69 | Nav2 | −1.211716661 | 1.10E−10 |
| chr7 | 120921238 | 120921471 | Intron | 3610 | Polr3e | −1.212053472 | 4.97E−05 |
| chr2 | 77176158 | 77176809 | Intergenic | −5848 | Ccdc141 | −1.212687093 | 0.000990885 |
| chr10 | 130330673 | 130331144 | Intron | 8056 | Tespa1 | −1.213363906 | 0.000480198 |
| chr17 | 35068536 | 35068926 | Intron | 1406 | Ly6g6c | −1.217549748 | 0.00957151 |
| chr1 | 98589287 | 98590071 | Intergenic | 168555 | Slco6d1 | −1.218066724 | 8.35E−07 |
| chr3 | 143646814 | 143647217 | Intergenic | 65128 | Gm6260 | −1.218681738 | 0.007429658 |
| chr14 | 53080582 | 53080784 | Intergenic | −584988 | Olfr1507 | −1.219711124 | 0.014335401 |
| chr6 | 134252045 | 134252542 | Intron | −144036 | Bcl2l14 | −1.222329209 | 0.000133984 |
| chr19 | 29384329 | 29384611 | Intron | 17032 | Cd274 | −1.222867305 | 0.031507626 |
| chr9 | 92499780 | 92499988 | Intergenic | −42339 | Plod2 | −1.222896135 | 0.037321188 |
| chr16 | 17024475 | 17024868 | Intron | 41289 | Mapk1 | −1.223148634 | 0.002054733 |
| chr18 | 32543071 | 32543479 | Intron | 16759 | Gypc | −1.223152929 | 1.74E−07 |
| chr13 | 43774078 | 43774541 | Intergenic | −10803 | Cd83 | −1.228412645 | 0.001597313 |
| chr10 | 24640265 | 24640412 | 3' UTR | 44896 | Ctgf | −1.228638076 | 0.006168951 |
| chr11 | 88578789 | 88579049 | Intron | −40332 | 0610039H22Rik | −1.229314 | 0.000636567 |
| chr13 | 107966881 | 107967228 | Intergenic | −76990 | Zswim6 | −1.230077011 | 0.018602031 |
| chr5 | 105198008 | 105198437 | Intergenic | 41311 | Gbp10 | −1.231975074 | 0.006493323 |
| chr12 | 109441330 | 109441700 | Intergenic | −11308 | Dlk1 | −1.232209699 | 0.015933818 |
| chr3 | 138864124 | 138864732 | Intron | 122220 | Tspan5 | −1.23283432 | 1.73E−05 |
| chr5 | 111235771 | 111236129 | Intron | −94747 | Pitpnb | −1.233463098 | 0.020423473 |
| chr11 | 88589290 | 88590044 | Intron | −29584 | 0610039H22Rik | −1.233868587 | 0.000763705 |
| chr2 | 67565462 | 67565935 | Intergenic | −109759 | Mir7224 | −1.234012712 | 6.26E−05 |
| chr6 | 145469131 | 145469719 | Intergenic | −34500 | Lmntd1 | −1.234687449 | 0.022667945 |
| chr6 | 59313079 | 59313839 | Intergenic | 104589 | Tigd2 | −1.235104043 | 0.009609487 |
| chr19 | 10869598 | 10869902 | Promoter-TSS | 29 | Tmem132a | −1.237019565 | 0.038027478 |
| chr7 | 68250361 | 68250814 | Intron | 13646 | Pgpep1l | −1.237643234 | 0.020287373 |
| chr2 | 72114048 | 72114701 | Intron | 59757 | Rapgef4 | −1.238753939 | 3.70E−05 |
| chr13 | 84791075 | 84791561 | Intergenic | −398067 | Ccnh | −1.239477111 | 0.00060728 |
| chr4 | 53159856 | 53160137 | Promoter-TSS | −101 | Abca1 | −1.240447046 | 0.004724526 |
| chr5 | 28402785 | 28403222 | Intron | −63981 | 9530036O11Rik | −1.242266521 | 1.24E−05 |
| chr15 | 11907114 | 11907497 | Promoter-TSS | 66 | Npr3 | −1.242442468 | 0.046956319 |
| chr5 | 15507124 | 15507439 | Intergenic | 21941 | Gm21190 | −1.242623462 | 0.002070681 |
| chr13 | 44320863 | 44321602 | Intergenic | −104745 | A330076C08Rik | −1.244739569 | 1.02E−07 |
| chr18 | 39656343 | 39656564 | Intergenic | −117107 | Pabpc2 | −1.244991531 | 0.011586205 |
| chr5 | 91083006 | 91083414 | Intron | 8593 | Ereg | −1.245961183 | 0.049285363 |
| chr13 | 9353845 | 9354225 | Intron | 77510 | Dip2c | −1.245983225 | 0.01978769 |
| chr5 | 90492501 | 90492790 | Intron | 1931 | Afp | −1.246046672 | 0.030018192 |
| chr2 | 61489828 | 61490068 | Intergenic | −88638 | Tank | −1.246113993 | 0.010606277 |
| chr9 | 96696301 | 96696700 | Intron | 35175 | Zbtb38 | −1.246447967 | 0.007747602 |
| chr12 | 79580542 | 79581051 | Intron | 283445 | Rad51b | −1.246602888 | 0.001071571 |
| chr6 | 86318618 | 86319320 | Intergenic | −46714 | Fam136a | −1.247177599 | 0.011395502 |
| chr6 | 47560909 | 47561311 | Intron | 33920 | Ezh2 | −1.251347339 | 0.000326278 |
| chr17 | 8190058 | 8190322 | Intron | 24672 | Fgfr1op | −1.252011692 | 0.020916187 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr3 | 60124382 | 60125059 | Intergenic | 42851 | Sucnr1 | −1.252097377 | 0.000234309 |
| chr18 | 39729887 | 39730275 | Intergenic | −43416 | Pabpc2 | −1.252156677 | 0.043005833 |
| chr18 | 69644515 | 69645090 | Intron | −280757 | Ccdc68 | −1.252237031 | 1.28E−05 |
| chr1 | 120236318 | 120237152 | Intron | 28545 | Steap3 | −1.252711071 | 2.15E−05 |
| chr4 | 154936489 | 154937171 | Intergenic | −8753 | Tnfrsf14 | −1.253770742 | 2.22E−12 |
| chr12 | 110375252 | 110375563 | Intergenic | −71772 | Ppp2r5c | −1.254131695 | 0.001560191 |
| chr6 | 134366343 | 134366828 | Intergenic | −29744 | Bcl2l14 | −1.255533458 | 5.47E−07 |
| chr19 | 17263336 | 17263533 | Intergenic | 76071 | Gcnt1 | −1.255593586 | 0.01692775 |
| chr18 | 61481678 | 61482004 | Intron | 2766 | A530050N04Rik | −1.255957367 | 0.001718316 |
| chr6 | 100438433 | 100439032 | Intergenic | −88668 | 1700049E22Rik | −1.257472454 | 4.17E−05 |
| chr9 | 123240508 | 123240684 | Intergenic | 20193 | Tmem158 | −1.257775419 | 0.031381868 |
| chr14 | 79141683 | 79142088 | Intron | 105482 | Zfp957 | −1.259257562 | 0.009459817 |
| chr9 | 31120325 | 31120857 | Intron | 11208 | St14 | −1.260443988 | 0.002160285 |
| chr10 | 117651785 | 117652365 | Intron | 22575 | Cpm | −1.260475264 | 0.025051859 |
| chr16 | 50230580 | 50230923 | Intron | −157899 | Gm4827 | −1.261230901 | 0.042867803 |
| chr6 | 54494713 | 54495301 | Intron | 42124 | Wipf3 | −1.261627389 | 0.000151395 |
| chr6 | 128902013 | 128902385 | Intergenic | −11075 | BC035044 | −1.261679518 | 0.002474515 |
| chr2 | 167823430 | 167823866 | Intergenic | −108679 | Ptpn1 | −1.263212761 | 0.047654341 |
| chr8 | 128534405 | 128534726 | Intergenic | −151089 | Itgb1 | −1.263358441 | 1.50E−06 |
| chr5 | 105313319 | 105313843 | Intergenic | −19882 | Gbp6 | −1.264998698 | 0.001667444 |
| chr15 | 55847018 | 55847241 | Intron | 59820 | Sntb1 | −1.268104393 | 0.006636155 |
| chr14 | 17981235 | 17981573 | Promoter-TSS | −240 | Thrb | −1.272791041 | 0.005769387 |
| chr16 | 29834715 | 29835058 | Intergenic | 144238 | Gm1968 | −1.273101091 | 0.000217795 |
| chr19 | 25056313 | 25056521 | Intron | 56888 | Dock8 | −1.273736966 | 0.005711262 |
| chr9 | 13425154 | 13425758 | Intergenic | −5905 | Phxr4 | −1.273931885 | 0.005496306 |
| chr16 | 26041316 | 26041937 | Intron | 64158 | P3h2 | −1.27437498 | 1.56E−05 |
| chr14 | 45005578 | 45006273 | Intergenic | 17814 | Ptger2 | −1.274763065 | 1.47E−07 |
| chr2 | 176830721 | 176831061 | Intergenic | 32291 | Gm14295 | −1.274941729 | 0.000210179 |
| chr19 | 21769858 | 21770389 | Intergenic | −8217 | Tmem2 | −1.27572619 | 0.000156359 |
| chr13 | 97857765 | 97858268 | Intergenic | 298016 | Gm5086 | −1.276355847 | 1.51E−06 |
| chr4 | 32405524 | 32405949 | Intergenic | −11699 | Bach2 | −1.276963497 | 5.45E−06 |
| chr10 | 121297511 | 121297738 | Intron | 13565 | Tbc1d30 | −1.278316303 | 0.000188587 |
| chr3 | 68980993 | 68981424 | Intron | 23361 | Ift80 | −1.279156489 | 0.009295682 |
| chr1 | 80213663 | 80214184 | Promoter-TSS | 21 | Fam124b | −1.279266007 | 3.27E−06 |
| chr18 | 34247535 | 34247753 | Intron | −25872 | Gm10548 | −1.282118793 | 0.0178875 |
| chr2 | 59441563 | 59441850 | Intergenic | −42947 | Dapl1 | −1.285427604 | 0.029200067 |
| chr6 | 50159851 | 50160268 | Intron | 49818 | Mpp6 | −1.285650612 | 0.044700638 |
| chr3 | 84460918 | 84461247 | Intron | 18409 | Fhdc1 | −1.286470613 | 0.015326824 |
| chr13 | 32428283 | 32428955 | Intergenic | −90075 | Gmds | −1.286879327 | 0.011488279 |
| chr4 | 101418836 | 101419530 | Promoter-TSS | −106 | Ak4 | −1.287016452 | 0.000564737 |
| chr1 | 143819037 | 143819316 | Intergenic | 41898 | Uchl5 | −1.287919733 | 0.032719547 |
| chr19 | 29185559 | 29186030 | Intergenic | 50519 | Mir101b | −1.289524839 | 0.000199208 |
| chr10 | 76961748 | 76962424 | Promoter-TSS | −139 | Pcbp3 | −1.292083986 | 2.12E−22 |
| chr19 | 10732043 | 10732451 | Intron | 6727 | Cd5 | −1.296795906 | 0.039443353 |
| chr14 | 53132369 | 53132839 | Intergenic | −636909 | Olfr1507 | −1.297876726 | 2.85E−09 |
| chr2 | 59534355 | 59534725 | Intergenic | 49887 | Dapl1 | −1.298916236 | 0.036114416 |
| chr15 | 85670977 | 85671252 | Intergenic | −32659 | Lncppara | −1.299195651 | 0.020343067 |
| chr14 | 61056980 | 61057399 | Intergenic | −10334 | Tnfrsf19 | −1.300595295 | 0.026109641 |
| chr12 | 54397940 | 54398526 | Intergenic | −6915 | Gm7550 | −1.300666151 | 3.68E−07 |
| chr9 | 83563810 | 83564547 | Intron | 15840 | Sh3bgrl2 | −1.301056938 | 9.04E−06 |
| chr6 | 61065800 | 61066301 | Intergenic | −114275 | Ccser1 | −1.301559774 | 0.009601978 |
| chr6 | 120206588 | 120207033 | Intron | 12987 | Ninj2 | −1.302523665 | 1.85E−05 |
| chr12 | 51567112 | 51567518 | Intergenic | −26026 | Coch | −1.303880746 | 9.10E−05 |
| chr7 | 140324130 | 140324573 | TTS | 1650 | Olfr525 | −1.305130291 | 7.03E−06 |
| chr13 | 43784992 | 43785197 | Promoter-TSS | −18 | Cd83 | −1.305499398 | 0.029845559 |
| chr18 | 30267934 | 30268150 | Intergenic | −4854 | Pik3c3 | −1.306721901 | 0.019205952 |
| chr12 | 100276774 | 100277262 | Intron | 409 | Gm10432 | −1.30789541 | 0.001812081 |
| chr7 | 120693885 | 120694343 | Intron | 16494 | BC030336 | −1.308258939 | 8.12E−05 |
| chr13 | 46930722 | 46931056 | Intron | −1171 | Kif13a | −1.30838008 | 0.002143163 |
| chr18 | 9393966 | 9394626 | Intron | 55854 | Ccny | −1.308654817 | 0.003549467 |
| chr1 | 83006167 | 83006511 | Intergenic | 32109 | Slc19a3 | −1.308777258 | 0.000816619 |
| chr5 | 102959991 | 102960383 | Intron | 98205 | Mapk10 | −1.309206376 | 0.022922441 |
| chr12 | 92885510 | 92885702 | Intergenic | 559213 | 4930559C10Rik | −1.309493859 | 0.020315564 |
| chr4 | 10769994 | 10770528 | Intron | 27541 | 1700123O12Rik | −1.309872992 | 0.002814897 |
| chr3 | 104616163 | 104616552 | Intergenic | −22307 | Slc16a1 | −1.310731458 | 0.001921515 |
| chr12 | 16557996 | 16558496 | Intron | 31524 | Lpin1 | −1.311291256 | 1.57E−09 |
| chr7 | 82664656 | 82665028 | Intron | 16228 | Efl1 | −1.311960281 | 0.035276892 |
| chr16 | 29865119 | 29865672 | Intergenic | 113729 | Gm1968 | −1.313086769 | 5.14E−05 |
| chr3 | 151748572 | 151748950 | Intron | 1198 | Ifi44 | −1.313231035 | 0.044244384 |
| chr5 | 103367058 | 103367681 | Intergenic | −57823 | Ptpn13 | −1.315649849 | 2.53E−15 |
| chr2 | 93746093 | 93746983 | Intron | 75731 | Ext2 | −1.316396099 | 0.034400784 |
| chr2 | 93746116 | 93746634 | Intron | 76193 | Ext2 | −1.317084207 | 0.000746432 |
| chr14 | 101804609 | 101805787 | Intron | −35425 | Lmo7 | −1.31715083 | 0.030966175 |
| chr11 | 31999910 | 32000173 | Promoter-TSS | −378 | Nsg2 | −1.318068438 | 0.015592752 |
| chr9 | 15501352 | 15501642 | Intergenic | −3998 | Smco4 | −1.320237159 | 0.038016214 |
| chr18 | 5397366 | 5397690 | Intergenic | −63089 | Zfp438 | −1.321911332 | 0.008155426 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr15 | 101479256 | 101479599 | Exon | 5949 | Krt86 | −1.322136844 | 0.048476853 |
| chr17 | 73540835 | 73541373 | Intron | −141808 | Capn13 | −1.322775728 | 0.002070737 |
| chr10 | 17347746 | 17348257 | Intergenic | −252219 | Gm20125 | −1.323078301 | 0.026421512 |
| chr6 | 116673439 | 116674255 | Promoter-TSS | −11 | Rassf4 | −1.323912089 | 0.000195999 |
| chr9 | 97310220 | 97310657 | Intergenic | 59520 | Trim42 | −1.324323519 | 0.004504475 |
| chr6 | 17851232 | 17851588 | Intron | 102240 | St7 | −1.325457643 | 0.040162612 |
| chr17 | 8506126 | 8506350 | Intergenic | −20563 | Pde10a | −1.32587235 | 0.014335401 |
| chr17 | 34304851 | 34305072 | Promoter-TSS | −906 | H2-Eb1 | −1.327002856 | 0.033546698 |
| chrX | 159021404 | 159021948 | Intergenic | −234106 | Rps6ka3 | −1.327501839 | 0.000312373 |
| chr18 | 7404844 | 7405311 | Intron | −107176 | Armc4 | −1.327556171 | 0.01199215 |
| chr2 | 3649125 | 3649520 | Intergenic | −64136 | Fam107b | −1.327979163 | 0.038243003 |
| chr19 | 10818542 | 10818846 | Intron | 11364 | Cd6 | −1.329505302 | 0.006400852 |
| chr1 | 159674085 | 159674602 | Intron | 150574 | Tnr | −1.329952754 | 0.001575794 |
| chr10 | 121796078 | 121796378 | Intron | 56291 | BC048403 | −1.330443972 | 0.022435249 |
| chr6 | 145992769 | 145993535 | Intergenic | 59005 | Sspn | −1.33177688 | 7.77E−10 |
| chr5 | 34224627 | 34225056 | Intron | −37131 | Mxd4 | −1.333365964 | 0.030519606 |
| chr18 | 11913497 | 11914242 | Intron | −73431 | Mir1901 | −1.334693213 | 1.35E−06 |
| chr11 | 3100119 | 3100548 | Intergenic | −23688 | Pisd-ps1 | −1.334835501 | 1.77E−07 |
| chr7 | 132317193 | 132317476 | Promoter-TSS | −179 | Chst15 | −1.335273279 | 0.033887019 |
| chr15 | 41914497 | 41914884 | Intergenic | −44970 | Abra | −1.335794375 | 0.007331461 |
| chr14 | 31570277 | 31570714 | Intron | 6888 | Colq | −1.337679399 | 0.00084706 |
| chr14 | 30184464 | 30184997 | Intron | 162097 | Chdh | −1.339190479 | 1.30E−06 |
| chr3 | 149117144 | 149117907 | Intergenic | −157212 | Gm1653 | −1.340393041 | 0.021142922 |
| chr5 | 149439525 | 149439995 | Promoter-TSS | 100 | Tex26 | −1.34105851 | 0.021648726 |
| chr16 | 97357193 | 97357518 | Intron | 627 | Bace2 | −1.342339793 | 0.046214456 |
| chr12 | 79550248 | 79550635 | Intron | 253090 | Rad51b | −1.3437959 | 0.007201184 |
| chr1 | 39196790 | 39197263 | Intron | 2754 | Npas2 | −1.345596525 | 1.67E−06 |
| chr12 | 40243841 | 40244126 | Intergenic | 20619 | Gm7008 | −1.346073185 | 0.007983729 |
| chr12 | 90781425 | 90781855 | Intergenic | −42603 | Dio2 | −1.347547316 | 0.035483715 |
| chr7 | 122932219 | 122932585 | Intergenic | 38057 | 4930413G21Rik | −1.348424517 | 0.026442131 |
| chr11 | 6006120 | 6006595 | Intron | 50599 | Ykt6 | −1.34884666 | 1.89E−06 |
| chr10 | 18193223 | 18193702 | Intron | 17428 | Ect2l | −1.350348125 | 8.11E−07 |
| chr3 | 144432032 | 144432559 | 3′ UTR | 137921 | Hs2st1 | −1.350548482 | 1.44E−05 |
| chr11 | 90238676 | 90239013 | Intergenic | −10632 | Mmd | −1.350838873 | 0.022997705 |
| chr13 | 95470105 | 95470463 | Intergenic | 8371 | S100z | −1.351208562 | 0.007257003 |
| chr8 | 81611240 | 81611512 | Intron | 268814 | Inpp4b | −1.351437454 | 0.021900508 |
| chr5 | 89198568 | 89198828 | Intron | 259200 | Gc | −1.352084615 | 0.028052079 |
| chr5 | 14929130 | 14929307 | Intergenic | 9257 | Speer4e | −1.352136778 | 0.026442131 |
| chr17 | 18597203 | 18597792 | Exon | 15770 | Vmn2r96 | −1.3528919 | 0.000144095 |
| chr4 | 136106756 | 136107157 | Intergenic | −36866 | Id3 | −1.353459419 | 2.18E−08 |
| chr17 | 32023207 | 32023476 | Intron | 11167 | Hsf2bp | −1.354528134 | 0.006753985 |
| chr10 | 119295827 | 119296187 | Intergenic | −24227 | 4930477N07Rik | −1.354912665 | 0.013016325 |
| chr17 | 23620296 | 23620768 | Intergenic | 19706 | Zscan10 | −1.355187099 | 1.22E−07 |
| chr1 | 128793958 | 128794218 | Intergenic | −201789 | Cxcr4 | −1.35588488 | 0.005110295 |
| chr11 | 88595646 | 88595938 | Intron | −23459 | 0610039H22Rik | −1.357322444 | 0.004764076 |
| chr4 | 45513905 | 45514311 | Intron | 16710 | Shb | −1.360281894 | 0.013131239 |
| chr12 | 69101812 | 69102508 | Intergenic | 57026 | Rps29 | −1.360594717 | 1.69E−06 |
| chr10 | 56378405 | 56378829 | Intron | 1317 | Gja1 | −1.360797419 | 0.015608066 |
| chr5 | 143630731 | 143631134 | Intron | 8485 | Cyth3 | −1.361576452 | 0.000746432 |
| chr3 | 94649099 | 94649526 | Intron | 9560 | Tuft1 | −1.362870748 | 0.004172233 |
| chr5 | 92336771 | 92337444 | Intron | 5280 | Art3 | −1.363201526 | 0.000636567 |
| chrX | 6399602 | 6400158 | Promoter-TSS | −152 | Shroom4 | −1.367331496 | 0.034133343 |
| chr15 | 83113035 | 83113185 | Intron | 9691 | Rrp7a | −1.368650108 | 0.030499164 |
| chr12 | 40381209 | 40381558 | Intron | 64407 | Zfp277 | −1.368652986 | 0.007535116 |
| chr1 | 89092489 | 89093073 | Intron | 22319 | Sh3bp4 | −1.369885841 | 0.035781518 |
| chr12 | 17724427 | 17725097 | Intron | 33948 | Hpcal1 | −1.370344695 | 1.71E−11 |
| chr14 | 53283446 | 53283717 | Intergenic | −787886 | Olfr1507 | −1.370747892 | 0.036554326 |
| chr14 | 20938432 | 20938897 | Intron | 9231 | Vcl | −1.37078345 | 0.003447517 |
| chr2 | 77148228 | 77148620 | Intron | 22211 | Ccdc141 | −1.374444915 | 7.07E−06 |
| chr6 | 59315953 | 59316258 | Intergenic | 107235 | Tigd2 | −1.375700952 | 0.004650323 |
| chr7 | 127628753 | 127629011 | Intergenic | −14449 | Zfp629 | −1.377215397 | 0.012533162 |
| chr12 | 69824989 | 69825449 | Intron | −18467 | 4931403G20Rik | −1.380743424 | 0.029238376 |
| chr6 | 100363922 | 100364048 | Intergenic | −76529 | Rybp | −1.381465948 | 0.047979754 |
| chr12 | 51543563 | 51543918 | Intergenic | −49601 | Coch | −1.381574621 | 0.006530241 |
| chr1 | 80153263 | 80153655 | Intergenic | 60485 | Fam124b | −1.381716937 | 0.040841883 |
| chr4 | 32401472 | 32401755 | Intergenic | −15822 | Bach2 | −1.381735546 | 0.01390331 |
| chr12 | 25958589 | 25959097 | Intergenic | 251662 | Gm29687 | −1.382398572 | 1.33E−11 |
| chr17 | 79461331 | 79461987 | Intergenic | 16226 | 4930429F11Rik | −1.383135065 | 0.008338866 |
| chr2 | 163123628 | 163123913 | Intergenic | −34169 | Gtsfl1 | −1.383876298 | 0.007797322 |
| chr6 | 134148021 | 134148308 | Intron | 112464 | Etv6 | −1.385770025 | 0.000746002 |
| chr13 | 43768924 | 43769212 | Intergenic | −16044 | Cd83 | −1.385780192 | 0.042026706 |
| chr19 | 32148755 | 32149062 | Intron | −45768 | Asah2 | −1.387818386 | 0.002217271 |
| chr10 | 116746601 | 116746939 | Intergenic | 17517 | 4930579P08Rik | −1.392925544 | 0.00266453 |
| chr16 | 22428825 | 22429305 | Intron | 10505 | Etv5 | −1.39322372 | 0.049620307 |
| chr8 | 13987139 | 13987443 | Intron | 1201 | Gm5907 | −1.393278497 | 0.013360209 |
| chr5 | 150859554 | 150860086 | Intergenic | −92787 | Kl | −1.394306374 | 0.000541165 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr3 | 96309523 | 96309752 | Intergenic | −15668 | Fcgr1 | −1.395340545 | 0.011836845 |
| chr3 | 138423664 | 138423869 | Intron | 8269 | Adh4 | −1.395835948 | 0.001401308 |
| chr13 | 112388698 | 112389102 | Intergenic | −75170 | Il6st | −1.397505102 | 0.001844861 |
| chr15 | 91609790 | 91610191 | Intergenic | −36729 | Slc2a13 | −1.398677685 | 0.027787341 |
| chr16 | 25248776 | 25249220 | Intergenic | −37819 | Tprg | −1.401225387 | 0.000890103 |
| chr6 | 100402573 | 100403026 | Intergenic | −115441 | Rybp | −1.401512312 | 0.002720972 |
| chr11 | 6704908 | 6705186 | Intergenic | 14990 | Gm11981 | −1.401565188 | 0.031274687 |
| chr4 | 6843780 | 6844637 | Intron | 146515 | Tox | −1.403569052 | 2.69E−08 |
| chr7 | 24461438 | 24461665 | Promoter-TSS | −932 | Plaur | −1.404403636 | 0.000210179 |
| chr3 | 84569459 | 84569805 | Intron | 12993 | Arfip1 | −1.406149807 | 0.031527524 |
| chr4 | 95448831 | 95449209 | Intergenic | −108487 | Fggy | −1.406472489 | 0.003005367 |
| chr6 | 67317901 | 67318136 | Intron | 21676 | Il12rb2 | −1.406957212 | 0.004861702 |
| chr6 | 134273902 | 134274300 | Intergenic | −122228 | Bcl2l14 | −1.407305917 | 0.000564737 |
| chr18 | 14667087 | 14667487 | Intron | 15627 | Ss18 | −1.408829939 | 3.74E−10 |
| chr1 | 91685076 | 91685391 | Intergenic | −116228 | Twist2 | −1.409806157 | 0.015660336 |
| chr9 | 92541856 | 92543018 | Non-Coding | 214 | Plod2 | −1.410638287 | 1.71E−10 |
| chr4 | 6934927 | 6935340 | Intron | 55590 | Tox | −1.413578617 | 5.01E−05 |
| chr17 | 88274334 | 88274762 | Intergenic | 149036 | Gm4832 | −1.414104733 | 0.000135578 |
| chr1 | 20743841 | 20744327 | Intergenic | 13179 | Il17a | −1.414371454 | 1.92E−07 |
| chr8 | 81558485 | 81559056 | Intron | 216208 | Inpp4b | −1.414552077 | 2.45E−12 |
| chr12 | 61994370 | 61994709 | Intergenic | 471372 | Lrfn5 | −1.416045492 | 0.020056938 |
| chr14 | 70962071 | 70962321 | Intron | 72089 | Gfra2 | −1.416512191 | 0.024451963 |
| chr5 | 137072039 | 137072505 | Promoter-TSS | 0 | Serpine1 | −1.416884408 | 2.15E−05 |
| chr9 | 115703783 | 115704264 | Intergenic | −205432 | Gadl1 | −1.417697665 | 0.00021257 |
| chr2 | 26623017 | 26623299 | Intergenic | −5299 | Fam69b | −1.419012669 | 0.024886986 |
| chr4 | 97996045 | 97996694 | Intron | 218743 | Nfia | −1.419123746 | 0.001398487 |
| chr13 | 41682816 | 41683179 | Intergenic | 32235 | Gm5082 | −1.419187237 | 0.018932329 |
| chr13 | 28502143 | 28502594 | Intron | 208505 | Mir6368 | −1.419598428 | 6.76E−05 |
| chr17 | 83365209 | 83365444 | Intron | 14395 | Eml4 | −1.419752287 | 0.008271741 |
| chr12 | 15717406 | 15717731 | Intergenic | 83533 | Mir6387 | −1.420475053 | 0.007449768 |
| chr5 | 22587370 | 22587901 | Intergenic | 37222 | 6030443J06Rik | −1.421303042 | 0.032472211 |
| chr19 | 55408529 | 55408894 | Intron | 92654 | Vti1a | −1.421861946 | 0.017056219 |
| chr1 | 78422651 | 78422946 | Intron | 66099 | Farsb | −1.422931446 | 0.010942106 |
| chr5 | 150259609 | 150260094 | Promoter-TSS | −79 | Fry | −1.423165942 | 0.00051647 |
| chr6 | 119635605 | 119636027 | Intron | −91469 | Wnt5b | −1.424511783 | 0.000224166 |
| chr6 | 134183750 | 134184417 | Intron | 148383 | Etv6 | −1.425810998 | 1.22E−05 |
| chr7 | 96817051 | 96817641 | Intron | −15797 | Gm15413 | −1.427364324 | 0.00029748 |
| chr4 | 6882666 | 6883025 | Intron | 107878 | Tox | −1.427792356 | 5.26E−05 |
| chr18 | 46380974 | 46381398 | Intergenic | −69258 | Ccdc112 | −1.430100702 | 0.004011754 |
| chr1 | 136858698 | 136859094 | Intron | 94734 | Nr5a2 | −1.430214764 | 0.008996106 |
| chr19 | 5364163 | 5364378 | TTS | 2093 | Banf1 | −1.433704662 | 0.005730797 |
| chr11 | 75563944 | 75564529 | Intron | 12807 | Mir3971 | −1.434481467 | 0.048388191 |
| chr15 | 53266913 | 53267856 | Intron | 78799 | Ext1 | −1.434483764 | 4.78E−07 |
| chr6 | 134366018 | 134366217 | Intergenic | −30212 | Bcl2l14 | −1.436096645 | 0.002812287 |
| chr19 | 47915360 | 47915536 | Intron | 3851 | Itprip | −1.438220634 | 0.019180335 |
| chr15 | 89282584 | 89282839 | Intron | 23021 | Mir6959 | −1.43918798 | 0.016927476 |
| chr9 | 31271188 | 31271685 | Promoter-TSS | 35 | Gm7244 | −1.439965348 | 8.30E−05 |
| chr6 | 146959876 | 146960466 | Intron | −5750 | 1700034J05Rik | −1.441170934 | 1.24E−07 |
| chr8 | 124681448 | 124681799 | Intron | −18254 | 2310022B05Rik | −1.441599503 | 0.034213343 |
| chr10 | 67840759 | 67841311 | Intergenic | 71627 | Zfp365 | −1.441696503 | 0.000279682 |
| chr6 | 100410107 | 100410626 | Intergenic | −117034 | 1700049E22Rik | −1.441699356 | 1.23E−06 |
| chr10 | 117526662 | 117526983 | Intergenic | −102678 | Cpm | −1.443429903 | 0.00011522 |
| chr4 | 102967753 | 102968213 | Non-Coding | −18396 | Tctex1d1 | −1.444088174 | 0.001921515 |
| chr5 | 100912366 | 100912798 | Intergenic | 66353 | Agpat9 | −1.444753951 | 1.03E−11 |
| chr2 | 18518845 | 18519508 | Intergenic | −126346 | Dnajc1 | −1.445038219 | 0.000144095 |
| chr19 | 17268789 | 17268968 | Intergenic | 70627 | Gcnt1 | −1.44557466 | 0.004436451 |
| chr8 | 83200723 | 83201192 | Intron | 35605 | Tbc1d9 | −1.445861606 | 0.021558192 |
| chr16 | 30678762 | 30679234 | Intergenic | 79275 | Fam43a | −1.445879505 | 0.016539327 |
| chr8 | 108759600 | 108759999 | Intron | 45155 | Zfhx3 | −1.446211679 | 0.027202365 |
| chr2 | 38546224 | 38546721 | Intron | 34596 | Nek6 | −1.446335629 | 0.046101938 |
| chr10 | 54254859 | 54255525 | Intergenic | 179270 | Gm16998 | −1.447468624 | 0.002277014 |
| chr1 | 127380855 | 127381344 | Intron | 176113 | Mgat5 | −1.447618265 | 0.001168637 |
| chr5 | 40953200 | 40953228 | Intergenic | 754293 | Rab28 | −1.447839864 | 0.048304219 |
| chr1 | 156985943 | 156986603 | Intergenic | −46647 | Ralgps2 | −1.449199905 | 0.000196794 |
| chr6 | 73279691 | 73280057 | Intergenic | 31369 | Suclg1 | −1.449959042 | 0.005928238 |
| chr5 | 103404402 | 103404915 | Intergenic | −20534 | Ptpn13 | −1.450160283 | 3.27E−05 |
| chr2 | 101992590 | 101992852 | Intron | 106459 | Commd9 | −1.451752281 | 0.0237233 |
| chr15 | 53115437 | 53115870 | Intron | 230530 | Ext1 | −1.451971859 | 0.003468453 |
| chr3 | 41031428 | 41031728 | Intergenic | 51468 | Pgrmc2 | −1.454145437 | 0.031538791 |
| chr7 | 45051038 | 45051183 | Intron | 1771 | Prr12 | −1.455740613 | 0.027810021 |
| chr13 | 89889007 | 89889454 | Intron | −146718 | Vcan | −1.455897005 | 0.002163727 |
| chr9 | 70039894 | 70040408 | Intergenic | −2063 | Gcnt3 | −1.456231757 | 8.22E−06 |
| chr2 | 163130687 | 163131599 | Intergenic | −41542 | Gtsf1l | −1.459077475 | 2.10E−14 |
| chr1 | 92004138 | 92004582 | Intron | 175981 | Hdac4 | −1.459913475 | 0.00234323 |
| chr6 | 8299151 | 8299464 | Intron | 40019 | Umad1 | −1.460110196 | 0.020916187 |
| chr7 | 82773831 | 82774455 | Intron | −18499 | 4933406J10Rik | −1.460497298 | 0.000154625 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr9 | 79756111 | 79756318 | Intron | 3639 | Cox7a2 | −1.462058387 | 0.000357247 |
| chr5 | 110594541 | 110594825 | Intron | −8822 | Galnt9 | −1.462682424 | 0.005632597 |
| chr12 | 73726214 | 73726572 | Intron | 141597 | Prkch | −1.462758496 | 0.006538564 |
| chr18 | 7409916 | 7410489 | Intron | −112301 | Armc4 | −1.464177292 | 1.66E−05 |
| chr5 | 115693268 | 115693647 | Intron | 38102 | Ccdc64 | −1.464650945 | 0.010166795 |
| chr18 | 30267072 | 30267897 | Intergenic | −5412 | Pik3c3 | −1.466442837 | 1.88E−08 |
| chr9 | 67813674 | 67814171 | Intergenic | 18408 | C2cd4a | −1.467107342 | 6.64E−05 |
| chr6 | 134342773 | 134343309 | Intergenic | −53288 | Bcl2l14 | −1.468285131 | 0.000203991 |
| chr5 | 148373371 | 148373684 | Intron | 19288 | Slc7a1 | −1.471296323 | 0.007522615 |
| chr6 | 115123270 | 115123884 | Intergenic | 11258 | Gm17733 | −1.471455121 | 0.006826746 |
| chr2 | 19579261 | 19580238 | Intergenic | −25839 | 4921504E06Rik | −1.4721567 | 5.63E−08 |
| chr4 | 140832888 | 140833188 | Intron | 12740 | Padi1 | −1.47223215 | 0.007762874 |
| chr4 | 10940657 | 10941344 | Intron | 66502 | 2610301B20Rik | −1.473205699 | 4.31E−10 |
| chr5 | 20791862 | 20792114 | Intron | 90136 | Phtf2 | −1.473375063 | 0.000366808 |
| chr3 | 116892941 | 116893331 | Intron | 31456 | Frrs1 | −1.473702344 | 0.029926315 |
| chr4 | 133185144 | 133185749 | Intron | −10209 | Mir7017 | −1.474601621 | 3.46E−08 |
| chr5 | 28382348 | 28382722 | Intron | 65346 | Rbm33 | −1.479227609 | 0.001689523 |
| chr1 | 159928814 | 159929077 | Intergenic | −115435 | 4930523C07Rik | −1.480149767 | 0.023361166 |
| chr3 | 109747691 | 109748205 | Intergenic | 173941 | Vav3 | −1.481722723 | 0.046107211 |
| chr14 | 103017120 | 103017347 | Intron | 16570 | 4933432I03Rik | −1.482650656 | 0.002132644 |
| chr1 | 161436514 | 161436927 | Intergenic | 41282 | Tnfsf4 | −1.484642614 | 0.000893424 |
| chr9 | 25497345 | 25497675 | Intron | 15913 | Eepd1 | −1.486360397 | 1.92E−05 |
| chr2 | 59513523 | 59514032 | Intergenic | 29124 | Dapl1 | −1.486795957 | 1.28E−06 |
| chr15 | 50674120 | 50674615 | Intron | 214682 | Trps1 | −1.49033243 | 0.013674885 |
| chr5 | 144165758 | 144166295 | Intron | −24260 | Bhlha15 | −1.491455026 | 1.61E−05 |
| chr11 | 75472762 | 75473111 | Intergenic | 4886 | Tlcd2 | −1.491606481 | 0.000651912 |
| chr18 | 67028587 | 67029099 | Intergenic | −59455 | Gnal | −1.492303433 | 0.007449768 |
| chr12 | 35681953 | 35682440 | Intron | 4108 | 9130015A21Rik | −1.495454037 | 0.000144459 |
| chr10 | 3510500 | 3510967 | Intergenic | −29546 | Iyd | −1.496280956 | 5.38E−06 |
| chr5 | 36996534 | 36996931 | Intergenic | −7750 | Wfs1 | −1.49907079 | 0.002476506 |
| chr16 | 21694045 | 21694403 | Exon | 441 | 2510009E07Rik | −1.501894055 | 0.017975644 |
| chr11 | 99168144 | 99168443 | Intergenic | −13216 | Ccr7 | −1.502056764 | 0.02188778 |
| chr7 | 98580478 | 98580780 | Intergenic | 75940 | Emsy | −1.502353826 | 0.004739713 |
| chr19 | 30924080 | 30924578 | Intron | 6633 | Gm6642 | −1.503104852 | 1.37E−07 |
| chr6 | 144804412 | 144804706 | Intergenic | 131691 | Sox5os3 | −1.50351339 | 0.005248428 |
| chr10 | 56377082 | 56377485 | Promoter-TSS | −17 | Gja1 | −1.505925139 | 0.026115229 |
| chr8 | 64826433 | 64826820 | Intron | 23298 | Klhl2 | −1.508570044 | 0.000988349 |
| chr12 | 17750403 | 17750908 | Intron | 59841 | Hpcal1 | −1.509794285 | 6.97E−06 |
| chr3 | 138424368 | 138424491 | Intron | 8932 | Adh4 | −1.513201184 | 0.007881082 |
| chr13 | 89324172 | 89324698 | Intergenic | −216201 | Hapln1 | −1.51386342 | 0.01574138 |
| chr10 | 13446659 | 13446973 | Intron | 27580 | Phactr2 | −1.516235699 | 0.008355949 |
| chr10 | 71263941 | 71264620 | Intron | 20982 | Ube2d1 | −1.51759923 | 6.09E−08 |
| chr5 | 102481054 | 102482028 | 5' UTR | 150 | Arhgap24 | −1.522152231 | 9.85E−07 |
| chr6 | 39226281 | 39226833 | Intergenic | −19784 | Kdm7a | −1.522825362 | 0.042163953 |
| chr9 | 44905706 | 44906215 | Intergenic | 14782 | Atp5l | −1.525484418 | 0.049567114 |
| chr10 | 71363340 | 71364347 | Intron | 16080 | Ipmk | −1.526810651 | 6.38E−06 |
| chr18 | 53926755 | 53927063 | Intron | 64796 | Csnk1g3 | −1.529121912 | 0.0080472 |
| chr4 | 63939238 | 63939530 | Intergenic | −78100 | Tnfsf8 | −1.535909283 | 0.001771012 |
| chr18 | 61614549 | 61614857 | Intergenic | −24950 | Bvht | −1.536789078 | 0.011953633 |
| chr5 | 89146923 | 89147779 | Intron | 260091 | Slc4a4 | −1.536948491 | 7.22E−05 |
| chr5 | 140944640 | 140944997 | Intron | 55778 | Card11 | −1.538674941 | 0.000890103 |
| chr2 | 101819376 | 101819718 | Intron | 19433 | Prr5l | −1.539179983 | 0.002211961 |
| chr19 | 21866280 | 21866592 | Intergenic | 88096 | Tmem2 | −1.540092417 | 6.16E−05 |
| chr19 | 10813072 | 10813258 | Intron | 16893 | Cd6 | −1.542574235 | 0.001471834 |
| chr15 | 58733035 | 58733373 | Intergenic | 90223 | Tmem65 | −1.543313865 | 0.018024716 |
| chr16 | 10669031 | 10669453 | Intron | 116294 | Socs1 | −1.546108859 | 8.71E−05 |
| chr3 | 101917738 | 101918040 | Intron | 6564 | Slc22a15 | −1.548759142 | 0.042086914 |
| chr8 | 104866995 | 104867546 | Promoter-TSS | −154 | Ces2d-ps | −1.548984094 | 0.000716372 |
| chr8 | 126886716 | 126887249 | Intergenic | 58939 | Tomm20 | −1.549259072 | 0.003322675 |
| chr6 | 53709696 | 53710099 | Intergenic | 110928 | Tril | −1.551472207 | 0.004600654 |
| chr1 | 40271073 | 40271478 | Intron | 4689 | Il1r1 | −1.551671759 | 0.001129694 |
| chr5 | 64298239 | 64298759 | Intron | 68142 | Tbc1d1 | −1.554227384 | 0.026638397 |
| chr14 | 71075612 | 71076117 | Intron | −175409 | Gm4251 | −1.554630287 | 0.000649388 |
| chr12 | 35770400 | 35770986 | Intergenic | −75575 | 9130015A21Rik | −1.55670476 | 0.002061258 |
| chr13 | 89521423 | 89521947 | Intergenic | −18951 | Hapln1 | −1.557289843 | 5.21E−06 |
| chr6 | 136690094 | 136690405 | Intergenic | −28356 | Plbd1 | −1.557886229 | 0.012808764 |
| chr9 | 73806514 | 73807169 | Intron | 126726 | Unc13c | −1.560400727 | 0.031274687 |
| chr13 | 89539207 | 89539705 | Intergenic | −1180 | Hapln1 | −1.561850082 | 9.52E−05 |
| chr2 | 92627598 | 92628043 | Intergenic | 28113 | Chst1 | −1.563343687 | 4.62E−06 |
| chr16 | 94185387 | 94185854 | Intron | 100360 | Sim2 | −1.563710761 | 6.81E−08 |
| chr1 | 69681079 | 69681320 | Intron | 4761 | Ikzf2 | −1.563842696 | 0.004957594 |
| chr1 | 69683238 | 69683402 | Intron | 2640 | Ikzf2 | −1.564029985 | 0.001471679 |
| chr13 | 97902736 | 97903663 | Intron | 302966 | Arhgef28 | −1.564408222 | 6.85E−07 |
| chr18 | 69647788 | 69648233 | Intron | −277549 | Ccdc68 | −1.567331406 | 0.005021261 |
| chr9 | 88637541 | 88638016 | Intergenic | −38535 | 9430037G07Rik | −1.568798866 | 0.035522753 |
| chr10 | 91028939 | 91029395 | Intron | 53576 | Apaf1 | −1.570619471 | 4.22E−05 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr2 | 61309240 | 61309586 | Intergenic | −269173 | Tank | −1.570710658 | 0.003595173 |
| chr11 | 113536595 | 113537403 | Intron | 28816 | Slc39a11 | −1.571112524 | 2.39E−10 |
| chr7 | 115474128 | 115474438 | 3′ UTR | 327326 | Sox6 | −1.574187886 | 0.01113749 |
| chr10 | 50426360 | 50426801 | Intergenic | −166089 | Ascc3 | −1.574331824 | 0.014470606 |
| chr18 | 60382526 | 60382785 | 5′ UTR | 6626 | Iigp1 | −1.5764309 | 0.028073248 |
| chr7 | 4690378 | 4690723 | Promoter-TSS | −378 | Brsk1 | −1.576733234 | 0.039548234 |
| chr9 | 52349046 | 52349531 | Intergenic | −181177 | Zc3h12c | −1.57805402 | 3.04E−10 |
| chr5 | 20082428 | 20082836 | Intron | 175114 | Magi2 | −1.578326638 | 0.045953855 |
| chr13 | 97927637 | 97928588 | Intron | 278053 | Arhgef28 | −1.583069027 | 3.37E−12 |
| chr4 | 10875558 | 10875698 | Intron | 1130 | 2610301B20Rik | −1.5840886 | 0.006293821 |
| chr12 | 110332691 | 110333192 | Intergenic | 53711 | Dio3 | −1.585322701 | 9.76E−05 |
| chr5 | 103746634 | 103747099 | Intergenic | −7296 | Aff1 | −1.586282837 | 0.005404704 |
| chrX | 153433522 | 153434075 | Intergenic | −64434 | Ubqln2 | −1.58756533 | 0.002541787 |
| chr8 | 40598540 | 40598941 | Intron | 36052 | Mtmr7 | −1.590747901 | 0.006251066 |
| chr1 | 10229041 | 10229238 | Intron | 3531 | Arfgef1 | −1.59098081 | 0.037798268 |
| chr2 | 101979090 | 101979285 | Intron | 92925 | Commd9 | −1.591321861 | 0.001699502 |
| chr10 | 124138477 | 124138827 | Intergenic | −330422 | 4930503E24Rik | −1.592457339 | 3.41E−09 |
| chr17 | 8193594 | 8193943 | Intron | 28250 | Fgfr1op | −1.595272629 | 0.013931248 |
| chr2 | 84511520 | 84511824 | Intergenic | −4799 | Gm13710 | −1.595852363 | 0.004711794 |
| chr6 | 85075028 | 85075463 | Promoter-TSS | −896 | Npm3-ps1 | −1.599151345 | 0.014208387 |
| chr1 | 165837630 | 165837885 | Intron | 49076 | Cd247 | −1.600783398 | 4.35E−05 |
| chr12 | 35799259 | 35799687 | Intergenic | −104355 | 9130015A21Rik | −1.601831109 | 1.57E−05 |
| chr7 | 79300599 | 79301228 | Intron | 27647 | Abhd2 | −1.603929417 | 8.30E−05 |
| chr5 | 15692012 | 15692269 | Intron | 11430 | Speer4cos | −1.603975319 | 0.02803968 |
| chr9 | 114451554 | 114451983 | Intron | 44776 | Ccr4 | −1.604828298 | 0.016472909 |
| chr6 | 37055137 | 37055517 | Intron | −243966 | Ptn | −1.604948169 | 0.000189695 |
| chr1 | 40315525 | 40315832 | 3′ UTR | −8949 | Il1rl2 | −1.605339539 | 0.004316481 |
| chr16 | 36540811 | 36541206 | Intron | 21126 | Casr | −1.605838168 | 2.62E−06 |
| chrX | 100789333 | 100789738 | Intron | 12264 | Dlg3 | −1.606231302 | 0.004395144 |
| chr2 | 19540860 | 19541259 | Intron | 12851 | 4921504E06Rik | −1.610771307 | 0.033527262 |
| chr9 | 7501192 | 7501448 | Intergenic | −1022 | Mmp10 | −1.611911381 | 0.005367967 |
| chr10 | 26879040 | 26879531 | Intron | 106773 | Arhgap18 | −1.614340235 | 1.44E−06 |
| chr3 | 61368890 | 61369041 | TTS | 4459 | Rap2b | −1.615928588 | 0.010043627 |
| chr6 | 67459381 | 67459730 | Intron | 32300 | Il23r | −1.616265233 | 4.76E−05 |
| chr14 | 101594149 | 101594658 | Intron | 14788 | Tbc1d4 | −1.616642779 | 0.002000233 |
| chr4 | 129036158 | 129036354 | Intergenic | −22015 | Rnf19b | −1.617181101 | 0.022765121 |
| chr3 | 65793402 | 65793986 | Intron | 127466 | Lekr1 | −1.618979343 | 0.000299107 |
| chr14 | 62118545 | 62118932 | Intron | 174241 | Dleu7 | −1.619381026 | 0.006409847 |
| chr12 | 35578983 | 35579328 | Intergenic | −44166 | Ahr | −1.6201022 | 0.002887018 |
| chr12 | 28835769 | 28835974 | Intron | 84043 | Tssc1 | −1.625589543 | 0.01998808 |
| chr6 | 37563980 | 37564354 | Intron | 33994 | Akr1d1 | −1.626651798 | 0.000369751 |
| chr8 | 108886569 | 108887553 | Intron | −49799 | Mir3108 | −1.627868647 | 7.61E−23 |
| chr7 | 67911847 | 67912307 | Intergenic | −40180 | Igf1r | −1.631233582 | 1.67E−06 |
| chr3 | 103987997 | 103988525 | Intron | −19945 | Phtf1os | −1.632131347 | 0.023990738 |
| chr3 | 55419322 | 55419714 | Intron | −42240 | Dclk1 | −1.63267737 | 0.00016105 |
| chr11 | 88566865 | 88567401 | Intron | −52118 | 0610039H22Rik | −1.633688789 | 2.51E−08 |
| chr6 | 67483099 | 67483561 | Intron | 8525 | Il23r | −1.635597179 | 0.00039443 |
| chr7 | 113263018 | 113263458 | Intron | 55773 | Arntl | −1.635731391 | 0.004623606 |
| chr14 | 53121795 | 53122105 | Intergenic | −626255 | Olfr1507 | −1.637060826 | 9.74E−05 |
| chr10 | 96535458 | 96535772 | Intergenic | −81386 | Btg1 | −1.638337551 | 0.000892345 |
| chr18 | 57414396 | 57414770 | Intergenic | −53903 | Ctxn3 | −1.641656617 | 0.030182225 |
| chr1 | 133363333 | 133364065 | 5′ UTR | 127 | Etnk2 | −1.64337772 | 7.66E−11 |
| chr4 | 95035464 | 95035836 | Intergenic | 16572 | Jun | −1.644120438 | 0.008476617 |
| chr7 | 29615738 | 29616298 | Intergenic | −110558 | Sipa1l3 | −1.644471502 | 0.000548563 |
| chr16 | 48675480 | 48675902 | Intergenic | 96265 | Trat1 | −1.645564875 | 0.000597751 |
| chr11 | 75318643 | 75319178 | Intron | 29473 | Rpa1 | −1.651248643 | 1.79E−05 |
| chr2 | 161511854 | 161512347 | Intergenic | −403014 | Chd6 | −1.65249511 | 0.001420648 |
| chr8 | 11007074 | 11007276 | Promoter-TSS | −675 | 9530052E02Rik | −1.65318214 | 0.001164575 |
| chr5 | 15508505 | 15508607 | Intergenic | 20621 | Gm21190 | −1.658406089 | 0.007137515 |
| chr5 | 135028899 | 135029306 | Intron | 5620 | Stx1a | −1.659299035 | 0.016306545 |
| chr2 | 65214325 | 65214709 | Intron | 24109 | Cobll1 | −1.660718719 | 0.025272967 |
| chr12 | 25851599 | 25851954 | Intergenic | 358729 | Gm29687 | −1.662873797 | 0.004803839 |
| chr16 | 95869462 | 95869778 | Intron | 29093 | 1600002D24Rik | −1.66344886 | 5.19E−07 |
| chr17 | 45766851 | 45767296 | Intergenic | −33229 | 1600014C23Rik | −1.665730855 | 0.031379644 |
| chr5 | 151247134 | 151247427 | Intergenic | −57087 | Stard13 | −1.669836445 | 0.000664129 |
| chr2 | 77102571 | 77102851 | Intron | 67924 | Ccdc141 | −1.671374263 | 0.008963868 |
| chr2 | 52952299 | 52952684 | Intron | 94623 | Fmnl2 | −1.679410527 | 0.003149128 |
| chr5 | 107840554 | 107841048 | Intron | 10639 | Ube2d2b | −1.680527552 | 0.001779376 |
| chr5 | 14933849 | 14934059 | 3′ UTR | 4521 | Speer4e | −1.681204051 | 0.023230382 |
| chr2 | 145832364 | 145832799 | Intron | 46465 | Rin2 | −1.682356772 | 3.37E−07 |
| chr2 | 72183742 | 72184124 | Intron | −101704 | Map3k20 | −1.684035638 | 0.004667559 |
| chr8 | 125648916 | 125649798 | Intergenic | −20461 | Map10 | −1.684335913 | 3.04E−06 |
| chr12 | 36468269 | 36469078 | Intron | 53057 | Mir3472 | −1.686938851 | 1.18E−08 |
| chr10 | 117530697 | 117531078 | Intergenic | −98613 | Cpm | −1.689540821 | 7.77E−10 |
| chr2 | 65818438 | 65818797 | Intergenic | −27150 | Csrnp3 | −1.689584663 | 9.96E−06 |
| chr5 | 15600319 | 15600651 | Intergenic | −18614 | Speer4d | −1.691496731 | 7.19E−06 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr10 | 128940487 | 128940779 | Intron | 6820 | Itga7 | −1.693205918 | 0.003909741 |
| chr4 | 32932027 | 32932486 | Intron | −8751 | Ankrd6 | −1.694393287 | 0.009461079 |
| chr12 | 35640907 | 35641437 | Intergenic | 45132 | 9130015A21Rik | −1.694409758 | 1.48E−05 |
| chr13 | 13492141 | 13492725 | Intron | 54831 | Nid1 | −1.695423943 | 0.015407911 |
| chr3 | 37128349 | 37128637 | Intergenic | −2539 | Il2 | −1.700200509 | 0.019168253 |
| chr4 | 122939192 | 122939504 | Intergenic | 21840 | Mfsd2a | −1.700565541 | 7.55E−06 |
| chr3 | 38283596 | 38284315 | Intergenic | −75836 | 5430434I15Rik | −1.706004848 | 0.035047946 |
| chr16 | 32972572 | 32972963 | Intron | 58667 | Lrch3 | −1.709203471 | 0.002015327 |
| chr1 | 190896160 | 190896467 | Intron | 15457 | Rps6kc1 | −1.709895898 | 0.004436451 |
| chr2 | 8964998 | 8965303 | Intergenic | −224365 | 1700061F12Rik | −1.710060534 | 0.000166619 |
| chr6 | 134862707 | 134863465 | Intergenic | 24699 | Gpr19 | −1.710327685 | 1.53E−22 |
| chr3 | 41077449 | 41077850 | Intron | 5397 | Pgrmc2 | −1.712882582 | 0.002410057 |
| chr14 | 76582375 | 76582890 | Intron | −25743 | Serp2 | −1.712919769 | 1.40E−09 |
| chr9 | 69702143 | 69702622 | Intergenic | 58558 | Foxb1 | −1.713706795 | 0.000134958 |
| chr8 | 125667351 | 125667582 | Intergenic | −2352 | Map10 | −1.713776767 | 0.00338553 |
| chrX | 159899117 | 159899472 | Intron | −43399 | Sh3kbp1 | −1.716396175 | 0.001864274 |
| chr15 | 53249000 | 53249340 | Intron | 97013 | Ext1 | −1.717571622 | 0.008323645 |
| chr5 | 75791830 | 75792069 | Intergenic | 186479 | Kdr | −1.718702714 | 0.005217087 |
| chr5 | 99499470 | 99500104 | Intron | 229273 | A930011G23Rik | −1.719511389 | 3.00E−10 |
| chr13 | 46907834 | 46908206 | Intron | 21698 | Kif13a | −1.719752125 | 0.012523287 |
| chr5 | 15006825 | 15007172 | Intergenic | 26009 | Gm17019 | −1.721046943 | 0.000446051 |
| chr11 | 32020013 | 32020561 | Intron | 19010 | Nsg2 | −1.727322335 | 9.05E−05 |
| chr6 | 17498788 | 17499062 | Intron | 34968 | Met | −1.727705212 | 0.009017325 |
| chr13 | 52084077 | 52084405 | Intergenic | −12500 | 4921525O09Rik | −1.732156311 | 6.73E−05 |
| chr4 | 102711464 | 102712225 | Intergenic | −48291 | Sgip1 | −1.73392797 | 1.14E−14 |
| chr6 | 50776945 | 50777602 | Intron | 1158 | C530044C16Rik | −1.734578503 | 0.012101769 |
| chr18 | 43523409 | 43523669 | Intergenic | −85253 | Dpysl3 | −1.734907612 | 0.043597089 |
| chr8 | 8440534 | 8441225 | Intergenic | 219894 | Efnb2 | −1.735975779 | 5.58E−06 |
| chr8 | 57742043 | 57742345 | Intergenic | −89139 | Galnt7 | −1.73671414 | 0.048855299 |
| chr2 | 166264698 | 166265339 | Intergenic | −8890 | Gm11468 | −1.737452007 | 8.08E−08 |
| chr5 | 150262642 | 150262978 | Intron | 2880 | Fry | −1.737658281 | 6.46E−05 |
| chr2 | 172971929 | 172972190 | Intergenic | −7783 | Spo11 | −1.7388498 | 0.003841213 |
| chr1 | 106145601 | 106146100 | Intergenic | 25674 | Gm20753 | −1.739530493 | 8.52E−07 |
| chr2 | 84498923 | 84499245 | Intergenic | 7789 | Gm13710 | −1.740902534 | 0.000226657 |
| chr7 | 76228831 | 76229376 | Promoter-TSS | −784 | Agbl1 | −1.743534867 | 0.000970187 |
| chr1 | 39234733 | 39235337 | Intron | 40763 | Npas2 | −1.752604267 | 1.63E−06 |
| chr14 | 48225937 | 48226831 | Intron | 27668 | Gm6498 | −1.760458427 | 1.00E−22 |
| chr5 | 150223443 | 150224083 | Intergenic | −36167 | Fry | −1.763750671 | 1.10E−06 |
| chr14 | 122290456 | 122290798 | Intron | −56989 | 1700108J01Rik | −1.767156184 | 3.57E−05 |
| chr17 | 46986658 | 46986914 | Intron | 23746 | Ubr2 | −1.768473924 | 0.032781245 |
| chr16 | 95778860 | 95779698 | Intergenic | 76872 | Ets2 | −1.768694192 | 1.13E−10 |
| chr10 | 38884741 | 38885169 | Intergenic | −63161 | Rfpl4b | −1.769095737 | 2.95E−06 |
| chr10 | 95193888 | 95194329 | Intron | −48283 | Gm29684 | −1.769725639 | 5.19E−05 |
| chr16 | 84851071 | 84851400 | Intron | −15610 | Atp5j | −1.769905391 | 0.010135776 |
| chr4 | 102886966 | 102887233 | Intron | −99280 | Tctex1d1 | −1.770803856 | 0.005217087 |
| chr2 | 68296682 | 68297161 | Intron | 175060 | Stk39 | −1.771284631 | 4.55E−08 |
| chrX | 134842956 | 134843395 | Intergenic | −33954 | Armcx2 | −1.772732546 | 0.002492801 |
| chr6 | 125433637 | 125434121 | Intergenic | −53375 | Plekhg6 | −1.781286599 | 1.18E−08 |
| chr4 | 35006548 | 35006871 | Intron | −95228 | Platr9 | −1.782852048 | 0.012540267 |
| chr3 | 104797730 | 104797937 | Intron | 8799 | Rhoc | −1.783046614 | 2.97E−06 |
| chr8 | 10993589 | 10994278 | Intron | −13917 | 9530052E02Rik | −1.783872005 | 1.49E−09 |
| chr5 | 75662352 | 75662775 | Intergenic | 87572 | Kit | −1.786091972 | 8.51E−08 |
| chr5 | 67300004 | 67300609 | Intergenic | −6649 | Slc30a9 | −1.786919338 | 1.16E−05 |
| chr4 | 144986117 | 144986444 | Intron | 93143 | Dhrs3 | −1.788597014 | 1.47E−07 |
| chr7 | 96920488 | 96921108 | Intergenic | −30729 | Nars2 | −1.789471465 | 1.02E−07 |
| chr11 | 99170707 | 99171249 | Intergenic | −15901 | Ccr7 | −1.797116625 | 2.04E−06 |
| chr14 | 54296928 | 54297272 | Intergenic | −14175 | Olfr49 | −1.797610985 | 0.017042889 |
| chr12 | 40239138 | 40239555 | Intergenic | 15982 | Gm7008 | −1.798044864 | 0.022119862 |
| chr8 | 34530378 | 34530378 | Intergenic | 110084 | B930018H19Rik | −1.799302513 | 1.92E−05 |
| chr13 | 53390244 | 53390595 | Intergenic | −3270 | Gm2762 | −1.799478077 | 0.000521215 |
| chr1 | 32104145 | 32104389 | Intergenic | −68539 | Khdrbs2 | −1.803884637 | 0.01689979 |
| chr17 | 52468395 | 52469017 | Intergenic | −134003 | Kcnh8 | −1.806848198 | 3.77E−10 |
| chr2 | 65161650 | 65162088 | Intron | 76757 | Cobll1 | −1.807381497 | 0.000669409 |
| chr5 | 76931179 | 76931668 | Intron | −19988 | Paics | −1.808106692 | 0.001052924 |
| chr3 | 27652557 | 27653164 | Intron | 57579 | Fndc3b | −1.812661408 | 0.017811795 |
| chr7 | 127922639 | 127923208 | Intron | 7190 | Prss8 | −1.812845231 | 3.58E−09 |
| chr15 | 6726464 | 6726786 | Intron | 18244 | Rictor | −1.813970357 | 0.004618657 |
| chr3 | 68495361 | 68496064 | Intron | 1531 | Schip1 | −1.816630185 | 0.02034242 |
| chr2 | 27187475 | 27188023 | TTS | 22242 | Dbh | −1.817175539 | 1.32E−05 |
| chr12 | 56696854 | 56697071 | Exon | 1491 | Pax9 | −1.817437238 | 0.045831306 |
| chr7 | 49250172 | 49250240 | Intron | 4017 | Nav2 | −1.827395363 | 0.014066848 |
| chr2 | 6569193 | 6569531 | Intron | 152300 | Celf2 | −1.832544871 | 0.001555076 |
| chr5 | 15552427 | 15552682 | Intergenic | −23332 | Gm21190 | −1.834250987 | 0.001274593 |
| chr10 | 51945751 | 51946549 | Intergenic | −76352 | Vgll2 | −1.839615739 | 0.014487938 |
| chr13 | 46909043 | 46909339 | Intron | 20527 | Kif13a | −1.843406429 | 0.004873869 |
| chr13 | 44469670 | 44470173 | Intergenic | 30194 | 1700029N11Rik | −1.845142967 | 0.000567642 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr2 | 178327433 | 178327713 | Intron | 80085 | Sycp2 | −1.850078298 | 0.027957498 |
| chr13 | 117127251 | 117127763 | Intergenic | −2518 | Gm6416 | −1.856735969 | 0.018216458 |
| chr11 | 32139548 | 32139950 | Intergenic | −38521 | Gm12108 | −1.857898997 | 0.000228524 |
| chr2 | 145843280 | 145843826 | Intron | 57437 | Rin2 | −1.863208042 | 0.022914704 |
| chr2 | 173173508 | 173173717 | Intergenic | 20539 | Pck1 | −1.86788366 | 0.002532543 |
| chr8 | 35865788 | 35866493 | Non-Coding | 16817 | 5430403N17Rik | −1.870639977 | 0.013912928 |
| chr1 | 160006066 | 160006437 | Intergenic | −38129 | 4930523C07Rik | −1.872083462 | 3.02E−08 |
| chr13 | 48552230 | 48552898 | Intergenic | −14292 | Mirlet7a-1 | −1.872125102 | 4.06E−07 |
| chr5 | 149391791 | 149392384 | Intergenic | −19719 | Medag | −1.873873955 | 6.83E−10 |
| chr5 | 74051486 | 74052237 | Intron | 16550 | Usp46 | −1.874273114 | 0.010942106 |
| chr11 | 3101415 | 3102128 | Intergenic | −22250 | Pisd-ps1 | −1.877973202 | 3.57E−24 |
| chr16 | 30769066 | 30769914 | Intergenic | 169767 | Fam43a | −1.880564257 | 3.97E−15 |
| chr13 | 28551649 | 28551985 | Intron | 159056 | Mir6368 | −1.882834887 | 0.00011962 |
| chr17 | 64826939 | 64827269 | Intergenic | 8967 | 4930583I09Rik | −1.883407479 | 0.000298159 |
| chr7 | 55960477 | 55960823 | Intron | 1843 | Nipa2 | −1.883779806 | 5.81E−09 |
| chr14 | 101480584 | 101480913 | Intron | 128443 | Tbc1d4 | −1.895181095 | 5.52E−06 |
| chr4 | 99099916 | 99100342 | Intron | 20786 | Dock7 | −1.897564845 | 3.40E−05 |
| chr8 | 119569968 | 119570182 | Intron | 5125 | Hsdl1 | −1.90495045 | 0.000643376 |
| chr3 | 109732574 | 109732797 | Intergenic | 158678 | Vav3 | −1.908330618 | 0.004436451 |
| chr4 | 6870526 | 6870786 | Intron | 120067 | Tox | −1.911035035 | 3.51E−07 |
| chr10 | 121300682 | 121300936 | Intron | 10380 | Tbc1d30 | −1.915509518 | 3.77E−08 |
| chr9 | 7509720 | 7510358 | 3' UTR | 7697 | Mmp10 | −1.922894607 | 6.37E−27 |
| chr11 | 63035509 | 63036201 | Intron | −25804 | Tekt3 | −1.923973421 | 0.041069167 |
| chr3 | 108856018 | 108856257 | 3' UTR | −15635 | Stxbp3 | −1.924284977 | 0.021990457 |
| chr11 | 34101891 | 34102198 | Intergenic | 54843 | Lcp2 | −1.925661659 | 0.000875189 |
| chr8 | 56443487 | 56444113 | Intergenic | 41168 | 4930518J21Rik | −1.927099225 | 1.11E−11 |
| chr3 | 68966842 | 68967268 | Intron | 37515 | Ift80 | −1.927684555 | 5.37E−05 |
| chr7 | 64185107 | 64185643 | Promoter-TSS | −84 | Trpm1 | −1.928129842 | 1.37E−07 |
| chr18 | 52558678 | 52559332 | Intergenic | −29138 | Lox | −1.933879847 | 0.047072499 |
| chr1 | 120136052 | 120136795 | Intron | 15236 | 3110009E18Rik | −1.937214093 | 4.48E−16 |
| chr2 | 9986159 | 9986464 | Intron | 62298 | Taf3 | −1.942425297 | 0.001782167 |
| chr2 | 104525357 | 104525868 | Intergenic | −31046 | Gm13884 | −1.947059973 | 0.018908403 |
| chr5 | 15004670 | 15004898 | Intergenic | −25885 | Gm10354 | −1.947619168 | 0.000165309 |
| chr17 | 51879802 | 51880006 | Intergenic | −2823 | Gm20098 | −1.954909363 | 0.001824752 |
| chr12 | 75283184 | 75283613 | Intergenic | −24915 | Rhoj | −1.955953575 | 4.78E−06 |
| chr7 | 128622622 | 128622997 | Intron | 11444 | Inpp5f | −1.956938191 | 0.022006323 |
| chr7 | 16535761 | 16536105 | Intron | −59153 | Npas1 | −1.95820533 | 0.000556531 |
| chr18 | 43437974 | 43438447 | Promoter-TSS | 76 | Dpysl3 | −1.960911095 | 0.001073816 |
| chr2 | 145730283 | 145730745 | Intron | 29319 | BC039771 | −1.962794454 | 0.002279627 |
| chr6 | 100479490 | 100479899 | Intergenic | −47706 | 1700049E22Rik | −1.963509888 | 3.62E−05 |
| chr16 | 30771420 | 30771911 | Intergenic | 171942 | Fam43a | −1.965883563 | 2.28E−06 |
| chr4 | 16739588 | 16740105 | Intergenic | 575736 | A530072M11Rik | −1.971214946 | 6.90E−09 |
| chr5 | 150406688 | 150407263 | Intron | 95244 | Gm5 | −1.977555121 | 7.07E−06 |
| chr3 | 135513299 | 135513646 | Intron | 27861 | Manba | −1.985204823 | 1.54E−11 |
| chr9 | 43261893 | 43262278 | Intron | 2206 | D630033O11Rik | −1.986945291 | 0.000802064 |
| chr9 | 94945622 | 94946183 | Intron | 194079 | Mir7656 | −1.986961711 | 0.000593185 |
| chr9 | 51103354 | 51103612 | Promoter-TSS | 162 | Mir34b | −1.993241363 | 0.028763021 |
| chr4 | 6940822 | 6941366 | Intron | 49629 | Tox | −1.998592058 | 1.42E−06 |
| chr8 | 104886364 | 104886906 | Intergenic | 19211 | Ces2d-ps | −2.000243581 | 2.54E−12 |
| chr5 | 15610822 | 15611155 | Intergenic | −8111 | Speer4d | −2.005813776 | 8.14E−05 |
| chr18 | 65322115 | 65322512 | Intron | 71575 | Alpk2 | −2.010459048 | 5.89E−05 |
| chr7 | 115494644 | 115495351 | Intron | 306612 | Sox6 | −2.013862821 | 4.75E−11 |
| chr3 | 146004688 | 146005226 | Intron | 17087 | Syde2 | −2.01503129 | 8.15E−06 |
| chr7 | 133734332 | 133734789 | Intron | 25227 | Bccip | −2.022369011 | 0.003296773 |
| chr6 | 83193506 | 83193918 | Exon | 7766 | Dctn1 | −2.029010982 | 5.48E−05 |
| chr5 | 86783086 | 86783503 | Intergenic | −20972 | Ythdc1 | −2.036335215 | 8.49E−08 |
| chr4 | 56070509 | 56070916 | Intergenic | −538237 | Klf4 | −2.045116287 | 0.001488476 |
| chr14 | 53039398 | 53039817 | Intergenic | −543912 | Olfr1507 | −2.046208939 | 4.49E−10 |
| chr13 | 60842762 | 60843267 | Intron | 21402 | 4930486L24Rik | −2.047388439 | 0.012837081 |
| chr11 | 60707531 | 60708104 | Intron | 8127 | Llgl1 | −2.048688837 | 0.018260539 |
| chr8 | 81562447 | 81562694 | Intron | 220008 | Inpp4b | −2.049061551 | 0.000151395 |
| chr19 | 32925585 | 32926102 | Intergenic | 168266 | Pten | −2.052163838 | 0.042342942 |
| chr2 | 4380420 | 4380756 | Intron | −20388 | Frmd4a | −2.052841052 | 4.06E−05 |
| chrX | 106043846 | 106044396 | Intron | 16897 | Atp7a | −2.059543124 | 0.002603336 |
| chr5 | 75667221 | 75667457 | Intergenic | 92348 | Kit | −2.070098993 | 7.84E−05 |
| chr1 | 151177183 | 151178256 | Intergenic | 39685 | C730036E19Rik | −2.086072024 | 7.07E−35 |
| chr10 | 13056886 | 13057397 | Intergenic | −33647 | Plagl1 | −2.094085962 | 1.11E−22 |
| chr12 | 28834123 | 28834792 | Intron | 82629 | Tssc1 | −2.098267553 | 5.17E−09 |
| chr4 | 63939640 | 63939885 | Intergenic | −78478 | Tnfsf8 | −2.10893011 | 2.27E−05 |
| chr10 | 68673539 | 68673984 | Intergenic | −49985 | Tmem26 | −2.109913722 | 7.10E−12 |
| chr11 | 8920854 | 8921388 | Intergenic | 90070 | Hus1 | −2.118157782 | 1.38E−05 |
| chr6 | 135074456 | 135074912 | Intron | 9022 | Gprc5a | −2.130271997 | 0.020430331 |
| chr4 | 150059780 | 150060253 | Intergenic | −8438 | Mir34a | −2.145360149 | 0.000110537 |
| chr18 | 16822069 | 16822286 | Non-Coding | 5770 | Gm15328 | −2.151214264 | 0.021869741 |
| chr5 | 64280178 | 64280493 | Intron | 49978 | Tbc1d1 | −2.159022841 | 0.024450759 |
| chr4 | 82755603 | 82755939 | Intergenic | 103890 | Zdhhc21 | −2.161171723 | 3.53E−06 |

TABLE 5-continued

Tox KO data: non-coding genomic locations epigenetically changed by Tox in an exhaustion specific manner

| Chromosome | Start | End | Annotation | Distance to TSS | Proximal Gene ID | Log2 Fold Change | Adjusted p-value |
|---|---|---|---|---|---|---|---|
| chr15 | 53140360 | 53140737 | Intron | 205635 | Ext1 | −2.177444396 | 1.24E−06 |
| chr14 | 22929550 | 22930064 | Intron | 164764 | Gm10248 | −2.183283927 | 0.03207167 |
| chr4 | 6869461 | 6869667 | Intron | 121159 | Tox | −2.188370995 | 0.003478602 |
| chr6 | 67105304 | 67105734 | Intergenic | −68112 | Gadd45a | −2.196702258 | 3.09E−06 |
| chr7 | 116432857 | 116433220 | Intron | 10420 | Pik3c2a | −2.198877955 | 0.000175201 |
| chr13 | 73685546 | 73685847 | Intron | −7673 | Slc6a18 | −2.213352335 | 6.77E−07 |
| chr19 | 38387127 | 38387741 | Intergenic | −8546 | Slc35g1 | −2.220669226 | 0.000556531 |
| chr7 | 49429017 | 49429225 | Intron | 182932 | Nav2 | −2.226913999 | 0.00631031 |
| chr3 | 55415683 | 55416005 | Intron | −45914 | Dclk1 | −2.237546828 | 4.34E−06 |
| chr19 | 21820182 | 21820508 | Intron | 42005 | Tmem2 | −2.239408942 | 0.020242255 |
| chr2 | 6622112 | 6622521 | Intron | 99346 | Celf2 | −2.244637947 | 5.75E−05 |
| chr6 | 61225439 | 61225722 | Intron | −44770 | A730020E08Rik | −2.249804351 | 9.12E−05 |
| chr3 | 62962506 | 62962922 | Intergenic | −332721 | Mme | −2.256096339 | 0.031310596 |
| chr8 | 125671334 | 125671672 | Exon | 1685 | Map10 | −2.257334114 | 3.44E−05 |
| chr6 | 137316391 | 137316725 | Intron | 64259 | Ptpro | −2.262194474 | 0.00034469 |
| chr15 | 73268260 | 73268612 | Intron | −13554 | Mir151 | −2.265926291 | 3.29E−06 |
| chr17 | 49661320 | 49661999 | Intron | 46487 | Kif6 | −2.267996964 | 0.005021261 |
| chr18 | 60375769 | 60376101 | Promoter-TSS | −94 | Iigp1 | −2.282508783 | 7.89E−05 |
| chr2 | 75147977 | 75148347 | Intergenic | 296017 | 9430019J16Rik | −2.285968211 | 0.000165733 |
| chr13 | 108714118 | 108714431 | Intron | 60097 | Pde4d | −2.290071942 | 0.04297038 |
| chr15 | 94255031 | 94255426 | Intron | 8051 | D630010B17Rik | −2.291976426 | 6.55E−05 |
| chr11 | 22342747 | 22343467 | Intergenic | −56312 | Ehbp1 | −2.305151939 | 0.01557413 |
| chr19 | 17011239 | 17011898 | Intron | 55450 | Prune2 | −2.315525181 | 0.017534973 |
| chr3 | 138334276 | 138334786 | Intergenic | 21245 | Adh6a | −2.319406139 | 5.15E−12 |
| chr12 | 20699436 | 20700121 | Intergenic | 116001 | 1700030C10Rik | −2.323119679 | 4.38E−08 |
| chr16 | 76142913 | 76143480 | Intron | 20583 | 4930578N18Rik | −2.334983435 | 1.20E−08 |
| chr5 | 15680623 | 15680871 | Promoter-TSS | 37 | Speer4cos | −2.33853039 | 4.33E−05 |
| chr1 | 36130214 | 36130603 | Intergenic | 13905 | Mir6897 | −2.354788463 | 0.029113064 |
| chr7 | 96707158 | 96707401 | Intron | 94270 | Gm15413 | −2.357095205 | 4.22E−05 |
| chr7 | 25386128 | 25386666 | TTS | 3715 | Lipe | −2.365627853 | 0.001566851 |
| chr9 | 63793766 | 63793989 | Intergenic | −35883 | Smad3 | −2.370077637 | 0.033357013 |
| chr10 | 61599617 | 61599880 | Intron | 4264 | Npffr1 | −2.381206649 | 1.26E−05 |
| chr16 | 24539055 | 24539403 | Intron | 9915 | Morf4l1-ps1 | −2.394791072 | 1.55E−06 |
| chr14 | 27956696 | 27957196 | Intron | 334539 | Erc2 | −2.399224748 | 0.018219288 |
| chr3 | 52651957 | 52652286 | Intergenic | −87603 | Gm2447 | −2.400650501 | 0.034366911 |
| chr15 | 25740244 | 25740684 | Intron | −102834 | Fam134b | −2.412124357 | 7.39E−08 |
| chr1 | 20740501 | 20740901 | Intergenic | 9796 | Il17a | −2.43762165 | 3.01E−08 |
| chr10 | 13059981 | 13060496 | Intergenic | −30550 | Plagl1 | −2.447142448 | 5.35E−19 |
| chr10 | 48540681 | 48541175 | Intergenic | 554915 | C130030K03Rik | −2.450031251 | 0.031152969 |
| chr5 | 20377328 | 20377921 | Intron | 470106 | Magi2 | −2.451110627 | 1.70E−11 |
| chr10 | 68354701 | 68354997 | Intergenic | −33707 | 4930545H06Rik | −2.466736202 | 0.012743816 |
| chr2 | 4401181 | 4401641 | 5′ UTR | 435 | Frmd4a | −2.467524016 | 6.95E−05 |
| chr11 | 106957436 | 106957796 | Intergenic | −36901 | Smurf2 | −2.475336282 | 0.047484622 |
| chr5 | 75640595 | 75640990 | Exon | 65801 | Kit | −2.512599357 | 4.19E−07 |
| chr13 | 110563976 | 110564354 | Intergenic | 169121 | Plk2 | −2.557962144 | 2.20E−12 |
| chr5 | 15482937 | 15483102 | Intergenic | 46203 | Gm21190 | −2.580972499 | 1.19E−05 |
| chr10 | 68356153 | 68356440 | Intergenic | −35154 | 4930545H06Rik | −2.600316852 | 8.56E−08 |
| chr2 | 168115043 | 168115291 | Intergenic | 34163 | Pard6b | −2.620809412 | 0.045624503 |
| chr15 | 76565886 | 76566232 | Intergenic | −10300 | Adck5 | −2.632858053 | 2.71E−06 |
| chr4 | 101871028 | 101871594 | Intergenic | 22478 | C130073F10Rik | −2.686808845 | 6.09E−08 |
| chr8 | 33435169 | 33435621 | Intergenic | −48916 | Hmgb1-rs17 | −2.68761644 | 0.004753106 |
| chr8 | 45439145 | 45439496 | Intergenic | −28781 | Tlr3 | −2.710401187 | 0.037790688 |
| chr5 | 96824852 | 96825273 | Intron | 31677 | Anxa3 | −2.726473564 | 2.05E−07 |
| chr11 | 96413614 | 96414193 | Intergenic | 48145 | Hoxb1 | −2.762257759 | 0.006480842 |
| chr1 | 164224369 | 164224934 | Intergenic | −24395 | Slc19a2 | −2.766334031 | 9.72E−16 |
| chr12 | 54774769 | 54775141 | Intron | 20707 | Snx6 | −2.81725024 | 3.62E−05 |
| chr14 | 48427420 | 48427858 | Intergenic | −18484 | Tmem260 | −2.865224923 | 1.29E−06 |
| chr5 | 89044829 | 89045151 | Intron | 157730 | Slc4a4 | −2.900861959 | 5.81E−10 |
| chr18 | 60273243 | 60273624 | Promoter-TSS | −166 | Gm4841 | −2.934128487 | 5.02E−06 |
| chr1 | 133763300 | 133763607 | Intergenic | −9706 | Atp2b4 | −2.94565942 | 3.84E−15 |
| chr1 | 107533669 | 107534059 | Intron | 4861 | Serpinb10 | −2.957440962 | 9.21E−08 |
| chr3 | 144996720 | 144997055 | Intergenic | −21842 | Clca4a | −3.01552193 | 0.035402147 |
| chr2 | 154334023 | 154354488 | Intron | 18464 | Cdk5rap1 | −3.04142506 | 4.51E−17 |
| chr7 | 62204012 | 62204259 | Intergenic | −118825 | Mir344i | −3.072712608 | 0.035662682 |
| chr4 | 100286014 | 100286569 | Intron | 190500 | Ror1 | −3.204109984 | 0.015016388 |
| chr1 | 108040935 | 108041202 | Intergenic | 123809 | D830032E09Rik | −3.342536211 | 1.86E−09 |
| chr12 | 86999979 | 87000390 | Intergenic | −11508 | Zdhhc22 | −3.347609246 | 0.049409459 |
| chr12 | 35294633 | 35295088 | Intergenic | 240129 | Ahr | −3.471801772 | 0.005140677 |
| chr16 | 30500199 | 30500526 | Intergenic | 50216 | Tmem44 | −3.47917482 | 0.040593975 |
| chr7 | 49335123 | 49335417 | Intron | 89081 | Nav2 | −3.578803837 | 8.25E−08 |
| chr15 | 79878804 | 79879067 | Intergenic | −13473 | Apobec3 | −4.09890424 | 0.040014386 |
| chr12 | 51735797 | 51736099 | Intron | −44034 | Strn3 | −4.13156699 | 0.030166715 |
| chr8 | 79227328 | 79227526 | Intron | 21156 | 1700011L22Rik | −4.138818645 | 0.033483578 |
| chr18 | 10290345 | 10290678 | Intergenic | −34668 | Greb1l | −4.253918967 | 0.027899313 |
| chr8 | 85132470 | 85132933 | Intergenic | −9606 | Zfp791 | −4.446755577 | 5.72E−14 |
| chr9 | 21791858 | 21792214 | Intron | 6510 | Kank2 | −4.842438769 | 0.005483251 |

TABLE 5-continued

| | | | Tox KO data: non-coding genomic locations epigenetically changed by Tox in an exhaustion specific manner | | | | |
|---|---|---|---|---|---|---|---|
| Chromosome | Start | End | Annotation | Distance to TSS | Proximal Gene ID | Log2 Fold Change | Adjusted p-value |
| chr6 | 119021188 | 119021547 | Intron | 87128 | Cacna1c | −4.928201788 | 0.006713317 |
| chr6 | 17211359 | 17211727 | Intergenic | 13436 | D830026I12Rik | −5.023431444 | 0.00297938 |
| chr6 | 134861551 | 134861828 | Intergenic | 26096 | Gpr19 | −5.37646787 | 4.62E−19 |
| chr4 | 6991166 | 6991492 | Promoter-TSS | −606 | Tox | −6.628180631 | 1.01E−13 |
| chr4 | 6990388 | 6991106 | Promoter-TSS | −24 | Tox | −8.588297015 | 2.69E−13 |

TABLE 6

| | | | ATAC-Seq of Tox vs. control GFP RV transduced in vitro activated CD8+ T cells | | | | |
|---|---|---|---|---|---|---|---|
| Chromosome | Start | End | Annotation | Distance to TSS | Proximal Gene ID | Log2 Fold Change | Adjusted p-value |
| chr8 | 86852633 | 86852864 | Intron | 32510 | N4bp1 | 1.458098792 | 0.000308513 |
| chr6 | 90391699 | 90392206 | Intron | 22458 | Zxdc | 1.378598783 | 0.000551207 |
| chr8 | 70339072 | 70339269 | Exon | 9405 | Gdf1 | 1.355034493 | 0.012060088 |
| chr18 | 55409385 | 55409746 | Intergenic | −419385 | Zfp608 | 1.297190262 | 0.00021212 |
| chr8 | 104427499 | 104427962 | Intron | 15317 | Dync1li2 | 1.279367435 | 0.000312533 |
| chr17 | 79616621 | 79616884 | Intron | 1852 | Rmdn2 | 1.278242709 | 0.008752207 |
| chr8 | 125648937 | 125649412 | Intergenic | −20644 | Map10 | 1.273934088 | 0.003081353 |
| chr8 | 70338714 | 70338959 | Intron | 9071 | Gdf1 | 1.263236934 | 0.008832549 |
| chr1 | 94074650 | 94075183 | Intergenic | −22363 | Pdcd1 | 1.201070984 | 3.75E−05 |
| chr2 | 144167119 | 144167825 | Intergenic | 21818 | Gm5535 | 1.175479965 | 1.10E−09 |
| chr11 | 111055279 | 111055661 | Intergenic | −10694 | Kcnj2 | 1.171436518 | 0.00064691 |
| chr5 | 146298815 | 146299130 | Intron | 67297 | Cdk8 | 1.161440103 | 0.010235572 |
| chr16 | 93392044 | 93392544 | Intergenic | 22574 | Mir802 | 1.158766161 | 9.78E−07 |
| chr10 | 63634013 | 63634213 | Intron | 176602 | Ctnna3 | 1.151607614 | 0.02919031 |
| chr3 | 100438539 | 100438759 | TTS | 12244 | 4930406D18Rik | 1.14654207 | 0.000409252 |
| chr2 | 89930136 | 89930539 | Exon | 526 | Olfr1258 | 1.134428469 | 0.027837442 |
| chr2 | 35996908 | 35997133 | Intergenic | −17396 | Ttll11 | 1.123772972 | 0.007762565 |
| chr14 | 76202569 | 76202907 | Intergenic | 91847 | Nufip1 | 1.120007012 | 0.000827133 |
| chr11 | 111053939 | 111054186 | Intergenic | −12102 | Kcnj2 | 1.116948724 | 0.001475821 |
| chr6 | 125240721 | 125240893 | TTS | −3780 | Cd27 | 1.112542994 | 0.007707415 |
| chr13 | 52551262 | 52551674 | Intergenic | −20632 | Diras2 | 1.112284629 | 0.013006851 |
| chr2 | 3789660 | 3789949 | Intergenic | 76346 | Fam107b | 1.097609402 | 0.027404436 |
| chr2 | 164017109 | 164017461 | 3' UTR | −7939 | Pabpc1l | 1.091920974 | 0.027416318 |
| chr10 | 28651986 | 28652303 | Intergenic | −16216 | Themis | 1.090339763 | 0.008834228 |
| chr17 | 86971070 | 86971588 | Intron | 8218 | Rhoq | 1.090010974 | 5.10E−05 |
| chr13 | 113396507 | 113396726 | Intergenic | 106228 | 4921509O07Rik | 1.088788257 | 0.011747979 |
| chr5 | 139449008 | 139449394 | Intron | 11333 | 3110082I17Rik | 1.086322214 | 0.038378284 |
| chr1 | 95450919 | 95451327 | Intergenic | 137495 | Fam174a | 1.083655032 | 0.013006851 |
| chr1 | 171119070 | 171119373 | Intergenic | −2440 | Cfap126 | 1.072745837 | 0.008829864 |
| chr4 | 84946546 | 84946729 | Intron | 62328 | Cntln | 1.068980981 | 0.046397637 |
| chr6 | 53521568 | 53521951 | Intergenic | −51615 | Creb5 | 1.066908425 | 0.027837442 |
| chr14 | 79226613 | 79227055 | Intron | 20533 | Zfp957 | 1.065230739 | 0.007762565 |
| chr1 | 181335502 | 181335834 | Intergenic | −16960 | Cnih3 | 1.039531414 | 0.013751277 |
| chr8 | 75203514 | 75203750 | Intergenic | −10312 | Rasd2 | 1.036413839 | 0.038346707 |
| chr16 | 14438699 | 14438939 | Intron | 77261 | Abcc1 | 1.030227231 | 0.032597605 |
| chr12 | 25250111 | 25250288 | Intergenic | 121025 | Gm17746 | 1.015114909 | 0.038101366 |
| chr13 | 19219430 | 19220030 | Intergenic | 176083 | Stard3nl | 1.014707553 | 7.53E−06 |
| chr2 | 148522092 | 148522603 | Intergenic | −78812 | Cd93 | 1.013388935 | 1.15E−07 |
| chr5 | 104960348 | 104960772 | Intron | 22157 | Abcg3 | 1.011492212 | 0.001475821 |
| chr16 | 92862543 | 92862782 | Intergenic | −36588 | Runx1 | 1.009934393 | 0.00777576 |
| chr9 | 46122370 | 46122837 | Intron | −106027 | Apoa1 | 1.006638021 | 0.007030729 |
| chr1 | 86210665 | 86210949 | Intron | 56027 | Armc9 | 1.001079088 | 0.049537782 |
| chr6 | 8640990 | 8641306 | Intron | 117310 | Ica1 | 0.996415714 | 0.010115045 |
| chr1 | 191107065 | 191107251 | Intron | 8744 | Batf3 | 0.993146898 | 0.024832005 |
| chr13 | 19300414 | 19300933 | Intergenic | 95140 | Stard3nl | 0.991164424 | 1.75E−06 |
| chr12 | 52824837 | 52825114 | Intron | 125592 | Akap6 | 0.990226085 | 0.025572054 |
| chr1 | 120289938 | 120290438 | Intergenic | −19106 | Steap3 | 0.990214641 | 0.026580973 |
| chr9 | 69597438 | 69597821 | Intergenic | 140685 | Mir3109 | 0.988464323 | 0.013331584 |
| chr7 | 29499096 | 29499464 | Intron | 6180 | Sipa1l3 | 0.98354891 | 0.009082411 |
| chr5 | 72832716 | 72833216 | Intron | 35482 | Tec | 0.983264655 | 0.04047618 |
| chr17 | 36431381 | 36431799 | Intergenic | 30739 | H2-M10.4 | 0.982457033 | 3.44E−05 |
| chr1 | 177368019 | 177368554 | Intergenic | −76375 | Zbtb18 | 0.978143078 | 0.002660748 |
| chr1 | 165680047 | 165680479 | Intron | 27831 | Rcsd1 | 0.975318779 | 2.22E−06 |
| chr10 | 60658085 | 60658544 | Intron | 38176 | Cdh23 | 0.96829644 | 0.018555137 |
| chr2 | 117320114 | 117320504 | Intron | 22568 | Rasgrp1 | 0.966527519 | 0.007294007 |
| chr9 | 115221281 | 115221756 | Intron | 60552 | Stmn1-rs1 | 0.966114346 | 1.13E−05 |
| chr17 | 72821938 | 72822316 | Intergenic | −14577 | Ypel5 | 0.963450498 | 0.036123863 |
| chr1 | 177670558 | 177671007 | Intergenic | −27839 | 2310043L19Rik | 0.96190908 | 0.041235515 |
| chr4 | 122930983 | 122931210 | Intergenic | 30092 | Mfsd2a | 0.957492796 | 0.004308052 |
| chr6 | 56909019 | 56909292 | Intron | −7269 | Nt5c3 | 0.950784516 | 0.042117068 |
| chr2 | 144441195 | 144441685 | Intergenic | −17840 | Zfp133-ps | 0.947541393 | 1.51E−06 |

TABLE 6-continued

ATAC-Seq of Tox vs. control GFP RV transduced in vitro activated CD8+ T cells

| Chromosome | Start | End | Annotation | Distance to TSS | Proximal Gene ID | Log2 Fold Change | Adjusted p-value |
|---|---|---|---|---|---|---|---|
| chr6 | 91153600 | 91154028 | Intergenic | −3001 | Hdac11 | 0.945575037 | 0.01908007 |
| chr17 | 71680708 | 71681319 | Intron | 7752 | Fam179a | 0.945011006 | 1.56E−05 |
| chr16 | 30504505 | 30505101 | Intergenic | 45775 | Tmem44 | 0.944892547 | 0.008838631 |
| chr9 | 83549929 | 83550131 | Intron | 1692 | Sh3bgrl2 | 0.940077846 | 0.049671897 |
| chr16 | 75912147 | 75912375 | Intergenic | −2995 | Samsn1 | 0.932664705 | 0.03685924 |
| chr12 | 110866356 | 110866759 | Intron | 16278 | Zfp839 | 0.930803258 | 0.007324132 |
| chr11 | 109765032 | 109765350 | Intergenic | −42935 | Fam20a | 0.924903907 | 0.002050843 |
| chr10 | 17566934 | 17567251 | Intergenic | −156136 | Cited2 | 0.920638367 | 0.007762565 |
| chr9 | 25497341 | 25497675 | Intron | 15911 | Eepd1 | 0.915849424 | 0.027462134 |
| chr16 | 94246091 | 94246355 | Intron | 41633 | Hlcs | 0.914623426 | 0.013660307 |
| chr7 | 139415614 | 139415816 | Intron | 26606 | Inpp5a | 0.914277555 | 0.041826107 |
| chr2 | 44323705 | 44324366 | Intron | −258711 | Arhgap15os | 0.91307601 | 2.80E−05 |
| chr17 | 85908735 | 85909221 | Intergenic | −220724 | Six2 | 0.912426257 | 2.64E−05 |
| chr6 | 71746892 | 71747257 | Intron | 39393 | Reep1 | 0.906486445 | 0.024174338 |
| chr17 | 15107002 | 15107730 | Intergenic | 54307 | Ermard | 0.896411885 | 3.04E−05 |
| chr18 | 82806232 | 82806599 | Intergenic | −47376 | 2210420H20Rik | 0.89627898 | 0.04876175 |
| chr4 | 111464923 | 111465237 | Intron | 50074 | Bend5 | 0.895599891 | 0.013006851 |
| chr16 | 75831408 | 75831806 | Intergenic | −64789 | Hspa13 | 0.895072677 | 0.032053561 |
| chr10 | 86847743 | 86847940 | Intron | 68836 | Nt5dc3 | 0.891466761 | 0.011924956 |
| chr19 | 18606466 | 18606746 | Intron | 25207 | Ostf1 | 0.891271873 | 0.027642235 |
| chr17 | 87561834 | 87562101 | Intron | −74012 | Epcam | 0.888996966 | 0.028192521 |
| chrX | 129737419 | 129738074 | Intergenic | −11996 | Diaph2 | 0.884281569 | 0.012947563 |
| chr2 | 173685907 | 173686453 | Intron | 14968 | Mir6340 | 0.883936232 | 0.000200899 |
| chr1 | 21029112 | 21029511 | Intron | 49914 | Tram2 | 0.882883377 | 0.001394846 |
| chr11 | 110642536 | 110642930 | Intergenic | 243611 | Map2k6 | 0.882580043 | 0.008752207 |
| chr3 | 101651431 | 101651767 | Intergenic | −46892 | Atp1a1 | 0.878569974 | 0.013331584 |
| chr6 | 122532915 | 122533284 | Intergenic | 19423 | Mfap5 | 0.877595123 | 0.00748912 |
| chr12 | 111269756 | 111270093 | Intergenic | −1172 | Amn | 0.877048939 | 0.035445222 |
| chr19 | 23388253 | 23388617 | Intron | 59887 | Mamdc2 | 0.876982004 | 0.049059337 |
| chr3 | 136325888 | 136326182 | Promoter-TSS | 31 | Bank1 | 0.873465992 | 0.019805 |
| chr5 | 125137703 | 125138316 | Intron | 41205 | Ncor2 | 0.870035632 | 9.44E−05 |
| chr5 | 22589244 | 22589618 | Intergenic | 39018 | 6030443J06Rik | 0.866635677 | 0.013006851 |
| chr2 | 90021307 | 90021809 | Exon | 506 | Olfr1264 | 0.865990784 | 0.028192521 |
| chr6 | 94253978 | 94254380 | Intron | −16737 | 4930511A08Rik | 0.865364439 | 0.007030729 |
| chr5 | 35687009 | 35687490 | Intergenic | −7469 | Htra3 | 0.864766682 | 0.020617833 |
| chr6 | 94184384 | 94184688 | Intron | 52906 | 4930511A08Rik | 0.864707578 | 0.049537782 |
| chr12 | 82303925 | 82304352 | Intron | −7211 | Sipa1l1 | 0.860947434 | 0.037533605 |
| chr2 | 102713241 | 102713865 | Intron | 7115 | Slc1a2 | 0.858229041 | 0.001148044 |
| chr6 | 8711927 | 8712566 | Intron | 46212 | Ica1 | 0.856569906 | 0.020905294 |
| chr3 | 153645701 | 153646139 | Intron | 79213 | St6galnac3 | 0.855879182 | 0.01510169 |
| chr2 | 66101966 | 66102415 | Intron | 22603 | Galnt3 | 0.844547558 | 0.018440961 |
| chr3 | 129658763 | 129659148 | Intergenic | 66131 | Egf | 0.840141725 | 0.039397068 |
| chr15 | 73006448 | 73006828 | Intron | 49174 | Trappc9 | 0.837924992 | 0.004923575 |
| chr11 | 110886189 | 110886520 | Intergenic | −81679 | Kcnj16 | 0.836533463 | 4.15E−05 |
| chr10 | 111128566 | 111128937 | Intergenic | −36051 | Osbpl8 | 0.833047555 | 0.049671897 |
| chr4 | 124969746 | 124969746 | Intergenic | −16966 | Rspo1 | 0.832179138 | 0.037520062 |
| chr14 | 70818982 | 70819426 | Intergenic | −33729 | 2410012E07Rik | 0.831644842 | 0.007324132 |
| chr19 | 17272907 | 17273327 | Intergenic | 66388 | Gcnt1 | 0.830138267 | 0.036169761 |
| chr13 | 98901731 | 98902025 | Intron | −10836 | Tnpo1 | 0.829676086 | 0.025402784 |
| chr3 | 35749640 | 35749846 | Intron | −4395 | Atp11b | 0.829664508 | 0.038388993 |
| chr2 | 163156024 | 163156427 | Intergenic | −66624 | Gtsf1l | 0.827097664 | 0.013331584 |
| chr15 | 84524675 | 84525287 | Intergenic | 32842 | Ldoc1l | 0.820184691 | 0.027837442 |
| chr8 | 26683237 | 26683619 | Intergenic | 140995 | 2310008N11Rik | 0.809047485 | 0.01251604 |
| chr4 | 107606023 | 107606042 | Intron | 77930 | Dmrtb1 | 0.806074879 | 0.013348005 |
| chr4 | 16015638 | 16015848 | Intergenic | −1866 | Osgin2 | 0.800718764 | 0.036123863 |
| chr7 | 109513516 | 109513777 | Intergenic | −5512 | Trim66 | 0.800541776 | 0.039113833 |
| chr7 | 139412415 | 139412796 | Intron | 23496 | Inpp5a | 0.79815991 | 0.003996925 |
| chr2 | 35985508 | 35985903 | Intergenic | −6081 | Ttll11 | 0.792883366 | 0.013464711 |
| chr8 | 88618597 | 88619165 | Intergenic | 17247 | Snx20 | 0.783359278 | 0.005981181 |
| chr7 | 47145953 | 47146681 | Intergenic | −12633 | Ptpn5 | 0.78102886 | 9.55E−05 |
| chr2 | 131145523 | 131145903 | TTS | 14307 | 1700037H04Rik | 0.777668888 | 0.03072441 |
| chr5 | 139320530 | 139320859 | Intron | 4770 | Adap1 | 0.777642741 | 0.044771365 |
| chr4 | 102787608 | 102788081 | Intron | 27709 | Sgip1 | 0.77455615 | 0.008832549 |
| chr13 | 107769911 | 107770311 | Intron | −9024 | Mir325 | 0.772376548 | 0.000317316 |
| chr5 | 65933776 | 65934171 | Intergenic | −33151 | Chrna9 | 0.770553267 | 0.001551006 |
| chr8 | 78717088 | 78717654 | Intron | 103781 | Lsm6 | 0.76757813 | 0.035472647 |
| chr6 | 94187061 | 94187375 | Intron | 50224 | 4930511A08Rik | 0.765168699 | 0.047429012 |
| chr5 | 134295649 | 134295984 | Intron | 18944 | Gtf2i | 0.763299537 | 0.038846255 |
| chr7 | 4948411 | 4948837 | Intergenic | 15724 | Sbk2 | 0.760159703 | 0.011007199 |
| chr5 | 34032218 | 34032726 | Intron | 36488 | Nat8l | 0.759885776 | 0.038203621 |
| chr18 | 74813826 | 74814308 | Intron | 34855 | Acaa2 | 0.759320655 | 0.008832549 |
| chr4 | 111455675 | 111456394 | Intron | 41028 | Bend5 | 0.758817893 | 1.93E−05 |
| chr14 | 60425641 | 60425998 | Intergenic | 47533 | Amer2 | 0.754823246 | 0.004508622 |
| chr13 | 83597435 | 83598069 | Intron | 93718 | Mef2c | 0.750543467 | 5.17E−06 |
| chr2 | 146497059 | 146497871 | Intron | 14539 | Ralgapa2 | 0.748207623 | 1.63E−10 |
| chr8 | 27252676 | 27252953 | Intergenic | −7513 | Eif4ebp1 | 0.747032387 | 0.018169475 |

TABLE 6-continued

ATAC-Seq of Tox vs. control GFP RV transduced in vitro activated CD8+ T cells

| Chromosome | Start | End | Annotation | Distance to TSS | Proximal Gene ID | Log2 Fold Change | Adjusted p-value |
|---|---|---|---|---|---|---|---|
| chr1 | 73910727 | 73911109 | 3' UTR | −46452 | 6030407O03Rik | 0.746894724 | 0.013006851 |
| chr10 | 86847119 | 86847525 | Intron | 68317 | Nt5dc3 | 0.745759073 | 1.51E−06 |
| chr12 | 103116698 | 103117041 | Intron | 125277 | Prima1 | 0.742190136 | 0.027095965 |
| chr5 | 118271706 | 118272260 | Intergenic | 26756 | 2410131K14Rik | 0.740341845 | 2.64E−05 |
| chr11 | 67633697 | 67634392 | Intron | 37489 | Gas7 | 0.73980755 | 0.018169475 |
| chrX | 78470498 | 78471124 | Intron | 101168 | 4930480E11Rik | 0.727041023 | 0.018555137 |
| chr5 | 22587436 | 22587905 | Intergenic | 37257 | 6030443J06Rik | 0.724395891 | 0.027751164 |
| chr10 | 43934627 | 43935158 | Intron | 33085 | Rtn4ip1 | 0.723903586 | 0.001148044 |
| chr10 | 44434710 | 44435032 | Intergenic | 23877 | Prdm1 | 0.723414837 | 0.011040627 |
| chr6 | 66954042 | 66954548 | Intron | 57404 | Gng12 | 0.720366293 | 0.002293634 |
| chr1 | 36024973 | 36025409 | Intergenic | −43209 | Hs6st1 | 0.718105346 | 0.00748912 |
| chr10 | 44402102 | 44402399 | Intergenic | 42574 | Mir1929 | 0.714216487 | 0.008832549 |
| chr3 | 138061350 | 138062004 | Intron | 5711 | Gm5105 | 0.710619725 | 1.34E−07 |
| chr14 | 99098490 | 99098843 | Promoter-TSS | −758 | Pibf1 | 0.710360859 | 0.026060269 |
| chr12 | 107926138 | 107926351 | Intron | 77170 | Bcl11b | 0.706200875 | 0.038595691 |
| chr8 | 90356601 | 90357166 | Intergenic | −8631 | Tox3 | 0.7051432 | 0.049671897 |
| chr14 | 48124800 | 48125203 | Intron | 4132 | Peli2 | 0.704141835 | 0.014071076 |
| chr8 | 27200822 | 27201244 | Intron | 1514 | Got1l1 | 0.704125029 | 0.012029357 |
| chr3 | 157581194 | 157581631 | Intron | 14520 | Ptger3 | 0.702510797 | 0.005905229 |
| chrX | 167110982 | 167111578 | Intergenic | −40910 | Gm8817 | 0.701510143 | 0.013006851 |
| chr3 | 100502470 | 100503004 | Intergenic | −13545 | Fam46c | 0.701078385 | 0.010314747 |
| chr3 | 135527490 | 135528222 | Intron | 42245 | Manba | 0.701055871 | 4.46E−05 |
| chr5 | 43853191 | 43853758 | Intergenic | −15335 | Cd38 | 0.695994048 | 0.000835876 |
| chr6 | 94555378 | 94555673 | Intron | 50890 | Mir7041 | 0.695104555 | 0.03022052 |
| chr6 | 115693285 | 115693663 | Intergenic | −16839 | Raf1 | 0.689935063 | 0.024286918 |
| chr13 | 98124185 | 98124892 | Intron | 81627 | Arhgef28 | 0.685425994 | 7.79E−06 |
| chr13 | 19272652 | 19273195 | Intergenic | 122890 | Stard3nl | 0.68497218 | 0.032468218 |
| chr18 | 55418918 | 55419708 | Intergenic | −429133 | Zfp608 | 0.684746625 | 0.007324132 |
| chr6 | 87189768 | 87190127 | Intron | 85201 | D6Ertd527e | 0.683863836 | 0.004716412 |
| chr8 | 68212117 | 68212595 | Intergenic | −64172 | Sh2d4a | 0.683375186 | 0.001764511 |
| chr11 | 46360092 | 46360469 | Exon | 29235 | Itk | 0.680205019 | 0.011685897 |
| chr4 | 132748718 | 132749115 | Intron | 8255 | Smpdl3b | 0.680000539 | 0.00159982 |
| chr6 | 71638301 | 71638912 | Intergenic | −5689 | Kdm3a | 0.678846083 | 8.30E−06 |
| chr10 | 95780929 | 95781532 | Intergenic | −159433 | Eea1 | 0.673152599 | 0.004032741 |
| chr9 | 56103261 | 56103434 | Intron | 13371 | Pstpip1 | 0.669452814 | 0.039113833 |
| chr2 | 58183739 | 58184030 | Intergenic | 19910 | Gm13546 | 0.663378887 | 0.018555137 |
| chr1 | 64986167 | 64986416 | Intergenic | −29467 | Plekhm3 | 0.66151924 | 0.047429012 |
| chr6 | 95712138 | 95712687 | Intron | 6434 | Suclg2 | 0.651816505 | 0.012390527 |
| chr8 | 91073659 | 91074275 | Intron | 3910 | Rbl2 | 0.646710073 | 6.49E−06 |
| chr14 | 105684370 | 105684694 | Intergenic | −60762 | Mir6390 | 0.646585147 | 0.007030729 |
| chr10 | 111996311 | 111996838 | Intron | 690 | Glipr1 | 0.645339217 | 9.55E−05 |
| chr4 | 138130231 | 138130631 | Intron | 8087 | 1700095J12Rik | 0.642956231 | 0.007707415 |
| chr1 | 120305829 | 120306291 | Intergenic | −34522 | C1ql2 | 0.642636913 | 0.00733836 |
| chrX | 163879251 | 163880000 | Intergenic | −29392 | Ap1s2 | 0.642171165 | 0.021574218 |
| chr17 | 84880946 | 84881314 | Intergenic | −75611 | Ppm1b | 0.640464306 | 0.023528715 |
| chr14 | 106026806 | 106027306 | Intergenic | −79142 | Trim52 | 0.63755534 | 0.018811737 |
| chr15 | 78457138 | 78457971 | Intron | 11080 | Tmprss6 | 0.624246578 | 0.0286532 |
| chr11 | 16987833 | 16988203 | Intron | 20700 | Plek | 0.620904721 | 0.039113833 |
| chr1 | 85680165 | 85680620 | Intron | 30404 | Sp100 | 0.618600496 | 0.013343101 |
| chr6 | 131263831 | 131264378 | Intergenic | −16742 | Klra2 | 0.616187035 | 2.77E−05 |
| chrX | 159021402 | 159021929 | Intergenic | −234117 | Rps6ka3 | 0.615572489 | 0.034799668 |
| chr15 | 63657406 | 63658598 | Intergenic | 150737 | Gsdmc | 0.610091818 | 0.013473212 |
| chr1 | 184276999 | 184277372 | Intergenic | 242724 | Dusp10 | 0.607823691 | 0.046397637 |
| chr11 | 100933877 | 100934480 | Intron | 5362 | Stat3 | 0.606793223 | 0.039397068 |
| chr6 | 115513029 | 115513552 | Intergenic | −31414 | Tsen2 | 0.605408058 | 0.024174338 |
| chr13 | 113549071 | 113549418 | Intergenic | −46400 | 4921509O07Rik | 0.602166227 | 0.010235572 |
| chr8 | 69188997 | 69189274 | Intergenic | −19911 | Zfp930 | 0.596107069 | 0.011310263 |
| chr10 | 117898258 | 117898770 | Intergenic | −26945 | 4933411E08Rik | 0.594167843 | 0.033538505 |
| chr1 | 80015491 | 80015820 | Intergenic | −156990 | Serpine2 | 0.58658288 | 0.028010344 |
| chr10 | 82966605 | 82967019 | Intergenic | −18685 | Chst11 | 0.581505567 | 0.010235572 |
| chr17 | 86904225 | 86904609 | Intergenic | −12931 | Tmem247 | 0.580594895 | 0.007762565 |
| chr6 | 140771204 | 140771810 | Intergenic | 144622 | Aebp2 | 0.580035457 | 0.007030729 |
| chr14 | 105897274 | 105897947 | Promoter-TSS | −593 | Spry2 | 0.578058747 | 0.044602915 |
| chr8 | 86838746 | 86839346 | Intergenic | 46212 | N4bp1 | 0.575566099 | 0.013464711 |
| chr15 | 28178949 | 28179348 | Intergenic | −24618 | Dnah5 | 0.572679066 | 0.029028806 |
| chr1 | 192736505 | 192736953 | Intron | 34490 | Hhat | 0.569934588 | 0.01216058 |
| chr2 | 72082308 | 72083424 | Intron | 28549 | Rapgef4 | 0.568751723 | 0.018208844 |
| chr3 | 138876952 | 138877492 | Intron | 135014 | Tspan5 | 0.566284193 | 0.03685924 |
| chr7 | 73696778 | 73697685 | Intergenic | −10668 | Gm4971 | 0.562636005 | 0.007762565 |
| chr19 | 57104300 | 57104621 | Intron | 14564 | Ablim1 | 0.561831287 | 0.038846255 |
| chr8 | 91082416 | 91082789 | Intron | 12545 | Rbl2 | 0.559955816 | 0.046397637 |
| chr10 | 122817705 | 122818169 | Intron | 138622 | Mir8104 | 0.558963988 | 0.008832549 |
| chr19 | 40356602 | 40357219 | Intron | 45400 | Sorbs1 | 0.558367067 | 0.005261538 |
| chr3 | 104840974 | 104841492 | Intron | −22670 | Mov10 | 0.558038725 | 0.026101606 |
| chr9 | 70371618 | 70372066 | Intron | 33911 | Mir5626 | 0.553189451 | 0.022358823 |
| chr6 | 30657202 | 30657687 | Intron | 18223 | Cpa1 | 0.549206386 | 0.022125818 |

TABLE 6-continued

ATAC-Seq of Tox vs. control GFP RV transduced in vitro activated CD8+ T cells

| Chromosome | Start | End | Annotation | Distance to TSS | Proximal Gene ID | Log2 Fold Change | Adjusted p-value |
|---|---|---|---|---|---|---|---|
| chr1 | 137806611 | 137807258 | Intergenic | −159521 | Mir181a-1 | 0.542533728 | 0.002600802 |
| chr14 | 20379649 | 20380347 | Intron | 8912 | Dnajc9 | 0.541748144 | 0.026101606 |
| chr2 | 144188046 | 144188496 | Intron | 1019 | Gm5535 | 0.536849705 | 0.040845098 |
| chr8 | 31170176 | 31170544 | Intergenic | −1636 | Mak16 | 0.536518197 | 0.001296439 |
| chr2 | 148374805 | 148375365 | Intergenic | −20292 | Sstr4 | 0.535499315 | 0.007030729 |
| chr19 | 61084075 | 61084789 | Intron | 56408 | Zfp950 | 0.535301134 | 0.00748912 |
| chr3 | 144617848 | 144618263 | Intergenic | 47628 | Sept15 | 0.533560547 | 0.024384617 |
| chr4 | 129924306 | 129925180 | Intergenic | 18517 | E330017L17Rik | 0.533076177 | 0.001551006 |
| chr14 | 121954668 | 121955051 | Exon | 10334 | Gpr183 | 0.531378941 | 0.019745643 |
| chr5 | 65867015 | 65867692 | Intron | 3784 | Rhoh | 0.530746123 | 0.003081353 |
| chr5 | 118081935 | 118082594 | Intron | 54440 | Tesc | 0.528913487 | 0.02073671 |
| chr2 | 57190853 | 57191353 | Intergenic | 9272 | 4930555B11Rik | 0.525432056 | 0.016064193 |
| chr10 | 77540595 | 77540981 | Intron | 10440 | Itgb2 | 0.524417005 | 0.013010395 |
| chr1 | 78591282 | 78591652 | Intergenic | −66358 | Utp14b | 0.523948663 | 0.038101366 |
| chr1 | 138954528 | 138955396 | Intergenic | −8747 | Dennd1b | 0.523835666 | 0.035153107 |
| chr8 | 111720085 | 111720553 | Intron | 11817 | Bcar1 | 0.523694339 | 0.041191672 |
| chr19 | 17380535 | 17381031 | Intergenic | −7939 | Gcnt1 | 0.521492643 | 0.000783812 |
| chr3 | 105625430 | 105625976 | Intron | 61868 | Ddx20 | 0.521402456 | 0.006484356 |
| chr3 | 144627877 | 144629136 | Intergenic | 58079 | Sept15 | 0.520924861 | 0.018555137 |
| chr1 | 98021900 | 98022240 | Intron | 25723 | B230216N24Rik | 0.519808832 | 0.039359357 |
| chr7 | 110956387 | 110957232 | Intron | −10622 | Mrvi1 | 0.519344382 | 4.69E−05 |
| chr4 | 86882089 | 86882366 | Intron | 7813 | Acer2 | 0.517975245 | 0.044446878 |
| chr11 | 83657316 | 83657827 | Intergenic | −5013 | Ccl4 | 0.515741475 | 0.028476381 |
| chr16 | 97204113 | 97204593 | Intergenic | −33618 | Dscam | 0.515238635 | 0.00748912 |
| chr10 | 116746314 | 116746953 | Intergenic | 17380 | 4930579P08Rik | 0.514631019 | 0.036230625 |
| chr3 | 152509277 | 152509670 | Intron | 112789 | Zzz3 | 0.513161865 | 0.002581166 |
| chr2 | 125454658 | 125454929 | Intron | 51645 | Fbn1 | 0.511267634 | 0.039113833 |
| chr2 | 166625295 | 166625996 | Intron | −47073 | Mir6364 | 0.506374903 | 0.001551006 |
| chr2 | 170306785 | 170307427 | Intergenic | −49255 | Bcas1os2 | 0.506137304 | 0.001732673 |
| chr16 | 89986708 | 89987480 | Intergenic | −12395 | Tiam1 | 0.504413588 | 0.027751164 |
| chr3 | 9801760 | 9802652 | Intron | 31473 | Pag1 | 0.502664562 | 0.002293634 |
| chr1 | 171231748 | 171232321 | Intron | 2315 | Fcer1g | 0.500550844 | 0.049671897 |
| chr12 | 113167811 | 113168662 | Intergenic | 11815 | 4930427A07Rik | 0.499627223 | 9.44E−05 |
| chr1 | 98129938 | 98130387 | Intergenic | −1305 | 1810006J02Rik | 0.499162469 | 0.014164181 |
| chr12 | 74894802 | 74895459 | Intergenic | 282202 | Kcnh5 | 0.497837351 | 0.007762565 |
| chr8 | 82874093 | 82874513 | Intron | 10947 | Rnf150 | 0.49312136 | 0.041691495 |
| chr13 | 119656988 | 119657495 | Intergenic | −22801 | 1700074H08Rik | 0.492521262 | 0.006088263 |
| chr6 | 129661320 | 129661788 | Promoter-TSS | −958 | Klrc2 | 0.491156252 | 0.041191672 |
| chr9 | 53247446 | 53247925 | Intron | 427 | Ddx10 | 0.49094067 | 0.025971912 |
| chr16 | 89871972 | 89872676 | Intron | −53972 | Tiam1 | 0.488036908 | 0.009471505 |
| chr8 | 86853570 | 86854254 | Intron | 31346 | N4bp1 | 0.485690448 | 0.001460098 |
| chr16 | 11399908 | 11400656 | Intron | −5366 | Snx29 | 0.483573606 | 0.013006851 |
| chr1 | 62875596 | 62876258 | Intergenic | −81195 | 4930487H11Rik | 0.479860039 | 2.64E−05 |
| chr5 | 149594199 | 149594561 | Intron | 41935 | Hsph1 | 0.478791501 | 0.031020786 |
| chr1 | 52034769 | 52035298 | Intron | 26793 | Stat4 | 0.478320957 | 0.014647905 |
| chr6 | 42343271 | 42344150 | Intergenic | −6118 | Zyx | 0.477061469 | 0.008838631 |
| chr17 | 73893315 | 73893792 | Intron | 56643 | Xdh | 0.468916205 | 0.032063145 |
| chr12 | 12496506 | 12497107 | Intergenic | −104331 | 4921511I17Rik | 0.468219481 | 0.014164181 |
| chr10 | 3510529 | 3511035 | Intergenic | −29497 | Iyd | 0.468169262 | 0.021959744 |
| chr7 | 68349883 | 68350716 | Exon | −67125 | 4933436H12Rik | 0.467777712 | 0.001394846 |
| chr3 | 15159462 | 15159912 | Intergenic | 172615 | Gm9733 | 0.467579947 | 0.038846255 |
| chr3 | 79152903 | 79153536 | Intergenic | −7344 | Rapgef2 | 0.466149143 | 0.000911408 |
| chr2 | 102034414 | 102034792 | Intron | 148341 | Commd9 | 0.465113969 | 0.039780036 |
| chr14 | 57712861 | 57713277 | Intron | 21349 | Lats2 | 0.462805697 | 0.039113833 |
| chr12 | 106008572 | 106009035 | Intergenic | −1460 | Vrk1 | 0.451277642 | 0.012060088 |
| chr15 | 86194774 | 86195302 | Intergenic | −8897 | Cerk | 0.450737624 | 0.003829653 |
| chr9 | 78100931 | 78101634 | Intron | 7374 | Fbxo9 | 0.449781847 | 0.013343101 |
| chr7 | 139151159 | 139151838 | Intron | 36996 | Stk32c | 0.448357079 | 0.002263516 |
| chr2 | 124751875 | 124752279 | Intergenic | 98496 | Sema6d | 0.447833976 | 0.039113833 |
| chr11 | 109790251 | 109790670 | Intron | 37586 | 1700012B07Rik | 0.445419374 | 0.026101606 |
| chr13 | 60839280 | 60839865 | Intergenic | 24844 | 4930486L24Rik | 0.445358901 | 0.007762565 |
| chr12 | 70219075 | 70219598 | Intron | 8347 | Pygl | 0.443795174 | 0.014647905 |
| chr2 | 30625945 | 30626611 | Intergenic | 31234 | Cstad | 0.443072344 | 0.00748912 |
| chr12 | 117994996 | 117995428 | Exon | 151351 | Cdca7l | 0.442999566 | 0.020580505 |
| chr17 | 74864814 | 74865227 | Intergenic | −140509 | Ltbp1 | 0.440735983 | 0.02073671 |
| chr2 | 92627574 | 92628045 | Intergenic | 28102 | Chst1 | 0.439210424 | 0.038388993 |
| chr1 | 192745491 | 192746334 | Intron | 25307 | Hhat | 0.435980721 | 0.007030729 |
| chr18 | 57249487 | 57250070 | Intron | −104955 | Prrc1 | 0.431575703 | 0.000106616 |
| chr6 | 3536128 | 3536712 | Intron | 38027 | Vps50 | 0.428189814 | 0.045141882 |
| chr3 | 105894580 | 105895297 | Intron | −9483 | Adora3 | 0.427110282 | 2.91E−05 |
| chr2 | 11540385 | 11540957 | Intron | 13258 | Pfkfb3 | 0.425572294 | 0.035596339 |
| chr1 | 122357125 | 122357315 | Intergenic | −789240 | Ddx18 | 0.424620865 | 0.038571732 |
| chr13 | 93786299 | 93786839 | Intron | −4208 | Mir5624 | 0.422888221 | 0.047429012 |
| chr3 | 108717974 | 108718611 | Intron | 4007 | Gpsm2 | 0.422790804 | 0.047429012 |
| chr7 | 58676967 | 58677796 | Intron | 19179 | Atp10a | 0.420347354 | 0.032582177 |
| chr13 | 19356129 | 19357017 | Intergenic | 39240 | Stard3nl | 0.418773824 | 0.027837442 |

TABLE 6-continued

ATAC-Seq of Tox vs. control GFP RV transduced in vitro activated CD8+ T cells

| Chromosome | Start | End | Annotation | Distance to TSS | Proximal Gene ID | Log2 Fold Change | Adjusted p-value |
|---|---|---|---|---|---|---|---|
| chr18 | 46380819 | 46381437 | Intergenic | −69200 | Ccdc112 | 0.418675267 | 0.013006851 |
| chr6 | 66929471 | 66930055 | Intron | 32872 | Gng12 | 0.418436835 | 0.000869155 |
| chr11 | 109495862 | 109496650 | Intron | −22660 | Slc16a6 | 0.413114194 | 0.005576349 |
| chr3 | 135665533 | 135666304 | Intron | 25629 | Nfkb1 | 0.411717987 | 4.69E−05 |
| chr16 | 91534582 | 91534715 | Intergenic | −12446 | Ifngr2 | 0.409048089 | 0.013006851 |
| chr13 | 99475426 | 99476000 | Intron | 40889 | Map1b | 0.408619868 | 0.027837442 |
| chr3 | 149339334 | 149339722 | Intergenic | 64791 | Gm1653 | 0.405221749 | 0.032468218 |
| chr9 | 87025776 | 87026125 | Intron | 3921 | Cyb5r4 | 0.40397114 | 0.025971912 |
| chr19 | 57994223 | 57994788 | Intron | −56662 | Mir5623 | 0.402380122 | 0.032597605 |
| chr4 | 119126856 | 119127676 | Intron | 18521 | Slc2a1 | 0.400953498 | 0.000402772 |
| chr14 | 105602867 | 105603411 | Intergenic | 13590 | 9330188P03Rik | 0.400321096 | 0.001434233 |
| chr10 | 85953271 | 85953877 | Intron | 4219 | Rtcb | 0.398005297 | 0.035153107 |
| chr8 | 117772250 | 117772971 | Intergenic | 29319 | Mphosph6 | 0.397640371 | 0.007294007 |
| chr2 | 131878461 | 131879153 | Intergenic | −19060 | Erv3 | 0.39420468 | 0.048380345 |
| chr4 | 134494857 | 134495655 | Intergenic | −1505 | Paqr7 | 0.393112624 | 0.014519071 |
| chr8 | 117287965 | 117288434 | Intron | 31180 | Cmip | 0.392423165 | 0.049537782 |
| chr16 | 92864278 | 92864623 | Intergenic | −38376 | Runx1 | 0.39087465 | 0.039113833 |
| chr13 | 99503471 | 99504055 | Intron | 12839 | Map1b | 0.389066254 | 0.027837442 |
| chr6 | 140722595 | 140723144 | Intergenic | 95984 | Aebp2 | 0.385462299 | 0.028055192 |
| chr17 | 86957911 | 86958304 | Intergenic | −5004 | Rhoq | 0.382388807 | 0.035472647 |
| chr10 | 11492079 | 11492227 | Intergenic | −117071 | Timm8a1 | 0.381960108 | 0.032597605 |
| chr16 | 17222261 | 17222514 | Intergenic | −11200 | Hic2 | 0.374621384 | 0.001551006 |
| chr3 | 105900713 | 105901184 | Intron | −3473 | Adora3 | 0.372734606 | 0.03198659 |
| chr6 | 125067368 | 125068106 | Promoter-TSS | −183 | Lpar5 | 0.372391803 | 0.047933903 |
| chr13 | 117260576 | 117261270 | Intron | 40350 | Emb | 0.372301568 | 0.002447601 |
| chr11 | 61493839 | 61494635 | Promoter-TSS | 29 | Mapk7 | 0.366534636 | 0.021781631 |
| chr9 | 90244329 | 90245050 | Intron | 26080 | Tbc1d2b | 0.366088345 | 0.016082026 |
| chr9 | 56223572 | 56223961 | Intron | −62696 | Tspan3 | 0.36502357 | 0.001838792 |
| chr18 | 50016606 | 50017611 | Intron | −36174 | Tnfaip8 | 0.360925838 | 0.007762565 |
| chr17 | 39847310 | 39847400 | Non-Coding | 4358 | Rn45s | 0.360355193 | 0.003498134 |
| chr5 | 36849943 | 36850470 | Intergenic | −18364 | Ppp2r2c | 0.359767946 | 0.038528911 |
| chr8 | 35425989 | 35426661 | Intergenic | 50584 | Ppp1r3b | 0.356334411 | 0.04307669 |
| chr5 | 113156582 | 113157440 | Intron | 6302 | 2900026A02Rik | 0.354834101 | 0.018811737 |
| chr17 | 36942376 | 36942958 | Promoter-TSS | −384 | Rnf39 | 0.352418241 | 0.043833559 |
| chr2 | 20899847 | 20900213 | Intron | 67691 | Arhgap21 | 0.34768341 | 0.019427929 |
| chr17 | 30518748 | 30519392 | Intron | 57217 | Btbd9 | 0.343900921 | 0.030608041 |
| chr1 | 120236411 | 120236893 | Intron | 28628 | Steap3 | 0.342686872 | 0.044771365 |
| chr16 | 11144170 | 11144318 | Intron | −9712 | Txndc11 | 0.340328269 | 0.000312533 |
| chr8 | 10534755 | 10535281 | Intron | 347436 | B930025P03Rik | 0.336835618 | 0.023847172 |
| chr16 | 57391113 | 57391420 | Intron | 37989 | Filip1l | 0.336186073 | 0.041612103 |
| chr6 | 3200762 | 3201380 | Intergenic | −87448 | Gm8579 | 0.335775218 | 0.000679578 |
| chr1 | 120055083 | 120056015 | Intron | 18231 | Tmem37 | 0.335592695 | 0.007707415 |
| chr13 | 44869566 | 44870029 | Intron | 132299 | Dtnbp1 | 0.33400662 | 0.013006851 |
| chr14 | 47361259 | 47362236 | Intergenic | −12113 | Lgals3 | 0.325435634 | 0.038571732 |
| chr16 | 18533187 | 18533334 | Intron | 34389 | Gnb1l | 0.319692693 | 0.037947883 |
| chr17 | 80174196 | 80175323 | Intron | 32546 | Srsf7 | 0.319678408 | 0.03357267 |
| chr19 | 38054248 | 38055370 | Promoter-TSS | −216 | Cep55 | 0.303325381 | 0.044713364 |
| chr17 | 39846780 | 39846920 | Non-Coding | 3853 | Rn45s | 0.295406153 | 0.005590089 |
| chr12 | 78350864 | 78351170 | Intron | 124362 | Gphn | 0.292704231 | 0.021957138 |
| chr16 | 35981589 | 35981821 | Intergenic | −1658 | Kpna1 | 0.286567785 | 0.026580973 |
| chr3 | 5860334 | 5860530 | Intergenic | −284184 | Pex2 | 0.276941305 | 0.009082411 |
| chr9 | 123461797 | 123462190 | 3' UTR | −16708 | Limd1 | 0.271263251 | 0.003996925 |
| chr12 | 54729197 | 54730213 | Intergenic | −33840 | Eapp | 0.267576453 | 0.048380345 |
| chr5 | 115489406 | 115490804 | Intergenic | −5621 | Sirt4 | 0.255543755 | 0.023418077 |
| chr1 | 94034912 | 94035712 | Intergenic | 14819 | Neu4 | 0.238230333 | 0.027837442 |
| chr15 | 78913625 | 78914309 | Promoter-TSS | 48 | Pdxp | −0.371596729 | 0.023087209 |
| chr4 | 148151321 | 148152207 | 5' UTR | 161 | Fbxo6 | −0.382303668 | 0.013006851 |
| chr14 | 31435839 | 31436386 | Promoter-TSS | −79 | Sh3bp5 | −0.428342997 | 0.009718597 |
| chr7 | 100932370 | 100933141 | Promoter-TSS | −594 | Arhgef17 | −0.429159379 | 0.047429012 |
| chr17 | 33978495 | 33979238 | Promoter-TSS | −75 | H2-K2 | −0.432829417 | 0.002293634 |
| chr1 | 174040854 | 174041307 | Promoter-TSS | −853 | Olfr433 | −0.439958261 | 0.038554319 |
| chr11 | 118145764 | 118146416 | Intergenic | −16871 | Dnah17 | −0.446220822 | 0.016134448 |
| chr18 | 89205960 | 89206638 | Intron | 8872 | Cd226 | −0.468086264 | 0.040845098 |
| chr18 | 4352855 | 4353542 | Promoter-TSS | −245 | Map3k8 | −0.51008756 | 0.000317316 |
| chr15 | 80681319 | 80681951 | Intron | 9788 | Fam83f | −0.516360827 | 0.039397068 |
| chr5 | 122707306 | 122708110 | Exon | 164 | P2rx4 | −0.516983476 | 0.032468218 |
| chr2 | 181483566 | 181483928 | Intergenic | −9459 | Abhd16b | −0.523510221 | 0.047478794 |
| chr17 | 32091197 | 32091659 | Promoter-TSS | −5 | Pdxk-ps | −0.527572638 | 0.040082654 |
| chr10 | 80696097 | 80696452 | Intron | 5546 | Mob3a | −0.541068696 | 0.038388993 |
| chr2 | 153262898 | 153263368 | Intron | 21601 | Pofut1 | −0.543675924 | 0.028055192 |
| chr7 | 136255467 | 136256110 | Intergenic | −12536 | C030029H02Rik | −0.561289156 | 0.00748912 |
| chr9 | 44734057 | 44734565 | Intron | 887 | Phldb1 | −0.570018497 | 0.020905294 |
| chr11 | 54155883 | 54156216 | Intergenic | 55125 | P4ha2 | −0.600661737 | 0.040239571 |
| chr17 | 56443245 | 56443775 | Intron | 18711 | Ptprs | −0.606674265 | 0.010969956 |
| chr19 | 53870126 | 53870401 | Intergenic | −21968 | Pdcd4 | −0.658832068 | 0.046397637 |
| chr6 | 136449900 | 136450427 | Intergenic | −34594 | E330021D16Rik | −0.666135834 | 0.046397637 |

TABLE 6-continued

ATAC-Seq of Tox vs. control GFP RV transduced in vitro activated CD8+ T cells

| Chromosome | Start | End | Annotation | Distance to TSS | Proximal Gene ID | Log2 Fold Change | Adjusted p-value |
|---|---|---|---|---|---|---|---|
| chr11 | 118153005 | 118153282 | Intergenic | −23924 | Dnah17 | −0.707184684 | 0.046397637 |
| chr15 | 80743660 | 80743928 | Intron | 32481 | Tnrc6b | −0.754538292 | 0.045141882 |
| chr5 | 63943108 | 63943615 | Intron | 25536 | Rell1 | −0.803367609 | 0.007074133 |
| chr11 | 119034210 | 119034503 | Intergenic | 6557 | Cbx8 | −0.826620958 | 0.049334164 |
| chr16 | 33043261 | 33043641 | Intron | 12735 | Iqcg | −0.928178558 | 0.021574218 |
| chr11 | 72957472 | 72957633 | Intergenic | −3617 | Atp2a3 | −0.942617805 | 0.038528911 |
| chr1 | 39205087 | 39205374 | Intron | 10958 | Npas2 | −0.997713108 | 0.021844477 |
| chr5 | 73265552 | 73265829 | Intergenic | −9072 | Fryl | −1.028837124 | 0.012060088 |
| chr1 | 134106782 | 134107018 | Intergenic | −4342 | Chit1 | −1.057139261 | 0.020181156 |
| chr10 | 40462233 | 40462601 | Intron | −107945 | Slc22a16 | −1.090716424 | 0.047478794 |
| chr11 | 6006122 | 6006575 | Intron | 50590 | Ykt6 | −1.102327929 | 1.59E−05 |
| chr16 | 4763261 | 4763535 | Intron | 21785 | Hmox2 | −1.133527605 | 0.029377755 |
| chr10 | 93007091 | 93007284 | Intergenic | −153689 | Cdk17 | −1.193698157 | 0.007762565 |

TABLE 7

MiST analysis following Tox immunoprecipitation and mass spectrometry in EL4 cells

| Protein ID | Abundance | Reproducibility | Specificity | MiST Score |
|---|---|---|---|---|
| Ppa1 | 8.43E−06 | 0.999227718 | 1 | 0.99380178 |
| Myef2 | 3.80E−06 | 0.998159011 | 1 | 0.99347202 |
| Rcn2 | 1.40E−05 | 0.992739626 | 1 | 0.99180004 |
| Acot8 | 2.29E−05 | 0.983302915 | 1 | 0.98888859 |
| Ing4 | 0.000240069 | 0.9772407 | 1 | 0.9870195 |
| Thoc5 | 3.93E−06 | 0.977038489 | 1 | 0.98695571 |
| Orc5 | 2.13E−06 | 0.970860992 | 1 | 0.98504975 |
| Eif5 | 1.08E−05 | 0.970620605 | 1 | 0.98497564 |
| Fubp1 | 4.54E−06 | 0.966336869 | 1 | 0.98365394 |
| Mrpl46 | 3.30E−05 | 0.961838021 | 1 | 0.98226608 |
| Ppie | 1.28E−05 | 0.952551811 | 1 | 0.97940089 |
| env | 0.000112971 | 0.946351241 | 1 | 0.97748842 |
| C1qc | 0.000820779 | 0.942980747 | 1 | 0.97645274 |
| Tox | 0.007039359 | 0.964062403 | 0.99044691 | 0.97644539 |
| Dync1li1 | 5.91E−06 | 0.940629338 | 1 | 0.97572241 |
| Sap130 | 5.37E−06 | 0.925539676 | 1 | 0.97106679 |
| Mphosph10 | 1.33E−05 | 0.923645066 | 1 | 0.97048229 |
| Rbm42 | 9.15E−06 | 0.919063903 | 1 | 0.96906884 |
| Rrp8 | 4.13E−06 | 0.918762391 | 1 | 0.96897579 |
| Meaf6 | 5.46E−05 | 0.916416448 | 1 | 0.96825229 |
| Acsl4 | 2.90E−06 | 0.914497025 | 1 | 0.96765979 |
| Kat7 | 3.67E−05 | 0.909595417 | 1 | 0.96614769 |
| Hcfc1 | 4.90E−07 | 0.901141106 | 1 | 0.96353907 |
| Ccar1 | 1.49E−06 | 0.896958769 | 1 | 0.9622487 |
| Rbm34 | 4.09E−05 | 0.895035417 | 1 | 0.96165552 |
| Dnajc9 | 5.16E−05 | 0.891794075 | 1 | 0.96065553 |
| Sdcbp | 5.96E−05 | 0.87963929 | 1 | 0.95690547 |
| Cdadc1 | 0.000339578 | 0.881826719 | 0.988291269 | 0.94955557 |
| Cacybp | 3.38E−05 | 0.836885361 | 1 | 0.94371444 |
| Jade2 | 4.26E−06 | 0.814781312 | 1 | 0.9368945 |
| Tox4; Tox3 | 1.98E−05 | 0.811732196 | 1 | 0.93595385 |
| Dlst | 0.000103907 | 0.941064348 | 0.938456667 | 0.93366863 |
| Utp14a | 3.20E−06 | 0.792470802 | 1 | 0.93001104 |
| Rpl36; Gm8973 | 0.002692672 | 0.855324089 | 0.969029421 | 0.92818855 |
| Pusl1 | 1.19E−05 | 0.776119274 | 1 | 0.92496615 |
| Acad9 | 7.35E−06 | 0.84555418 | 0.959445096 | 0.91858808 |
| Prrc2a | 7.11E−07 | 0.862140923 | 0.9481517 | 0.91596382 |
| Fxr1 | 1.59E−05 | 0.924066561 | 0.918643828 | 0.91484188 |
| Srrt | 2.30E−06 | 0.95280801 | 0.903230603 | 0.91314348 |
| Ikbkap | 1.13E−06 | 0.736904582 | 1 | 0.91286718 |
| Rpl37a | 0.001273114 | 0.731210374 | 1 | 0.91111792 |
| Cad | 2.65E−07 | 0.71384941 | 1 | 0.90575396 |
| Prrc2c | 7.52E−07 | 0.709944848 | 1 | 0.90454929 |
| Dmap1 | 6.59E−06 | 0.708606731 | 1 | 0.90413647 |
| Zfp219 | 8.26E−06 | 0.83639774 | 0.939721598 | 0.9022424 |
| Nusap1 | 2.24E−05 | 0.9664066 | 0.87676912 | 0.89919956 |
| Kntc1 | 2.82E−06 | 0.686171999 | 1 | 0.89721466 |
| Cdc73 | 4.06E−05 | 0.885704413 | 0.90816719 | 0.89582432 |
| Zwilch | 6.62E−05 | 0.729047997 | 0.977711957 | 0.8951649 |
| Rpl36a | 0.000922687 | 0.678673564 | 1 | 0.89490665 |
| Dhx30; mKIAA0890 | 2.07E−06 | 0.892053581 | 0.896902211 | 0.89006074 |
| Aldh18a1 | 9.69E−06 | 0.701787119 | 0.97877897 | 0.88748521 |
| Pno1 | 0.000115928 | 0.987554158 | 0.845302129 | 0.88415384 |

TABLE 7-continued

MiST analysis following Tox immunoprecipitation and mass spectrometry in EL4 cells

| Protein ID | Abundance | Reproducibility | Specificity | MiST Score |
|---|---|---|---|---|
| Metap2 | 1.54E−05 | 0.926625599 | 0.868116476 | 0.88099441 |
| Ogdh | 1.34E−05 | 0.850630425 | 0.901560078 | 0.88047353 |
| Ptcd3 | 1.85E−06 | 0.630909777 | 1 | 0.8801646 |
| Myo6 | 5.25E−07 | 0.630014089 | 1 | 0.87988825 |
| Kifc5b; Kifc1 | 1.73E−06 | 0.629935342 | 1 | 0.87986396 |
| Ash2l | 4.44E−06 | 0.628609744 | 1 | 0.87945499 |
| Hs2st1 | 6.47E−06 | 0.628232302 | 1 | 0.87933855 |
| Cd2ap | 5.85E−07 | 0.627669345 | 1 | 0.87916483 |
| Ing2 | 2.44E−05 | 0.625185331 | 1 | 0.87839858 |
| Gm10094; Sap18 | 2.26E−05 | 0.624688907 | 1 | 0.8782454 |
| Dido1 | 3.41E−07 | 0.623916753 | 1 | 0.87800704 |
| Eif5b | 7.46E−06 | 0.771388601 | 0.933258429 | 0.87775456 |
| Snx9 | 5.29E−06 | 0.621064905 | 1 | 0.87712719 |
| Mars | 3.23E−07 | 0.619389585 | 1 | 0.87661027 |
| Wdhd1 | 1.64E−06 | 0.6193885 | 1 | 0.87660994 |
| Dlgap5 | 6.65E−06 | 0.809596572 | 0.91381838 | 0.87621651 |
| Tagln2 | 1.75E−05 | 0.615745876 | 1 | 0.87548618 |
| Rrp1b | 4.86E−06 | 0.954558871 | 0.847338617 | 0.87536917 |
| Ttc37 | 2.58E−07 | 0.61392652 | 1 | 0.87492475 |
| Rif1 | 1.07E−07 | 0.611495657 | 1 | 0.87417476 |
| Afg3l1 | 2.15E−06 | 0.609855951 | 1 | 0.87366887 |
| Safb; Safb2; mKIAA0138 | 3.18E−06 | 0.608864164 | 1 | 0.87336288 |
| Cdc23 | 6.55E−06 | 0.757918965 | 0.930696669 | 0.87184265 |
| Cdc27 | 6.71E−06 | 0.597218956 | 1 | 0.86977001 |
| Terf2ip | 2.33E−05 | 0.5954903 | 1 | 0.86923676 |
| Eif4h; mKIAA0038 | 1.07E−05 | 0.595140398 | 1 | 0.86912873 |
| Ppp1r10 | 1.37E−05 | 0.650009672 | 0.973612315 | 0.86796854 |
| Trip12 | 1.40E−06 | 0.585400125 | 1 | 0.86612351 |
| Eif4g2 | 4.84E−06 | 0.886817017 | 0.864276373 | 0.86607978 |
| Zfr | 2.44E−06 | 0.991149322 | 0.816622646 | 0.86560231 |
| Utp18 | 1.83E−05 | 0.582259088 | 1 | 0.86515451 |
| Cdk9 | 1.60E−05 | 0.580704761 | 1 | 0.86467494 |
| Sltm | 2.12E−06 | 0.987658334 | 0.81563826 | 0.86385042 |
| Taf6 | 1.15E−06 | 0.577778572 | 1 | 0.86377203 |
| Ddx55 | 2.21E−06 | 0.57441018 | 1 | 0.86273279 |
| Chtop | 0.000478777 | 0.936415926 | 0.836704966 | 0.86248488 |
| Tsr1 | 5.30E−06 | 0.961967696 | 0.82388032 | 0.86157412 |
| Anln | 4.57E−07 | 0.567265827 | 1 | 0.86052853 |
| Tpm4 | 0.000138206 | 0.979007906 | 0.812367381 | 0.8589401 |
| Thoc2 | 1.60E−06 | 0.899672521 | 0.847976345 | 0.85887224 |
| Dap3 | 2.69E−06 | 0.56146138 | 1 | 0.8587377 |
| Larp7 | 9.12E−06 | 0.896409901 | 0.848957867 | 0.85853851 |
| Trim21 | 4.56E−06 | 0.559858906 | 1 | 0.8582433 |
| Pdlim1 | 1.21E−05 | 0.559458022 | 1 | 0.85811966 |
| Snrpb2 | 7.46E−05 | 0.558234995 | 1 | 0.85774269 |
| Pml | 8.97E−06 | 0.557463864 | 1 | 0.85750438 |
| Hsd17b10 | 1.27E−05 | 0.557178512 | 1 | 0.85741636 |
| Mrpl3 | 7.04E−05 | 0.554806065 | 1 | 0.85668474 |
| Utp11l | 4.22E−05 | 0.553063587 | 1 | 0.85614696 |
| Rbm28 | 8.77E−06 | 0.958473436 | 0.815373315 | 0.85466442 |
| Mcm5 | 4.18E−06 | 0.756949241 | 0.899750816 | 0.85032976 |
| Cnot1 | 5.57E−07 | 0.931138332 | 0.821294043 | 0.85028939 |
| Tmem214 | 1.26E−06 | 0.532242113 | 1 | 0.84972267 |
| Mrto4; mg684 | 0.000165982 | 0.997015257 | 0.789906046 | 0.8490986 |
| Orc3 | 7.41E−07 | 0.527933369 | 1 | 0.84839329 |
| Tceb1 | 0.000119597 | 0.950033883 | 0.809194155 | 0.84782535 |
| Supt6h; Supt6 | 2.72E−07 | 0.524473174 | 1 | 0.84732571 |
| Trrap | 9.36E−08 | 0.524472849 | 1 | 0.84732561 |
| Cdc16 | 4.84E−06 | 0.524245254 | 1 | 0.84725542 |
| Dhx29 | 5.88E−07 | 0.927947738 | 0.818299003 | 0.84725187 |
| Arhgef2 | 1.33E−05 | 0.942704392 | 0.811232435 | 0.84696061 |
| Cpt1a | 7.71E−07 | 0.522073805 | 1 | 0.84658544 |
| Tmem160 | 3.49E−05 | 0.939944857 | 0.811736048 | 0.84645457 |
| Wdr82 | 0.000129966 | 0.950914848 | 0.806640245 | 0.84634649 |
| Ccnk | 1.18E−05 | 0.974529842 | 0.795224257 | 0.84580594 |
| Spty2d1 | 1.04E−05 | 0.847769677 | 0.852135293 | 0.84570971 |
| Skap2 | 4.76E−06 | 0.515638907 | 1 | 0.8446001 |
| Copg1 | 3.36E−06 | 0.514269675 | 1 | 0.84417764 |
| Nop2 | 8.30E−05 | 0.981097554 | 0.789110499 | 0.84364166 |
| Orc1 | 1.58E−06 | 0.866076349 | 0.839401153 | 0.84262843 |
| Gnl2 | 7.98E−06 | 0.893856202 | 0.826736349 | 0.84251754 |
| Mark2 | 2.81E−06 | 0.891483689 | 0.826376998 | 0.84153918 |
| Zmym4 | 1.92E−06 | 0.502805309 | 1 | 0.84064053 |
| Rps6ka3; Rps6ka2; Rps6ka1 | 1.04E−06 | 0.502780979 | 1 | 0.84063302 |
| Nob1 | 2.40E−05 | 0.955457461 | 0.796030216 | 0.84047411 |
| Nop14 | 1.27E−06 | 0.500778368 | 1 | 0.84001516 |

TABLE 7-continued

MiST analysis following Tox immunoprecipitation and mass spectrometry in EL4 cells

| Protein ID | Abundance | Reproducibility | Specificity | MiST Score |
|---|---|---|---|---|
| Sptbn1 | 1.19E−05 | 0.99637859 | 0.776825259 | 0.83993424 |
| Sptbn1 | 1.09E−05 | 0.99637859 | 0.776825259 | 0.83993423 |
| Dnajb11 | 2.91E−05 | 0.78316614 | 0.871540193 | 0.83907994 |
| Dynll2; Dynll1; BC048507 | 0.00029675 | 0.495868366 | 1 | 0.83850204 |
| Nsf | 2.87E−06 | 0.807738025 | 0.859490281 | 0.83840061 |
| Dnajb6 | 2.48E−05 | 0.944187671 | 0.796374426 | 0.837233 |
| Lsg1 | 2.90E−06 | 0.885849996 | 0.82166613 | 0.83657167 |
| Ddx23 | 7.90E−06 | 0.836626288 | 0.842768413 | 0.83585053 |
| Rpl28 | 0.001902351 | 0.980700719 | 0.777371305 | 0.83548273 |
| Polr2b | 7.04E−07 | 0.485505971 | 1 | 0.83530316 |
| Zcchc8 | 2.87E−06 | 0.482855959 | 1 | 0.83448557 |
| Rrbp1 | 1.36E−06 | 0.674725849 | 0.913247209 | 0.83421327 |
| Camk2d; Camk2b; Camk2a; Camk2g | 5.81E−06 | 0.824347731 | 0.845865579 | 0.83418535 |
| Sugp1 | 7.71E−06 | 0.905766757 | 0.806544371 | 0.8323505 |
| Atxn2 | 2.51E−06 | 0.831471454 | 0.83822819 | 0.83114771 |
| Gm20517; Med20 | 2.20E−05 | 0.471845808 | 1 | 0.83108872 |
| Samd1 | 2.47E−06 | 0.886481 | 0.810857752 | 0.8293571 |
| Ap3m1 | 1.64E−05 | 0.981843551 | 0.767410738 | 0.82899602 |
| Sorbs1 | 1.52E−05 | 0.99675664 | 0.760480869 | 0.82884666 |
| Csrp1 | 5.52E−05 | 0.965511262 | 0.772915934 | 0.82773112 |
| Parp2 | 2.87E−06 | 0.459979352 | 1 | 0.82742745 |
| Aars | 4.49E−06 | 0.459033739 | 1 | 0.82713571 |
| Sfxn1 | 3.71E−05 | 0.95355686 | 0.77726522 | 0.8270242 |
| Ipo4 | 1.65E−06 | 0.940326502 | 0.782271137 | 0.82637363 |
| Tfip11 | 5.43E−06 | 0.971785661 | 0.767188433 | 0.82574041 |
| Baz1a | 4.09E−07 | 0.453669869 | 1 | 0.82548077 |
| Tbl1x | 5.34E−06 | 0.453089015 | 1 | 0.82530159 |
| Stau1 | 1.96E−05 | 0.951217088 | 0.775707875 | 0.82523463 |
| Cpsf3 | 1.17E−05 | 0.871469352 | 0.811340132 | 0.82505634 |
| Ep400 | 2.31E−06 | 0.451316601 | 1 | 0.82475473 |
| Pds5a | 1.76E−06 | 0.865424777 | 0.813121426 | 0.82441239 |
| Chd4; Chd5 | 4.94E−07 | 0.879353863 | 0.804549943 | 0.82283408 |
| Lmnb1 | 1.67E−05 | 0.963960656 | 0.765938606 | 0.82246945 |
| Ddx18 | 4.72E−05 | 0.985664842 | 0.755986781 | 0.82234395 |
| Nmt1 | 6.96E−06 | 0.947674717 | 0.771640514 | 0.82135341 |
| Otud4 | 9.24E−07 | 0.993001973 | 0.74665444 | 0.81820999 |
| Supt16; Supt16h | 4.95E−06 | 0.800114911 | 0.832565622 | 0.81759154 |
| Ap3d1 | 1.02E−06 | 0.426530242 | 1 | 0.81710738 |
| Lrrfip1 | 8.42E−06 | 0.995647066 | 0.743479192 | 0.81684946 |
| Tdrd3 | 8.62E−06 | 0.626723663 | 0.907018501 | 0.81513336 |
| Rpl3 | 0.000661388 | 0.924253385 | 0.77253894 | 0.81474701 |
| Dnmt1 | 4.05E−06 | 0.928501083 | 0.770040821 | 0.81434115 |
| Rpa2 | 0.000292057 | 0.977172115 | 0.747082313 | 0.81362105 |
| Ahnak | 6.22E−06 | 0.496666549 | 0.961324756 | 0.8122343 |
| Wrnip1 | 3.59E−06 | 0.409809537 | 1 | 0.81194856 |
| Ythdf1 | 3.50E−05 | 0.832974645 | 0.808731327 | 0.81139129 |
| Isy1 | 3.22E−05 | 0.855961542 | 0.797370003 | 0.81069512 |
| Ckap5 | 1.02E−06 | 0.924162851 | 0.765380454 | 0.80980793 |
| Rpl8 | 0.003543828 | 0.995291482 | 0.732772836 | 0.80942151 |
| Ssb | 3.74E−05 | 0.807156754 | 0.817142453 | 0.80919162 |
| Ptpn11 | 4.22E−05 | 0.395706865 | 1 | 0.80759769 |
| Srsf5 | 0.000504669 | 0.996402216 | 0.729368308 | 0.80741225 |
| Pds5b | 2.47E−06 | 0.845219305 | 0.797180476 | 0.80725072 |
| Add3 | 3.22E−06 | 0.394079363 | 1 | 0.80709533 |
| Rps23 | 0.004789919 | 0.996609359 | 0.72833887 | 0.80679601 |
| Tpx2 | 1.91E−05 | 0.991982306 | 0.727175833 | 0.80454272 |
| Dst | 1.97E−08 | 0.384586607 | 1 | 0.80416651 |
| LRWD1 | 9.87E−06 | 0.965297093 | 0.737377833 | 0.80330305 |
| Tra2b | 3.65E−05 | 0.381485157 | 1 | 0.80320983 |
| Nup98 | 5.87E−07 | 0.381392182 | 1 | 0.80318093 |
| Yars | 2.51E−06 | 0.378644862 | 1 | 0.80233331 |
| Rpl13 | 0.003758422 | 0.953335588 | 0.739309478 | 0.80095907 |
| Zc3h11a | 1.22E−05 | 0.957200596 | 0.737101828 | 0.80061585 |
| Dnaja2 | 0.000331734 | 0.945619771 | 0.741883128 | 0.80032235 |
| Rftn1 | 4.96E−06 | 0.37048216 | 1 | 0.79981489 |
| Rpl5 | 0.001032564 | 0.983739918 | 0.722948665 | 0.79910797 |
| Paf1 | 9.64E−06 | 0.572696811 | 0.906814851 | 0.79832485 |
| Rpl7a | 0.004612374 | 0.888117505 | 0.764126777 | 0.79785493 |
| Rars | 4.81E−06 | 0.980265049 | 0.721134163 | 0.79678589 |
| Rpl14; Rpl14-ps1 | 0.00405256 | 0.996828786 | 0.713527182 | 0.79670576 |
| Rcc1 | 2.79E−05 | 0.986444142 | 0.716716462 | 0.79566408 |
| Eif2a | 8.58E−05 | 0.991574735 | 0.711714971 | 0.79381879 |
| Usp10 | 3.26E−06 | 0.612760787 | 0.880787897 | 0.79284402 |
| Cycs | 8.14E−05 | 0.95656664 | 0.725869726 | 0.79272095 |
| Racgap1 | 8.29E−06 | 0.868451125 | 0.765424107 | 0.79264915 |
| Luzp1; mFLJ00226 | 7.26E−06 | 0.855975554 | 0.770439479 | 0.79223815 |

TABLE 7-continued

MiST analysis following Tox immunoprecipitation and mass spectrometry in EL4 cells

| Protein ID | Abundance | Reproducibility | Specificity | MiST Score |
|---|---|---|---|---|
| Acad12; Acad10 | 5.24E−06 | 0.624485107 | 0.874367539 | 0.79206011 |
| Ppan | 4.70E−05 | 0.958864454 | 0.723147795 | 0.79156378 |
| Rcc2 | 3.74E−05 | 0.958317871 | 0.721819573 | 0.79048457 |
| Terf2 | 6.86E−06 | 0.994482517 | 0.705473366 | 0.79043678 |
| Slc25a11 | 2.29E−05 | 0.955832276 | 0.71978884 | 0.78832552 |
| Xrn2 | 8.55E−06 | 0.804357991 | 0.786548604 | 0.78735556 |
| Numa1 | 1.43E−06 | 0.775346939 | 0.799449319 | 0.7872483 |
| Smarca4 | 6.52E−07 | 0.594128673 | 0.87920895 | 0.78601305 |
| Wdr36 | 3.46E−06 | 0.886428331 | 0.746876068 | 0.78548077 |
| Brd1 | 3.10E−06 | 0.320995465 | 1 | 0.78454675 |
| Eif3h | 0.000105475 | 0.95611456 | 0.713642985 | 0.78420006 |
| Rpl26 | 0.004987151 | 0.982738255 | 0.700103828 | 0.78316213 |
| Rpl32 | 0.000129703 | 0.314674271 | 1 | 0.78259723 |
| Bag6 | 1.40E−06 | 0.764554448 | 0.796763691 | 0.78207747 |
| BC005685 | 0.000233668 | 0.958882994 | 0.704836126 | 0.77901778 |
| Rpl21 | 0.005659709 | 0.996976282 | 0.68672457 | 0.77838738 |
| Csnk2a2 | 2.87E−05 | 0.912905181 | 0.724510614 | 0.77831808 |
| Ap3b1 | 4.13E−06 | 0.696401697 | 0.820933553 | 0.777619 |
| Slc25a3 | 6.71E−05 | 0.974819277 | 0.695545132 | 0.77756454 |
| Lztfl1 | 6.33E−05 | 0.893691609 | 0.730210392 | 0.77629758 |
| Polb | 8.62E−05 | 0.985754979 | 0.688733403 | 0.77626913 |
| Rbm15 | 8.04E−06 | 0.986935475 | 0.687188453 | 0.77557381 |
| Gtpbp4 | 4.52E−05 | 0.968179949 | 0.695213941 | 0.77528894 |
| Acaca | 2.64E−07 | 0.28987807 | 1 | 0.77494608 |
| Xrcc5 | 2.92E−05 | 0.736617118 | 0.798838897 | 0.77488071 |
| Thoc1 | 9.29E−06 | 0.998582563 | 0.680694153 | 0.77471538 |
| Ywhah | 6.28E−05 | 0.819130813 | 0.760568906 | 0.77410439 |
| Sin3a | 5.49E−06 | 0.284352165 | 1 | 0.77324121 |
| Cd3eap | 0.000223715 | 0.993164344 | 0.680332451 | 0.77279703 |
| Tcof1 | 0.00014243 | 0.983538866 | 0.681274607 | 0.77047265 |
| Acin1 | 2.27E−05 | 0.611809866 | 0.847722498 | 0.76988408 |
| Hnrnph1; Hnrnph2 | 8.52E−05 | 0.928427693 | 0.704145016 | 0.76914675 |
| Elmo1 | 5.93E−06 | 0.595056364 | 0.854130353 | 0.76910767 |
| Srrm2 | 1.10E−06 | 0.860539396 | 0.733828988 | 0.76854934 |
| Rpl34; Gm2178 | 0.006579136 | 0.936739749 | 0.6989711 | 0.76820321 |
| Pfkl | 3.37E−06 | 0.50075397 | 0.894304717 | 0.76755247 |
| Rps24 | 0.001473736 | 0.996056637 | 0.671176071 | 0.76742005 |
| Zw10 | 2.83E−06 | 0.582363686 | 0.856640411 | 0.76691225 |
| Umps | 2.41E−06 | 0.791674561 | 0.761491121 | 0.76626515 |
| Emg1 | 7.66E−05 | 0.938993224 | 0.69516591 | 0.76625122 |
| Gm20425; Srprb | 5.88E−06 | 0.920115777 | 0.703207581 | 0.76593919 |
| Hp1bp3 | 1.65E−05 | 0.778969839 | 0.766410332 | 0.76571761 |
| Slc25a4 | 0.00018643 | 0.959277443 | 0.684305074 | 0.76506495 |
| Srp72 | 3.55E−05 | 0.872294688 | 0.722648861 | 0.76451231 |
| Kdm1a | 3.25E−06 | 0.739627036 | 0.782081972 | 0.76432216 |
| Eif3a | 1.17E−05 | 0.794796627 | 0.756833673 | 0.76403573 |
| Soat1 | 5.75E−06 | 0.249348604 | 1 | 0.76244156 |
| Raver1 | 4.89E−05 | 0.838762089 | 0.733939934 | 0.76190672 |
| Pnn | 7.35E−05 | 0.680517596 | 0.805150749 | 0.76189942 |
| Leo1 | 7.69E−06 | 0.974418555 | 0.67071599 | 0.76041992 |
| Abcf1 | 1.12E−05 | 0.747206829 | 0.772811648 | 0.7603059 |
| Dld | 1.87E−05 | 0.898163866 | 0.704258174 | 0.75988663 |
| Thoc6 | 3.97E−05 | 0.994320809 | 0.660795086 | 0.75975968 |
| Gatad2a | 1.98E−05 | 0.907980336 | 0.69956541 | 0.75969838 |
| Rsl1d1 | 0.000211084 | 0.983596495 | 0.664844248 | 0.75922767 |
| Rpl6 | 0.003170388 | 0.972759137 | 0.669122251 | 0.75883427 |
| Pabpn1 | 8.22E−05 | 0.992345149 | 0.660318188 | 0.75882346 |
| Cwc27 | 1.14E−05 | 0.434600192 | 0.910094271 | 0.75796599 |
| Nol7 | 0.000127902 | 0.971882803 | 0.666316229 | 0.7566222 |
| Abcf2 | 2.89E−05 | 0.917128335 | 0.689663582 | 0.75573306 |
| Rpl23 | 0.002902851 | 0.994037438 | 0.654982555 | 0.75570476 |
| Bclaf1 | 6.73E−05 | 0.871911775 | 0.709928876 | 0.75567469 |
| Cwc15 | 9.35E−05 | 0.814297568 | 0.735852396 | 0.75566996 |
| Rbm25 | 9.24E−06 | 0.601057173 | 0.830681539 | 0.75488473 |
| Pop1 | 2.18E−06 | 0.90562992 | 0.692518143 | 0.75414212 |
| Ap2a1 | 2.47E−06 | 0.845966576 | 0.718835441 | 0.75377497 |
| Actr5 | 9.00E−06 | 0.979090586 | 0.657746867 | 0.75297093 |
| Rrp1 | 9.00E−06 | 0.975954634 | 0.659046694 | 0.75289444 |
| Top3b | 8.10E−07 | 0.541258742 | 0.853717037 | 0.75222613 |
| Rpl10; Rpl10l | 0.001088488 | 0.94373055 | 0.672532396 | 0.75220336 |
| Ebna1bp2 | 9.40E−05 | 0.983892308 | 0.654202525 | 0.75202323 |
| Hist1h3i; Hist1h3a; H3f3a | 0.004003116 | 0.949510377 | 0.6695937 | 0.75198947 |
| Gatad2b | 1.65E−05 | 0.862564841 | 0.708220692 | 0.7516196 |

TABLE 7-continued

| MiST analysis following Tox immunoprecipitation and mass spectrometry in EL4 cells | | | | |
| --- | --- | --- | --- | --- |
| Protein ID | Abundance | Reproducibility | Specificity | MiST Score |
| Ccdc86 | 3.82E−05 | 0.963796654 | 0.661951586 | 0.75113484 |
| Cnot10 | 8.51E−06 | 0.946002803 | 0.669104067 | 0.75054782 |
| Ymel11 | 1.45E−05 | 0.987677897 | 0.649846956 | 0.75020494 |
| Paxbp1 | 1.83E−06 | 0.516171307 | 0.861879886 | 0.75008163 |

TABLE 8

| Epigenetic-modulating genes Gene ID |
| --- |
| 44M2.3 |
| A1CF |
| AARS2 |
| AARSD1 |
| ABCE1 |
| ABCF1 |
| ABCF2 |
| ABCF3 |
| ABT1 |
| ACAD8 |
| ACAD9 |
| ACADL |
| ACADM |
| ACADS |
| ACADSB |
| ACADVL |
| ACAP1 |
| ACAP2 |
| ACAP3 |
| ACAT1 |
| ACIN1 |
| ACOX1 |
| ACOX2 |
| ACOX3 |
| ACOXL |
| ACRC |
| ACTB |
| ACTL6A |
| ACTL6B |
| ACTR |
| ACTR3B |
| ACTR5 |
| ACTR6 |
| ACTR8 |
| ADAD1 |
| ADAD2 |
| ADAP1 |
| ADAP2 |
| ADAR |
| ADARB1 |
| ADARB2 |
| ADAT1 |
| ADNP |
| AEBP2 |
| AES |
| AFF1 |
| AFF2 |
| AFF3 |
| AFF4 |
| AGAP1 |
| AGAP2 |
| AGAP3 |
| AGAP4 |
| AGAP5 |
| AGAP6 |
| AGAP7P |
| AGFG1 |
| AGFG2 |
| AICDA |
| AIMP1 |
| AIRE |
| AJUBA |
| AKAP1 |

TABLE 8-continued

| Epigenetic-modulating genes Gene ID |
| --- |
| ALKBH1 |
| ALKBH8 |
| ALS2 |
| ALX1 |
| ALX3 |
| ALX4 |
| ALYREF |
| ANGEL1 |
| ANGEL2 |
| ANHX |
| ANKRD27 |
| ANKRD32 |
| ANKUB1 |
| ANO9 |
| ANP32A |
| ANP32B |
| ANP32E |
| AOX1 |
| APBB1 |
| APEX1 |
| APITD1 |
| APOBEC1 |
| APOBEC2 |
| APOBEC3A |
| APOBEC3B |
| APOBEC3C |
| APOBEC3D |
| APOBEC3F |
| APOBEC3G |
| APOBEC3H |
| APPL1 |
| APPL2 |
| APTX |
| AQR |
| AR |
| ARAP1 |
| ARAP2 |
| ARAP3 |
| ARFGAP1 |
| ARFGAP2 |
| ARFGAP3 |
| ARFGEF1 |
| ARFGEF2 |
| ARGFX |
| ARHGAP5 |
| ARID1A |
| ARID1B |
| ARID2 |
| ARID3A |
| ARID3B |
| ARID3C |
| ARID4A |
| ARID4B |
| ARID5A |
| ARID5B |
| ARL14EP |
| ARL14EPL |
| ARL6IP4 |
| ARNT |
| ARNT2 |
| ARNTL |
| ARNTL2 |
| ARRB1 |

TABLE 8-continued

| Epigenetic-modulating genes Gene ID |
| --- |
| ARX |
| ASAP1 |
| ASAP2 |
| ASAP3 |
| ASCL1 |
| ASCL2 |
| ASCL3 |
| ASCL4 |
| ASCL5 |
| ASF1A |
| ASF1B |
| ASH1L |
| ASH2L |
| ASXL1 |
| ASXL2 |
| ASXL3 |
| ATAD2 |
| ATAD2B |
| ATAD5 |
| ATAT1 |
| ATF2 |
| ATF7 |
| ATF7IP |
| ATM |
| ATN1 |
| ATOH1 |
| ATOH7 |
| ATOH8 |
| ATP5A1 |
| ATP5B |
| ATP6V1A |
| ATP6V1B1 |
| ATP6V1B2 |
| ATR |
| ATRX |
| ATXN3 |
| ATXN3L |
| ATXN7 |
| ATXN7L3 |
| AURKA |
| AURKB |
| AURKC |
| BABAM1 |
| BACE2 |
| BACH2 |
| BAHCC1 |
| BAHD1 |
| BANP |
| BAP1 |
| BARD1 |
| BARHL1 |
| BARHL2 |
| BARX1 |
| BARX2 |
| BAZ1A |
| BAZ1B |
| BAZ2A |
| BAZ2B |
| BCL11A |
| BCL11B |
| BCLAF1 |
| BCOR |
| BCORL1 |
| BDP1 |
| BHLHA15 |
| BHLHE22 |
| BHLHE23 |
| BHMG1 |
| BICC1 |
| BLM |
| BMI1 |
| BMS1 |
| BNC1 |
| BNC2 |
| BOLL |
| BPTF |
| BRCA1 |

TABLE 8-continued

| Epigenetic-modulating genes Gene ID |
| --- |
| BRCA2 |
| BRCC3 |
| BRD1 |
| BRD2 |
| BRD3 |
| BRD4 |
| BRD7 |
| BRD8 |
| BRD9 |
| BRDT |
| BRE |
| BRF1 |
| BRF2 |
| BRIP1 |
| BRIX1 |
| BRMS1 |
| BRMS1L |
| BRPF1 |
| BRPF3 |
| BRWD1 |
| BRWD3 |
| BSX |
| BTBD8 |
| BTF3 |
| BTF3L4 |
| BUB1 |
| BZW1 |
| BZW2 |
| C11orf30 |
| C12orf50 |
| C14orf169 |
| C17orf49 |
| C1D |
| C3orf67 |
| CABIN1 |
| CAMTA1 |
| CAMTA2 |
| CARD8 |
| CARHSP1 |
| CARM1 |
| CARMIL2 |
| CARMIL3 |
| CASZ1 |
| CBX1 |
| CBX2 |
| CBX3 |
| CBX4 |
| CBX5 |
| CBX6 |
| CBX7 |
| CBX8 |
| CC2D1A |
| CC2D1B |
| CCDC101 |
| CCDC108 |
| CCDC130 |
| CCDC94 |
| CCNO |
| CD2BP2 |
| CDC45 |
| CDC5L |
| CDC6 |
| CDC73 |
| CDCA4 |
| CDCA5 |
| CDIP1 |
| CDK1 |
| CDK17 |
| CDK2 |
| CDK2AP1 |
| CDK2AP2 |
| CDK3 |
| CDK5 |
| CDK7 |
| CDK9 |
| CDKN2AIP |
| CDKN2AIPNL |

TABLE 8-continued

Epigenetic-modulating genes
Gene ID

TABLE 8-continued

Epigenetic-modulating genes
Gene ID

| | |
|---|---|
| CDR2 | CSNK2A1 |
| CDX1 | CSRP2BP |
| CDX2 | CSTF2 |
| CDX4 | CSTF2T |
| CDY1 | CSTF3 |
| CDY1B | CT45A1 |
| CDY2A | CT45A10 |
| CDY2B | CT45A2 |
| CDYL | CT45A3 |
| CDYL2 | CT45A5 |
| CEBBP | CT45A6 |
| CEBPA | CT45A7 |
| CEBPB | CT45A8 |
| CEBPD | CT45A9 |
| CEBPE | CT47A1 |
| CECR2 | CT47B1 |
| CENPA | CTBP1 |
| CENPC | CTBP2 |
| CFAP20 | CTCF |
| CHAF1A | CTCFL |
| CHAF1B | CTGLF11P |
| CHD1 | CTIF |
| CHD1L | CTR9 |
| CHD2 | CTTN |
| CHD3 | CUL1 |
| CHD4 | CUL2 |
| CHD5 | CUL3 |
| CHD6 | CUL4A |
| CHD7 | CUL4B |
| CHD8 | CUL5 |
| CHD9 | CUX1 |
| CHEK1 | CUX2 |
| CHERP | CWC22 |
| CHRAC1 | CXorf23 |
| CHTF18 | CXXC1 |
| CHTOP | CYB5R1 |
| CHUK | CYB5R2 |
| CIITA | CYB5R3 |
| CIR1 | CYB5R4 |
| CIT | CYB5RL |
| CLNS1A | DACH1 |
| CLOCK | DACH2 |
| CLPX | DAPK3 |
| CLUH | DARS |
| CMIP | DARS2 |
| CMSS1 | DAXX |
| CNBP | DAZ1 |
| CNOT6 | DAZ3 |
| CNOT6L | DAZ4 |
| COA1 | DAZL |
| COIL | DBP |
| COPS5 | DBX1 |
| CORT | DBX2 |
| CPEB1 | DCC |
| CPEB2 | DCLRE1A |
| CPEB3 | DCLRE1B |
| CPEB4 | DCLRE1C |
| CPSF1 | DCP1A |
| CPSF2 | DCP1B |
| CPSF3 | DDB1 |
| CPSF3L | DDB2 |
| CPSF4 | DDIT3 |
| CPSF4L | DDN |
| CPSF6 | DDX11 |
| CPSF7 | DDX11L8 |
| CRAMP1 | DDX12P |
| CRB2 | DDX21 |
| CREB5 | DDX50 |
| CREBBP | DEAF1 |
| CRLF3 | DEDD |
| CRTC1 | DEDD2 |
| CRTC2 | DEF6 |
| CRTC3 | DEK |
| CRX | DENND6A |
| CRY1 | DENND6B |
| CRY2 | DENR |
| CSDC2 | DEPDC1 |

TABLE 8-continued

| Epigenetic-modulating genes Gene ID |
| --- |
| DEPDC1B |
| DEPDC4 |
| DEPDC5 |
| DEPDC7 |
| DICER1 |
| DIDO1 |
| DIEXF |
| DKC1 |
| DLX1 |
| DLX2 |
| DLX3 |
| DLX4 |
| DLX5 |
| DLX6 |
| DMAP1 |
| DMBX1 |
| DMC1 |
| DMTF1 |
| DNA2 |
| DNAJC1 |
| DNAJC2 |
| DNASE2 |
| DNASE2B |
| DND1 |
| DNMT1 |
| DNMT3A |
| DNMT3B |
| DNMT3L |
| DNTT |
| DNTTIP2 |
| DOT1 |
| DOT1L |
| DPF1 |
| DPF2 |
| DPF3 |
| DPPA3 |
| DPRX |
| DPY30 |
| DR1 |
| DRAP1 |
| DRGX |
| DROSHA |
| DSCC1 |
| DTX3L |
| DUX1 |
| DUX3 |
| DUX4 |
| DUX4L2 |
| DUX4L3 |
| DUX4L4 |
| DUX4L5 |
| DUX4L6 |
| DUX4L7 |
| DUX4L9 |
| DUX5 |
| DUXA |
| DZIP1 |
| DZIP1L |
| DZIP3 |
| E2F1 |
| E2F2 |
| E2F3 |
| E2F4 |
| E2F5 |
| E2F6 |
| E2F7 |
| E2F8 |
| EARS2 |
| EDA2R |
| EDAR |
| EDC3 |
| EED |
| EEF1A1 |
| EEF1A1P5 |
| EEF1A2 |
| EEF1B2 |
| EEF1D |

TABLE 8-continued

| Epigenetic-modulating genes Gene ID |
| --- |
| EEF1G |
| EEF2 |
| EEFSEC |
| EFCC1 |
| EFL1 |
| EFTUD2 |
| EHF |
| EHMT1 |
| EHMT2 |
| EID1 |
| EID2 |
| EID2B |
| EIF1AX |
| EIF1AY |
| EIF2A |
| EIF2B3 |
| EIF2B5 |
| EIF2S1 |
| EIF2S2 |
| EIF2S3 |
| EIF2S3L |
| EIF3A |
| EIF3B |
| EIF3C |
| EIF3CL |
| EIF3D |
| EIF3E |
| EIF3F |
| EIF3G |
| EIF3H |
| EIF3I |
| EIF3J |
| EIF3L |
| EIF4B |
| EIF4E |
| EIF4E1B |
| EIF4E2 |
| EIF4E3 |
| EIF4G1 |
| EIF4G2 |
| EIF4G3 |
| EIF4H |
| EIF5 |
| EIF5A |
| EIF5A2 |
| EIF5AL1 |
| ELF1 |
| ELF2 |
| ELF3 |
| ELF4 |
| ELF5 |
| ELK1 |
| ELK3 |
| ELK4 |
| ELL |
| ELL2 |
| ELL3 |
| ELMSAN1 |
| ELP2 |
| ELP3 |
| ELP4 |
| ELP5 |
| ELP6 |
| EMC2 |
| EMG1 |
| EMX1 |
| EMX2 |
| EN1 |
| EN2 |
| ENOX1 |
| ENOX2 |
| ENY2 |
| EOMES |
| EP300 |
| EP400 |
| EPAS1 |
| EPC1 |

TABLE 8-continued

Epigenetic-modulating genes
Gene ID

| |
| --- |
| EPC2 |
| EPM2AIP1 |
| EPRS |
| ERAL1 |
| ERBB4 |
| ERCC1 |
| ERCC2 |
| ERCC3 |
| ERCC4 |
| ERCC6 |
| ERCC6L |
| ERCC6L2 |
| ERF |
| ERG |
| ERH |
| ESR1 |
| ESR2 |
| ESRP1 |
| ESRP2 |
| ESRRA |
| ESRRB |
| ESRRG |
| ESX1 |
| ETFA |
| ETFBKMT |
| ETS1 |
| ETS2 |
| ETV1 |
| ETV2 |
| ETV3 |
| ETV3L |
| ETV4 |
| ETV5 |
| ETV6 |
| ETV7 |
| EVX1 |
| EVX2 |
| EWSR1 |
| EXD1 |
| EXO1 |
| EXOSC1 |
| EXOSC10 |
| EXOSC2 |
| EXOSC3 |
| EXOSC4 |
| EXOSC5 |
| EXOSC6 |
| EXOSC7 |
| EXOSC8 |
| EXOSC9 |
| EYA1 |
| EYA2 |
| EYA3 |
| EYA4 |
| EZH1 |
| EZH2 |
| FAM133A |
| FAM133B |
| FAM175A |
| FAM175B |
| FAM200A |
| FAM200B |
| FAM32A |
| FANCM |
| FBL |
| FBLIM1 |
| FBLL1 |
| FBRS |
| FBRSL1 |
| FEV |
| FHL2 |
| FHL3 |
| FHL5 |
| FIGLA |
| FIZ1 |
| FLI1 |
| FMR1 |

TABLE 8-continued

Epigenetic-modulating genes
Gene ID

| |
| --- |
| FOXA1 |
| FOXA2 |
| FOXA3 |
| FOXB1 |
| FOXB2 |
| FOXC1 |
| FOXC2 |
| FOXD1 |
| FOXD2 |
| FOXD3 |
| FOXD4 |
| FOXD4L1 |
| FOXD4L3 |
| FOXD4L4 |
| FOXD4L5 |
| FOXD4L6 |
| FOXE1 |
| FOXE3 |
| FOXF1 |
| FOXF2 |
| FOXG1 |
| FOXH1 |
| FOXI1 |
| FOXI2 |
| FOXI3 |
| FOXJ1 |
| FOXJ2 |
| FOXJ3 |
| FOXK1 |
| FOXK2 |
| FOXL1 |
| FOXL2 |
| FOXM1 |
| FOXN1 |
| FOXO1 |
| FOXO3 |
| FOXO4 |
| FOXO6 |
| FOXP1 |
| FOXP2 |
| FOXP3 |
| FOXP4 |
| FOXQ1 |
| FOXR1 |
| FOXR2 |
| FOXS1 |
| FRG1 |
| FRG1B |
| FUBP1 |
| FUBP3 |
| FUS |
| FXR1 |
| FXR2 |
| G2E3 |
| G3BP1 |
| G3BP2 |
| GABPA |
| GADD45A |
| GADD45B |
| GADD45G |
| GAR1 |
| GATAD1 |
| GATAD2A |
| GATAD2B |
| GBX1 |
| GBX2 |
| GCDH |
| GCFC2 |
| GCH1 |
| GCM1 |
| GCM2 |
| GCN5 |
| GEMIN2 |
| GEN1 |
| GFI1 |
| GFI1B |
| GFM2 |

TABLE 8-continued

| Epigenetic-modulating genes Gene ID |
| --- |
| GIT1 |
| GIT2 |
| GLYR1 |
| GMEB1 |
| GMEB2 |
| GMPPA |
| GNE |
| GNPTAB |
| GON4L |
| GPATCH2 |
| GPATCH2L |
| GPATCH4 |
| GPBP1 |
| GPBP1L1 |
| GPKOW |
| GPN1 |
| GPN2 |
| GPN3 |
| GPR171 |
| GPR34 |
| GPR87 |
| GRHL1 |
| GRHL2 |
| GRHL3 |
| GRSF1 |
| GSC |
| GSC2 |
| GSE1 |
| GSG2 |
| GSPT1 |
| GSPT2 |
| GSX1 |
| GSX2 |
| GTF2A2 |
| GTF2B |
| GTF2E2 |
| GTF2F1 |
| GTF2H1 |
| GTF2H2 |
| GTF2H2C |
| GTF2H3 |
| GTF2H4 |
| GTF2I |
| GTF2IRD1 |
| GTF2IRD2B |
| GTF3C3 |
| GTF3C4 |
| GTF3C5 |
| GTPBP1 |
| GTPBP2 |
| H1FNT |
| H1FOO |
| H1FX |
| H2AFB1 |
| H2AFB2 |
| H2AFJ |
| H2AFV |
| H2AFX |
| H2AFY |
| H2AFY2 |
| H2AFZ |
| H2BFM |
| H2BFS |
| H2BFWT |
| H3F3A |
| H3F3C |
| HABP4 |
| HAT1 |
| HBO1 |
| HCFC1 |
| HCFC2 |
| HCLS1 |
| HDAC1 |
| HDAC10 |
| HDAC11 |
| HDAC2 |
| HDAC3 |

TABLE 8-continued

| Epigenetic-modulating genes Gene ID |
| --- |
| HDAC4 |
| HDAC5 |
| HDAC6 |
| HDAC7 |
| HDAC8 |
| HDAC9 |
| HDGF |
| HDGFL1 |
| HDGFRP2 |
| HDGFRP3 |
| HEATR1 |
| HELLS |
| HELZ |
| HELZ2 |
| HEMK1 |
| HERC1 |
| HESX1 |
| HIF1A |
| HIF1AN |
| HIF3A |
| HILS1 |
| HINFP |
| HINT3 |
| HIRA |
| HIRIP3 |
| HIST1H1A |
| HIST1H1B |
| HIST1H1C |
| HIST1H1D |
| HIST1H1E |
| HIST1H1T |
| HIST1H2AA |
| HIST1H2AB |
| HIST1H2AC |
| HIST1H2AD |
| HIST1H2AG |
| HIST1H2AH |
| HIST1H2AJ |
| HIST1H2BA |
| HIST1H2BB |
| HIST1H2BC |
| HIST1H2BD |
| HIST1H2BH |
| HIST1H2BJ |
| HIST1H2BK |
| HIST1H2BL |
| HIST1H2BM |
| HIST1H2BN |
| HIST1H2BO |
| HIST1H3A |
| HIST1H4A |
| HIST2H2AA3 |
| HIST2H2AB |
| HIST2H2AC |
| HIST2H2BC |
| HIST2H2BD |
| HIST2H2BE |
| HIST2H2BF |
| HIST2H3A |
| HIST2H3PS2 |
| HIST3H2A |
| HIST3H2BB |
| HIST3H3 |
| HIVEP1 |
| HIVEP2 |
| HIVEP3 |
| HJURP |
| HKR1 |
| HLCS |
| HLF |
| HLTF |
| HLX |
| HMG20A |
| HMG20B |
| HMGA1 |
| HMGA2 |
| HMGB1 |

TABLE 8-continued

| Epigenetic-modulating genes Gene ID |
| --- |
| HMGB1P1 |
| HMGB2 |
| HMGB3 |
| HMGB4 |
| HMGN1 |
| HMGN2 |
| HMGN2P46 |
| HMGN3 |
| HMGN4 |
| HMGN5 |
| HMGXB4 |
| HMX2 |
| HMX3 |
| HNF1A |
| HNF1B |
| HNF4A |
| HNF4G |
| HNRNPF |
| HNRNPH1 |
| HNRNPH2 |
| HNRNPH3 |
| HNRNPK |
| HNRNPM |
| HOMEZ |
| HOXA1 |
| HOXA10 |
| HOXA11 |
| HOXA13 |
| HOXA2 |
| HOXA3 |
| HOXA4 |
| HOXA5 |
| HOXA6 |
| HOXA7 |
| HOXA9 |
| HOXB1 |
| HOXB13 |
| HOXB2 |
| HOXB3 |
| HOXB4 |
| HOXB5 |
| HOXB6 |
| HOXB7 |
| HOXB8 |
| HOXB9 |
| HOXC10 |
| HOXC11 |
| HOXC12 |
| HOXC13 |
| HOXC4 |
| HOXC5 |
| HOXC6 |
| HOXC8 |
| HOXC9 |
| HOXD1 |
| HOXD10 |
| HOXD11 |
| HOXD12 |
| HOXD13 |
| HOXD3 |
| HOXD4 |
| HOXD8 |
| HOXD9 |
| HP1BP3 |
| HR |
| HSPA1A |
| HSPA1B |
| HSPBAP1 |
| HTATSF1 |
| HTR2C |
| HUWE1 |
| HYI |
| HYPM |
| ID1 |
| ID2 |
| ID2B |
| ID3 |

TABLE 8-continued

| Epigenetic-modulating genes Gene ID |
| --- |
| ID4 |
| IFI16 |
| IFI35 |
| IGF2BP1 |
| IGF2BP2 |
| IGF2BP3 |
| IKBKAP |
| IKBKG |
| IKZF1 |
| IKZF2 |
| IKZF3 |
| IKZF4 |
| IL1A |
| IL4I1 |
| ILF2 |
| ILF3 |
| IMP3 |
| IMP4 |
| INCENP |
| ING1 |
| ING2 |
| ING3 |
| ING4 |
| ING5 |
| INO80 |
| INO80B |
| INO80C |
| INO80D |
| INO80E |
| INTS6 |
| INTS6L |
| INTS9 |
| IRAK1 |
| IRAK2 |
| IRAK3 |
| IRAK4 |
| IRF1 |
| IRF2 |
| IRF3 |
| IRF4 |
| IRF5 |
| IRF6 |
| IRF7 |
| IRF8 |
| IRF9 |
| IRX1 |
| IRX2 |
| IRX3 |
| IRX4 |
| IRX5 |
| IRX6 |
| ISG15 |
| ISL1 |
| ISL2 |
| ISX |
| IVD |
| IVNS1ABP |
| JADE1 |
| JADE2 |
| JADE3 |
| JAK2 |
| JARID2 |
| JDP2 |
| JMJD1C |
| JMJD4 |
| JMJD6 |
| JMJD7 |
| JMJD8 |
| JUN |
| JUNB |
| JUND |
| KANSL1 |
| KANSL2 |
| KANSL3 |
| KARS |
| KAT2A |
| KAT2B |

TABLE 8-continued

| Epigenetic-modulating genes Gene ID |
| --- |
| KAT5 |
| KAT6A |
| KAT6B |
| KAT7 |
| KAT8 |
| KDM1A |
| KDM1B |
| KDM2A |
| KDM2B |
| KDM3A |
| KDM3B |
| KDM4A |
| KDM4B |
| KDM4C |
| KDM4D |
| KDM4E |
| KDM5A |
| KDM5B |
| KDM5C |
| KDM5D |
| KDM6A |
| KDM6B |
| KDM7A |
| KDM8 |
| KEAP1 |
| KHDRBS1 |
| KHDRBS2 |
| KHDRBS3 |
| KHNYN |
| KHSRP |
| KIAA0430 |
| KIAA0907 |
| KIAA1586 |
| KIAA1958 |
| KIN |
| KLF13 |
| KLHL6 |
| KMT2A |
| KMT2B |
| KMT2C |
| KMT2D |
| KMT2E |
| KMT5A |
| KRBOX4 |
| KRCC1 |
| L1RE1 |
| L1TD1 |
| L3MBTL1 |
| L3MBTL2 |
| L3MBTL3 |
| L3MBTL4 |
| LAMA1 |
| LARP1 |
| LARP1B |
| LARP4 |
| LARP4B |
| LARP6 |
| LARP7 |
| LAS1L |
| LBR |
| LBX1 |
| LBX2 |
| LCOR |
| LCORL |
| LDB1 |
| LDB2 |
| LDB3 |
| LEF1 |
| LEO1 |
| LEUTX |
| LIG1 |
| LIG3 |
| LIG4 |
| LIMD1 |
| LIN28A |
| LIN28B |
| LIN9 |

TABLE 8-continued

| Epigenetic-modulating genes Gene ID |
| --- |
| LITAF |
| LOC102724159 |
| LOC102725121 |
| LOC285556 |
| LOC81691 |
| LRPPRC |
| LRRC16A |
| LRRC71 |
| LRRC73 |
| LRRFIP1 |
| LRRFIP2 |
| LRWD1 |
| LSM1 |
| LSM11 |
| LSM14A |
| LSM14B |
| LSM2 |
| LSM3 |
| LSM4 |
| LSM5 |
| LSM6 |
| LSM7 |
| LSM8 |
| LUC7L |
| LUC7L2 |
| LUC7L3 |
| LYL1 |
| MAK16 |
| MAOA |
| MAOB |
| MAP3K14 |
| MAP3K7 |
| MAPKAPK3 |
| MARVELD2 |
| MASTL |
| MATR3 |
| MAX |
| MAZ |
| MBD1 |
| MBD2 |
| MBD3 |
| MBD4 |
| MBD5 |
| MBD6 |
| MBIP |
| MBNL1 |
| MBNL2 |
| MBNL3 |
| MBTD1 |
| MCEE |
| MCM10 |
| MCM2 |
| MCM3 |
| MCM4 |
| MCM5 |
| MCM6 |
| MCM7 |
| MCM8 |
| MCM9 |
| MCMBP |
| MCMDC2 |
| MCPH1 |
| MCRS1 |
| MDC1 |
| MDM2 |
| MDM4 |
| MEAF6 |
| MECOM |
| MECP2 |
| MED25 |
| MED27 |
| MEIOB |
| MEN1 |
| MEOX1 |
| MEOX2 |
| METAP1 |
| METAP1D |

TABLE 8-continued

TABLE 8-continued

| Epigenetic-modulating genes Gene ID | | Epigenetic-modulating genes Gene ID |
|---|---|---|
| METAP2 | 5 | MTA3 |
| METTL14 | | MTERF1 |
| METTL25 | | MTERF2 |
| METTL4 | | MTF2 |
| MEX3A | | MTIF3 |
| MEX3B | | MTO1 |
| MEX3C | 10 | MTRF1 |
| MEX3D | | MTRF1L |
| MGA | | MUM1 |
| MGEA5 | | MUTYH |
| MGMT | | MVP |
| MIER1 | | MXD1 |
| MIER2 | | MXD3 |
| MIER3 | 15 | MXD4 |
| MIF4GD | | MXI1 |
| MINA | | MYB |
| MIXL1 | | MYBBP1A |
| MKX | | MYBL1 |
| MLH1 | | MYBL2 |
| MLH3 | 20 | MYC |
| MLL1 | | MYCBP |
| MLL2 | | MYCBP2 |
| MLL3 | | MYCL |
| MLL4 | | MYCLP1 |
| MLL5 | | MYCN |
| MLLT1 | 25 | MYEF2 |
| MLLT10 | | MYF5 |
| MLLT3 | | MYF6 |
| MLLT6 | | MYO1C |
| MLXIP | | MYOD1 |
| MLXIPL | | MYOG |
| MMS19 | 30 | MYSM1 |
| MNDA | | MYT1 |
| MNT | | MYT1L |
| MNX1 | | N4BP1 |
| MOF | | N6AMT1 |
| MORF | | NAA60 |
| MORF4L1 | | NABP1 |
| MORF4L2 | 35 | NABP2 |
| MOV10 | | NACA |
| MOV10L1 | | NACA2 |
| MOZ | | NACAD |
| MPG | | NACAP1 |
| MPHOSPH8 | | NANOG |
| MPND | 40 | NANOGP1 |
| MRGBP | | NANOGP8 |
| MRM1 | | NANOS1 |
| MRM3 | | NANOS2 |
| MRPL1 | | NANOS3 |
| MRPL11 | | NAP1L1 |
| MRPL13 | 45 | NAP1L2 |
| MRPL16 | | NAP1L4 |
| MRPL18 | | NARS |
| MRPL23 | | NARS2 |
| MRPL39 | | NASP |
| MRPL4 | | NAT10 |
| MRPL44 | 50 | NBN |
| MRPS11 | | NCAPD2 |
| MRPS15 | | NCAPD3 |
| MRPS6 | | NCBP1 |
| MRPS7 | | NCBP2 |
| MRTO4 | | NCBP2L |
| MSH2 | | NCL |
| MSH3 | 55 | NCOA1 |
| MSH4 | | NCOA2 |
| MSH5 | | NCOA3 |
| MSH6 | | NCOA6 |
| MSL1 | | NCOR1 |
| MSL2 | | NCOR2 |
| MSL3 | 60 | NDN |
| MSL3P1 | | NEDD8 |
| MSS51 | | NEIL2 |
| MST1 | | NEIL3 |
| MSX1 | | NEK6 |
| MSX2 | | NEK9 |
| MTA1 | 65 | NEUROD1 |
| MTA2 | | NEUROD2 |

TABLE 8-continued

| Epigenetic-modulating genes Gene ID |
| --- |
| NEUROD4 |
| NEUROD6 |
| NEUROG1 |
| NEUROG2 |
| NEUROG3 |
| NFAT5 |
| NFATC1 |
| NFATC2 |
| NFATC3 |
| NFATC4 |
| NFE2 |
| NFE2L1 |
| NFE2L2 |
| NFE2L3 |
| NFIA |
| NFIB |
| NFIC |
| NFIL3 |
| NFIX |
| NFRKB |
| NFX1 |
| NFXL1 |
| NFYA |
| NFYB |
| NFYC |
| NHLH1 |
| NHLH2 |
| NHP2 |
| NIPBL |
| NKX1-1 |
| NKX1-2 |
| NKX2-1 |
| NKX2-2 |
| NKX2-3 |
| NKX2-4 |
| NKX2-5 |
| NKX2-6 |
| NKX2-8 |
| NKX3-1 |
| NKX3-2 |
| NKX6-1 |
| NKX6-2 |
| NKX6-3 |
| NLRC3 |
| NLRC5 |
| NLRP1 |
| NLRP10 |
| NLRP11 |
| NLRP12 |
| NLRP13 |
| NLRP14 |
| NLRP2 |
| NLRP3 |
| NLRP4 |
| NLRP5 |
| NLRP6 |
| NLRP7 |
| NLRP8 |
| NLRP9 |
| NLRX1 |
| NMI |
| NMU |
| NNT |
| NO66 |
| NOBOX |
| NOC2L |
| NOC3L |
| NOCT |
| NOD1 |
| NOD2 |
| NOM1 |
| NONO |
| NOP10 |
| NOP56 |
| NOP58 |
| NOP9 |
| NOTO |

TABLE 8-continued

| Epigenetic-modulating genes Gene ID |
| --- |
| NOVA1 |
| NOVA2 |
| NPAS1 |
| NPAS2 |
| NPAS3 |
| NPAS4 |
| NPM1 |
| NPM2 |
| NPRL2 |
| NR0B1 |
| NR1D1 |
| NR1D2 |
| NR1H2 |
| NR1H3 |
| NR1H4 |
| NR1I2 |
| NR1I3 |
| NR2C1 |
| NR2C2 |
| NR2E1 |
| NR2E3 |
| NR2F1 |
| NR2F2 |
| NR2F6 |
| NR3C1 |
| NR3C2 |
| NR4A1 |
| NR4A2 |
| NR4A3 |
| NR5A1 |
| NR5A2 |
| NR6A1 |
| NSA2 |
| NSD1 |
| NSD2 |
| NSD3 |
| NSL1 |
| NSUN2 |
| NTHL1 |
| NUCB1 |
| NUCB2 |
| NUDT21 |
| NUFIP1 |
| NUP35 |
| NUP98 |
| NUPR1 |
| NUPR2 |
| NYNRIN |
| OAS1 |
| OAS2 |
| OAS3 |
| OASL |
| OCEL1 |
| OCLN |
| OGG1 |
| OGT |
| OLIG1 |
| OLIG2 |
| OLIG3 |
| ONECUT1 |
| ONECUT2 |
| ONECUT3 |
| OPN4 |
| OPTN |
| ORC1 |
| ORC2 |
| ORC3 |
| ORC4 |
| ORC5 |
| ORC6 |
| OSR1 |
| OSR2 |
| OTP |
| OTUD1 |
| OTUD3 |
| OTUD4 |
| OTUD5 |

TABLE 8-continued

| Epigenetic-modulating genes Gene ID |
| --- |
| OTUD6A |
| OTUD6B |
| OTUD7A |
| OTUD7B |
| OTX1 |
| OTX2 |
| OVCA2 |
| OXNAD1 |
| P2RX1 |
| P2RX2 |
| P2RX3 |
| P2RX4 |
| P2RX5 |
| P2RX6 |
| P2RX7 |
| P2RY12 |
| P2RY13 |
| P2RY14 |
| P3H4 |
| PA2G4 |
| PADI1 |
| PADI2 |
| PADI3 |
| PADI4 |
| PAF1 |
| PAGR1 |
| PAIP1 |
| PAK2 |
| PAOX |
| PAPD5 |
| PAPD7 |
| PARG |
| PARN |
| PARP1 |
| PARP10 |
| PARP11 |
| PARP12 |
| PARP14 |
| PARP15 |
| PARP2 |
| PARP3 |
| PARP9 |
| PARS2 |
| PASD1 |
| PATL1 |
| PATL2 |
| PAX1 |
| PAX2 |
| PAX3 |
| PAX4 |
| PAX5 |
| PAX6 |
| PAX7 |
| PAX8 |
| PAX9 |
| PAXBP1 |
| PAXIP1 |
| PBK |
| PBRM1 |
| PCAF |
| PCBP1 |
| PCBP2 |
| PCBP3 |
| PCBP4 |
| PCF11 |
| PCGF1 |
| PCGF2 |
| PCGF3 |
| PCGF5 |
| PCGF6 |
| PCNA |
| PDCD11 |
| PDCD2 |
| PDCD2L |
| PDCD4 |
| PDE12 |
| PDLIM1 |

TABLE 8-continued

| Epigenetic-modulating genes Gene ID |
| --- |
| PDLIM2 |
| PDLIM3 |
| PDLIM4 |
| PDLIM5 |
| PDLIM7 |
| PDP1 |
| PDS5A |
| PDS5B |
| PDX1 |
| PELO |
| PELP1 |
| PEO1 |
| PEPD |
| PER1 |
| PER2 |
| PER3 |
| PES1 |
| PGR |
| PHC1 |
| PHC2 |
| PHC3 |
| PHF1 |
| PHF10 |
| PHF11 |
| PHF12 |
| PHF13 |
| PHF14 |
| PHF19 |
| PHF2 |
| PHF20 |
| PHF20L1 |
| PHF21A |
| PHF23 |
| PHF3 |
| PHF6 |
| PHF7 |
| PHF8 |
| PHIP |
| PHOX2A |
| PHOX2B |
| PHTF1 |
| PHTF2 |
| PINX1 |
| PIR |
| PITX1 |
| PITX2 |
| PITX3 |
| PIWIL4 |
| PKM |
| PKN1 |
| PLEKHA3 |
| PLEKHA8 |
| PLEKHA8P1 |
| PLEKHD1 |
| PMRT1 |
| PMRT10 |
| PMRT2 |
| PMRT3 |
| PMRT5 |
| PMRT6 |
| PMRT7 |
| PMRT8 |
| PMS1 |
| PMS2 |
| PMS2P1 |
| PMS2P11 |
| PMS2P2 |
| PMS2P3 |
| PMS2P5 |
| PNKP |
| PNLDC1 |
| PNPT1 |
| POGZ |
| POLA2 |
| POLB |
| POLD2 |
| POLD4 |

TABLE 8-continued

| Epigenetic-modulating genes Gene ID |
| --- |
| POLDIP3 |
| POLE2 |
| POLE3 |
| POLE4 |
| POLG |
| POLL |
| POLM |
| POLN |
| POLQ |
| POLR2D |
| POLRMT |
| POP4 |
| POT1 |
| PPAN |
| PPAN-P2RY11 |
| PPARA |
| PPARD |
| PPARG |
| PPARGC1A |
| PPARGC1B |
| PPM1G |
| PPOX |
| PPP1R37 |
| PPP2CA |
| PPP4C |
| PPP4R2 |
| PPRC1 |
| PQBP1 |
| PRDM1 |
| PRDM10 |
| PRDM11 |
| PRDM12 |
| PRDM13 |
| PRDM14 |
| PRDM16 |
| PRDM2 |
| PRDM4 |
| PRDM5 |
| PRDM6 |
| PRDM7 |
| PRDM8 |
| PRDM9 |
| PREB |
| PRICKLE4 |
| PRIM1 |
| PRKAA1 |
| PRKAA2 |
| PRKAB1 |
| PRKAB2 |
| PRKAG1 |
| PRKAG2 |
| PRKAG3 |
| PRKCA |
| PRKCB |
| PRKCD |
| PRKDC |
| PRKRIP1 |
| PRM2 |
| PRM3 |
| PRMT1 |
| PRMT2 |
| PRMT5 |
| PRMT6 |
| PRMT7 |
| PRMT8 |
| PRMT9 |
| PROP1 |
| PROX1 |
| PROX2 |
| PRPF31 |
| PRPF39 |
| PRPF4 |
| PRPF40A |
| PRPF40B |
| PRPF8 |
| PRR14 |
| PRRX1 |

TABLE 8-continued

| Epigenetic-modulating genes Gene ID |
| --- |
| PRRX2 |
| PSIP1 |
| PSMC3IP |
| PSMD14 |
| PSPC1 |
| PTAFR |
| PTOV1 |
| PUM1 |
| PUM2 |
| PUM3 |
| PURA |
| PURB |
| PURG |
| PWP1 |
| PWP2 |
| PYHIN1 |
| QARS |
| QKI |
| QRICH1 |
| RAD1 |
| RAD23A |
| RAD23B |
| RAD50 |
| RAD51 |
| RAD51B |
| RAD51C |
| RAD51D |
| RAD52 |
| RAD54B |
| RAD54L |
| RAD54L2 |
| RAE1 |
| RAG1 |
| RAG2 |
| RAI1 |
| RARA |
| RARB |
| RARG |
| RAVER1 |
| RAVER2 |
| RAX |
| RAX2 |
| RB1 |
| RBBP4 |
| RBBP5 |
| RBBP6 |
| RBBP7 |
| RBBP8 |
| RBBP8NL |
| RBCK1 |
| RBFOX1 |
| RBFOX2 |
| RBFOX3 |
| RBL1 |
| RBL2 |
| RBM11 |
| RBM12 |
| RBM12B |
| RBM15 |
| RBM15B |
| RBM17 |
| RBM20 |
| RBM22 |
| RBM26 |
| RBM27 |
| RBM43 |
| RBM7 |
| RBM8A |
| RBMX2 |
| RBPJ |
| RBPJL |
| RBPMS |
| RBX1 |
| RCBTB1 |
| RCBTB2 |
| RCC1 |
| RCC2 |

TABLE 8-continued

| Epigenetic-modulating genes Gene ID |
| --- |
| RCCD1 |
| RCL1 |
| RCOR1 |
| RCOR2 |
| RCOR3 |
| RECQL |
| RECQL4 |
| RECQL5 |
| REST |
| REXO1 |
| REXO1L1P |
| REXO4 |
| RFC1 |
| RFC2 |
| RFC3 |
| RFC4 |
| RFC5 |
| RFX1 |
| RFX2 |
| RFX3 |
| RFX4 |
| RFX5 |
| RFX6 |
| RFX7 |
| RFX8 |
| RGP1 |
| RHOXF1 |
| RHOXF2 |
| RHOXF2B |
| RIC8A |
| RIC8B |
| RILP |
| RILPL1 |
| RILPL2 |
| RIMKLA |
| RIMKLB |
| RING1 |
| RLF |
| RLIM |
| RMI1 |
| RNF168 |
| RNF2 |
| RNF20 |
| RNF40 |
| RNF8 |
| RNH1 |
| RNPC3 |
| RNPS1 |
| RORA |
| RORB |
| RORC |
| ROSA |
| RPA3 |
| RPF1 |
| RPF2 |
| RPGR |
| RPL10A |
| RPL12 |
| RPL13 |
| RPL13A |
| RPL18 |
| RPL23 |
| RPL30 |
| RPL34 |
| RPL35 |
| RPL35A |
| RPL37 |
| RPL39 |
| RPL39L |
| RPL39P5 |
| RPL5 |
| RPL7A |
| RPL9 |
| RPLP0 |
| RPLP0P6 |
| RPLP1 |
| RPLP2 |

TABLE 8-continued

| Epigenetic-modulating genes Gene ID |
| --- |
| RPP25 |
| RPP25L |
| RPP30 |
| RPS13 |
| RPS14 |
| RPS26 |
| RPS26P11 |
| RPS27A |
| RPS3 |
| RPS5 |
| RPS6KA3 |
| RPS6KA4 |
| RPS6KA5 |
| RPS9 |
| RREB1 |
| RRN3 |
| RRN3P1 |
| RRNAD1 |
| RRP8 |
| RRP9 |
| RSF1 |
| RSL1D1 |
| RTCA |
| RTEL1 |
| RTEL1-TNFRSF6B |
| RUNX2 |
| RUNX3 |
| RUVBL1 |
| RUVBL2 |
| RXRA |
| RXRB |
| RXRG |
| RYBP |
| SAFB |
| SAGE1 |
| SAGE2P |
| SALL1 |
| SALL2 |
| SALL3 |
| SALL4 |
| SAMD1 |
| SAMD11 |
| SAMD13 |
| SAMD4A |
| SAMD4B |
| SAMD7 |
| SAP130 |
| SAP18 |
| SAP25 |
| SAP30 |
| SAP30L |
| SATB1 |
| SATB2 |
| SBDS |
| SBNO1 |
| SBNO2 |
| SCMH1 |
| SCML1 |
| SCML2 |
| SCML4 |
| SEBOX |
| SENP1 |
| SENP3 |
| SERBP1 |
| SERGEF |
| SERTAD1 |
| SERTAD2 |
| SET |
| SETBP1 |
| SETD1A |
| SETD1B |
| SETD2 |
| SETD3 |
| SETD4 |
| SETD5 |
| SETD6 |
| SETD7 |

TABLE 8-continued

Epigenetic-modulating genes
Gene ID

| |
|---|
| SETD8 |
| SETDB1 |
| SETDB2 |
| SETMAR |
| SETX |
| SF1 |
| SF3A1 |
| SF3A3 |
| SF3B1 |
| SF3B3 |
| SFMBT1 |
| SFMBT2 |
| SFPQ |
| SHARPIN |
| SHOX |
| SHOX2 |
| SHPRH |
| SIM1 |
| SIM2 |
| SIN3A |
| SIN3B |
| SIRT1 |
| SIRT2 |
| SIRT3 |
| SIRT4 |
| SIRT5 |
| SIRT6 |
| SIRT7 |
| SIX1 |
| SIX2 |
| SIX3 |
| SIX4 |
| SIX5 |
| SIX6 |
| SKP1 |
| SLBP |
| SLC2A4RG |
| SLX1A |
| SMAD1 |
| SMAD2 |
| SMAD3 |
| SMAD4 |
| SMAD5 |
| SMAD6 |
| SMAD7 |
| SMAD9 |
| SMAP1 |
| SMAP2 |
| SMARCA1 |
| SMARCA2 |
| SMARCA4 |
| SMARCA5 |
| SMARCAD1 |
| SMARCAL1 |
| SMARCB1 |
| SMARCC1 |
| SMARCC2 |
| SMARCD1 |
| SMARCD2 |
| SMARCD3 |
| SMARCE1 |
| SMC5 |
| SMC6 |
| SMEK1 |
| SMEK2 |
| SMOX |
| SMYD1 |
| SMYD2 |
| SMYD3 |
| SMYD4 |
| SMYD5 |
| SNAI2 |
| SNAPC1 |
| SNAPC4 |
| SNAPC5 |
| SND1 |
| SNRNP35 |

TABLE 8-continued

Epigenetic-modulating genes
Gene ID

| |
|---|
| SNRNP70 |
| SNRPA |
| SNRPB2 |
| SNRPC |
| SNRPD1 |
| SNRPD3 |
| SNRPF |
| SNRPG |
| SNRPGP15 |
| SNU13 |
| SNURFL |
| SNW1 |
| SOHLH1 |
| SOHLH2 |
| SOX1 |
| SOX10 |
| SOX11 |
| SOX12 |
| SOX13 |
| SOX14 |
| SOX15 |
| SOX17 |
| SOX18 |
| SOX2 |
| SOX21 |
| SOX3 |
| SOX30 |
| SOX4 |
| SOX5 |
| SOX6 |
| SOX7 |
| SOX8 |
| SOX9 |
| SP1 |
| SP100 |
| SP110 |
| SP140 |
| SP140L |
| SP2 |
| SP3 |
| SP4 |
| SP5 |
| SP6 |
| SP7 |
| SP8 |
| SP9 |
| SPAG7 |
| SPDEF |
| SPEN |
| SPI1 |
| SPIB |
| SPIC |
| SPO11 |
| SPOCD1 |
| SPOP |
| SPRY1 |
| SPRY2 |
| SPRY3 |
| SPRY4 |
| SPTY2D1 |
| SRBD1 |
| SRC1 |
| SRCAP |
| SRP19 |
| SRP54 |
| SRPRA |
| SRRM1 |
| SRSF1 |
| SRSF10 |
| SRSF12 |
| SRSF2 |
| SRSF3 |
| SRSF7 |
| SRSF8 |
| SRY |
| SS18 |
| SS18L1 |

TABLE 8-continued

| Epigenetic-modulating genes Gene ID |
| --- |
| SS18L2 |
| SSB |
| SSBP1 |
| SSRP1 |
| ST18 |
| STAG1 |
| STAG2 |
| STAG3 |
| STAG3L1 |
| STAG3L2 |
| STAG3L3 |
| STAG3L4 |
| STAT1 |
| STAT2 |
| STAT3 |
| STAT4 |
| STAT5A |
| STAT5B |
| STAT6 |
| STK17A |
| STK17B |
| STK31 |
| STK4 |
| STRBP |
| SUDS3 |
| SUFU |
| SUGP1 |
| SUGP2 |
| SUPT16H |
| SUPT3H |
| SUPT4H1 |
| SUPT6H |
| SUPT7L |
| SURF6 |
| SUV39H1 |
| SUV39H2 |
| SUV420H1 |
| SUV420H2 |
| SUZ12 |
| SWAP70 |
| SYNCRIP |
| T |
| TAB2 |
| TAB3 |
| TADA1 |
| TADA2A |
| TADA2B |
| TADA3 |
| TAF1 |
| TAF10 |
| TAF12 |
| TAF13 |
| TAF15 |
| TAF1B |
| TAF1L |
| TAF2 |
| TAF3 |
| TAF4 |
| TAF5 |
| TAF5L |
| TAF6 |
| TAF6L |
| TAF7 |
| TAF7L |
| TAF8 |
| TAF9 |
| TAF9B |
| TAL1 |
| TAL2 |
| TARBP1 |
| TARS |
| TARS2 |
| TARSL2 |
| TBL1XR1 |
| TBL3 |
| TBP |
| TBPL1 |

TABLE 8-continued

| Epigenetic-modulating genes Gene ID |
| --- |
| TBPL2 |
| TBR1 |
| TBX1 |
| TBX10 |
| TBX15 |
| TBX18 |
| TBX19 |
| TBX2 |
| TBX20 |
| TBX21 |
| TBX22 |
| TBX3 |
| TBX4 |
| TBX5 |
| TBX6 |
| TCEA1 |
| TCEA2 |
| TCEA3 |
| TCEANC |
| TCEANC2 |
| TCERG1 |
| TCERG1L |
| TCF12 |
| TCF20 |
| TCF3 |
| TCF4 |
| TCF7 |
| TCF7L1 |
| TCF7L2 |
| TCFL5 |
| TDG |
| TDRD1 |
| TDRD10 |
| TDRD12 |
| TDRD15 |
| TDRD3 |
| TDRD5 |
| TDRD6 |
| TDRD7 |
| TDRKH |
| TEAD1 |
| TEAD2 |
| TEAD3 |
| TEAD4 |
| TEF |
| TERF1 |
| TERF2 |
| TERT |
| TET1 |
| TET2 |
| TET3 |
| TEX10 |
| TFAM |
| TFAP2A |
| TFAP2B |
| TFAP2C |
| TFAP2D |
| TFAP2E |
| TFAP4 |
| TFCP2 |
| TFCP2L1 |
| TFDP1 |
| TFDP2 |
| TFDP3 |
| TFPT |
| THAP1 |
| THAP12 |
| THAP2 |
| THAP3 |
| THAP5 |
| THAP6 |
| THAP7 |
| THAP8 |
| THOC1 |
| THOC2 |
| THOC5 |
| THOC7 |

TABLE 8-continued

| Epigenetic-modulating genes Gene ID |
| --- |
| THRA |
| THRB |
| TIP60 |
| TIPARP |
| TIPIN |
| TLE1 |
| TLE2 |
| TLE3 |
| TLE4 |
| TLE6 |
| TLK1 |
| TLK2 |
| TLR7 |
| TMEM62 |
| TNFAIP3 |
| TNFRSF19 |
| TNP1 |
| TNP2 |
| TNRC18 |
| TOE1 |
| TONSL |
| TOP1 |
| TOP1MT |
| TOP2A |
| TOP2B |
| TOP3B |
| TOPBP1 |
| TOX |
| TOX2 |
| TOX3 |
| TOX4 |
| TP53 |
| TP53BP1 |
| TP63 |
| TP73 |
| TRA2A |
| TRA2B |
| TRAPPC1 |
| TRAPPC2 |
| TRAPPC2B |
| TRAPPC4 |
| TRERF1 |
| TRIM16 |
| TRIM24 |
| TRIM27 |
| TRIM28 |
| TRIM33 |
| TRIM66 |
| TRMT10B |
| TRMT10C |
| TRMT2A |
| TRMT2B |
| TRMT6 |
| TRNT1 |
| TROVE2 |
| TRRAP |
| TRUB2 |
| TSC22D1 |
| TSC22D2 |
| TSC22D3 |
| TSC22D4 |
| TSEN2 |
| TSFM |
| TSHZ1 |
| TSHZ2 |
| TSHZ3 |
| TSR1 |
| TSSK6 |
| UBR2 |
| UBR5 |
| UBR7 |
| UBTF |
| UBTFL1 |
| UBTFL6 |
| UCHL5 |
| UHMK1 |
| UHRF1 |

TABLE 8-continued

| Epigenetic-modulating genes Gene ID |
| --- |
| UHRF2 |
| UIMC1 |
| unassigned |
| UNCX |
| UPF1 |
| UPF2 |
| URI1 |
| USP11 |
| USP12 |
| USP15 |
| USP16 |
| USP17L2 |
| USP21 |
| USP22 |
| USP3 |
| USP36 |
| USP44 |
| USP46 |
| USP49 |
| USP7 |
| UTP6 |
| UTY |
| VAX1 |
| VAX2 |
| VDR |
| VENTX |
| VGLL1 |
| VGLL2 |
| VGLL3 |
| VPS72 |
| VRK1 |
| VSX1 |
| WAC |
| WDHD1 |
| WDR3 |
| WDR4 |
| WDR5 |
| WDR77 |
| WDR82 |
| WHSC1 |
| WHSC1L1 |
| WIZ |
| WRN |
| WRNIP1 |
| WSB2 |
| WTIP |
| WWTR1 |
| XAB2 |
| XDH |
| XPA |
| XPC |
| XPNPEP1 |
| XPNPEP2 |
| XPNPEP3 |
| XPO5 |
| XPOT |
| XRCC2 |
| XRCC3 |
| XRCC5 |
| XRCC6 |
| XRN1 |
| YAF2 |
| YAP1 |
| YARS |
| YEATS2 |
| YEATS4 |
| YLPM1 |
| YRDC |
| YWHAB |
| YWHAE |
| YWHAZ |
| YY1 |
| YY1AP1 |
| YY2 |
| ZBED1 |
| ZBED4 |
| ZBED5 |

TABLE 8-continued

| Epigenetic-modulating genes Gene ID |
| --- |
| ZBED6 |
| ZBED8 |
| ZBED9 |
| ZBTB16 |
| ZBTB2 |
| ZBTB33 |
| ZBTB44 |
| ZBTB47 |
| ZBTB7C |
| ZC3H10 |
| ZC3H11A |
| ZC3H12A |
| ZC3H12B |
| ZC3H12C |
| ZC3H12D |
| ZC3H14 |
| ZC3H15 |
| ZC3H3 |
| ZC3H7A |
| ZC3H7B |
| ZC3HAV1 |
| ZC3HAV1L |
| ZCCHC13 |
| ZCCHC3 |
| ZCCHC7 |
| ZCCHC8 |
| ZCCHC9 |
| ZCRB1 |
| ZCWPW1 |
| ZFAND1 |
| ZFAND2A |
| ZFAND2B |
| ZFAND4 |
| ZFAND5 |
| ZFAND6 |
| ZFP1 |
| ZFP14 |
| ZFP28 |
| ZFP30 |
| ZFP36 |
| ZFP36L1 |
| ZFP36L2 |
| ZFP37 |
| ZFP42 |
| ZFP57 |
| ZFP64 |
| ZFP69 |
| ZFP69B |
| ZFP82 |
| ZFP90 |
| ZFP92 |
| ZFPL1 |
| ZFPM1 |
| ZFPM2 |
| ZFR |
| ZFR2 |
| ZGPAT |
| ZGRF1 |
| ZHX1 |
| ZHX2 |
| ZHX3 |
| ZIK1 |
| ZIM3 |
| ZKSCAN5 |
| ZKSCAN7 |
| ZMAT1 |
| ZMAT2 |
| ZMAT3 |
| ZMAT4 |
| ZMAT5 |
| ZMYM1 |
| ZMYM2 |
| ZMYM3 |
| ZMYM4 |
| ZMYM5 |
| ZMYM6 |
| ZMYND10 |

TABLE 8-continued

| Epigenetic-modulating genes Gene ID |
| --- |
| ZMYND11 |
| ZMYND12 |
| ZMYND15 |
| ZMYND19 |
| ZMYND8 |
| ZNF10 |
| ZNF112 |
| ZNF12 |
| ZNF121 |
| ZNF124 |
| ZNF132 |
| ZNF133 |
| ZNF134 |
| ZNF135 |
| ZNF136 |
| ZNF140 |
| ZNF154 |
| ZNF155 |
| ZNF157 |
| ZNF16 |
| ZNF160 |
| ZNF169 |
| ZNF17 |
| ZNF175 |
| ZNF177 |
| ZNF180 |
| ZNF181 |
| ZNF182 |
| ZNF184 |
| ZNF19 |
| ZNF2 |
| ZNF20 |
| ZNF207 |
| ZNF211 |
| ZNF214 |
| ZNF217 |
| ZNF219 |
| ZNF221 |
| ZNF222 |
| ZNF223 |
| ZNF224 |
| ZNF225 |
| ZNF226 |
| ZNF227 |
| ZNF23 |
| ZNF230 |
| ZNF233 |
| ZNF234 |
| ZNF235 |
| ZNF236 |
| ZNF248 |
| ZNF25 |
| ZNF250 |
| ZNF251 |
| ZNF254 |
| ZNF256 |
| ZNF26 |
| ZNF264 |
| ZNF266 |
| ZNF277 |
| ZNF28 |
| ZNF283 |
| ZNF284 |
| ZNF285 |
| ZNF286A |
| ZNF286B |
| ZNF292 |
| ZNF30 |
| ZNF300 |
| ZNF302 |
| ZNF304 |
| ZNF311 |
| ZNF316 |
| ZNF317 |
| ZNF320 |
| ZNF324 |
| ZNF324B |

TABLE 8-continued

TABLE 8-continued

| Epigenetic-modulating genes Gene ID |
| --- |
| ZNF329 |
| ZNF333 |
| ZNF334 |
| ZNF335 |
| ZNF337 |
| ZNF34 |
| ZNF341 |
| ZNF343 |
| ZNF346 |
| ZNF347 |
| ZNF35 |
| ZNF350 |
| ZNF354A |
| ZNF354B |
| ZNF354C |
| ZNF355P |
| ZNF37A |
| ZNF382 |
| ZNF385A |
| ZNF385B |
| ZNF385C |
| ZNF385D |
| ZNF395 |
| ZNF404 |
| ZNF41 |
| ZNF415 |
| ZNF416 |
| ZNF417 |
| ZNF418 |
| ZNF419 |
| ZNF420 |
| ZNF425 |
| ZNF426 |
| ZNF429 |
| ZNF432 |
| ZNF439 |
| ZNF440 |
| ZNF445 |
| ZNF45 |
| ZNF454 |
| ZNF461 |
| ZNF468 |
| ZNF470 |
| ZNF471 |
| ZNF480 |
| ZNF483 |
| ZNF487 |
| ZNF490 |
| ZNF491 |
| ZNF514 |
| ZNF516 |
| ZNF521 |
| ZNF527 |
| ZNF528 |
| ZNF529 |
| ZNF530 |
| ZNF532 |
| ZNF534 |
| ZNF536 |
| ZNF540 |
| ZNF541 |
| ZNF543 |
| ZNF546 |
| ZNF547 |
| ZNF548 |
| ZNF549 |
| ZNF550 |
| ZNF551 |
| ZNF552 |
| ZNF554 |
| ZNF555 |
| ZNF556 |
| ZNF557 |
| ZNF558 |
| ZNF559 |
| ZNF559-ZNF177 |
| ZNF560 |

| Epigenetic-modulating genes Gene ID |
| --- |
| ZNF561 |
| ZNF564 |
| ZNF565 |
| ZNF566 |
| ZNF567 |
| ZNF568 |
| ZNF569 |
| ZNF570 |
| ZNF571 |
| ZNF573 |
| ZNF574 |
| ZNF577 |
| ZNF578 |
| ZNF579 |
| ZNF582 |
| ZNF583 |
| ZNF584 |
| ZNF586 |
| ZNF587 |
| ZNF589 |
| ZNF592 |
| ZNF593 |
| ZNF595 |
| ZNF596 |
| ZNF598 |
| ZNF599 |
| ZNF605 |
| ZNF606 |
| ZNF607 |
| ZNF610 |
| ZNF611 |
| ZNF613 |
| ZNF614 |
| ZNF616 |
| ZNF618 |
| ZNF619 |
| ZNF620 |
| ZNF623 |
| ZNF624 |
| ZNF629 |
| ZNF630 |
| ZNF639 |
| ZNF649 |
| ZNF655 |
| ZNF665 |
| ZNF668 |
| ZNF669 |
| ZNF670 |
| ZNF674 |
| ZNF677 |
| ZNF681 |
| ZNF684 |
| ZNF687 |
| ZNF689 |
| ZNF69 |
| ZNF699 |
| ZNF7 |
| ZNF70 |
| ZNF701 |
| ZNF704 |
| ZNF705A |
| ZNF705B |
| ZNF705D |
| ZNF705E |
| ZNF705F |
| ZNF705G |
| ZNF711 |
| ZNF720 |
| ZNF726 |
| ZNF728 |
| ZNF738 |
| ZNF74 |
| ZNF747 |
| ZNF749 |
| ZNF761 |
| ZNF765 |
| ZNF77 |

TABLE 8-continued

| Epigenetic-modulating genes Gene ID |
| --- |
| ZNF772 |
| ZNF773 |
| ZNF775 |
| ZNF776 |
| ZNF778 |
| ZNF780A |
| ZNF782 |
| ZNF787 |
| ZNF789 |
| ZNF790 |
| ZNF791 |
| ZNF792 |
| ZNF793 |
| ZNF8 |
| ZNF80 |
| ZNF805 |
| ZNF806 |
| ZNF81 |
| ZNF813 |
| ZNF816 |
| ZNF821 |
| ZNF831 |
| ZNF837 |
| ZNF84 |
| ZNF846 |
| ZNF860 |
| ZNF862 |
| ZNF879 |
| ZNF880 |
| ZNF888 |
| ZNF891 |

TABLE 8-continued

| Epigenetic-modulating genes Gene ID |
| --- |
| ZNF93 |
| ZNFX1 |
| ZNHIT1 |
| ZNHIT2 |
| ZRANB3 |
| ZRSR1 |
| ZRSR2 |
| ZSCAN10 |
| ZZEF1 |
| ZZZ3 |

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of making an improved cell therapy composition, comprising the steps of:
   (a) obtaining a sample comprising lymphocytes from a subject;
   (b) reducing or eliminating expression of one or more genes required for the induction and/or maintenance of exhausted CD8+ T lymphocytes ($T_{EX}$) in the lymphocytes; and
   (c) engineering the lymphocytes to target a therapeutically relevant antigen;
   wherein the one or more genes required for the induction and/or maintenance of $T_{EX}$ is a transcription factor or a gene involved in epigenetic modification of DNA; and
   wherein the transcription factor is TOX.

2. The method of claim 1, wherein the sample comprising T cells from the subject comprises blood, ascites, pleural effusion, lymph, mucus, broncho-alveolar lavage, or tissue.

3. The method of claim 2, wherein the sample comprising T cells from the subject comprises CD8+ T cells, tumor-associated lymphocytes, or tumor-infiltrating lymphocytes (TILs).

4. The method of claim 1, wherein expression of the one or more genes required for the induction and/or maintenance of $T_{EX}$ in the lymphocytes is reduced.

5. The method of claim 1, wherein expression of the one or more genes required for the induction and/or maintenance of $T_{EX}$ in the lymphocytes is eliminated.

6. The method of claim 4, wherein expression of the one or more genes required for the induction and/or maintenance of $T_{EX}$ in the lymphocytes is reduced by a method selected from the group consisting of RNA interference, clustered interspersed short palindromic repeat (CRISPR)/CRISPR-associated protein (Cas) system, meganucleases, transcription activator-like effector nucleases (TALENs), Zinc-finger nucleases (ZFNs), antisense, ribozymes and CRISPR inhibition system comprising dead Cas9.

7. The method of claim 5, wherein expression of the one or more genes required for the induction and/or maintenance of $T_{EX}$ in the lymphocytes is eliminated by a method selected from the group consisting of RNA interference, clustered interspersed short palindromic repeat (CRISPR)/CRISPR-associated protein (Cas) system, meganucleases, transcription activator-like effector nucleases (TALENs), Zinc-finger nucleases (ZFNs), antisense, ribozymes and CRISPR inhibition system comprising dead Cas9.

8. The method of claim 1, wherein the engineering the lymphocytes to target a therapeutically relevant antigen comprises introduction of a recombinant T cell receptor capable of binding a desired antigen/MHC or neo-antigen/MHC combination or introduction of a chimeric antigen receptor capable of binding a desired therapeutically relevant antigen.

9. A method of reducing or preventing T cell exhaustion in a lymphocyte obtained from a subject, comprising the steps of:
   reducing or eliminating expression of one or more genes required for the induction and/or maintenance of exhausted CD8+ T lymphocytes ($T_{EX}$) in the lymphocyte;
   wherein the gene required for induction and/or maintenance of exhausted CD8+ T lymphocytes is TOX; and
   wherein the lymphocyte is a CD8+ T cell.

* * * * *

SEQUENCE LISTING

```
<160> NUMBER OF SEQ ID NOS: 60

<210> SEQ ID NO 1
<211> LENGTH: 87
<212> TYPE: DNA
<213> ORGANISM: Homo Sapiens

<400> SEQUENCE: 1
cccctgatcc tggagtcgcc cagccccaac cagacctctc tgtacttctg tgccagcagt      60
tcctattacg agcagtactt cgggccg                                          87

<210> SEQ ID NO 2
<211> LENGTH: 87
<212> TYPE: DNA
<213> ORGANISM: Homo Sapiens

<400> SEQUENCE: 2
agtgcccatc ctgaagacag cagcttctac atctgcagtg ctaggagcac cgggactatg      60
attcgggctg agcagttctt cgggcca                                          87

<210> SEQ ID NO 3
<211> LENGTH: 87
<212> TYPE: DNA
<213> ORGANISM: Homo Sapiens

<400> SEQUENCE: 3
ctgactgtga gcaacatgag ccctgaagac agcagcatat atctctgcag cgtccaaggg      60
ggatctcctg aagctttctt tggacaa                                          87

<210> SEQ ID NO 4
```

<211> LENGTH: 87
<212> TYPE: DNA
<213> ORGANISM: Homo Sapiens

<400> SEQUENCE: 4
ctaaacctga gctctctgga gctgggggac tcagctttgt atttctgtgc cagcagcgtg        60
ttaggggatg agcagttctt cgggcca        87

<210> SEQ ID NO 5
<211> LENGTH: 87
<212> TYPE: DNA
<213> ORGANISM: Homo Sapiens

<400> SEQUENCE: 5
ctgaatgtga acgccttgtt gctgggggac tcggccctct atctctgtgc cagcagcttt        60
aggtccgggg agctgttttt tggagaa        87

<210> SEQ ID NO 6
<211> LENGTH: 87
<212> TYPE: DNA
<213> ORGANISM: Homo Sapiens

<400> SEQUENCE: 6
ctgctggggt tggagtcggc tgctccctcc caaacatctg tgtacttctg tgccagccgg        60
cagggttttg gctacacctt cggttcg        87

<210> SEQ ID NO 7
<211> LENGTH: 87
<212> TYPE: DNA
<213> ORGANISM: Homo Sapiens

<400> SEQUENCE: 7
actctgacga tccagcgcac acagcaggag gactcggccg tgtatctctg tgccagcagc        60
ttagggtaca ccatatattt tggagag        87

<210> SEQ ID NO 8
<211> LENGTH: 87
<212> TYPE: DNA
<213> ORGANISM: Homo Sapiens

<400> SEQUENCE: 8
cacgccctgc agccagaaga ctcagccctg tatctctgcg ccagcagcca agtgcctagc        60
ggcccctacg agcagtactt cgggccg        87

<210> SEQ ID NO 9
<211> LENGTH: 87
<212> TYPE: DNA
<213> ORGANISM: Homo Sapiens

<400> SEQUENCE: 9
accagtgccc atcctgaaga cagcagcttc tacatctgca gtgctccggg gatcgggcga        60
cgggggactg aagctttctt tggacaa        87

<210> SEQ ID NO 10
<211> LENGTH: 87
<212> TYPE: DNA
<213> ORGANISM: Homo Sapiens

<400> SEQUENCE: 10
gctgctccct cccagacatc tgtgtacttc tgtgccagca gtctaacagg ggtggtcata        60

-continued

```
tacaccgggg agctgttttt tggagaa                                          87

<210> SEQ ID NO 11
<211> LENGTH: 87
<212> TYPE: DNA
<213> ORGANISM: Homo Sapiens

<400> SEQUENCE: 11
ctgaagatcc agccctcaga acccagggac tcagctgtgt acttctgtgc cagcagtccc      60
ttgggctacg agcagtactt cgggccg                                          87

<210> SEQ ID NO 12
<211> LENGTH: 87
<212> TYPE: DNA
<213> ORGANISM: Homo Sapiens

<400> SEQUENCE: 12
agcaccttgg agctggggga ctcggccctt tatctttgcg ccagcagcgg gggacaggcc      60
agctcctacg agcagtactt cgggccg                                          87

<210> SEQ ID NO 13
<211> LENGTH: 87
<212> TYPE: DNA
<213> ORGANISM: Homo Sapiens

<400> SEQUENCE: 13
atccggtcca caaagctgga ggactcagcc atgtacttct gtgccagcag aggacaagac      60
cagaacactg aagctttctt tggacaa                                          87

<210> SEQ ID NO 14
<211> LENGTH: 87
<212> TYPE: DNA
<213> ORGANISM: Homo Sapiens

<400> SEQUENCE: 14
ctcaggctgg agtcggctgc tccctcccag acatctgtgt acttctgtgc cagcagtgaa      60
acagacactg aagctttctt tggacaa                                          87

<210> SEQ ID NO 15
<211> LENGTH: 87
<212> TYPE: DNA
<213> ORGANISM: Homo Sapiens

<400> SEQUENCE: 15
cacctacaca ccctgcagcc agaagactcg gccctgtatc tctgcgccag cagccaaatc      60
ggggataaga cggctttctt tggacaa                                          87

<210> SEQ ID NO 16
<211> LENGTH: 87
<212> TYPE: DNA
<213> ORGANISM: Homo Sapiens

<400> SEQUENCE: 16
aagatccagc ctgcagagct tggggactcg gccgtgtatc tctgtgccag cagccataca      60
aacaccgggg agctgttttt tggagaa                                          87

<210> SEQ ID NO 17
<211> LENGTH: 87
<212> TYPE: DNA
```

-continued

<213> ORGANISM: Homo Sapiens

<400> SEQUENCE: 17

```
ttggagtcgg ctgctccctc ccaaacatct gtgtacttct gtgccagcag ttacgggga      60 caggggcctg aagctttctt tggacaa                                          87
```

<210> SEQ ID NO 18
<211> LENGTH: 87
<212> TYPE: DNA
<213> ORGANISM: Homo Sapiens

<400> SEQUENCE: 18

```
gagatccagc gcacagagca gggggactcg gccatgtatc tctgtgccag cagtctagtc      60
gggggagggg aagctttctt tggacaa                                          87
```

<210> SEQ ID NO 19
<211> LENGTH: 87
<212> TYPE: DNA
<213> ORGANISM: Homo Sapiens

<400> SEQUENCE: 19

```
cacgccctgc agccagaaga ctcagccctg tatctctgcg ccagcagcct ggacaggggg      60
tataatcagc cccagcattt tggtgat                                          87
```

<210> SEQ ID NO 20
<211> LENGTH: 87
<212> TYPE: DNA
<213> ORGANISM: Homo Sapiens

<400> SEQUENCE: 20

```
caacctgcaa agcttgagga ctcggccgtg tatctctgtg ccagcagctt caatggggag      60
atgaacactg aagctttctt tggacaa                                          87
```

<210> SEQ ID NO 21
<211> LENGTH: 87
<212> TYPE: DNA
<213> ORGANISM: Homo Sapiens

<400> SEQUENCE: 21

```
ttggagatcc agcgcacaga gcaggggac tcggccatgt atctctgtgc cagcagcctt      60
tcctcttcac ccctccactt tgggaac                                          87
```

<210> SEQ ID NO 22
<211> LENGTH: 87
<212> TYPE: DNA
<213> ORGANISM: Homo Sapiens

<400> SEQUENCE: 22

```
tctaagaagc tcctcctcag tgactctggc ttctatctct gtgccttcgt cagcagggga      60
ggcgactatg gctacacctt cggttcg                                          87
```

<210> SEQ ID NO 23
<211> LENGTH: 87
<212> TYPE: DNA
<213> ORGANISM: Homo Sapiens

<400> SEQUENCE: 23

```
ctgagctctc tggagctggg ggactcagct ttgtatttct gtgccagcag cgcctccgcg      60
tgggccgctg aagctttctt tggacaa                                          87
```

-continued

```
<210> SEQ ID NO 24
<211> LENGTH: 87
<212> TYPE: DNA
<213> ORGANISM: Homo Sapiens

<400> SEQUENCE: 24
atgagctcct tggagctggg ggactcagcc ctgtacttct gtgccagcag ctcgaggact      60
aggtggaatg agcagttctt cgggcca                                          87

<210> SEQ ID NO 25
<211> LENGTH: 87
<212> TYPE: DNA
<213> ORGANISM: Homo Sapiens

<400> SEQUENCE: 25
ctgaagatcc agccctcaga acccagggac tcagctgtgt acttctgtgc cagcagcagt      60
gctaactatg ctacacctt cggttcg                                          87

<210> SEQ ID NO 26
<211> LENGTH: 87
<212> TYPE: DNA
<213> ORGANISM: Homo Sapiens

<400> SEQUENCE: 26
gaactgaaca tgagctcctt ggagctgggg gactcagccc tgtacttctg tgccagcagt      60
tcatctgata cgcagtattt tggccca                                         87

<210> SEQ ID NO 27
<211> LENGTH: 87
<212> TYPE: DNA
<213> ORGANISM: Homo Sapiens

<400> SEQUENCE: 27
tctctggagc tggggactc agctttgtat ttctgtgcca gcagcgtagg ggacaggggg      60
tctggaaaca ccatatattt tggagag                                        87

<210> SEQ ID NO 28
<211> LENGTH: 87
<212> TYPE: DNA
<213> ORGANISM: Homo Sapiens

<400> SEQUENCE: 28
tccgctacca gctcccagac atctgtgtac ttctgtgcca tcagtgacct cggcggcccg      60
gccgcagata cgcagtattt tggccca                                         87

<210> SEQ ID NO 29
<211> LENGTH: 87
<212> TYPE: DNA
<213> ORGANISM: Homo Sapiens

<400> SEQUENCE: 29
cccagcccca accagacctc tctgtacttc tgtgccagca gtttatgggg cggcgggagc      60
tcctacaatg agcagttctt cgggcca                                         87

<210> SEQ ID NO 30
<211> LENGTH: 87
<212> TYPE: DNA
<213> ORGANISM: Homo Sapiens
```

-continued

<400> SEQUENCE: 30

```
cagcctgcag aactggagga ttctggagtt tatttctgtg ccagcagcca actgacaggg      60
gctgacactg aagctttctt tggacaa                                         87
```

<210> SEQ ID NO 31
<211> LENGTH: 11
<212> TYPE: PRT
<213> ORGANISM: Homo Sapiens

<400> SEQUENCE: 31

```
Cys Ala Ser Ser Ser Tyr Tyr Glu Gln Tyr Phe
1               5                   10
```

<210> SEQ ID NO 32
<211> LENGTH: 16
<212> TYPE: PRT
<213> ORGANISM: Homo Sapiens

<400> SEQUENCE: 32

```
Cys Ser Ala Arg Ser Thr Gly Thr Met Ile Arg Ala Glu Gln Phe Phe
1               5                   10                  15
```

<210> SEQ ID NO 33
<211> LENGTH: 12
<212> TYPE: PRT
<213> ORGANISM: Homo Sapiens

<400> SEQUENCE: 33

```
Cys Ser Val Gln Gly Gly Ser Pro Glu Ala Phe Phe
1               5                   10
```

<210> SEQ ID NO 34
<211> LENGTH: 12
<212> TYPE: PRT
<213> ORGANISM: Homo Sapiens

<400> SEQUENCE: 34

```
Cys Ala Ser Ser Val Leu Gly Asp Glu Gln Phe Phe
1               5                   10
```

<210> SEQ ID NO 35
<211> LENGTH: 12
<212> TYPE: PRT
<213> ORGANISM: Homo Sapiens

<400> SEQUENCE: 35

```
Cys Ala Ser Ser Phe Arg Ser Gly Glu Leu Phe Phe
1               5                   10
```

<210> SEQ ID NO 36
<211> LENGTH: 11
<212> TYPE: PRT
<213> ORGANISM: Homo Sapiens

<400> SEQUENCE: 36

```
Cys Ala Ser Arg Gln Gly Phe Gly Tyr Thr Phe
1               5                   10
```

<210> SEQ ID NO 37
<211> LENGTH: 11
<212> TYPE: PRT
<213> ORGANISM: Homo Sapiens

<400> SEQUENCE: 37

-continued

```
Cys Ala Ser Ser Leu Gly Tyr Thr Ile Tyr Phe
1               5                   10

<210> SEQ ID NO 38
<211> LENGTH: 15
<212> TYPE: PRT
<213> ORGANISM: Homo Sapiens

<400> SEQUENCE: 38

Cys Ala Ser Ser Gln Val Pro Ser Gly Pro Tyr Glu Gln Tyr Phe
1               5                   10                  15

<210> SEQ ID NO 39
<211> LENGTH: 15
<212> TYPE: PRT
<213> ORGANISM: Homo Sapiens

<400> SEQUENCE: 39

Cys Ser Ala Pro Gly Ile Gly Arg Arg Gly Thr Glu Ala Phe Phe
1               5                   10                  15

<210> SEQ ID NO 40
<211> LENGTH: 17
<212> TYPE: PRT
<213> ORGANISM: Homo Sapiens

<400> SEQUENCE: 40

Cys Ala Ser Ser Leu Thr Gly Val Val Ile Tyr Thr Gly Glu Leu Phe
1               5                   10                  15

Phe

<210> SEQ ID NO 41
<211> LENGTH: 12
<212> TYPE: PRT
<213> ORGANISM: Homo Sapiens

<400> SEQUENCE: 41

Cys Ala Ser Ser Pro Leu Gly Tyr Glu Gln Tyr Phe
1               5                   10

<210> SEQ ID NO 42
<211> LENGTH: 15
<212> TYPE: PRT
<213> ORGANISM: Homo Sapiens

<400> SEQUENCE: 42

Cys Ala Ser Ser Gly Gly Gln Ala Ser Ser Tyr Glu Gln Tyr Phe
1               5                   10                  15

<210> SEQ ID NO 43
<211> LENGTH: 14
<212> TYPE: PRT
<213> ORGANISM: Homo Sapiens

<400> SEQUENCE: 43

Cys Ala Ser Arg Gly Gln Asp Gln Asn Thr Glu Ala Phe Phe
1               5                   10

<210> SEQ ID NO 44
<211> LENGTH: 12
<212> TYPE: PRT
<213> ORGANISM: Homo Sapiens

<400> SEQUENCE: 44
```

-continued

```
Cys Ala Ser Ser Glu Thr Asp Thr Glu Ala Phe Phe
1               5                   10

<210> SEQ ID NO 45
<211> LENGTH: 13
<212> TYPE: PRT
<213> ORGANISM: Homo Sapiens

<400> SEQUENCE: 45

Cys Ala Ser Ser Gln Ile Gly Asp Lys Thr Ala Phe Phe
1               5                   10

<210> SEQ ID NO 46
<211> LENGTH: 13
<212> TYPE: PRT
<213> ORGANISM: Homo Sapiens

<400> SEQUENCE: 46

Cys Ala Ser Ser His Thr Asn Thr Gly Glu Leu Phe Phe
1               5                   10

<210> SEQ ID NO 47
<211> LENGTH: 14
<212> TYPE: PRT
<213> ORGANISM: Homo Sapiens

<400> SEQUENCE: 47

Cys Ala Ser Ser Tyr Gly Gly Gln Gly Pro Glu Ala Phe Phe
1               5                   10

<210> SEQ ID NO 48
<211> LENGTH: 13
<212> TYPE: PRT
<213> ORGANISM: Homo Sapiens

<400> SEQUENCE: 48

Cys Ala Ser Ser Leu Val Gly Gly Arg Glu Ala Phe Phe
1               5                   10

<210> SEQ ID NO 49
<211> LENGTH: 15
<212> TYPE: PRT
<213> ORGANISM: Homo Sapiens

<400> SEQUENCE: 49

Cys Ala Ser Ser Leu Asp Arg Gly Tyr Asn Gln Pro Gln His Phe
1               5                   10                  15

<210> SEQ ID NO 50
<211> LENGTH: 15
<212> TYPE: PRT
<213> ORGANISM: Homo Sapiens

<400> SEQUENCE: 50

Cys Ala Ser Ser Phe Asn Gly Glu Met Asn Thr Glu Ala Phe Phe
1               5                   10                  15

<210> SEQ ID NO 51
<211> LENGTH: 12
<212> TYPE: PRT
<213> ORGANISM: Homo Sapiens

<400> SEQUENCE: 51

Cys Ala Ser Ser Leu Ser Ser Ser Pro Leu His Phe
```

-continued

```
1               5                10

<210> SEQ ID NO 52
<211> LENGTH: 14
<212> TYPE: PRT
<213> ORGANISM: Homo Sapiens

<400> SEQUENCE: 52

Cys Ala Phe Val Ser Arg Gly Gly Asp Tyr Gly Tyr Thr Phe
1               5                10

<210> SEQ ID NO 53
<211> LENGTH: 14
<212> TYPE: PRT
<213> ORGANISM: Homo Sapiens

<400> SEQUENCE: 53

Cys Ala Ser Ser Ala Ser Ala Trp Ala Ala Glu Ala Phe Phe
1               5                10

<210> SEQ ID NO 54
<211> LENGTH: 14
<212> TYPE: PRT
<213> ORGANISM: Homo Sapiens

<400> SEQUENCE: 54

Cys Ala Ser Ser Ser Arg Thr Arg Trp Asn Glu Gln Phe Phe
1               5                10

<210> SEQ ID NO 55
<211> LENGTH: 12
<212> TYPE: PRT
<213> ORGANISM: Homo Sapiens

<400> SEQUENCE: 55

Cys Ala Ser Ser Ser Ala Asn Tyr Gly Tyr Thr Phe
1               5                10

<210> SEQ ID NO 56
<211> LENGTH: 11
<212> TYPE: PRT
<213> ORGANISM: Homo Sapiens

<400> SEQUENCE: 56

Cys Ala Ser Ser Ser Ser Asp Thr Gln Tyr Phe
1               5                10

<210> SEQ ID NO 57
<211> LENGTH: 16
<212> TYPE: PRT
<213> ORGANISM: Homo Sapiens

<400> SEQUENCE: 57

Cys Ala Ser Ser Val Gly Asp Arg Gly Ser Gly Asn Thr Ile Tyr Phe
1               5                10               15

<210> SEQ ID NO 58
<211> LENGTH: 16
<212> TYPE: PRT
<213> ORGANISM: Homo Sapiens

<400> SEQUENCE: 58

Cys Ala Ile Ser Asp Leu Gly Gly Pro Ala Ala Asp Thr Gln Tyr Phe
1               5                10               15
```

-continued

```
<210> SEQ ID NO 59
<211> LENGTH: 17
<212> TYPE: PRT
<213> ORGANISM: Homo Sapiens

<400> SEQUENCE: 59

Cys Ala Ser Ser Leu Trp Gly Gly Gly Ser Ser Tyr Asn Glu Gln Phe
1               5                   10                  15

Phe

<210> SEQ ID NO 60
<211> LENGTH: 15
<212> TYPE: PRT
<213> ORGANISM: Homo Sapiens

<400> SEQUENCE: 60

Cys Ala Ser Ser Gln Leu Thr Gly Ala Asp Thr Glu Ala Phe Phe
1               5                   10                  15
```